(12) United States Patent  (10) Patent No.: US 8,241,628 B2
Diefenbach-Streiber et al.  (45) Date of Patent: Aug. 14, 2012

(54) COMPOSITIONS AND METHODS FOR ANTIBODIES TARGETING COMPLEMENT PROTEIN C5

(75) Inventors: Beate Diefenbach-Streiber, Windach (DE); Adina Eberth, Munich (DE); Braydon Charles Guild, Concord, MA (US); Yong-In Kim, Westborough, MA (US); Michael Roguska, Ashland, MA (US); Igor Splawski, Winchester, MA (US)

(73) Assignee: Novartis AG, Basel (CH)

( * ) Notice: Subject to any disclaimer, the term of this patent is extended or adjusted under 35 U.S.C. 154(b) by 196 days.

(21) Appl. No.: 12/535,205

(22) Filed: Aug. 4, 2009

(65) Prior Publication Data

US 2010/0034809 A1    Feb. 11, 2010

Related U.S. Application Data

(60) Provisional application No. 61/086,355, filed on Aug. 5, 2008.

(51) Int. Cl.
*A61K 39/395* (2006.01)
*C07K 16/18* (2006.01)
*C07H 21/00* (2006.01)
*C12N 15/74* (2006.01)
*C12N 5/16* (2006.01)

(52) U.S. Cl. ............. 424/133.1; 530/387.1; 530/387.3; 530/388.1

(58) Field of Classification Search .............. 424/133.1; 530/387.1, 387.3, 388.1
See application file for complete search history.

(56) References Cited

U.S. PATENT DOCUMENTS

| | | | |
|---|---|---|---|
| 6,074,642 A | 6/2000 | Wang et al. | |
| 6,355,245 B1 | 3/2002 | Evans et al. | |
| 7,011,952 B2 | 3/2006 | Hageman et al. | |
| 7,108,982 B1 | 9/2006 | Hageman | |
| 7,344,846 B2 | 3/2008 | Hageman et al. | |
| 7,351,524 B2 | 4/2008 | Hageman et al. | |
| 2005/0169921 A1 | 8/2005 | Bell et al. | |
| 2005/0191298 A1 | 9/2005 | Bell et al. | |
| 2006/0115476 A1 | 6/2006 | Tedesco | |
| 2006/0263819 A1 | 11/2006 | Hageman et al. | |
| 2007/0116710 A1 | 5/2007 | Bell et al. | |
| 2007/0196367 A1 | 8/2007 | Dinu | |
| 2008/0131418 A1 | 6/2008 | Hageman et al. | |
| 2008/0274453 A1 | 11/2008 | Hageman | |

FOREIGN PATENT DOCUMENTS

| | | |
|---|---|---|
| EP | 1153302 B1 | 10/2006 |
| EP | 1804064 A1 | 7/2007 |
| EP | 1287364 B1 | 10/2008 |
| EP | 2026073 A1 | 2/2009 |
| JP | 3734266 B2 | 10/2005 |
| WO | 95/29697 A1 | 11/1995 |
| WO | 01/84144 A1 | 11/2001 |
| WO | WO 02/30985 A2 | 4/2002 |
| WO | WO 02/086085 A2 | 10/2002 |
| WO | 2005/074607 A2 | 8/2005 |
| WO | 2007056227 A2 | 5/2007 |
| WO | 2007/106585 A1 | 9/2007 |
| WO | 2008/069889 A2 | 6/2008 |

OTHER PUBLICATIONS

De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Rudikoff et al. (Proc. Natl. Acad. Sci. USA. 1982; 79 (6): 1979-1983).*
Cicchetti et al.; "Immune parameters relevant to neural xenograft survival in the primate brain"; Xenotransplantation; 10(1): 41-49 (2003).
Holers; "The spectrum of complement alternative pathway-mediated diseases"; Immunological Reviews; 223:300-316 (2008).
Rother et al.; "Discovery and development of the complement inhibitor eculizumab for the treatment of paroxysmal nocturnal hemoglobinuria"; Nature Biotechnology—Perspective; 25(11):1256-1264 (2007).

* cited by examiner

*Primary Examiner* — Lynn Bristol
(74) *Attorney, Agent, or Firm* — Matthew Beaudet; Karen A. Lacourse

(57) ABSTRACT

The present invention relates to antibodies targeting complement protein C5 and compositions and methods of use thereof.

20 Claims, 73 Drawing Sheets

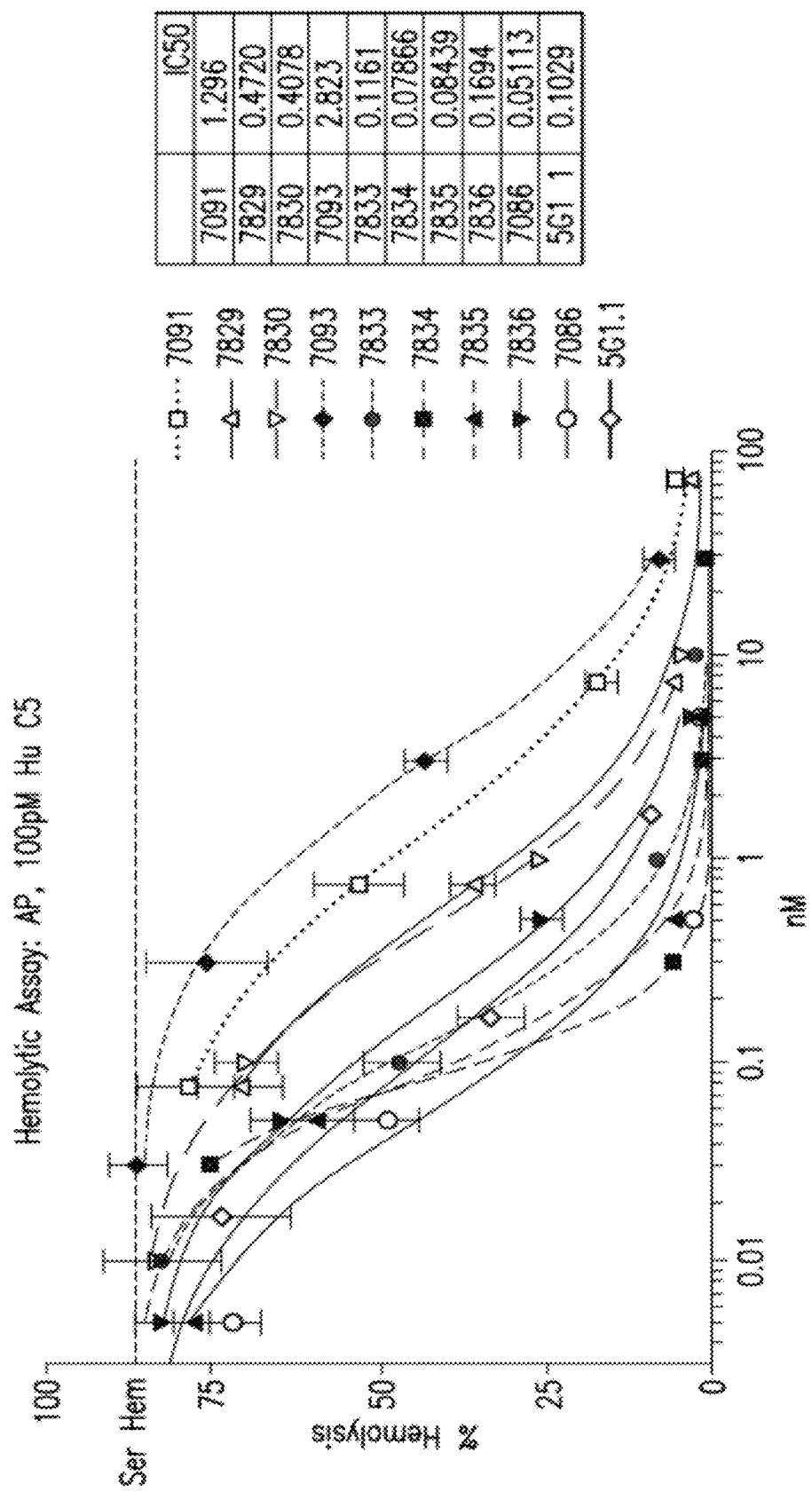

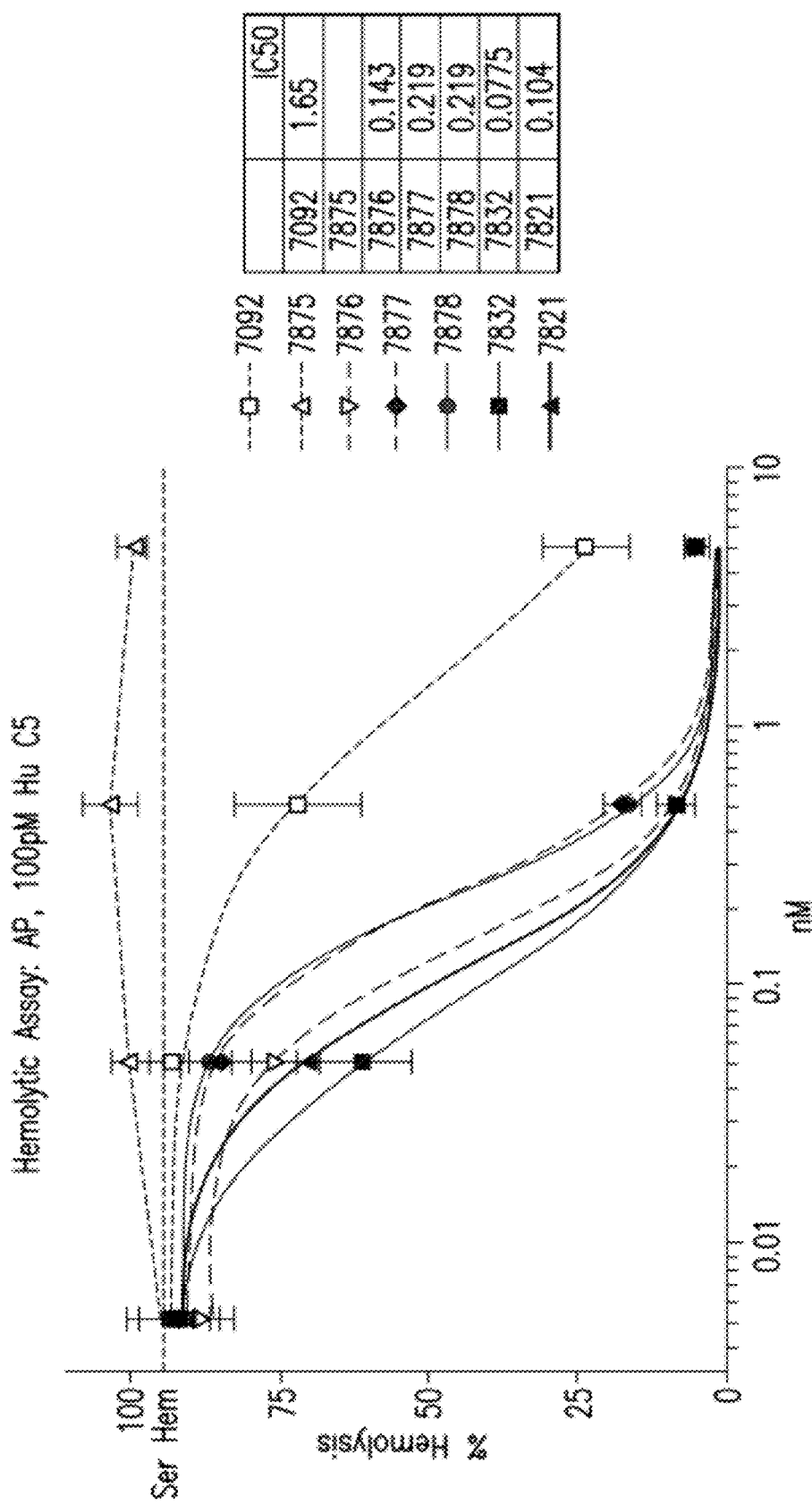

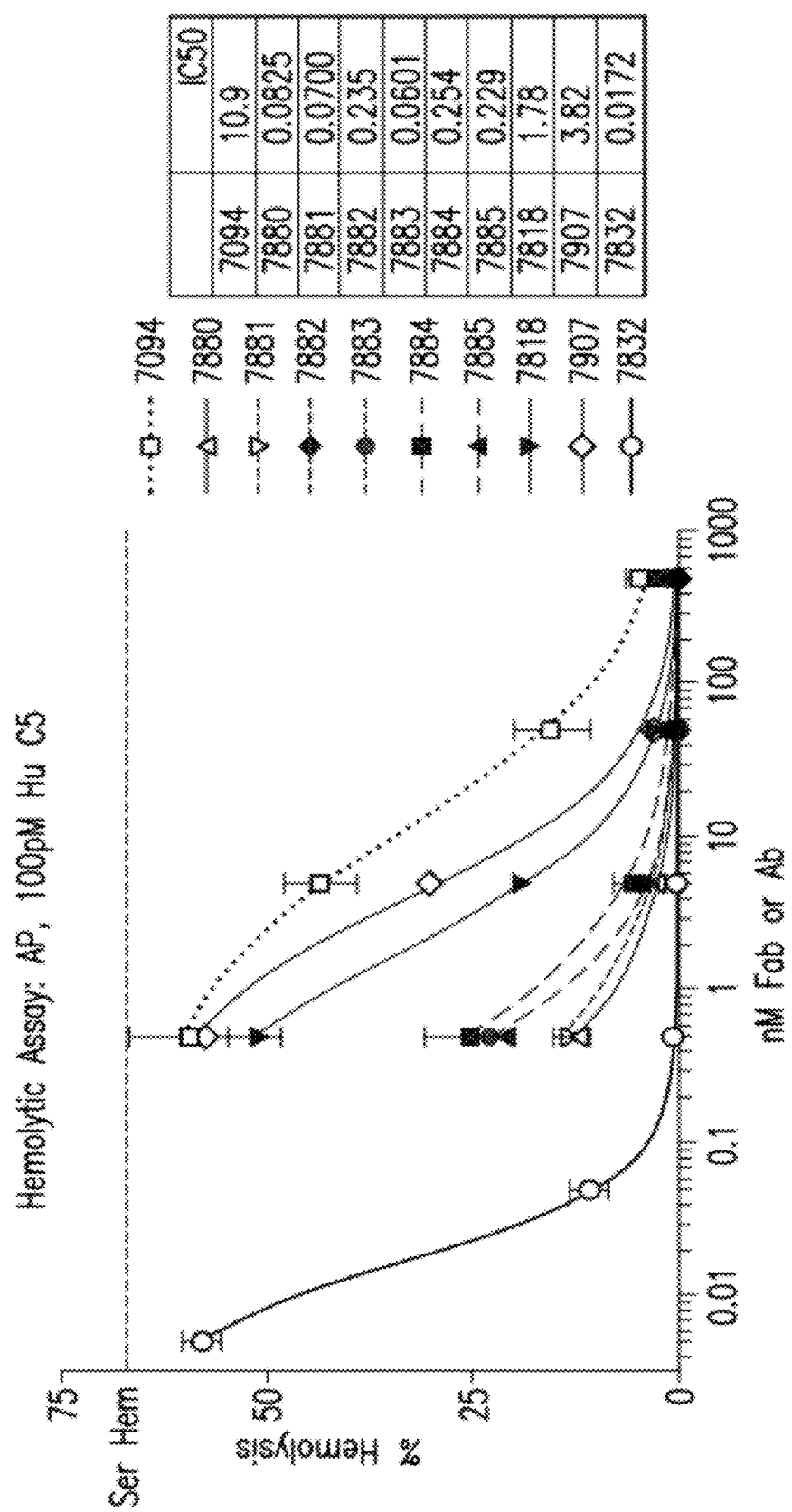

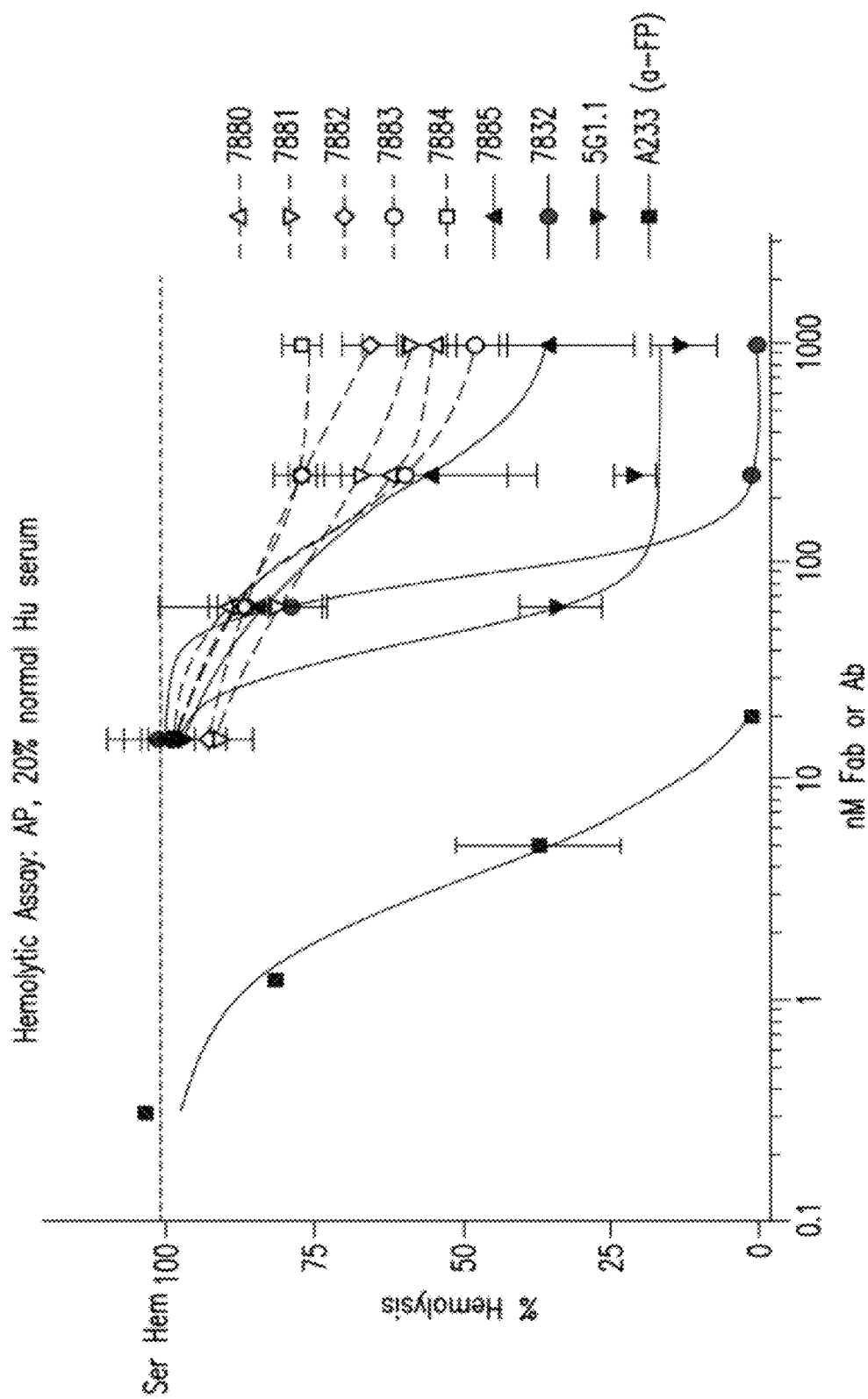

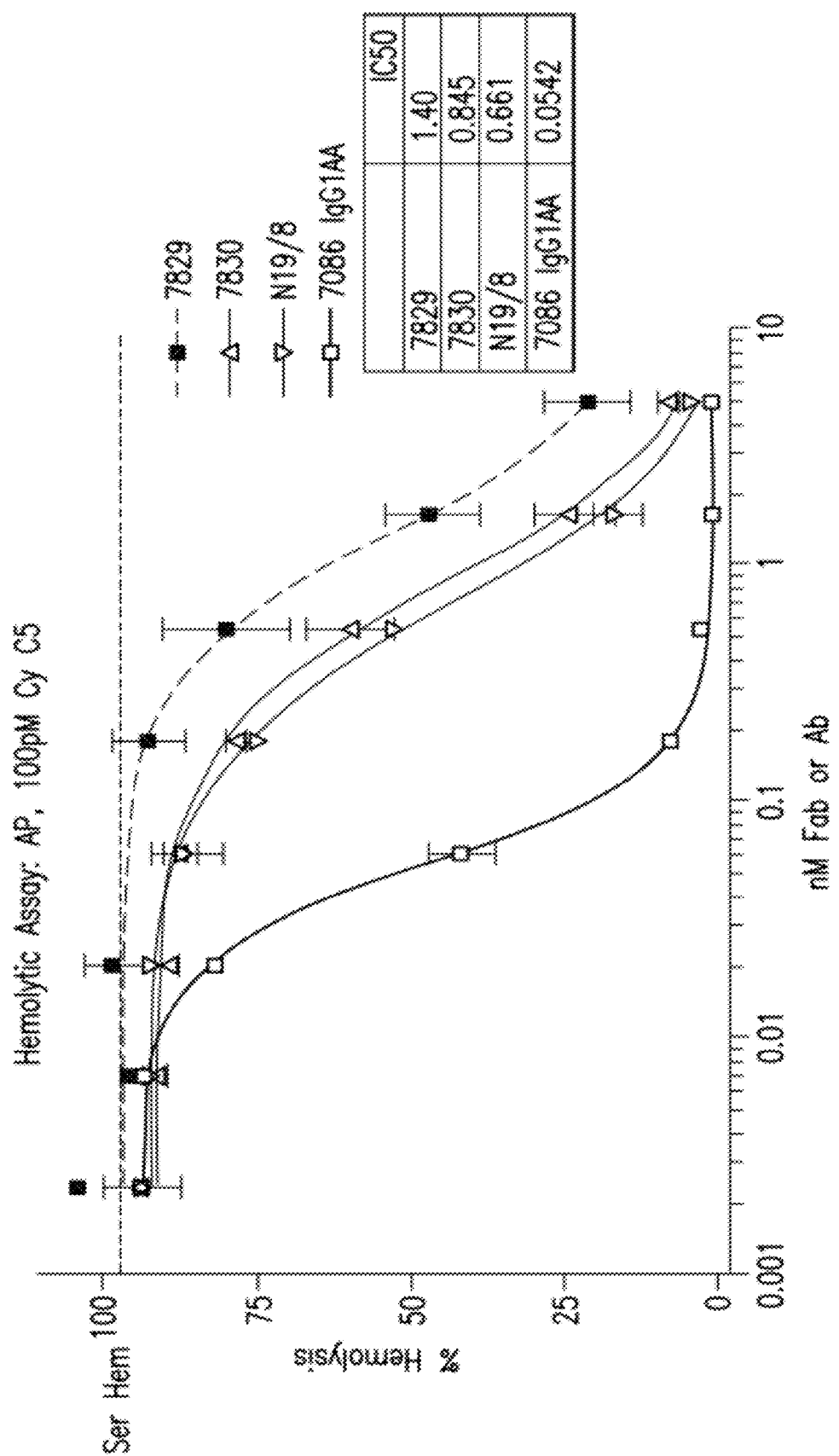

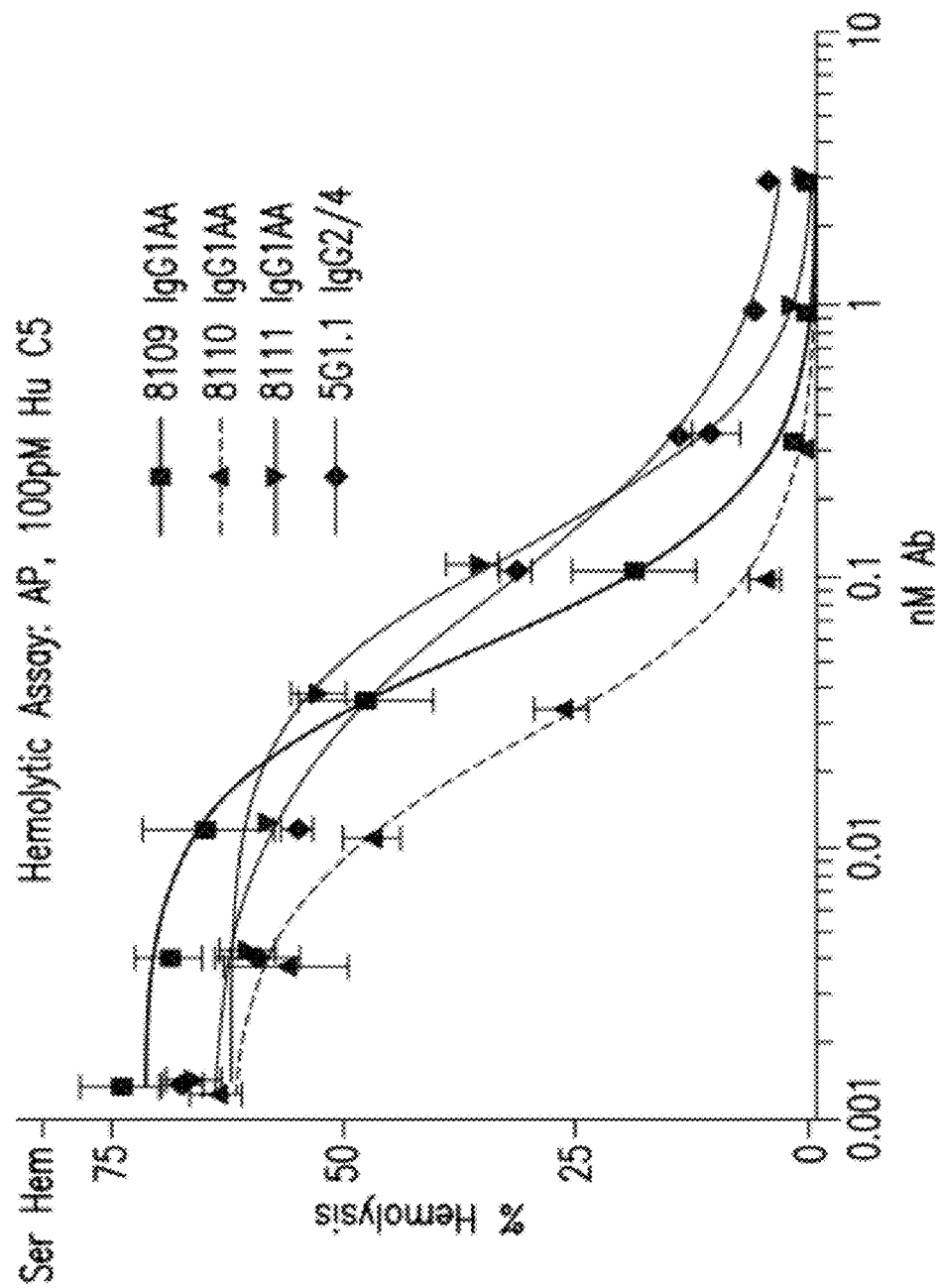

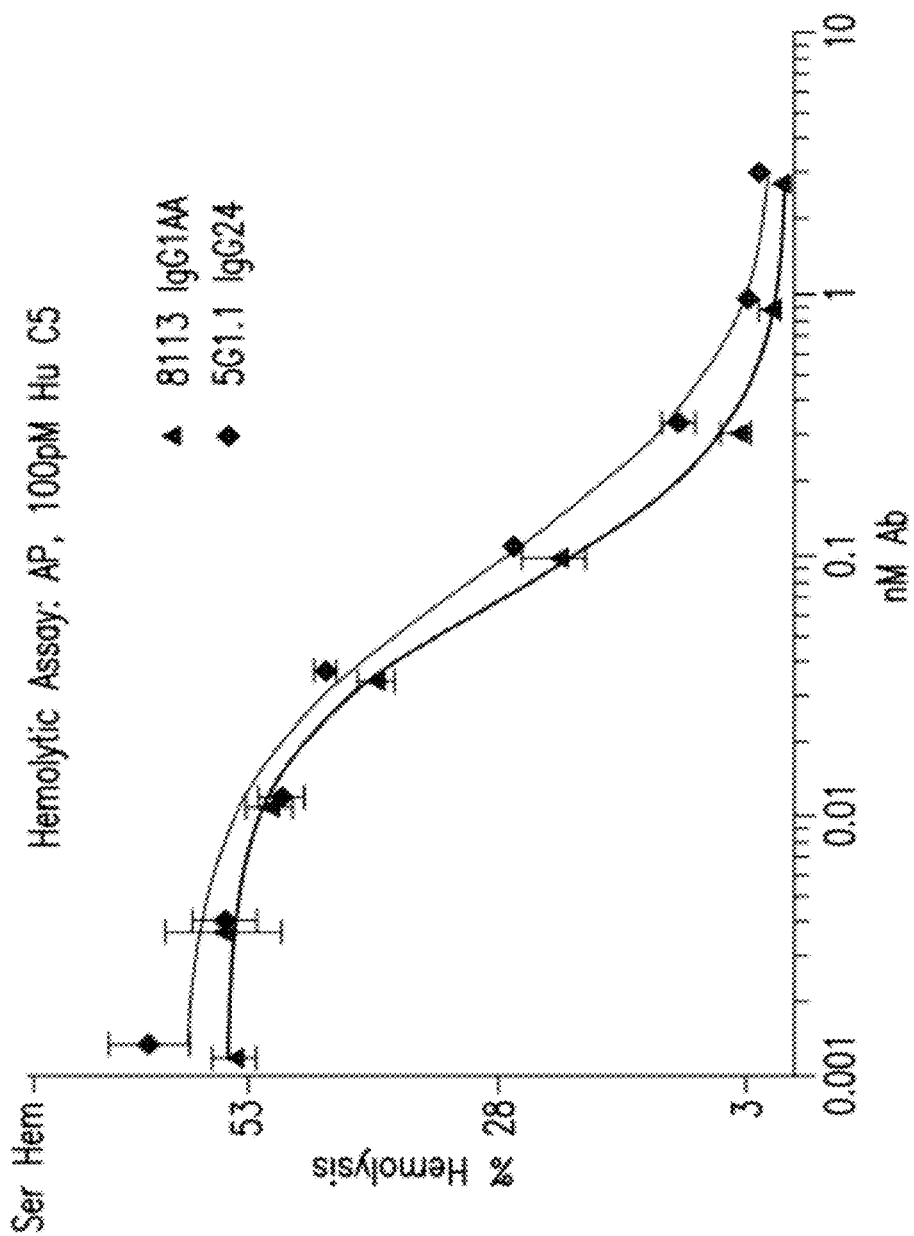

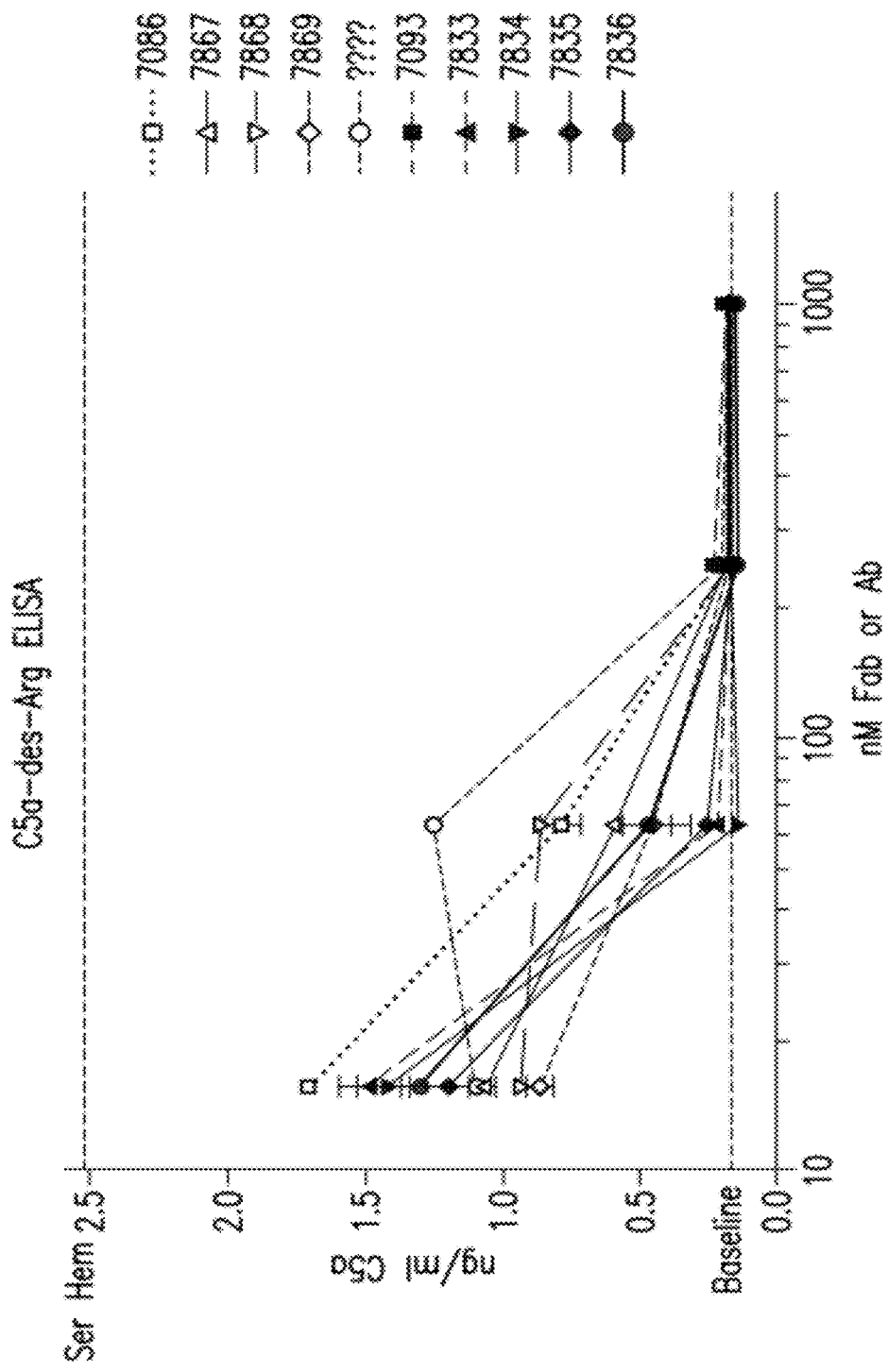

| Rows: unlabelled Fab (100-fold excess) | | | | | | | | | |
|---|---|---|---|---|---|---|---|---|---|
| | | | | Columns: biotinylated Fab | | | | | |
| MOR0 | 7086 | 7832 | 7834 | 7871 | 7872 | 7873 | 7876 | 7878 | |
| 7086 | 691 | 2597 | 853 | 1191 | 825 | 694 | 1002 | 495 | |
| 7832 | 668 | 1186 | 404 | 586 | 3601 | 499 | 595 | 251 | |
| 7834 | 618 | 1727 | 391 | 625 | 609 | 455 | 756 | 560 | |
| 7871 | 426 | 1384 | 422 | 758 | 619 | 1009 | 392 | 451 | |
| 7872 | 1553 | 3199 | 773 | 1486 | 944 | 882 | 842 | 781 | |
| 7873 | 800 | 3342 | 965 | 1414 | 1491 | 922 | 1188 | 691 | |
| 7876 | 892 | 2535 | 652 | 978 | 1366 | 1394 | 621 | 701 | |
| 7878 | 850 | 2643 | 784 | 1228 | 2218 | 891 | 1180 | 643 | |
| 100% | 36816 | 37112 | 37340 | 43250 | 41651 | 33768 | 38078 | 37405 | | competition with identical Fab
biotinylated Fab without competition = 100% signal

FIG. 19

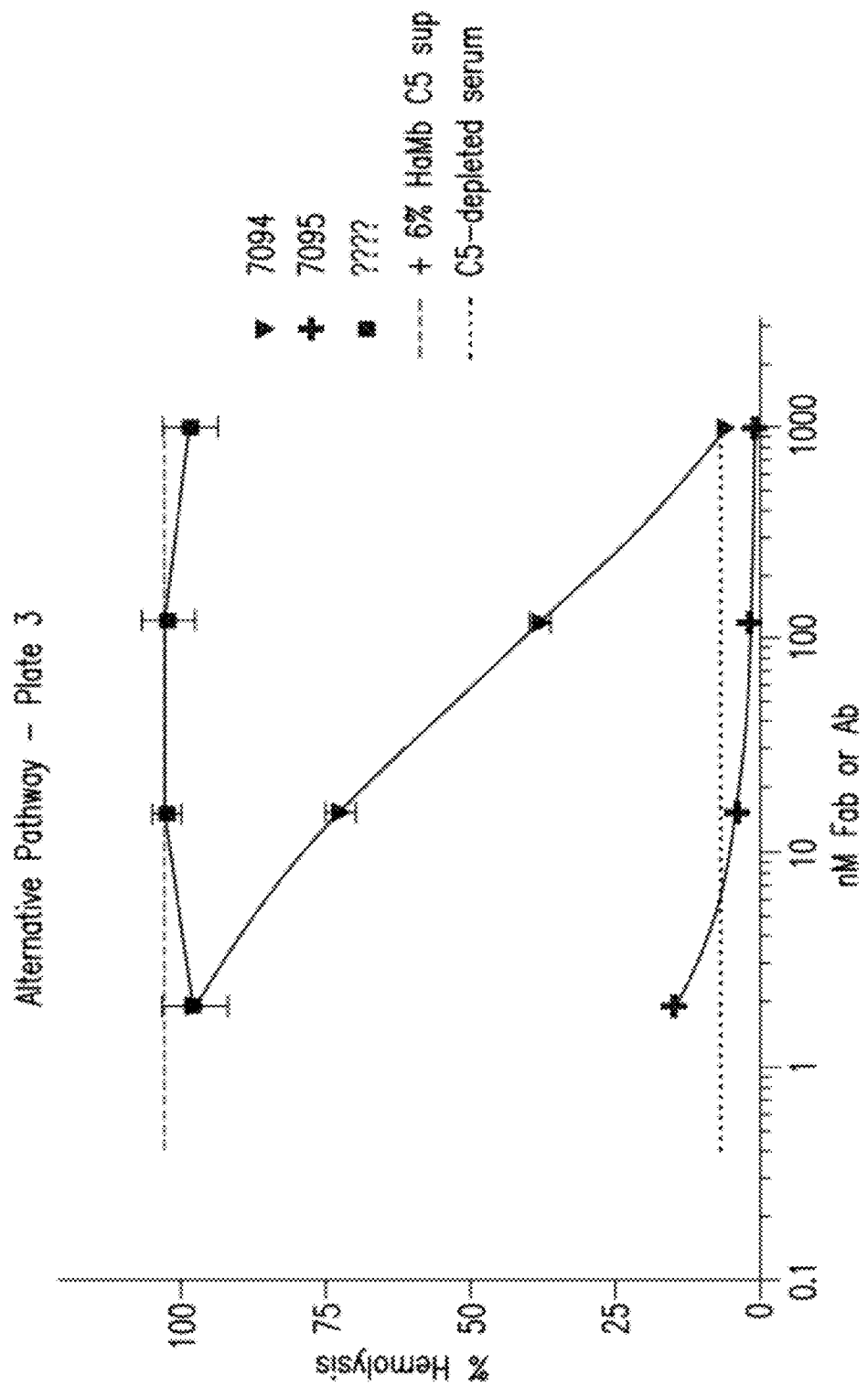

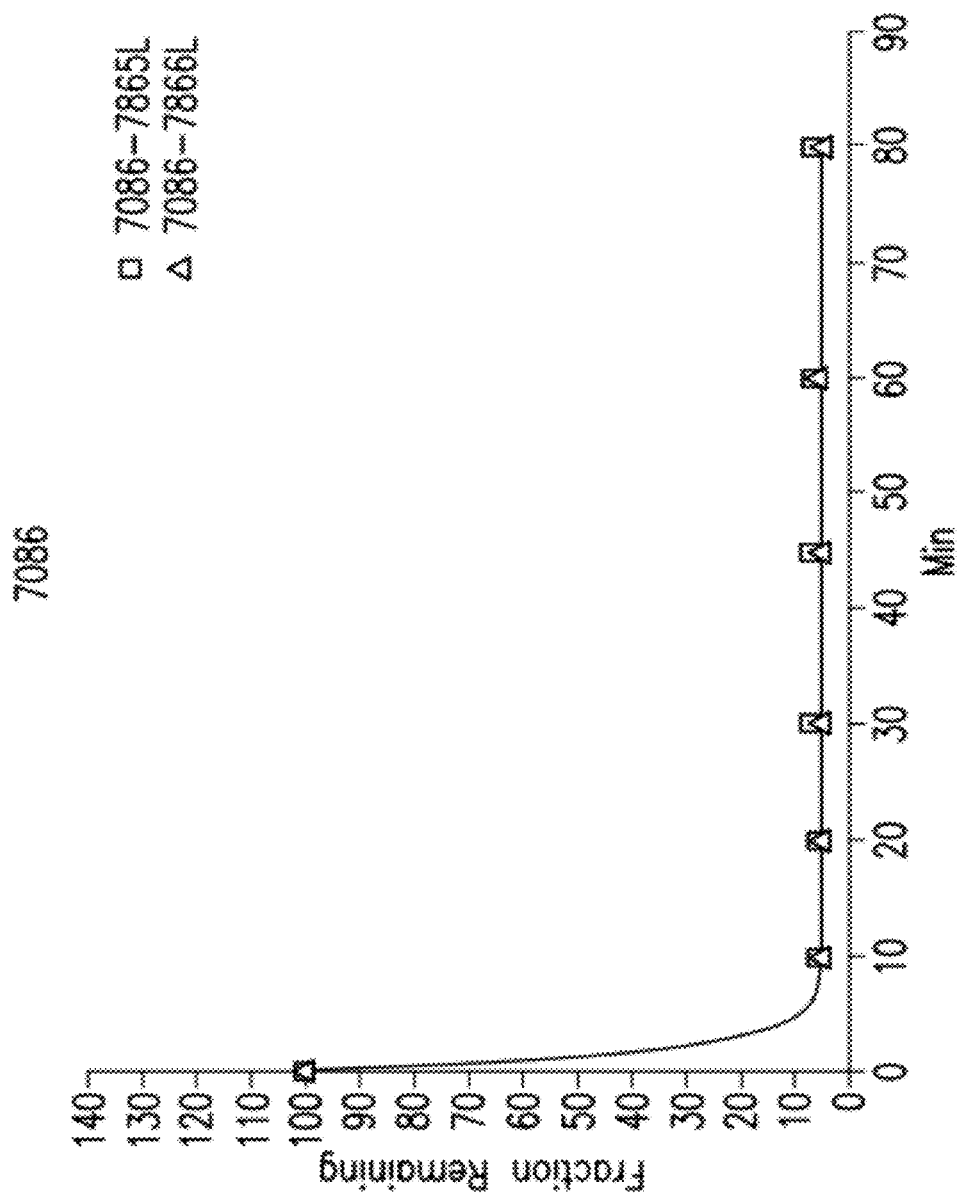

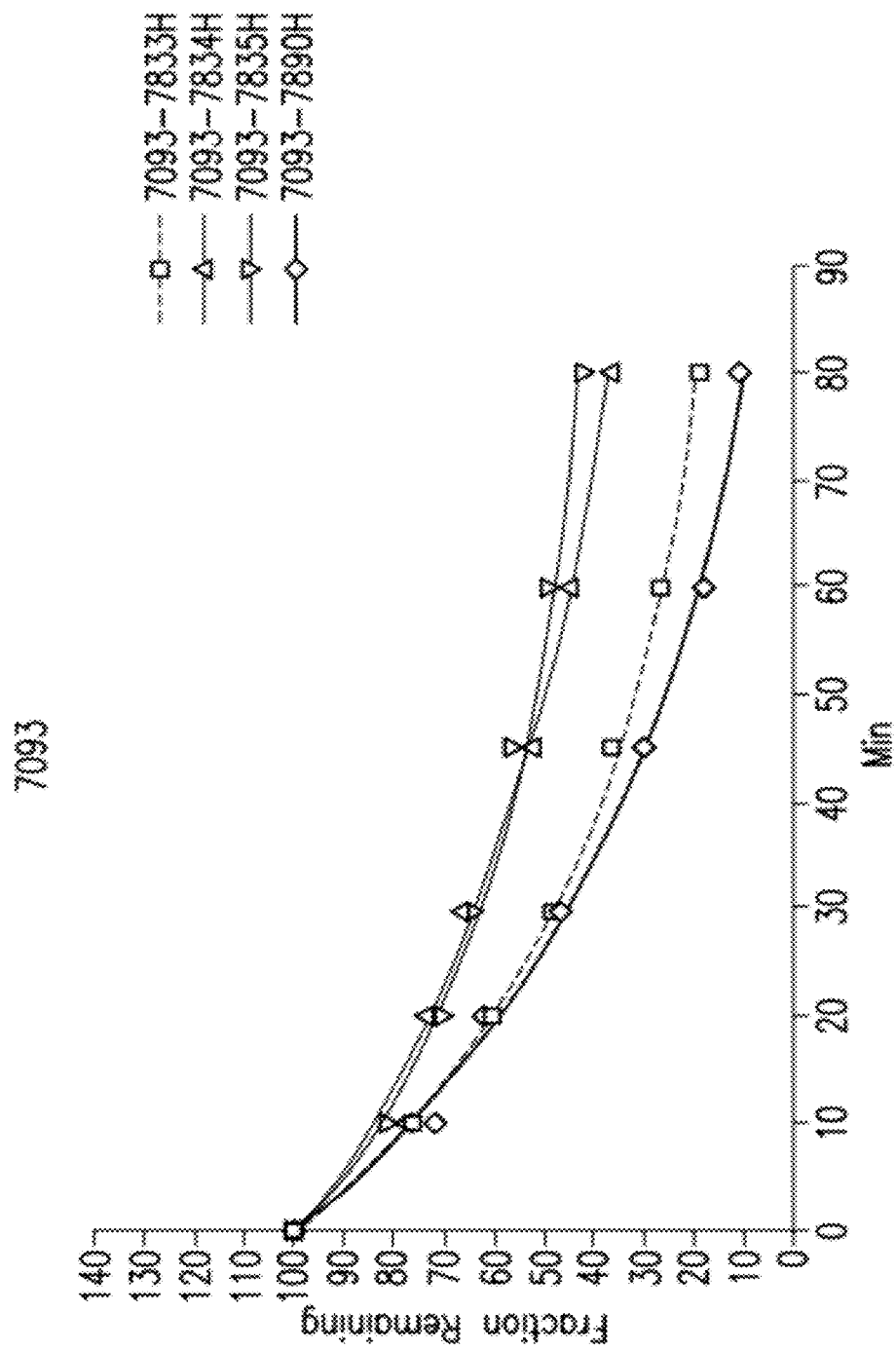

COMPOSITIONS AND METHODS FOR ANTIBODIES TARGETING COMPLEMENT PROTEIN C5

This application claims priority to U.S. Provisional Application Ser. No. 61/086,355 filed 5 Aug. 2008, the contents of which are incorporated herein by reference in their entirety.

1. INTRODUCTION

The present invention relates to antibodies targeting complement protein C5 and compositions and methods of use thereof.

2. BACKGROUND OF THE INVENTION

The normal role of complement, which is part of the innate immune system, is in host defense. Complement defends against bacterial infection, links adaptive and innate immunity, and disposes immune complexes and the products of inflammatory injury.

The defensive functions are accomplished by biologically active products generated in the course of complement activation, which opsonise infectious agents, promote inflammation or lyse susceptible targets (Marzari et al., Eur J Immunol 32:2773-2782 (2002)). The complement system consists of about 25-30 plasma proteins which play a role in the immune system. The complement cascade is activated by at least three major pathways. The classical pathway is typically activated by immune-complexes, the alternative pathway can be activated by unprotected cell surfaces, and the mannose binding lectin (MBL) pathway is initiated by binding of MBL to cell surface carbohydrates (Trendelenburg, Swiss Med Wkly 137: 413-417 (2007)).

All three pathways lead to the cleavage of C5 by the C5 convertase. The result of this cleavage is release of C5a fragment, a potent inflammatory molecule, and C5b which initiates the membrane attack complex (MAC). The complement products, once released, do not differentiate between foreign and self targets and, if not tightly regulated, often cause extensive damage of bystander cells and tissues in clinical conditions associated with unrestricted complement activation (Marzari et al., 2002).

C5 is expressed intracellularly as a single pro-C5 peptide of 1676 amino acids that consist of an 18 residue signal sequence and an Arg-rich linker sequence (RPRR) situated between the mature N-terminal β chain and the C-terminal α chain. The mature C5 has a molecular weight of about 190 kDa, and consists of two polypeptide chains (α, 115 kDa and β, 75 kDa) which are connected by disulfide bonds. The C5 convertase cleaves C5 between residues 74 and 75 of the alpha chain to release the 74 amino acid C5a peptide and the C5b fragment which is subsequently incorporated into the membrane-attack complex (MAC).

Macular degeneration is a medical condition predominantly found in the elderly in which the center of the inner lining of the eye, known as the macula area of the retina, suffers thinning, atrophy, and in some cases, bleeding. This can result in loss of central vision, which entails inability to see fine details, to read, or to recognize faces. Pathogenesis of new choroidal vessel formation is poorly understood, but factors such as inflammation, ischemia, and local production of angiogenic factors are thought to be important.

Despite current treatment options for treating diseases and disorders associated with the classical or alternative component pathways, particularly AMD, there remains a need for finding specific targets that lead to treatments which are effective and well-tolerated.

3. SUMMARY OF THE INVENTION

The present invention provides isolated complement C5-binding molecules (e.g., C5-binding antibodies or antigen binding fragments thereof), pharmaceutical compositions comprising such molecules, methods of making such molecules and compositions, and methods of use thereof.

In some embodiments, the present invention provides isolated antibodies or antigen binding fragments thereof that specifically bind to a C5 protein, wherein said antibody has an affinity constant ($K_A$) of at least $1 \times 10^7$ $M^{-1}$, $10^8$ $M^{-1}$, $10^9$ $M^{-1}$, $10^{10}$ $M^{-1}$, or $10^{11}$ $M^{-1}$.

In some embodiments, the present invention provides isolated antibodies or antigen binding fragments thereof that specifically bind to a C5 protein, and inhibit the alternative complement pathway as measured by in vitro hemolytic assay with an $IC_{50}$ range from about 20 pM to about 200 pM.

In some embodiments, the present invention provides isolated antibodies or antigen binding fragments thereof that specifically bind to a C5 protein, and cross compete with an antibody described in Table 1 below. In some embodiments, the present invention provides isolated antibodies or antigen binding fragments thereof that bind to the same epitope of C5 protein as an antibody described in Table 1 below.

In some embodiments, the antibodies of the invention are isolated monoclonal antibodies that specifically bind to a C5 protein. In some embodiments, the antibodies of the invention are isolated human or humanized monoclonal antibodies that specifically bind to a C5 protein. In some embodiments, the antibodies of the invention are isolated chimeric antibodies that specifically bind to a C5 protein. In some embodiments, the antibodies of the invention comprise a human heavy chain constant region and a human light chain constant region.

In some embodiments, the present invention provides isolated antibodies or antigen binding fragments thereof that specifically bind to a C5 protein, wherein said antibodies are single chain antibodies. In some embodiments, the antibodies of the invention are Fab fragments. In some embodiments, the antibodies of the invention are scFv.

In some embodiments, the present invention provides isolated antibodies or antigen-binding fragments thereof that specifically bind to both human C5 and cynomolgus C5. In some embodiments, the antibodies of the invention are an IgG isotype.

In some embodiments, the present invention provides isolated antibodies or antigen binding fragments thereof comprising a framework in which amino acids have been substituted into the antibody framework from the respective human VH or VL germline sequences.

In some embodiments, the present invention provides isolated monoclonal antibodies or antigen binding fragments thereof that specifically bind to a C5 protein, wherein said antibodies comprise at least one complementarity determining (CDR) sequence having at least 90%, 95%, 97%, 98% or at least 99% sequence identity to SEQ ID NO: 1, 2, 3, 4, 5, 6, 17, 18, 19, 20, 21, 22, 33, 34, 35, 36, 37, 38, 49, 50, 61, 62, 63, 64, 65, 66, 77, 78, 89, 95, 101, 107, 113, 119, 120, 131, 132, 133, 134, 135, 136, 145, 146, 147, 148, 149, 150, 159, 160, 161, 162, 163, 164, 173, 174, 175, 176, 177, 178, 195, 196, 197, 198, 199, 200, 209, 226, 235, 236, 237, 238, 239, or 240.

In some embodiments, the present invention provides isolated monoclonal antibodies or antigen binding fragments thereof that specifically bind to a C5 protein, wherein said antibodies comprise at least one heavy chain CDR sequence that is identical to SEQ ID NO: 1, 2, 3, 17, 18, 19, 33, 34, 35, 49, 61, 62, 63, 77, 77, 95, 107, 113, 119, 132, 131, 133, 145, 146, 147, 159, 160, 161, 173, 174, 175, 195, 196, 197, 226, 235, 236, or 237.

In some embodiments, the present invention provides isolated monoclonal antibodies or antigen binding fragments thereof that specifically bind to a C5 protein, wherein said antibodies comprise at least one light chain CDR sequence that is identical to SEQ ID NO: 4, 5, 6, 20, 21, 22, 36, 37, 38, 50, 64, 65, 66, 78, 89, 101, 120, 134, 135, 136, 148, 149, 150, 162, 163, 164, 176, 177, 178, 198, 199, 200, 209, 238, 239, or 240.

In some embodiments, the present invention provides isolated monoclonal antibodies or antigen binding fragments thereof that specifically bind to a C5 protein, wherein said antibodies comprise a heavy chain CDR 1 selected from the group consisting SEQ ID NOs: 1, 17, 33, 61, 131, 145, 159, 173, 195, and 235; a heavy chain CDR2 selected from the group consisting SEQ ID NOs: 2, 18, 34, 49, 62, 77, 95, 107, 113, 119, 132, 146, 160, 174, 196, 226, and 236; and a heavy chain CDR3 selected from the group consisting SEQ ID NOs: 3, 19, 35, 63, 133, 147, 161, 175, 197, and 237. In some embodiments, such antibodies or antigen binding fragments thereof further comprise a light chain CDR1 selected from the group consisting SEQ ID NOs: 4, 20, 36, 64, 134, 148, 162, 176, 198, and 238; a light chain CDR2 selected from the group consisting SEQ ID NOs: 5, 21, 37, 65, 135, 149, 163, 177, 199, and 239; and a light chain CDR3 selected from the group consisting SEQ ID NOs: 6, 22, 38, 50, 66, 78, 89, 101, 120, 136, 150, 164, 178, 200, 209, and 240.

In some embodiments, the present invention provides isolated monoclonal antibodies or antigen binding fragments thereof that specifically bind to a C5 protein, wherein said antibodies comprise a light chain CDR 1 selected from the group consisting SEQ ID NOs: 4, 20, 36, 64, 134, 148, 162, 176, 198, and 238; a light chain CDR2 selected from the group consisting SEQ ID NOs: 5, 21, 37, 65, 135, 149, 163, 177, 199, and 239; and a light chain CDR3 selected from the group consisting SEQ ID NOs: 6, 22, 38, 50, 66, 78, 89, 101, 120, 136, 150, 164, 178, 200, 209, and 240.

In some embodiments, the present invention provides isolated monoclonal antibodies or antigen binding fragments thereof that specifically bind to a C5 protein, wherein said antibodies comprise a heavy chain variable region having at least 90%, 95%, 97%, 98% or at least 99% sequence identity to SEQ ID NO: 7, 23, 39, 51, 67, 79, 96, 108, 114, 121, 137, 151, 165, 179, 187, 201, 210, 218, 227, 241, 253, 257, 273, 277, or 281. In some embodiments, such antibodies or antigen binding fragments thereof further comprise a light chain variable region having at least 90%, 95%, 97%, 98% or at least 99% sequence identity to SEQ ID NO: 8, 24, 40, 52, 68, 80, 90, 102, 122, 138, 152, 166, 180, 188, 202, 211, 219, 228, 242, 261, 265, 269, 285, and 289.

In some embodiments, the present invention provides isolated monoclonal antibodies or antigen binding fragments thereof that specifically bind to a C5 protein, wherein said antibodies comprise a light chain variable region having at least 90%, 95%, 97%, 98% or at least 99% sequence identity to SEQ ID NO: 8, 24, 40, 52, 68, 80, 90, 102, 122, 138, 152, 166, 180, 188, 202, 211, 219, 228, 242, 261, 265, 269, 285, and 289.

In some embodiments, the present invention provides isolated monoclonal antibodies or antigen binding fragments thereof that specifically bind to a C5 protein, wherein said antibodies comprise a heavy chain having at least 90%, 95%, 97%, 98% or at least 99% sequence identity to SEQ ID NO: 9, 25, 41, 53, 69, 81, 97, 109, 115, 123, 139, 153, 167, 181, 189, 203, 212, 220, 229, 243, 249, 254, 258, 274, 278, or 282. In some embodiments, such antibodies further comprise a light chain having at least 90%, 95%, 97%, 98% or at least 99% sequence identity to SEQ ID NO: 10, 26, 42, 54, 70, 82, 91, 103, 124, 140, 154, 168, 182, 190, 204, 213, 221, 230, 244, 251, 262, 266, 270, 286, or 290.

In some embodiments, the present invention provides isolated monoclonal antibodies or antigen binding fragments thereof that specifically bind to a C5 protein, wherein said antibodies comprise a light chain having at least 90%, 95%, 97%, 98% or at least 99% sequence identity to SEQ ID NO: 10, 26, 42, 54, 70, 82, 91, 103, 124, 140, 154, 168, 182, 190, 204, 213, 221, 230, 244, 251, 262, 266, 270, 286, or 290.

The present invention also comprises pharmaceutical compositions comprising one or more C5-binding molecules of the invention (e.g., C5 binding antibodies or antigen binding fragments thereof) and a pharmaceutically acceptable carrier.

In some embodiments, the present invention provides nucleic acids comprising a nucleotide sequence encoding a polypeptide comprising a heavy chain variable region having at least 90%, 95%, 97%, 98% or at least 99% sequence identity to SEQ ID NO: 7, 23, 39, 51, 67, 79, 96, 108, 114, 121, 137, 151, 165, 179, 187, 201, 210, 218, 227, 241, 253, 257, 273, 277, or 281.

In some embodiments, the present invention provides nucleic acids comprising a nucleotide sequence encoding a polypeptide comprising a light chain variable region having at least 90%, 95%, 97%, 98% or at least 99% sequence identity to SEQ ID NO: 8, 24, 40, 52, 68, 80, 90, 102, 122, 138, 152, 166, 180, 188, 202, 211, 219, 228, 242, 261, 265, 269, 285, and 289.

The present invention also provides vectors and host cells comprising such nucleic acids. In one embodiment, the present invention provides isolated host cells comprising (1) a recombinant DNA segment encoding a heavy chain of the antibodies of the invention, and (2) a second recombinant DNA segment encoding a light chain of the antibodies of the invention; wherein said DNA segments are respectively operably linked to a first and a second promoter, and are capable of being expressed in said host cell. In another embodiment, the present invention provides isolated host cells comprising a recombinant DNA segment encoding a heavy chain, and a light chain of the antibodies of the invention, respectively, wherein said DNA segment is operably linked to a promoter, and is capable of being expressed in said host cells. In some embodiments, the host cells are non-human mammalian cell line. In some embodiments, the antibodies or antigen binding fragments thereof are a human monoclonal antibody, or an antigen binding fragment thereof.

The present invention further provides treatment of diagnostic methods using the C5 binding molecules (e.g., C5 binding antibodies or antigen binding fragments thereof) of the invention. In one embodiment, the present invention provides methods of treating age related macular degeneration comprising administering to a subject in need thereof an effective amount of a composition comprising an antibody or an antigen binding fragment thereof of the invention.

In another embodiment, the present invention provides methods of treating a disease comprising administering to a subject in need thereof an effective amount of a composition comprising an antibody or an antigen binding fragment thereof of the invention, wherein said disease is asthma, arthritis, autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, Alzheimer's disease, glomerulonephritis, or MPGN II.

The present invention also provides methods of treating paroxysmal nocturnal hemoglobinuria (PNH) comprising administering to a subject in need thereof an effective amount of a composition comprising an antibody or antigen binding fragment thereof of the invention.

The present invention further provides methods of ameliorating a symptom associated with extracorporeal circulation comprising administering to a subject in need thereof an effective amount of a composition comprising an antibody or antigen binding fragment thereof of the invention.

3.1. Definitions

Unless defined otherwise, all technical and scientific terms used herein have the same meaning as commonly understood by those of ordinary skill in the art to which this invention pertains.

The term "antibody" as used herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen binding portion" of an antibody, as used herein, refers to one or more fragments of an intact antibody that retain the ability to specifically bind to a given antigen (e.g., C5). Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies.

Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding portions can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody.

Specific binding between two entities means a binding with an equilibrium constant ($K_A$) of at least $1 \times 10^7$ M$^{-1}$, $10^8$ M$^{-1}$, $10^9$ M$^{-1}$, $10^{10}$ M$^{-1}$, or $10^{11}$ M$^{-1}$. The phrase "specifically (or selectively) binds" to an antibody (e.g., a C5-binding antibody) refers to a binding reaction that is determinative of the presence of a cognate antigen (e.g., a human C5 or cynomolgus C5) in a heterogeneous population of proteins and other biologics. In addition to the equilibrium constant (KA) noted above, an C5-binding antibody of the invention typically also has a dissociation rate constant (Kd) of about $1\times10^{-2}$ s$^{-1}$, $1\times10^{-3}$ s$^{-1}$, $1\times10^{-4}$ s$^{-1}$, $1\times10^{-4}$ s$^{-1}$, or lower, and binds to C5 with an affinity that is at least two-fold greater than its affinity for binding to a non-specific antigen (e.g., C3, C4, BSA). The phrases "an antibody recognizing an antigen" and "an antibody specific for an antigen" are used interchangeably herein with the term "an antibody which binds specifically to an antigen".

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "complement C5 protein" or "C5" are used interchangeably, and refers to the C5 protein in different species. For example, human C5 has the sequence as set in SEQ ID NO: 296, cynomolgus C5 has the sequence as set in SEQ ID NO: 297 (*Macaca fascicularis*) (see Table 1). Human C5 can be obtained from Quidel (Cat. Number A403). Cynomolgus C5 can be produced as illustrated in the Example section below.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The terms "cross-block", "cross-blocked" and "cross-blocking" are used interchangeably herein to mean the ability of an antibody or other binding agent to interfere with the binding of other antibodies or binding agents to C5 in a standard competitive binding assay.

The ability or extent to which an antibody or other binding agent is able to interfere with the binding of another antibody or binding molecule to C5, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, the term "high affinity" for an IgG antibody refers to an antibody having a KD of $10^{-8}$ M or less, $10^{-9}$ M or less, or $10^{-10}$ M, or $10^{-11}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but is not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (N) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, $M=5$, $N=-4$, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds C5 is substantially free of antibodies that specifically bind antigens other than C5). An isolated antibody that specifically binds C5 may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to after the Fc function, for example, to enhance or reduce effector functions or binding to Fc receptors.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e. Kd/Ka) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "treating" includes the administration of compositions or antibodies to prevent or delay the onset of the symptoms, complications, or biochemical indicia of a disease (e.g., AMD), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

4. BRIEF DESCRIPTION OF THE FIGURES

FIG. 1 shows variable-region alignments of selected antibodies with their most closely related human germline sequences. Specifically, the sequences of 8109 VH (SEQ ID NO: 7) and VL (SE ID NO: 8) are aligned with germline sequences SEQ ID NOs: 298 and 299, respectively. The sequences of 8110 VH (SEQ ID NO: 23) and VL (SEQ ID NO: 24) are aligned with germline sequences SEQ ID NOs: 300 and 301, respectively. The sequences of 8111 VH (SEQ ID NO: 39) and VL (SEQ ID NO: 40) are aligned with germline sequences SEQ ID NOs:302 and 303, respectively. The sequences of 8113 VH (SEQ ID NO: 51) and VL (SEQ ID NO: 52) are aligned with germline sequences SEQ ID NOs: 304 and 305, respectively. The sequences of 8114 VH (SEQ ID NO: 67) and VL (SEQ ID NO: 68) are aligned with germline sequences SEQ ID NOs: 306 and 307, respectively.

FIG. 19 shows epitope binning of some affinity improved Fabs.

5. DETAILED DESCRIPTION OF THE INVENTION

Figure 1:
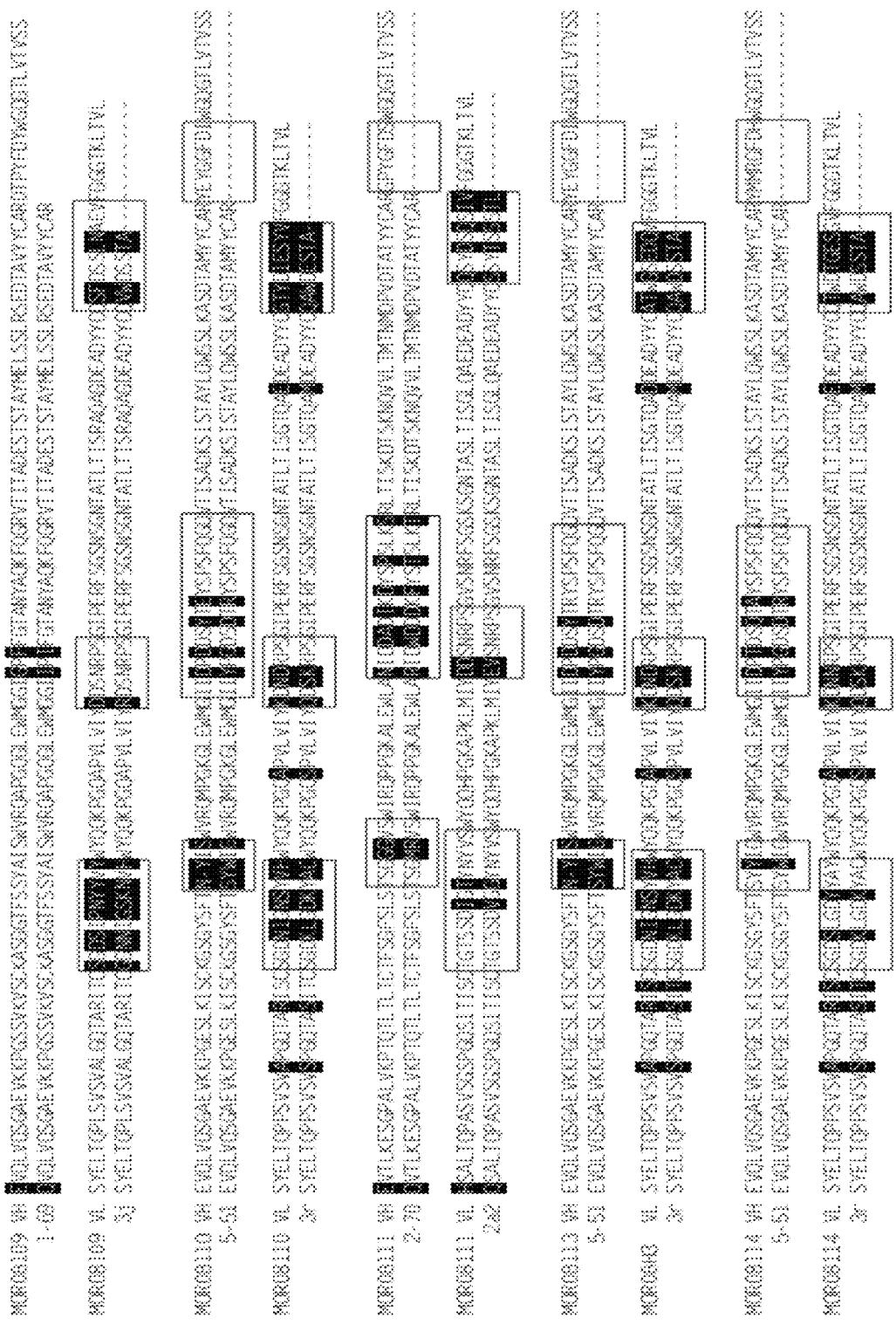

The present invention provides antibodies that specifically bind to complement C5 protein (e.g., human C5, cynomolgus C5), pharmaceutical compositions, production methods, and methods of use of such antibodies and compositions.

5.1. C5 Antibodies

The present invention provides antibodies that specifically bind to C5 (e.g., human C5, cynomologus C5). In some embodiments, the present invention provides antibodies that specifically bind to both human and cynomologus C5. Antibodies of the invention include, but are not limited to, the human monoclonal antibodies, isolated as described, in the Examples (see Section 6 below).

The present invention provides antibodies that specifically bind a C5 protein (e.g., human and/or cynomologus C5), said antibodies comprising a VH domain having an amino acid sequence of SEQ ID NO: 7, 23, 39, 51, 67, 79, 96, 108, 114, 121, 137, 151, 165, 179, 187, 201, 210, 218, 227, 241, 253, 257, 273, 277, or 281. The present invention also provides antibodies that specifically bind to a C5 protein (e.g., human and/or cynomologus C5), said antibodies comprising a VH CDR having an amino acid sequence of any one of the VH CDRs listed in Table 1, infra. In particular, the invention provides antibodies that specifically bind to a C5 protein (e.g., human and/or cynomologus C5), said antibodies comprising (or alternatively, consisting of) one, two, three, four, five or more VH CDRs having an amino acid sequence of any of the VH CDRs listed in Table 1, infra.

The present invention provides antibodies that specifically bind to a C5 protein (e.g., human and/or cynomologus C5), said antibodies comprising a VL domain having an amino acid sequence of SEQ ID NO: 8, 24, 40, 52, 68, 80, 90, 102, 122, 138, 152, 166, 180, 188, 202, 211, 219, 228, 242, 261, 265, 269, 285, or 289. The present invention also provides antibodies that specifically bind to a C5 protein (e.g., human and/or cynomologus C5), said antibodies comprising a VL CDR having an amino acid sequence of any one of the VL CDRs listed in Table 1, infra. In particular, the invention provides antibodies that specifically bind to a C5 protein (e.g., human and/or cynomologus C5), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 60, 70, 80, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to a C5 protein (e.g., human and/or cynomologus C5). Such nucleic acid sequences can be optimized for expression in mammalian cells (for example, Table 1 shows the optimized nucleic acid sequences for the heavy chain and light chain of antibodies 8109, 8110, 8111, 8113, 8114, 8112, 8125, 8126, 8127, 8128, 8129, 8130, 8131, 8132, and 8091).

TABLE 1

Examples of C5 Antibodies of the Present Invention and C5 Proteins

| | Sequence Identifier (SEQ ID NO:) or comments/details |
|---|---|
| Antibody 8109 | |
| CDRH1 | 1: SYAIS |
| CDRH2 | 2: GIGPFFGTANYAQKFQG |
| CDRH3 | 3: DTPYFDY |

TABLE 1-continued

Examples of C5 Antibodies of the Present Invention and C5 Proteins

| | Sequence Identifier (SEQ ID NO:) or comments/details |
|---|---|
| CDRL1 | 4: SGDSIPNYYVY |
| CDRL2 | 5: DDSNRPS |
| CDRL3 | 6: QSFDSSLNAEV |
| VH | 7: EVQLVQSGAEVKKPGSSVKVSCKASGGTFSSYAI SWVRQAPGQGLEWMGGIGPFFGTANYAQKFQGRVTI TADESTSTAYMELSSLRSEDTAVYYCARDTPYFDYW GQGTLVTVSS |
| VL | 8: SYELTQPLSVSVALGQTARITCSGDSIPNYYVYW YQQKPGQAPVLVIYDDSNRPSGIPERFSGSNSGNTA TLTISRAQAGDEADYYCQSFDSSLNAEVFGGGTKLT VL |
| Heavy chain | 9: EVQLVQSGAEVKKPGSSVKVSCKASGGTFSSYAI SWVRQAPGQGLEWMGGIGPFFGTANYAQKFQGRVTI TADESTSTAYMELSSLRSEDTAVYYCARDTPYFDYW GQGTLVTVSSASTKGPSVFPLAPSSKSTSGGTAALG CLVKDYFPEPVTVSWNSGALTSGVHTFPAVLQSSGL YSLSSWTVPSSSLGTQTYICNVNHKPSNTKVDKRVE PKSCDKTHTCPPCPAPEAAGGPSVFLFPPKPKDTLM ISRTPEVTCVVVDVSHEDPEVKFNWYVDGVEVHNAK TKPREEQYNSTYRVVSVLTVLHQDWLNGKEYKCKVS NKALPAPIEKTISKAKGQPREPQVYTLPPSREEMTK NQVSLTCLVKGFYPSDIAVEWESNGQPENNYKTTPP VLDSDGSFFLYSKLTVDKSRWQQGNVFSCSVMHEAL HNHYTQKSLSLSPGK |
| Light chain | 10: SYELTQPLSVSVALGQTARITCSGDSIPNYYVY WYQQKPGQAPVLVIYDDSNRPSGIPERFSGSNSGNT ATLTISRAQAGDEADYYCQSFDSSLNAEVFGGGTKL TVLGQPKAAPSVTLFPPSSEELQANKATLVCLISDF YPGAVTVAWKADSSPVKAGVETTTPSKQSNNKYAAS SYLSLTPEQWKSHRSYSCQVTHEGSTVEKTVAPTEC S |
| PN encoding SEQ ID NO: 7 | 11: GAGGTGCAATTGGTTCAGTCTGGCGCGGAAGTG AAAAAACCGGGCAGCAGCGTGAAAGTGAGCTGCAAA GCCTCCGGAGGCACTTTTTCTTCTTATGCCATTTCT TGGGTGCGCCAAGCCCCTGGGCAGGGTCTCGAGTGG ATGGGCGGTATCGGTCCGTTTTTTGGCACTGCGAAT TACGCGCAGAAGTTTCAGGGCCGGGTGACCATTACC GCGGATGAAAGCACCAGCACCGCGTATATGGAACTG AGCAGCCTGCGTAGCGAAGATACGGCCGTGTATTAT TGCGCGCGTGATACTCCTTATTTTGATTATTGGGGC CAAGGCACCCTGGTGACGGTTAGCTCA |
| PN encoding SEQ ID NO: 8 | 12: TCCTATGAACTCACACAGCCCCTGAGCGTGAGC GTGGCCCTGGGCCAGACCGCCCGGATCACCTGCTCC GGCGACAGCATCCCCAACTACTACGTGTACTGGTAC CAGCAGAAGCCCGGCCAGGCCCCCGTGCTGGTGATC TACGACGACAGCAACCGGCCCAGCGGCATCCCCGAG CGGTTCAGCGGCAGCAACAGCGGCAACACCGCCACC CTGACCATTTCCAGAGCACAGGCAGGCGACGAGGCC GACTACTACTGCCAGAGCTTCGACAGCAGCCTGAAC GCCGAGGTGTTCGGCGGAGGGACCAAGTTAACCGTC CTA |
| PN encoding SEQ ID NO: 9 | 13: GAGGTGCAATTGGTTCAGTCTGGCGCGGAAGTG AAAAAACCGGGCAGCAGCGTGAAAGTGAGCTGCAAA GCCTCCGGAGGCACTTTTTCTTCTTATGCCATTTCT TGGGTGCGCCAAGCCCCTGGGCAGGGTCTCGAGTGG ATGGGCGGTATCGGTCCGTTTTTTGGCACTGCGAAT TACGCGCAGAAGTTTCAGGGCCGGGTGACCATTACC GCGGATGAAAGCACCAGCACCGCGTATATGGAACTG AGCAGCCTGCGTAGCGAAGATACGGCCGTGTATTAT TGCGCGCGTGATACTCCTTATTTTGATTATTGGGGC CAAGGCACCCTGGTGACGGTTAGCTCAGCCTCCACC AAGGGTCCATCGGTCTTCCCCCTGGCACCCTCCTCC AAGAGCACCTCTGGGGGCACAGCGGCCCTGGGCTGC CTGGTCAAGGACTACTTCCCCGAACCGGTGACGGTG TCGTGGAACTCAGGCGCCCTGACCAGCGGCGTGCAC |

TABLE 1-continued

Examples of C5 Antibodies of the Present Invention and C5 Proteins

| | Sequence Identifier (SEQ ID NO:) or comments/details |
|---|---|
| | ACCTTCCCGGCTGTCCTACAGTCCTCAGGACTCTAC<br>TCCCTCAGCAGCGTGGTGACCGTGCCCTCCAGCAGC<br>TTGGGCACCCAGACCTACATCTGCAACGTGAATCAC<br>AAGCCCAGCAACACCAAGGTGGACAAGAGAGTTGAG<br>CCCAAATCTTGTGACAAAACTCACACATGCCCACCG<br>TGCCCAGCACCTGAAGCAGCGGGGGGACCGTCAGTC<br>TTCCTCTTCCCCCCAAAACCCAAGGACACCCTCATG<br>ATCTCCCGGACCCCTGAGGTCACATGCGTGGTGGTG<br>GACGTGAGCCACGAAGACCCTGAGGTCAAGTTCAAC<br>TGGTACGTGGACGGCGTGGAGGTGCATAATGCCAAG<br>ACAAAGCCCGCGGAGGAGCAGTACAACAGCACGTAC<br>CGGGTGGTCAGCGTCCTCACCGTCCTGCACCAGGAC<br>TGGCTGAATGGCAAGGAGTACAAGTGCAAGGTCTCC<br>AACAAAGCCCTCCCAGCCCCCATCGAGAAAACCATC<br>TCCAAAGCCAAAGGGCAGCCCCGAGAACCACAGGTG<br>TACACCCTGCCCCCATCCCGGGAGGAGATGACCAAG<br>AACCAGGTCAGCCTGACCTGCCTGGTCAAAGGCTTC<br>TATCCCAGCGACATCGCCGTGGAGTGGGAGAGCAAT<br>GGGCAGCCGGAGAACAACTACAAGACCACGCCTCCC<br>GTGCTGGACTCCGACGGCTCCTTCTTCCTCTACAGC<br>AAGCTCACCGTGGACAAGAGCAGGTGGCAGCAGGGG<br>AACGTCTTCTCATGCTCCGTGATGCATGAGGCTCTG<br>CACAACCACTACACGCAGAAGAGCCTCTCCCTGTCT<br>CCGGGTAAA |
| PN encoding SEQ ID NO: 10 | 14: TCCTATGAACTCACACAGCCCCTGAGCGTGAGC<br>GTGGGCCCTGGGCCAGACCGCCCGGATCACCTGCTCC<br>GGCGACAGCATCCCCAACTACTACGTGTACTGGTAC<br>CAGCAGAAGCCCGGCCAGGCCCCCGTGCTGGTGATC<br>TACGACGACAGCAACCGGCCCAGCGGCATCCCCGAG<br>CGGTTCAGCGGCAGCAACAGCGGCAACACCGCCACC<br>CTGACCATTTCCAGAGCAGGCAGGCGACGAGGCC<br>GACTACTACTGCCAGAGCTTCGACAGCAGCCTGAAC<br>GCCGAGGTGTTCGGCGGAGGGACCAAGTTAACCGTC<br>CTAGGTCAGCCCAAGGCTGCCCCCTCGGTCACTCTG<br>TTCCCGCCCTCCTCTGAGGAGCTTCAAGCCAACAAG<br>GCCACACTGGTGTGTCTCATAAGTGACTACTACCCG<br>GGAGCCGTGACAGTGGCCTGGAAGGCAGATAGCAGC<br>CCCGTCAAGGCGGGAGTGGAGACCACCACACCCTCC<br>AAACAAAGCAACAACAAGTACGCGGCCAGCAGCTAT<br>CTGAGCCTGACGCCTGAGCAGTGGAAGTCCCACAGA<br>AGCTACAGCTGCCAGGTCACGCATGAAGGGAGCACC<br>GTGGAGAAGACAGTGGCCCCTACAGAATGTTCA |
| Optimized PN encoding SEQ ID NO: 9 | 15: GAGGTGCAGCTGGTGCAGAGCGGAGCCGAGGTG<br>AAGAAGCCCGGTAGCAGCGTCAAGGTGTCCTGCAAG<br>GCCAGCGGCGGCACCTTCAGCAGCTACGCCATCAGC<br>TGGGTGCGGCAGGCCCCAGGCCAGGGCCTGGAGTGG<br>ATGGGCGGCATCGGCCCATTCTTCGGCACCGCCAAC<br>TACGCCCAGAAGTTCCAGGGCAGGGTCACCATCACC<br>GCCGACGAGAGCACCAGCACCGCCTACATGGAGCTG<br>TCCAGCCTGAGAAGCGAGGACACCGCCGTGTACTAC<br>TGCGCCAGAGACACCCCTACTTCGACTACTGGGGC<br>CAGGGCACCCTGGTGACCGTGAGCAGCGCTAGCACC<br>AAGGGCCCCAGCGTGTTCCCCCTGGCCCCCAGCAGC<br>AAGAGCACCTCCGGCGGCACAGCCGCCCTGGGCTGC<br>CTGGTGAAGGACTACTTCCCCGAGCCCGTGACCGTG<br>TCCTGGAACAGCGGAGCCCTGACCAGCGGCGTGCAC<br>ACCTTCCCCGCCGTGCTGCAGAGCAGCGGCCTGTAC<br>AGCCTGTCCAGCGTGGTGACAGTGCCCAGCAGCAGC<br>CTGGGCACCCAGACCTACATCTGCAACGTGAACCAC<br>AAGCCCAGCAACACCAAGGTGGACAAGAGAGTGGAG<br>CCCAAGAGCTGCGACAAGACCCACACCTGCCCCCCC<br>TGCCCAGCCCCCGAAGCTGCAGGCGGCCCTTCCGTG<br>TTCCTGTTCCCCCCCAAGCCCAAGGACACCCTGATG<br>ATCAGCAGGACCCCCGAGGTGACCTGCGTGGTGGTG<br>GACGTGAGCCACGAGGACCCAGAGGTGAAGTTCAAC<br>TGGTACGTGGACGGCGTGGAGGTGCACAACGCCAAG<br>ACCAAGCCAGAGGAGCAGTACAACAGCACCTAC<br>AGGGTGGTGTCCGTGCTGACCGTGCTGCACCAGGAC<br>TGGCTGAACGGCAAAGAATACAAGTGCAAGGTCTCC<br>AACAAGGCCCTGCCTGCCCCCATCGAAAAGACCATC<br>AGCAAGGCCAAGGGCCAGCCACGGGAGCCCCAGGTG<br>TACACCCTGCCCCCTTCTCGGGAGGAGATGACCAAG |
| | AACCAGGTGTCCCTGACCTGTCTGGTGAAGGGCTTC<br>TACCCCAGCGACATCGCCGTGGAGTGGGAGAGCAAC<br>GGCCAGCCCGAGAACAACTACAAGACCACCCCCCCA<br>GTGCTGGACAGCGACGGCAGCTTCTTCCTGTACAGC<br>AAGCTGACCGTGGACAAGAGCAGGTGGCAGCAGGGC<br>AACGTGTTCAGCTGCAGCGTGATGCACGAGGCCCTG<br>CACAACCACTACACCCAGAAGAGCCTGAGCCTGTCA<br>CCCGGCAAG |
| Optimized PN encoding SEQ ID NO: 10 | 16: AGCTACGAGCTGACCCAGCCCCTGAGCGTGAGC<br>GTGGCCCTGGGCCAGACCGCCAGGATCACCTGCAGC<br>GGCGACAGCATCCCCAACTACTACGTGTACTGGTAT<br>CAGCAGAAGCCCGGCCAGGCCCCCGTGCTGGTGATC<br>TACGACGACAGCAACAGGCCCAGCGGCATCCCCGAG<br>AGGTTCAGCGGCAGCAACAGCGGCAACACCGCCACC<br>CTGACCATCAGCGGAACCCAGGCCGGCGACGAGGCC<br>GACTACTACTGCCAGAGCTTCGACAGCTCACTGAAC<br>GCCGAGGTGTTCGGCGGAGGGACCAAGCTGACCGTG<br>CTGGGCCAGCCTAAGGCTGCCCCCAGCGTGACCCTG<br>TTCCCCCCCAGCAGCGAGGAGCTGCAGGCCAACAAG<br>GCCACCCTGGTGTGCCTGATCAGCGACTTCTACCCA<br>GGCGCCGTGACCGTGGCCTGGAAGGCCGACAGCAGC<br>CCCGTGAAGGCCGGCGTGGAGACCACCACCCCCAGC<br>AAGCAGAGCAACAACAAGTACGCCGCCAGCAGCTAC<br>CTGAGCCTGACCCCCGAGCAGTGGAAGAGCCACAGG<br>TCCTACAGCTGCCAGGTGACCCACGAGGGCAGCACC<br>GTGGAAAAGACCGTGGCCCCAACCGAGTGCAGC |
| Antibody 8110 | |
| CDRH1 | 17: NYIS |
| CDRH2 | 18: IIDPDDSYTEYSPSFQG |
| CDRH3 | 19: YEYGGFDI |
| CDRL1 | 20: SGDNIGNSYVH |
| CDRL2 | 21: KDNDRPS |
| CDRL3 | 22: GTYDIESYV |
| VH | 23: EVQLVQSGAEVKKPGESLKISCKGSYSFTNYI<br>SWVRQMPGKGLEWMGIIDPDDSYTEYSPSFQGQVTI<br>SADKSISTAYLQWSSLKASDTAMYYCARYEYGGFDI<br>WGQGTLVTVSS |
| VL | 24: SYELTQPPSVSVAPGQTARISCSGDNIGNSYVH<br>WYQQKPGQAPVLVIYKDNDRPSGIPERFSGSNSGNT<br>ATLTISGTQAEDEADYYCGTYDIESYVFGGGTKLTV<br>L |
| Heavy chain | 25: EVQLVQSGAEVKKPGESLKISCKGSYSFTNYI<br>SWVRQMPGKGLEWMGIIDPDDSYTEYSPSFQGQVTI<br>SADKSISTAYLQWSSLKASDTAMYYCARYEYGGFDI<br>WGQGTLVTVSSASTKGPSVFPLAPSSKSTSGGTAAL<br>GCLVKDYFPEPVTVSWNSGALTSGVHTFPAVLQSSG<br>LYSLSSWTVPSSSLGTQTYICNVNHKPSNTKVDKRV<br>EPKSCDKTHTCPPCPAPEAAGGPSVFLFPPKPKDTL<br>MISRTPEVTCVVVDVSHEDPEVKFNWYVDGVEVHNA<br>KTKPREEQYNSTYRVVSVLTVLHQDWLNGKEYKCKV<br>SNKALPAPIEKTISKAKGQPREPQVYTLPPSREEMT<br>KNQVSLTCLVKGFYPSDIAVEWESNGQPENNYKTTP<br>PVLDSDGSFFLYSKLTVDKSRWQQGNVFSCSVMHEA<br>LHNHYTQKSLSLSPGK |
| Light chain | 26: SYELTQPPSVSVAPGQTARISCSGDNIGNSYVH<br>WYQQKPGQAPVLVIYKDNDRPSGIPERFSGSNSGNT<br>ATLTISGTQAEDEADYYCGTYDIESYVFGGGTKLTV<br>LGQPKAAPSVTLFPPSSEELQANKATLVCLISDFYP<br>GAVTVAWKADSSPVKAGVETTTPSKQSNNKYAASSY<br>LSLTPEQWKSHRSYSCQVTHEGSTVEKTVAPTECS |

TABLE 1-continued

Examples of C5 Antibodies of the Present Invention and C5 Proteins

| | Sequence Identifier (SEQ ID NO:) or comments/details |
|---|---|
| PN encoding SEQ ID NO: 23 | 27: GAGGTGCAATTGGTTCAGAGCGGCGCGGAAGTG AAAAAACCGGGCGAAAGCCTGAAAATTAGCTGCAAA GGTTCCGGATATTCCTTTACTAATTATATTTCTTGG GTGCGCCAGATGCCTGGGAAGGGTCTCGAGTGGATG GGCACATTGATCCTGATGATTCTTATACTGAGTATT CTCCTTCTTTTCAGGGTCAGGTCACCATTAGCGCGG ATAAAAGCATTAGCACCGCGTATCTTCAATGGAGCA GCCTGAAAGCGAGCGATACGGCCATGTATTATTGCG CGCGTTATGAGTATGGTGGTTTTGATATTTGGGGCC AAGGCACCCTGGTGACGGTTAGCTCA |
| PN encoding SEQ ID NO: 24 | 28: AGTTACGAACTGACCCAGCCGCCTTCAGTGAGC GTTGCACCAGGTCAGACCGCGCGTATCTCGTGTAGC GGCGATAATATTGGTAATTCTTATGTTCATTGGTAC CAGCAGAAACCCGGGCAGGCGCCAGTTCTTGTGATT TATAAGGATAATGATCGTCCCTCAGGCATCCCGGAA CGCTTTAGCGGATCCAACAGCGGCAACACCGCGACC CTGACCATTAGCGGCACTCAGGCGGAAGACGAAGCG GATTATTATTGCGGTACTTATGATATVGAGTCTTAT GTGTTTGGCGGCGGCACGAAGTTAACCGTCCTA |
| PN encoding SEQ ID NO: 25 | 29: GAGGTGCAATTGGTTCAGAGCGGCGCGGAAGTG AAAAAACCGGGCGAAAGCCTGAAAATTAGCTGCAAA GGTTCCGGATATTCCTTTACTAATTATATTTCTTGG GTGCGCCAGATGCCTGGGAAGGGTCTCGAGTGGATG GGCATTATTGATCCTGATGATTCTTATACTGAGTAT TCTCCTTCTTTTCAGGGTCAGGTCACCATTAGCGCG GATAAAAGCATTAGCACCGCGTATCTTCAATGGAGC AGCCTGAAAGCGAGCGATACGGCCATGTATTATTGC GCGCGTTATGAGTATGGTGGTTTTGATATTTGGGGC CAAGGCACCCTGGTGACGGTTAGCTCAGCTCCACC AAGGGTCCATCGGTCTTCCCCCTGGCACCCTCCTCC AAGAGCACCTCTGGGGGCACAGCGGCCCTGGGCTGC CTGGTCAAGGACTACTTCCCCGAACCGGTGACGGTG TCGTGGAACTCAGGCGCCCTGACCAGCGGCGTGCAC ACCTTCCCGGCTGTCCTACAGTCCTCAGGACTCTAC TCCCTCAGCAGCGTGGTGACCGTGCCCTCCAGCAGC TTGGGCACCCAGACCTACATCTGCAACGTGAATCAC AAGCCCAGCAACACCAAGGTGGACAAGAGAGTTGAG CCCAAATCTTGTGACAAAACTCACACATGCCCACCG TGCCCAGCACCTGAAGCAGCGGGGGGACCGTCAGTC TTCCTCTTCCCCCCAAAACCCAAGGACACCCTCATG ATCTCCCGGACCCCTGAGGTCACATGCGTGGTGGTG GACGTGAGCCACGAAGACCCTGAGGTCAAGTTCAAC TGGTACGTGGACGCGTGGAGGTGCATAATGCCAAG ACAAAGCCGCGGGAGGAGCAGTACAACAGCACGTAC CGGGTGGTCAGCGTCCTCACCGTCCTGCACCAGGAC TGGCTGAATGGCAAGGAGTACAAGTGCAAGGTCTCC AACAAAGCCCTCCCAGCCCCCATCGAGAAAACCATC TCCAAAGCCAAAGGGCAGCCCCGAGAACCACAGGTG TACACCCTGCCCCCATCCCGGGAGGAGATGACCAAG AACCAGGTCAGCCTGACCTGCCTGGTCAAAGGCTTC TATCCCAGCGACATCGCCGTGGAGTGGGAGAGCAAT GGGCAGCCGGAGAACAACTACAAGACCACGCCTCCC GTGCTGGACTCCGACGGCTCCTTCTTCCTCTACAGC AAGCTCACCGTGGACAAGAGCAGGTGGCAGCAGGGG AACGTCTTCTCATGCTCCGTGATGCATGAGGCTCTG CACAACCACTACACGCAGAAGAGCCTCTCCCTGTCT CCGGGTAAA |
| PN encoding SEQ ID NO: 26 | 30: AGTTACGAACTGACCCAGCCGCCTTCAGTGAGC GTTGCACCAGGTCAGACCGCGCGTATCTCGTGTAGC GGCGATAATATTGGTAATTCTTATGTTCATTGGTAC CAGCAGAAACCCGGGCAGGCGCCAGTTCTTGTGATT TATAAGGATAATGATCGTCCCTCAGGCATCCCGGAA CGCTTTAGCGGATCCAACAGCGGCAACACCGCGACC CTGACCATTAGCGGCACTCAGGCGGAAGACGAAGCG GATTATTATTGCGGTACTTATGATATTGAGTCTTAT GTGTTTGGCGGCGGCACGAAGTTAACCGTCCTAGGT CAGCCCAAGGCTGCCCCCTCGGTCACTCTGTTCCCG CCCTCCTCTGAGGAGCTTCAAGCCAACAAGGCCACA CTGGTGTGTCTCATAAGTGACTTCTACCCGGGAGCC GTGACAGTGGCCTGGAAGGCAGATAGCAGCCCCGTC AAGGCGGAGTGGAGACCACCACACCCTCCAAACAA AGCAACAACAAGTACGCGGCCAGCAGCTATCTGAGC CTGACGCCTGAGCAGTGGAAGTCCCACAGAAGCTAC AGCTGCCAGGTCACGCATGAAGGGAGCACCGTGGAG AAGACAGTGGCCCCTACAGAATGTTCA |
| Optimized PN encoding SEQ ID NO: 25 | 31: GAGGTGCAGCTGGTGCAGAGCGGAGCCGAGGTG AAAAAGCCCGGTGAGAGCCTGAAGATCAGCTGCAAG GGCAGCGGCTACAGCTTCACCAACTACATCAGCTGG GTGCGGCAGATGCCCGGCAAGGGCCTGGAGTGGATG GGCATCATCGACCCCGACGACAGCTACACCGAGTAC AGCCCCAGCTTCCAGGGCCAGGTGACCATCAGCGCC GACAAGAGCATCAGCACCGCCTACCTGCAGTGGAGC AGCCTGAAGGCCAGCGACACCGCCATGTACTACTGC GCCAGATACGAGTACGGCGGCTTCGACATCTGGGGC CAGGGCACCCTGGTGACCGTCAGCTCAGCTAGCACC AAGGGCCCCAGCGTGTTCCCCCTGGCCCCCAGCAGC AAGAGCACCTCCGGCGGCACAGCCGCCCTGGGCTGC CTGGTGAAGGACTACTTCCCCGAGCCCGTGACCGTG TCCTGGAACAGCGGAGCCCTGACCAGCGGCGTGCAC ACCTTCCCCGCCGTGCTGCAGAGCAGCGGCCTGTAC AGCCTGTCCAGCGTGGTGACAGTGCCCAGCAGCAGC CTGGGCACCCAGACCTACATCTGCAACGTGAACCAC AAGCCCAGCAACACCAAGGTGGACAAGAGAGTGGAG CCCAAGAGCTGCGACAAGACCCACACCTGCCCCCCC TGCCCAGCCCCCGAAGCTGCAGGCGGCCCTTCCGTG TTCCTGTTCCCCCCCAAGCCCAAGGACACCCTGATG ATCAGCAGGACCCCCGAGGTGACCTGCGTGGTGGTG GACGTGAGCCACGAGGACCCCGAGGTGAAGTTCAAC TGGTACGTGGACGGCGTGGAGGTGCACAACGCCAAG ACCAAGCCCAGAGAGGAGCAGTACAACAGCACCTAC AGGGTGGTGTCCGTGCTGACCGTGCTGCACCAGGAC TGGCTGAACGGCAAAGAATACAAGTGCAAGGTCTCC AACAAGGCCCTGCCTGCCCCCATCGAAAAGACCATC AGCAAGGCCAAGGGCCAGCCACGGGAGCCCCAGGTG TACACCCTGCCCCCTTCTCGGGAGGAGATGACCAAG AACCAGGTGTCCCTGACCTGTCTGGTGAAGGGCTTC TACCCCAGCGACATCGCCGTGGAGTGGGAGAGCAAC GGCCAGCCCGAGAACAACTACAAGACCACCCCCCCA GTGCTGGACAGCGACGGCAGCTTCTTCCTGTACAGC AAGCTGACCGTGGACAAGAGCAGGTGGCAGCAGGGC AACGTGTTCAGCTGCAGCGTGATGCACGAGGCCCTG CACAACCACTACACCCAGAAGAGCCTGAGCCTGTCA CCCGGCAAG |
| Optimized PN encoding SEQ ID NO: 26 | 32: AGCTACGAGCTGACCCAGCCCCCCAGCGTGAGC GTGGCCCCAGGCCAGACCGCCAGGATCAGCTGCAGC GGCGACAACATCGGCAACAGCTACGTGCACTGGTAT CAGCAGAAGCCCGGCCAGGCCCCCGTGCTGGTGATC TACAAGGACAACGACAGGCCCAGCGGCATCCCCGAG AGGTTCAGCGGCAGCAACTCCGGCAACACCGCCACC CTGACCATCAGCGGCACCCAGGCCGAGGACGAGGCC GACTACTACTGCGGCACCTACGACATCGAGTCATAC GTGTTCGGCGGAGGGACCAAGCTGACCGTGCTGGGC CAGCCTAAGGCTGCCCCCAGCGTGACCCTGTTCCCC CCCAGCAGCGAGGAGCTGCAGGCCAACAAGGCCACC CTGGTGTGCCTGATCAGCGACTTCTACCCAGGCGCC GTGACCGTGGCCTGGAAGGCCGACAGCAGCCCCGTG AAGGCCGGCGTGGAGACCACCACCCCCAGCAAGCAG AGCAACAACAAGTACGCCGCCAGCAGCTACCTGAGC CTGACCCCCGAGCAGTGGAAGAGCCACAGGTCCTAC AGCTGCCAGGTGACCCACGAGGGCAGCACCGTGGAA AAGACCGTGGCCCCAACCGAGTGCAGC |

Antibody 8111

| | |
|---|---|
| CDRH1 | 33: TSGGGVS |
| CDRH2 | 34: NIDDADIKDYSPSLKS |
| CDRH3 | 35: GPYGFDS |
| CDRL1 | 36: TGTSSDIGTYNYVS |

TABLE 1-continued

Examples of C5 Antibodies of the Present Invention and C5 Proteins

| | Sequence Identifier (SEQ ID NO:) or comments/details |
|---|---|
| CDRL2 | 37:DDSNRPS |
| CDRL3 | 38:QSYDSQSIV |
| VH | 39:EVTLKESGPALVKPTQTLTLTCTFSGFSLSTSG GGVSWIRQPPGKALEWLANIDDADIKDYSPSLKSRL TISKDTSKNQVVLTMTNMDPVDTATYYCARGPYGFD SWGQGTLVTVSS |
| VL | 40:ESALTQPASVSGSPGQSITISCTGTSSDIGTYN YVSWYQQHPGKAPKLMIYDDSNRPSGVSNRFSGSKS GNTASLTISGLQAEDEADYYCQSYDSQSIVFGGGTK LTVL |
| Heavy chain | 41:EVTLKESGPALVKPTQTLTLTCTFSGFSLSTSG GGVSWIRQPPGKALEWLANIDDADIKQYSPSLKSRL TISKDTSKNQVVLTMTNMDPVDTATYYCARGPYGFD SWGQGTLVTVSSASTKGPSVFPLAPSSKSTSGGTAA LGCLVKQYFPEPVTVSWNSGALTSGVHTFPAVLQSS GLYSLSSWTVPSSSLGTQTYICNVNHKPSNTKVDKR VEPKSCDKTHTCPPCPAPEAAGGPSVFLFPPKPKDT LMISRTPEVTCVWDVSHEDPEVKFNWYVDGVEVHNA KTKPREEQYNSTYRVVSVLTVLHQDWLNGKEYKCKV SNKALPAPIEKTISKAKGQPREPQVYTLPPSREEMT KNQVSLTCLVKGFYPSDIAVEWESNGQPENNYKTTP PVLDSDGSFFLYSKLTVDKSRWQQGNVFSCSVMHEA LHNHYTQKSLSLSPGK |
| Light chain | 42:ESALTQPASVSGSPGQSITISCTGTSSDIGTYN YVSWYQQHPGKAPKLMIYDDSNRPSGVSNRFSGSKS GNTASLTISGLQAEDEADYYCQSYDSQSIVFGGGTK LTVLGQPKAAPSVTLFPPSSEELQANKATLVCLISD FYPGAVTVAWKADSSPVKAGVETTTPSKQSNNKYAA SSYLSLTPEQWKSHRSYSCQVTHEGSTVEKTVAPTE CS |
| PN encoding SEQ ID NO: 39 | 43:GAGGTGACATGAAAGAAAGCGGCCCGGCCCTGG TGAAACCGACCCAAACCCTGACCCTGACCTGTACCT TTTCCGGATTTAGCCTGTCTACTTCTGGTGGTGGTG TGTCTTGGATTCGCCAGCCGCCTGGGAAAGCCCTCG AGTGGCTGGCTAATATTGATGATGCTGATATTAAGG ATTATTCTCCTTCTCTTAAGTCTCGTCTGACCATTA GCAAAGATACTTCGAAAAATCAGGTGGTGCTGACTA TGACCAACATGGACCCGGTGGATACGGCCACCTATT ATTGCGCGCGTGGTCCTTATGGTTTTGATTCTTGGG GCCAAGGCACCCTGGTGACGGTTAGCTCA |
| PN encoding SEQ ID NO: 40 | 44:GAAAGCGCACTGACCCAGCCAGCTCAGTGAGCG GCTCACCAGGTCAGAGCATTACCATCTCGTGTACGG GTACTAGCAGCGATATTGGTACTTATAATTATGTGT CTTGGTACCAGCAGCATCCCGGGAAGGCGCCGAAAC TTATGATTTATGATGATTCTAATCGTCCCTCAGGCG TGAGCAACCGTTTTAGCGGATCCAAAAGCGGCAACA CCGCGAGCCTGACCATTAGCGGCCTGCAAGCGGAAG ACGAAGCGGATTATTATTGCCAGTCTTATGATTCT AGTCTATTGTGTTTGGCGGCGGCACGAAGTTAACCG TCCTA |
| PN encoding SEQ ID NO: 41 | 45:GAGGTGACATTGAAAGAAAGCGGCCCGGCCCTG GTGAAACCGACCCAAACCCTGACCCTGACCTGTACC TTTTCCGGATTTAGCCTGTCTACTTCTGGTGGTGGT GTGTCTTGGATTCGCCAGCCGCCTGGGAAAGCCCTC GAGTGGCTGGCTAATATTGATGATGCTGATATTAAG GATTATTCTCCTTCTCTTAAGTCTCGTCTGACCATT AGCAAAGATACTTCGAAAAATCAGGTGGTGCTGACT ATGACCAACATGGACCCGGTGGATACGGCCACCTAT TATTGCGCGCGTGGTCCTTATGGTTTTGATTCTTGG GGCCAAGGCACCCTGGTGACGGTTAGCTCAGCCTCC ACCAAGGGTCCATCGGTCTTCCCCCTGGCACCCTCC TCCAAGAGCACCTCTGGGGGCACAGCGGCCCTGGGC TGCCTGGTCAAGGACTACTTCCCCGAACCGGTGACG GTGTCGTGGAACTCAGGCGCCCTGACCAGCGGCGTG CACACCTTCCCGGCTGTCCTACAGTCCTCAGGACTC TACTCCCTCAGCAGCGTGGTGACCGTGCCCTCCAGC AGCTTGGGCACCCAGACCTACATCTGCAACGTGAAT CACAAGCCCAGCAACACCAAGGTGGACAAGAGAGTT GAGCCCAAATCTTGTGACAAAACTCACACATGCCCA CCGTGCCCAGCACCTGAAGCAGCGGGGGACCGTCA GTCTTCCTCTTCCCCCCAAAACCCAAGGACACCCTC ATGATCTCCCGGACCCCTGAGGTCACATGCGTGGTG GTGGACGTGAGCCACGAAGACCCTGAGGTCAAGTTC AACTGGTACGTGGACGGCGTGGAGGTGCATAATGCC AAGACAAAGCCGCGGGAGGAGCAGTACAACAGCACG TACCGGGTGGTCAGCGTCCTCACCGTCCTGCACCAG GACTGGCTGAATGGCAAGGAGTACAAGTGCAAGGTC TCCAACAAACCCCTCCCAGCCCCCATCGAGAAAACC ATCTCCAAAGCCAAAGGGCAGCCCCGAGAACCACAG GTGTACACCCTGCCCCCATCCCGGGAGGAGATGACC AAGAACCAGGTCAGCCTGACCTGCCTGGTCAAAGGC TTCTATCCCAGCGACATCGCCGTGGAGTGGGAGAGC AATGGGCAGCCGGAGAACAACTACAAGACCACGCCT CCCGTGCTGGACTCCGACGGCTCCTTCTTCCTCTAC AGCAAGCTCACCGTGGACAAGAGCAGGTGGCAGCAG GGGAACGTCTTCTCATGCTCCGTGATGCATGAAGCT CTGCACAACCACTACACGCAGAAGAGCCTCTCCCTG TCTCCGGGTAAA |
| PN encoding SEQ ID NO: 42 | 46:GAAAGCGCACTGACCCAGCCAGCTTCAGTGAGC GGCTCACCAGGTCAGAGCATTACCATCTCGTGTACG GGTACTAGCAGCGATATTGGTACTTATAATTATGTG TCTTGGTACCAGCAGCATCCCGGGAAGGCGCCGAAA CTTATGATTTATGATGATTCTAATCGTCCCTCAGGC GTGAGCAACCGTTTTAGCGGATCCAAAAGCGGCAAC ACCGCGAGCCTGACCATTAGCGGCCTGCAAGCGGAA GACGAAGCGGATTATTATTGCCAGTCTTATGATTCT CAGTCTATTGTGTTTGGCGGCGGCACGAAGTTAACC GTCCTAGGTCAGCCCAAGGCTGCCCCCTCGGTCACT CTGTTCCCGCCCTCCTCTGAGGAGCTTCAAGCCAAC AAGGCCACACTGGTGTGTCTCATAAGTGACTTCTAC CCGGGAGCCGTGACAGTGGCCTGGAAGGCAGATAGC AGCCCCGTCAAGGCGGGAGTGGAGACCACCACACCC TCCAAACAAAGCAACAACAAGTACGCGGCCAGCAGC TATCTGAGCCTGACGCCTGAGCAGTGGAAGTCCCAC AGAAGCTACAGCTGCCAGGTCACGCATGAAGGGAGC ACCGTGGAGAAGACAGTGGCCCCTACAGAATGTTCA |
| Optimized PN encoding SEQ ID NO: 41 | 47:GAGGTGACCCTGAAGGAGAGCGGCCCCAGCCCTG GTGAAGCCCACCCAGACCCTGACCCTGACTTGCACC TTCAGCGGCTTCAGCCTGAGCACCAGCGGAGGGGGC GTGAGCTGGATCAGGCAGCCCCCAGGTAAGGCCCTG GAGTGGCTGGCCAATATCGACGACGCCGATATCAAG GACTACAGCCCCAGCCTGAAGAGCAGGCTGACCATC AGCAAGGACACCAGCAAGAACCAGGTGGTGCTGACC ATGACCAATATGGACCCCGTGGACACCGCCACCTAC TACTGCGCCAGAGGCCCCTACGGCTTCGACAGCTGG GGCCAGGGCACCCTGGTGACCGTCAGCTCAGCTAGC ACCAAGGGCCCAGCGTGTTCCCCCTGGCCCCCAGC AGCAAGAGCACCTCCGGCGGCACAGCCGCCCTGGGC TGCCTGGTGAAGGACTACTTCCCCGAGCCCGTGACC GTGTCCTGGAACAGCGGAGCCCTGACCAGCGGCGTG CACACCTTCCCCGCCGTGCTGCAGAGCAGCGGCCTG TACAGCCTGTCCAGCGTGGTGACAGTGCCCAGCAGC AGCCTGGGCACCCAGACCTACATCTGCAACGTGAAC CACAAGCCCAGCAACACCAAGGTGGACAAGAGAGTG GAGCCCAAGAGTGCCAAGACCCACACCTGCCCC CCTGCCCAGCCCCGAAGCTGCAGGCGGCCTTCC GTGTTCCTGTTCCCCCCAAGCCCAAGGACACCCTG ATGATCAGCAGGACCCCCGAGGTGACCTGCGTGGTG GTGGACGTGAGCCACGAGGACCCAGAGGTGAAGTTC AACTGGTACGTGGACGGCGTGGAGGTGCACAACGCC AAGACCAAGCCCAGAGAGGAGCAGTACAACAGCACC TACAGGGTGGTGTCCGTGCTGACCGTGCTGCACCAG GACTGGCTGAACGGCAAGGAATACAAGTGCAAGGTC TCCAACAAGGCCCTGCCTGCCCCCATCGAAAAGACC ATCAGCAAGGCCAAGGGCCAGCCACGGGAGCCCCAG GTGTACACCCTGCCCCCTTCTCGGGAGGAGATGACC AAGAACCAGGTGTCCCTGACCTGTCTGGTGAAGGGC |

TABLE 1-continued

Examples of C5 Antibodies of the
Present Invention and C5 Proteins

| | Sequence Identifier (SEQ ID NO:) or comments/details |
|---|---|
| | TTCTACCCCAGCGACATCGCCGTGGAGTGGGAGAGC<br>AACGGCCAGCCCGAGAACAACTACAAGACCACCCCC<br>CCAGTGCTGGACAGCGACGGCAGCTTCTTCCTGTAC<br>AGCAAGCTGACCGTGGACAAGAGCAGGTGGCAGCAG<br>GGCAACGTGTTCAGCTGCAGCGTGATGCACGAGGCC<br>CTGCACAACCACTACACCCAGAAGAGCCTGAGCCTG<br>TCACCCGGCAAG |
| Optimized PN encoding SEQ ID NO: 42 | 48:GAGAGCGCCCTGACCCAGCCCGCCAGCGTGAGC<br>GGCAGCCCAGGCCAGTCTATCACAATCAGCTGCACC<br>GGCACCTCCAGCGATATCGGCACCTACAACTACGTG<br>AGCTGGTATCAGCAGCACCCCGGCAAGGCCCCCAAG<br>CTGATGATCTACGACGACAGCAACAGGCCCAGCGGC<br>GTGAGCAACAGGTTCAGCGGCAGCAAGAGCGGCAAC<br>ACCGCCAGCCTGACAATCAGCGGCCTGCAGGCCGAG<br>GACGAGGCCGACTACTACTGCCAGAGCTACGACAGC<br>CAGTCAATCGTGTTCGGCGGAGGGACCAAGCTGACC<br>GTGCTGGGCCAGCCTAAGGCTGCCCCCAGCGTGACC<br>CTGTTCCCCCCAGCAGCGAGGAGCTGCAGGCCAAC<br>AAGGCCACCCTGGTGTGCCTGATCAGCGACTTCTAC<br>CCAGGCGCCGTGACCGTGGCCTGGAAGGCCGACAGC<br>AGCCCCGTGAAGGCCGGCGTGGAGACCACCACCCCC<br>AGCAAGCAGAGCAACAACAAGTACGCCGCCAGCAGC<br>TACCTGAGCCTGACCCCCGAGCAGTGGAAGAGCCAC<br>AGGTCCTACAGCTGCCAGGTGACCCACGAGGGCAGC<br>ACCGTGGAAAAGACCGTGGCCCCAACCGAGTGCAGC |
| Antibody 8113 | |
| CDRH1 | SEQ ID NO: 17 |
| CDRH2 | 49:IIDPDDSYTRYSPSFQG |
| CDRH3 | SEQ ID NO: 19 |
| CDRL1 | SEQ ID NO: 20 |
| CDRL2 | SEQ ID NO: 21 |
| CDRL3 | 50:ATWGSEDQV |
| VH | 51:EVQLVQSGAEVKKPGESLKISCKGSGYSFTNYI<br>SWVRQMPGKGLEWMGIIDPDDSYTRYSPSFQGQVTI<br>SADKSISTAYLQWSSLKASDTAMYYCARYEYGGFDI<br>WGQGTLVTVSS |
| VL | 52:SYELTQPPSVSVAPGQTARISCSGDNIGNSYVH<br>WYQQKPGQAPVLVIYKDNDRPSGIPERFSGSNSGNT<br>ATLTISGTQAEDEADYYCATWGSEDQVFGGGTKLTV<br>L |
| Heavy chain | 53:EVQLVQSGAEVKKPGESLKISCKGSGYSFTNYI<br>SWVRQMPGKGLEWMGIIDPDDSYTRYSPSFQGQVTI<br>SADKSISTAYLQWSSLKASDTAMYYCARYEYGGFDI<br>WGQGTLVTVSSASTKGPSVFPLAPSSKSTSGGTAAL<br>GCLVKDYFPEPVTVSWNSGALTSGVHTFPAVLQSSG<br>LYSLSSVVTVPSSSLGTQTYICNVNHKPSNTKVDKRV<br>EPKSCDKTHTCPPCPAPEAAGGPSVFLFPPKPKDTL<br>MISRTPEVTCVWVDVSHEDPEVKFNWYVDGVEVHNAK<br>TKPREEQYNSTYRVVSVLTVLHQDWLNGKEYKCKVS<br>NKALPAPIEKTISKAKGQPREPQVYTLPPSREEMTK<br>NQVSLTCLVKGFYPSDIAVEWESNGQPENNYKTTPP<br>VLDSDGSFFLYSKLTVDKSRWQQGNVFSCSVMHEAL<br>HNHYTQKSLSLSPGK |
| Light chain | 54:SYELTQPPSVSVAPGQTARISCSGDNIGNSYVH<br>WYQQKPGQAPVLVIYKDNDRPSGIPERFSGSNSGNT<br>ATLTISGTQAEDEADYYCATWGSEDQVFGGGTKLTV<br>LGQPKAAPSVTLFPPSSEELQANKATLVCLISDFYP<br>GAVTVAWKADSSPVKAGVETTTPSKQSNNKYAASSY<br>LSLTPEQWKSHRSYSCQVTHEGSTVEKTVAPTECS |
| PN encoding SEQ ID NO: 51 | 55:GAGGTGCAATTGGTTCAGAGCGGCGCGGAAGTG<br>AAAAAACCGGGCGAAAGCCTGAAAATTAGCTGCAAA |

TABLE 1-continued

Examples of C5 Antibodies of the
Present Invention and C5 Proteins

| | Sequence Identifier (SEQ ID NO:) or comments/details |
|---|---|
| | GGTTCCGGATATTCCTTTACTAATTATATTTCTTGG<br>GTGCGCCAGATGCCTGGGAAGGGTCTCGAGTGGATG<br>GGCATTATCGATCCGGATGATAGCTATACCCGTTAT<br>TCTCCGAGCTTTCAGGGACAGGTGACCATTAGCGCG<br>GATAAAAGCATTAGCACCGCGTATCTTCAATGGAGC<br>AGCCTGAAAGCGAGCGATACGGCCATGTATTATTGC<br>GCGCGTTATGAGTATGGTGGTTTTGATATTTGGGGC<br>CAAGGCACCCTGGTGACGGTTAGCTCA |
| PN encoding SEQ ID NO: 52 | 56:AGTTACGAACTGACCCAGCCGCCTTCAGTGAGC<br>GTTGCACCAGGTCAGACCGCGCGTATCTCGTGTAGC<br>GGCGATAATATTGGTAATTCTTATGTTCATTGGTAC<br>CAGCAGAAACCCGGGCAGGCGCCAGTTCTTGTGATT<br>TATAAGGATAATGATCGTCCCTCAGGCATCCCGGAA<br>CGCTTTAGCGGATCCAACAGCGGCAACACCGCGACC<br>CTGACCATTAGCGGCACTCAGGCGGAAGACGAAGCG<br>GATTATTATTGCGCTACTTGGGGTTCTGAGGATCAG<br>GTGTTTGGCGGCGGCACGAAGTTAACCGTCCTA |
| PN encoding SEQ ID NO: 53 | 57:GAGGTGCAATTGGTTCAGAGCGGCGCGGAAGTG<br>AAAAAACCGGGCGAAAGCCTGAAAATTAGCTGCAAA<br>GGTTCCGGATATTCCTTTACTAATTATATTTCTTGG<br>GTGCGCCAGATGCCTGGGAAGGGTCTCGAGTGGATG<br>GGCATTATCGATCCGGATGATAGCTATACCCGTTAT<br>TCTCCGAGCTTTCAGGGACAGGTGACCATTAGCGCG<br>GATAAAAGCATTAGCACCGCGTATCTTCAATGGAGC<br>AGCCTGAAAGCGAGCGATACGGCCATGTATTATTGC<br>GCGCGTTATGAGTATGGTGGTTTTGATATTTGGGGC<br>CAAGGCACCCTGGTGACGGTTAGCTCAGCCTCCACC<br>AAGGGTCCATCGGTCTTCCCCCTGGCACCCTCCTCC<br>AAGAGCACCTCTGGGGGCACAGCGGCCCTGGGCTGC<br>CTGGTCAAGGACTACTTCCCCGAACCGGTGACGGTG<br>TCGTGGAACTCAGGCGCCCTGACCAGCGGCGTGCAC<br>ACCTTCCCGGCTGTCCTACAGTCCTCAGGACTCTAC<br>TCCCTCAGCAGCGTGGTGACCGTGCCCTCCAGCAGC<br>TTGGGCACCCAGACCTACATCTGCAACGTGAATCAC<br>AAGCCCAGCAACACCAAGGTGGACAAGAGAGTTGAG<br>CCCAAATCTTGTGACAAAACTCACACATGCCCACCG<br>TGCCCAGCACCTGAAGCAGCGGGGGGACCGTCAGTC<br>TTCCTCTTCCCCCCAAAACCCAAGGACACCCCTCATG<br>ATCTCCCGGACCCCTGAGGTCACATGCGTGGTGGTG<br>GACGTGAGCCACGAAGACCCTGAGGTCAAGTTCAAC<br>TGGTACGTGGACGGCGTGGAGGTGCATAATGCCAAG<br>ACAAAGCCGCGGGAGGAGCAGTACAACAGCACGTAC<br>CGGGTGGTCAGCGTCCTCACCGTCCTGCACCAGGAC<br>TGGCTGAATGGCAAGGAGTACAAGTGCAAGGTCTCC<br>AACAAAGCCCTCCCAGCCCCCATCGAGAAAACCATC<br>TCCAAAGCCAAAGGGCAGCCCCGAGAACCACAGGTG<br>TACACCCTGCCCCCATCCCGGGAGGAGATGACCAAG<br>AACCAGGTCAGCCTGACCTGCCTGGTCAAAGGCTTC<br>TATCCCAGCGACATCGCCGTGGAGTGGGAGAGCAAT<br>GGGCAGCCGGAGAACAACTACAAGACCACGCCTCCC<br>GTGCTGGACTCCGACGGCTCCTTCTTCCTCTACAGC<br>AAGCTCACCGTGGACAAGAGCAGGTGGCAGCAGGGG<br>AACGTCTTCTCATGCTCCGTGATGCATGAGGCTCTG<br>CACAACCACTACACGCAGAAGAGCCTCTCCCTGTCT<br>CCGGGTAAA |
| PN encoding SEQ ID NO: 54 | 58:AGTTACGAACTGACCCAGCCGCCTTCAGTGAGC<br>GTTGCACCAGGTCAGACCGCGCGTATCTCGTGTAGC<br>GGCGATAATATTGGTAATTCTTATGTTCATTGGTAC<br>CAGCAGAAACCCGGGCAGGCGCCAGTTCTTGTGATT<br>TATAAGGATAATGATCGTCCCTCAGGCATCCCGGAA<br>CGCTTTAGCGGATCCAACAGCGGCAACACCGCGACC<br>CTGACCATTAGCGGCACTCAGGCGGAAGACGAAGCG<br>GATTATTATTGCGCTACTTGGGGTTCTGAGGATCAG<br>GTGTTTGGCGGCGGCACGAAGTTAACCGTCCTAGGT<br>CAGCCCAAGGCTGCCCCCTCGGTCACTCTGTTCCCG<br>CCCTCCTCTGAGGAGCTTCAAGCCAACAAGGCCACA<br>CTGGTGTGTCTCATAAGTGACTTCTACCCGGGAGCC<br>GTGACAGTGGCCTGGAAGGCAGATAGCAGCCCCGTC<br>AAGGCGGGAGTGGAGACCACCACACCCTCCAAACAA<br>AGCAACAACAAGTACGCGGCCAGCAGCTATCTGAGC<br>CTGACGCCTGAGCAGTGGAAGTCCCACAGAAGCTAC |

TABLE 1-continued

Examples of C5 Antibodies of the
Present Invention and C5 Proteins

| | Sequence Identifier (SEQ ID NO:) or comments/details |
|---|---|
| | AGCTGCCAGGTCACGCATGAAGGGAGCACCGTGGAG<br>AAGACAGTGGCCCCTACAGAATGTTCA |
| Optimized PN encoding SEQ ID NO: 53 | 59: GAGGTGCAGCTGGTGCAGAGCGGAGCCGAGGTG<br>AAAAAGCCCGGTGAGAGCCTGAAGATCAGCTGCAAG<br>GGCAGCGGCTACAGCTTCACCAACTACATCAGCTGG<br>GTGCGGCAGATGCCCGGCAAGGGCCTGGAGTGGATG<br>GGCATCATCGACCCCGACGACAGCTACACCAGGTAC<br>AGCCCCAGCTTCCAGGGCCAGGTGACCATCAGCGCC<br>GACAAGAGCATCAGCACCGCCTACCTGCAGTGGAGC<br>AGCCTGAAGGCCAGCGACACCGCCATGTACTACTGC<br>GCCAGATACGAGTACGGCGGCTTCGACATCTGGGGC<br>CAGGGCACCCTGGTGACCGTCAGCTCAGCTAGCACC<br>AAGGGCCCCAGCGTGTTCCCCCTGGCCCCCAGCAGC<br>AAGAGCACCTCCGGCGGCACAGCCGCCCTGGGCTGC<br>CTGGTGAAGGACTACTTCCCCGAGCCCGTGACCGTG<br>TCCTGGAACAGCGGAGCCCTGACCAGCGGCGTGCAC<br>ACCTTCCCCGCCGTGCTGCAGAGCAGCGGCCTGTAC<br>AGCCTGTCCAGCGTGGTGACAGTGCCCAGCAGCAGC<br>CTGGGCACCCAGACCTACATCTGCAACGTGAACCAC<br>AAGCCCAGCAACACCAAGGTGGACAAGAGAGTGGAG<br>CCCAAGAGCTGCGACAAGACCCACACCTGCCCCCCC<br>TGCCCAGCCCCCGAAGCTGCAGGCGGCCCTTCCGTG<br>TTCCTGTTCCCCCCCAAGCCCAAGGACACCCTGATG<br>ATCAGCAGGACCCCCGAGGTGACCTGCGTGGTGGTG<br>GACGTGAGCCACGAGGACCCAGAGGTGAAGTTCAAC<br>TGGTACGTGGACGGCGTGGAGGTGCACAACGCCAAG<br>ACCAAGCCCAGAGAGGAGCAGTACAACAGCACCTAC<br>AGGGTGGTGTCCGTGCTGACCGTGCTGCACCAGGAC<br>TGGCTGAACGGCAAAGAATACAAGACCAAGTCTCC<br>AACAAGGCCCTGCCTGCCCCCATCGAAAAGACCATC<br>AGCAAGGCCAAGGGCCAGCCACGGGAGCCCCAGGTG<br>TACACCCTGCCCCCTTCTCGGGAGGAGATGACCAAG<br>AACCAGGTGTCCCTGACCTGTCTGGTGAAGGGCTTC<br>TACCCCAGCGACATCGCCGTGGAGTGGGAGAGCAAC<br>GGCCAGCCCGAGAACAACTACAAGACCACCCCCCCA<br>GTGCTGGACAGCGACGGCAGCTTCTTCCTGTACAGC<br>AAGCTGACCGTGGACAAGAGCAGGTGGCAGCAGGGC<br>AACGTGTTCAGCTGCAGCGTGATGCACGAGGCCCTG<br>CACAACCACTACACCCAGAAGAGCCTGAGCCTGTCA<br>CCCGGCAAG |
| Optimized PN encoding SEQ ID NO: 54 | 60: AGCTACGAGCTGACCCAGCCCCCCAGCGTGAGC<br>GTGGCCCCAGGCCAGACCGCCAGGATCAGCTGCAGC<br>GGCGACAATATCGGCAACAGCTACGTGCACTGGTAT<br>CAGCAGAAGCCCGGCCAGGCCCCCGTGCTGGTGATC<br>TACAAGGACAACGACAGGCCCAGCGGCATCCCCGAG<br>AGGTTCAGCGGCAGCAACTCCGGCAACACCGCCACC<br>CTGACAATCAGCGGCACCCAGGCCGAGGACGAGGCC<br>GACTACTACTGCGCCACCTGGGGCTCAGAGGACCAG<br>GTGTTCGGCGGAGGGACCAAGCTGACCGTGCTGGGC<br>CAGCCTAAGGCTGCCCCCAGCGTGACCCTGTTCCCC<br>CCCAGCAGCGAGGAGCTGCAGGCCAACAAGGCCACC<br>CTGGTGTGCCTGATCAGCGACTTCTACCCAGGCGCC<br>GTGACCGTGGCCTGGAAGGCCGACAGCAGCCCCGTG<br>AAGGCCGGTGGAGACTACAACACCCCCAGCAAGCAG<br>AGCAACAACAAGTACGCCGCCAGCAGCTACCTGAGC<br>CTGACCCCCGAGCAGTGGAAGAGCCACAGGTCCTAC<br>AGCTGCCAGGTGACCCACGAGGGCAGCACCGTGGAA<br>AAGACCGTGGCCCCAACCGAGTGCAGC |

Antibody 8114

| | |
|---|---|
| CDRH1 | 61: SYYIG |
| CDRH2 | 62: IIDPTDSQTAYSPSFQG |
| CDRH3 | 63: YMMRGFDH |
| CDRL1 | 64: SGDSLGDYYAY |
| CDRL2 | 65: KDNNRPS |
| CDRL3 | 66: QTWDTGESGV |

TABLE 1-continued

Examples of C5 Antibodies of the
Present Invention and C5 Proteins

| | Sequence Identifier (SEQ ID NO:) or comments/details |
|---|---|
| VH | 67: EVQLVQSGAEVKKPGESLKISCKGSGYSFTSYY<br>IGWVRQMPGKGLEWMGIIDPTDSQTAYSPSFQGQVT<br>ISADKSISTAYLQWSSLKASDTAMYYCARYMMRGFD<br>HWGQGTLVTVSS |
| VL | 68: SYELTQPPSVSVAPGQTARISCSGDSLGDYYAY<br>WYQQKPGQAPVLVIYKDNNRPSGIPERFSGSNSGNT<br>ATLTISGTQAEDEADYYCQTWDTGESGVFGGGTKLT<br>VL |
| Heavy chain | 69: EVQLVQSGAEVKKPGESLKISCKGSGYSFTSYY<br>IGWVRQMPGKGLEWMGIIDPTDSQTAYSPSFQGQVT<br>ISADKSISTAYLQWSSLKASDTAMYYCARYMMRGFD<br>HWGQGTLVTVSSASTKGPSVFPLAPSSKSTSGGTAA<br>LGCLVKDYFPEPVTVSWNSGALTSGVHTFPAVLQSS<br>GLYSLSSVVTVPSSSLGTQTYICNVNHKPSNTKVDK<br>RVEPKSCDKTHTCPPCPAPEAAGGPSVFLFPPKPKD<br>TLMISRTPEVTCVVVDVSHEDPEVKFNWYVDGVEVHN<br>AKTKPREEQYNSTYRVVSVLTVLHQDWLNGKEYKCK<br>VSNKALPAPIEKTISKAKGQPREPQVYTLPPSREEM<br>TKNQVSLTCLVKGFYPSDIAVEWESNGQPENNYKTT<br>PPVLDSDGSFFLYSKLTVDKSRWQQGNVFSCSVMHE<br>ALHNHYTQKSLSLSPGK |
| Light chain | 70: SYELTQPPSVSVAPGQTARISCSGDSLGDYYAY<br>WYQQKPGQAPVLVIYKDNNRPSGIPERFSGSNSGNT<br>ATLTISGTQAEDEADYYCQTWDTGESGVFGGGTKLT<br>VLGQPKAAPSVTLFPPSSEELQANKATLVCLISDFY<br>PGAVTVAWKADSSPVKAGVETTTPSKQSNNKYAASS<br>YLSLTPEQWKSHRSYSCQVTHEGSTVEKTVAPTECS |
| PN encoding SEQ ID NO: 67 | 71: GAGGTGCAATTGGTTCAGAGCGGCGCGGAAGTG<br>AAAAAACCGGGCGAAAGCCTGAAAATTAGCTGCAAA<br>GGTTCCGGATATTCCTTTACTTCTTATTATATTGGT<br>TGGGTGCGCCAGATGCCTGGGAAGGGTCTCGAGTGG<br>ATGGGCATTATTGATCCTACTGATTCTCAGACTGCT<br>TATTCTCCTTCTTTTCAGGGTCAGGTGACCATTAGC<br>GCGGATAAAAGCATTAGCACCGCGTATCTTCAATGG<br>AGCAGCCTGAAAGCGAGCGATACGGCCATGTATTAT<br>TGCGCGCGTTATATGATGCGTGGTTTTGATCATTGG<br>GGCCAAGGCACCCTGGTGACGGTTAGCTCA |
| PN encoding SEQ ID NO: 68 | 72: AGTTACGAACTGACCCAGCCGCCTTCAGTGAGC<br>GTTGCACCAGGTCAGACCGCGCGTATCTCGTGTAGC<br>GGCGATTCTCTTGGTGATTATTATGCTTATTGGTAC<br>CAGCAGAAACCCGGGCAGGCGCCAGTTCTTGTGATT<br>TATAAGGATAATAATCGTCCCTCAGGCATCCCGGAA<br>CGCTTTAGCGGATCCAACAGCGGCAACACCGCGACC<br>CTGACCATTAGCGGCACTCAGGCGGAAGACGAAGCG<br>GATTATTATTGCCAGACTTGGGATACTGGTGAGTCT<br>GGTGTGTTTGGCGGCGGCACGAAGTTAACCGTCCTA |
| PN encoding SEQ ID NO: 69 | 73: GAGGTGCAATTGGTTCAGAGCGGCGCGGAAGTG<br>AAAAAACCGGGCGAAAGCCTGAAAATTAGCTGCAAA<br>GGTTCCGGATATTCCTTTACTTCTTATTATATTGGT<br>TGGGTGCGCCAGATGCCTGGGAAGGGTCTCGAGTGG<br>ATGGGCATTATTGATCCTACTGATTCTCAGACTGCT<br>TATTCTCCTTCTTTTCAGGGTCAGGTGACCATTAGC<br>GCGGATAAAAGCATTAGCACCGCGTATCTTCAATGG<br>AGCAGCCTGAAAGCGAGCGATACGGCCATGTATTAT<br>TGCGCGCGTTATATGATGCGTGGTTTTGATCATTGG<br>GGCCAAGGCACCCTGGTGACGGTTAGCTCAGCCTCC<br>ACCAAGGGTCCATCGGTCTTCCCCCTGGCACCCTCC<br>TCCAAGAGCACCTCTGGGGGCACAGCGGCCCTGGGC<br>TGCCTGGTCAAGGACTACTTCCCCGAACCGGTGACG<br>GTGTCGTGGAACTCAGGCGCCCTGACCAGCGGCGTG<br>CACACCTTCCCGGCTGTCCTACAGTCCTCAGGACTC<br>TACTCCCTCAGCAGCGTGGTGACCGTGCCCTCCAGC<br>AGCTTGGGCACCCAGACCTACATCTGCAACGTGAAT<br>CACAAGCCCAGCAACACCAAGGTGGACAAGAGAGTT<br>GAGCCCAAATCTTGTGACAAAACTCACACATGCCCA<br>CCGTGCCCAGCACCTGAACTCAGCGGGGGACCGTCA<br>GTCTTCCTCTTCCCCCCAAAACCCAAGGACACCCTC |

TABLE 1-continued

Examples of C5 Antibodies of the Present Invention and C5 Proteins

| | Sequence Identifier (SEQ ID NO:) or comments/details |
|---|---|
| | ATGATCTCCCGGACCCCTGAGGTCACATGCGTGGTG<br>GTGGACGTGAGCCACGAAGACCCTGAGGTCAAGTTC<br>AACTGGTACGTGGACGGCGTGGAGGTGCATAATGCC<br>AAGACAAAGCCGCGGGAGGAGCAGTACAACAGCACG<br>TACCGGGTGGTCAGCGTCCTCACCGTCCTGCACCAG<br>GACTGGCTGAATGGCAAGGAGTACAAGTGCAAGGTC<br>TCCAACAAAGCCCTCCCAGCCCCCATCGAGAAAACC<br>ATCTCCAAAGCCAAAGGGCAGCCCCGAGAACCACAG<br>GTGTACACCCTGCCCCCATCCCGGGAGGAGATGACC<br>AAGAACCAGGTCAGCCTGACCTGCCTGGTCAAAGGC<br>TTCTATCCCAGCGACATCGCCGTGGAGTGGGAGAGC<br>AATGGGCAGCCGGAGAACAACTACAAGACCACGCCT<br>CCCGTGCTGGACTCCGACGGCTCCTTCTTCCTCTAC<br>AGCAAGCTCACCGTGGACAAGAGCAGGTGGCAGCAG<br>GGGAACGTCTTCTCATGCTCCGTGATGCATGAGGCT<br>CTGCACAACCACTACACGCAGAAGAGCCTCTCCCTG<br>TCTCCGGGTAAA |
| PN encoding<br>SEQ ID NO: 70 | 74:AGTTACGAACTGACCCAGCCGCCTTCAGTGAGC<br>GTTGCACCAGGTCAGACCGCGCGTATCTCGTGTAGC<br>GGCGATTCTCTTGGTGATTATTATGCTTATTGGTAC<br>CAGCAGAAACCCGGGCAGGCGCCAGTTCTTGTGATT<br>TATAAGGATAATAATCGTCCCTCAGGCATCCCGGAA<br>CGCTTTAGCGGATCCAACAGCGGCAACACCGCGACC<br>CTGACCATTAGCGGCACTCAGGCGGAAGACGAAGCG<br>GATTATTATTGCCAGACTTGGGATACTGGTGAGTCT<br>GGTGTGTTTGGCGGCGGCACGAAGTTAACCGTCCTA<br>GGTCAGCCCAAGGCTGCCCCCTCGGTCACTCTGTTC<br>CCGCCCTCCTCTGAGGAGCTTCAAGCCAACAAGGCC<br>ACACTGGTGTGTCTCATAAGTGACTTCTACCCGGGA<br>GCCGTGACAGTGGCCTGGAAGGCAGATAGCAGCCCC<br>GTCAAGGCGGGAGTGGAGACCACCACACCCTCCAAA<br>CAAAGCAACAACAAGTACGCGGCCAGCAGCTATCTG<br>AGCCTGACGCCTGAGCAGTGGAAGTCCCACAGAAGC<br>TACAGCTGCCAGGTCACGCATGAAGGGAGCACCGTG<br>GAGAAGACAGTGGCCCCTACAGAATGTTCA |
| Optimized PN<br>encoding<br>SEQ ID NO: 69 | 75:GAGGTGCAGCTGGTGCAGAGCGGAGCCGAGGTG<br>AAAAAGCCCGGTGAGAGCCTGAAGATCAGCTGCAAG<br>GGCAGCGGCTACAGCTTCACCAGCTACTACATCGGC<br>TGGGTGCGGCAGATGCCCGGCAAGGGCCTGGAGTGG<br>ATGGGCATCATCGACCCCACCGACAGCCAGACCGCC<br>TACAGCCCCAGCTTCCAGGGCCAGGTGACCATCAGC<br>GCCGACAAGAGCATCAGCACCGCCTACCTGCAGTGG<br>AGCAGCCTGAAGGCCAGCGACACCGCCATGTACTAC<br>TGCGCCCGGTACATGATGAGGGGCTTCGACCACTGG<br>GGTCAGGGCACCCTGGTGACCGTCAGCTCAGCTAGC<br>ACCAAGGGCCCCAGCGTGTTCCCCCTGGCCCCCAGC<br>AGCAAGAGCACCTCCGGCGGCACAGCCGCCCTGGGC<br>TGCCTGGTGAAGGACTACTTCCCCGAGCCCGTGACC<br>GTGTCCTGGAACAGCGGAGCCCTGACCAGCGGCGTG<br>CACACCTTCCCCGCCGTGCTGCAGAGCAGCGGCCTG<br>TACAGCCTGTCCAGCGTGGTGACAGTGCCCAGCAGC<br>AGCCTGGGCACCCAGACCTACATCTGCAACGTGAAC<br>CACAAGCCCAGCAACACCAAGGTGGACAAGAGAGTG<br>GAGCCCAAGAGCTGCGACAAGACCCACACCTGCCCC<br>CCCTGCCCAGCCCCCGAAGCTGCAGGCGGCCCTTCC<br>GTGTTCCTGTTCCCCCCCAAGCCCAAGGACACCCTG<br>ATGATCAGCAGGACCCCCGAGGTGACCTGCGTGGTG<br>GTGGACGTGAGCCACGAGGACCCAGAGGTGAAGTTC<br>AACTGGTACGTGGACGGCGTGGAGGTGCACAACGCC<br>AAGACCAAGCCCAGAGAGGAGCAGTACAACAGCACC<br>TACAGGGTGGTGTCCGTGCTGACCGTGCTGCACCAG<br>GACTGGCTGAACGGCAAAGAATACAAGTGCAAGGTC<br>TCCAACAAGGCCCTGCCTGCCCCCATCGAAAAGACC<br>ATCAGCAAGGCCAAGGGCCAGCCACGGGAGCCCCAG<br>GTGTACACCCTGCCCCCTTCTCGGGAGGAGATGACC<br>AAGAACCAGGTGTCCCTGACCTGTCTGGTGAAGGGC<br>TTCTACCCCAGCGACATCGCCGTGGAGTGGGAGAGC<br>AACGGCCAGCCCGAGAACAACTACAAGACCACCCCC<br>CCAGTCCTGGACAGCGACGGCAGCTTCTTCCTGTAC<br>AGCAAGCTGACCGTGGACAAGAGCAGGTGGCAGCAG<br>GGCAACGTGTTCAGCTGCAGCGTGATGCACGAGGCC<br>CTGCACAACCACTACACCCAGAAGAGCCTGAGCCTG<br>TCACCCGGCAAG |
| Optimized PN<br>encoding<br>SEQ ID NO: 70 | 76:AGCTACGAGCTGACCCAGCCCCCCAGCGTGAGC<br>GTGGCCCCAGGCCAGACCGCCAGGATCAGCTGCAGC<br>GGCGACAGCCTGGGCGACTACTACGCCTACTGGTAT<br>CAGCAGAAGCCCGGCCAGGCCCCCGTGCTGGTGATC<br>TACAAGGACAACAACAGGCCCAGCGGCATCCCCGAG<br>AGGTTCAGCGGCAGCAACAGCGGCAACACCGCCACC<br>CTGACAATCAGCGGCACCCAGGCCGAGGACGAGGCC<br>GACTACTACTGCCAGACCTGGGACACCGGCGAGTCA<br>GGCGTGTTCGGCGAGGGACCAAGCTGACCGTGCTG<br>GGTCAGCCTAAGGCTGCCCCCAGCGTGACCCTGTTC<br>CCCCCCAGCAGCGAGGAGCTGCAGGCCAACAAGGCC<br>ACCCTGGTGTGCCTGATCAGCGACTTCTACCCAGGC<br>GCCGTGACCGTGGCCTGGAAGGCCGACAGCAGCCCC<br>GTGAAGGCCGGCGTGGAGACCACCACCCCCAGCAAG<br>CAGAGCAACAACAAGTACGCCGCCAGCAGCTACCTG<br>AGCCTGACCCCCGAGCAGTGGAAGAGCCACAGGTCC<br>TACAGCTGCCAGGTGACCCACGAGGGCAGCACCGTG<br>GAAAAGACCGTGGCCCCAACCGAGTGCAGC |
| Antibody 8112 | |
| CDRH1 | SEQ ID NO: 61 |
| CDRH2 | 77:IIDPSQSHTTYSPSFQG |
| CDRH3 | SEQ ID NO: 63 |
| CDRL1 | SEQ ID NO: 64 |
| CDRL2 | SEQ ID NO: 65 |
| CDRL3 | 78:QTWDILPHGLV |
| VH | 79:EVQLVQSGAEVKKPGESLKISCKGSGYSFTSYY<br>IGVWRQMPGKGLEWMGIIDPSDSHTTYSPSFQGQVT<br>ISADKSISTAYLQWSSLKASDTAMYYCARYMMRGFD<br>HWGQGTLVTVSS |
| VL | 80:SYELTQPPSVSVAPGQTARISCSGDSLGDYYAY<br>WYQQKPGQAPVLVIYKDNNRPSGIPERFSGSNSGNT<br>ATLTISGTQAEDEADYYCQTWDILPHGLVFGGGTKL<br>TVL |
| Heavy chain | 81:EVQLVQSGAEVKKPGESLKISCKGSGYSFTSYY<br>IGVWRQMPGKGLEWMGIIDPSDSHTTYSPSFQGQVT<br>ISADKSISTAYLQWSSLKASDTAMYYCARYMMRGFD<br>HWGQGTLVTVSSASTKGPSVFPLAPSSKSTSGGTAA<br>LGCLVKDYFPEPVTVSWNSGALTSGVHTFPAVLQSS<br>GLYSLSSVVTVPSSSLGTQTYICNVNHKPSNTKVDK<br>RVEPKSCDKTHTCPPCPAPEAAGGPSVFLFPPKPKD<br>TLMISRTPEVTCVVVDVSHEDPEVKFNWYVDGVEVHN<br>AKTKPREEQYNSTYRVVSVLTVLHQDWLNGKEYKCK<br>VSNKALPAPIEKTISKAKGQPREPQVYTLPPSREEM<br>TKNQVSLTCLVKGFYPSDIAVEWESNGQPENNYKTT<br>PPVLDSDGSFFLYSKLTVDKSRWQQGNVFSCSVMHE<br>ALHNHYTQKSLSLSPGK |
| Light chain | 82:SYELTQPPSVSVAPGQTARISCSGDSLGDYYAY<br>WYQQKPGQAPVLVIYKDNNRPSGIPERFSGSNSGNT<br>ATLTISGTQAEDEADYYCQTWDILPHGLVFGGGTKL<br>TVLGQPKAAPSVTLFPPSSEELQANKATLVCLISDF<br>YPGAVTVAWKADSSPVKAGVETTTPSKQSNNKYAAS<br>SYLSLTPEQWKSHRSYSCQVTHEGSTVEKTVAPTEC<br>S |
| PN encoding<br>SEQ ID NO: 79 | 83:GAGGTGCAATTGGTTCAGAGCGGCGCGGAAGTG<br>AAAAAACCGGGCGAAAGCCTGAAAATTAGCTGCAAA<br>GGTTCCGGATATTCCTTTACTTCTTATTATATTGGT<br>TGGGTGCGCCAGATGCCTGGGAAGGGTCTCGAGTGG<br>ATGGGCATTATCGATCCGTCTGATAGCCATACCACT |

TABLE 1-continued

Examples of C5 Antibodies of the Present Invention and C5 Proteins

| | Sequence Identifier (SEQ ID NO:) or comments/details |
|---|---|
| | TATTCTCCGAGCTTTCAGGGCCAGGTGACCATTAGC GCGGATAAAAGCATTAGCACCGCGTATCTTCAATGG AGCAGCCTGAAAGCGAGCGATACGGCCATGTATTAT TGCGCGCGTTATATGATGCGTGGTTTTGATCATTGG GGCCAAGGCACCCTGGTGACGGTTAGCTCA |
| PN encoding SEQ ID NO: 80 | 84:AGTTACGAACTGACCCAGCCGCCTTCAGTGAGC GTTGCACCAGGTCAGACCGCGCGTATCTCGTGTAGC GGCGATTCTCTTGGTGATTATTATGCTTATTGGTAC CAGCAGAAACCCGGGCAGGCGCCAGTTCTTGTGATT TATAAGGATAATAATCGTCCCTCAGGCATCCCGGAA CGCTTTAGCGGATCCAACAGCGGCAACACCGCGACC CTGACCATTAGCGGCACTCAGGCGGAAGACGAAGCG GATTATTATTGCCAGACTTGGGATATTCTTCCTCAT GGTCTTGTGTTTGGCGGCGGCACGAAGTTAACCGTC CTA |
| PN encoding SEQ ID NO: 81 | 85:GAGGTGCAATTGGTTCAGAGCGGCGCGGAAGTG AAAAAACCGGGCGAAAGCCTGAAAATTAGCTGCAAA GGTTCCGGATATTCCTTTACTTCTTATTATATTGGT TGGGTGCGCCAGATGCCTGGGAAGGGTCTCGAGTGG ATGGGCATTATCGATCCGTCTGATAGCCATACCACT TATTCTCCGAGCTTTCAGGGCCAGGTGACCATTAGC GCGGATAAAAGCATTAGCACCGCGTATCTTCAATGG AGCAGCCTGAAAGCGAGCGATACGGCCATGTATTAT TGCGCGCGTTATATGATGCGTGGTTTTGATCATTGG GGCCAAGGCACCCTGGTGACGGTTAGCTCAGCCTCC ACCAAGGGTCCATCGGTCTTCCCCCTGGCACCCTCC TCCAAGAGCACCTCTGGGGGCACAGCGGCCCTGGGC TGCCTGGTCAAGGACTACTTCCCCGAACCGGTGACG GTGTCGTGGAACTCAGGCGCCCTGACCAGCGGCGTG CACACCTTCCCGGCTGTCCTACAGTCCTCAGGACTC TACTCCCTCAGCAGCGTGGTGACCGTGCCCTCCAGC AGCTTGGGCACCCAGACCTACATCTGCAACGTGAAT CACAAGCCCAGCAACACCAAGGTGGACAAGAGAGTT GAGCCCAAATCTTGTGACAAAACTCACACATGCCCA CCGTGCCCAGCACCTGAAGCAGCGGGGGGACCGTCA GTCTTCCTCTTCCCCCCAAAACCCAAGGACACCCTC ATGATCTCCCGGACCCCTGAGGTCACATGCGTGGTG GTGGACGTGAGCCACGAAGACCCTGAGGTCAAGTTC AACTGGTACGTGGACGGCGTGGAGGTGCATAATGCC AAGACAAAGCCGCGGGAGGAGCAGTACAACAGCACG TACCGGGTGGTCAGCGTCCTCACCGTCCTGCACCAG GACTGGCTGAATGGCAAGGAGTACAAGTGCAAGGTC TCCAACAAAGCCCTCCCAGCCCCCATCGAGAAAACC ATCTCCAAAGCCAAAGGGCAGCCCCGAGAACCACAG GTGTACACCCTGCCCCCATCCCGGGAGGAGATGACC AAGAACCAGGTCAGCCTGACCTGCCTGGTCAAAGGC TTCTATCCCAGCGACATCGCCGTGGAGTGGGAGAGC AATGGGCAGCCGGAGAACAACTACAAGACCACGCCT CCCGTGCTGGACTCCGACGGCTCCTTCTTCCTCTAC AGCAAGCTCACCGTGGACAAGAGCAGGTGGCAGCAG GGGAACGTCTTCTCATGCTCCGTGATGCATGAGGCT CTGCACAACCACTACACGCAGAAGAGCCTCTCCCTG TCTCCGGGTAAA |
| PN encoding SEQ ID NO: 82 | 86:AGTTACGAACTGACCCAGCCGCCTTCAGTGAGC GTTGCACCAGGTCAGACCGCGCGTATCTCGTGTAGC GGCGATTCTCTTGGTGATTATTATGCTTATTGGTAC CAGCAGAAACCCGGGCAGGCGCCAGTTCTTGTGATT TATAAGGATAATAATCGTCCCTCAGGCATCCCGGAA CGCTTTAGCGGATCCAACAGCGGCAACACCGCGACC CTGACCATTAGCGGCACTCAGGCGGAAGACGAAGCG GATTATTATTGCCAGACTTGGGATATTCTTCCTCAT GGTCTTGTGTTTGGCGGCGGCACGAAGTTAACCGTC CTAGGTCAGCCCAAGGCTGCCCCCTCGGTCACTCTG TTCCCGCCCTCCTCTGAGGAGCTTCAAGCCAACAAG GCCACACTGGTGTGTCTCATAAGTGACTTCTACCCG GGAGCCGTGACAGTGGCCTGGAAGGCAGATAGCAGC CCCGTCAAGGCGGGAGTGGAGACCACCACACCCTCC AAACAAAGCAACAACAAGTACGCGGCCAGCAGCTAT CTGAGCCTGACGCCTGAGCAGTGGAAGTCCCACAGA AGCTACAGCTGCCAGGTCACGCATGAAGGGAGCACC GTGGAGAAGACAGTGGCCCCTACAGAATGTTCA |
| Optimized PN encoding SEQ ID NO: 81 | 87:GAGGTGCAGCTGGTGCAGAGCGGGAGCCGAGGTG AAAAAGCCCGGTGAGAGCCTGAAGATCAGCTGCAAG GGCAGCGGCTACAGCTTCACCAGCTACTACATCGGC TGGGTGCGGCAGATGCCCGGCAAGGGCCTGGAGTGG ATGGGCATTATCGATCCGTCTGATAGCCATACCACT TATTCTCCGAGCTTTCAGGGCCAGGTGACCATCAGC GCCGACAAGAGCATCAGCACCGCCTACCTGCAGTGG AGCAGCCTGAAGGCCAGCGACACCGCCATGTACTAC TGCGCCCGGTACATGATGAGGGGCTTCGACCACTGG GGTCAGGGCACCCTGGTGACCGTCAGCTCAGCTAGC ACCAAGGGCCCCAGCGTGTTCCCCCTGGCCCCCAGC AGCAAGAGCACCTCCGGCGGCACAGCCGCCCTGGGC TGCCTGGTGAAGGACTACTTCCCCGAGCCCGTGACC GTGTCCTGGAACAGCGGAGCCCTGACCAGCGGCGTG CACACCTTCCCCGCCGTGCTGCAGAGCAGCGGCCTG TACAGCCTGTCCAGCGTGGTGACAGTGCCCAGCAGC AGCCTGGGCACCCAGACCTACATCTGCAACGTGAAC CACAAGCCCAGCAACACCAAGGTGGACAAGAGAGTG GAGCCCAAGAGCTGCGACAAGACCCACACCTGCCCC CCCTGCCCAGCCCCCGAAGCTGCAGGCGGCCCTTCC GTGTTCCTGTTCCCCCCCAAGCCCAAGGACACCCTG ATGATCAGCAGGACCCCCGAGGTGACCTGCGTGGTG GTGGACGTGAGCCACGAGGACCCAGAGGTGAAGTTC AACTGGTACGTGGACGGCGTGGAGGTGCACAACGCC AAGACCAAGCCCAGAGAGGAGCAGTACAACAGCACC TACAGGGTGGTGTCCGTGCTGACCGTGCTGCACCAG GACTGGCTGAACGGCAAAGAATACAAGTGCAAGGTC TCCAACAAGGCCCTGCCTGCCCCCATCGAAAAGACC ATCAGCAAGGCCAAGGGCCAGCCACGGGAGCCCCAG GTGTACACCCTGCCCCCCTTCTCGGGAGGAGATGACC AAGAACCAGGTGTCCCTGACCTGTCTGGTGAAGGGC TTCTACCCCAGCGACATCGCCGTGGAGTGGGAGAGC AACGGCCAGCCCGAGAACAACTACAAGACCACCCCC CCAGTGCTGGACAGCGACGGCAGCTTCTTCCTGTAC AGCAAGCTGACCGTGGACAAGAGCAGGTGGCAGCAG GGCAACGTGTTCAGCTGCAGCGTGATGCACGAGGCC CTGCACAACCACTACACCCAGAAGAGCCTGAGCCTG TCACCCGGCAAG |
| Optimized PN encoding SEQ ID NO: 82 | 88:AGCTACGAGCTGACCCAGCCCCCCAGCGTGAGC GTGGCCCCAGGCCAGACCGCCAGGATCAGCTGCAGC GGCGACAGCCTGGGCGACTACTACGCCTACTGGTAT CAGCAGAAGCCCGGCCAGGCCCCCGTGCTGGTGATC TACAAGGACAACAACAGGCCCAGCGGCATCCCCGAG AGGTTCAGCGGCAGCAACAGCGGCAACACCGCCACC CTGACAATCAGCGGCACCCAGGCCGAGGACGAGGCC GACTACTACTGCCAGACTTGGGATATTCTTCCTCAT GGTCTTGTGTTCGGCGGAGGGACCAAGCTGACCGTG CTGGGTCAGCCTAAGGCTGCCCCCAGCGTGACCCTG TTCCCCCCCAGCAGCGAGGAGCTGCAGGCCAACAAG GCCACCCTGGTGTGCCTGATCAGCGACTTCTACCCA GGCGCCGTGACCGTGGCCTGGAAGGCCGACAGCAGC CCCGTGAAGGCCGGCGTGGAGACCACCACCCCCAGC AAGCAGAGCAACAACAAGTACGCCGCCAGCAGCTAC CTGAGCCTGACCCCCGAGCAGTGGAAGAGCCACAGG TCCTACAGCTGCCAGGTGACCCACGAGGGCAGCACC GTGGAAAAGACCGTGGCCCCAACCGAGTGCAGC |

Antibody 8125

| | |
|---|---|
| CDRH1 | SEQ ID NO: 61 |
| CDRH2 | SEQ ID NO: 77 |
| CDRH3 | SEQ ID NO: 63 |
| CDRL1 | SEQ ID NO: 64 |
| CDRL2 | SEQ ID NO: 65 |
| CDRL3 | 89:QAWTDSPTGLV |
| VH | SEQ ID NO: 79 |

TABLE 1-continued

Examples of C5 Antibodies of the Present Invention and C5 Proteins

| | Sequence Identifier (SEQ ID NO:) or comments/details |
|---|---|
| VL | 90: SYELTQPPSVSVAPGQTARISCSGDSLGDYYAYWYQQKPGQAPVLVIYKDNNRPSGIPERFSGSNSGNTATLTISGTQAEDEADYYCQAWTDSPTGLVFGGGTKLTVL |
| Heavy chain | SEQ ID NO: 81 |
| Light chain | 91: SYELTQPPSVSVAPGQTARISCSGDSLGDYYAYWYQQKPGQAPVLVIYKDNNRPSGIPERFSGSNSGNTATLTISGTQAEDEADYYCQAWTDSPTGLVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| PN encoding SEQ ID NO: 79 | SEQ ID NO: 83 |
| PN encoding SEQ ID NO: 90 | 92: AGTTACGAACTGACCCAGCCGCCTTCAGTGAGCGTTGCACCAGGTCAGACCGCGCGTATCTCGTGTAGCGGCGATTCTCTTGGTGATTATTATGCTTATTGGTACCAGCAGAAACCGGGCAGGCGCCAGTTCTTGTGATTTATAAGGATAATAATCGTCCCTCAGGCATCCCGGAACGCTTTAGCGGATCCAACAGCGGCAACACCGCGACCCTGACCATTAGCGGCACTCAGGCGGAAGACGAAGCGGATTATTATTGCCAGGCTTGGACTGATTCTCCTACTGGTCTTGTGTTTGGCGGCGGCACGAAGTTAACCGTCCTA |
| PN encoding SEQ ID NO: 81 | SEQ ID NO: 85 |
| PN encoding SEQ ID NO: 91 | 93: AGTTACGAACTGACCCAGCCGCCTTCAGTGAGCGTTGCACCAGGTCAGACCGCGCGTATCTCGTGTAGCGGCGATTCTCTTGGTGATTATTATGCTTATTGGTACCAGCAGAAACCGGGCAGGCGCCAGTTCTTGTGATTTATAAGGATAATAATCGTCCCTCAGGCATCCCGGAACGCTTTAGCGGATCCAACAGCGGCAACACCGCGACCCTGACCATTAGCGGCACTCAGGCGGAAGACGAAGCGGATTATTATTGCCAGGCTTGGACTGATTCTCCTACTGGTCTTGTGTTTGGCGGCGGCACGAAGTTAACCGTCCTAGGTCAGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTATCTGAGCCTGACGCCTGAGCAGTGGAAGTCCCACAGAAGCTACAGCTGCCAGGTCACGCATGAAGGGAGCACCGTGGAGAAGACAGTGGCCCCTACAGAATGTTCA |
| Optimized PN encoding SEQ ID NO: 81 | SEQ ID NO: 87 |
| Optimized PN encoding SEQ ID NO: 91 | 94: AGCTACGAGCTGACCCAGCCCCCCAGCGTGAGCGTGGCCCCAGGCCAGACCGCCAGGATCAGCTGCAGCGGCGACAGCCTGGGCGACTACTACGCCTACTGGTATCAGCAGAAGCCCGGCCAGGCCCCCGTGCTGGTGATCTACAAGGACAACAACAGGCCCAGCGGCATCCCCGAGAGGTTCAGCGGCAGCAACAGCGGCAACACCGCCACCCTGACAATCAGCGGCACCCAGGCCGAGGACGAGGCCGACTACTACTGCCAGGCTTGGACTGATTCTCCTACTGGTCTTGTGTTCGGCGGAGGGACCAAGCTGACCGTGCTGGGTCAGCCTAAGGCTGCCCCCAGCGTGACCCTGTTCCCCCCCAGCAGCGAGGAGCTGCAGGCCAACAAGGCCACCCTGGTGTGCCTGATCAGCGACTTCTACCCAGGCGCCGTGACCGTGGCCTGGAAGGCCGACAGCAGCCCCGTGAAGGCCGGCGTGGAGACCACCACCCCCAGCAAGCAGAGCAACAACAAGTACGCCGCCAGCAGCTACCTGAGCCTGACCCCCGAGCAGTGGAAGAGCCACAGGTCCTACAGCTGCCAGGTGACCCACGAGGGCAGCACCGTGGAAAAGACCGTGGCCCCAACCGAGTGCAGC |

TABLE 1-continued

Examples of C5 Antibodies of the Present Invention and C5 Proteins

| | Sequence Identifier (SEQ ID NO:) or comments/details |
|---|---|
| Antibody 8125 | |
| CDRH1 | SEQ ID NO: 61 |
| CDRH2 | SEQ ID NO: 62 |
| CDRH3 | SEQ ID NO: 63 |
| CDRL1 | SEQ ID NO: 64 |
| CDRL2 | SEQ ID NO: 65 |
| CDRL3 | SEQ ID NO: 89 |
| VH | SEQ ID NO: 67 |
| VL | SEQ ID NO: 90 |
| Heavy chain | SEQ ID NO: 69 |
| Light chain | SEQ ID NO: 91 |
| PN encoding SEQ ID NO: 79 | SEQ ID NO: 71 |
| PN encoding SEQ ID NO: 90 | SEQ ID NO: 92 |
| PN encoding SEQ ID NO: 81 | SEQ ID NO: 73 |
| PN encoding SEQ ID NO: 91 | SEQ ID NO: 93 |
| Optimized PN encoding SEQ ID NO: 81 | SEQ ID NO: 75 |
| Optimized encoding SEQ ID NO: 91 | PN SEQ ID NO: 94 |
| Antibody 8127 | |
| CDRH1 | SEQ ID NO: 61 |
| CDRH2 | 95: IIDPTDSYTVYSPSFQG |
| CDRH3 | SEQ ID NO: 63 |
| CDRL1 | SEQ ID NO: 64 |
| CDRL2 | SEQ ID NO: 65 |
| CDRL3 | SEQ ID NO: 89 |
| VH | 96: EVQLVQSGAEVKKPGESLKISCKGSGYSFTSYYIGVVRQMPGKGLEWMGIIDPTDSYTVYSPSFQGQVTISADKSISTAYLQWSSLKASDTAMYYCARYMMRGFDHWGQGTLVTSS |
| VL | SEQ ID NO: 90 |
| Heavy chain | 97: EVQLVQSGAEVKKPGESLKISCKGSGYSFTSYYIGVWRQMPGKGLEWMGIIDPTDSYTVYSPSFQGQVTISADKSISTAYLQWSSLKASDTAMYYCARYMMRGFDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEM |

TABLE 1-continued

Examples of C5 Antibodies of the
Present Invention and C5 Proteins

| | Sequence Identifier (SEQ ID NO:) or comments/details |
|---|---|
| | TKNQVSLTCLVKGFYPSDIAVEWESNGQPENNYKTT PPVLDSDGSFFLYSKLTVDKSRWQQGNVFSCSVMHE ALHNHYTQKSLSLSPGK |
| Light chain | SEQ ID NO: 91 |
| PN encoding SEQ ID NO: 96 | 98:GAGGTGCAATTGGTTCAGAGCGGCGCGGAAGTG AAAAAAACCGGGCGAAAGCCTGAAAATTAGCTGCAAA GGTTCCGGATATTCCTTTACTTCTTATTATATTGGT TGGGTGCGCCAGATGCCTGGGAAGGGTCTCGAGTGG ATGGGCATTATTGATCCTACTGATTCTTATACTGTT TATTCTCCTTCTTTTCAGGGTCAGGTGACCATTAGC GCGGATAAAAGCATTAGCACCGCGTATCTTCAATGG AGCAGCCTGAAAGCGAGCGATACGGCCATGTATTAT TGCGCGCGTTATATGATGCGTGGTTTTGATCATTGG GGCCAAGGCACCCTGGTGACGGTTAGCTCAGC |
| PN encoding SEQ ID NO: 90 | SEQ ID NO: 92 |
| PN encoding SEQ ID NO: 97 | 99:GAGGTGCAATTGGTTCAGAGCGGCGCGGAAGTG AAAAAAACCGGGCGAAAGCCTGAAAATTAGCTGCAAA GGTTCCGGATATTCCTTTACTTCTTATTATATTGGT TGGGTGCGCCAGATGCCTGGGAAGGGTCTCGAGTGG ATGGGCATTATTGATCCTACTGATTCTTATACTGTT TATTCTCCTTCTTTTCAGGGTCAGGTGACCATTAGC GCGGATAAAAGCATTAGCACCGCGTATCTTCAATGG AGCAGCCTGAAAGCGAGCGATACGGCCATGTATTAT TGCGCGCGTTATATGATGCGTGGTTTTGATCATTGG GGCCAAGGCACCCTGGTGACGGTTAGCTCAGCGCCT CCACCAAGGGTCCATCGGTCTTCCCCCTGGCACCCT CCTCCAAGAGCACCTCTGGGGGCACAGCGGCCCTGG GCTGCCTGGTCAAGGACTACTTCCCCGAACCGGTGA CGGTGTCGTGGAACTCAGGCGCCCTGACCAGCGGCG TGCACACCTTCCCGGCTGTCCTACAGTCCTCAGGAC TCTACTCCCTCAGCAGCGTGGTGACCGTGCCCTCCA GCAGCTTGGGCACCCAGACCTACATCTGCAACGTGA ATCACAAGCCCAGCAACACCAAGGTGGACAAGAGAG TTGAGCCCAAATCTTGTGACAAAACTCACACATGCC CACCGTGCCCAGCACCTGAAGCAGCGGGGGGACCGT CAGTCTTCCTCTTCCCCCCAAAACCCAAGGACACCC TCATGATCTCCCGGACCCCTGAGGTCACATGCGTGG TGGTGGACGTGAGCCACGAAGACCCTGAGGTCAAGT TCAACTGGTACGTGGACGGCGTGGAGGTGCATAATG CCAAGACAAAGCCGCGGGAGGAGCAGTACAACAGCA CGTACCGGGTGGTCAGCGTCCTCACCGTCCTGCACC AGGACTGGCTGAATGGCAAGGAGTACAAGTGCAAGG TCTCCAACAAAGCCCTCCCAGCCCCCATCGAGAAAA CCATCTCCAAAGCCAAAGGGCAGCCCCGAGAACCAC AGGTGTACACCCTGCCCCCATCCCGGGAGGAGATGA CCAAGAACCAGGTCAGCCTGACCTGCCTGGTCAAAG GCTTCTATCCCAGCGACATCGCCGTGGAGTGGGAGA GCAATGGGCAGCCGGAGAACAACTACAAGACCACGC CTCCCGTGCTGGACTCCGACGGCTCCTTCTTCCTCT ACAGCAAGCTCACCGTGGACAAGAGCAGGTGGCAGC AGGGGAACGTCTTCTCATGCTCCGTGATGCATGAGG CTCTGCACAACCACTACACGCAGAAGAGCCTCTCCC TGTCTCCGGGTAAA |
| PN encoding SEQ ID NO: 91 | SEQ ID NO: 93 |
| Optimized PN encoding SEQ ID NO: 97 | 100:GAGGTGCAGCTGGTGCAGAGCGGAGCCGAGGT GAAAAAGCCCGGTGAGAGCCTGAAGATCAGCTGCAA GGGCAGCGGCTACAGCTTCACCAGCTACTACATCGG CTGGGTGCGGCAGATGCCCGGCAAGGGCCTGGAGTG GATGGGCATTATTGATCCTACTGATTCTTATACTGT TTATTCTCCTTCTTTTCAGGGTCAGGTGACCATCAG CGCCGACAAGAGCATCAGCACCGCCTACCTGCAGTG GAGCAGCCTGAAGGCCAGCGACACCGCCATGTACTA CTGCGCCCGGTACATGATGAGGGCTTCGACCACTG GGGTCAGGGCACCCTGGTGACCGTCAGCTCAGCTAG CACCAAGGGCCCCAGCGTGTTCCCCCTGGCCCCCAG CAGCAAGAGCACCTCCGGCGGCACAGCCGCCCTGGG |

TABLE 1-continued

Examples of C5 Antibodies of the
Present Invention and C5 Proteins

| | Sequence Identifier (SEQ ID NO:) or comments/details |
|---|---|
| | CTGCCTGGTGAAGGACTACTTCCCCGAGCCCGTGAC CGTGTCCTGGAACAGCGGAGCCCTGACCAGCGGCGT GCACACCTTCCCCGCCGTGCTGCAGAGCAGCGGCCT GTACAGCCTGTCCAGCGTGGTGACAGTGCCCAGCAG CAGCCTGGGCACCCAGACCTACATCTGCAACGTGAA CCACAAGCCCAGCAACACCAAGGTGGACAAGAGAGT GGAGCCCAAGAGCTGCGACAAGACCCACACCTGCCC CCCCTGCCCAGCCCCCGAAGCTGCAGGCGGCCCTTC CGTGTTCCTGTTCCCCCCCAAGCCCAAGGACACCCT GATGATCAGCAGGACCCCCGAGGTGACCTGCGTGGT GGTGGACGTGAGCCACGAGGACCCAGAGGTGAAGTT CAACTGGTACGTGGACGGCGTGGAGGTGCACAACGC CAAGACCAAGCCCAGAGAGGAGCAGTACAACAGCAC CTACAGGGTGGTGTCCGTGCTGACCGTGCTGCACCA GGACTGGCTGAACGGCAAAGAATACAAGTGCAAGGT CTCCAACAAGGCCCTGCCTGCCCCCATCGAAAAGAC CATCAGCAAGGCCAAGGGCCAGCCACGGGAGCCCCA GGTGTACACCCTGCCCCCTTCTCGGGAGGAGATGAC CAAGAACCAGGTGTCCCTGACCTGTCTGGTGAAGGG CTTCTACCCCAGCGACATCGCCGTGGAGTGGGAGAG CAACGGCCAGCCCGAGAACAACTACAAGACCACCCC CCCAGTGCTGGACAGCGACGGCAGCTTCTTCCTGTA CAGCAAGCTGACCGTGGACAAGAGCAGGTGGCAGCA GGGCAACGTGTTCAGCTGCAGCGTGATGCACGAGGC CCTGCACAACCACTACACCCAGAAGAGCCTGAGCCT GTCACCCGGCAAG |
| Optimized PN encoding SEQ ID NO: 91 | SEQ ID NO: 94 |
| Antibody 8128 | |
| CDRH1 | SEQ ID NO: 17 |
| CDRH2 | SEQ ID NO: 49 |
| CDRH3 | SEQ ID NO: 19 |
| CDRL1 | SEQ ID NO: 20 |
| CDRL2 | SEQ ID NO: 21 |
| CDRL3 | 101:STWDIEPTYV |
| VH | SEQ ID NO: 51 |
| VL | 102:SYELTQPPSVSVAPGQTARISCSGDNIGNSYV HWYQQKPGQAPVLVIYKDNDRPSGIPERFSGSNSGN TATLTISGTQAEDEADYYCSTWDIEPTYVFGGGTKL TVL |
| Heavy chain | SEQ ID NO: 53 |
| Light chain | 103:SYELTQPPSVSVAPGQTARISCSGDNIGNSYV HWYQQKPGQAPVLVIYKDNDRPSGIPERFSGSNSGN TATLTISGTQAEDEADYYCSTWDIEPTYVFGGGTKL TVLGQPKAAPSVTLFPPSSEELQANKATLVCLISDF YPGAVTVAWKADSSPVKAGVETTTPSKQSNNKYAAS SYLSLTPEQWKSHRSYSCQVTHEGSTVEKTVAPTEC S |
| PN encoding SEQ ID NO: 51 | SEQ ID NO: 55 |
| PN encoding SEQ ID NO: 102 | 104:AGTTACGAACTGACCCAGCCGCCTTCAGTGAG CGTTGCACCAGGTCAGACCGCGCGTATCTCGTGTAG CGGCGATAATATTGGTAATTCTTATGTTCATTGGTA CCAGCAGAAACCCGGGCAGGCGCCAGTTCTTGTGAT TTATAAGGATAATGATCGTCCCTCAGGCATCCCGGA ACGCTTTAGCGGATCCAACAGCGGCAACACCGCGAC CCTGACCATTAGCGGCACTCAGGCGGAAGACGAAGC |

TABLE 1-continued

Examples of C5 Antibodies of the Present Invention and C5 Proteins

| | Sequence Identifier (SEQ ID NO:) or comments/details |
|---|---|
| | GGATTATTATTGCTCTACTTGGGATATTGAGCCTAC<br>TTATGTGTTTGGCGGCGGCACGAAGTTAACCGTCCT<br>A |
| PN encoding<br>SEQ ID NO: 53 | SEQ ID NO: 57 |
| PN encoding<br>SEQ ID NO: 103 | 105:AGTTACGAACTGACCCAGCCGCCTTCAGTGAG<br>CGTTGCACCAGGTCAGACCGCGCGTATCTCGTGTAG<br>CGGCGATAATATTGGTAATTCTTATGTTCATTGGTA<br>CCAGCAGAAACCCGGCAGGCGCCAGTTCTTGTGAT<br>TTATAAGGATAATGATCGTCCCTCAGGCATCCCGGA<br>ACGCTTTAGCGGATCCAACAGCGGCAACACCGCGAC<br>CCTGACCATTAGCGGCACTCAGGCGGAAGACGAAGC<br>GGATTATTATTGCTCTACTTGGGATATTGAGCCTAC<br>TTATGTGTTTGGCGGCGGCACGAAGTTAACCGTCCT<br>AGGTCAGCCCAAGGCTGCCCCCTCGGTCACTCTGTT<br>CCCGCCCTCCTCTGAGGAGCTTCAAGCCAACAAGGC<br>CACACTGGTGTGTCTCATAAGTGACTTCTACCCGGG<br>AGCCGTGACAGTGGCCTGGAAGGCAGATAGCAGCCC<br>CGTCAAGGCGGGAGTGGAGACCACCACACCCTCCAA<br>ACAAAGCAACAACAAGTACGCGGCCAGCAGCTATCT<br>GAGCCTGACGCCTGAGCAGTGGAAGTCCACAGAAG<br>CTACAGCTGCCAGGTCACGCATGAAGGGAGCACCGT<br>GGAGAAGACAGTGGCCCCTACAGAATGTTCA |
| Optimized PN<br>encoding<br>SEQ ID NO: 53 | SEQ ID NO: 59 |
| Optimized PN<br>encoding<br>SEQ ID NO: 103 | 106:AGCTACGAGCTGACCCAGCCCCCCAGCGTGAG<br>CGTGGCCCCAGGCCAGACCGCCAGGATCAGCTGCAG<br>CGGCGACAATATCGGCAACAGCTACGTGCACTGGTA<br>TCAGCAGAAGCCCGGCCAGGCCCCCGTGCTGGTGAT<br>CTACAAGGACAACGACAGGCCCAGCGGCATCCCCGA<br>GAGGTTCAGCGGCAGCAACTCCGGCAACACCGCCAC<br>CCTGACAATCAGCGGCACCCAGGCCGAGGACGAGGC<br>CGACTACTACTGCTCTACTTGGGATATTGAGCCTAC<br>TTATGTGTTCGGCGGAGGGACCAAGCTGACCGTGCT<br>GGGCCAGCCTAAGGCTGCCCCCAGCGTGACCCTGTT<br>CCCCCCCAGCAGCGAGGAGCTGCAGGCCAACAAGGC<br>CACCCTGGTGTGCCTGATCAGCGACTTCTACCCAGG<br>CGCCGTGACCGTGGCCTGGAAGGCCGACAGCAGCCC<br>CGTGAAGGCCGGCGTGGAGACCACCACCCCCAGCAA<br>GCAGAGCAACAACAAGTACGCCAGCAGCTACCT<br>GAGCCTGACCCCCGAGCAGTGGAAGAGCCACAGGTC<br>CTACAGCTGCCAGGTGACCCACGAGGGCAGCACCGT<br>GGAAAAGACCGTGGCCCCAACCGAGTGCAGC |

Antibody 8129

| | |
|---|---|
| CDRH1 | SEQ ID NO: 17 |
| CDRH2 | 107:IIDPQDSYTEYSPSFQG |
| CDRH3 | SEQ ID NO: 19 |
| CDRL1 | SEQ ID NO: 20 |
| CDRL2 | SEQ ID NO: 21 |
| CDRL3 | SEQ ID NO: 22 |
| VH | 108:EVQLVQSGAEVKKPGESLKISCKGSGYSFTNY<br>ISWVRQMPGKGLEWMGIIDPQDSYTEYSPSFQGQVT<br>ISADKSISTAYLQWSSLKASDTAMYYCARYEYGGFD<br>IWGQGTLVTVSS |
| VL | SEQ ID NO: 24 |
| Heavy chain | 109:EVQLVQSGAEVKKPGESLKISCKGSGYSFTNY<br>ISWVRQMPGKGLEWMGIIDPQDSYTEYSPSFQGQVT<br>ISADKSISTAYLQWSSLKASDTAMYYCARYEYGGFD<br>IWGQGTLVTVSSASTKGPSVFPLAPSSKSTSGGTAA |
| | LGCLVKDYFPEPVTVSWNSGALTSGVHTFPAVLQSS<br>GLYSLSSWTVPSSSLGTQTYICNVNHKPSNTKVDKR<br>VEPKSCDKTHTCPPCPAPEAAGGPSVFLFPPKPKDT<br>LMISRTPEVTCVVVDVSHEDPEVKFNWYVDGVEVHN<br>AKTKPREEQYNSTYRVVSVLTVLHQDWLNGKEYKCK<br>VSNKALPAPIEKTISKAKGQPREPQVYTLPPSREEM<br>TKNQVSLTCLVKGFYPSDIAVEWESNGQPENNYKTT<br>PPVLDSDGSFFLYSKLTVDKSRWQQGNVFSCSVMHE<br>ALHNHYTQKSLSLSPGK |
| Light chain | SEQ ID NO: 26 |
| PN encoding<br>SEQ ID NO: 108 | 110:GAGGTGCAATTGGTVCAGAGCGGCGCGGAAGT<br>GAAAAAACCGGGCGAAAGCCTGAAAATTAGCTGCAA<br>AGGTTCCGGATATTCCTTTACTAATTATATTTCTTG<br>GGTGCGCCAGATGCCTGGGAAGGGTCTCGAGTGGAT<br>GGGCATTATTGATCCTCAGGATTCTTATACTGAGTA<br>TTCTCCTTCTTTTCAGGGTCAGGTCACCATTAGCGC<br>GGATAAAAGCATTAGCACCGCGTATCTTCAATGGAG<br>CAGCCTGAAAGCGAGCGATACGGCCATGTATTATTG<br>CGCGCGTTATGAGTATGGTGGTTTTGATATTTGGGG<br>CCAAGGCACCCTGGTGACGGTTAGCTCA |
| PN encoding<br>SEQ ID NO: 24 | SEQ ID NO: 28 |
| PN encoding<br>SEQ ID NO 109 | 111:GAGGTGCAATTGGTTCAGAGCGGCGCGGAAGT<br>GAAAAAACCGGGCGAAAGCCTGAAAATTAGCTGCAA<br>AGGTTCCGGATATTCCTTTACTAATTATATTTCTTG<br>GGTGCGCCAGATGCCTGGGAAGGGTCTCGAGTGGAT<br>GGGCATTATTGATCCTCAGGATTCTTATACTGAGTA<br>TTCTCCTTCTTTTCAGGGTCAGGTCACCATTAGCGC<br>GGATAAAAGCATTAGCACCGCGTATCTTCAATGGAG<br>CAGCCTGAAAGCGAGCGATACGGCCATGTATTATTG<br>CGCGCGTTATGAGTATGGTGGTTTTGATATTTGGGG<br>CCAAGGCACCCTGGTGACGGTTAGCTCAGCTCCAC<br>CAAGGGTCCATCGGTCTTCCCCCTGGCACCCTCCTC<br>CAAGAGCACCTCTGGGGGCACAGCGGCCCTGGGCTG<br>CCTGGTCAAGGACTACTTCCCCGAACCGGTGACGGT<br>GTCGTGGAACTCAGGCGCCCTGACCAGCGGCGTGCA<br>CACCTTCCCGGCTGTCCTACAGTCCTCAGGACTCTA<br>CTCCCTCAGCAGCGTGGTGACCGTGCCCTCCAGCAG<br>CTTGGGCACCCAGACCTACATCTGCAACGTGAATCA<br>CAAGCCCAGCAACACCAAGGTGGACAAGAGAGTTGA<br>GCCCAAATCTTGTGACAAAACTCACACATGCCCACC<br>GTGCCCAGCACCTGAAGCAGCGGGGGGACCGTCAGT<br>CTTCCTCTTCCCCCCAAAACCCAAGGACACCCTCAT<br>GATCTCCCGGACCCCTGAGGTCACATGCGTGGTGGT<br>GGACGTGAGCCACGAAGACCCTGAGGTCAAGTTCAA<br>CTGGTACGTGGACGGCGTGGAGGTGCATAATGCCAA<br>GACAAAGCCGCGGGAGGAGCAGTACAACAGCACGTA<br>CCGGGTGGTCAGCGTCCTCACCGTCCTGCACCAGGA<br>CTGGCTGAATGGCAAGGAGTACAAGTGCAAGGTCTC<br>CAACAAAGCCCTCCCAGCCCCCATCGAGAAAACCAT<br>CTCCAAAGCCAAAGGGCAGCCCCGAGAACCACAGGT<br>GTACACCCTGCCCCCATCCCGGGAGGAGATGACCAA<br>GAACCAGGTCAGCCTGACCTGCCTGGTCAAAGGCTT<br>CTATCCCAGCGACATCGCCGTGGAGTGGGAGAGCAA<br>TGGGCAGCCGGAGAACAACTACAAGACCACGCCTCC<br>CGTGCTGGACTCCGACGGCTCCTTCTTCCTCTACAG<br>CAAGCTCACCGTGGACAAGAGCAGGTGGCAGCAGGG<br>GAACGTCTTCTCATGCTCCGTGATGCATGAGGCTCT<br>GCACAACCACTACACGCAGAAGAGCCTCTCCCTGTC<br>TCCGGGTAAA |
| PN encoding<br>SEQ ID NO: 26 | SEQ ID NO: 30 |
| Optimized PN<br>encoding<br>SEQ ID NO: 109 | 112:GAGGTGCAGCTGGTGCAGAGCGGAGCCGAGGT<br>GAAAAAGCCCGGTGAGAGCCTGAAGATCAGCTGCAA<br>GGGCAGCGGCTACAGCTTCACCAACTACATCAGCTG<br>GGTGCGGCAGATGCCCGGCAAGGGCCTGGAGTGGAT<br>GGGCATCATCGACCCCAGGACAGCTACACCGAGTA<br>CAGCCCCAGCTTCCAGGGCCAGGTGACCATCAGCGC |

TABLE 1-continued

Examples of C5 Antibodies of the Present Invention and C5 Proteins

| | Sequence Identifier (SEQ ID NO:) or comments/details |
|---|---|
| | CGACAAGAGCATCAGCACCGCCTACCTGCAGTGGAG |
| | CAGCCTGAAGGCCAGCGACACCGCCATGTACTACTG |
| | CGCCAGATACGAGTACGGCGGCTTCGACATCTGGGG |
| | CCAGGGCACCCTGGTGACCGTCAGCTCAGCTAGCAC |
| | CAAGGGCCCCAGCGTGTTCCCCCTGGCCCCCAGCAG |
| | CAAGAGCACCTCCGGCGGCACAGCCGCCCTGGGCTG |
| | CCTGGTGAAGGACTACTTCCCCGAGCCCGTGACCGT |
| | GTCCTGGAACAGCGGAGCCCTGACCAGCGGCGTGCA |
| | CACCTTCCCCGCCGTGCTGCAGAGCAGCGGCCTGTA |
| | CAGCCTGTCCAGCGTGGTGACAGTGCCCAGCAGCAG |
| | CCTGGGCACCCAGACCTACATCTGCAACGTGAACCA |
| | CAAGCCCAGCAACACCAAGGTGGACAAGAGAGTGGA |
| | GCCCAAGAGCTGCGACAAGACCCACACCTGCCCCCC |
| | CTGCCCAGCCCCCGAAGCTGCAGGCGGCCCTTCCGT |
| | GTTCCTGTTCCCCCCCAAGCCCAAGGACACCCTGAT |
| | GATCAGCAGGACCCCCGAGGTGACCTGCGTGGTGGT |
| | GGACGTGAGCCACGAGGACCCAGAGGTGAAGTTCAA |
| | CTGGTACGTGGACGGCGTGGAGGTGCACAACGCCAA |
| | GACCAAGCCCAGAGAGGAGCAGTACAACAGCACCTA |
| | CAGGGTGGTGTCCGTGCTGACCGTGCTGCACCAGGA |
| | CTGGCTGAACGGCAAAGAATACAAGTGCAAGGTCTC |
| | CAACAAGGCCCTGCCTGCCCCCATCGAAAAGACCAT |
| | CAGCAAGGCCAAGGGCCAGCCACGGGAGCCCCAGGT |
| | GTACACCCTGCCCCCTTCTCGGGAGGAGATGACCAA |
| | GAACCAGGTGTCCCTGACCTGTCTGGTGAAGGGCTT |
| | CTACCCCAGCGACATCGCCGTGGAGTGGGAGAGCAA |
| | CGGCCAGCCCGAGAACAACTACAAGACCACCCCCCC |
| | AGTGCTGGACAGCGACGGCAGCTTCTTCCTGTACAG |
| | CAAGCTGACCGTGGACAAGAGCAGGTGGCAGCAGGG |
| | CAACGTGTTCAGCTGCAGCGTGATGCACGAGGCCCT |
| | GCACAACCACTACACCCAGAAGAGCCTGAGCCTGTC |
| | ACCCGGCAAG |
| Optimized PN encoding SEQ ID NO: 26 | SEQ ID NO: 32 |
| Antibody 8130 | |
| CDRH1 | SEQ ID NO: 17 |
| CDRH2 | SEQ ID NO: 107 |
| CDRH3 | SEQ ID NO: 19 |
| CDRL1 | SEQ ID NO: 20 |
| CDRL2 | SEQ ID NO: 21 |
| CDRL3 | SEQ ID NO: 101 |
| VH | SEQ ID NO: 108 |
| VL | SEQ ID NO: 102 |
| Heavy chain | SEQ ID NO: 109 |
| Light chain | SEQ ID NO: 103 |
| PN encoding SEQ ID NO: 108 | SEQ ID NO: 110 |
| PN encoding SEQ ID NO: 102 | SEQ ID NO: 104 |
| PN encoding SEQ ID NO: 109 | SEQ ID NO: 111 |
| PN encoding SEQ ID NO: 103 | SEQ ID NO: 105 |
| Optimized PN encoding SEQ ID NO: 109 | SEQ ID NO: 112 |
| Optimized PN encoding SEQ ID NO: 103 | SEQ ID NO: 106 |
| Antibody 8131 | |
| CDRH1 | SEQ ID NO: 17 |
| CDRH2 | 113: IIDPEDSHTEYSPSFQG |
| CDRH3 | SEQ ID NO: 19 |
| CDRL1 | SEQ ID NO: 20 |
| CDRL2 | SEQ ID NO: 21 |
| CDRL3 | SEQ ID NO: 22 |
| VH | 114: EVQLVQSGAEVKKPGESLKISCKGSGYSFTNY ISWVRQMPGKGLEWMGIIDPEDSHTEYSPSFQGQVT ISADKSISTAYLQWSSLKASDTAMYYCARYEYGGFD IWGQGTLVTVSS |
| VL | SEQ ID NO: 24 |
| Heavy chain | 115: EVQLVQSGAEVKKPGESLKISCKGSGYSFTNY ISWVRQMPGKGLEWMGIIDPEDSHTEYSPSFQGQVT ISADKSISTAYLQWSSLKASDTAMYYCARYEYGGFD IWGQGTLVTVSSASTKGPSVFPLAPSSKSTSGGTAA LGCLVKDYFPEPVTVSWNSGALTSGVHTFPAVLQSS GLYSLSSWTVPSSSLGTQTYICNVNHKPSNTKVDKR VEPKSCDKTHTCPPCPAPEAAGGPSVFLFPPKPKDT LMISRTPEVTCVVVDVSHEDPEVKFNWYVDGVEVHNA KTKPREEQYNSTYRVVSVLTVLHQDWLNGKEYKCKV SNKALPAPIEKTISKAKGQPREPQVYTLPPSREEMT KNQVSLTCLVKGFYPSDIAVEWESNGQPENNYKTTP PVLDSDGSFFLYSKLTVDKSRWQQGNVFSCSVMHEA LHNHYTQKSLSLSPGK |
| Light chain | SEQ ID NO: 26 |
| PN encoding SEQ ID NO: 114 | 116: GAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTGAGGATTCTCATACTGAGTA TTCTCCTTCTTTTCAGGGTCAGGTGACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACCGGTTAGCTCA |
| PN encoding SEQ ID NO: 24 | SEQ ID NO: 28 |
| PN encoding SEQ ID NO: 115 | 117: GAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTGAGGATTCTCATACTGAGTA TTCTCCTTCTTTTCAGGGTCAGGTGACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACCGGTTAGCTCAGCCTCCAC CAAGGGTCATCGGTCTTCCCCCTGGCACCCTCCTC CAAGAGCACCTCTGGGGGCACAGCGGCCCTGGGCTG CCTGGTCAAGGACTACTTCCCCGAACCGGTGACGGT GTCGTGGAACTCAGGCGCCCTGACCAGCGGCGTGCA CACCTTCCCGGCTGTCCTACAGTCCTCAGGACTCTA CTCCCTCAGCAGCGTGGTGACCGTGCCCTCCAGCAG CTTGGGCACCCAGACCTACATCTGCAACGTGAATCA CAAGCCCAGCAACACCAAGGTGGACAAGAGAGTTGA |

TABLE 1-continued

Examples of C5 Antibodies of the Present Invention and C5 Proteins

| Sequence Identifier (SEQ ID NO:) | or comments/details |
|---|---|
| | GCCCAAATCTTGTGACAAAACTCACACATGCCCACC GTGCCCAGCACCTGAAGCAGCGGGGGGACCGTCAGT CTTCCTCTTCCCCCCAAAACCCAAGGACACCCTCAT GATCTCCCGGACCCCTGAGGTCACATGCGTGGTGGT GGACGTGAGCCACGAAGACCCTGAGGTCAAGTTCAA CTGGTACGTGGACGGCGTGGAGGTGCATAATGCCAA GACAAAGCCGCGGGAGGAGCAGTACAACAGCACGTA CCGGGTGGTCAGCGTCCTCACCGTCCTGCACCAGGA CTGGCTGAATGGCAAGGAGTACAAGTGCAAGGTCTC CAACAAAGCCCTCCCAGCCCCCATCGAGAAAACCAT CTCCAAAGCCAAAGGGCAGCCCCGAGAACCACAGGT GTACACCCTGCCCCCATCCCGGGAGGAGATGACCAA GAACCAGGTCAGCCTGACCTGCCTGGTCAAAGGCTT CTATCCCAGCGACATCGCCGTGGAGTGGGAGAGCAA TGGGCAGCCGGAGAACAACTACAAGACCACGCCTCC CGTGCTGGACTCCGACGGCTCCTTCTTCCTCTACAG CAAGCTCACCGTGGACAAGAGCAGGTGGCAGCAGGG GAACGTCTTCTCATGCTCCGTGATGCATGAGGCTCT GCACAACCACTACACGCAGAAGAGCCTCTCCCTGTC TCCGGGTAAA |
| PN encoding SEQ ID NO: 26 | SEQ ID NO: 30 |
| Optimized PN encoding SEQ ID NO: 115 | 118:GAGGTGCAGCTGGTGCAGAGCGGAGCCGAGGT GAAAAAGCCCGGTGAGAGCCTGAAGATCAGCTGCAA GGGCGGCTACAGCTTCACCAACTACATCAGCTGG GGTGCGGCAGATGCCCGGCAAGGGCCTGGAGTGGAT GGGCATCATCGACCCCGAGGACAGCCATACCGAGTA CAGCCCCAGCTTCCAGGGCCAGGTGACCATCAGCGC CGACAAGAGCATCAGCACCGCCTACCTGCAGTGGAG CAGCCTGAAGGCCAGCGACACCGCCATGTACTACTG CGCCAGATACGAGTACGGCGGCTTCGACATCTGGGG CCAGGGCACCCTGGTGACCGTCAGCTCAGCTAGCAC CAAGGGCCCCAGCGTGTTCCCCCTGGCCCCCAGCAG CAAGAGCACCTCCGGCGGCACAGCCGCCCTGGGCTG CCTGGTGAAGGACTACTTCCCCGAGCCCGTGACCGT GTCCTGGAACAGCGGAGCCCTGACCAGCGGCGTGCA CACCTTCCCCGCCGTCCTGCAGAGCAGCGGCCTGTA CAGCCTGTCCAGCGTGGTGACAGTGCCCAGCAGCAG CCTGGGCACCCAGACCTACATCTGCAACGTGAACCA CAAGCCCAGCAACACCAAGGTGGACAAGAGAGTGGA GCCCAAGAGCTGCGACAAGACCCACACCTGCCCCCC CTGCCCAGCCCCCGAAGCTGCAGGCGGCCCTTCCGT GTTCCTGTTCCCCCCCAAGCCCAAGGACACCCTGAT GATCAGCAGGACCCCCGAGGTGACCTGCGTGGTGGT GGACGTGAGCCACGAGGACCCAGAGGTGAAGTTCAA CTGGTACGTGGACGGCGTGGAGGTGCACAACGCCAA GACCAAGCCCAGAGAGGAGCAGTACAACAGCACCTA CAGGGTGGTGTCCGTGCTGACCGTGCTGCACCAGGA CTGGCTGAACGGCAAAGAATACAAGTGCAAGGTCTC CAACAAGGCCCTGCCTGCCCCCATCGAAAAGACCAT CAGCAAGGCCAAGGGCCAGCCACGGGAGCCCCAGGT GTACACCCTGCCCCCTTCTCGGGAGGAGATGACCAA GAACCAGGTGTCCCTGACCTGTCTGGTGAAGGGCTT CTACCCCAGCGACATCGCCGTGGAGTGGGAGAGCAA CGGCCAGCCCGAGAACAACTACAAGACCACCCCCCC AGTGCTGGACAGCGACGGCAGCTTCTTCCTGTACAG CAAGCTGACCGTGGACAAGAGCAGGTGGCAGCAGGG CAACGTGTTCAGCTGCAGCGTGATGCACGAGGCCCT GCACAACCACTACACCCAGAAGAGCCTGAGCCTGTC ACCCGGCAAG |
| Optimized PN encoding SEQ ID NO: 26 | SEQ ID NO: 32 |
| Antibody 8132 | |
| CDRH1 | SEQ ID NO: 17 |
| CDRH2 | SEQ ID NO: 113 |
| CDRH3 | SEQ ID NO: 19 |

TABLE 1-continued

Examples of C5 Antibodies of the Present Invention and C5 Proteins

| Sequence Identifier (SEQ ID NO:) | or comments/details |
|---|---|
| CDRL1 | SEQ ID NO: 20 |
| CDRL2 | SEQ ID NO: 21 |
| CDRL3 | SEQ ID NO: 101 |
| VH | SEQ ID NO: 114 |
| VL | SEQ ID NO: 102 |
| Heavy chain | SEQ ID NO: 115 |
| Light chain | SEQ ID NO: 103 |
| PN encoding SEQ ID NO: 114 | SEQ ID NO: 116 |
| PN encoding SEQ ID NO: 102 | SEQ ID NO: 104 |
| PN encoding SEQ ID NO: 115 | SEQ ID NO: 117 |
| PN encoding SEQ ID NO: 103 | SEQ ID NO: 105 |
| Optimized PN encoding SEQ ID NO: 115 | SEQ ID NO: 11S |
| Optimized PN encoding SEQ ID NO: 103 | SEQ ID NO: 106 |
| Antibody 8091 | |
| CDRH1 | SEQ ID NO: 1 |
| CDRH2 | 119:NIGPFFGIANYAQKFQG |
| CDRH3 | SEQ ID NO: 3 |
| CDRL1 | SEQ ID NO: 4 |
| CDRL2 | SEQ ID NO: 5 |
| CDRL3 | 120:QTYDDGSTAEV |
| VH | 121:QVQLVQSGAEVKKPGSSVKVSCKASGGTFSSY AISWVRQAPGQGLEWMGNIGPFFGIANYAQKFQGRV TITADESTSTAYMELSSLRSEDTAVYYCARDTPYFD YWGQGTLVTVSS |
| VL | 122:DIELTQPPSVSVAPGQTARISCSGDSIPNYYV YWYQQKPGQAPVLVIYDDSNRPSGIPERFSGSNSGN TATLTISGTQAEDEADYYCQTYDDGSTAEVFGGGTK LTVL |
| Heavy chain | 123:QVQLVQSGAEVKKPGSSVKVSCKASGGTFSSY AISWVRQAPGQGLEWMGNIGPFFGIANYAQKFQGRV TITADESTSTAYMELSSLRSEDTAVYYCARDTPYFD YWGQGTLVTVSSASTKGPSVFPLAPCSRSTSESTAA LGCLVKDYFPEPVTVSWNSGALTSGVHTFPAVLQSS GLYSLSSVVTVPSSNFGTQTYTCNVDHKPSNTKVDK TVERKCCVECPPCPAPPVAGPSVFLFPPKPKDTLMI SRTPEVTCVVVDVSHEDPEVQFNWYVDGVEVHNAKT KPREEQFNSTFRWSVLTVVHQDWLNGKEYKCKVSNK GLPAPIEKTISKTKGQPREPQVYTLPPSREEMTKNQ VSLTCLVKGFYPSDIAVEWESNGQPENNYKTTPPML DSDGSFFLYSKLTVDKSRWQQGNVFSCSVMHEALHN HYTQKSLSLSPGK |

TABLE 1-continued

Examples of C5 Antibodies of the Present Invention and C5 Proteins

| | Sequence Identifier (SEQ ID NO:) or comments/details |
|---|---|
| Light chain | 124: DIELTQPPSVSVAPGQTARISCSGDSIPNYYV YWYQQKPGQAPVLVIYDDSNRPSGIPERFSGSNSGN TATLTISGTQAEDEADYYCQTYDDGSTAEVFGGGTK LTVLGQPKAAPSVTLFPPSSEELQANKATLVCLISD FYPGAVTVAWKADSSPVKAGVETTTPSKQSNNKYAA SSYLSLTPEQWKSHRSYSCQVTHEGSTVEKTVAPTE CS |
| PN encoding SEQ ID NO: 121 | 125: CAGGTGCAATTGGTTCAGTCTGGCGCGGAAGT GAAAAAACCGGGCAGCAGCGTGAAAGTGAGCTGCAA AGCCTCCGGAGGCACTTTTTCTTCTTATGCCATTTC TTGGGTGCGCCAAGCCCCTGGGCAGGGTCTCGAGTG GATGGGCAATATCGGTCCGTTTTTTGGCATTGCGAA TTACGCGCAGAAGTTTCAGGGCCGGGTGACCATTAC CGCGGATGAAAGCACCAGCACCGCGTATATGAACT GAGCAGCCTGCGTAGCGAAGATACGGCCGTGTATTA TTGCGCGCGTGATACTCCTTATTTTGATTATTGGGG CCAAGGCACCCTGGTGACGGTTAGCTCA |
| PN encoding SEQ ID NO: 122 | 126: GATATCGAACTGACCCAGCCGCCTTCAGTGAG CGTTGCACCAGGTCAGACCGCGCGTATCTCGTGTAG CGGCGATTCTATTCCTAATTATTATGTTTATTGGTA CCAGCAGAAACCCGGGCAGGCGCCAGTTCTTGTGAT TTATGATGATTCTAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGACTTATGATGATGGTTCTAC TGCTGAGGTGTTTGGCGGCGGCACGAAGTTAACCGT TCTT |
| PN encoding SEQ ID NO: 123 | 127: CAGGTGCAATTGGTTCAGTCTGGCGCGGAAGT GAAAAAACCGGGCAGCAGCGTGAAAGTGAGCTGCAA AGCCTCCGGAGGCACTTTTTCTTCTTATGCCATTTC TTGGGTGCGCCAAGCCCCTGGGCAGGGTCTCGAGTG GATGGGCAATATCGGTCCGTTTTTTGGCATTGCGAA TTACGCGCAGAAGTTTCAGGGCCGGGTGACCATTAC CGCGGATGAAAGCACCAGCACCGCGTATATGAACT GAGCAGCCTGCGTAGCGAAGATACGGCCGTGTATTA TTGCGCGCGTGATACTCCTTATTTTGATTATTGGGG CCAAGGCACCCTGGTGACGGTTAGCTCAGCTTCCAC CAAGGGCCCCAGCGTGTTCCCCCTGGCCCCCTGCAG CAGAAGCACCAGCGAGAGCACAGCCGCCCTGGGCTG CCTGGTGAAGGACTACTTCCCCGAGCCCGTGACCGT GAGCTGGAACAGCGGAGCCCTGACCAGCGGCGTGCA CACCTTCCCCGCCGTGCTGCAGAGCAGCGGCCTGTA CAGCCTGAGCAGCGTGGTGACCGTGCCCAGCAGCAA CTTCGGCACCCAGACCTACACCTGCAACGTGGACCA CAAGCCCAGCAACACCAAGGTGGACAAGACCGTGGA GCGGAAGTGCTGCGTGGAGTGCCCCCCCTGCCCTGC CCCTCCTGTGGCCGGACCCTCCGTGTTCCTGTTCCC CCCCAAGCCCAAGGACACCCTGATGATCAGCCGGAC CCCCGAGGTGACCTGCGTGGTGGTGGACGTGAGCCA CGAGGACCCCGAGGTGCAGTTCAACTGGTACGTGGA CGGCGTGGAGGTGCACAACGCCAAGACCAAGCCCCG GGAGGAACAGTTCAACAGCACCTTCCGGGTGGTGTC CGTGCTGACCGTGGTGCACCAGGACTGGCTGAACGG CAAAGAATACAAGTGCAAGGTGTCCAACAAGGGCCT GCCTGCCCCATCGAGAAACCATCAGCAAGACAAA GGGCCAGCCCAGGGAACCCCAGGTGTACACCCTGCC CCCCAGCCGGGAGGAAATGACCAAGAACCAGGTGTC CCTGACCTGTCTGGTGAAGGGCTTCTACCCCAGCGA CATCGCCGTGGAGTGGGAGAGCAACGGCCAGCCCGA GAACAACTACAAGACCACCCCCCCCATGCTGGACAG CGACGGCAGCTTCTTCCTGTACAGCAAGCTGACAGT GGACAAGAGCCGGTGGCAGCAGGGCAACGTGTTCAG CTGCAGCGTGATGCACGAGGCCCTGCACAACCACTA CACCCAGAAGAGCCTGAGCCTGTCCCCCGGCAAA |
| PN encoding SEQ ID NO: 124 | 128: GATATCGAACTGACCCAGCCGCCTTCAGTGAG CGTTGCACCAGGTCAGACCGCGCGTATCTCGTGTAG CGGCGATTCTATTCCTAATTATTATGTTTATTGGTA CCAGCAGAAACCCGGGCAGGCGCCAGTTCTTGTGAT TTATGATGATTCTAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGACTTATGATGATGGTTCTAC TGCTGAGGTGTTTGGCGGCGGCACGAAGTTAACCGT TCTTGGTCAGCCCAAGGCTGCCCCCTCGGTCACTCT GTTCCCGCCCTCCTCTGAGGAGCTTCAAGCCAACAA GGCCACACTGGTGTGTCTCATAAGTGACTTCTACCC GGGAGCCGTGACAGTGGCCTGGAAGGCAGATAGCAG CCCCGTCAAGGCGGGAGTGGAGACCACCACACCCTC CAAACAAAGCAACAACAAGTACGCGGCCAGCAGCTA TCTGAGCCTGACGCCTGAGCAGTGGAAGTCCCACAG AAGCTACAGCTGCCAGGTCACGCATGAAGGGAGCAC CGTGGAGAAGACAGTGGCCCCTACAGAATGTTCA |
| Optimized PN encoding SEQ ID NO: 123 | 129: CAGGTGCAGCTGGTGCAGTCCGGCGCCGAGGT GAAGAAGCCCGGCTCCTCCGTGAAGGTGTCCTGCAA GGCCTCCGGCGGCACCTTCTCCTCCTACGCCATCTC CTGGGTGCGGCAGGCCCCCGGCCAGGGCCTGGAGTG GATGGGCAACATCGGCCCCTTCTTCGGCATCGCCAA CTACGCCCAGAAGTTCCAGGGCCGGGTGACCATCAC CGCCGACGAGTCCACCTCCACCGCCTACATGGAGCT GTCCTCCCTGCGGTCCGAGGACACCGCCGTGTACTA CTGCGCCCGGGACACCCCCTACTTCGACTACTGGGG CCAGGGCACCCTGGTGACCGTGTCCTCCGCCTCCAC CAAGGGCCCCTCCGTGTTCCCCCTGGCCCCCTGCTC CCGGTCCACCTCCGAGTCCACCGCCGCCCTGGGCTG CCTGGTGAAGGACTACTTCCCCGAGCCCGTGACCGT GTCCTGGAACTCCGGCGCCCTGACCTCCGGCGTGCA CACCTTCCCCGCCGTGCTGCAGTCCTCCGGCCTGTA CTCCCTGTCCTCCGTGGTGACCGTGCCCTCCTCCAA CTTCGGCACCCAGACCTACACCTGCAACGTGGACCA CAAGCCCTCCAACACCAAGGTGGACAAGACCGTGGA GCGGAAGTGCTGCGTGGAGTGCCCCCCCTGCCCCGC CCCCCCCGTGGCCGGCCCCTCCGTGTTCCTGTTCCC CCCCAAGCCCAAGGACACCCTGATGATCTCCCGGAC CCCCGAGGTGACCTGCGTGGTGGTGGACGTGTCCCA CGAGGACCCCGAGGTGCAGTTCAACTGGTACGTGGA CGGCGTGGAGGTGCACAACGCCAAGACCAAGCCCCG GGAGGAGCAGTTCAACTCCACCTTCCGGGTGGTGTC CGTGCTGACCGTGGTGCACCAGGACTGGCTGAACGG CAAGGAGTACAAGTGCAAGGTGTCCAACAAGGGCCT GCCCGCCCCCATCGAGAAGACCATCTCCAAGACCAA GGGCCAGCCCCGGGAGCCCCAGGTGTACACCCTGCC CCCCTCCCGGGAGGAGATGACCAAGAACCAGGTGTC CCTGACCTGCCTGGTGAAGGGCTTCTACCCCTCCGA CATCGCCGTGGAGTGGGAGTCCAACGGCCAGCCCGA GAACAACTACAAGACCACCCCCCCCATGCTGGACTC CGACGGCTCCTTCTTCCTGTACTCCAAGCTGACCGT GGACAAGTCCCGGTGGCAGCAGGGCAACGTGTTCTC CTGCTCCGTGATGCACGAGGCCCTGCACAACCACTA CACCCAGAAGTCCCTGTCCCTGTCCCCCGGCAAG |
| Optimized PN encoding SEQ ID NO: 124 | 130: GACATCGAGCTGACCCAGCCCCCCTCCGTGTC CGTGGCCCCCGGCCAGACCGCCCGGATCTCCTGCTC CGGCGACTCCATCCCCAACTACTACGTGTACTGGTA CCAGCAGAAGCCCGGCCAGGCCCCCGTGCTGGTGAT CTACGACGACTCCAACCGCCCTCCGGCATCCCCGA GCGGTTCTCCGGCTCCAACTCCGGCAACACCGCCAC CCTGACCATCTCCGGCACCCAGGCCGAGGACGAGGC CGACTACTACTGCCAGACCTACGACGACGGCTCCAC CGCCGAGGTGTTCGGCGGCGGCACCAAGCTGACCGT GCTGGGCCAGCCTAAGGCTGCCCCCAGCGTGACCCT GTTCCCCCCCAGCAGCGAGGAGCTGCAGGCCAACAA GGCCACCCTGGTGTGCCTGATCAGCGACTTCTACCC AGGCGCCGTGACCGTGGCCTGGAAGGCCGACAGCAG CCCCGTGAAGGCCGGCGTGGAGACCACCACCCCCAG CAAGCAGAGCAACAACAAGTACGCCGCCAGCAGCTA CCTGAGCCTGACCCCCGAGCAGTGGAAGAGCCACAG GTCCTACAGCTGCCAGGTGACCCACGAGGGCAGCAC CGTGGAAAAGACCGTGGCCCCCAACCGAGTGCAGC |

TABLE 1-continued

Examples of C5 Antibodies of the Present Invention and C5 Proteins

| | Sequence Identifier (SEQ ID NO:) or comments/details |
|---|---|
| Antibody 6525 | |
| CDRH1 | 131: SYWIS |
| CDRH2 | 132: IIDPDDSKTNYSPSFQG |
| CDRH3 | 133: RSYYPMDY |
| CDRL1 | 134: TGTSSDVVGVYNFVS |
| CDRL2 | 135: YVDNRPS |
| CDRL3 | 136: QSFDGFGIDMV |
| VH | 137: QVQLVQSGAEVKKPGESLKISCKGSGYSFTSY WISWVRQMPGKGLEWMGIIDPDDSKTNYSPSFQGQV TISADKSISTAYLQWSSLKASDTAMYYCARRSYYPM DYWGQGTLVTVSS |
| VL | 138: DIALTQPASVSGSPGQSITISCTGTSSDWGVY NFVSWYQQHPGKAPKLMIYYVDNRPSGVSNRFSGSK SGNTASLTISGLQAEDEADYYCQSFDGFGIDMVFGG GTKLTVL |
| Heavy chain | 139: QVQLVQSGAEVKKPGESLKISCKGSGYSFTSY WISWVRQMPGKGLEWMGIIDPDDSKTNYSPSFQGQV TISADKSISTAYLQWSSLKASDTAMYYCARRSYYPM DYWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVD KKVEPKSX (X can be G, EF or CEF) |
| Light chain | 140: DIALTQPASVSGSPGQSITISCTGTSSDWGVY NFVSWYQQHPGKAPKLMIYYVDNRPSGVSNRFSGSK SGNTASLTISGLQAEDEADYYCQSFDGFGIDMVFGG GTKLTVLGQPKAAPSVTLFPPSSEELQANKATLVCL ISDFYPGAVTVAWKADSSPVKAGVETTTPSKQSNNK YAASSYLSLTPEQWKSHRSYSCQVTHEGSTVEKTVA PTEX (X can be CS or A) |
| PN encoding SEQ ID NO: 137 | 141: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTGGATTTC TTGGGTGCGCCAGATGCCTGGGAAGGGTCTCGAGTG GATGGGCATTATCGATCCGGATGATAGCAAGACCAA TTATTCTCCGAGCTTTCAGGGCCAGGTGACCATTAG CGCGGATAAAAGCATTAGCACCGCGTATCTTCAATG GAGCAGCCTGAAAGCGAGCGATACGGCCATGTATTA TTGCGCGCGTCGTTCTTATTATCCTATGGATTATTG GGGCCAAGGCACCCTGGTGACGGTTAGCTCA |
| PN encoding SEQ ID NO: 138 | 142: GATATCGCACTGACCCAGCCAGCTTCAGTGAG CGGCTCACCAGGTCAGAGCATTACCATCTCGTGTAC GGGTACTAGCAGCGATGTTGTTGGTGTTTATAATTT TGTGTCTTGGTACCAGCAGCATCCCGGGAAGGCGCC GAAACTTATGATTTATTATGTTGATAATCGTCCCTC AGGCGTGAGCAACCGTTTTAGCGGATCCAAAAGCGG CAACACCGCGAGCCTGACCATTAGCGGCCTGCAAGC GGAAGACGAAGCGGATTATTATTGCCAGTCTTTTGA TGGTTTTGGTATTGATATGGTGTTTGGCGGCGGCAC GAAGTTAACCGTTCTT |
| PN encoding SEQ ID NO: 139 | 143: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTGGATTTC TTGGGTGCGCCAGATGCCTGGGAAGGGTCTCGAGTG GATGGGCATTATCGATCCGGATGATAGCAAGACCAA TTATTCTCCGAGCTTTCAGGGCCAGGTGACCATTAG CGCGGATAAAAGCATTAGCACCGCGTATCTTCAATG GAGCAGCCTGAAAGCGAGCGATACGGCCATGTATTA TTGCGCGCGTCGTTCTTATTATCCTATGGATTATTG GGGCCAAGGCACCCTGGTGACGGTTAGCTCAGCGTC GACCAAAGGTCCAAGCGTGTTTCCGCTGGCTCCAGAG CAGCAAAAGCACCAGCGGCGGCACGGCTGCCCTGGG CTGCCTGGTTAPAGATTATTTCCCGGAACCAGTCAC CGTGAGCTGGAACAGCGGGGCGCTGACCAGCGGCGT GCATACCTTTCCGGCGGTGCTGCAAAGCAGCGGCCT GTATAGCCTGAGCAGCGTTGTGACCGTGCCGAGCAG CAGCTTAGGCACTCAGACCTATATTTGCAACGTGAA CCATAAACCGAGCAACACCAAAGTGGATAAAAAAGT GGAACCGAAAAGC X (X can be TGC, GAATTC orTGCGAATTC) |
| PN encoding SEQ ID NO: 140 | 144: GATATCGCACTGACCCAGCCAGCTTCAGTGAG CGGCTCACCAGGTCAGAGCATTACCATCTCGTGTAC GGGTACTAGCAGCGATGTTGTTGGTGTTTATAATTT TGTGTCTTGGTACCAGCAGCATCCCGGGAAGGCGCC GAAACTTATGATTTATTATGTTGATAATCGTCCCTC AGGCGTGAGCAACCGTTTTAGCGGATCCAAAAGCGG CAACACCGCGAGCCTGACCATTAGCGGCCTGCAAGC GGAAGACGAAGCGGATTATTATTGCCAGTCTTTTGA TGGTTTTGGTATTGATATGGTGTTTGGCGGCGGCAC GAAGTTAACCGTTCTTGGCCAGCCGAAAGCCGCACC GAGTGTGACGCTGTTTCCGCCGAGCAGCGAAGAATT GCAGGCGAACAAAGCGACCCTGGTGTGCCTGATTAG CGACTTTTATCCGGGAGCCGTGACAGTGGCCTGGAA GGCAGATAGCAGCCCCGTCAAGGCGGGAGTGGAGAC CACCACACCCTCCAAACAAAGCAACAACAAGTACGC GGCCAGCAGCTATCTGAGCCTGACGCCTGAGCAGTG GAAGTCCCACAGAAGCTACAGCTGCCAGGTCACGCA TGAGGGGAGCACCGTGAAAAAACCGTTGCGCCGAC TGAGX (X can be TGCAGC orGCC) |
| Antibody 6755 | |
| CDRH1 | 145: SYWIA |
| CDRH2 | 146: IIYPGDSDTNYSPSFQG |
| CDRH3 | 147: SKYGSFDY |
| CDRL1 | 148: TGTSSDVGGYNYVS |
| CDRL2 | 149: NVNSRPS |
| CDRL3 | 150: QSYDDGQDNEV |
| VH | 151: QVQLVQSGAEVKKPGESLKISCKGSGYSFTSY WIAWVRQMPGKGLEWMGIIYPGDSDTNYSPSFQGQV TISADKSISTAYLQWSSLKASDTAMYYCARSKYGSF DYWGQGTLVTVSS |
| VL | 152: DIALTQPASVSGSPGQSITISCTGTSSDVGGY NYVSWYQQHPGKAPKLMIYNVNSRPSGVSNRFSGSK SGNTASLTISGLQAEDEADYYCQSYDDGQDNEVFGG GTKLTVL |
| Heavy chain | 153: QVQLVQSGAEVKKPGESLKISCKGSGYSFTSY WIAWVRQMPGKGLEWMGIIYPGDSDTNYSPSFQGQV TISADKSISTAYLQWSSLKASDTAMYYCARSKYGSF DYWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVD KKVEPKSX (X can be G, EF or CEF) |
| Light chain | 154: DIALTQPASVSGSPGQSITISCTGTSSDVGGY NYVSWYQQHPGKAPKLMIYNVNSRPSGVSNRFSGSK SGNTASLTISGLQAEDEADYYCQSYDDGQDNEVFGG GTKLTVLGQPKAAPSVTLFPPSSEELQANKATLVCL ISDFYPGAVTVAWKADSSPVKAGVETTTPSKQSNNK YAASSYLSLTPEQWKSHRSYSCQVTHEGSTVEKTVA PTEX (X can be CS or A) |
| PN encoding SEQ ID NO: 151 | 155: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTGGATTGC TTGGGTGCGCCAGATGCCTGGGAAGGGTCTCGAGTG |

TABLE 1-continued

Examples of C5 Antibodies of the
Present Invention and C5 Proteins

| | Sequence Identifier (SEQ ID NO:) or comments/details |
|---|---|
| | GATGGGCATTATCTATCCGGGTGATAGCGATACCAA<br>TTATTCTCCGAGCTTTCAGGGCCAGGTGACCATTAG<br>CGCGGATAAAAGCATTAGCACCGCGTATCTTCAATG<br>GAGCAGCCTGAAAGCGAGCGATACGGCCATGTATTA<br>TTGCGCGCGTTCTAAGTATGGTTCTTTTGATTATTG<br>GGGCCAAGGCACCCTGGTGACGGTTAGCTCA |
| PN encoding SEQ ID NO: 152 | 156: GATATCGCACTGACCCAGCCAGCTTCAGTGAG<br>CGGCTCACCAGGTCAGAGCA1TACCATCTCGTGTAC<br>GGGTACTAGCAGCGATGTTGGTGGTTATAATTATGT<br>GTCTTGGTACCAGCAGCATCCCGGGAAGGCGCCGAA<br>ACTTATGATTTATAATGTTAATTCTCGTCCCTCAGG<br>CGTGAGCAACCGTTTTAGCGGATCAAAAGCGGCAA<br>CACCGCGAGCCTGACCATTAGCGGCCTGCAAGCGGA<br>AGACGAAGCGGATTATTATTGCCAGTCTTATGATGA<br>TGGTCAGGATAATGAGGTGTTTGGCGGCGGCACGAA<br>GTTAACCGTTCTT |
| PN encoding SEQ ID NO: 153 | 157: CAGGTGCAATTGGTTCAGAGCGGCGCGGAAGT<br>GAAAAAACCGGGCGAAAGCCTGAAAATTAGCTGCAA<br>AGGTTCCGGATATTCCTTTACTTCTTATTGGATTGC<br>TTGGGTGCGCCAGATGCCTGGGAAGGGTCTCGAGTG<br>GATGGGCATTATCTATCCGGGTGATAGCGATACCAA<br>TTATTCTCCGAGCTTTCAGGGCCAGGTGACCATTAG<br>CGCGGATAAAAGCATTAGCACCGCGTATCTTCAATG<br>GAGCAGCCTGAAAGCGAGCGATACGGCCATGTATTA<br>TTGCGCGCGTTCTAAGTATGGTTCTTTTGATTATTG<br>GGGCCAAGGCACCCTGGTGACGGTTAGCTCAGCGTC<br>GACCAAAGGTCCAAGCGTGTTTCCGCTGGCTCCGAG<br>CAGCAAAGCACCAGCGGCGGCACGGCTGCCCTGGGC<br>TGCCTGGTTAAAGATTATTTCCCGGAACCAGTCACC<br>GTGAGCTGGAACAGCGGGCGCTGACCAGCGGCGTG<br>CATACCTTTCCGGCGGTGCTGCAAAGCAGCGGCCTG<br>TATAGCCTGAGCAGCGTTGTGACCGTGCCGAGCAGC<br>AGCTTAGGCACTCAGACCTATATTTGCAACGTGAAC<br>CATAAACCGAGCAACACCAAAGTGGATAAAAAAGTG<br>GAACCGAAAAGC X (X can be TGC, GAATTC or TGCGAATTC) |
| PN encoding SEQ ID NO: 154 | 158: GATATCGCACTGACCCAGCCAGCTTCAGTGAG<br>CGGCTCACCAGGTCAGAGCATTACCATCTCGTGTAC<br>GGGTACTAGCAGCGATGTTGGTGGTTATAATTATGT<br>GTCTTGGTACCAGCAGCATCCCGGGAAGGCGCCGAA<br>ACTTATGATTTATAATGTTAATTCTCGTCCCTCAGG<br>CGTGAGCAACCGTTTTAGCGGATCAAAAGCGGCAA<br>CACCGCGAGCCTGACCATTAGCGGCCTGCAAGCGGA<br>AGACGAAGCGGATTATTATTGCCAGTCTTATGATGA<br>TGGTCAGGATAATGAGGTGTTTGGCGGCGGCACGAA<br>GTTAACCGTTCTTGGCCAGCCGAAAGCCGCACCGAG<br>TGTGACGCTGTTTCCGCCGAGCAGCGAAGAATTGCA<br>GGCGAACAAAGCGACCCTGGTGTGCCTGATTAGCGA<br>CTTTTATCCGGGAGCCGTGACAGTGGCCTGGAAGGC<br>AGATAGCAGCCCCGTCAAGGCGGGAGTGGAGACCAC<br>CACACCCTCCAAACAAAGCAACAACAAGTACGCGGC<br>CAGCAGCTATCTGAGCCTGACGCCTGAGCAGTGGAA<br>GTCCCACAGAAGCTACAGCTGCCAGGTCACGCATGA<br>GGGGAGCACCGTGGAAAAAACCGTTGCGCCCGACTGA<br>GX (X can be TGCAGC or GCC) |

Antibody 6757

| CDRH1 | 159: SYAMH |
| CDRH2 | 160: AISSSGSSTYYADSVKG |
| CDRH3 | 161: ESWFLDL |
| CDRL1 | 162: RASQSISNWLA |
| CDRL2 | 163: LASSLQS |
| CDRL3 | 164: QQYYQFSDT |

TABLE 1-continued

Examples of C5 Antibodies of the
Present Invention and C5 Proteins

| | Sequence Identifier (SEQ ID NO:) or comments/details |
|---|---|
| VH | 165: QVQLVESGGGLVQPGGSLRLSCAASGFTFTSY<br>AMHWVRQAPGKGLEVWSAISSSGSSTYYADSVKGRF<br>TISRDNSKNTLYLQMNSLRAEDTAVYYCARESWFLD<br>LWGQGTLVTVSS |
| VL | 166: DIQMTQSPSSLSASVGDRVTITCRASQSISNW<br>LAWYQQKPGKAPKLLIYLASSLQSGVPSRFSGSGSG<br>TDFTLTISSLQPEOFAVYYCQQYYDFSDTFGQGTKV<br>EIK |
| Heavy chain | 167: QVQLVESGGGLVQPGGSLRLSCAASGFTFTSY<br>AMHWVRQAPGKGLEVWSAISSSGSSTYYADSVKGRF<br>TISRDNSKNTLYLQMNSLRAEDTAVYYCARESWFLD<br>LWGQGTLVTVSSASTKGPSVFPLAPSSKSTSGGTAA<br>LGCLVKDYFPEPVTVSWNSGALTSGVHTFPAVLQSS<br>GLYSLSSWTVPSSSLGTQTYICNVNHKPSNTKVDKK<br>VEPKSX (X can be C, EF or CEF) |
| Light chain | 168: DIQMTQSPSSLSASVGORVTITCRASQSISNW<br>LAWYQQKPGKAPKLLIYLASSLQSGVPSRFSGSGSG<br>TDFTLTISSLQPEDFAVYYCQQYYDFSDTFGQGTKV<br>EIKRTVAAPSVFIFPPSDEQLKSGTASVVCLLNNFY<br>PREAKVQWKVDNALQSGNSQESVTEQDSKDSTYSLS<br>STLTLSKADYEKHKVYACEVTHQGLSSPVTKSFNRG<br>EX (X can be C or A) |
| PN encoding SEQ ID NO: 165 | 169: CAGGTGCAATTGGTGGAAAGCGGCGGCGGCCT<br>GGTGCAACCGGGCGGCAGCCTGCGTCTGAGCTGCGC<br>GGCCTCCGGATTTACCTTTACTTCTTATGCTATGCA<br>TTGGGTGCGCCAAGCCCCTGGGAAGGGTCTCGAGTG<br>GGTGAGCGCTATCTCTTCTTCTGGTAGCTCTACCTA<br>TTATGCGGATAGCGTGAAAGGCCGTTTTACCATTTC<br>ACGTGATAATTCGAAAAACACCCTGTATCTGCAAAT<br>GAACAGCCTGCGTGCGGAAGATACGGCCGTGTATTA<br>TTGCGCGCGTGAGTCTTGGTTTCTTGATCTTTGGGG<br>CCAAGGCACCCTGGTGACGGTTAGCTCA |
| PN encoding SEQ ID NO: 166 | 170: GATATCCAGATGACCCAGAGCCCGTCTAGCCT<br>GAGCGCGAGCGTGGGTGATCGTGTGACCATTACCTG<br>CAGAGCGAGCCAGTCTATTTCTAATTGGCTGGCTTG<br>GTACCAGCAGAAACCAGGTAAAGCACCGAAACTATT<br>AATTTATCTTGCTTCTCTTTTGCAAAGCGGGGTCCC<br>GTCCCGTTTTAGCGGCTCTGGATCCGGCACTGATTT<br>TACCCTGACCATTAGCAGCCTGCAACCTGAAGACTT<br>TGCGGTTTATTATTGCCAGCAGTATTATGATTTTTC<br>TGATACCTTTGGCCAGGGTACGAAAGTTGAATTAA<br>A |
| PN encoding SEQ ID NO: 167 | 171: CAGGTGCAATTGGTGGAAAGCGGCGGCGGCCT<br>GGTGCAACCGGGCGGCAGCCTGCGTCTGAGCTGCGC<br>GGCCTCCGGATTTACCTTTACTTCTTATGCTATGCA<br>TTGGGTGCGCCAAGCCCCTGGGAAGGGTCTCGAGTG<br>GGTGAGCGCTATCTCTTCTTCTGGTAGCTCTACCTA<br>TTATGCGGATAGCGTGAAAGGCCGT1TTACCATTTC<br>ACGTGATAATTCGAAAAACACCCTGTATCTGCAAAT<br>GAACAGCCTGCGTGCGGAAGATACGGCCGTGTATTA<br>TTGCGCGCGTGAGTCTTGGTTTCTTGATCTTTGGGG<br>CCAAGGCACCCTGGTGACGGTTAGCTCAGCGTCGAC<br>CAAAGGTCCAAGCGTGTTTCCGCTGGCTCCGAGCAG<br>CAAAGCACCAGCGGCGGCACGGCTGCCCTGGGCTG<br>CCTGGTTAAAGATTATTTCCCGGAACCAGTCACCGT<br>GAGCTGGAACAGCGGGGCGCTGACCAGCGGCGTGCA<br>TACCTTTCCGGCGGTGCTGCAAAGCAGCGGCCTGTA<br>TAGCCTGAGCAGCGTTGTGACCGTGCCGAGCAGCAG<br>CTTAGGCACTCAGACCTATATTTGCAACGTGAACCA<br>TAAACCGAGCAACACCAAAGTGGATAAAAAAGTGGA<br>ACCGAAAAGCX (X can be TGC, GAATTC or TGCGAATTC) |
| PN encoding SEQ ID NO: 168 | 172: GATATCCAGATGACCCAGAGCCCGTCTAGCCT<br>GAGCGCGAGCGTGGGTGATCGTGTGACCATTACCTG<br>CAGAGCGAGCCAGTCTATTTCTAATTGGCTGGCTTG<br>GTACCAGCAGAAACCAGGTAAAGCACCGAAACTATT<br>AATTTATCTTGCTTCTCTTTTGCAAAGCGGGGTCCC |

TABLE 1-continued

Examples of C5 Antibodies of the Present Invention and C5 Proteins

| | Sequence Identifier (SEQ ID NO:) or comments/details |
|---|---|
| | GTCCCGTTTTAGCGGCTCTGGATCCGGCACTGATTT TACCCTGACCATTAGCAGCCTGCAACCTGAAGACTT TGCGGTTTATTATTGCCAGCAGTATTATGATTTTTC TGATACCTTTGGCCAGGGTACGAAAGTTGAAATTAA ACGTACGGTGGCTGCTCCGAGCGTGTTTATTTTTCC GCCGAGCGATGAACAACTGAAAAGCGGCACGGCGAG CGTGGTGTGCCTGCTGAACAACTTTTATCCGCGTGA AGCGAAAGTTCAGTGGAAAGTAGACAACGCGCTGCA AAGCGGCAACAGCCAGGAAAGCGTGACCGAACAGGA TAGCAAAGATAGCACCTATTCTCTGAGCAGCACCCT GACCCTGAGCAAAGCGGATTATGAAAAACATAAAGT GTATGCGTGCGAAGTGACCCATCAAGGTCTGAGCAG CCCGGTGACTAAATCTTTTAATCGTGGCGAGX (X can be TGC or GCC) |
| Antibody 6763 | |
| CDRH1 | 173:NYGMH |
| CDRH2 | 174:VSYAGSFTNYADSVKG |
| CDRH3 | 175:SWLGYPDIFDY |
| CDRL1 | 176:TGTSSDVGGYNYVS |
| CDRL2 | 177:DVNNRPS |
| CDRL3 | 178:SSYDKFQTV |
| VH | 179:QVQLVESGGGLVQPGGSLRLSCAASGFTFSNY GMHWVRQAPGKGLEWVSVSYAGSFTNYADSVKGRFT ISRDNSKNTLYLQMNSLRAEDTAVYYCARSWLFGYP DIFDYWGQGTLVTVSS |
| VL | 180:DIALTQPASVSGSPGQSITISCTGTSSDVGGY NYVSWYQQHPGKAPKLMIYDVNNRPSGVSNRFSGSK SGNTASLTISGLQAEDEADYYCSSYDKFQTVFGGGT KLTVL |
| Heavy chain | 181:QVQLVESGGGLVQPGGSLRLSCMSGFTFSNYG MHWVRQAPGKGLEWISVSYAGSFTNYADSVKGRFTI SRDNSKNTLYLQMNSLRAEDTAVYYCARSWLFGYPD IFDYWGQGTLVTVSSASTKGPSVFPLAPSSKSTSGG TAALGCLVKDYFPEPVTVSWNSGALTSGVHTFPAVL QSSGLYSLSSWTVPSSSLGTQTYICNVNHKPSNTKV DKKVEPKSX (X can be C, EF or CEF) |
| Light chain | 182:DIALTQPASVSGSPGQSITISCTGTSSDVGGY NYVSWYQQHPGKAPKLMIYDVNNRPSGVSNRFSGSK SGNTASLTISGLQAEDEADYYCSSYDKFQTVFGGGT KLTVLGQPKAAPSVTLFPPSSEELQANKATLVCLIS DFYPGAVTVAWKADSSPVKAGVETTTPSKQSNNKYA ASSYLSLTPEQWKSHRSYSCQVTHEGSTVEKTVAPT EX (X can be CS or A) |
| PN encoding SEQ ID NO: 179 | 183:CAGGTGCAATTGGTGGAAAGCGGCGGCGGCCT GGTGCAACCGGGCGGCAGCCTGCGTCTGAGCTGCGC GGCCTCCGGATTTACCTTTTCTAATTATGGTATGCA TTGGGTGCGCCAAGCCCCTGGGAAGGGTCTCGAGTG GGTGAGCGTTTCTTATGCTGGTAGCTTTACCAATTA TGCGGATAGCGTGAAAGGCCGTTTTACCATTTCACG TGATAATTCGAAAAACACCCTGTATCTGCAAATGAA CAGCCTGCGTGCGGAAGATACGGCCGTGTATTATTG CGCGCGTTCTTGGCTTTTTGGTTATCCTGATATTTT TGATTATTGGGGCCAAGGCACCCTGGTGACGGTTAG CTCA |
| PN encoding SEQ ID NO: 180 | 184:GATATCGCACTGACCCAGCCAGCTTCAGTGAG CGGCTCACCAGGTCAGAGCATTACCATCTCGTGTAC GGGTACTAGCAGCGATGTTGGTGGTTATAATTATGT GTCTTGGTACCAGCAGCATCCCGGGAAGGCGCCGAA ACTTATGATTTATGATGTTAATAATCGTCCCTCAGG CGTGAGCAACCGTTTTAGCGGATCCAAAAGCGGCAA CACCGCGAGCCTGACCATTAGCGGCCTGCAAGCGGA |

TABLE 1-continued

Examples of C5 Antibodies of the Present Invention and C5 Proteins

| | Sequence Identifier (SEQ ID NO:) or comments/details |
|---|---|
| | AGACGAAGCGGATTATTATTGCTCTTCTTATGATAA GTTTCAGACTGTGTTTGGCGGCGGCACGAAGTTAAC CGTTCTT |
| PN encoding SEQ ID NO: 181 | 185:CAGGTGCAATTGGTGGAAAGCGGCGGCGGCCT GGTGCAACCGGGCGGCAGCCTGCGTCTGAGCTGCGC GGCCTCCGGATTTACCTTTTCTAATTATGGTATGCA TTGGGTGCGCCAAGCCCCTGGGAAGGGTCTCGAGTG GGTGAGCGTTTCTTATGCTGGTAGCTTTACCAATTA TGCGGATAGCGTGAAAGGCCGTTTTACCATTTCACG TGATAATTCGAAAAACACCCTGTATCTGCAAATGAA CAGCCTGCGTGCGGAAGATACGGCCGTGTATTATTG CGCGCGTTCTTGGCTTTTTGGTTATCCTGATATTTT TGATTATTGGGGCCAAGGCACCCTGGTGACGGTTAG CTCAGCGTCGACCAAGGGTCCAAGCGTGTTTCCGCT GGCTCCGAGCAGCAAAAGCACCAGCGGCGGCACGGC TGCCCTGGGCTGCCTGGTTAAGATTATTCCCGGA ACCAGTCACCGTGAGCTGGAACAGCGGGGCGCTGAC CAGCGGCGTGCATACCTTTCCGGCGGTGCTGCAAAG CAGCGGCCTGTATAGCCTGAGCAGCGTTGTGACCGT GCCGAGCAGCAGCTTAGGCACTCAGACCTATATTTG CAACGTGAACCATAAACCGAGCAACACCAAAGTGGA TAAAAAAGTGGAACCGAAAAGCX (X can be TGC, GAATTC or TGCGAATTC) |
| PN encoding SEQ ID NO: 182 | 186:GATATCGCACTGACCCAGCCAGCTTCAGTGAG CGGCTCACCAGGTCAGAGCA1TACCATCTCGTGTAC GGGTACTAGCAGCGATGTTGGTGGTTATAATTATGT GTCTTGGTACCAGCAGCATCCCGGGAAGGCGCCGAA ACTTATGATTTATGATGTTAATAATCGTCCCTCAGG CGTGAGCAACCGTTTTAGCGGATCCAGACGGCAAC ACCGCGAGCCTGACCATTAGCGGCCTGCAAGCGGAA GACGAAGCGGATTATTATTGCTCTTCTTATGATAAG TTTCAGACTGTGTTTGGCGGCGGCACGAAGTTAACC GTTCTTGGCCAGCCGAAAGCCGCACCGAGTGTGACG CTGTTTCCGCCGAGCAGCGAAGAATTGCAGGCGAAC AAAGCGACCCTGGTGTGCCTGATTAGCGACTTTTAT CCGGGAGCCGTGACAGTGGCCTGGAAGGCAGATAGC AGCCCCGTCAAGGCGGGAGTGGAGACCACCACACCC TCCAAACAAAGCAACAACAAGTACGCGCCAGCAGC TATCTGAGCCTGACGCCTGAGCAGTGGAAGTCCCAC AGAAGCTACAGCTGCCAGGTCACGCATGAGGGGAGC ACCGTGGAAAAAACCGTTGCGCCGACTGAGX (X can be TGCAGC or GCC) |
| Antibody 7085 | |
| CDRH1 | SEQ ID NO: 1 |
| CDRH2 | SEQ ID NO: 2 |
| CDRH3 | SEQ ID NO: 3 |
| CDRL1 | SEQ ID NO: 4 |
| CDRL2 | SEQ ID NO: 5 |
| CDRL3 | SEQ ID NO: 6 |
| VH | 187:QVQLVQSGAEVKKPGSSVKVSCKASGGTFSSY AISWVRQAPGQGLEWMGGIGPFFGTANYAQKFQGRV TITADESTSTAYMELSSLRSEDTAVYYCARDTPYFD YWGQGTLVTVSS |
| VL | 188:DIELTQPPSVSVAPGQTARISCSGDSIPNYYV YWYQQKPGQAPVLVIYDDSNRPSGIPERFSGSNSGN TATLTISGTQAEDEADYYCQSFDSSLNAEVFGGGTK LTVL |
| Heavy chain | 189:QVQLVQSGAEVKKPGSSVKVSCKASGGTFSSY AISWVRQAPGQGLEWMGGIGPFFGTANYAQKFQGRV TITADESTSTAYMELSSLRSEDTAVYYCAROTPYFD YWGQGTLVTVSSASTKGPSVFPLAPSSKSTSGGTAA LGCLVKDYFPEPVTVSWNSGALTSGVHTFPPAVLQSS |

TABLE 1-continued

Examples of C5 Antibodies of the Present Invention and C5 Proteins

| | Sequence Identifier (SEQ ID NO:) or comments/details |
|---|---|
| | GLYSLSSVVTVPSSSLGTQTYICNVNHKPSNTKVDK KVEPKSX (X can be G, EF or CEF) |
| Light chain | 190:DIELTQPPSVSVAPGQTARISCSGDSIPNYYV YWYQQKPGQAPVLVIYDDSNRPSGIPERFSGSNSGN TATLTISGTQAEDEADYYCQSFDSSLNAEVFGGGTK LTVLGQPKAAPSVTLFPPSSEELQANKATLVCLISD FYPGAVTVAWKADSSPVKAGVETTTPSKQSNNKYAA SSYLSLTPEQWKSHRSYSCQVTHEGSTVEKTVAPTE X (X can be CS or A) |
| PN encoding SEQ ID NO: 187 | 191:CAGGTGCAATTGGTTCAGTCTGGCGCGGAAGT GAAAAAACCGGGCAGCAGCGTGAAAGTGAGCTGCAA AGCCTCCGGAGGCACTTTTTCTTCTTATGCCATTTC TTGGGTGCGCCAAGCCCCTGGGCAGGGTCTCGAGTG GAT GGGCGGTATCGGTCCGTTTTTTGGCACTGCGA ATTACGCGCAGAAGTTTCAGGGCCGGGTGACCATTA CCGCGGATGAAAGCACCAGCACCGCGTATATGGAAC TGAGCAGCCTGCGTAGCGAAGATACGGCCGTGTATT ATTGCGCGCGTGATACTCCTTATTTTGATTATTGGG GCCAAGGCACCCTGGTGACGGTTAGCTCA |
| PN encoding SEQ ID NO: 188 | 192:GATATCGAACTGACCCAGCCGCCTTCAGTGAG CGTTGCACCAGGTCAGACCGCGCGTATCTCGTGTAG CGGCGATTCTATTCCTAATTATTATGTTTATTGGTA CCAGCAGAAACCCGGGCAGGCGCCAGTTCTTGTGAT TTATGATGATTCTAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGTCTTTTGATTCTTCTCTTAA TGCTGAGGTGTTTGGCGGCGGCACGAAGTTAACCGT TCTT |
| PN encoding SEQ ID NO: 189 | 193:CAGGTGCAATTGGTTCAGTCTGGCGCGGAAGT GAAAAAACCGGGCAGCAGCGTGAAAGTGAGCTGCAA AGCCTCCGGAGGCACTTTTTCTTCTTATGCCATTTC TTGGGTGCGCCAAGCCCCTGGGCAGGGTCTCGAGTG GATGGGCGGTATCGGTCCGTTTTTTGGCACTGCGAA TTACGCGCAGAAGTTTCAGGGCCGGGTGACCATTAC CGCGGATGAAAGCACCAGCACCGCGTATATGGAACT GAGCAGCCTGCGTAGCGAAGATACGGCCGTGTATTA TTGCGCGCGTGATACTCCTTATTTTGATTATTGGGG CCAAGGCACCCTGGTGACGGTTAGCTCAGCGTCGAC CAAAGGTCCAAGCGTGTTTTCCGCTGGCTCCGAGCAG CAAAAGCACCAGCGGCGGCACGGCTGCCCTGGGCTG CCTGGTTAAAGATTATTTCCCGGAACCAGTCACCGT GAGCTGGAACAGCGGGGCGCTGACCAGCGGCGTGCA TACCTTTCCGGCGGTGCTGCAAAGCAGCGGCCTGTA TAGCCTGAGCAGCGTTGTGACCGTGCCGAGCAGCAG CTTAGGCACTCAGACCTATATTTGCAACGTGAACCA TAAACCGAGCAACACCAAAGTGGATAAAAAAGTGGA ACCGAAAAGCX (X can be TGC, GAATTC or TGCGAATTC) |
| PN encoding SEQ ID NO: 190 | 194:GATATCGAACTGACCCAGCCGCCTTCAGTGAG CGTTGCACCAGGTCAGACCGCGCGTATCTCGTGTAG CGGCGATTCTATTCCTAATTATTATGTTTATTGGTA CCAGCAGAAACCCGGGCAGGCGCCAGTTCTTGTGAT TTATGATGATTCTAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGTCTTTTGATTCTTCTCTTAA TGCTGAGGTGTTTGGCGGCGGCACGAAGTTAACCGT TCTTGGCCAGCCGAAAGCCGCACCGAGTGTGACGCT GTTTCCGCCGAGCAGCGAAGAATTGCAGGCGAACAA AGCGACCCTGGTGTGCCTGATTAGCGACTTTTATCC GGGAGCCGTGACAGTGGCCTGGAAGGCAGATAGCAG CCCCGTCAAGGCGGGAGTGGAGACCACCACACCCTC CAAACAAAGCAACAACAAGTACGCGGCCAGCTCATA TCTGAGCCTGACGCCTGAGCAGTGGAAGTCCCACAG AAGCTACAGCTGCCAGGTCACGCATGAGGGGAGCAC CGTGGAAAAAACCGTTGCGCCGACTGAGX (X can be TGCAGC or GCC) |

TABLE 1-continued

Examples of C5 Antibodies of the Present Invention and C5 Proteins

| | Sequence Identifier (SEQ ID NO:) or comments/details |
|---|---|
| Antibody 7087 | |
| CDRH1 | 195:SYYIS |
| CDRH2 | 196:GIIPIFGTANYAQKFQG |
| CDRH3 | 197:GEIWHTHQPYKSGVYGAAY |
| CDRL1 | 198:RASQGISNWLN |
| CDRL2 | 199:GTSSLQS |
| CDRL3 | 200:QQLDSFPAT |
| VH | 201:QTQLVQSGAEVKKPGSSVKVSCKASGGTFSSY YISWVRQAPGQGLEWMGGIPTFGTANYAQKFQGRVT ITADESTSTAYMELSSLRSEDTAVYYCARGEIWHVH QPYKSGVYGAAYWGQGTLVTVSS |
| VL | 202:DIQMTQSPSSLSASVGDRVTITCRASQGISNW LNWYQQKPGKAPKLLIYGTSSLQSGVPSRFSGSGSG TDFTLTISSLQPEDFATYYCQQLDSFPATFGQGTKV EIK |
| Heavy chain | 203:QVQLVQSGAEVKKPGSSVKVSCKASGGTFSSY YISWVRQAPGQGLEWMGGIFTFGTANYAQKFQGRVT ITADESTSTAYMELSSLRSEDTAVYYCARGEIWHVH QPYKSGVYGAAYWGQGTLVTVSSASTKGPSVFPLAP SSKSTSGGTAALGCLVKDYFPEPVTVSWNSGALTSG VHTFPAVLQSSGLYSLSSVVTVPSSSLGTQTYICNV NHKPSNTKVDKKVEPKSX(X can be C, EF or CEF) |
| Light chain | 204:DIQMTQSPSSLSASVGDRVTITCRASQGISNW LNWYQQKPGKAPKLLIYGTSSLQSGVPSRFSGSGSG TDFTLTISSLQPEDFATYYCQQLDSFPATFGQGTKV EIKRTVAAPSVFIFPPSDEQLKSGTASVVCLLNNFY PREAKVQWKVDNALQSGNSQESVTEQDSKDSTYSLS STLTLSKADYEKHKVYACEVTHQGLSSPVTKSFNRG EX (X can be C or A) |
| PN encoding SEQ ID NO: 201 | 205:CAGGTGCAATTGGTTCAGTCTGGCGCGGAAGT GAAAAAACCGGGCAGCAGCGTGAAAGTGAGCTGCAA AGCCTCCGGAGGCACTTTTTCTTCTTATTATATTTC TTGGGTGCGCCAAGCCCCTGGGCAGGGTCTCGAGTG GATGGGCGGTATCATTCCGATTTTTGGCACTGCGAA TTACGCGCAGAAGTTTCAGGGCCGGGTGACCATTAC CGCGGATGAAAGCACCAGCACCGCGTATATGGAACT GAGCAGCCTGCGTAGCGAAGATACGGCCGTGTATTA TTGCGCGCGTGTGGAGATTTGGCATGTTCATCAGCC TTATAAGTCTGGTGTTTATGGTGCTGCTTATTGGGG CCAAGGCACCCTGGTGACGGTTAGCTCA |
| PN encoding SEQ ID NO: 202 | 206:GATATCCAGATGACCCAGAGCCCGTCTAGCCT GAGCGCGAGCGTGGGTGATCGTGTGACCATTACCTG CAGAGCGAGCCAGGGTATTTCTAATTGGCTGAATTG GTACCAGCAGAAACCAGGTAAAGCACCGAAACTATT AATTTATGGTACTTCTTCTTTGCAAAGCGGGGTCCC GTCCCGTTTTAGCGGCTCTGGATCCGGCACTGATTT TACCCTGACCATTAGCAGCCTGCAACCTGAAGACTT TGCGACTTATTATTGCCAGCAGCTTGATTCTTTTCC TGCTACCTTTGGCCAGGGTACGAAAGTTGAAATTAA A |
| PN encoding SEQ ID NO: 203 | 207:CAGGTGCAATTGGTTCAGTCTGGCGCGGAAGT GAAAAAACCGGGCAGCAGCGTGAAAGTGAGCTGCAA AGCCTCCGGAGGCACTTTTTCTTCTTATTATATTTC TTGGGTGCGCCAAGCCCCTGGGCAGGGTCTCGAGTG GATGGGCGGTATCATTCCGATTTTTGGCACTGCGAA TTACGCGCAGAAGTTTCAGGGCCGGGTGACCATTAC CGCGGATGAAAGCACCAGCACCGCGTATATGGAACT GAGCAGCCTGCGTAGCGAAGATACGGCCGTGTATTA TTGCGCGCGTGTGGAGATTTGGCATGTTCATCAGCC TTATAAGTCTGGTGTTTATGGTGCTGCTTATTGGGG |

TABLE 1-continued

Examples of C5 Antibodies of the Present Invention and C5 Proteins

| | Sequence Identifier (SEQ ID NO:) or comments/details |
|---|---|
| | CCAAGGCACCCTGGTGACGGTTAGCTCAGCGTCGAC CAAAGGTCCAAGCGTGTTTCCGCTGGCTCCGAGCAG CAAAAGCACCAGCGGCGGCACGGCTGCCCTGGGCTG CCTGGTTAAAGATTATTTCCCGGAACCAGTCACCGT GAGCTGGAACAGCGGGGCGCTGACCAGCGGCGTGCA TACCTTTCCGGCGGTGCTGCAAAGCAGCGGCCTGTA TAGCCTGAGCAGCGTTGTGACCGTGCCGAGCAGCAG CTTAGGCACTCAGACCTATATTTGCAACGTGAACCA TAAACCGAGCAACACCAAAGTGGATAAAAAAGTGGA ACCGAAAAGCX (X can be TGC, GAATTC or TGCGAATTC) |
| PN encoding SEQ ID NO: 204 | 208: GATATCCAGATGACCCAGAGCCCGTCTAGCCT GAGCGCGAGCGTGGGTGATCGTGTGACCATTACCTG CAGAGCGAGCCAGGGTATTTCTAATTGGCTGAATTG GTACCAGCAGAAACCAGGTAAAGCACCGAAACTATT AATTTATGGTACTTCTTCTTTGCAAAGCGGGGTCCC GTCCCGTTTTAGCGGCTCTGGATCCGGCACTGATTT TACCCTGACCATTAGCAGCCTGCAACCTGAAGACTT TGCGACTTATTATTGCCAGCAGCTTGATTCTTTTCC TGCTACCTTTGGCCAGGGTACGAAAGTTGAAATTAA ACGTACGGTGGCTGCTCCGAGCGTGTTTATTTTTCC GCCGAGCGATGAACAACTGAAAAGCGGCACGGCGAG CGTGGTGTGCCTGCTGAACAACTTTTATCCGCGTGA AGCGAAAGTTCAGTGGAAAGTAGACAACGCGCTGCA AAGCGGCAACAGCCAGGAAAGCGTGACCGAACAGGA TAGCAAAGATAGCACCTATTCTCTGAGCAGCACCCT GACCCTGAGCAAAGCGGATTATGAAAAACATAAAGT GTATGCGTGCGAAGTGACCCATCAAGGTCTGAGCAG CCCGGTGACTAAATCTTTTAATCGTGGCGAGX (X can be TGC or GCC) |

Antibody 7091

| | |
|---|---|
| CDRH1 | SEQ ID NO: 61 |
| CDRH2 | SEQ ID NO: 77 |
| CDRH3 | SEQ ID NO: 63 |
| CDRL1 | SEQ ID NO: 64 |
| CDRL2 | SEQ ID NO: 65 |
| CDRL3 | 209: QSWTDSPNTLV |
| VH | 210: QVQLVQSGAEVKKPGESLKISCKGSGYSFTSY YIGWIRQMPGKGLEWMGIIDPSDSHTTYSPSFQGQV TISADKSISTAYLQWSSLKASDTAMYYCARYMMRGF DHWGQGTLVTVSS |
| VL | 211: DIELTQPPSVSVAPGQTARISCSGDSLGDYYA YWYQQKPGQAPVLVIYKDNNRPSGIPERFSGSNSGN TATLTISGTQAEDEADYYCQSWTDSPNTLVFGGGTK LTVL |
| Heavy chain | 212: QVQLVQSGAEVKKPGESLKISCKGSGYSFTSY YIGWVRQMPGKGLEWMGIIDPSDSHTTYSPSFQGQV TISADKSISTAYLQWSSLKASDTAMYYCARYMMRGF DHWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK KVEPKSX (X can be C, EF or CEF) |
| Light chain | 213: DIELTQPPSVSVAPGQTARISCSGDSLGDYYA YWYQQKPGQAPVLVIYKDNNRPSGIPERFSGSNSGN TATLTISGTQAEDEADYYCQSWTDSPNTLVFGGGTK LTVLGQPKAAPSVTLFPPSSEELQANKATLVCLISD FYPGAVTVAWKADSSPVKAGVETTTPSKQSNNKYAA SSYLSLTPEQWKSHRSYSCQVTHEGSTVEKTVAPTE X (X can be CS or A) |
| PN encoding SEQ ID NO: 210 | 214: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTATATTGG TTGGGTGCGCCAGATGCCTGGGAAGGGTCTCGAGTG GATGGGCATTATCGATCCGTCTGATAGCCATACCAC TTATTCTCCGAGCTTTCAGGGCCAGGTGACCATTAG CGCGGATAAAAGCATTAGCACCGCGTATCTTCAATG GAGCAGCCTGAAAGCGAGCGATACGGCCATGTATTA TTGCGCGCGTTATATGATGCGTGGTTTTGATCATTG GGGCCAAGGCACCCTGGTGACGGTTAGCTCA |
| PN encoding SEQ ID NO: 211 | 215: GATATCGAACTGACCCAGCCGCCTTCAGTGAG CGTTGCACCAGGTCAGACCGCGCGTATCTCGTGTAG CGGCGATTCTCTTGGTGATTATTATGCTTATTGGTA CCAGCAGAAACCCGGGCAGGCGCCAGTTCTTGTGAT TTATAAGGATAATAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGTCTTGGACTGATTCTCCTAA TACTCTTGTGTTTGGCGGCGGCACGAAGTTAACCGT TCTT |
| PN encoding SEQ ID NO: 212 | 216: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTATATTGG TTGGGTGCGCCAGATGCCTGGGAAGGGTCTCGAGTG GATGGGCATTATCGATCCGTCTGATAGCCATACCAC TTATTCTCCGAGCTTTCAGGGCCAGGTGACCATTAG CGCGGATAAAAGCATTAGCACCGCGTATCTTCAATG GAGCAGCCTGAAAGCGAGCGATACGGCCATGTATTA TTGCGCGCGTTATATGATGCGTGGTTTTGATCATTG GGGCCAAGGCACCCTGGTGACGGTTAGCTCAGCGTC GACCAAAGGTCCAAGCGTGTTTCCGCTGGCTCCGAG CAGCAAAAGCACCAGCGGCGGCACGGCTGCCCTGGG CTGCCTGGTTAAAGATTATTTCCCGGAACCAGTCAC CGTGAGCTGGAACAGCGGGGCGCTGACCAGCGGCGT GCATACCTTTCCGGCGGTGCTGCAAAGCAGCGGCCT GTATAGCCTGAGCAGCGTTGTGACCGTGCCGAGCAG CAGCTTAGGCACTCAGACCTATATTTGCAACGTGAA CCATAAACCGAGCAACACCAAAGTGGATAAAAAAGT GGAACCGAAAAGCX (X can be TGC, GAATTC or TGCGAATTC) |
| PN encoding SEQ ID NO: 213 | 217: GATATCGAACTGACCCAGCCGCCTTCAGTGAG CGTTGCACCAGGTCAGACCGCGCGTATCTCGTGTAG CGGCGATTCTCTTGGTGATTATTATGCTTATTGGTA CCAGCAGAAACCCGGGCAGGCGCCAGTTCTTGTGAT TTATAAGGATAATAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGTCTTGGACTGATTCTCCTAA TACTCTTGTGTTTGGCGGCGGCACGAAGTTAACCGT TCTTGGCCAGCCGAAAGCCGCACCGAGTGTGACGCT GTTTCCGCCGAGCAGCGAAGAATTGCAGGCGAACAA AGCGACCCTGGTGTGCCTGATTAGCGACTTTTATCC GGGAGCCGTGACAGTGGCCTGGAAGGCAGATAGCAG CCCCGTCAAGGCGGGAGTGGAGACCACCACACCCTC CAAACAAAGCAACAACAAGTACGCGGCCAGCAGCTA TCTGAGCCTGACGCCTGAGCAGTGGAAGTCCCACAG AAGCTACAGCTGCCAGGTCACGCATGAGGGGAGCAC CGTGGAAAAAACCGTTGCGCCGACTGAGX (X can be TGCAGC or GCC) |

Antibody 7092

| | |
|---|---|
| CDRH1 | SEQ ID NO: 17 |
| CDRH2 | SEQ ID NO: 49 |
| CDRH3 | SEQ ID NO: 19 |
| CDRL1 | SEQ ID NO: 20 |
| CDRL2 | SEQ ID NO: 21 |
| CDRL3 | SEQ ID NO: 22 |

TABLE 1-continued

Examples of C5 Antibodies of the
Present Invention and C5 Proteins

Sequence Identifier
(SEQ ID NO:) or comments/details

| | |
|---|---|
| VH | 218:QVQLVQSGAEVKKPGESLKISCKGSGYSFTNY ISVWRQMPGKGLEWMGIIDPDDSYTRYSPSFQGQVT ISADKSISTAYLQWSSLKASDTAMYYCARYEYGGFD IWGQGTLVTVSS |
| VL | 219:DIELTQPPSVSVAPGQTARISCSGDNIGNSYV HWYQQKPGQAPVLVIYKDNDRPSGIPERFSGSNSGN TATLTISGTQAEDEADYYCGTYDIESYVFGGGTKLT VL |
| Heavy chain | 220:QVQLVQSGAEVKKPGESLKISCKGSGYSFTNY ISVWRQMPGKGLEWMGIIDPDDSYTRYSPSFQGQVT ISADKSISTAYLQWSSLKASDTAMYYCARYEYGGFD IWGQGTLVTVSSASTKGPSVFPLAPSSKSTSGGTAA LGCLVKDYFPEPVTVSWNSGALTSGVHTFPAVLQSS GLYSLSSWTVPSSSLGTQTYICNVNHKPSNTKVDKK VEPKSX (X can be C, EF or CEF) |
| Light chain | 221:DIELTQPPSVSVAPGQTARISCSGDNIGNSYV HWYQQKPGQAPVLVIYKDNDRPSGIPERFSGSNSGN TATLTISGTQAEDEADYYCGTYDIESYVFGGGTKLT VLGQPKAAPSVTLFPPSSEELQANKATLVCLISDFY PGAVTVAWKADSSPVKAGVETTTPSKQSNNKYAASS YLSLTPEQWKSHRSYSCQVTHEGSTVEKTVAPTEX (X can be CS or A) |
| PN encoding SEQ ID NO: 218 | 222:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATCGATCCGGATAGCTACACCCGTTA TTCTCCGAGCTTTCAGGGACAGGTGACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCA |
| PN encoding SEQ ID NO: 219 | 223:GATATCGAACTGACCCAGCCGCCTTCAGTGAG CGTTGCACCAGGTCAGACCGCGCGTATCTCGTGTAG CGGCGATAATATTGGTAATTCTTATGTTCATTGGTA CCAGCAGAAACCCGGGCAGGCGCCAGTTCTTGTGAT TTATAAGGATAATGATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCGGTACTTATGATATTGAGTCTTA TGTGTTTGGCGGCGGCACGAAGTTAACCGTTCTT |
| PN encoding SEQ ID NO: 220 | 224:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATCGATCCGGATAGCTACACCCGTTA TTCTCCGAGCTTTCAGGGACAGGTGACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCAGCGTCGAC CAAAGGTCCAAGCGTGTTTCCGCTGGCTCCAGCAG CAAAAGCACCAGCGGCGGCACGGCTGCCCTGGGCTG CCTGGTTAAAGATTATTTCCCGGAACCAGTCACCGT GAGCTGGAACAGCGGGGCGTGACCAGCGGCGTGCA TACCTTTCCGGCGGTGCTGCAAAGCAGCGGCCTGTA TAGCCTGAGCAGCGTTGTGACCGTGCCGAGCAGCAG CTTAGGCACTCAGACCTATATTTGCAACGTGAACCA TAAACCGAGCAACACCAAAGTGGATAAAAAAGTGGA ACCGAAAAGCX (X can be TCC, GAATTC or TGCGAATTC) |
| PN encoding SEQ ID NO: 221 | 225:GATATCGAACTGACCCAGCCGCCTTCAGTGAG CGTTGCACCAGGTCAGACCGCGCGTATCTCGTGTAG CGGCGATAATATTGGTAATTCTTATGTTCATTGGTA CCAGCAGAAACCCGGGCAGGCGCCAGTTCTTGTGAT TTATAAGGATAATGATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCGGTACTTATGATATTGAGTCTTA TGTGTTTGGCGGCGGCACGAAGTTAACCGTTCTTGG CCAGCCGAAAGCCGCACCGAGTGTGACGCTGTTTCC GCCGAGCAGCGAAGAATTGCAGGCGACAAAGCGAC CGTGACAGTGGCCTGGAAGGCAGATAGCAGCCCCGT CAAGGCGGGAGTGGAGACCACCACACCCTCCAAACA AAGCAACAACAAGTACGCGGCCAGCAGCTATCTGAG CCTGACGCCTGAGCAGTGGAAGTCCCACAGAAGCTA CAGCTGCCAGGTCACGCATGAGGGGAGCACCGTGGA AAAAAACCGTTGCGCCGACTGAGX (X can be TGCAGC or GCC) |

Antibody 7093

| | |
|---|---|
| CDRH1 | SEQ ID NO: 33 |
| CDRH2 | 226:HIFSDDDKYYSTSLKT |
| CDRH3 | SEQ ID NO: 35 |
| CDRL1 | SEQ ID NO: 36 |
| CDRL2 | SEQ ID NO: 37 |
| CDRL3 | SEQ ID NO: 38 |
| VH | 227:QVQLKESGPALVKPTQTLTLTCTFSGFSLSTS GGGVSWIRQPPGKALEWLAHIFSDDDKYYSTSLKTR LTISKDTSKNQVVLTMTNMDPVDTATYYCARGPYDF DSWGQGTLVTVSS |
| VL | 228:DIALTQPASVSGSPGQSITISCTGTSSDIGTY NYVSWYQQHPGKAPKLMIYDDSNRPSGVSNRFSGSK SGNTASLTISGLQAEDEADYYCQSYDSQSIVFGGGT KLTVL |
| Heavy chain | 229:QVQLKESGPALVKPTQTLTLTCTFSGFSLSTS GGGVSWIRQPPGKALEWLAHIFSDDDKYYSTSLKTR LTISKDTSKNQVVLTMTNMDPVDTATYYCARGPYDF DSWGQGTLVTVSSASTKGPSVFPLAPSSKSTSGGTA ALGDLVKDYFPEPVTVSWNSGALTSGVHTFPAVLQS SGLYSLSSVVTVPSSSLGTQTYICNVNHKPSNTKVD KKVEPKSX (X can be C, EF or CEF) |
| Light chain | 230:DIALTQPASVSGSPGQSITISCTGTSSDIGTY NYVSWYQQHPGKAPKLMIYDDSNRPSGVSNRFSGSK SGNTASLTISGLQAEDEADYYCQSYDSQSIVFGGGT KLTVLGQPKAAPSVTLFPPSSEELQANKATLVCLIS DFYPGAVTVAWKADSSPVKAGVETTTPSKQSNNKYA ASSYLSLTPEQWKSHRSYSCQVTHEGSTVEKTVAPT EX (X can be CS orA) |
| PN encoding SEQ ID NO: 227 | 231:CAGGTGCAATTGAAAGAAAGCGGCCCCGGCCCT GGTGAAACCGACCCAAACCCTGACCCTGACCTGTAC CTTTTCCGGATTTAGCCTGTCTACTTCTGGTGGTGG TGTGTCTTGGATTCGCCAGCCGCCTGGGAAAGCCCT CGAGTGGCTGGCTCATATCTTTTCTGATGATGATAA GTATTATAGCACCAGCCTGAAAACGCGTCTGACCAT TAGCAAAGATACTTCGAAAAATCAGGTGGTGCTGAC TATGACCAACATGGACCCGGTGGATACGGCCACCTA TTATTGCGCGCGTGGTCCTTATGGTTTTGATTCTTG GGGCCAAGGCACCCTGGTGACGGTTAGCTCA |
| PN encoding SEQ ID NO: 228 | 232:GATATCGCACTGACCCAGCCAGCTTCAGTGAG CGGCTCACCAGGTCAGAGCATTACCATCTCGTGTAC GGGTACTAGCAGCGATATTGGTACTTATAATTATGT GCTTGGTACCAGCAGCATCCCGGGAAGGCGCCGAA ACTTATGATTTATGATGATTCTAATCGTCCCTCAGG CGTGAGCAACCGTTTTAGCGGATCCAAAAGCGGCAA CACCGCGAGCCTGACCATTAGCGGCCTGCAAGCGGA AGACGAAGCGGATTATTATTGCCAGTCTTATGATTC |

TABLE 1-continued

Examples of C5 Antibodies of the Present Invention and C5 Proteins

Sequence Identifier (SEQ ID NO:) or comments/details

| | |
|---|---|
| | TCAGTCTATTGTGTTTGGCGGCGGCACGAAGTTAAC<br>CGTTCTT |
| PN encoding<br>SEQ ID NO: 229 | 233: CAGGTGCAATTGAAAGAAAGCGGCCCGGCCCT<br>GGTGAAACCGACCCAAACCCTGACCCTGACCTGTAC<br>CTTTTCCGGATTTAGCCTGTCTACTTCTGGTGGTGG<br>TGTGTCTTGGATTCGCCAGCCGCCTGGGAAAGCCCT<br>CGAGTGGCTGGCTCATATCTTTTCTGATGATGATAA<br>GTATTATAGCACCAGCTGAAAACGCGTCTGACCAT<br>TAGCAAAGATACTTCGAAAAATCAGGTGGTGCTGAC<br>TATGACCAACATGGACCCGGTGGATACGGCCACCTA<br>TTATTGCGCGCGTGGTCCTTATGGTTTTGATTCTTG<br>GGGCCAAGGCACCCTGGTGACGGTTAGCTCAGCGTC<br>GACCAAAGGTCCAAGCGTGTTTCCGCTGGCTCCGAG<br>CAGCAAAAGCACCAGCGGCGGCACGGCTGCCCTGGG<br>CTGCCTGGTTAAAGATTATTTCCCGGAACCAGTCAC<br>CGTGAGCTGGAACAGCGGGGCGCTGACCAGCGGCGT<br>GCATACCTTTCCGGCGGTGCTGCAAAGCAGCGGCCT<br>GTATAGCCTGAGCAGCGTTGTGACCGTGCCGAGCAG<br>CAGCTTAGGCACTCAGACCTATATTTGCAACGTGAA<br>CCATAAACCGAGCAACACCAAAGTGGATAAAAAAGT<br>GGAACCGAAAAGCX (X can be TGC, GAATTC<br>or TGCGAATTC) |
| PN encoding<br>SEQ ID NO: 230 | 234: GATATCGCACTGACCCAGCCAGCTTCAGTGAG<br>CGGCTCACCAGGTCAGAGCATTACCATCTCGTGTAC<br>GGGTACTAGCAGCGATATTGGTACTTATAATTATGT<br>GTCTTGGTACCAGCAGCATCCCGGGAAGGCGCCGAA<br>ACTTATGATTTATGATGATTCTAATCGTCCCTCAGG<br>CGTGAGCAACCGTTTTAGCGGATCCAAAAGCGGCAA<br>CACCGCGAGCCTGACCATTAGCGGCCTGCAAGCGGA<br>AGACGAAGCGGATTATTATTGCCAGTCTTATGATTC<br>TCAGTCTATTGTTTGGCGGCGGCACGAAGTTAAC<br>CGTTCTTGGCCAGCCGAAAGCCGCACCGAGTGTGAC<br>GCTGTTTCCGCCGAGCAGCGAAGAATTGCAGGCGAA<br>CAAAGCCACCCTGGTGTGCCTGATTAGCGACTTTTA<br>TCCGGGAGCCGTGACAGTGGCCTGGAAGGCAGATAG<br>CAGCCCCGTCAAGGCGGGAGTGGAGACCACCACACC<br>CTCCAAACAAAGCAACAACAAGTACGCGGCCAGCAG<br>CTATCTGAGCCTGACGCCTGAGCAGTGGAAGTCCCA<br>CAGAAGCTACAGCTGCCAGGTCACGCATGAGGGGAG<br>CACCGTGGAAAAAACCGTTGCGCCGACTGAGX (X<br>can be TGCAGC or GCC) |

Antibody 7094

| | |
|---|---|
| CDRH1 | 235: TSGMSVG |
| CDRH2 | 236: LIDWDEDKSYSTSLKT |
| CDRH3 | 237: YNWYNPPGFDN |
| CDRL1 | 238: SGSSSNIGSNYVS |
| CDRL2 | 239: RNDKRPS |
| CDRL3 | 240: QSADSSSMV |
| VH | 241: QVQLKESGPALVKPTQTLTLTCTFSGFSLSTS<br>GMSVGWIRQPPGKALEWLALIDWDEQKSYSTSLKTR<br>LTISKDTSKNQVVLTMTNMDPVDTATYYCARYNWYN<br>PPGFDNWGQGTLVTVSS |
| VL | 242: DIVLTQPPSVSGAPGQRVTISCSGSSSNIGSN<br>YVSWYQQLPGTAPKLLIYRNDKRPSGVPDRFSGSKS<br>GTSASLAITGLQSEDEADYYCQSADSSSMVFGGGTK<br>LTVL |
| Heavy chain | 243: QVQLKESGPALVKPTQTLTLTCTFSGFSLSTS<br>GMSVGWIRQPPGKALEWLALIDWDEQKSYSTSLKTR<br>LTISKDTSKNQVVLTMTNMDPVDTATYYCARYNWYN<br>PPGFDNWGQGTLVTVSSASTKGPSVFPLAPSSKSTS |

TABLE 1-continued

Examples of C5 Antibodies of the Present Invention and C5 Proteins

Sequence Identifier (SEQ ID NO:) or comments/details

| | |
|---|---|
| | GGTAALGCLVKDYFPEPVTVSWNSGALTSGVHTFPA<br>VLQSSGLYSLSSVVTVPSSSLGTQTYICNVNHKPSN<br>TKVDKKVEPKSX (X can be C, EF or CEF) |
| Light chain | 244: DIVLTQPPSVSGAPGQRVTISCSGSSSNIGSN<br>YVSWYQQLPGTAPKLLIYRNDKRPSGVPDRFSGSKS<br>GTSASLAITGLQSEDEADYYCQSADSSSMVFGGGTK<br>LTVLGQPKAAPSVTLFPPSSEELQANKATLVCLISD<br>FYPGAVTVAWKADSSPVKAGVETTTPSKQSNNKYAA<br>SSYLSLTPEQWKSHRSYSCQVTHEGSTVEKTVAPTE<br>X (X can be CS orA) |
| PN encoding<br>SEQ ID NO: 241 | 245: CAGGTGCAATTGAAAGAAAGCGGCCCGGCCCT<br>GGTGAAACCGACCCAAACCCTGACCCTGACCTGTAC<br>CTTTTCCGGATTTAGCCTGTCTACTTCTGGTATGTC<br>TGTGGGTTGGATTCGCCAGCCGCCTGGGAAAGCCCT<br>CGAGTGGCTGGCTCTTATCGATTGGGATGAGGATAA<br>GTCTTATAGCACCAGCCTGAAAACGCGTCTGACCAT<br>TAGCAAAGATACTTCGAAAAATCAGGTGGTGCTGAC<br>TATGACCAACATGGACCCGGTGGATACGGCCACCTA<br>TTATTGCGCGCGTTATAATTGGTATAATCCTCCTGG<br>TTTTGATAATTGGGGCCAAGGCACCCTGGTGACGGT<br>TAGCTCA |
| PN encoding<br>SEQ ID NO: 242 | 246: GATATCGTGCTGACCCAGCCGCCTTCAGTGAG<br>TGGCGCACCAGGTCAGCGTGTGACCATCTCGTGTAG<br>CGGCAGCAGCAGCAACATTGGTTCTAATTATGTGTC<br>TTGGTACCAGCAGTTGCCCGGGACGGCGCCGAAACT<br>TCTGATTTATCGTAATGATAAGCGTCCCTCAGGCGT<br>GCCCGGATCGTTTTAGCGGATCCAAAAGCGGCACCAG<br>CGCGAGCCTTGCGATTACGGGCCTGCAAAGCGAAGA<br>CGAAGCGGATTATTATTGCCAGTCTGCTGATTCTTC<br>TTCTATGGTGTTTGGCGGCGGCACGAAGTTAACCGT<br>TCTT |
| PN encoding<br>SEQ ID NO: 243 | 247: CAGGTGCAATTGAAAGAAAGCGGCCCGGCCCT<br>GGTGAAACCGACCCAAACCCTGACCCTGACCTGTAC<br>CTTTTCCGGATTTAGCCTGTCTACTTCTGGTATGTC<br>TGTGGGTTGGATTCGCCAGCCGCCTGGGAAAGCCCT<br>CGAGTGGCTGGCTCTTATCGATTGGGATGAGGATAA<br>GTCTTATAGCACCAGCCTGAAAACGCGTCTGACCAT<br>TAGCAAAGATACTTCGAAAAATCAGGTGGTGCTGAC<br>TATGACCAACATGGACCCGGTGGATACGGCCACCTA<br>TTATTGCGCGCGTTATAATTGGTATAATCCTCCTGG<br>TTTTGATAATTGGGGCCAAGGCACCCTGGTGACGGT<br>TAGCTCAGCGTCGACCAAAGGTCCAAGCGTGTTTCC<br>GCTGGCTCCGAGCAGCAAAAGCACCAGCGGCGGCAC<br>GGCTGCCCTGGGCTGCCTGGTTAAAGATTATTTCCC<br>GGAACCAGTCACCGTGAGCTGGAACAGCGGGGCGCT<br>GACCAGCGGCGTGCATACCTTTCCGGCGGTGCTGCA<br>AAGCAGCGGCCTGTATAGCCTGAGCAGCGTTGTGAC<br>CGTGCCGAGCAGCAGCTTAGGCACTCAGACCTATAT<br>TTGCAACGTGAACCATAAACCGAGCAACACCAAAGT<br>GGATAAAAAAGTGGAACCGAAAAGCX (X can be<br>TGC, GAATTC or TGCGAATTC) |
| PN encoding<br>SEQ ID NO: 244 | 248: GATATCGTGCTGACCCAGCCGCCTTCAGTGAG<br>TGGCGCACCAGGTCAGCGTGTGACCATCTCGTGTAG<br>CGGCAGCAGCAGCAACATTGGTTCTAATTATGTGTC<br>TTGGTACCAGCAGTTGCCCGGGACGGCGCCGAAACT<br>TCTGATTTATCGTAATGATAAGCGTCCCTCAGGCGT<br>GCCCGGATCGTTTTAGCGGATCCAAAAGCGGCACCAG<br>CGCGAGCCTTGCGATTACGGGCCTGCAAAGCGAAGA<br>CGAAGCGGATTATTATTGCCAGTCTGCTGATTCTTC<br>TTCTATGGTGTTTGGCGGCGGCACGAAGTTAACCGT<br>TCTTGGCCAGCCGAAAGCCGCACCGAGTGTGACGCT<br>GTTTCCGCCGAGCAGCGAAGAATTGCAGGCGAACAA<br>AGCGACCCTGGTGTGCCTGATTAGCGACTTTTATCC<br>GGGAGCCGTGACAGTGGCCTGGAAGGCAGATAGCAG<br>CCCCGTCAAGGCGGGAGTGGAGACCACCACACCCTC<br>CAAACAAAGCAACAACAAGTACGCGGCCAGCAGCTA<br>TCTGAGCCTGACGCCTGAGCAGTGGAAGTCCCACAG |

TABLE 1-continued

Examples of C5 Antibodies of the Present Invention and C5 Proteins

| | Sequence Identifier (SEQ ID NO:) or comments/details |
|---|---|
| | AAGCTACAGCTGCCAGGTCACGCATGAGGGGAGCAC CGTGGAAAAAACCGTTGCGCCGACTGAGX (X can be TGCAGC or GCC) |
| Antibody 7821 | |
| CDRH1 | SEQ ID NO: 1 |
| CDRH2 | SEQ ID NO: 119 |
| CDRH3 | SEQ ID NO: 3 |
| CDRL1 | SEQ ID NO: 4 |
| CDRL2 | SEQ ID NO: 5 |
| CDRL3 | SEQ ID NO: 6 |
| VH | SEQ ID NO: 121 |
| VL | SEQ ID NO: 188 |
| Heavy chain | 249:QVQLVQSGAEVKKPGSSVKVSCKASGGTFSSY AISWVRQAPGQGLEWMGNIGPFFGIANYAQKFQGRV TITADESTSTAYMELSSLRSEDTAVYYCARDTPYFD YWGQGTLVTVSSASTKGPSVFPLAPSSKSTSGGTAA LGCLVKDYFPEPVTVSWNSGALTSGVHTFPAVLQSS GLYSLSSVVTVPSSSLGTQTYICNVNHKPSNTKVDK KVEPKSX (X can be C, EF or CEF) |
| Light chain | SEQ ID NO: 190 |
| PN encoding SEQ ID NO: 121 | SEQ ID NO: 125 |
| PN encoding SEQ ID NO: 188 | SEQ ID NO: 192 |
| PN encoding SEQ ID NO: 249 | 250:CAGGTGCAATTGGTTCAGTCTGGCGCGGAAGT GAAAAAACCGGGCAGCAGCGTGAAAGTGAGCTGCA AGCCTCCGGAGGCACTTTTTCTTCTTATGCCATTTC TTGGGTGCGCCAAGCCCCTGGGCAGGGTCTCGAGTG GATGGGCAATATCGGTCCGTTTTTTGGCATTGCGAA TTACGCGCAGAAGTTTCAGGGCCGGGTGACCATTAC CGCGGATGAAAGCACCAGCACCGCGTATATGGAACT GAGCAGCCTGCGTAGCGAAGATACGGCCGTGTATTA TTGCGCGCGTGATACTCCTTATTTTGATTATTGGGG CCAAGGCACCCTGGTGACGGTTAGCTCAGCGTCGAC CAAAGGTCCAAGCGTGTTTCCGCTGGCTCCGAGCAG CAAAAGCACCAGCGGCGGCACGGCTGCCCTGGGCTG CCTGGTTAAAGATTATTTCCCGGAACCAGTCACCGT GAGCTGGAACAGCGGGGCGCTGACCAGCGGCGTGCA TACCTTTCCGGCGGTGCTGCAAAGCAGCGGCCTGTA TAGCCTGAGCAGCGTTGTGACCGTGCCGAGCAGCAG CTTAGGCACTCAGACCTATATTTGCAACGTGAACCA TAAACCGAGCAACACCAAAGTGGATAAAAAAGTGGA ACCGAAAAGC X (X can be TGC, GAATTC or TGCGAATTC) |
| PN encoding SEQ ID NO: 190 | SEQ ID NO: 194 |
| Antibody 7865 | |
| CDRH1 | SEQ ID NO: 1 |
| CDRH2 | SEQ ID NO: 2 |
| CDRH3 | SEQ ID NO: 3 |
| CDRL1 | SEQ ID NO: 4 |
| CDRL2 | SEQ ID NO: 5 |
| CDRL3 | SEQ ID NO: 120 |
| VH | SEQ ID NO: 187 |
| VL | SEQ ID NO: 122 |
| Heavy chain | SEQ ID NO: 189 |
| Light chain | 251:DIELTQPPSTSTAPGQTARISCSGDSIPNYYT YWYQQKPGQAPVLVIYDDSNRPSGIPERFSGSNSGN TATLTISGTQAEDEADYYCQTYDDGSTAEVFGGGTK LTVLGQPKAAPSVTLFPPSSEELQANKATLVCLISD FYPGAVTVAWKADSSPVKAGVETTTPSKQSNNKYAA SSYLSLTPEQWKSHRSYSCQVTHEGSTVEKTVAPTE X (X can be CS or A) |
| PN encoding SEQ ID NO: 187 | SEQ ID NO: 191 |
| PN encoding SEQ ID NO: 122 | SEQ ID NO: 126 |
| PN encoding SEQ ID NO: 189 | SEQ ID NO: 193 |
| PN encoding SEQ ID NO: 251 | 252:GATATCGAACTGACCCAGCCGCCTTCAGTGAG CGTTGCACCAGGTCAGACCGCGCGTATCTCGTGTAG CGGCGATTCTATTCCTAATTATTATGTTTATTGGTA CCAGCAGAAACCCGGGCAGGCGCCAGTTCTTGTGAT TTATGATGATTCTAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGACTTATGATGATGGTTCTAC TGCTGAGGTGTTTGGCGGCGGCACGAAGTTAACCGT TCTTGGCCAGCCGAAAGCCGCACCGAGTGTGACGCT GTTTCCGCCGAGCAGCGAAGAATTGCAGGCGAACAA AGCGACCCTGGTGTGCCTGATTAGCGACTTTTATCC GGGAGCCGTGACAGTGGCCTGGAAGGCAGATAGCAG CCCCGTCAAGGCGGGAGTGGAGACCACCACACCCTC CAAACAAAGCAACAACAAGTACGCGGCCAGCAGCTA TCTGAGCCTGACGCCTGAGCAGTGGAAGTCCCACAG AAGCTACAGCTGCCAGGTCACGCATGAGGGGAGCAC CGTGGAAAAAACCGTTGCGCCGACTGAGX (X can be TGCAGC or GCC) |
| Antibody 7829 | |
| CDRH1 | SEQ ID NO: 61 |
| CDRH2 | SEQ ID NO: 62 |
| CDRH3 | SEQ ID NO: 63 |
| CDRL1 | SEQ ID NO: 64 |
| CDRL2 | SEQ ID NO: 65 |
| CDRL3 | SEQ ID NO: 209 |
| VH | 253:QTQLTQSGAETKKPGESLKISCKGSGYSFTSY YIGWIRQMPGKGLEWMGIIDPTDSQTAYSPSFQGQV TISADKSISTAYLQWSSLKASDTAMYYCARYMMRGF DHWGQGTLVTVSS |
| VL | SEQ ID NO: 211 |
| Heavy chain | 254:QVQLVQSGAEVKKPGESLKISCKGSGYSFTSY YIGWVRQMPGKGLEWMGIIDPTDSQTAYSPSFQGQV TISADKSISTAYLQWSSLKASDTAMYYCARYMMRGF DHWGQGTLVTVSSASTKGPSVFPLAPSSKSTSGGTA ALGCLVKDYFPEPVTVSWNSGALTSGVHTFPAVLQS SGLYSLSSWTVPSSSLGTQTYICNVNHKPSNTKVDK KVEP KSX (X can be C, EF or CEF) |

TABLE 1-continued

Examples of C5 Antibodies of the
Present Invention and C5 Proteins

| | Sequence Identifier (SEQ ID NO:) or comments/details |
|---|---|
| Light chain | SEQ ID NO: 213 |
| PN encoding SEQ ID NO: 253 | 255: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTATATTGG TTGGGTGCGCCAGATGCCTGGGAAGGGTCTCGAGTG GATGGGCATTATTGATCCTACTGATTCTCAGACTGC TTATTCTCCTTCTTTTCAGGGTCAGGTGACCATTAG CGCGGATAAAAGCATTAGCACCGCGTATCTTCAATG GAGCAGCCTGAAAGCGAGCGATACGGCCATGTATTA TTGCGCGCGTTATATGATGCGTGGTTTTGATCATTG GGGCCAAGGCACCCTGGTGACGGTTAGCTCA |
| PN encoding SEQ ID NO :211 | SEQ ID NO: 215 |
| PN encoding SEQ ID NO: 254 | 256: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTATATTGG TTGGGTGCGCCAGATGCCTGGGAAGGGTCTCGAGTG GATGGGCATTATTGATCCTACTGATTCTCAGACTGC TTATTCTCCTTCTTTTCAGGGTCAGGTGACCATTAG CGCGGATAAAAGCATTAGCACCGCGTATCTTCAATG GAGCAGCCTGAAAGCGAGCGATACGGCCATGTATTA TTGCGCGCGTTATATGATGCGTGGTTTTGATCATTG GGGCCAAGGCACCCTGGTGACGGTTAGCTCAGCGTC GACCAAAGGTCCAAGCGTGTTTCCGCTGGCTCCGAG CAGCAAAAGCACCAGCGGCGGCACGGCTGCCCTGGG CTGCCTGGTTAAAGATTATTTCCCGGAACCAGTCAC CGTGAGCTGGAACAGCGGGGCGCTGACCAGCGGCGT GCATACCTTTCCGGCGGTGCTGCAAAGCAGCGGCCT GTATAGCCTGAGCAGCGTTGTGACCGTGCCGAGCAG CAGCTTAGGCACTCAGACCTATATTTGCAACGTGAA CCATAAACCGAGCAACACCAAAGTGGATAAAAAAGT GGAACCGAAAAGCX (X can be TGC, GAATTC or TGCGAATTC) |
| PN encoding SEQ ID NO: 213 | SEQ ID NO: 217 |
| Antibody 7830 | |
| CDRH1 | SEQ ID NO: 61 |
| CDRH2 | SEQ ID NO: 95 |
| CDRH3 | SEQ ID NO: 63 |
| CDRL1 | SEQ ID NO: 64 |
| CDRL2 | SEQ ID NO: 65 |
| CDRL3 | SEQ ID NO: 209 |
| VH | 257: QVQLVQSGAEVKKPGESLKISCKGSGYSFTSY YIGWIRQMPGKGLEWMGIIDPTDSYTVYSPSFQGQV TISADKSISTAYLQWSSLKASDTAMYYCARYMMRGF DHWGQGTLVTVSS |
| VL | SEQ ID NO: 211 |
| Heavy chain | 258: QVQLVQSGAEVKKPGESLKISCKGSGYSFTSY YIGWVRQMPGKGLEWMGIIDPTDSYTVYSPSFQGQV TISADKSISTAYLQWSSLKASDTAMYYCARYMMRGF DHWGQGTLVTVSSASTKGPSVFPLAPSSKSTSGGTA ALGCLVKDYFPEPVTVSWNSGALTSGVHTFPAVLQS SGLYSLSSWTVPSSSLGTQTYICNVNHKPSNTKVDK KVEPKSX (X can be C, EF or CEF) |
| Light chain | SEQ ID NO: 213 |
| PN encoding SEQ ID NO: 257 | 259: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTATATTGG |

TABLE 1-continued

Examples of C5 Antibodies of the
Present Invention and C5 Proteins

| | Sequence Identifier (SEQ ID NO:) or comments/details |
|---|---|
| | TTGGGTGCGCCAGATGCCTGGGAAGGGTCTCGAGTG GATGGGCATTATTGATCCTACTGATTCTTATACTGT TTATTCTCCTTCTTTTCAGGGTCAGGTGACCATTAG CGCGGATAAAAGCATTAGCACCGCGTATCTTCAATG GAGCAGCCTGAAAGCGAGCGATACGGCCATGTATTA TTGCGCGCGTTATATGATGCGTGGTTTTGATCATTG GGGCCAAGGCACCCTGGTGACGGTTAGCTCA |
| PN encoding SEQ ID NO :211 | SEQ ID NO: 215 |
| PN encoding SEQ ID NO: 258 | 260: CAGGTGCAATTGGTTCAGAGCGGCGCGGAAGT GAAAAAACCGGGCGAAAGCCTGAAAATTAGCTGCAA AGGTTCCGGATATTCCTTTACTTCTTATTATATTGG TTGGGTGCGCCAGATGCCTGGGAAGGGTCTCGAGTG GATGGGCATTATTGATCCTACTGATTCTTATACTGT TTATTCTCCTTCTTTTCAGGGTCAGGTGACCATTAG CGCGGATAAAAGCATTAGCACCGCGTATCTTCAATG GAGCAGCCTGAAAGCGAGCGATACGGCCATGTATTA TTGCGCGCGTTATATGATGCGTGGTTTTGATCATTG GGGCCAAGGCACCCTGGTGACGGTTAGCTCAGCGTC GACCAAAGGTCCAAGCGTGTTTCCGCTGGCTCCGAG CAGCAAAAGCACCAGCGGCGGCACGGCTGCCCTGGG CTGCCTGGTTAAAGATTATTTCCCGGAACCAGTCAC CGTGAGCTGGAACAGCGGGGCGCTGACCAGCGGCGT GCATACCTTTCCGGCGGTGCTGCAAAGCAGCGGCCT GTATAGCCTGAGCAGCGTTGTGACCGTGCCGAGCAG CAGCTTAGGCACTCAGACCTATATTTGCAACGTGAA CCATAAACCGAGCAACACCAAAGTGGATAAAAAAGT GGAACCGAAAAGCX (X can be TGC, GAATTC or TGCGAATTC) |
| PN encoding SEQ ID NO: 213 | SEQ ID NO: 217 |
| Antibody 7871 | |
| CDRH1 | SEQ ID NO: 61 |
| CDRH2 | SEQ ID NO: 77 |
| CDRH3 | SEQ ID NO: 63 |
| CDRL1 | SEQ ID NO: 64 |
| CDRL2 | SEQ ID NO: 65 |
| CDRL3 | SEQ ID NO: 66 |
| VH | SEQ ID NO: 210 |
| VL | 261: DIELTQPPSVSVAPGQTARISCSGDSLGDYYA YWYQQKPGQAPVLVIYKDNNRPSGIPERFSGSNSGN TATLTISGTQAEDEADYYCQTWDTGESGVFGGGTKL TVL |
| Heavy chain | SEQ ID NO: 212 |
| Light chain | 262: DIELTQPPSVSVAPGQTARISCSGDSLGDYYA YWYQQKPGQAPVLVIYKDNNRPSGIPERFSGSNSGN TATLTISGTQAEDEADYYCQTWDTGESGVFGGGTKL TVLGQPKMPSVTLFPPSSEELQANKATLVCLISDFY PGAVTVAWKADSSPVKAGVETTTPSKQSNNKYAASS YLSLTPEQWKSHRSYSCQVTHEGSTVEKTVAPTEX (X can be CS orA) |
| PN encoding SEQ ID NO: 210 | SEQ ID NO: 214 |
| PN encoding SEQ ID NO: 261 | 263: GATATCGAACTGACCCAGCCGCCTTCAGTGAG CGTTGCACCAGGTCAGACCGCGCGCATCTCGTGTAG CGGCGATTCTCTTGGTGATTATTATGCTTATTGGTA CCAGCAGAAACCCGGGCAGGCGCCAGTTCTTGTGAT TTATAAGGATAATAATCGTCCCTCAGGCATCCCGGA |

TABLE 1-continued

Examples of C5 Antibodies of the
Present Invention and C5 Proteins

| | Sequence Identifier (SEQ ID NO:) or comments/details |
|---|---|
| | ACGCTTTAGCGGATCCAACAGCGGCAACACCGCGAC CCTGACCATTAGCGGCACTCAGGCGGAAGACGAAGC GGATTATTATTGCCAGACTTGGGATACTGGTGAGTC TGGTGTGTTTGGCGGCGGCACGAAGTTAACCGTTCT T |
| PN encoding SEQ ID NO: 212 | SEQ ID NO: 216 |
| PN encoding SEQ ID NO: 262 | 264: GATATCGAACTGACCCAGCCGCCTTCAGTGAG CGTTGCACCAGGTCAGACCGCGCGTATCTCGTGTAG CGGCGATTCTCTTGGTGATTATTATGCTTATTGGTA CCAGCAGAAACCCGGGCAGGCGCCAGTTCTTGTGAT TTATAAGGATAATAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGACTTGGGATACTGGTGAGTC TGGTGTGTTTGGCGGCGGCACGAAGTTAACCGTTCT TGGCCAGCCGAAAGCCGCACCGAGTGTGACGCTGTT TCCGCCGAGCAGCGAAGAATTGCAGGCGAACAAAGC GACCCTGGTGTGCCTGATTAGCGACTTTTATCCGGG AGCCGTGACAGTGGCCTGGAAGGCAGATAGCAGCCC CGTCAAGGCGGGAGTGGAGACCACCACACCCTCCAA ACAAAGCAACAACAAGTACGCGGCCAGCAGCTATCT GAGCCTGACGCTGAGCAGTGGAAGTCCCACAGAAG CTACAGCTGCCAGGTCACGCATGAGGGGAGCACCGT GGAAAAAACCGTTGCGCCGACTGAGX (X can be TGCAGC or GCC) |
| Antibody 7872 | |
| CDRH1 | SEQ ID NO: 61 |
| CDRH2 | SEQ ID NO: 77 |
| CDRH3 | SEQ ID NO: 63 |
| CDRL1 | SEQ ID NO: 64 |
| CDRL2 | SEQ ID NO: 65 |
| CDRL3 | SEQ ID NO: 78 |
| VH | SEQ ID NO: 210 |
| VL | 265: DIELTQPPSVSVAPGQTARISCSGDSLGDYYA YWYQQKPGQAPVLVIYKDNNRPSGIPERFSGSNSGN TATLTISGTQAEDEADYYCQTWDILPHGLVFGGGTK LTVL |
| Heavy chain | SEQ ID NO: 212 |
| Light chain | 266: DIELTQPPSVSVAPGQTARISCSGDSLGDYYA YWYQQKPGQAPVLVIYKDNNRPSGIPERFSGSNSGN TATLTISGTQAEDEADYYCQTWDILPHGLVFGGGTK LTVLGQPKAAPSVTLFPPSSEELQANKATLVCLISD FYPGAVTVAWKADSSPVKAGVETTTPSKQSNNKYAA SSYLSLTPEQWKSHRSYSCQVTHEGSTVEKTVAPTE X (X can be CS orA) |
| PN encoding SEQ ID NO: 210 | SEQ ID NO: 214 |
| PN encoding SEQ ID NO: 265 | 267: GATATCGAACTGACCCAGCCGCCTTCAGTGAG CGTTGCACCAGGTCAGACCGCGCGTATCTCGTGTAG CGGCGATTCTCTTGGTGATTATTATGCTTATTGGTA CCAGCAGAAACCCGGGCAGGCGCCAGTTCTTGTGAT TTATAAGGATAATAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGACTTGGGATATTCTTCCTCA TGGTCTTGTGTTTGGCGGCGGCACGAAGTTAACCGT TCTT |

TABLE 1-continued

Examples of C5 Antibodies of the
Present Invention and C5 Proteins

| | Sequence Identifier (SEQ ID NO:) or comments/details |
|---|---|
| PN encoding SEQ ID NO :212 | SEQ ID NO: 216 |
| PN encoding SEQ ID NO: 266 | 268: GATATCGAACTGACCCAGCCGCCTTCAGTGAG CGTTGCACCAGGTCAGACCGCGCGTATCTCGTGTAG CGGCGATTCTCTTGGTGATTATTATGCTTATTGGTA CCAGCAGAAACCCGGGCAGGCGCCAGTTCTTGTGAT TTATAAGGATAATAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGACTTGGGATATTCTTCCTCA TGGTCTTGTGTTTGGCGGCGGCACGAAGTTAACCGT TCTTGGCCAGCCGAAAGCCGCACCGAGTGTGACGCT GTTTCCGCCGAGCAGCGAAGAATTGCAGGCGAACAA AGCGACCCTGGTGTGCCTGATTAGCGACTTTTATCC GGGAGCCGTGACAGTGGCCTGGAAGGCAGATAGCAG CCCCGTCAAGGCGGGAGTGGAGACCACCACACCCTC CAAACAAAGCAACAACAAGTACGCGGCCAGCAGCTA TCTGAGCCTGACGCCTGAGCAGTGGAAGTCCCACAG AAGCTACAGCTGCCAGGTCACGCATGAGGGGAGCAC CGTGGAAAAAACCGTTGCGCCGACTGAGX (X can be TGCAGC or GCC) |
| Antibody 7873 | |
| CDRH1 | SEQ ID NO: 61 |
| CDRH2 | SEQ ID NO: 77 |
| CDRH3 | SEQ ID NO: 63 |
| CDRL1 | SEQ ID NO: 64 |
| CDRL2 | SEQ ID NO: 65 |
| CDRL3 | SEQ ID NO: 89 |
| VH | SEQ ID NO: 210 |
| VL | 269: DIELTQPPSVSVAPGQTARISCSGDSLGDYYA YWYQQKPGQAPVLVIYKDNNRPSGIPERFSGSNSGN TATLTISGTQAEDEADYYCQAWTDSPTGLVFGGGTK LTVL |
| Heavy chain | SEQ ID NO: 212 |
| Light chain | 270: DIELTQPPSVSVAPGQTARISCSGDSLGDYYA YWYQQKPGQAPVLVIYKDNNRPSGIPERFSGSNSGN TATLTISGTQAEDEADYYCQAWTDSPTGLVFGGGTK LTVLGQPKAAPSVTLFPPSSEELQANKATLVCLISD FYPGAVTVAWKADSSPVKAGVETTTPSKQSNNKYAA SSYLSLTPEQWKSHRSYSCQVTHEGSTVEKTVAPTE X (X can be CS or A) |
| PN encoding SEQ ID NO: 210 | SEQ ID NO: 214 |
| PN encoding SEQ ID NO: 269 | 271: GATATCGAACTGACCCAGCCGCCTTCAGTGAG CGTTGCACCAGGTCAGACCGCGCGTATCTCGTGTAG CGGCGATTCTCTTGGTGATTATTATGCTTATTGGTA CCAGCAGAAACCCGGGCAGGCGCCAGTTCTTGTGAT TTATAAGGATAATAATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCCAGGCTTGGACTGATTCTCCTAC TGGTCTTGTGTTTGGCGGCGGCACGAAGTTAACCGT TCTT |
| PN encoding SEQ ID NO :212 | SEQ ID NO: 216 |
| PN encoding SEQ ID NO: 270 | 272: GATATCGAACTGACCCAGCCGCCTTCAGTGAG CGTTGCACCAGGTCAGACCGCGCGTATCTCGTGTAG CGGCGATTCTCTTGGTGATTATTATGCTTATTGGTA |

TABLE 1-continued

Examples of C5 Antibodies of the Present Invention and C5 Proteins

Sequence Identifier (SEQ ID NO:) or comments/details

CCAGCAGAAACCCGGGCAGGCGCCAGTTCTTGTGAT
TTATAAGGATAATAATCGTCCCTCAGGCATCCCGGA
ACGCTTTAGCGGATCCAACAGCGGCAACACCGCGAC
CCTGACCATTAGCGGCACTCAGGCGGAAGACGAAGC
GGATTATTATTGCCAGGCTTGGACTGATTCTCCTAC
TGGTCTTGTGTTTGGCGGCGGCACGAAGTTAACCGT
TCTTGGCCAGCCGAAAGCCGCACCGAGTGTGACGCT
GTTTCCGCCGAGCAGCGAAGAATTGCAGGCGAACAA
AGCGACCCTGGTGTGCCTGATTAGCGACTTTTATCC
GGGAGCCGTGACAGTGGCCTGGAAGGCAGATAGCAG
CCCCGTCAAGGCGGGAGTGGAGACCACCACACCCTC
CAAACAAAGCAACAACAAGTACGCGGCCAGCAGCTA
TCTGAGCCTGACGCCTGAGCAGTGGAAGTCCCACAG
AAGCTACAGCTGCCAGGTCACGCATGAGGGGAGCAC
CGTGGAAAAAACCGTTGCGCCGACTGAGX (X can
be TGCAGC or GCC)

Antibody 7832

| | |
|---|---|
| CDRH1 | SEQ ID NO: 17 |
| CDRH2 | SEQ ID NO: 18 |
| CDRH3 | SEQ ID NO: 19 |
| CDRL1 | SEQ ID NO: 20 |
| CDRL2 | SEQ ID NO: 21 |
| CDRL3 | SEQ ID NO: 22 |
| VH | 273:QVQLVQSGAEVKKPGESLKISCKGSGYSFTNY ISVWRQMPGKGLEWMGIIDPDDSYTEYSPSFQGQVT ISADKSISTAYLQWSSLKASDTAMYYCARYEYGGFD IWGQGTLVTVSS |
| VL | SEQ ID NO: 219 |
| Heavy chain | 274:QVQLVQSGAEVKKPGESLKISCKGSGYSFTNY ISVWRQMPGKGLEWMGIIDPDDSYTEYSPSFQGQVT ISADKSISTAYLQWSSLKASDTAMYYCARYEYGGFD IWGQGTLVTVSSASTKGPSVFPLAPSSKSTSGGTAA LGCLVKDYFPEPVTVSWNSGALTSGVHTFPAVLQSS GLYSLSSWTVPSSSLGTQTYICNVNHKPSNTKVDKK VEPKSX (X can be C, EF or CEF) |
| Light chain | SEQ ID NO: 221 |
| PN encoding SEQ ID NO: 273 | 275:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTGATGATTCTTATACTGAGTA TTCTCCTTCTTTTCAGGGTCAGGTCACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCA |
| PN encoding SEQ ID NO :219 | SEQ ID NO: 223 |
| PN encoding SEQ ID NO: 274 | 276:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTGATGATTCTTATACTGAGTA TTCTCCTTCTTTTCAGGGTCAGGTCACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCAGCGTCGAC CAAAGGTCCAAGCGTGTTTCCGCTGGCTCCGAGCAG CAAAAGCACCAGCGGCGGCACGGCTGCCCTGGGCTG |

CCTGGTTAAAGATTATTTCCCGGAACCAGTCACCGT
GAGCTGGAACAGCGGGGCGCTGACCAGCGGCGTGCA
TACCTTTCCGGCGGTGCTGCAAAGCAGCGGCCTGTA
TAGCCTGAGCAGCGTTGTGACCGTGCCGAGCAGCAG
CTTAGGCACTCAGACCTATATtTGCAACGTGAACCA
TAAACCGAGCAACACCAAAGTGGATAAAAAGTGGA
ACCGAAAAGCX (X can be TGC, GAATTC or
TGCGAATTC)

Antibody 7909

| | |
|---|---|
| CDRH1 | SEQ ID NO: 17 |
| CDRH2 | SEQ ID NO: 107 |
| CDRH3 | SEQ ID NO: 19 |
| CDRL1 | SEQ ID NO: 20 |
| CDRL2 | SEQ ID NO: 21 |
| CDRL3 | SEQ ID NO: 22 |
| VH | 277:QVQLVQSGAEVKKPGESLKISCKGSGYSFTNY ISVWRQMPGKGLEWMGIIDPQDSYTEYSPSFQGQVT ISADKSISTAYLQWSSLKASDTAMYYCARYEYGGFD IWGQGTLVTVSS |
| VL | SEQ ID NO: 219 |
| Heavy chain | 278:QVQLVQSGAEVKKPGESLKISCKGSGYSFTNY ISVWRQMPGKGLEWMGIIDPQDSYTEYSPSFQGQVT ISADKSISTAYLQWSSLKASDTAMYYCARYEYGGFD IWGQGTLVTVSSASTKGPSVFPLAPSSKSTSGGTAA LGCLVKDYFPEPVTVSWNSGALTSGVHTFPAVLQSS GLYSLSSWTVPSSSLGTQTYICNVNHKPSNTKVDKK VEPKSX (X can be C, EF or CEF) |
| Light chain | SEQ ID NO: 221 |
| PN encoding SEQ ID NO: 277 | 279:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTCAGGATTCTTATACTGAGTA TTCTCCTTCTTTTCAGGGTCAGGTCACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCA |
| PN encoding SEQ ID NO: 219 | SEQ ID NO: 223 |
| PN encoding SEQ ID NO: 278 | 280:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTCAGGATTCTTATACTGAGTA TTCTCCTTCTTTTCAGGGTCAGGTCACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCAGCGTCGAC CAAAGGTCCAAGCGTGTTTCCGCTGGCTCCGAGCAG CAAAAGCACCAGCGGCGGCACGGCTGCCCTGGGCTG CCTGGTTAAAGATTATTTCCCGGAACCAGTCACCGT GAGCTGGAACAGCGGGGCGCTGACCAGCGGCGTGCA TACCTTTCCGGCGGTGCTGCAAAGCAGCGGCCTGTA TAGCCTGAGCAGCGTTGTGACCGTGCCGAGCAGCAG CTTAGGCACTCAGACCTATATtTGCAACGTGAACCA TAAACCGAGCAACACCAAAGTGGATAAAAAGTGGA ACCGAAAAGCX (X can be TGC, GAATTC or TGCGAATTC) |

TABLE 1-continued

Examples of C5 Antibodies of the
Present Invention and C5 Proteins

| | Sequence Identifier (SEQ ID NO:) or comments/details |
|---|---|
| Antibody 7910 | |
| CDRH1 | SEQ ID NO: 17 |
| CDRH2 | SEQ ID NO: 113 |
| CDRH3 | SEQ ID NO: 19 |
| CDRL1 | SEQ ID NO: 20 |
| CDRL2 | SEQ ID NO: 21 |
| CDRL3 | SEQ ID NO: 22 |
| VH | 281:QVQLVQSGAEVKKPGESLKISCKGSGYSFTNY ISVWRQMPGKGLEWMGIIDPEDSHTEYSPSFQGQVT ISADKSISTAYLQWSSLKASDTAMYYCARYEYGGFD IWGQGTLVTVSS |
| VL | SEQ ID NO: 219 |
| Heavy chain | 282:QVQLVQSGAEVKKPGESLKISCKGSGYSFTNY ISVWRQMPGKGLEWMGIIDPEDSHTEYSPSFQGQVT ISADKSISTAYLQWSSLKASDTAMYYCARYEYGGFD IWGQGTLVTVSSASTKGPSVFPLAPSSKSTSGGTAA LGCLVKDYFPEPVTVSWNSGALTSGVHTFPAVLQSS GLYSLSSWTVPSSSLGTQTYICNVNHKPSNTKVDKK VEPKSX (X can be C, EF or CEF) |
| Light chain | SEQ ID NO: 221 |
| PN encoding SEQ ID no: 281 | 283:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTGAGGATTCTCATACTGAGTA TTCTCCTTCTTTTCAGGGTCAGGTGACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCA |
| PN encoding SEQ ID NO: 219 | SEQ ID NO: 223 |
| PN encoding SEQ ID NO: 282 | 284:CAGGTGCAATTGGTTCAGAGCGGCGCGGAAGT GAAAAAACCGGGCGAAAGCCTGAAAATTAGCTGCAA AGGTTCCGGATATTCCTTTACTAATTATATTTCTTG GGTGCGCCAGATGCCTGGGAAGGGTCTCGAGTGGAT GGGCATTATTGATCCTGAGGATTCTCATACTGAGTA TTCTCCTTCTTTTCAGGGTCAGGTGACCATTAGCGC GGATAAAAGCATTAGCACCGCGTATCTTCAATGGAG CAGCCTGAAAGCGAGCGATACGGCCATGTATTATTG CGCGCGTTATGAGTATGGTGGTTTTGATATTTGGGG CCAAGGCACCCTGGTGACGGTTAGCTCAGCGTCGAC CAAAGGTCCAAGCGTGTTTCCGCTGGCTCCGAGCAG CAAAAGCACCAGCGGCGGCAGGCTGCCCTGGGCTG CCTGGTTAAAGATTATTTCCCGGAACCAGTCACCGT GAGCTGGAACAGCGGGGCGCTGACCAGCGGCGTGCA TACCTTTCCGGCGGTGCTGCAAAGCAGCGGCCTGTA TAGCCTGAGCAGCGTTGTGACCGTGCCGAGCAGCAG CTTAGGCACTCAGACCTATATTTGCAACGTGAACCA TAAACCGAGCAACACCAAAGTGGATAAAAAGTGGA ACCGAAAAGCX (X can be TGC, GAATTC or TGCGAATTC) |
| Antibody 7875 | |
| CDRH1 | SEQ ID NO: 17 |
| CDRH2 | SEQ ID NO: 49 |
| CDRH3 | SEQ ID NO: 19 |
| CDRL1 | SEQ ID NO: 20 |
| CDRL2 | SEQ ID NO: 21 |
| CDRL3 | SEQ ID NO: 50 |
| VH | SEQ ID NO: 218 |
| VL | 285:DIELTQPPSVSVAPGQTARISCSGDNIGNSYV HWYQQKPGQAPVLVIYKDNDRPSGIPERFSGSNSGN TATLTISGTQAEDEADYYCATWGSEDQVFGGGTKLT VL |
| Heavy chain | SEQ ID NO: 220 |
| Light chain | 286:DIELTQPPSVSVAPGQTARISCSGDNIGNSYV HWYQQKPGQAPVLVIYKDNDRPSGIPERFSGSNSGN TATLTISGTQAEDEADYYCATWGSEDQVFGGGTKLT VLGQPKMPSVTLFPPSSEELQANKATLVCLISDFYP GAVTVAWKADSSPVKAGVETTTPSKQSNNKYAASSY LSLTPEQWKSHRSYSCQVTHEGSTVEKTVAPTEX (X can be CS or A) |
| PN encoding SEQ ID NO :218 | SEQ ID NO: 222 |
| PN encoding SEQ ID NO: 285 | 287:GATATCGAACTGACCCAGCCGCCTTCAGTGAG CGTTGCACCAGGTCAGACCGCGCGTATCTCGTGTAG CGGCGATAATATTGGTAATTCTTATGTTCATTGGTA CCAGCAGAAACCCGGGCAGGCGCCAGTTCTTGTGAT TTATAAGGATAATGATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCGCTACTTGGGGTTCTGAGGATCA GGTGTTTGGCGGCGGCACGAAGTTAACCGTTCTT |
| PN encoding SEQ ID NO: 220 | SEQ ID NO: 224 |
| PN encoding SEQ ID NO: 286 | 288:GATATCGAACTGACCCAGCCGCCTTCAGTGAG CGTTGCACCAGGTCAGACCGCGCGTATCTCGTGTAG CGGCGATAATATTGGTAATTCTTATGTTCATTGGTA CCAGCAGAAACCCGGGCAGGCGCCAGTTCTTGTGAT TTATAAGGATAATGATCGTCCCTCAGGCATCCCGGA ACGCTTTAGCGGATCCAACAGCGGCAACACCGCGAC CCTGACCATTAGCGGCACTCAGGCGGAAGACGAAGC GGATTATTATTGCGCTACTTGGGGTTCTGAGGATCA GGTGTTTGGCGGCGGCACGAAGTTAACCGTTCTTGG CCAGCCGAAAGCCGCACCGAGTGTGACGCTGTTTCC GCCGAGCAGCGAAGAATTGCAGGCGAACAAAGCGAC CCTGGTGTGCCTGATTAGCGACTTTTATCCGGGAGC CGTGACAGTGGCCTGGAAGGCAGATAGCAGCCCCGT CAAGGCGGGAGTGGAGACCACCACACCCTCCAAACA AAGCAACAACAAGTACGCGGCCAGCAGCTATCTGAG CCTGACGCCTGAGCAGTGGAAGTCCCACAGAAGCTA CAGCTGCCAGGTCACGCATGAGGGGAGCACCGTGGA AAAAACCGTTGCGCCGACTGAGX (X can be TGCAGC or GCC) |
| Antibody 7878 | |
| CDRH1 | SEQ ID NO: 17 |
| CDRH2 | SEQ ID NO: 49 |
| CDRH3 | SEQ ID NO: 19 |
| CDRL1 | SEQ ID NO: 20 |
| CDRL2 | SEQ ID NO: 21 |

TABLE 1-continued

Examples of C5 Antibodies of the
Present Invention and C5 Proteins

| | Sequence Identifier
(SEQ ID NO:) or comments/details |
|---|---|
| CDRL3 | SEQ ID NO: 101 |
| VH | SEQ ID NO: 218 |
| VL | 289: DIELTQPPSVSVAPGQTARISCSGDNIGNSYV
HWYQQKPGQAPVLVIYKDNDRPSGIPERFSGSNSGN
TATLTISGTQAEDEADYYCSTWDIEPTYVFGGGTKL
TVL |
| Heavy chain | SEQ ID NO: 220 |
| Light chain | 290: DIELTQPPSVSVAPGQTARISCSGDNIGNSYV
HWYQQKPGQAPVLVIYKDNDRPSGIPERFSGSNSGN
TATLTISGTQAEDEADYYCSTWDIEPTYVFGGGTKL
TVLGQPKAAPSVTLFPPSSEELQANKATLVCLISDF
YPGAVTVAWKADSSPVKAGVETTTPSKQSNNKYAAS
SYLSLTPEQWKSHRSYSCQVTHEGSTVEKTVAPTEX
(X can be CS or A) |
| PN encoding
SEQ ID NO: 218 | SEQ ID NO: 222 |
| PN encoding
SEQ ID NO: 289 | 291: GATATCGAACTGACCCAGCCGCCTTCAGTGAG
CGTTGCACCAGGTCAGACCGCGCGTATCTCGTGTAG
CGGCGATAATATTGGTAATTCTTATGTTCATTGGTA
CCAGCAGAAACCCGGGCAGGCGCCAGTTCTTGTGAT
TTATAAGGATAATGATCGTCCCTCAGGCATCCCGGA
ACGCTTTAGCGGATCCAACAGCGGCAACACCGCGAC
CCTGACCATTAGCGGCACTCAGGCGGAAGACGAAGC
GGATTATTATTGCTCTACTTGGGATATTGAGCCTAC
TTATGTGTTTGGCGGCGGCACGAAGTTAACCGTTCT
T |
| PN encoding
SEQ ID NO: 220 | SEQ ID NO: 224 |
| PN encoding
SEQ ID NO: 290 | 292: GATATCGAACTGACCCAGCCGCCTTCAGTGAG
CGTTGCACCAGGTCAGACCGCGCGTATCTCGTGTAG
CGGCGATAATATTGGTAATTCTTATGTTCATTGGTA
CCAGCAGAAACCCGGGCAGGCGCCAGTTCTTGTGAT
TTATAAGGATAATGATCGTCCCTCAGGCATCCCGGA
ACGCTTTAGCGGATCCAACAGCGGCAACACCGCGAC
CCTGACCATTAGCGGCACTCAGGCGGAAGACGAAGC
GGATTATTATTGCTCTACTTGGGATATTGAGCCTAC
TTATGTGTTTGGCGGCGGCACGAAGTTAACCGTTCT
TGGCCAGCCGAAAGCCGCACCGAGTGTGACGCTGTT
TCCGCCGAGCAGCGAAGAATTGCAGGCGAACAAAGC
GACCCTGGTGTGCCTGATTAGCGACTTTTATCCGGG
AGCCGTGACAGTGGCCTGGAAGGCAGATAGCAGCCC
CGTCAAGGCGGGAGTGGAGACCACCACACCCTCCAA
ACAAAGCAACAACAAGTACGCGGCCAGCAGCTATCT
GAGCCTGACGCCTGAGCAGTGAAGGTCCACAGAAG
CTACAGCTGCCAGGTCACGCATGAGGGGAGCACCGT
GGAAAAAACCGTTGCGCCGACTGAGX (X can be
TGCAGC or GCC) |
| Human
(Homo sapiens)
C5 | 296: MGLLGILCFLIFLGKTWGQEQTYVISAPKIFR
VGASENIVIQVYGYTEAFDATISIKSYPDKKFSYSS
GHVHLSSENKFQNSAILTIQPKQLPGGQNPVSYVYL
EVVSKHFSKSKRMPITYONGFLFIHTOKPVYTPQS
VKVRVYSLNOOLKPAKRETVLTFIDPEGSEVOMVEE
IDHIGIISFPDFKIPSNPRYGMWTIKAKYKEDFSTT
GTAYFEVKEYVLPHFSVSIEPEYNFIGYKNFKNFEI
TIKARYFYNKVVTEADVYITFGIREDLKDDQKEMMQ
TAMQNTMLINGIAQVTFDSETAVKELSYYSLEDLNN
KYLYIAVTVIESTGGFSEEAEIPGIKYVLSPYKLNL
VATPLFLKPGIPYPIKVQVKDSLDQLVGGVPVTLNA
QTIDVNQETSDLDPSKSVTRVDDGVASFVLNLPSGV
TVLEFNVKTDAPDLPENQAREGYRAIAYSSLSQSYL
YIDWTDNHKALLVGEHLNIIVTPKSPYIDKITHYN
YLILSKGKIIHFGTREKFSDASYQSINIPVTQNMVP
SSRLLVYYIVTGEQTAELVSDSVWLNIEEKCGNQLQ
VHLSPDADAYSPGQTVSLNMATGMDSWVALAAVDSA
VYGVQRGAKKPLERVFQFLEKSDLGCGAGGGLNNAN | |

TABLE 1-continued

Examples of C5 Antibodies of the
Present Invention and C5 Proteins

| | Sequence Identifier
(SEQ ID NO:) or comments/details |
|---|---|
| | VFHLAGLTFLTNANADOSQENDEPCKEILRPRRTLQ
KKIEEIAAKYKHSVVKKCCYDGACVNNDETCEQRAA
RISLGPRCIKAFTECCVVASQLRANISHKDMQLGRL
HMKTLLPVSKPEIRSYFPESWLWEVHLVPRRKQLQF
ALPDSLTTWEIQGVGISNTGICVADTVKAKVFKDVF
LEMNIPYSVVRGEQIQLKGTVYNYRTSGMQFCVKMS
AVEGICTSESPVIDHQGTKSSKCVRQKVEGSSSHLV
TFTVLPLEIGLHNINFSLETWFGKEILVKTLRVVPE
GVKRESYSGVTLDPRGIYGTISRRKEFPYRIPLDLV
PKTEIKRILSVKGLLVGEILSAVLSQEGINILTHLP
KGSAEAELMSVVPVFYVFHYLETGNHWNIFHSDPLI
EKQKLKKKLKEGMLSIMSYRNADYSYSVWKGGSAST
WLTAFALRVLGQVNKYVEQNQNSICNSLLWLVENYQ
LDNGSFKENSQYQPIKLQGTLPVEARENSLYLTAFT
VIGIRKAFDICPLVKIDTALIKADNFLLENTLPAQS
TFTLAISAYALSLGDKTHPQFRSIVSALKREALVKG
NPPIYRFWKDNLQHKDSSVPNTGTARMVETTAYALL
TSLNLKDINYVNPVIKWLSEEQRYGGGFYSTQDTIN
AIEGLTEYSLLVKQLRLSMDIDVSYKHKGALHNYKM
TDKNFLGRPVEVLLNDDLIVSTGFGSGLATVHVTTV
VHKTSTSEEVCSFYLKIDTQDIEASHYRGYGNSDYK
RIVACASYKPSREESSSGSSHAVMDISLPTGISANE
EDLKALVEGVDQLFTDYQIKDGHVILQLNSIPSSDF
LCVRFRIFELFEVGFLSPATFTVYEYHRPDKQCTMF
YSTSNIKIQKVCEGAACKCVEADCGQMQEELDLTIS
AETRKQTACKPEIAYAYKVSITSITVENVFVKYKAT
LLDIYKTGEAVAEKOSEITFIKKVTCTNAELVKGRQ
YLIMGKEALQIKYNFSFRYIYPLDSLTWIEYWPRDT
TCSSCQAFLANLDEFAEDIFLNGC |
| Cynomolgus
Macaque
(Macaca
fascicularis)
C5 | 297: MGLLGILCFLIFLGKTWGQEQTYVISAPKIFR
VGASENIVIQVYGYTEAFDATSIKSYPDKKFSYSSG
HVHLSSENKFQNSAVLTIQPKQLPGGQNQVSYVYLE
VVSKHFSKSKKIPITYDNGFLFIHTDKPVYTPDQSV
KVRVYSLNDDLKPAKRETVLTFIDPEGSEIDMVEEI
DHIGIISFPDFKIPSNPRYGMWTIQAKYKEDFSTTG
TAFFEVKEYVLPHFSVSVEPESNFIGYKNFKNFEIT
IKARYFYNKVVTEADVYITFGIREDLKDDQKEMMQT
AMQNTMLINGIAQVTFDSETAVKELSYYSLEDLNNK
YLYIAVTVIESTGGFSEEAEIPGIKYVLSPYKLNLV
ATPLFLKPGIPYSIKVQVKDALDQLVGGVPVTLNAQ
TIDVNQETSDLEPRKSVTRVDDGVASFVVNLPSGVT
VLEFNVKTDAPDLPDENQAREGYRAIAYSSLSQSYL
YIDWTDNHKALLVGEYLNIIVTPKSPYIDKITHYNY
LILSKGKIIHFGTREKLSDASYQSINIPVTQNMVPS
SRLLVYYIVTGEQTAELVSDSVWLNIEEKCGNQLQV
HLSPDADTYSPGQTVSLNMVTGMDSWVALTAVDSAV
YGVQRRAKKPLERVFQFLEKSDLGCGAGGGLNNANV
FHLAGLTFLTNANADDSQENDEPCKEIIRPRRMLQE
KIEEIAAKYKHLVVKKCCYDGVRINHDETCEQRAAR
ISVGPRCVKAFTECCVVASQLRANNSHKDLQLGRLH
MKTLLPVSKPEIRSYFPESWLWEVHLVPRRKQLQFA
LPDSVTTWEIQGVGISNGICVADTIKAKVFKDVFL
EMNIPYSVVRGEQVQLKGTVYNYRTSGMQFCVKMSA
VEGICTSESPVIDHQGTKSSKCVRQKVEGSSNHLVT
FTVLPLEIGLQNINFSLETSFGKEILVKSLRWPEGV
KRESYSGITLDPRGIYGTISRRKEFPYRIPLDLVPK
TEIKRILSVKGLLVGEILSAVLSREGINILTHLPKG
SAEAELMSVVPVFYVFHYLETGNHWNIFHSDPLIEK
RNLEKKLKEGMVSIMSYRNADYSYSVWKGGSASTWL
TAFALRVLGQVNKYVEQNQNSICNSLLWLVENYQLD
NGSFKENSQYQPIKLQGTLPVEARENSLYLTAFTVI
GIRKAFDICPLVKINTALIKADTFLLENTLPAQSTF
TLAISAYALSLGDKTHPQFRSIVSALKREALVKGNP
PIYRFWKDSLQHKDSSVPNTGTARMVETTAYALLTS
LNLKDINYVNPIIKWLSEEQRYGGGFYSTQDTINAI
EGLTEYSLLVKQLRLNMDIDVAYKHKGPLHNYKMTD
KNFLGRPVEVLLNDDLVVSTGFGSGLATVHVTVVH
KTSTSEEVCSFYLKIDTQDIEASHYRGYGNSDYKRI
VACASYKPSKEESSSGSSHAVMDISLPTGINANEED
LKALVEGVDQLFTDYQIKDGHVILQLNSIPSSDFLC
VRFRIFELFEVGFLSPATFTVYEYHRPDKQCTMFYS
TSNIKIQKVCEGATCKCIEADCGQMQKELDLTISAE
TRKQTACNPEIAYAYKVIITSITVENVFVKYKATLL |

TABLE 1-continued

Examples of C5 Antibodies of the
Present Invention and C5 Proteins

Sequence Identifier
(SEQ ID NO:) or comments/details

DIYKTGEAVAEKDSEITFIKKVTCTNAELVKGRQYL
IMGKEALQIKYNFTFRYIYPLDSLTWIEYWPRDTTC
SSCQAFLANLDEFAEDIFLNGC

Other antibodies of the invention include those where the amino acids or nucleic acids encoding the amino acids have been mutated, yet have at least 60, 70, 80, 90 or 95 percent identity to the sequences described in Table 1. In some embodiments, it include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each of these antibodies can bind to C5, the VH, VL, full length light chain, and full length heavy chain sequences (amino acid sequences and the nucleotide sequences encoding the amino acid sequences) can be "mixed and matched" to create other C5-binding antibodies of the invention. Such "mixed and matched" C5-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or antigen binding region thereof having: a heavy chain variable region comprising an amino acid sequence selected from the group consisting of SEQ ID NOs: 7, 23, 39, 51, 67, 79, 96, 108, 114, 121, 137, 151, 165, 179, 187, 201, 210, 218, 227, 241, 253, 257, 273, 277, and 281; and a light chain variable region comprising an amino acid sequence selected from the group consisting of SEQ ID NOs: 8, 24, 40, 52, 68, 80, 90, 102, 122, 138, 152, 166, 180, 188, 202, 211, 219, 228, 242, 261, 265, 269, 285, and 289; wherein the antibody specifically binds to C5 (e.g., human and/or cynomologus C5).

In another aspect, the invention provides (i) an isolated monoclonal antibody having: a full length heavy chain comprising an amino acid sequence that has been optimized for expression in the cell of a mammalian selected from the group consisting of SEQ ID NOs: 9, 25, 41, 53, 69, 81, 97, 109, 115, 123, 139, 153, 167, 181, 189, 203, 212, 220, 229, 243, 249, 254, 258, 274, 278, and 282; and a full length light chain comprising an amino acid sequence that has been optimized for expression in the cell of a mammalian selected from the group consisting of SEQ ID NOs: 10, 26, 42, 54, 70, 82, 91, 103, 124, 140, 154, 168, 182, 190, 204, 213, 221, 230, 244, 251, 262, 266, 270, 286, and 290; or (ii) a functional protein comprising an antigen binding portion thereof.

In another aspect, the present invention provides C5-binding antibodies that comprise the heavy chain and light chain CDR1s, CDR2s and CDR3s as described in Table 1, or combinations thereof. The amino acid sequences of the VH CDR1s of the antibodies are shown in SEQ ID NOs: 1, 17, 33, 61, 131, 145, 159, 173, 195, and 235. The amino acid sequences of the VH CDR2s of the antibodies and are shown in SEQ ID NOs: 2, 18, 34, 49, 62, 77, 95, 107, 113, 119, 132, 146, 160, 174, 196, 226, and 236. The amino acid sequences of the VH CDR3s of the antibodies are shown in SEQ ID NOs: 3, 19, 35, 63, 133, 147, 161, 175, 197, and 237. The amino acid sequences of the VL CDR1s of the antibodies are shown in SEQ ID NOs: 4, 20, 36, 64, 134, 148, 162, 176, 198, and 238. The amino acid sequences of the VL CDR2s of the antibodies are shown in SEQ ID NOs: 5, 21, 37, 65, 135, 149, 163, 177, 199, and 239. The amino acid sequences of the VL CDR3s of the antibodies are shown in SEQ ID NOs: 6, 22, 38, 50, 66, 78, 89, 101, 120, 136, 150, 164, 178, 200, 209, and 240. The CDR regions are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antibodies can bind to C5 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other C5-binding binding molecules of the invention. Such "mixed and matched" C5-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, the present invention provides an isolated monoclonal antibody or antigen binding region thereof comprising a heavy chain variable region CDR1 comprising an amino acid sequence selected from the group consisting of SEQ ID NOs: 1, 17, 33, 61, 131, 145, 159, 173, 195, and 235; a heavy chain variable region CDR2 comprising an amino acid sequence selected from the group consisting of SEQ ID NOs: 2, 18, 34, 49, 62, 77, 95, 107, 113, 119, 132, 146, 160, 174, 196, 226, and 236; a heavy chain variable region CDR3 comprising an amino acid sequence selected from the group consisting of SEQ ID NOs: 3, 19, 35, 63, 133, 147, 161, 175, 197, and 237; a light chain variable region CDR1 comprising an amino acid sequence selected from the group consisting of SEQ ID NOs: 4, 20, 36, 64, 134, 148, 162, 176, 198, and 238; a light chain variable region CDR2 comprising an amino acid sequence selected from the group consisting of SEQ ID NOs: 5, 21, 37, 65, 135, 149, 163, 177, 199, and 239; and a light chain variable region CDR3 comprising an amino acid sequence selected from the group consisting of SEQ ID NOs: 6, 22, 38, 50, 66, 78, 89, 101, 120, 136, 150, 164, 178, 200, 209, and 240; wherein the antibody specifically binds C5.

In a specific embodiment, an antibody that specifically binds to C5 comprising a heavy chain variable region CDR1 of SEQ ID NO:1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6. In another specific embodiment, an antibody that specifically binds to C5 comprising a heavy chain variable region CDR1 of SEQ ID NO: 17; a heavy chain variable region CDR2 of SEQ ID NO: 18; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 22.

In another specific embodiment, an antibody that specifically binds to C5 comprising a heavy chain variable region CDR1 of SEQ ID NO: 33; a heavy chain variable region CDR2 of SEQ ID NO: 34; a heavy chain variable region CDR3 of SEQ ID NO: 35; a light chain variable region CDR1 of SEQ ID NO: 36; a light chain variable region CDR2 of SEQ ID NO: 37; and a light chain variable region CDR3 of SEQ ID NO: 38. In another specific embodiment, an antibody that specifically binds to C5 comprising a heavy chain variable region CDR1 of SEQ ID NO: 17; a heavy chain variable region CDR2 of SEQ ID NO: 49; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 50.

In another specific embodiment, an antibody that specifically binds to C5 comprising a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 66. In another specific embodiment, an antibody that specifically binds to C5 comprising a heavy chain variable region CDR1 of SEQ ID NO: 61; a heavy chain variable region CDR2 of SEQ ID NO: 77; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 78.

In another specific embodiment, an antibody that specifically binds to C5 comprising a heavy chain variable region CDR1 of SEQ ID NO: 61; a heavy chain variable region CDR2 of SEQ ID NO: 77; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 89. In another specific embodiment, an antibody that specifically binds to C5 comprising a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 89.

In another specific embodiment, an antibody that specifically binds to C5 comprising a heavy chain variable region CDR1 of SEQ ID NO: 61; a heavy chain variable region CDR2 of SEQ ID NO: 95; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 89. In another specific embodiment, an antibody that specifically binds to C5 comprising a heavy chain variable region CDR1 of SEQ ID NO: 17; a heavy chain variable region CDR2 of SEQ ID NO: 49; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 101.

In another specific embodiment, an antibody that specifically binds to C5 comprising a heavy chain variable region CDR1 of SEQ ID NO: 17; a heavy chain variable region CDR2 of SEQ ID NO: 107; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 22. In another specific embodiment, an antibody that specifically binds to C5 comprising a heavy chain variable region CDR1 of SEQ ID NO: 17; a heavy chain variable region CDR2 of SEQ ID NO: 107; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 101.

In another specific embodiment, an antibody that specifically binds to C5 comprising a heavy chain variable region CDR1 of SEQ ID NO: 17; a heavy chain variable region CDR2 of SEQ ID NO: 113; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 22. In another specific embodiment, an antibody that specifically binds to C5 comprising a heavy chain variable region CDR1 of SEQ ID NO: 17; a heavy chain variable region CDR2 of SEQ ID NO: 113; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 101.

In another specific embodiment, an antibody that specifically binds to C5 comprising a heavy chain variable region CDR1 of SEQ ID NO: 1; a heavy chain variable region CDR2 of SEQ ID NO: 119; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 120. In another specific embodiment, an antibody that specifically binds to C5 comprising a heavy chain variable region CDR1 of SEQ ID NO: 131; a heavy chain variable region CDR2 of SEQ ID NO: 132; a heavy chain variable region CDR3 of SEQ ID NO: 133; a light chain variable region CDR1 of SEQ ID NO: 134; a light chain variable region CDR2 of SEQ ID NO: 135; and a light chain variable region CDR3 of SEQ ID NO: 136.

In another specific embodiment, an antibody that specifically binds to C5 comprising a heavy chain variable region CDR1 of SEQ ID NO: 145; a heavy chain variable region CDR2 of SEQ ID NO: 146; a heavy chain variable region CDR3 of SEQ ID NO: 147; a light chain variable region CDR1 of SEQ ID NO: 148; a light chain variable region CDR2 of SEQ ID NO: 149; and a light chain variable region CDR3 of SEQ ID NO: 150. In another specific embodiment, an antibody that specifically binds to C5 comprising a heavy chain variable region CDR1 of SEQ ID NO: 159; a heavy chain variable region CDR2 of SEQ ID NO: 160; a heavy chain variable region CDR3 of SEQ ID NO: 161; a light chain variable region CDR1 of SEQ ID NO: 162; a light chain variable region CDR2 of SEQ ID NO: 163; and a light chain variable region CDR3 of SEQ ID NO: 164.

In another specific embodiment, an antibody that specifically binds to C5 comprising a heavy chain variable region CDR1 of SEQ ID NO: 173; a heavy chain variable region CDR2 of SEQ ID NO: 174; a heavy chain variable region CDR3 of SEQ ID NO: 175; a light chain variable region CDR1 of SEQ ID NO: 176; a light chain variable region CDR2 of SEQ ID NO: 177; and a light chain variable region CDR3 of SEQ ID NO: 178. In another specific embodiment, an antibody that specifically binds to C5 comprising a heavy chain variable region CDR1 of SEQ ID NO: 195; a heavy chain variable region CDR2 of SEQ ID NO: 196; a heavy chain variable region CDR3 of SEQ ID NO: 197; a light chain variable region CDR1 of SEQ ID NO: 198; a light chain variable region CDR2 of SEQ ID NO: 199; and a light chain variable region CDR3 of SEQ ID NO: 200.

In another specific embodiment, an antibody that specifically binds to C5 comprising a heavy chain variable region CDR1 of SEQ ID NO: 61; a heavy chain variable region CDR2 of SEQ ID NO: 77; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 209. In another specific embodiment, an antibody that specifically binds to C5 comprising a heavy chain variable region CDR1 of SEQ ID NO: 17; a heavy chain variable region CDR2 of SEQ ID NO: 49; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 22.

In another specific embodiment, an antibody that specifically binds to C5 comprising a heavy chain variable region CDR1 of SEQ ID NO: 33; a heavy chain variable region CDR2 of SEQ ID NO: 226; a heavy chain variable region CDR3 of SEQ ID NO: 35; a light chain variable region CDR1 of SEQ ID NO: 36; a light chain variable region CDR2 of SEQ ID NO: 37; and a light chain variable region CDR3 of SEQ ID NO: 38. In another specific embodiment, an antibody that specifically binds to C5 comprising a heavy chain variable region CDR1 of SEQ ID NO: 235; a heavy chain variable region CDR2 of SEQ ID NO: 236; a heavy chain variable region CDR3 of SEQ ID NO: 237; a light chain variable region CDR1 of SEQ ID NO: 238; a light chain variable region CDR2 of SEQ ID NO: 239; and a light chain variable region CDR3 of SEQ ID NO: 240.

In another specific embodiment, an antibody that specifically binds to C5 comprising a heavy chain variable region CDR1 of SEQ ID NO: 1; a heavy chain variable region CDR2 of SEQ ID NO: 119; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6. In another specific embodiment, an antibody that specifically binds to C5 comprising a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 120.

In another specific embodiment, an antibody that specifically binds to C5 comprising a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 209. In another specific embodiment, an antibody that specifically binds to C5 comprising a heavy chain variable region CDR1 of SEQ ID NO: 61; a heavy chain variable region CDR2 of SEQ ID NO: 95; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 209.

In another specific embodiment, an antibody that specifically binds to C5 comprising a heavy chain variable region CDR1 of SEQ ID NO: 61; a heavy chain variable region CDR2 of SEQ ID NO: 77; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 66. In another specific embodiment, an antibody that specifically binds to C5 comprising a heavy chain variable region CDR1 of SEQ ID NO: 61; a heavy chain variable region CDR2 of SEQ ID NO: 77; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 78.

In another specific embodiment, an antibody that specifically binds to C5 comprising a heavy chain variable region CDR1 of SEQ ID NO: 61; a heavy chain variable region CDR2 of SEQ ID NO: 77; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 89. In another specific embodiment, an antibody that specifically binds to C5 comprising a heavy chain variable region CDR1 of SEQ ID NO: 17; a heavy chain variable region CDR2 of SEQ ID NO: 107; a heavy chain variable region CDR3 of SEQ ID NO: 19; a light chain variable region CDR1 of SEQ ID NO: 20; a light chain variable region CDR2 of SEQ ID NO: 21; and a light chain variable region CDR3 of SEQ ID NO: 22.

In certain embodiments, an antibody that specifically binds to C5 is an antibody that is described in Table 1.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, the present invention provides an antibody or an antigen-binding fragment thereof comprising amino acid sequences that are homologous to the sequences described in Table 1, and said antibody binds to a C5 protein (e.g., human and/or cynomologus C5), and retains the desired functional properties of those antibodies described in Table 1.

For example, the invention provides an isolated monoclonal antibody (or a functional antigen binding fragment thereof) comprising a heavy chain variable region and a light chain variable region, wherein the heavy chain variable region comprises an amino acid sequence that is at least 80%, at least 90%, or at lest 95% identical to an amino acid sequence selected from the group consisting of SEQ ID NOs: 7, 23, 39, 51, 67, 79, 96, 108, 114, 121, 137, 151, 165, 179, 187, 201, 210, 218, 227, 241, 253, 257, 273, 277, or 281; the light chain variable region comprises an amino acid sequence that is at least 80%, at least 90%, or at least 95% identical to an amino acid sequence selected from the group consisting of SEQ ID NOs: 8, 24, 40, 52, 68, 80, 90, 102, 122, 138, 152, 166, 180, 188, 202, 211, 219, 228, 242, 261, 265, 269, 285, or 289; the antibody specifically binds to C5 (e.g., human and/or cynomologus C5), and the antibody can inhibit red blood cell lysis in a hemolytic assay. In a specific example, such antibodies have an $IC_{50}$ value in a hemolytic assay of 20-200 pM when using human C5-depleted serum that is reconstituted with 100 pM human C5.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except an amino acid substitution in no more than 1, 2, 3, 4 or 5 amino acid position. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 7, 23, 39, 51, 67, 79, 96, 108, 114, 121, 137, 151, 165, 179, 187, 201, 210, 218, 227, 241, 253, 257, 273, 277, or 281; and 8, 24, 40, 52, 68, 80, 90, 102, 122, 138, 152, 166, 180, 188, 202, 211, 219, 228, 242, 261, 265, 269, 285, or 289 respectively, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 9, 25, 41, 53, 69, 81, 97, 109, 115, 123, 139, 153, 167, 181, 189, 203, 212, 220, 229, 243, 249, 254, 258, 274, 278, and 282 and full length light chains of any of SEQ ID NOs 10, 26, 42, 54, 70, 82, 91, 103, 124, 140, 154, 168, 182, 190, 204, 213, 221, 230, 244, 251, 262, 266, 270, 286, and 290 respectively, can be obtained by mutagenesis (e.g., site-directed or PCR-mediated mutagenesis) of nucleic acid molecules encoding such polypeptides respectively, followed by testing of the encoded altered antibody for retained function using the functional assays described herein.

In other embodiments, the full length heavy chain and/or full length light chain nucleotide sequences may be 60%, 70%, 80%, 90%, 95%, 96%, 97%, 98% or 99% identical to the sequences set forth above.

In other embodiments, the variable regions of heavy chain and/or light chain nucleotide sequences may be 60%, 70%, 80%, 90%, 95%, 96%, 97%, 98% or 99% identical to the sequences set forth above As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the C5-binding antibodies of the invention. Accordingly, the invention provides an isolated monoclonal antibody, or a functional antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 1, 17, 33, 61, 131, 145, 159, 173, 195, and 235, and conservative modifications thereof; the heavy chain variable region CDR2 amino acid sequences are selected from the group consisting of SEQ ID NOs: 2, 18, 34, 49, 62, 77, 95, 107, 113, 119, 132, 146, 160, 174, 196, 226, and 236, and conservative modifications thereof; the heavy chain variable region CDR3 amino acid sequences are selected from the group consisting of SEQ ID NOs: 3, 19, 35, 63, 133, 147, 161, 175, 197, and 237, and conservative modifications thereof; the light chain variable regions CDR1 amino acid sequences are selected from the group consisting of SEQ ID NOs: 4, 20, 36, 64, 134, 148, 162, 176, 198, and 238, and conservative modifications thereof; the light chain variable regions CDR2 amino acid sequences are selected from the group consisting of SEQ ID NOs: 5, 21, 37, 65, 135, 149, 163, 177, 199, and 239, and conservative modifications thereof; the light chain variable regions of CDR3 amino acid sequences are selected from the group consisting of SEQ ID NOs: 6, 22, 38, 50, 66, 78, 89, 101, 120, 136, 150, 164, 178, 200, 209, and 240, and conservative modifications thereof; the antibody or the antigen-binding fragment thereof specifically binds to C5, and inhibits red blood cell lysis in a hemolytic assay as described herein.

In other embodiments, an antibody of the invention optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the C5-binding antibodies of the invention. Accordingly, the invention provides an isolated monoclonal antibody optimized for expression in a mammalian cell consisting of a full length heavy chain and a full length light chain wherein: the full length heavy chain has amino acid sequences selected from the group of SEQ ID NOs: 9, 25, 41, 53, 69, 81, 97, 109, 115, 123, 139, 153, 167, 181, 189, 203, 212, 220, 229, 243, 249, 254, 258, 274, 278, and 282, and conservative modifications thereof; and the full length light chain has amino acid sequences selected from the group of SEQ ID NOs: 10, 26, 42, 54, 70, 82, 91, 103, 124, 140, 154, 168, 182, 190, 204, 213, 221, 230, 244, 251, 262, 266, 270, 286, and 290, and conservative modifications thereof; the antibody specifically binds to C5 (e.g., human and/or cynomologus C5); and the antibody inhibits red blood cell lysis in a hemolytic assay as described herein. In a specific embodiment, such antibodies have an $IC_{50}$ value in a hemolytic assay of 20-200 pM when using human C5-depleted serum that is reconstituted with 100 pM human C5.

Antibodies that Bind to the Same Epitope

The present invention provides antibodies that bind to the same epitope as do the C5-binding antibodies described in Table 1. Additional antibodies can therefore be identified based on their ability to cross-compete (e.g., to competitively inhibit the binding of, in a statistically significant manner) with other antibodies of the invention in C5 binding assays. The ability of a test antibody to inhibit the binding of antibodies of the present invention to a C5 protein (e.g., human and/or cynomolgus C5) demonstrates that the test antibody can compete with that antibody for binding to C5; such an antibody may, according to non-limiting theory, bind to the same or a related (e.g., a structurally similar or spatially proximal) epitope on the C5 protein as the antibody with which it competes. In a certain embodiment, the antibody that binds to the same epitope on C5 as the antibodies of the present invention is a human monoclonal antibody. Such human monoclonal antibodies can be prepared and isolated as described herein.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or an antigen binding fragment thereof, comprising a heavy chain variable region comprising CDR1 sequences having an amino acid sequence selected from the group consisting of SEQ ID NOs: 1, 17, 33, 61, 131, 145, 159, 173, 195, and 235; CDR2 sequences having an amino acid sequence selected from the group consisting of SEQ ID NOs: 2, 18, 34, 49, 62, 77, 95, 107, 113, 119, 132, 146, 160, 174, 196, 226, and 236; CDR3 sequences having an amino acid sequence selected from the group consisting of SEQ ID NOs: 3, 19, 35, 63, 133, 147, 161, 175, 197, and 237, respectively; and a light chain variable region having CDR1 sequences having an amino acid sequence selected from the group consisting of SEQ ID NOs: 4, 20, 36, 64, 134, 148, 162, 176, 198, and 238; CDR2 sequences having an amino acid sequence selected from the group consisting of SEQ ID NOs: 5, 21, 37, 65, 135, 149, 163, 177, 199, and 239; and CDR3 sequences consisting of an amino acid sequence selected from the group consisting of SEQ ID NOs: 6, 22, 38, 50, 66, 78, 89, 101, 120, 136, 150, 164, 178, 200, 209, and 240, respectively. Thus, such antibodies contain the VH and VL CDR sequences of monoclonal antibodies, yet may contain different framework sequences from these antibodies.

Such framework sequences can be obtained from public DNA databases or published references that include germine antibody gene sequences. For example, germine DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated C5-binding monoclonal antibodies, or an antigen binding fragment thereof, consisting of a heavy chain variable region having: a VH CDR1 region consisting of an amino acid sequence selected from the group having SEQ ID NOs: 1, 17, 33, 61, 131, 145, 159, 173, 195, and 235 or an amino acid sequence having one, two, three, four or five amino acid substitutions, deletions or additions as compared to SEQ ID NOs: 1, 17, 33, 61, 131, 145, 159, 173, 195, and 235; a VH CDR2 region having an amino acid sequence selected from the group consisting of SEQ ID NOs: 2, 18, 34, 49, 62, 77, 95, 107, 113, 119, 132, 146, 160, 174, 196, 226, and 236, or an amino acid sequence having one, two, three, four or five amino acid substitutions, deletions or additions as compared to SEQ ID NOs: 2, 18, 34, 49, 62, 77, 95, 107, 113, 119, 132, 146, 160, 174, 196, 226, and 236; a VH CDR3 region having an amino acid sequence selected from the group consisting of SEQ ID NOs: 3, 19, 35, 63, 133, 147, 161, 175, 197, and 237, or an amino acid sequence having one, two, three, four or five amino acid substitutions, deletions or additions as compared to SEQ ID NOs: 3, 19, 35, 63, 133, 147, 161, 175, 197, and 237; a VL CDR1 region having an amino acid sequence selected from the group consisting of SEQ ID NOs: 4, 20, 36, 64, 134, 148, 162, 176, 198, and 238, or an amino acid sequence having one, two, three, four or five amino acid substitutions, deletions or additions as compared to SEQ ID NOs: 4, 20, 36, 64, 134, 148, 162, 176, 198, and 238; a VL CDR2 region having an amino acid sequence selected from the group consisting of SEQ ID NOs: 5, 21, 37, 65, 135, 149, 163, 177, 199, and 239, or an amino acid sequence having one, two, three, four or five amino acid substitutions, deletions or additions as compared to SEQ ID NOs: 5, 21, 37, 65, 135, 149, 163, 177, 199, and 239; and a VL CDR3 region having an amino acid sequence selected from the group consisting of SEQ ID NOs: 6, 22, 38, 50, 66, 78, 89, 101, 120, 136, 150, 164, 178, 200, 209, and 240, or an amino acid sequence having one, two, three, four or five amino acid substitutions, deletions or additions as compared to SEQ ID NOs: 6, 22, 38, 50, 66, 78, 89, 101, 120, 136, 150, 164, 178, 200, 209, and 240.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to C5. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target C5 protein (e.g., human and/or cynomolgus C5). Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (SciI Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

In some embodiments, the Fabs are converted to silent IgG1 format by changing the Fc region. For example, antibodies 6525-7910 in Table 1 can be converted to silent IgG1 formate by substituting the "X" in the amino acid sequences for the heavy chain with:

```
                                        (SEQ ID NO: 293)
CDKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQ

GNVFSCSVMHEALHNHYTQKSLSLSPGK
``` and substituting the "X" in the amino acid sequence for the light chain with: CS if the light chain is lambda, or C if the light chain is kappa. As used herein, a "silent IgG1" is an IgG1 Fc sequence in which the amino acid sequence has been altered to reduce Fc-mediated effector functions (for example ADCC and/or CDC). Such an antibody will typically have reduced binding to Fc receptors and/or C1q.

In some other embodiments, the Fabs are converted to IgG2 format. For example, antibodies 6525-7910 in Table 1 can be converted to IgG2 format by substituting the constant sequence

```
                                        (SEQ ID NO: 294)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSX
``` with the constant sequence for the heavy chain of IgG2:

```
                                        (SEQ ID NO: 295)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK
``` and substituting the "X" in the amino acid sequence for the light chain with CS if the light chain is lambda, or C if the light chain is kappa.

Human or Humanized Antibodies

The present invention provides fully human antibodies that specifically bind to a C5 protein (e.g., human and/or cynomolgus C5). Compared to the chimeric or humanized antibodies, the human C5-binding antibodies of the invention have further reduced antigenicity when administered to human subjects.

The human C5-binding antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("lest antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Using one of the mouse or chimeric C5-binding antibodies described above as the reference antibody, this method can be readily employed to generate human antibodies that bind to human C5 with the same binding specificity and the same or better binding affinity. In addition, such human C5-binding antibodies can also be commercially obtained from companies which customarily produce human antibodies, e.g., KaloBios, Inc. (Mountain View, Calif.).

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for C5. In certain embodiments herein, the camelid antibody or nanobody is naturally produced in the camelid animal, i.e., is produced by the camelid following immunization with C5 or a peptide fragment thereof, using techniques described herein for other antibodies. Alternatively, the C5-binding camelid nanobody is engineered, i.e., produced by selection for example from a library of phage displaying appropriately mutagenized camelid nanobody proteins using panning procedures with C5 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising an C5-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for C5 and a second binding specificity for a second target epitope. For example, the second target epitope is another epitope of C5 different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poijak et al., 1994

Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to C5. The antigen-binding portions can be linked together via protein fusion or covalent or non covalent linkage. Alternatively, methods of linkage has been described for the bispecific molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280B1. Pentamerizing modules are described for example in PCT/EP97/05897.

Antibodies with Extended Half Life

The present invention provides for antibodies that specifically bind to C5 protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The strategies for increasing half life is especially useful in nanobodies, fibronectin-based binders, and other antibodies or proteins for which increased in vivo half life is desired.

Antibody Conjugates

The present invention provides antibodies or fragments thereof that specifically bind to a C5 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)$_2$ fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a C5 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149 Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.2. Methods of Producing Antibodies of the Invention

5.2.1. Nucleic Acids Encoding the Antibodies

The invention provides substantially purified nucleic acid molecules which encode polypeptides comprising segments or domains of the C5-binding antibody chains described above. Some of the nucleic acids of the invention comprise the nucleotide sequence encoding the heavy chain variable region shown in SEQ ID NO: 7, 23, 39, 51, 67, 79, 96, 108, 114, 121, 137, 151, 165, 179, 187, 201, 210, 218, 227, 241, 253, 257, 273, 277, or 281, and/or the nucleotide sequence encoding the light chain variable region shown in SEQ ID NO: 8, 24, 40, 52, 68, 80, 90, 102, 122, 138, 152, 166, 180, 188, 202, 211, 219, 228, 242, 261, 265, 269, 285, or 289. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting C5 antigen binding capacity.

Also provided in the invention are polynucleotides which encode at least one CDR region and usually all three CDR regions from the heavy or light chain of the C5-binding antibody set forth above. Some other polynucleotides encode all or substantially all of the variable region sequence of the heavy chain and/or the light chain of the C5-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a mature heavy chain variable region sequence that is substantially identical (e.g., at least 80%, 90%, or 99%) to the mature heavy chain variable region sequence set forth in SEQ ID NO: 7, 23, 39, 51, 67, 79, 96, 108, 114, 121, 137, 151, 165, 179, 187, 201, 210, 218, 227, 241, 253, 257, 273, 277, or 281. Some other nucleic acid sequences comprising nucleotide encoding a mature light chain variable region sequence that is substantially identical (e.g., at least 80%, 90%, or 99%) to the mature light chain variable region sequence set forth in SEQ ID NO: 8, 24, 40, 52, 68, 80, 90, 102, 122, 138, 152, 166, 180, 188, 202, 211, 219, 228, 242, 261, 265, 269, 285, or 289.

The polynucleotide sequences can be produced by de novo solid-phase DNA synthesis or by PCR mutagenesis of an existing sequence (e.g., sequences as described in the Examples below) encoding an C5-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the C5-binding antibodies described above. Various expression vectors can be employed to express the polynucleotides encoding the C5-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the C5-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an C5-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an C5-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted C5-binding antibody sequences. More often, the inserted C5-binding antibody sequences are linked to a signal sequences before inclusion in the vector. Vectors to be used to receive sequences encoding C5-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the C5-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express C5-binding polypeptides of the invention. Insect cells in combination with baculovirus vectors can also be used.

In some preferred embodiments, mammalian host cells are used to express and produce the C5-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express C5-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

5.2.2. Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6180370 to Queen et al.

In a certain embodiment, the antibodies of the invention are human monoclonal antibodies. Such human monoclonal antibodies directed against C5 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy ($\mu$ and $\gamma$) and $\kappa$ light chain immunoglobulin sequences, together with targeted mutations that inactivate the endogenous $\mu$ and $\kappa$ chain loci (see e.g., Lonberg, et al., 1994 Nature 368(6474): 856-859). Accordingly, the mice exhibit reduced expression of mouse IgM or K, and in response to immunization, the introduced human heavy and light chain transgenes undergo class switching and somatic mutation to generate high affinity human IgG$\kappa$ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise C5-binding antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise C5-binding antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise C5-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al; U.S. Pat. Nos. 5,427,908 and 5,580,717 to Dower et al; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

5.2.3. Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, LecI3 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)—N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

5.2.4. Methods of Engineering Altered Antibodies

As discussed above, the C5-binding antibodies having VH and VL sequences or full length heavy and light chain sequences shown herein can be used to create new C5-binding antibodies by modifying full length heavy chain and/or light chain sequences, VH and/or VL sequences, or the constant region(s) attached thereto. Thus, in another aspect of the invention, the structural features of a C5-binding antibody of the invention are used to create structurally related C5-binding antibodies that retain at least one functional property of the antibodies of the invention, such as binding to human C5 and also inhibiting one or more functional properties of C5 (e.g., inhibit red blood cell lysis in a hemolytic assay).

For example, one or more CDR regions of the antibodies of the present invention, or mutations thereof, can be combined recombinantly with known framework regions and/or other CDRs to create additional, recombinantly-engineered, C5-binding antibodies of the invention, as discussed above.

Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an C5-binding antibody consisting of: a heavy chain variable region antibody sequence having a CDR1 sequence selected from the group consisting of SEQ ID NOs: 1, 17, 33, 61, 131, 145, 159, 173, 195, and 235, a CDR2 sequence selected from the group consisting of SEQ ID NOs: 2, 18, 34, 49, 62, 77, 95, 107, 113, 119, 132, 146, 160, 174, 196, 226, and 236, and/or a CDR3 sequence selected from the group consisting of SEQ ID NOs: 3, 19, 35, 63, 133, 147, 161, 175, 197, and 237; and a light chain variable region antibody sequence having a CDR1 sequence selected from the group consisting of SEQ ID NOs: 4, 20, 36, 64, 134, 148, 162, 176, 198, and 238, a CDR2 sequence selected from the group consisting of SEQ ID NOs: 5, 21, 37, 65, 135, 149, 163, 177, 199, and 239, and/or a CDR3 sequence selected from the group consisting of SEQ ID NOs: 6, 22, 38, 50, 66, 78, 89, 101, 120, 136, 150, 164, 178, 200, 209, and 240; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing an C5-binding antibody optimized for expression in a mammalian cell consisting of: a full length heavy chain antibody sequence having a sequence selected from the group of SEQ ID NOs: 9, 25, 41, 53, 69, 81, 97, 109, 115, 123, 139, 153, 167, 181, 189, 203, 212, 220, 229, 243, 249, 254, 258, 274, 278, and 282; and a full length light chain antibody sequence having a sequence selected from the group of 10, 26, 42, 54, 70, 82, 91, 103, 124, 140, 154, 168, 182, 190, 204, 213, 221, 230, 244, 251, 262, 266, 270, 286, and 290; altering at least one amino acid residue within the full length heavy chain antibody sequence and/or the full length light chain antibody sequence to create at least one altered antibody sequence; and expressing the altered antibody sequence as a protein.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the C5-binding antibodies described herein, which functional properties include, but are not limited to, specifically binding to human and/or cynomolgus C5; and the antibody inhibit red blood cell lysis in a hemolytic assay.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an C5-binding antibody coding sequence and the resulting modified C5-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

5.3. Characterization of the Antibodies of the Invention

The antibodies of the invention can be characterized by various functional assays. For example, they can be characterized by their ability to inhibit red blood cell lysis in hemolytic assays, their affinity to a C5 protein (e.g., human and/or cynomolgus C5), the epitope binning, their resistance to proteolysis, and their ability to block the complement cascade, for example, their ability to inhibit MAC formation.

Various methods can be used to measure presence of complement pathway molecules and activation of the complement system (see, e.g., U.S. Pat. No. 6,087,120; and Newell et al., J Lab Clin Med, 100:437-44, 1982). For example, the complement activity can be monitored by (i) measurement of inhibition of complement-mediated lysis of red blood cells (hemolysis); (ii) measurement of ability to inhibit cleavage of C3 or C5; and (iii) inhibition of alternative pathway mediated hemolysis.

The two most commonly used techniques are hemolytic assays (see, e.g., Baatrup et al., Ann Rheum Dis, 51:892-7, 1992) and immunological assays (see, e.g., Auda et al., Rheumatol Int, 10:185-9, 1990). The hemolytic techniques measure the functional capacity of the entire sequence—either the classical or alternative pathway. Immunological techniques measure the protein concentration of a specific complement component or split product. Other assays that can be employed to detect complement activation or measure activities of complement components in the methods of the present invention include, e.g., T cell proliferation assay (Chain et al., J Immunol Methods, 99:221-8, 1987), and delayed type hypersensitivity (DTH) assay (Forstrom et al., 1983, Nature 303:627-629; Halliday et al., 1982, in Assessment of Immune Status by the Leukocyte Adherence Inhibition Test, Academic, New York pp. 1-26; Koppi et al., 1982, Cell. Immunol. 66:394-406; and U.S. Pat. No. 5,843,449).

In hemolytic techniques, all of the complement components must be present and functional. Therefore hemolytic techniques can screen both functional integrity and deficiencies of the complement system (see, e.g., Dijk et al., J Immunol Methods 36: 29-39, 1980; Minh et al., Clin Lab Haematol. 5:23-34 1983; and Tanaka et al., J Immunol 86:161-170, 1986). To measure the functional capacity of the classical pathway, sheep red blood cells coated with hemolysin (rabbit IgG to sheep red blood cells) or chicken red blood cells that are sensitized with rabbit anti-chicken antibodies are used as target cells (sensitized cells). These Ag-Ab complexes activate the classical pathway and result in lysis of the target cells when the components are functional and present in adequate concentration. To determine the functional capacity of the alternative pathway, rabbit red blood cells are used as the target cell (see, e.g., U.S. Pat. No. 6,087,120).

To test the ability of an antibody to inhibit MAC (membrane attack complex) formation, a MAC deposition assay can be performed. Briefly, zymosan can be used to activate the alternative pathway and IgM can be used to active the classic pathway. Fabs are pre-incubated with human serum and added to plates coated with zymosan or IgM. Percentage inhibition of MAC deposition can be calculated for each sample relative to baseline (EDTA treated human serum) and positive control (human serum).

The ability of an antibody to bind to C5 can be detected by labelling the antibody of interest directly, or the antibody may be unlabelled and binding detected indirectly using various sandwich assay formats known in the art.

In some embodiments, the C5-binding antibodies of the invention block or compete with binding of a reference C5-binding antibody to a C5 polypeptide. These can be fully human C5-binding antibodies described above. They can also be other mouse, chimeric or humanized C5-binding antibodies which bind to the same epitope as the reference antibody. The capacity to block or compete with the reference antibody binding indicates that a C5-binding antibody under test binds to the same or similar epitope as that defined by the reference antibody, or to an epitope which is sufficiently proximal to the epitope bound by the reference C5-binding antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as a C5 polypeptide. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of a C5-binding antibody with the reference C5-binding antibody for binding to a C5 protein. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using I-125 label (see Morel et al., Molec. Immunol. 25:7-15, 1988); solid phase direct biotin-avidin EIA (Cheung et al., Virology 176: 546-552, 1990); and direct labeled RIA (Moldenhauer et al., Scand. J. Immunol. 32:77-82, 1990). Typically, such an assay involves the use of purified antigen bound to a solid surface or cells bearing either of these, an unlabelled test C5-binding antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected C5-binding monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using a C5 polypeptide coated-ELISA plates. Biotinylated MAb binding can be detected with a strep-avidin-alkaline phosphatase probe. To determine the isotype of a purified C5-binding antibody, isotype ELISAs can be performed. For example, wells of microtiter plates can be coated with 1 μg/ml of anti-human IgG overnight at 4° C. After blocking with 1% BSA, the plates are reacted with 1 μg/ml or less of the monoclonal C5-binding antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal C5-binding antibodies to live cells expressing a C5 polypeptide, flow cytometry can be used. Briefly, cell lines expressing C5 (grown under standard growth conditions) can be mixed with various concentrations of a C5-binding antibody in PBS containing 0.1% BSA and 10% fetal calf serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

C5-binding antibodies of the invention can be further tested for reactivity with a C5 polypeptide or antigenic fragment by Western blotting. Briefly, purified C5 polypeptides or fusion proteins, or cell extracts from cells expressing C5 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Examples of functional assays are also described in the Example section below.

5.4. Prophylactic and Therapeutic Uses

The present invention provides methods of treating a disease or disorder associated with increased complement activity by administering to a subject in need thereof an effective amount of the antibodies of the invention. In a specific embodiment, the present invention provides a method of treating age-related macular degeneration (AMD) by administering to a subject in need thereof an effective amount of the antibodies of the invention.

The antibodies of the invention can be used, inter alia, to prevent progression of dry AMD to wet AMD, to slow and/or prevent progression of geographic atrophy, and to improve vision lost due to dry AMD progression. It can also be used in combination with anti-VEGF therapies for the treatment of wet AMD patients.

In some embodiments, the present invention provides methods of treating a complement related disease or disorder by administering to a subject in need thereof an effective amount of the antibodies of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, post-ischemic reperfusion conditions, myocardial infarction, balloon angioplasty, post-pump syndrome in cardiopulmonary bypass or renal bypass, hemodialysis, renal ischemia, mesenteric artery reperfusion after acrotic reconstruction, infectious disease or sepsis, immune complex disorders and autoimmune diseases, rheumatoid arthritis, systemic lupus erythematosus (SLE), SLE nephritis, proliferative nephritis, hemolytic anemia, and myasthenia gravis. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gasses and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, and immune complex-associated inflammation.

In a specific embodiment, the present invention provides methods of treating a complement related disease or disorder by administering to a subject in need thereof an effective amount of the antibodies of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimers disease and other neurodegenerative conditions, aHUS, glomerulonephritis, bullous pemphigoid or MPGN II.

In a specific embodiment, the present invention provides methods of treating glomerulonephritis by administering to a subject in need thereof an effective amount of a composition comprising an antibody of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH by administering to a subject in need thereof an effective amount of a composition comprising an antibody of the present invention.

In a specific embodiment, the present invention provides methods of reducing the dysfunction of the immune and hemostatic systems associated with extracorporeal circulation by administering to a subject in need thereof an effective amount of a composition comprising an antibody of the present invention. The antibodies of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient.

Subjects to be treated with therapeutic agents of the present invention can also be administered other therapeutic agents with know methods of treating conditions associated with macular degeneration, such as antibiotic treatments as described in U.S. Pat. No. 6,218,368. In other treatments, immunosuppressive agents such as cyclosporine, are agents capable of suppressing immune responses. These agents include cytotoxic drugs, corticosteroids, nonsteroidal antiinflammatory drugs (NSAIDs), specific T-lymphocyte immunosuppressants, and antibodies or fragments thereof (see Physicians' Desk Reference, 53rd edition, Medical Economics Company Inc., Montvale, N.J. (1999). Immunosuppressive treatment is typically continued at intervals for a period of a week, a month, three months, six months or a year. In some patients, treatment is administered for up to the rest of a patient's life.

When the therapeutic agents of the present invention are administered together with another agent, the two can be administered sequentially in either order or simultaneously. In some aspects, an antibody of the present invention is administered to a subject who is also receiving therapy with a second agent (e.g., verteporfin). In other aspects, the binding molecule is administered in conjunction with surgical treatments.

Suitable agents for combination treatment with C5-binding antibodies include agents known in the art that are able to modulate the activities of complement components (see, e.g., U.S. Pat. No. 5,808,109). Other agents have been reported to diminish complement-mediated activity. Such agents include: amino acids (Takada, Y. et al. Immunology 1978, 34, 509); phosphonate esters (Becker, L. Biochem. Biophy. Acta 1967, 147, 289); polyanionic substances (Conrow, R. B. et al. J. Med. Chem. 1980, 23, 242); sulfonyl fluorides (Hansch, C.; Yoshimoto, M. J. Med. Chem. 1974, 17, 1160, and references cited therein); polynucleotides (DeClercq, P. F. et al. Biochem. Biophys. Res. Commun. 1975, 67, 255); pimaric acids (Glovsky, M. M. et al. J. Immunol. 1969, 102, 1); porphines (Lapidus, M. and Tomasco, J. Immunopharmacol. 1981, 3, 137); several antiinflammatories (Burge, J. J. et a! J. Immunol. 1978, 120, 1625); phenols (Muller-Eberhard, H. J. 1978, in Molecular Basis of Biological Degradative Processes, Berlin, R. D. et al., eds. Academic Press, New York, p. 65); and benzamidines (Vogt, W. et al Immunology 1979, 36, 138). Some of these agents function by general inhibition of proteases and esterases. Others are not specific to any particular intermediate step in the complement pathway, but, rather, inhibit more than one step of complement activation. Examples of the latter compounds include the benzamidines, which block C1, C4 and C5 utilization (see, e.g., Vogt et al. Immunol. 1979, 36, 138).

Additional agents known in the art that can inhibit activity of complement components include K-76, a fungal metabolite from Stachybotrys (Corey et al., J. Amer. Chem. Soc. 104: 5551, 1982). Both K-76 and K-76 COOH have been shown to inhibit complement mainly at the C5 step (Hong et al., J. Immunol. 122: 2418, 1979; Miyazaki et al., Microbiol. Immunol. 24: 1091, 1980), and to prevent the generation of a chemotactic factor from normal human complement (Bumpers et al., Lab. Clinc. Med. 102: 421, 1983). At high concentrations of K-76 or K-76 COOH, some inhibition of the reactions of C2, C3, C6, C7, and C9 with their respective preceding intermediaries is exhibited. K-76 or K-76 COOH has also been reported to inhibit the C3b inactivator system of complement (Hong et al., J. Immunol. 127: 104-108, 1981). Other suitable agents for practicing methods of the present invention include griseofulvin (Weinberg, in Principles of Medicinal Chemistry, 2d Ed., Foye, W. O., ed., Lea & Febiger, Philadelphia, Pa., p. 813, 1981), isopannarin (Djura et al., Aust. J. Chem. 36: 1057, 1983), and metabolites of *Siphonodictyon coralli-phagum* (Sullivan et al., Tetrahedron 37: 979, 1981).

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related disease as described above with a C5-binding antibody of the invention and an anti-angiogenic, such as anti-VEGF agent.

5.5. Diagnostic Uses

In one aspect, the invention encompasses diagnostic assays for determining C5 protein and/or nucleic acid expression as well as C5 protein function, in the context of a biological sample (e.g., blood, serum, cells, tissue) or from individual is afflicted with a disease or disorder, or is at risk of developing a disorder associated with AMD.

Diagnostic assays, such as competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers. In an assay of this form, competitive binding between antibodies and C5-binding antibodies results in the bound C5 protein, preferably the C5 epitopes of the invention, being a measure of antibodies in the serum sample, most particularly, neutralising antibodies in the serum sample.

A significant advantage of the assay is that measurement is made of neutralising antibodies directly (i.e., those which interfere with binding of C5 protein, specifically, epitopes). Such an assay, particularly in the form of an ELISA test has considerable applications in the clinical environment and in routine blood screening.

Immunologic techniques employ polyclonal or monoclonal antibodies against the different epitopes of the various complement components (e.g., C3, C4, C5) to detect, e.g., the split products of complement components (see, e.g., Hugli et al., Immunoassays Clinical Laboratory Techniques 443-460, 1980; Gorski et al., J Immunol Meth 47: 61-73, 1981; Linder et al., J Immunol Meth 47: 49-59, 1981; and Burger et al., J Immunol 141: 553-558, 1988). Binding of the antibody with the split product in competition with a known concentration of labeled split product could then be measured. Various assays such as radio-immunoassays, ELISA's, and radial diffusion assays are available to detect complement split products.

The immunologic techniques provide high sensitivity to detect complement activation, since they allow measurement of split-product formation in blood from a test subject and control subjects with or without macular degeneration-related disorders. Accordingly, in some methods of the present invention, diagnosis of a disorder associated with ocular disorders is obtained by measurement of abnormal complement activation through quantification of the soluble split products of complement components in blood plasma from a test subject. The measurements can be performed as described, e.g., in Chenoweth et al., N Engl J Med 304: 497-502, 1981; and Bhakdi et al., Biochim Biophys Acta 737: 343-372, 1983. Preferably, only the complement activation formed in vivo is measured. This can be accomplished by collecting a biological sample from the subject (e.g., serum) in medium containing inhibitors of the complement system, and subsequently measuring complement activation (e.g., quantification of the split products) in the sample.

In the clinical diagnosis or monitoring of patients with disorders associated with ocular diseases or disorders, the detection of complement proteins in comparison to the levels in a corresponding biological sample from a normal subject is indicative of a patient with disorders associated with macular degeneration.

In vivo diagnostic or imaging is described in US2006/0067935. Briefly, these methods generally comprise administering or introducing to a patient a diagnostically effective amount of a C5 binding molecule that is operatively attached to a marker or label that is detectable by non-invasive methods. The antibody-marker conjugate is allowed sufficient time to localize and bind to complement proteins within the eye. The patient is then exposed to a detection device to identify the detectable marker, thus forming an image of the location of the C5 binding molecules in the eye of a patient. The presence of C5 binding antibody or an antigen-binding fragment thereof is detected by determining whether an antibody-marker binds to a component of the eye. Detection of an increased level in selected complement proteins or a combination of protein in comparison to a normal individual without AMD disease is indicative of a predisposition for and/or on set of disorders associated with macular degeneration. These aspects of the invention are also preferred for use in eye imaging methods and combined angiogenic diagnostic and treatment methods.

The invention also pertains to the field of predictive medicine in which diagnostic assays, prognostic assays, pharmacogenomics, and monitoring clinical trials are used for prognostic (predictive) purposes to thereby treat an individual prophylactically.

The invention also provides for prognostic (or predictive) assays for determining whether an individual is at risk of developing a disorder associated with dysregulation of complement pathway activity. For example, mutations in a C5 gene can be assayed in a biological sample. Such assays can be used for prognostic or predictive purpose to thereby prophylactically treat an individual prior to the onset of a disorder characterized by or associated with C5 protein, nucleic acid expression or activity.

Another aspect of the invention provides methods for determining C5 nucleic acid expression or C5 protein activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs) on the expression or activity of C5 protein in clinical trials.

5.6. Pharmaceutical Compositions

The invention provides pharmaceutical compositions comprising the C5-binding antibodies (intact or binding fragments) formulated together with a pharmaceutically acceptable carrier. The compositions can additionally contain one or more other therapeutical agents that are suitable for treating or preventing a complement-associated disease (e.g., AMD). Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. In a specific embodiment, the antibodies of the invention are formulated so that they can be administered intravitreally into the eye. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the C5-binding antibody is employed in the pharmaceutical compositions of the invention. The C5-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. An exemplary treatment regime entails systemic administration once per every two weeks or once a month or once every 3 to 6 months. For intravitreal administration with an antibody, the dosage ranges from about 0.0001 to about 10 mg. An exemplary treatment regime entails systemic administration once per every two weeks or once a month or once every 3 to 6 months.

Antibody is usually administered on multiple occasions. Intervals between single dosages can be weekly, monthly or yearly. Intervals can also be irregular as indicated by measuring blood levels of C5-binding antibody in the patient. In some methods of systemic administration, dosage is adjusted to achieve a plasma antibody concentration of 1-1000 µg/ml and in some methods 25-500 µg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

6. EXAMPLES

The following examples are provided to further illustrate the invention but not to limit its scope. Other variants of the invention will be readily apparent to one of ordinary skill in the art and are encompassed by the appended claims.

Example 1

Generation of Cynomolgus C5 and Human C5

1. Generation of Cynomolgus C5

Cynomolgus C5 was purified successfully from cynomolgus serum by affinity chromatography using MOR07086 hu IgG1. Cynomolgus C5 was quality tested by SDS-PAGE, Western blot, mass spectrometry and hemolytic assays. Quality of purified cynomolgus C5 was shown to be high by SDS-PAGE and Western blot. Lack of C3 contamination was confirmed by SDS and Western blot. In addition, the identity of cynomolgus C5 sequence was determined by mass spectrometric analysis and the activity of purified cynomolgus C5 was tested in hemolytic assays. In hemolytic assays the new preparation was equipotent to human C5 (e.g., Sample 6, which was used in affinity maturation pannings, reconstituted complement activity of 20% human C5-depleted serum with similar activity to purified human C5).

2. Quality Control of Human and Cynomolgus Biotinylated and Non-Biotinylated C5 Proteins Bioactivity of purified human C5 was characterized and confirmed by the alternative pathway hemolytic activity. C5 was spiked into C5-depleted human serum at varying concentrations to obtain an EC50. EC50 values ranging between 0.02-0.1 nM were considered acceptable.

Before using, the bioactivity of every purified human C5 protein lot was tested in the hemolytic assay. The same quality control was done for cynomolgus C5 after purification from cynomolgus serum. After biotinylation of human and cynomolgus C5, the bioactivity of the material was also tested in hemolytic assays, in order to analyze if there was a loss of activity caused by biotinylation.

Example 2

Generation of C5-Specific Antibodies from the HuCAL GOLD® Library

C5 antibodies were generated by selection of clones having high binding affinities, using as the source of antibody variant proteins a commercially available phage display library, the MorphoSys HuCAL GOLD® library.

HuCAL GOLD® library is a Fab library (Knappik et al., 2000) in which all six CDRs are diversified by appropriate mutation, and which employs the CysDisplay™ technology for linking the Fab to the phage surface (WO01/05950, Löhning et al., 2001).

1. Selection by Panning of C5 Specific Antibodies from the Library

For the selection of antibodies against C5, two different panning strategies were applied. The six different pools were individually subjected to three rounds of: (a) a solid phase panning where the antigens (human and cynomolgus C5) were directly coated on MaxiSorp® 96 well microliter plates (Nunc, Wiesbaden, Germany); or (b) a solution panning with biotinylated human and cyno C5 where the phage-antigen complex was captured by Streptavidin magnetic beads (Dynabeads M-280; Dynal) for each panning pool.

The HuCAL GOLD® library was amplified in 2×YT medium containing 34 µg/ml chloramphenicol and 1% glucose (2×YT-CG). After infection with VCSM13 helper phage at an OD600 nm of 0.5 (30 min at 37° C. without shaking; 30 min at 37° C. shaking at 250 rpm), cells were spun down (4120 g; 5 min; 4° C.), resuspended in 2×YT/34 µg/ml chloramphenicol/50 tag/ml kanamycin/0.25 mM IPTG and grown overnight at 22° C. Phage were PEG-precipitated from the supernatant, resuspended in PBS/20% glycerol and stored at −80° C. Phage amplification between two panning rounds was conducted as follows: mid-log phase E. coli TG1 cells were infected with eluted phage and plated onto LB-agar supplemented with 1% of glucose and 34 µg/ml of chloramphenicol (LB-CG plates). After overnight incubation at 30° C., the TG1 colonies were scraped off the agar plates and used to inoculate 2×YT-CG until an OD600 nm of 0.5 was reached. VCSM13 helper phage were added for infection as described above.

Taken together 354 clones derived from all panning strategies were sequenced, resulting in 64 unique clones with the desired profile: binding to human and cynomolgus C5 and no binding to the counter targets C3 and C4.

45 clones derived from solid phase pannings and 19 clones from solution pannings were selected for protein expression and purification. Four Fabs from solid phase pannings (MOR06525, MOR06756, MOR06757 and MOR06763) and 6 Fabs from solution pannings (MOR07086, MOR07087, MOR07091, MOR07092, MOR07093 and MOR07094) entered affinity maturation.

Solid Phase Panning Against C5 on Directly Coated Protein

The first panning variant was solid phase panning alternating human C5 (first and third round of selection) and cynomolgus C5 (second round of selection).

Three wells of a MaxiSorp® plate (F96 Nunc-Innmuno® plate) were coated with 200 µl of 50 nM C5 each o/n at 4° C. The coated wells were washed 2× with 400 µl PBS and blocked with 350 µl 5% MPBS for 2 h at RT on a microtiter plate shaker. For each panning about $10^{13}$ HuCAL GOLD® phage-antibodies were blocked with equal volume of PBST/5% milk powder for 2 h at room temperature. The coated wells were washed 2× with 400 µl PBS after the blocking procedure. 200 µl of pre-blocked HuCAL GOLD® phage-antibodies were added to each coated well and incubated for 2 h at RT on a shaker. Washing was performed by adding five times 350 µl PBS/0.05% Tween, followed by washing another five times with PBS. For some panning conditions a more stringent wash procedure was applied.

Elution of phage from the plate was performed with 200 µl 20 mM DTT in 10 mM Tris/HCl pH8 per well for 10 min. The DTT phage eluate was added to 15 ml of E. coli TG1, which were grown to an OD600 of 0.6-0.8 at 37° C. in 2YT medium and incubated in 50 ml plastic tubes for 45 min at 37° C. without shaking for phage infection. After centrifugation for 5 min at 4120×g, the bacterial pellets were each resuspended in 600 µl 2×YT medium, plated on 3×YT-CG agar plates and incubated overnight at 37° C. Colonies were scraped off the plates and phages were rescued and amplified as described above.

The second and third rounds of solid phase panning were performed according to the protocol of the first round. In the second selection round for some panning conditions the output of the first round was used for selections on cynomolgus C5 in order to enrich for cynomolgus cross-reactive antibodies.

For some panning conditions washing stringency was increased and antigen concentration was decreased within the three round of selection in order to generate high affinity antibodies.

The HuCAL GOLD® phagemid library was used to select specific Fab antibody fragments against human C5. First strategy was a solid phase panning on directly coated human C5 protein (panning procedure described above).

After the 3rd panning round, the enriched phage pools were subcloned from the pMORPH® 23 library vector (allowing efficient antibody display on the phage surface) into the pMORPH®×9_Fab_MH expression vector which mediates periplasmic expression of soluble Fabs. Single clones were picked and soluble Fabs were expressed from these single clones.

In total, 6624 clones were analyzed in primary screening which was performed by binding of the Fabs directly from the bacterial lysates to human C5 immobilized on Maxisorp microliter plates. 1660 hits were obtained from the primary screening on human C5 with signals >5-fold over background. 384 hits were further analyzed in a secondary screening to confirm binding on human C5 and to screen for binding to the counter targets human C3 and C4.

Many primary hits could be confirmed on human C5 and showed no cross-reactivity to human C3 and C4, but only 6 Fabs had weak cross-reactivity to cynomolgus C5.

As a first consequence new soild phase pannings were performed alternating on human and cynomolgus C5. In parallel, quality controls of the purified cynomolgus C5 batch revealed a high amount of cynomolgus C3 within the cynomolgus C5 batch. Considering this results, a new method to screen for cynomolgus cross-rective antibodies was applied. Cynomolgus C5 was captured from cynomolgus serum using an C5-binding polyclonal antibody (see Example 3, section 3). Using this method the initial primary hits were screened again on cynomolgus C5 and 56 clones were confirmed for binding to cynomolgus C5.

For the alternating solid phase pannings, the 1st round output of the most successful 12 human solid phase pannings was used for selections on cynomolgus C5 (protein batch contaminated with cynomolgus C3; not known during pannings). 376 clones were confirmed in a secondary screening for binding to human C5 and 361 clones for binding to cynomolgus C5 captured from cynomolgus serum.

Solution Panning on Biotinylated C5 Protein

The second panning variant was solution panning against biologically active (in hemolytic assays) biotinylated human C5 and biotinylated cynomolgus C5.

For this panning 200 µl of Streptavidin magnetic beads (Dynabeads® M-280; Dynal) were washed once with PBS and blocked with Chemiblocker for 2 h at RT. 300 µl of the PBS diluted phage were blocked also with Chemiblocker for 1-2 h at RT on a rotator. The blocked phages were twice pre-adsorbed against 50 µl blocked Streptavidin magnetic beads for 30 min. The phage supernatant was transferred to a new blocked 2 ml reaction tube and human biotinylated C5 was added and incubated for 1 h at RT on a rotator. 100 µl of the blocked Streptavidin magnetic beads were added to each panning pool an incubated for 10 min on a rotator. The beads were collected with a particle separator (Dynal MPC-E) for approx. 2.5 min and the solution was removed carefully.

Beads were then washed 7× in PBS/0.05% Tween using a rotator, followed by washing another three times with PBS. Elution of phage from the Dynabeads was performed by adding 200 µl 20 mM DTT in 10 mM Tris/HCl pH 8 to each tube and incubation for 10 min. Dynabeads were removed by the magnetic particle separator and the supernatant was added to 15 ml of an *E. coli* TG-1 culture grown to OD600 nm of 0.6-0.8. Beads were then washed once with 200 µl PBS and together with additionally removed phages the PBS was added to the 15 ml *E. coli* TG-1 culture. For phage infection, the culture was incubated in 50 ml plastic tubes for 45 min at 37° C. without shaking. After centrifugation for 5 min at 4120×g, the bacterial pellets were resuspended each in 600 µl 2×YT medium, plated on 3×YT-CG agar plates and incubated overnight at 37° C. Colonies were scraped off the plates and phages were rescued and amplified as described above. The second and third rounds of selection were performed in an identical way to the first round of selection.

A further panning strategy was solution panning using human C5 and alternating human and cynomolgus C5 (protein batch contaminated with cynomolgus C3, not known during pannings). Therefore the proteins were biotinylated and the retained bio-functionality after the biotinylation procedure was confirmed in hemolytic bioassays.

The phage-antigen complex was captured on Streptavidin magnetic beads via the biotin moiety of the antigen. After washing only specific bound phage were eluted (panning procedure described above).

First screening was done on directly coated proteins (see Example 3, section 1) and only 80 clones could be confirmed on human C5. Due to the fact that during the pannings the antigen was kept in solution, a new screening method was developed. In a solution ELISA the Fabs were incubated with biotinylated antigen on a NeutrAvidin plate. Using this solution screening procedure, a significantly higher amount of human and cynomolgus C5 specific clones could be selected. These results confirmed that many Fabs derived from solution pannings recognize C5 only in solution or when captured (e.g. via a polyclonal C5-binding antibody).

2. Subcloning and Expression of Selected Fab Fragments

To facilitate rapid expression of soluble Fabs, the Fab-encoding inserts of the selected HuCAL GOLD® phages were subcloned via XbaI and EcoRI into the *E. coli* expression vector pMORP®x9_MH. Fab fragments carry a C-terminal Myc tag and as a second C-terminal tag the 6×His-tag (Chen et al., Gene 139:73-75 (1994)). After transformation of the expression plasmids into *E. coli* TG1 F-cells chloramphenicol-resistant single clones were picked into the wells of a sterile 384-well microtiter plate pre-filled with 60 µl 2×YT-CG medium and grown o/n at 30° C. 5 µl of each *E. coli* TG-1 o/n culture were transferred to a fresh, sterile 96-well microtiter plate pre-filled with 40 µl 2×YT medium supplemented with 34 µg/ml chloramphenicol per well. The microtiter plates were incubated at 30° C. shaking at 400 rpm on a microplate shaker until the cultures were slightly turbid (~2-4 h) with an OD600 nm of ~0.5. To these expression plates, 10 µl 2×YT medium supplemented with 34 µg/ml chloramphenicol and 3 mM IPTG (isopropyl-β-D-thiogalactopyranoside) was added per well (end concentration 0.5 mM IPTG). The microtiter plates were sealed with a gas-permeable tape, and incubated o/n at 30° C. shaking at 400 rpm. To each well of the expression plates, 15 µl BEL buffer was added containing 2.5 mg/ml lysozyme, 4 mM EDTA and 10U/µl Benzonase and incubated for 1 h at 22° C. on a microtiter plate shaker (400 rpm) followed by an optional freezing step for at least 2 h at −80° C. The BEL extracts were used for binding analysis by ELISA or Fab SET screening after affinity maturation.

Expression of Fab fragments encoded by pMORPH®x 9_Fab_MH in TG-1 cells was carried out in shaker flask cultures using 750 ml of 2×YT medium supplemented with 34 µg/ml chloramphenicol. Cultures were shaken at 30° C. until the OD600 nm reached 0.5. Expression was induced by addition of 0.75 mM IPTG for 20 h at 30° C. Cells were disrupted using lysozyme and Fab fragments isolated by Ni-NTA chromatography (Qiagen, Hilden, Germany). Buffer exchange to 1× Dulbecco's PBS (pH 7.2) was performed using PD10 columns. Samples were filtered sterile (0.2 µm, Millipore). Purity of samples was determined in denatured, reduced state by SDS-PAGE (15% Criterion Gels, BioRad) and in native state by size exclusion chromatography (HP-SEC). Protein concentrations were determined by UV-spectrophotometry (Krebs et al., J. Immunol. Methods 254:67-84 (2001)).

On Fab level, the overall expression rates and the percentage of monomeric fraction in SEC (Size Exclusion Chromatography) ranged from acceptable to good for most of the identified antibody fragments. 64 parental Fabs were expressed and 61 Fabs could be purified. 60 affinity matured Fabs were purified in the mg scale. Most of the Fabs were good expressors and had no aggregation tendency.

Example 3

Identification of C5-Specific Antibodies from the HUCAL GOLD® Library

Below four different Enzyme Linked Immunosorbent Assay (ELISA) methods describe the screening of C5-binding antibodies (as bacterial BEL lysates or purified Fabs) on specific and counter antigens.

1. Screening on Directly Coated Protein

MaxiSorp® (Nunc, Rochester, N.Y., USA) 384 well plates were coated with 20 µl per well of 2.5 µg/ml antigen (human C5 and the counter proteins human C3 and C4) in PBS, pH 7.4 o/n at 4° C. In parallel, plates were coated with 20 µl per well of 5 µg/ml sheep anti-human IgG, Fd fragment specific (The Binding Site, Birmingham, UK), diluted in PBS, pH 7.4 to check for Fab expression level.

The plates were blocked with PBS/0.05% Tween 20 (PBST) containing 5% milk powder for 1-2 h at RT. After washing the wells with PBST, BEL-extracts, purified HuCAL GOLD® Fabs or control Fabs diluted in PBS were added and incubated for 1 h at RT. To detect Fab binding, anti-HIS6 antibody coupled to peroxidase was applied (Roche).

For detection of POD-conjugates fluorogenic substrate QuantaBlu™ (Pierce) was used according to manufacturer's instructions. Between all incubation steps, the wells of the microtiter plates were washed three times and five times with PBST after the final incubation with the secondary antibody. Fluorescence was measured in a Tecan GENios Pro plate reader.

2. Solution Screening with Biotinylated Proteins

The ELISA method described below was used for screening of HuCAL GOLD® Fabs after solution pannings using biotinylated complement proteins.

NeutrAvidin plates were blocked with 1× Chemiblocker (Chemicon) diluted in PBS o/n at 4° C. These plates were used to screen for binding to human C5 and to the counter targets C3 and C4. In parallel, MaxiSorp® 384 well plates (Nunc, Rochester, N.Y., USA) were coated with 20 µl per well of 5 µg/ml sheep anti-human IgG, Fd fragment specific (The Binding Site, Birmingham, UK), diluted in PBS, pH 7.4. These plates were used to check for Fab expression levels and for non-specific biotin binding. On the next day, coated MaxiSorp® plates were washed 2× with PBST and blocked with 3% BSA in TBS for 1-2 h at RT. Periplasmic BEL extracts containing Fabs or purified HuCAL GOLD Fabs were added to both blocked NeutrAvidin and MaxiSorp® plates.

Subsequently, 20 µl per well of biotinylated human C5 (to detect specific binding) and in parallel, biotinylated human C3 and C4 (to detect unwanted binding) were added to wells of the NeutrAvidin plates. The biotinylated antigens were incubated with the HuCAL GOLD®Fabs for 1-2 h at RT. Biotinylated unrelated antigen Transferrin was then added to the MaxiSorp® plates to check for biotin binding Fabs (in this case the HuCAL®-Fab fragments were previously captured via anti-Fd antibody).

Following secondary antibodies were applied for detection: Alkaline phosphatase (AP)-conjugated Streptavidin-AP AffiniPure F(ab')2 fragment, goat anti-human, was added to the MaxiSorp® expression plates; anti-HIS6 Peroxidase conjugated mouse antibody, Roche, was added to the NeutrAvidin plates and Streptavidin-Alkaline Phosphatase, ZYMED, was added to the MaxiSorp® plates with the biotinylated Transferrin.

For detection of AP-conjugates, fluorogenic substrate AttoPhos® (Roche Diagnostics, Mannheim, Germany) and for detection of POD-conjugates, fluorogenic substrate QuantaBlu™ (Pierce) were used according to manufacturer's instructions. Fluorescence was measured in a Tecan GENios Pro plate reader.

Using this method it was possible to screen for anti-human C5 Fabs which recognize human C5 in solution and to exclude antibodies binding to the biotin moiety of the target antigens.

3. Determination of Cross-Reactivity to Cynomolgus C5

A polyclonal C5-binding antibody (US Biological Cat#C7850-24) was used to capture cynomolgus C5 from cynomolgus serum.

384 well MaxiSorp® plates were coated with 20 µl/well of 5 µg/ml polyclonal C5-binding in PBS and incubated o/n at 4° C. On the next day the plates were washed 3× with PBST and blocked with 100 µl/well of diluent (4% BSA/0.1% Tween20/0.1% Triton-X 100/PBS) for 2 hours at RT. Cynomolgus serum was diluted 1:20 in diluent (4% BSN 0.1% Tween20/0.1% Triton-X 100/PBS) (~approx. concentration of cynomolgus C5 4 µg/ml) and 20 µl/well was added to the 2×PBST washed MaxiSorp® plates. After 1 h incubation at RT the plates were washed 3×PBST and BEL lysates containing Fab fragments or purified Fabs were added and incubated for 1 h at RT. The plates were washed again and detection antibody anti-HIS6—POD (Roche #1965085), was added. POD substrate, BM Blue, soluble, (Roche Applied Science) was added and the reaction was stopped with 1M H2SO4. Absorbance was read at 450 nm using the BMG Reader device.

Example 4

Affinity Maturation

1. Construction of Affinity Maturation Libraries of Selected C5-Binding Fabs

To increase affinity and biological activity of selected antibody fragments, L-CDR3 and H-CDR2 regions were optimized in parallel by cassette mutagenesis using trinucleotide directed mutagenesis (see e.g., Virnekas et al., Nucleic Acids Res. 22:5600-5607 (1994)), while the framework regions were kept constant. Prior to cloning for affinity maturation, all parental Fab fragments were transferred from the corresponding expression vector (pMORPH®x9_MH) into the CysDisplay™ vector pMORPH® 25 via XbaI/EcoRI. pMORPH™25 was created from the HuCAL GOLD® display vector pMORPH®23 by removal of one BssHII site interfering with library cloning for H-CDR2 optimization. For optimizing L-CDR3 of parental Fabs, the L-CDR3, framework 4 and the constant region of the light chains (405 bp) of the binders were removed by BpiI/SphI and replaced by a repertoire of diversified L-CDR3s together with framework 4 and the constant domain.

10 parental C5-binding Fabs were divided in 7 pools according to different selection criteria and only Fabs with same framework were put together: (1) MOR07086; (2) MOR06525+6756 (same framework); (3) MOR06757; (4) MOR06763; (5) MOR07087; (6) MOR07091+7092 (same framework); (7) MOR07093+7094 (same framework).

Approximately 1.5 µg of the single Fab vector fragment and of the Fab pool were ligated with a 3 to 5-fold molar excess of the insert fragment carrying the diversified L-CDR3s. In a second library set, the H-CDR2 (XhoI/BssHII) was diversified while the connecting framework regions were kept constant. In order to monitor the cloning efficiency, the parental H-CDR2 was replaced by a dummy before the diversified H-CDR2 cassette was cloned in.

Ligation mixtures of the different libraries were electroporated into E. coli TOP10 F' cells (Invitrogen) yielding from $2 \times 10^7$ to $2 \times 10^8$ independent colonies. The libraries were amplified. For quality control, several single clones per library were randomly picked and sequenced using primers CFR84 (VL) and OCAL_Seq_Hp (VH).

As described above, seven maturation sub pools were generated and kept separate during the subsequent selection process.

14 different affinity maturation libraries (one LCDR3 and one HCDR3 library for each lead or pool) were generated by standard cloning procedures and transformation of the diversified clones into electro-competent E. coli TOP10F' cells (Invitrogen). Library sizes were good, being in the range of $2 \times 10^7$-$5 \times 10^8$. Sequencing of randomly picked clones showed a diversity of 100%. No parental binders but derivatives of all respective parental input binders were found. Finally phages of all 14 libraries were prepared separately.

Table 2. Overview of maturation libraries

TABLE 2

Overview of maturation libraries

| MOR0 | Maturation | VH/VL Type | Library Size |
|---|---|---|---|
| 6757 | HCDR2 | VH3 | 3.70 × 10E7 |
| 6763 | HCDR2 | VH3 | 4.95 × 10E7 |
| 7086 | HCDR2 | VH1A | 1.58 × 10E8 |
| 7087 | HCDR2 | VH1A | 7.85 × 10E7 |
| 6525 + 6756 | HCDR2 | VH5 | 5.22 × 10E7 |
| 7091 + 7092 | HCDR2 | VH5 | 3.51 × 10E7 |
| 7093 + 7094 | HCDR2 | VH2 | 2.01 × 10E7 |
| 6757 | LCDR3 | Vkappa1 | 1.89 × 10E7 |
| 6763 | LCDR3 | Vlambda2 | 7.35 × 10E7 |
| 7086 | LCDR3 | Vlambda3 | 7.54 × 10E7 |
| 7087 | LCDR3 | Vkappa1 | 5.46 × 10E7 |
| 6525 + 6756 | LCDR3 | Vlambda2 | 8.50 × 10E7 |
| 7091 + 7092 | LCDR3 | Vlambda3 | 4.93 × 10E8 |
| 7093 + 7094 | LCDR3 | Vlambda2 | 1.33 × 10E8 |

2. Preparation of Antibody-Phages for Affinity Maturation

The HuCAL® maturation libraries were amplified in 2×YT medium containing 34 µg/ml chloramphenicol and 1% glucose (2×YT-CG). After infection with VCSM13 helper phage at an OD600 nm of 0.5 (30 min at 37° C. without shaking; 30 min at 37° C. shaking at 250 rpm), cells were spun down (4120×g; 5 min; 4° C.), resuspended in 2×YT/34 µg/ml chloramphenicol/50 µg/ml kanamycin/0.25 mM IPTG and grown o/n at 22° C. Phages were PEG-precipitated twice from the supernatant, resuspended in PBS and used for the maturation pannings described below.

3. Standard Solution Maturation Panning on Biotinylated C5 Protein

About $10^{12}$ phages rescued from the generated affinity maturation libraries, as described above, were subjected to pannings performed under very stringent conditions to select for affinity improved C5 specific Fabs.

Solution pannings using the respective phage pools were either performed using biotinylated human C5 or alternating biotinylated human and cynomolgus C5 proteins. In order to increase panning stringency and to select for improved off-rates, antigen concentration was decreased and prolonged washing periods were applied (washing conditions are listed in Table 3).

Table 3. Increased washing conditions within the selection rounds of solution maturation pannings

TABLE 3

Increased washing conditions within the selection rounds of solution maturation pannings

| Selection Rd. | Washing conditions (modified: stringent) |
|---|---|
| 1st round | 4× PBS/0.05% Tween 5 min on rotator |
| | 3× PBS/0.05% Tween 15 min on rotator-> transfer magnetic beads with the captured antigen and phages to a fresh blocked tube |
| | 4× PBS quick |
| | 3× PBS 5 min on rotator-> transfer magnetic beads with the captured antigen and phages to a fresh blocked tube |
| 2nd round | 3× PBS/0.05% Tween quick |
| | 7× PBS/0.05% Tween 15 min on rotator-> transfer magnetic beads with the captured antigen and phages to a fresh blocked tube |
| | 3× PBS quick |
| | 7× PBS 15 min on rotator-> transfer magnetic beads with the captured antigen and phages to a fresh blocked tube |
| 3rd round | 5× PBS/0.05% Tween quick |
| | 8× PBS/0.05% Tween 15 min on rotator |
| | 1× PBS/0.05% Tween o/n on rotator |
| | 3× PBS/0.05% Tween quick |
| | 6× PBS/0.05% Tween 15 min on rotator -> transfer magnetic beads with the captured antigen and phages to a fresh blocked tube |
| | 5× PBS quick |
| | 8× PBS 15 min on rotator -> transfer magnetic beads with the captured antigen and phages to a fresh blocked tube |

Pre-blocked phage (1:2 mixture with 2× Chemiblocker incubated for 1 h at RD were incubated with low concentration of biotinylated C5 protein for 1-2 h at RT. The panning strategy is similar to a standard solution panning described above. The phage antigen complex was captured via the biotin moiety of C5 to pre-blocked Streptavidin magnetic beads 30 min at RT. Beads were then washed more stringently compared to a normal panning. Elution and amplification of phage was performed as described above.

The second and third rounds of selection were performed in an identical way to the first round, but at higher stringency washing conditions and lower antigen concentrations. For each antibody lead or pool several different pannings were performed. For each panning strategy different stringency conditions were applied. Panning strategies are summarized in Table 4.

TABLE 4

Overview of solution maturation pannings 1783 and 1784 on biotinylated human C5 and biotinylated cynomolgus C5

| Panning # | Library | Panning mode | Antigen 1st round | Antigen 2nd round | Antigen 3rd round | Antigen Conc. | Washing |
|---|---|---|---|---|---|---|---|
| 1783.1 | MOR06525 + 6756 HCDR2 | solution Streptavidin beads | human C5 | human C5 | human C5 | 50 nM human/ 5 nM human/ 0.25 nM human | modified (more stringent) |
| 1783.2 | MOR07086 HCDR2 | | | | | | |
| 1783.3 | MOR06763 HCDR2 | | | | | | |
| 1783.4 | MOR07087 HCDR2 | | | | | | |
| 1783.5 | MOR06525 + 6756 LCDR3 | | | | | | |
| 1783.6 | MOR07086 LCDR3 | | | | | | |
| 1783.7 | MOR06763 LCDR3 | | | | | | |
| 1783.8 | MOR07087 LCDR3 | | | | | | |
| 1783.9 | MOR06525 + 6756 HCDR2 | solution Streptavidin beads | human C5 | cyno C5 | human C5 | 25 nM human/ 5 nm cyno/ 0.25 nM human | modified (more stringent) |
| 1783.10 | MOR07086 HCDR2 | | | | | | |
| 1783.11 | MOR06763 HCDR2 | | | | | | |
| 1783.12 | MOR06525 + 6756 LCDR3 | | | | | | |
| 1783.13 | MOR07086 LCDR3 | | | | | | |
| 1783.14 | MOR06763 LCDR3 | | | | | | |
| 1784.1 | MOR06757 HCDR2 | solution Streptavidin beads | human C5 | human C5 | human C5 | 50 nM human/ 5 nM human/ 0.25 nM human | modified (more stringent) |
| 1784.2 | MOR07091 + 7092 HCDR2 | | | | | | |
| 1784.3 | MOR07093 + 7094 HCDR2 | | | | | | |
| 1784.4 | MOR06757 LCDR3 | | | | | | |
| 1784.5 | MOR07091 + 7092 LCDR3 | | | | | | |
| 1784.6 | MOR07093 + 7094 LCDR3 | | | | | | |
| 1784.7 | MOR06757 HCDR2 | solution Streptavidin beads | human C5 | cyno C5 | human C5 | 25 nM human/ 5 nM cyno/ 0.25 nM human | modified (more stringent) |
| 1784.8 | MOR07091 + 7092 HCDR2 | | | | | | |
| 1784.9 | MOR07093 + 7094 HCDR2 | | | | | | |
| 1784.10 | MOR07087 HCDR2 | | | | | | |
| 1784.11 | MOR06757 LCDR3 | | | | | | |
| 1784.12 | MOR07091 + 7092 LCDR3 | | | | | | |
| 1784.13 | MOR07093 + 7094 LCDR3 | | | | | | |
| 1784.14 | MOR07087 LCDR3 | | | | | | |

After maturation pannings, the enriched phagemid pools were sub-cloned into pMORPH®×9_MH expression vector.
4. Cross-Combination of Optimized VL (L-CDR3) with Optimized VH(H-CDR2)

For further improvement of affinity and potency, the independently optimized heavy and light chains from matured antibodies, derived from the same parental clone, were combined (see e.g., Rauchenberger et al, J. Biol. Chem. 278: 38194-38205 (2003); Chen et al., J. Mol. Biol. 293:865-881 (1999); and Schier et al., J. Mol. Biol. 263:551-567 (1996)). This procedure, called cross-cloning, was applied for binders deriving from the same parental clones.
5. Affinity Screening and Maturation Panning Outcome A total of 2640 clones derived from all pannings were screened as bacterial lysates for improved affinities on human C5. Preliminary affinities were estimated by solution equilibrium titration (SET). Based on their estimated affinities, clones derived from each parental Fab or Fab pools were sequenced. Table 5 shows number of sequenced clones and number of obtained unique sequences for each panning condition.

sors. Parental Fabs MOR06525, MOR06757, MOR06763, MOR07087 and MOR07094 yielded only HCDR2 improved clones and parentals MOR06756 and MOR07093 yielded only LCDR3 improved clones. MOR07086, MOR07091 and MOR07092 had matured clones for both VH and VL. This later allowed cross-cloning of VH and VL matured chains. From all data, 60 clones with best affinity and highest diversity in the matured CDRs were selected for Fab expression. Selected VH and VL amino acid, as well as nucleotide sequences, are listed in Table 1.

Example 5

IgG Conversion

1. Conversion into Human IgG2 Format

In order to express full length immunoglobulin (Ig), variable domain fragments of heavy (VH) and light chains (VL) were subcloned from the pMORPH®×9_MH Fab expression vectors into pMORPH®2_h_Ig vector series for human IgG2. Restriction enzymes MfeI, and BlpI were used for

TABLE 5

Overview of affinity improved clones selected for sequence analysis

| Parental/Maturation | Antigen | Sequenced clones | Unique Sequences | Parental of unique |
|---|---|---|---|---|
| MOR06525 + 6756 HCDR2 | hu/hu/hu | 10 | 9 | 6525 |
| MOR07086 HCDR2 | hu/hu/hu | 10 | 4 | 7086 |
| MOR06763 HCDR2 | hu/hu/hu | 22 | 10 | 6763 (8×), 7086 (2×) |
| MOR07087 HCDR2 | hu/hu/hu | 10 | 4 | 7087 |
| MOR06757 HCDR2 | hu/hu/hu | 10 | 0 | |
| MOR07091 + 7092 HCDR2 | hu/hu/hu | 24 | 7 | 7092 |
| MOR07093 + 7094 HCDR2 | hu/hu/hu | 10 | 10 | 7093 |
| MOR06525 + 6756 LCDR3 | hu/hu/hu | 20 | 5 | 6756 |
| MOR07086 LCDR3 | hu/hu/hu | 10 | 5 | 7086 |
| MOR06763 LCDR3 | hu/hu/hu | 10 | 8 | 7086 |
| MOR07087 LCDR3 | hu/hu/hu | 6 | 1 | 7086 |
| MOR06757 LCDR3 | hu/hu/hu | 16 | 0 | |
| MOR07091 + 7092 LCDR3 | hu/hu/hu | 6 | 6 | 7091 (1×), 7092 (5×) |
| MOR07093 + 7094 LCDR3 | hu/hu/hu | 10 | 9 | 7094 |
| MOR06525 + 6756 HCDR2 | hu/cyno/hu | 10 | 8 | 6525 |
| MOR07086 HCDR2 | hu/cyno/hu | 10 | 6 | 7086 |
| MOR06763 HCDR2 | hu/cyno/hu | 22 | 5 | 6763 |
| MOR06757 HCDR2 | hu/cyno/hu | 15 | 2 | 6757 |
| MOR07091 + 7092 HCDR2 | hu/cyno/hu | 15 | 6 | 7091 (3×), 7092 (3×) |
| MOR07093 + 7094 HCDR2 | hu/cyno/hu | 10 | 10 | 7093 |
| MOR07087 HCDR2 | hu/cyno/hu | 10 | 6 | 7087 (5×), 7086 (1×) |
| MOR06525 + 6756 LCDR3 | hu/cyno/hu | 12 | 0 | |
| MOR07086 LCDR3 | hu/cyno/hu | 10 | 1 | 7086 |
| MOR06763 LCDR3 | hu/cyno/hu | 10 | 0 | |
| MOR06757 LCDR3 | hu/cyno/hu | 9 | 1 | 7094 |
| MOR07091 + 7092 LCDR3 | hu/cyno/hu | 11 | 9 | 7091 (6×), 7092 (3×) |
| MOR07093 + 7094 LCDR3 | hu/cyno/hu | 10 | 7 | 7094 |
| MOR07087 LCDR3 | hu/cyno/hu | 10 | 0 | |
| Sum | | 338 | 139 | |

6. Sequence Analysis and Selection of Affinity Optimized Fabs for Protein Production A very good diversity was maintained by recovering derivatives of all 10 parental Fabs. The nucleotide sequences of the heavy chain (VH) for 188 HCDR2 improved clones and the light chain (VL) variable regions for 150 improved LCDR3 clones were determined. 87 unique HCDR2 and 52 unique LCDR3 sequences were selected for a detailed analysis of sequence diversity within the matured CDRs. Fabs containing possible glycosylations sites in the CDRs were omitted from further characterizations.

The VH and VL sequence analysis and affinity data showed that all 10 parental Fabs yielded affinity-improved successubcloning of the VH domain fragment into pMORPH®2_h_IgG2. Subcloning of the VL domain fragment into pMORPH®2_h_IgK was performed via the EcoRV and BsiWI sites, whereas subcloning into pMORPH®2_h_Igλ2 was done using EcoRV and HpaI.

All ten parental Fabs (MOR06525, 6756, 6757, 6763, 7086, 7087, MOR07091, 7092, 7093 and 7094) were converted into human IgG2. The IgGs were also expressed.

2. Conversion into Human IgG1AA Format

In order to express full length immunoglobulin, variable domain fragments of Fab heavy (VH) and light chains (VL) were subcloned from the Fab expression vectors into IgG1 expression vectors. Restriction enzymes MfeI, and BlpI were used for subcloning of the VH domain fragment into pMORPH®2_h_IgG1AA, in which leucines at positions 234 and 235 were mutated to alanines to abrogate FcRγ binding and attenuate effector functions. The restrictions enzymes EcoRV and HpaI were used to subclone of the VL domain fragment into pMORPH®2 h_Igλ2.

Following matured Fabs with desired profile were subcloned into human IgG1AA format: MOR07832, 7834, 7872, 7876, 7829, 7871, 7865, 7873, 7830, 7878, 7910. Cross-cloning on IgG level was achieved by transfecting cells with combinations of light and heavy chain constructs. For example, MOR08114 was the product of the germlined heavy chain from MOR07829 and the germlined light chain from MOR07871. Table 6 summarizes the most relevant cross-cloned germlined IgGs.

TABLE 6

Overview of most relevant cross-cloned germlined IgGs

| MOR0 Nr. | VH/VL germlined | VH/VL VH | VH/VL VL | matured CDRs matured VH | matured VL | format |
|---|---|---|---|---|---|---|
| 8114 | yes | 7829 | 7871 | 7091/HCDR2 | 7091/LCDR3 | huIg1AA |
| 8125 | yes | 7091 | 7873 | — | 7091/LCDR3 | huIg1AA |
| 8126 | yes | 7829 | 7873 | 7091/HCDR2 | 7091/LCDR3 | huIg1AA |
| 8127 | yes | 7830 | 7873 | 7091/HCDR2 | 7091/LCDR3 | huIg1AA |
| 8128 | yes | 7092 | 7878 | — | 7092/LCDR3 | huIg1AA |
| 8129 | yes | 7909 | 7092 | 7092/HCDR2 | — | huIg1AA |
| 8130 | yes | 7909 | 7878 | 7092/HCDR2 | 7092/LCDR3 | huIg1AA |
| 8131 | yes | 7910 | 7092 | 7092/HCDR2 | — | huIg1AA |
| 8132 | yes | 7910 | 7878 | 7092/HCDR2 | 7092/LCDR3 | huIg1AA |

3. Transient Expression and Purification of Human IgG

Eukaryotic HKB11 and HEK293 cells were transfected with an equimolar ratio of IgG heavy and light chain expression vector DNA. Cell culture supernatant was harvested at 3 or 7 days post transfection and subjected to standard protein A affinity chromatography (rProteinA FF or MabSelect SuRe™, GE Healthcare). As not otherwise stated, buffer exchange was performed to 1× Dulbcecco's PBS (pH 7.2, Invitrogen) and samples were sterile filtered (0.2 μm). Purity of IgG was analyzed under denaturing, reducing and non-reducing conditions in SDS-PAGE or by using Agilent Bio-Analyzer and in native state by HP-SEC.

Example 6

Germlining

IgG constructs were germlined via site-directed mutagenesis using QuickChange® Site-Directed Mutagenesis Kit (Stratagene). The N-terminal DI of MOR08111 Vλ2 were changed to ES to match human germline sequence as well as to avoid a terminal Q (N-terminal Q can form pyroglutamine). N-terminal DI of MOR08110VA3, MOR08113VA3, and MOR08114VA3 were germlined to SY, the most commonly found sequence in human A3 genes. N-terminal QVQ of MOR08111VH2 was germlined to EVT to match a A2 gene and avoid terminal Q. N-terminal Q in MOR08109VH5, MOR08110VH5, MOR08113VH5 and MOR08114VH5 was also mutated to E.

Framework sequences for MOR08109VA3 were synthesized to match the human A3j gene and cloned into the expression vector using NheI and HpaI restriction sites. Sequence alignments of the antibodies variable domains with their respective closest related human germline sequences are shown in FIG. 1.

Example 7

Affinity Determination

1. Kon/Koff and $K_D$ Determination of Anti-Human C5 Antibodies Using Surface Plasmon Resonance (Biacore)

It was determined that anti-Fab antibodies used to immobilize Fabs to the Biacore™ chip were influencing differently the binding affinity of each Fab for human C5, thus making the comparison of the Fabs to each other difficult. Biacore™ analysis was performed on IgG antibodies.

A CM4 chip was coated with 50 μg/ml goat anti-human Fc antibody (500-2000 RU) in 10 mM acetate buffer, pH 4.5, using standard EDC-NHS amine coupling chemistry. Each anti-human C5 IgG was captured on the chip in HBS-EP buffer at constant flow rate of 10 μl/min for a contact time leading to a ligand density around 20 RU. After capturing the anti-hu C5 IgG, different concentrations of human or cynomolgus C5, in the range between 0.156 nM to 2.5 nM, were injected. Each cycle was completed with two regeneration steps with phosphoric acid. All running conditions were carried out at 25° C. in 1×HBS-EP buffer. The resulting signals were adjusted by double referencing, substracting the refraction index values from the reference flow cell and the binding step with no analyte. Data were collected at 10 Hz and analyzed using the Biacore™ T100 Evaluation Software Version 1.1 (GE). This program uses a global fitting analysis method for the determination of rate and affinity constants for each interaction.

The specificity of the antibodies were measured. Preferably, the Kon and Koff values for binding to human and cynomolgus C5 are as follows: Kon $>1\times10^5$, Koff $<1\times10^{-4}$). These measurements were performed in Biacore™ for the germlined IgGs and resulting data are listed in Table 7.

TABLE 7

$K_D$, Kon and Koff values of the germlined IgGs determined in Biacore

| antiC5 final IgG | C5 sample | ka [1/Ms] | kd [1/s] | KD [pM] |
|---|---|---|---|---|
| MOR08109 | huC5 | 2.13E+06 | 2.56E−05 | 12 |
| | cynoC5 | 1.23E+06 | 4.49E−05 | 37 |
| MOR08110 | huC5 | 4.15E+06 | 4.69E−05 | 12 |
| | cynoC5 | 1.81E+06 | 9.24E−05 | 60 |
| MOR08111 | huC5 | 1.00E+06 | 3.07E−05 | 31 |
| | cynoC5 | 8.91E+05 | 1.28E−04 | 144 |
| MOR08113 | huC5 | 2.51E+06 | 6.77E−05 | 28 |
| | cynoC5 | 1.53E+06 | 1.27E−04 | 83 |
| MOR08114 | huC5 | 2.09E+06 | 3.12E−05 | 15 |
| | cynoC5 | 1.06E+06 | 3.13E−05 | 31 |
| 5G1.1 | huC5 | 1.29E+06 | 7.22E−05 | 56 |

2. Determination of Picomolar Affinities Using Solution Equilibrium Titration (SET) for Purified Fabs or Fabs Bacterial Lysates (Meso Scale Discovery (MSD))

For $K_D$ determination by solution equilibrium titration (SET), monomer fractions (at least 90% monomer content, analyzed by analytical SEC; Superdex™ 75, Amersham Pharmacia) of Fab protein were used. Affinity determination in solution was basically performed as described in the literature (Friguet et al., J. Immunol. Methods 77:305-319 (1985)). In order to improve the sensitivity and accuracy of the SET method, it was transferred from classical ELISA to ECL based technology (Haenel et a, Anal Biochem 339:182-184 (2005)).

1 mg/ml goat-anti-human (Fab)$_2$ fragment specific antibodies (Dianova) were labelled with ECL Sulfo-TAGTM NHS-Ester (Meso Scale Discovery, Gaithersburg, Md., USA) according to manufacturer's instructions. Experiments were carried out in polypropylene microliter plates and PBS pH 7.4 with 0.5% BSA and 0.02% Tween 20 as assay buffer. Unlabelled antigen was diluted in $2^n$ series, starting with a concentration at least 10 times higher than the $K_D$. Wells without antigen were used to determine Bmax values; wells with neither antigen nor Fab were used to determine background. After addition of e.g. 10 pM Fab (final concentration in 60 µl final volume), the mixture was incubated over night at RT. The applied Fab concentration was similar to or below the expected $K_D$.

Streptavidin MSD plates were coated with 0.2 µg/ml biotinylated human C5 (30 µl/well) and blocked with 5% BSA in PBS. Subsequently the equilibrated samples were transferred to those plates (30 µl per well) and incubated for 20 min. After washing, 30 µl/well of the ECL Sulfo-tag labeled detection antibody (goat anti-human (Fab)2) in a final dilution of 1:1500 was added to the MSD plate and incubated for 30 min on an Eppendorf shaker (700 rpm).

After washing and adding 30 µl/well MSD Read Buffer T with surfactant Electrochemiluminescence signals were detected using a Sector® Imager 6000 (Mesa Scale Discovery, Gaithersburg, Md., USA).

Data were evaluated with XLfit (IDBS) software applying customized fitting models. For data evaluation i.e. $K_D$ determination of Fab molecules the following fit model was used (model of Abraham et al 16, modified according to et al., 200515): y=Bmax−(Bmax/(2*cFab)*(x+cFab+KD−sqrt((x+cFab+KD)*(x+cFab+KD)−4*x*cFab))); cFab: applied Fab concentration; x: applied total soluble antigen concentration (binding sites); sqrt: square root. Using the assay conditions described above (monomeric) affinities for the affinity-optimized C5-binding Fabs were determined in solution.

Parental Fabs

In order to further characterize the C5-binding antibodies, affinity of the parental Fabs to human C5 was determined. Because characterization focus was on efficacy in hemolytic assays, affinity measurements were done only for the most relevant Fabs. For a reliable determination of monovalent affinities only Fab batches were used for measurements which showed 90% monomeric fraction in a qualitative size exclusion chromatography.

Affinities of the 10 parental Fabs which entered affinity maturation are summarized in Table 8. Affinities ranged from 72 pM to 3.7 nM.

TABLE 8

Affinities of the 10 parental Fabs determined in SET

| MOR0 Number | SET KD [pM] |
|---|---|
| 6525 | 72 |
| 6756 | 1521 |
| 6757 | 1186 |
| 6763 | 820 |
| 7086 | 108 |
| 7087 | 3793 |
| 7091 | 324 |
| 7092 | 229 |
| 7093 | 576 |
| 7094 | 1364 |
| 3207 (negative control) | no binding |

(n = 1)

Matured Fabs

Monovalent affinities of the purified Fabs to human C5 were measured in SET. Affinities were in the low pM range and best affinities were obtained for derivatives of MOR07086, 7091, 7092 and 7093. Subsequently affinity measurements of these derivatives to cynomolgus C5 showed affinities in the mid to low pM range.

The affinity maturation process was very successful resulting in a repertoire of binders with markedly improved affinity. Table 9 summarizes affinities to human and cynomolgus C5 of the best improved binders. Certain Fabs have $K_D$ to human C5≦30 pM and to cynomolgus C5≦150 pM.

TABLE 9

Overview of affinities to human and cynomolgus C5 for the best affinity improved Fabs

| MOR | Matured | SET hu C5 (n = 1-2) KD [pM] | SET cyno C5 (n = 1) KD [pM] |
|---|---|---|---|
| 6525 | | 273/29 | |
| 7813 | HCDR2 | 437 | |
| 7814 | HCDR2 | 137 | |
| 7816 | HCDR2 | 116 | |
| 6757 | | 3650/1245 | |
| 7818 | HCDR2 | 491 | 70 |
| 7907 | HCDR2 | 179 | |
| 6763 | | 673/962 | |
| 7820 | HCDR2 | 62 | |
| 7086 | | 12/65 | 10 |
| 7821 | HCDR2 | 7 | 39 |
| 7822 | HCDR2 | 5 | 14 |
| 7823 | HCDR2 | 5 | 15 |
| 7824 | HCDR2 | 55/130 | |
| 7864 | LCDR3 | 22 | 974 |
| 7865 | LCDR3 | 10 | 88 |
| 7866 | LCDR3 | 10 | 191 |
| 7867 | LCDR3 | 19 | 154 |
| 7868 | LCDR3 | | 384 |
| 7869 | LCDR3 | 2 | 83 |
| 7870 | LCDR3 | 12 | 500 |
| 7087 | | 120 | |
| 7827 | HCDR2 | 361 | |
| 7828 | HCDR2 | 2477/1730 | |
| 7091 | | 135/138 | 704 |
| 7829 | HCDR2 | 429 | 116 |
| 7830 | HCDR2 | 399 | 75 |
| 7908 | HCDR2 | 15* | 39* |
| 7871 | LCDR3 | 3 | 4 |
| 7872 | LCDR3 | 2 | 3 |
| 7873 | LCDR3 | 13,13 | 6 |
| 7874 | LCDR3 | 35 | 8 |
| 7092 | | 96 | 481 |
| 7831 | HCDR2 | 10 | 36 |
| 7832 | HCDR2 | 4 | 13 |
| 7909 | HCDR2 | 7 | 18 |
| 7910 | HCDR2 | 27 | 31 |
| 7876 | LCDR3 | 78 | 60 |
| 7877 | LCDR3 | 29 | 144 |
| 7878 | LCDR3 | 33 | 70 |
| 7879 | LCDR3 | 25 | 122 |
| 7093 | | 431/992 | 3146 |
| 7833 | HCDR2 | 47 | 107 |
| 7834 | HCDR2 | 4 | 15 |
| 7835 | HCDR2 | 29 | 28 |
| 7836 | HCDR2 | 11 | |
| 7890 | HCDR2 | 46 | |
| 7094 | | | |
| 7880 | LCDR3 | 13 | 13 |
| 7881 | LCDR3 | 88 | |
| 7882 | LCDR3 | 70 | |
| 7883 | LCDR3 | 49 | |
| 7884 | LCDR3 | 83 | |
| 7885 | LCDR3 | 35 | | criterion: KD hu C5 ≦ 30 pM; cy ≦ 150 pM
*scattering (no reliable measurement)

3. $K_D$ Determination of IgG Molecules Using Solution Equilibrium Titration (Set)

Affinities of the germlined IgGs (human IgG1AA format) to human and cynomolgus C5 were determined in SET as described below. Similar data sets between two independent measurements showed higher affinities of the lead IgGs to human C5 than reference IgG 5G1.1 (see U.S. Pat. No. 6,355,245). Final IgGs had affinities for human C5 ranging from 1 to 14 pM and affinities to cynomolgus C5 ranging from 3 to 29 pM.

TABLE 10

$K_D$ values determination for the final lead IgGs (human IgG1AA format) in SET

| | | 1st measurement | | 2nd measurement | |
|---|---|---|---|---|---|
| | | human C5 KD [pM] | cyno C5 KD [pM] | human C5 KD [pM] | cyno C5 KD [pM] |
| hu IgG1AA germlined | MOR08109 | 4 | 13 | 2 | 6 |
| | MOR08110 | 7 | 18 | 3 | 8 |
| | MOR08111 | 5 | 14 | 3 | 17 |
| | MOR08113 | 14 | 29 | 8 | 16 |
| | MOR08114 | 1 | 5 | 2 | 4 |
| hu IgG2/4 (reference IgG) | 5G1.1 | 24 | no binding | 19 | no binding |

For $K_D$ determination by solution equilibrium titration (SET), monomer fractions of IgG protein were used (at least 90% monomer content, analyzed by analytical SEC MALS; Tosoh TSKgel G3000SWXL, Wyatt Treos miniDAWN). Affinity determination in solution was basically performed as described in the literature (Friguet et al., J. Immunol. Methods 77:305-319 (1985)). In order to improve the sensitivity and accuracy of the SET method, it was transferred from classical ELISA to ECL based technology (Haenel et al., Anal Biochem 339:182-184 (2005)).

1 mg/ml goat-anti-human (Fab)$_2$ fragment specific antibodies (Dianova) were labelled with ECL Sulfo-TAGTM NHS-Ester (Meso Scale Discovery, Gaithersburg, Md., USA) according to the manufacturer's instructions. The experiments were carried out in polypropylene microliter plates and PBS pH 7.4 with 0.5% BSA and 0.02% Tween 20 as assay buffer. Unlabeled antigen was diluted in 2n or 1.75n series, respectively, starting with a concentration at least 10 timer higher than the $K_D$. Wells without antigen were used to determine Bmax values; wells containing neither antigen nor IgG were used to determine background. After addition of e.g. 10 pM IgG (final concentration in 60 μl final volume), the mixture was incubated overnight at RT. The applied IgG concentration was similar to or below the expected $K_D$.

Streptavidin MSD plates were coated with 0.2 μg/ml biotinylated human C5 (30 μl/well) and blocked with 5% BSA in PBS. Subsequently the equilibrated samples were transferred to those plates (30 μl per well) and incubated for 20 min. After washing, 30 μl/well of the ECL Sulfo-tag labeled detection antibody (goat anti-human (Fab)$_2$) in a final dilution of 1:1500 was added to the MSD plate and incubated for 30 min on an Eppendorf shaker (700 rpm).

Electrochemiluminescence signals were detected after washing and adding 30 μl/well MSD Read Buffer T with surfactant using a Sector® Imager 6000 (Meso Scale Discovery, Gaithersburg, Md., USA).

Data were evaluated with XLfit (IDBS) software applying customized fitting models. For data evaluation i.e. $K_D$ determination of IgG molecules the following fit model for IgG was used (modified according to Piehler et al., 199717):

y=Bmax/(cIgG/2)*(cIgG/2−((x+cIgG+KD)/2−((x+cIgG+KD)^2/4−x*cIgG^0.5) ^2/(2*IgG)); cIgG=applied IgG concentration, complete molecule (not binding sites); x=applied total soluble antigen concentration (binding sites); sqrt: square root.

Example 8

Characterization by Hemolytic Assays

The hemolytic assay is a basic functional assay that tests for complement activation and has been used to evaluate the ability of anti-human C5 mAbs and Fab molecules to block lysis of red blood cells (RBCs) by complement pathways (see e.g., Evans et al., Mol. Immunol. 32: 1183-1195 (1995); Thomas et ai., Mol Immunol 33:1389-1401 (1996); Rinder et al., J Clin Invest 96:1564-1572 (1995)). Briefly, for classical pathway assays, sensitized red blood cells are used as targets for lysis by complement proteins present in serum. This assay is of interest for the characterization and screening of high-affinity anti-human C5 mAbs.

1. Classical Pathway

The desired number of chicken red blood cells was washed four times with cold gelatin veronal buffer (GVB++) and resuspended to 5×10$^7$ cells/ml. To sensitize the cells rabbit anti-chRBC IgG was added to RBC cell suspension to a final concentration of 1 μg/ml IgG. After 15 minutes incubation on ice, the sensitized chRBCs were centrifuged, washed twice with GVB++ and diluted to 8.33×10$^7$ cells/ml.

Round-bottom 96 well plates were used for hemolytic assay. Antibodies were diluted in GVB++ buffer and added to the wells (when calculating the required concentration of C5-binding Abs, it was considered that the sample will be diluted two-fold when serum is added). 50 μl of 40% human serum (diluted in GVB++) was added to 50 μl antibody dilutions, resulting in a final serum assay concentration of 20%.

The control and blank wells were prepared as described here: control wells: i) 0% lysis control→100 μl GVB++, ii) 100% lysis control→100 μl 0.1% NP-40, iii) 20% serum control→100 μl of 20% serum (0% Ab control). blank wells: i) 20% serum blank→100 μl 20% serum, ii) GVB++ blank→100 μl GVB++, iii) NP-40 blank→100 μl 0.1% NP-40.

2.5×10$^6$ (30 μl) sensitized chRBCs/well were added to all sample and control wells. To the blank wells PBS was added instead of cells. Assay plate was incubated 30 min at 37° C., centrifuged (2.000 rpm, 5 min) and 85 μl supernatant was transferred to a new, flat-bottomed 96-well plate. The new plate was centrifuged (2.000 rpm, 3 min) to get rid of any bubbles. Hemoglobin release was measured by reading absorbance at 415 nm. Percentage of hemolysis was calculated with respect to the control and blank wells using the following calculation algorithms:

$$\% \text{ Hemolysis} = 100 \times \frac{ODsample - ODnegativecontrol}{ODpositivecontrol - ODnegativecontrol}$$

where $ODsample = \lfloor AverageOD_{sample} \rfloor - \lfloor AverageOD_{20\% \text{ Serum Blank}} \rfloor$ $ODnegativecontrol = \lfloor AverageOD_{0\% \text{ Lysis}} \rfloor - \lfloor AverageOD_{GVB++Blank} \rfloor$ $ODpositivecontrol = \lfloor AverageOD_{100\% \text{ Lysis}} \rfloor - \lfloor AverageOD_{NP-40 \text{ Blank}} \rfloor$ Using this procedure, anti human-05 antibodies which were able to inhibit red blood cell lysis could be identified. To screen for cross-reactivity to cynomolgus C5, the classical pathway was performed using 5% cynomolgus serum.

2. Alternative Pathway

Hemolytic assays undergoing the alternative pathway were done in a similar way to the classical pathway hemolytic assays. In the alternative pathway RBCs cells from rabbit were used and there was no need to sensitize the cells. The rabbit RBCs are different from chicken RBCs in that they are sensitive to lysis caused by the complement alternative pathway.

The working buffer was GVB++supplemented with 10 mM EGTA and 5 mM Mg++, since the C5 convertase of the alternative pathway is Mg++dependent and the C5 convertase of the classical pathway is Ca++dependent.

Hemolytic assays of the alternative pathway were run with: i) 20% human serum, ii) 100 pM human C5 added to 20% human C5-depleted serum, iii) 0.025% cynomolgus serum added to 20% human C5-depleted serum, iv) 100 pM cynomolgus C5 added to 20% human C5-depleted serum, v) 10% cynomolgus serum. These settings were used to screen for antibodies with high affinity to the human and cynomolgus C5 proteins which were able to inhibit very effectively the red blood cell lysis induced by the alternative complement pathway.

3. Hemolytic Assays with Parental Fabs

Hemolytic assays were used as a basic bio-functional assay to evaluate the ability of anti-human C5 mAbs to block complement mediated lysis of red blood cells. C5 convertase cleaves C5 into C5a peptide and C5b fragment, that is subsequently incorporated into the membrane-attack complex (MAC), which leads to cell lysis. C5 convertase of the classical pathway, formed by a C3bC4bC2a complex has a different structure than the C5 convertase of the alternative pathway which is formed by a C3bC3bBb complex. HuCAL GOLD® generated antibodies should be inhibitory in both classical and alternative pathway, but with focus on the alternative pathway because mainly the alternative pathway (factor H, factor B and factor H-related genes) is implicated in AMD.

The classical and alternative pathway assays were performed with 20% human serum (~80 nM C5). To increase sensitivity of alternative pathway assays, new assay formats were developed. 10-100 pM purified human C5 or 0.025% cynomolgus serum (~100 pM cynomolgus C5) were added to human C5-depleted serum (but containing all other serum and complement components).

Figure 2:
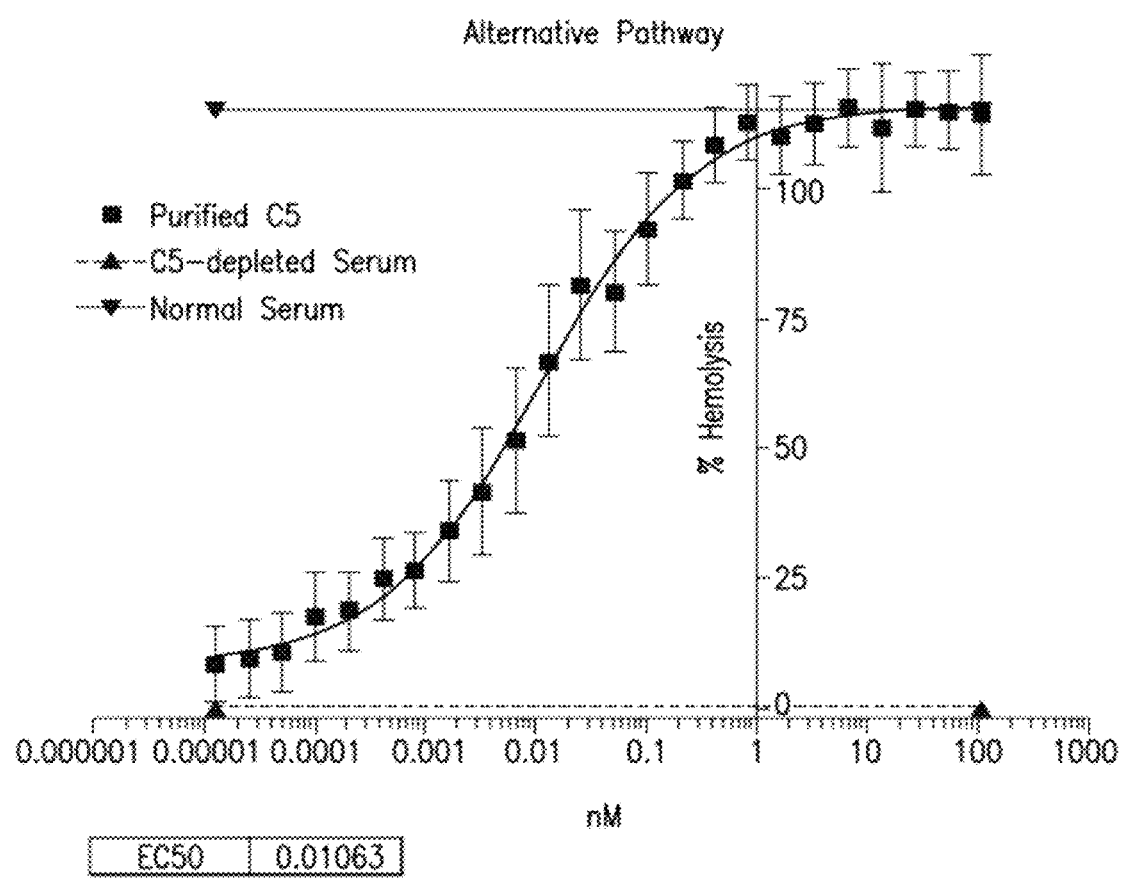
FIG. 2 shows a hemolytic assay in which human C5 is titrated into human C5-depleted serum to determine C5 activity.
Figure 3:
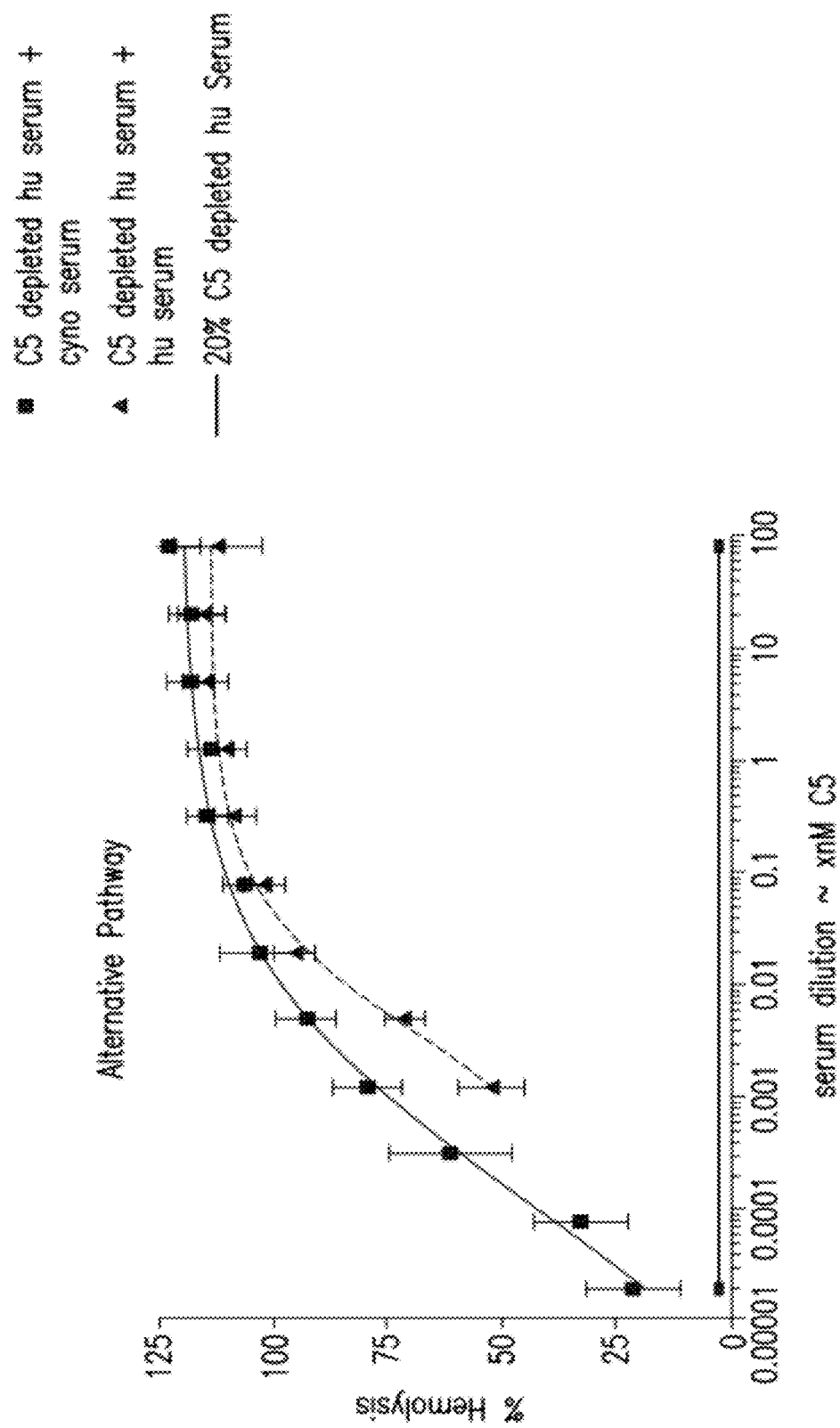
FIG. 3 shows titration of cynomolgus serum into human C5-depleted serum to determine optimal cynomolgus C5 concentration for alternative pathway hemolytic assay.

FIG. 2 shows that considerable hemolysis could be observed between 10 and 100 pM purified human C5 added to human C5-depleted serum. Cynomolgus serum was added to human C5-depleted serum to test for cross-reactivity. FIG. 3 shows that 0.025% of cynomolgus serum (~100 pM C5) added to human C5 depleted serum restores hemolytic activity.

Classical Pathway

First Fab selection was done in the classical pathway (20% human serum). Approximately half of the 61 purified parental Fabs were weak to strong inhibitors of the classical pathway. IC50 values of the best inhibitory Fabs were between 35 and 900 nM.

Figure 4:
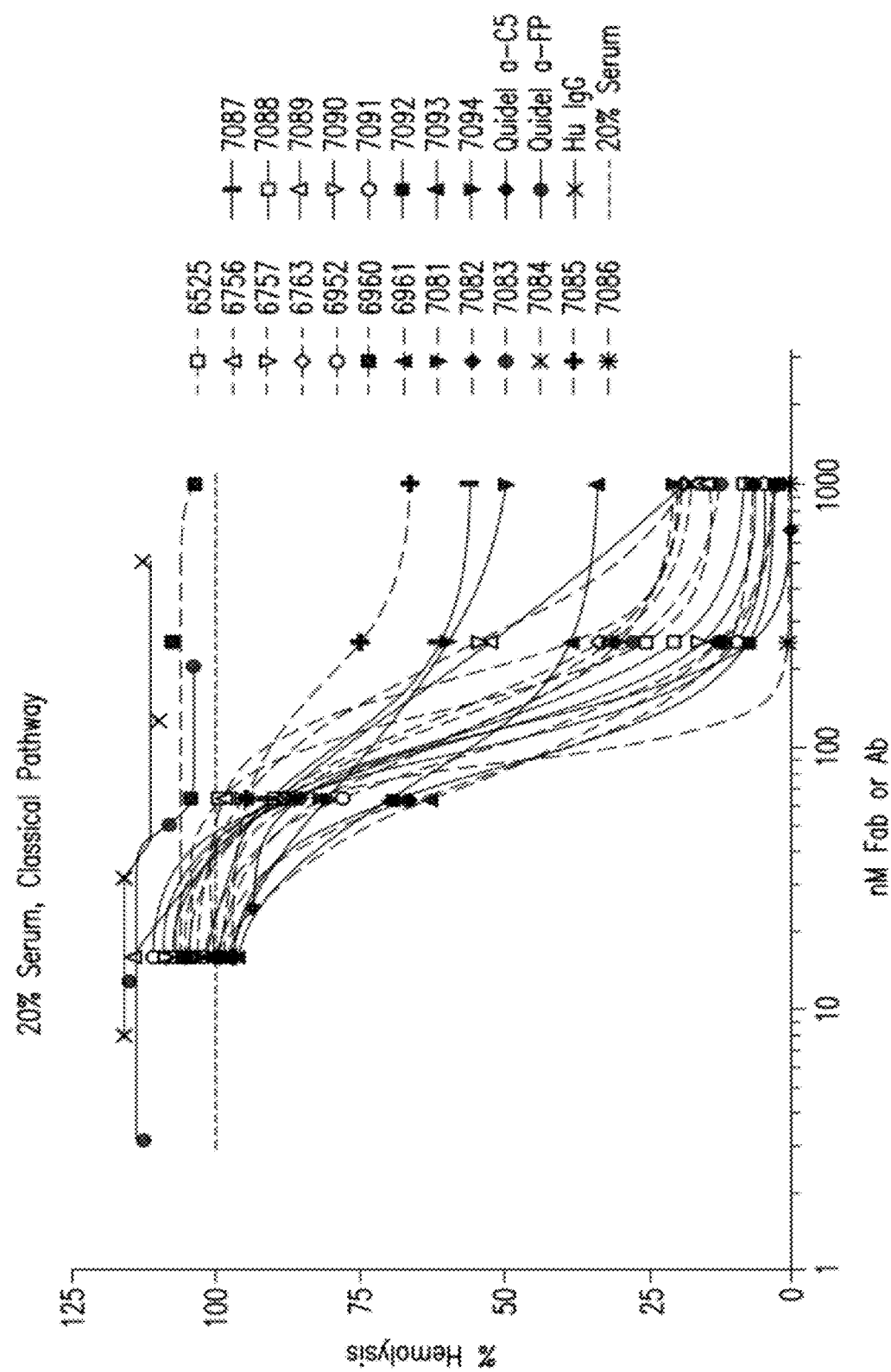
FIG. 4 shows examples of classical pathway hemolytic assays with 20% human serum.

Assays were done showing congruent results (as shown in FIG. 4). % hemolysis was calculated with respect to the control and blank wells. Fab inhibition of cell lysis was compared to a maximum lysis caused by 20% human serum (=100%). An irrelevant human Fab (hen egg white lysozyme binder MOR03207) was used as negative control and anti-human C5 IgG monoclonal antibody (Quidel) as positive control. FIG. 4 show an example with the best inhibitory Fabs.

Alternative Pathway

Figure 5:
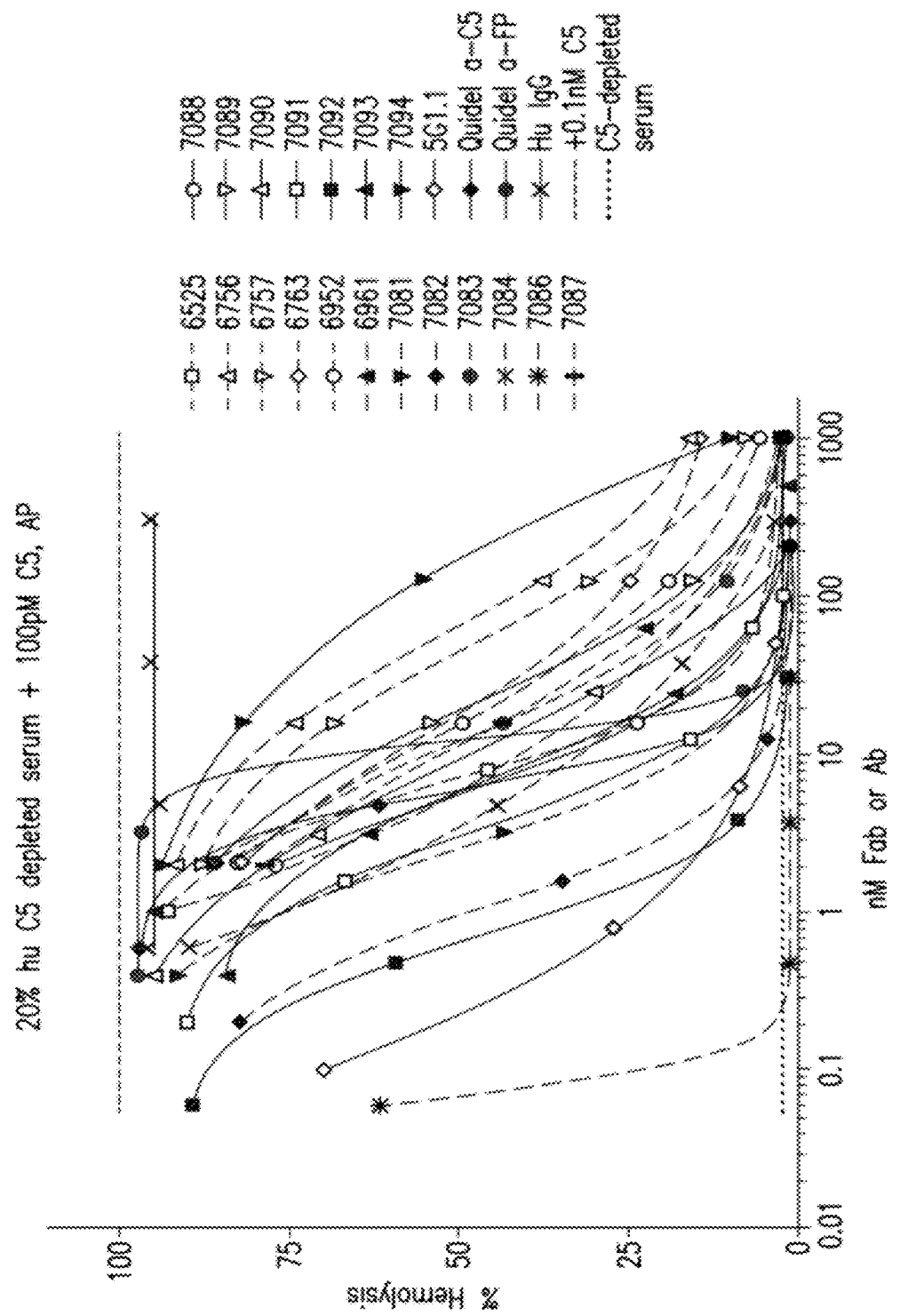
FIG. 5 shows example of alternative pathway hemolytic assays with 100 pM purified human C5 added to human C5-depleted serum.

Fabs which showed inhibitory activity in the classical pathway were further evaluated in the alternative pathway. Hemolytic assays were run with 100 pM purified human C5 or 0.025% cynomolgus serum added to human C5-depleted serum. $IC_{50}$ values for the human alternative assays were between 0.1 and 90 nM (examples of assays with the most relevant Fabs are shown in FIG. 5.

The positive control of the classical pathway (anti-human C5 antibody, Quidel) was not inhibitory in the alternative pathway. Therefore an anti-complement factor P antibody (Quidel) was used as positive control. As shown in FIG. 5, MOR07086 had best inhibitory activity and NVS data revealed a better potency than for the reference antibody 5G1.1.

Figure 6:
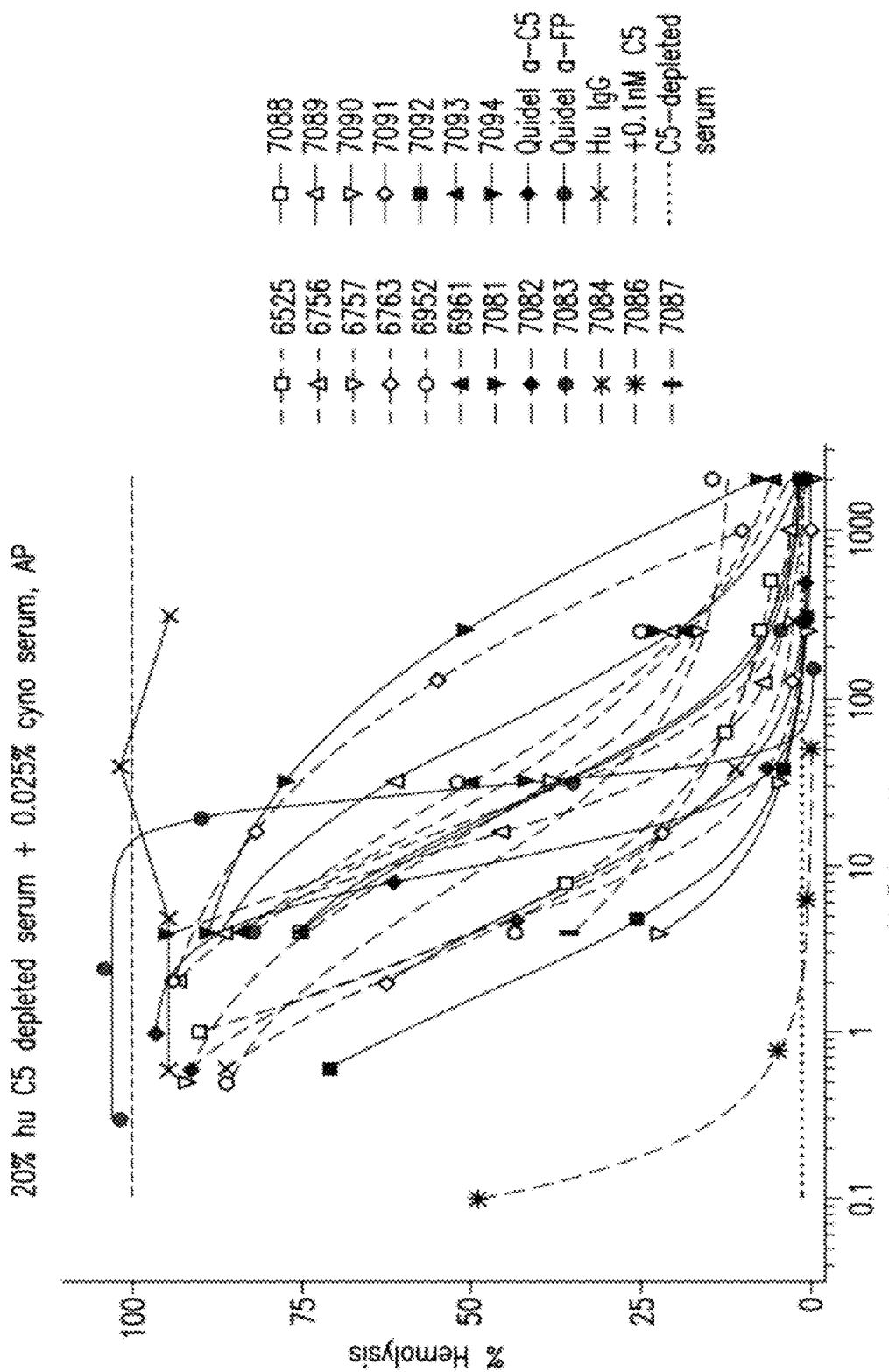
FIG. 6 shows examples of alternative pathway hemolytic assays with 0.025% cynomolgus serum added to human C5-depleted serum.

To test for cynomolgus cross-reactivity, hemolytic assays of the alternative pathway were performed with 0.025% cynomolgus serum added to human C5-depleted serum. A comparison to 5G1.1 was not possible, since 5G1.1 does not recognize cynomolgus C5. The anti-Factor P antibody was used as positive control. Results of assays revealed $IC_{50}$ values between 0.1 and 400 nM for the best inhibitory Fabs. Again, MOR07086 showed best potency (shown in FIG. 6).

A consistent inhibitory activity of the Fabs was noticed in both classical and alternative pathway. Table 11 below summarizes the results of hemolytic assays for the most relevant 22 Fabs. To have a reliable comparison between different experiments, lysis caused by 20% human serum was normalized to 100%.

TABLE 11

Summary of hemolytic assays with the most relevant Fabs

| | MOR IC50 [nM] | | | NVS IC50 [nM] | | |
|---|---|---|---|---|---|---|
| MOR-Nr | CP [human] normalized | AP (0.1 nM C5) [human] normalized | AP (0.025% cyno serum) [cyno] normalized | CP [human] normalized | AP (0.1 nM C5) [human] normalized | AP (0.025% cyno serum) [cyno] normalized |
| 6525 | 190 | 15 | 11 | 185 | 7 | 5 |
| 6756 | 320 | 80 | 400 | 225 | 70 | 2500 |
| 6757 | 500 | 90 | 30 | 305 | 130 | 25 |
| 6763 | 250 | 45 | 110 | 195 | 20 | 360 |
| 6764 | n.t. | 50 | n.t. | n.t | 25 | 30% inh |
| 6776 | >4000 | 40 | | n.t. | 20* | 50% inh |
| 6952 | 90 | 20 | >1000 | 110 | 15 | 200 |
| 6961 | 100 | 25 | 600 | 85 | 15 | 30 |
| 7081 | 180 | 5 | 40% inh | 170 | 3 | 10 |

TABLE 11-continued

Summary of hemolytic assays with the most relevant Fabs

| | MOR IC50 [nM] | | | NVS IC50 [nM] | | |
| --- | --- | --- | --- | --- | --- | --- |
| MOR-Nr | CP [human] normalized | AP (0.1 nM C5) [human] normalized | AP (0.025% cyno serum) [cyno] normalized | CP [human] normalized | AP (0.1 nM C5) [human] normalized | AP (0.025% cyno serum) [cyno] normalized |
| 7082 | 70 | 2.5 | 1 | 90 | 1 | 1 |
| 7083 | 100 | 30 | 300 | 140 | 10 | 5 |
| 7084 | 120 | 10 | 1.2 | 160 | 5 | 1.5 |
| 7086 | 35 | 0.2/0.2 | 0.2/0.4 | 85 | 0.1 | 0.1 |
| 7087 | >4000 | 50 | 100 | 775 | 10 | 1 |
| 7088 | 110 | 15 | 230 | 130 | 5 | 15 |
| 7089 | 150 | 75 | 900 | 250 | 20 | 50 |
| 7090 | 105 | 20 | 10 | 120 | 10 | 1 |
| 7091 | 82 | 7 | 40 | 110 | 3 | 4 |
| 7092 | 100 | 1 | 1.5 | 90 | 0.5 | 1.5 |
| 7093 | >4000 | 7 | 190 | 230 | 5 | 15 |
| 7094 | | | | 770 | 40 | 190 |
| 7095* | 120* | 0.5** | 1.3** | n.t. | | |

*not pure as MH
**as pMx9_FS

4. Hemolytic Assays with Matured Fabs

Classical Pathway (1) Classical Pathway Using 20% Human Serum

Figures 1, 7:
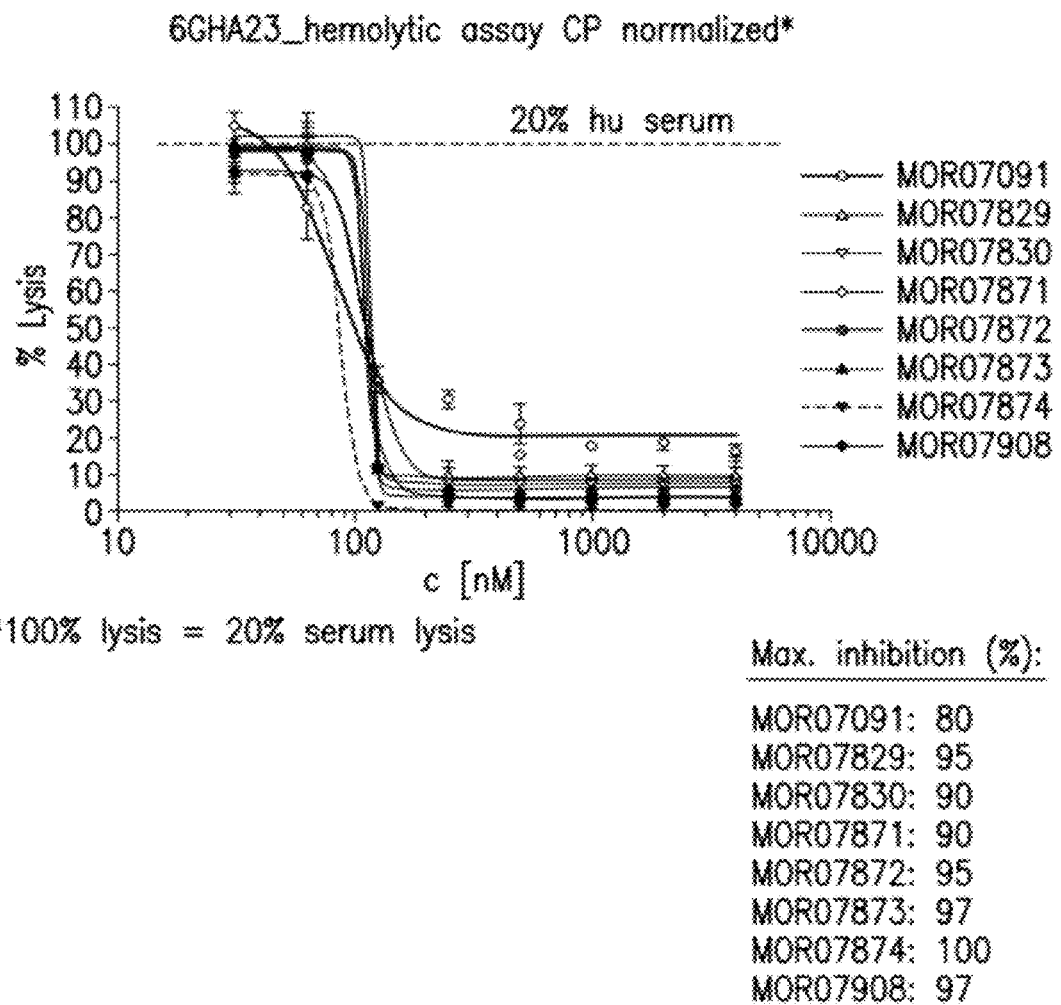
FIG. 7 shows examples of classical pathway hemolytic assays (20% human serum) with matured Fabs in comparison to their respective parentals.
Figures 2, 7:
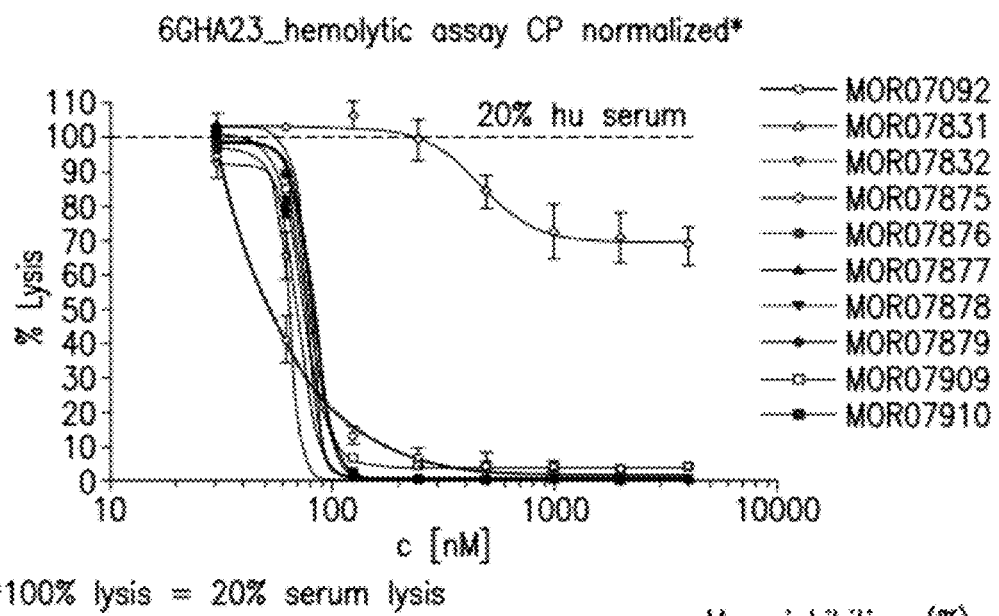
Figures 3, 7:
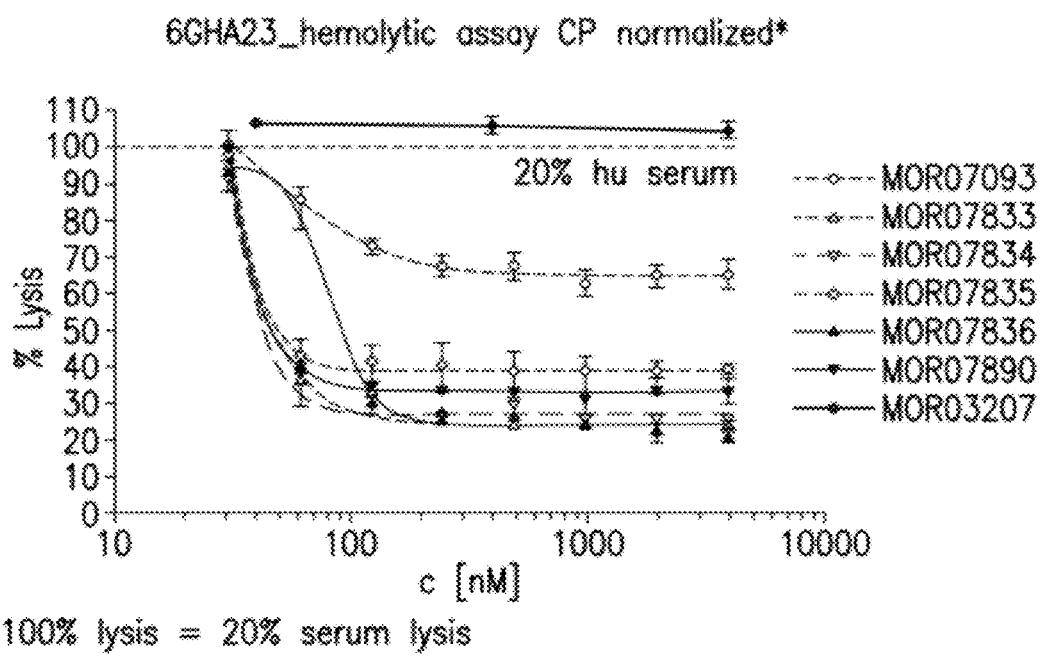
Figures 4, 7:
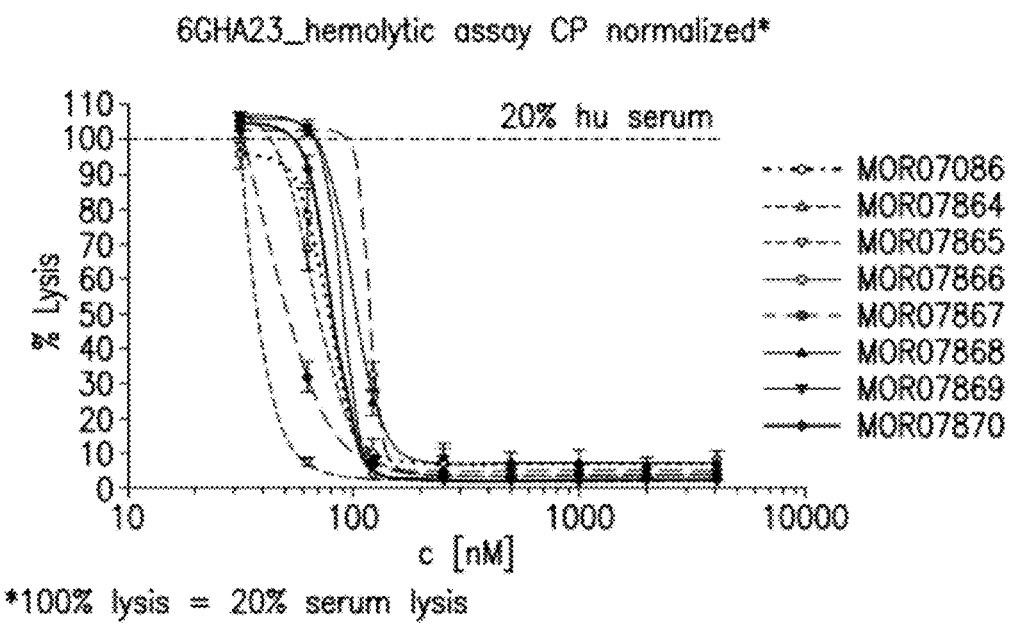

Matured Fabs were tested in the classical pathway with 20% human serum. Derivatives of MOR07086, 7091, 7092 and 7093 showed highest potency (IC50 values in the low nM range). Descendants of MOR07091, 7092 and 7093 showed strongly improved potency. FIG. 7 shows examples of hemolytic assays with derivatives of MOR07086, 7091, 7092 and 7093.

(2) Classical Pathway Using 5% Cynomolgus Serum

Figures 1, 8:
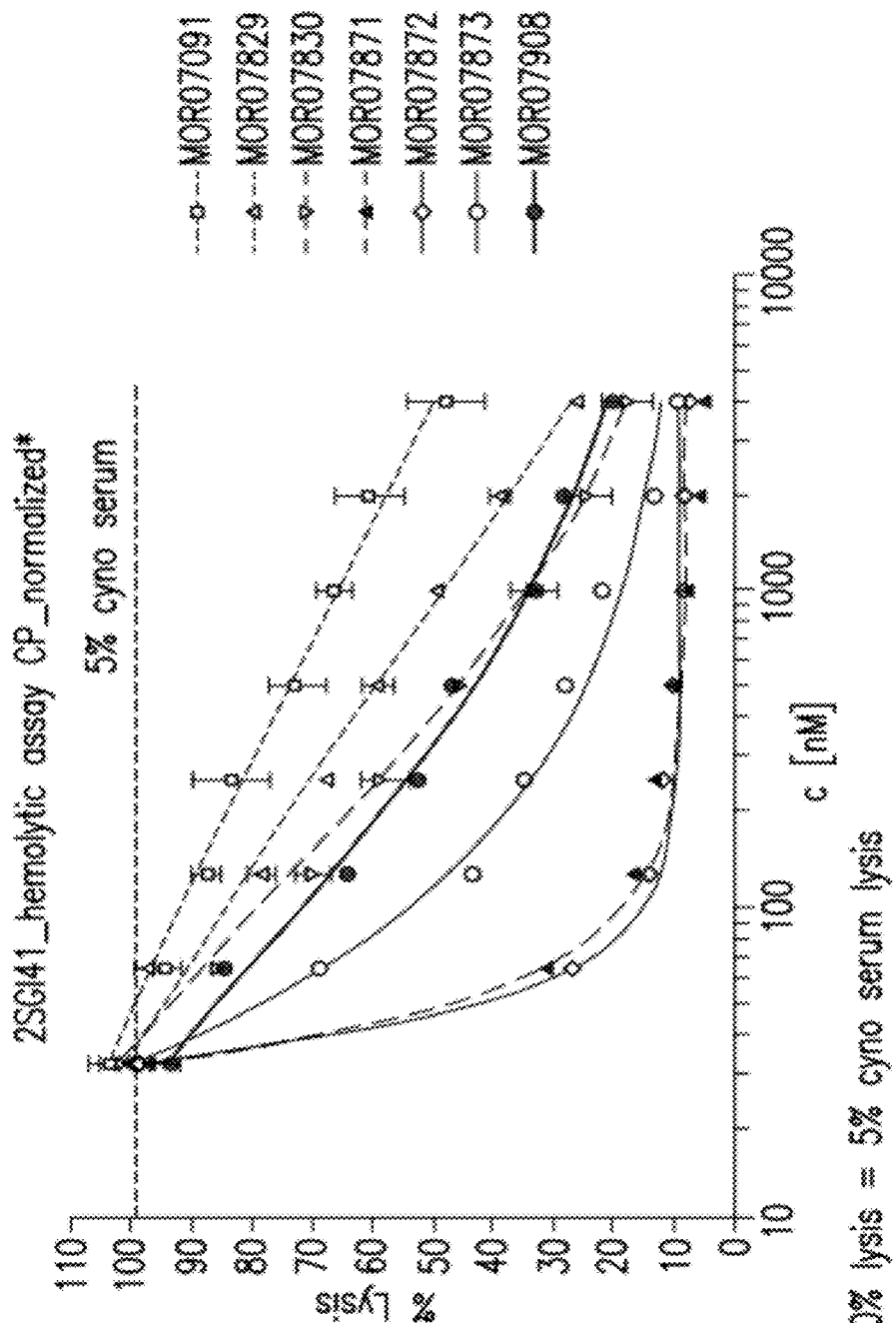
FIG. 8 shows examples of classical pathway hemolytic assays (5% cynomolgus serum) with matured Fabs.
Figures 2, 8:
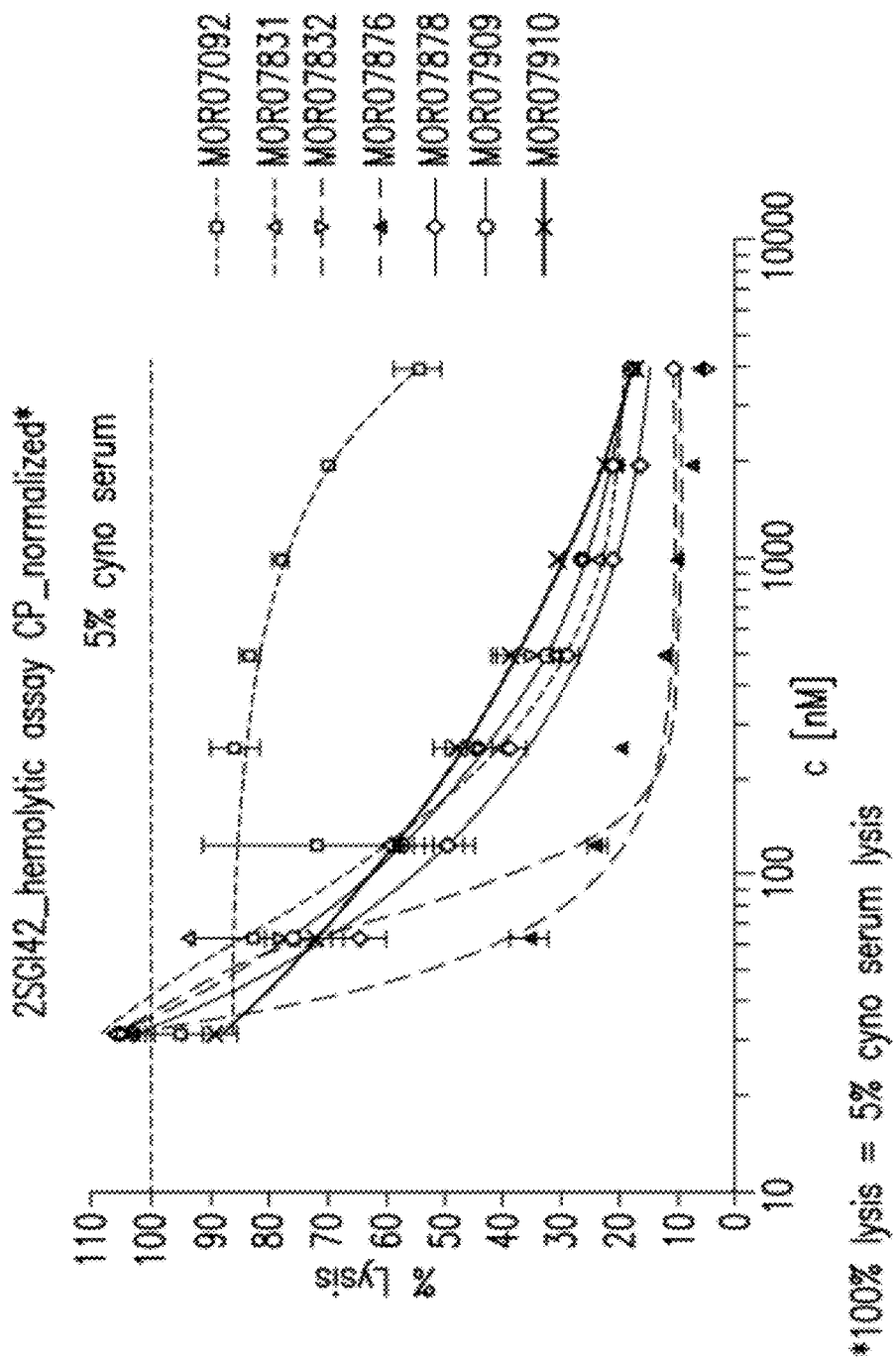
Figures 3, 8:
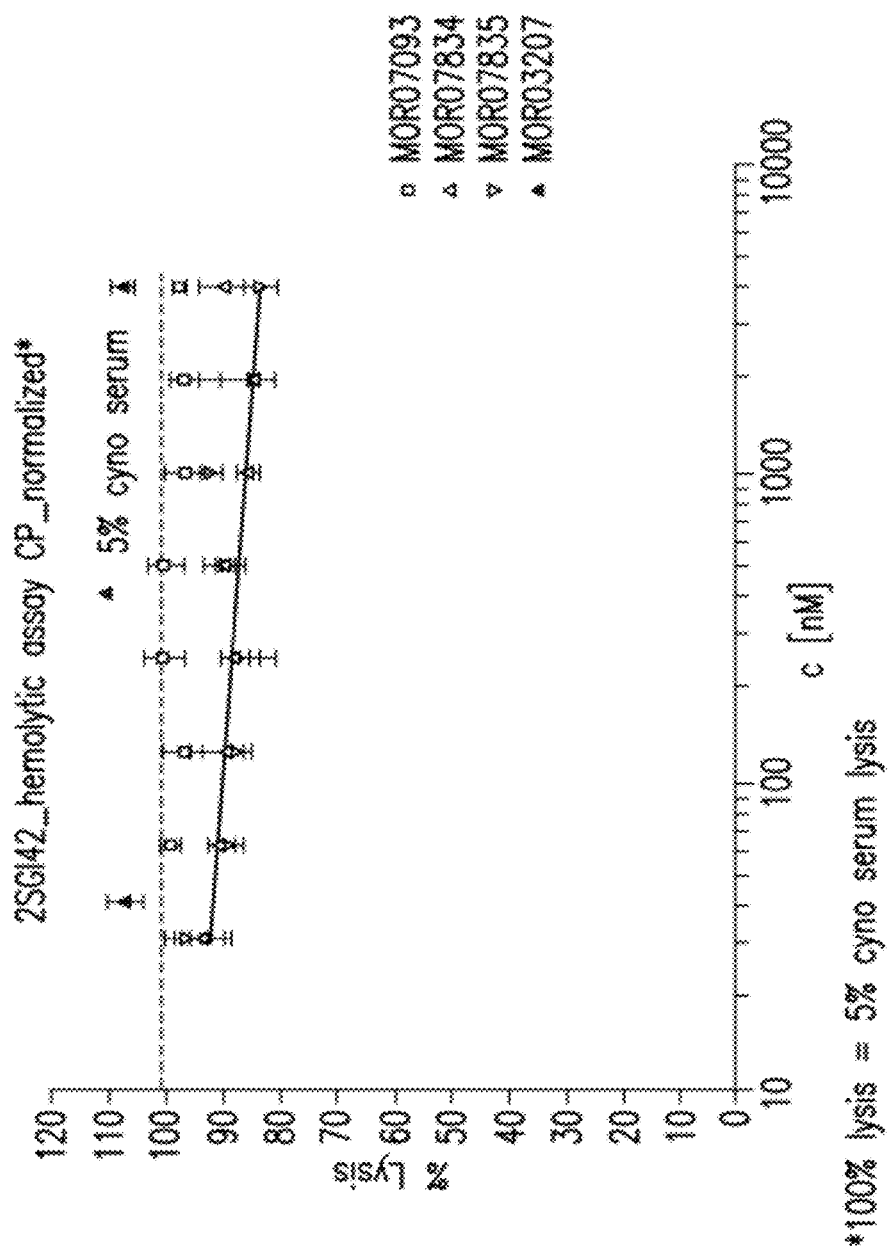
Figures 4, 8:
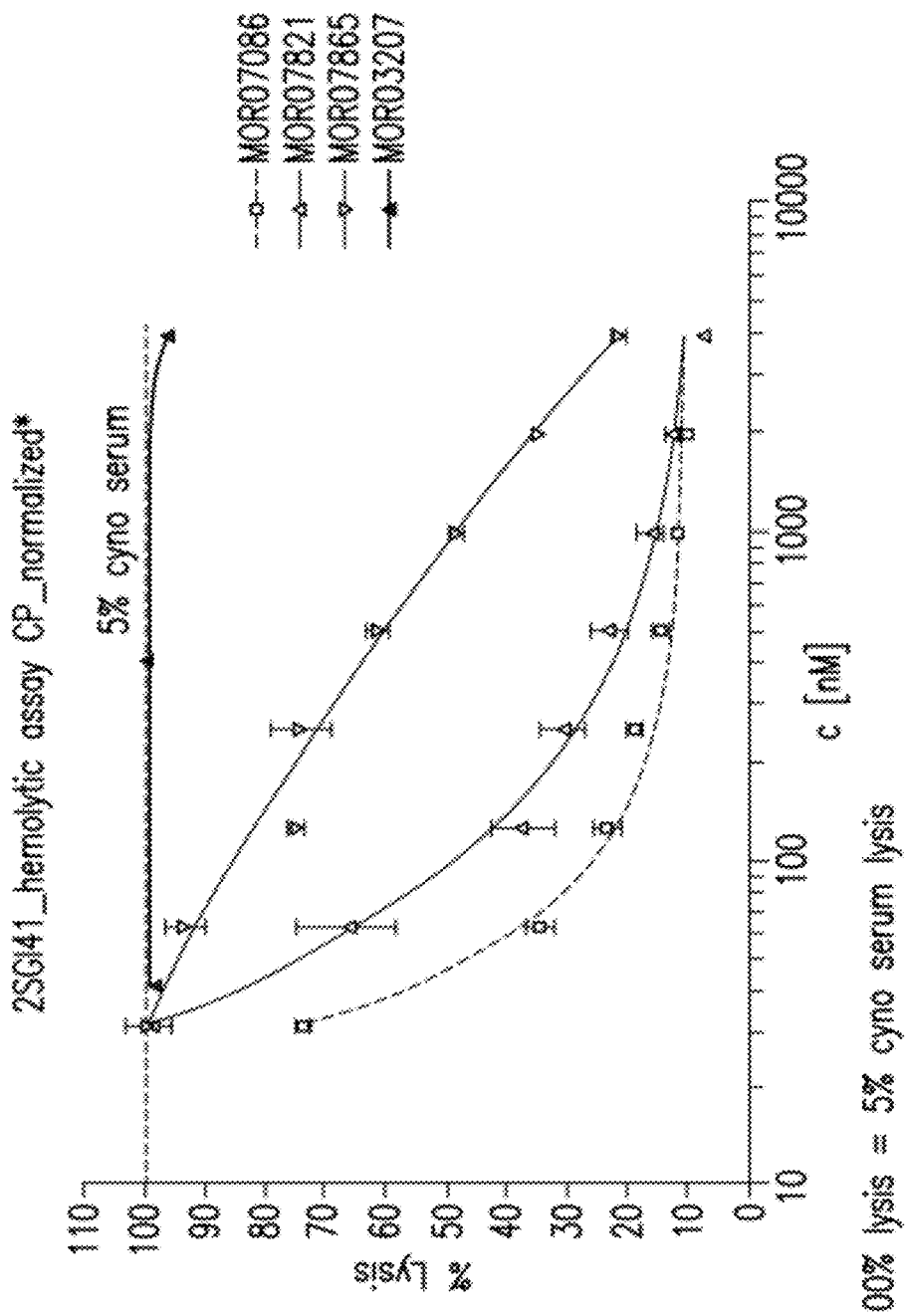
Figure 9A:
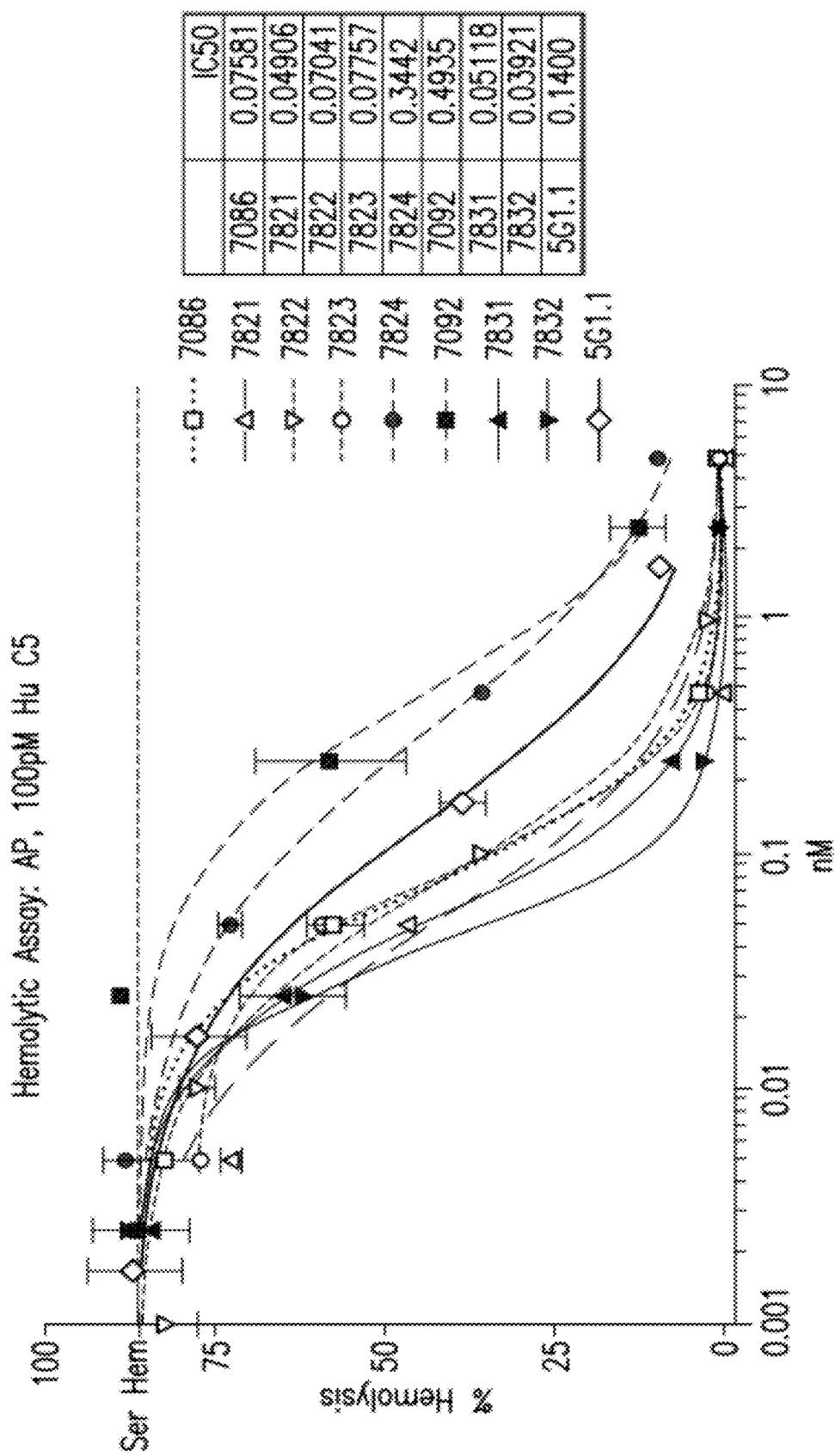
FIG. 9 shows affinity matured Fab characterization in alternative pathway hemolytic assay using 100 pM human C5 added to 20% human C5-depleted serum.
Figure 9C:
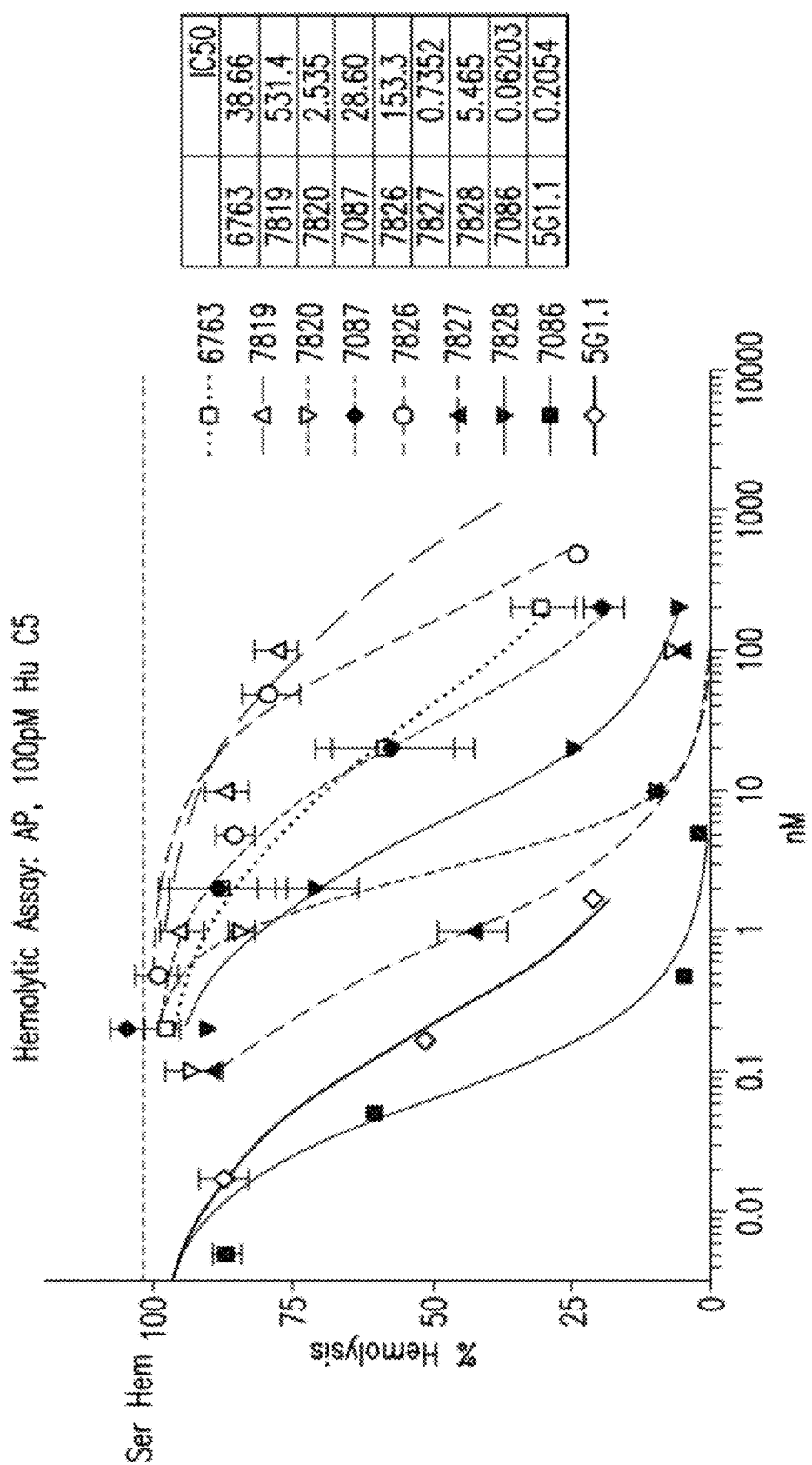
Figure 9D:
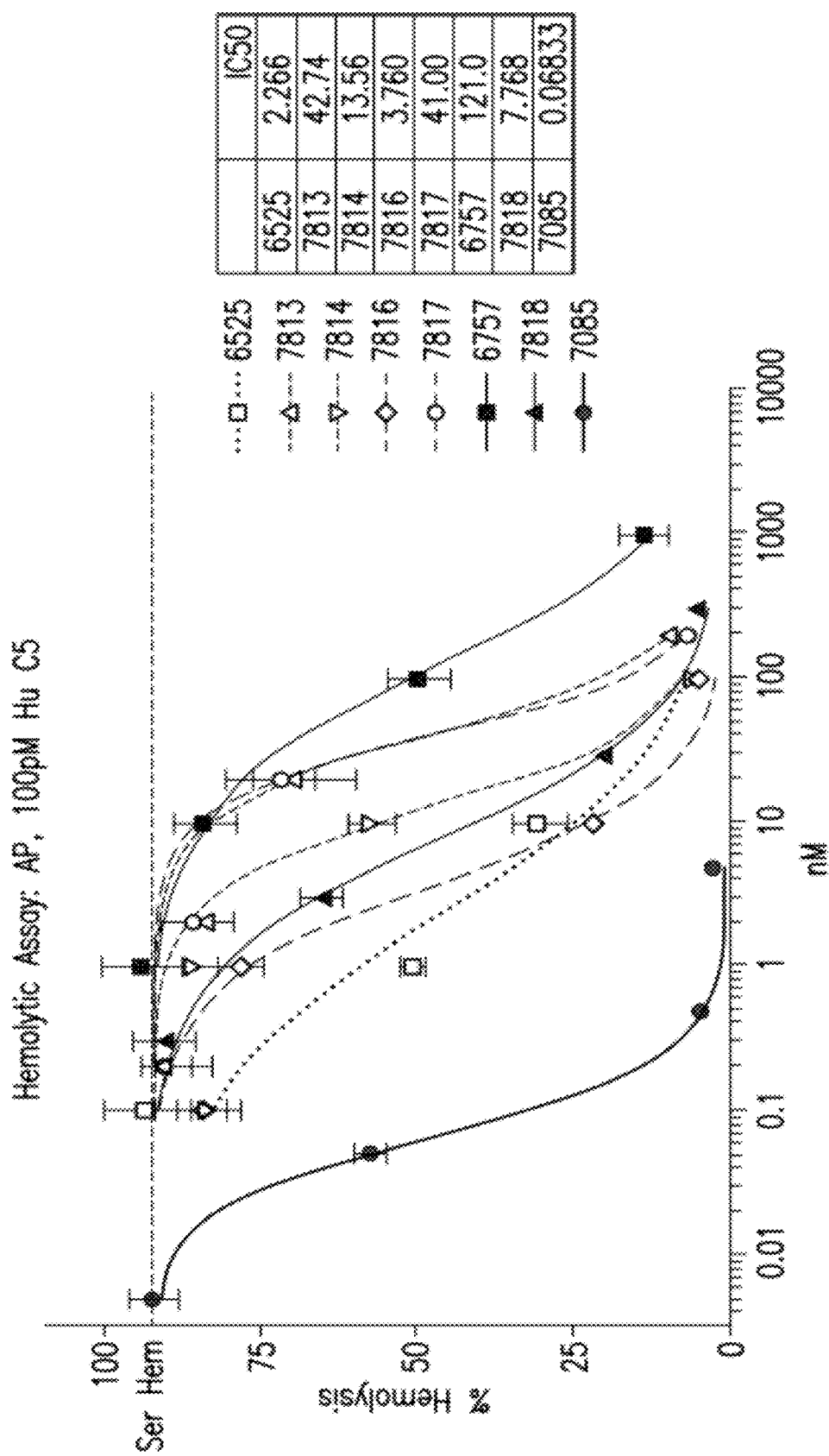
Figure 9E:
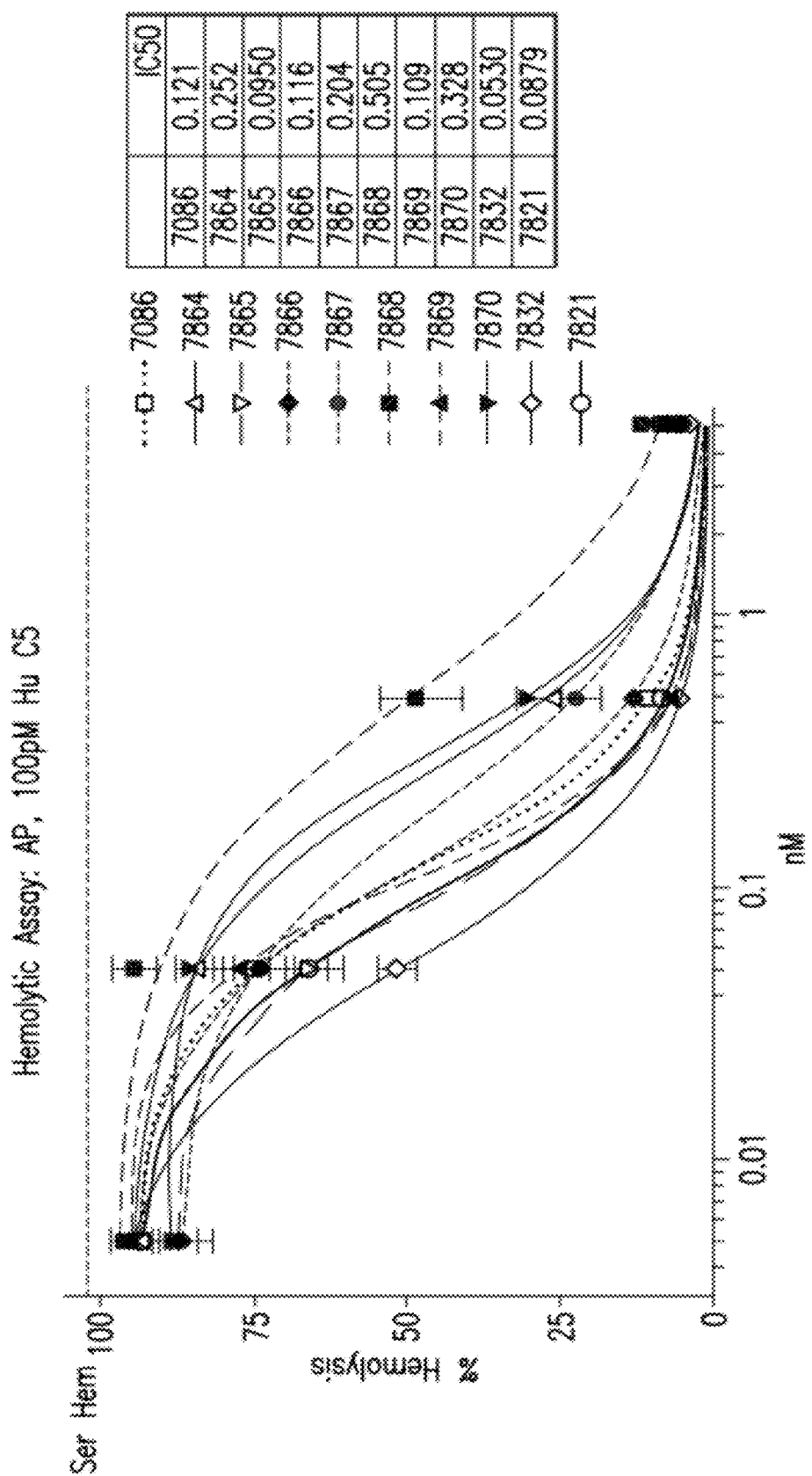
Figure 9F:
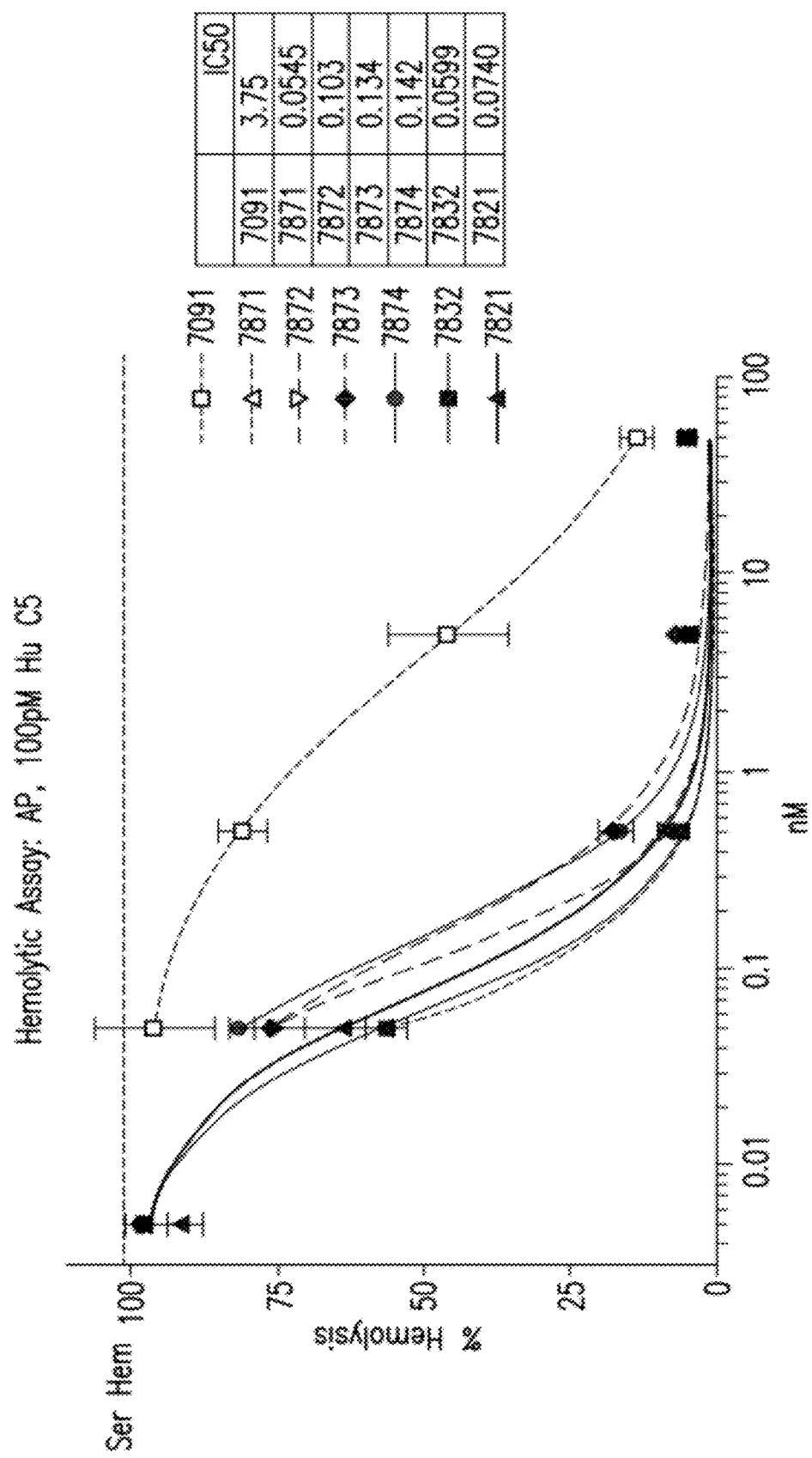
Figure 9I:
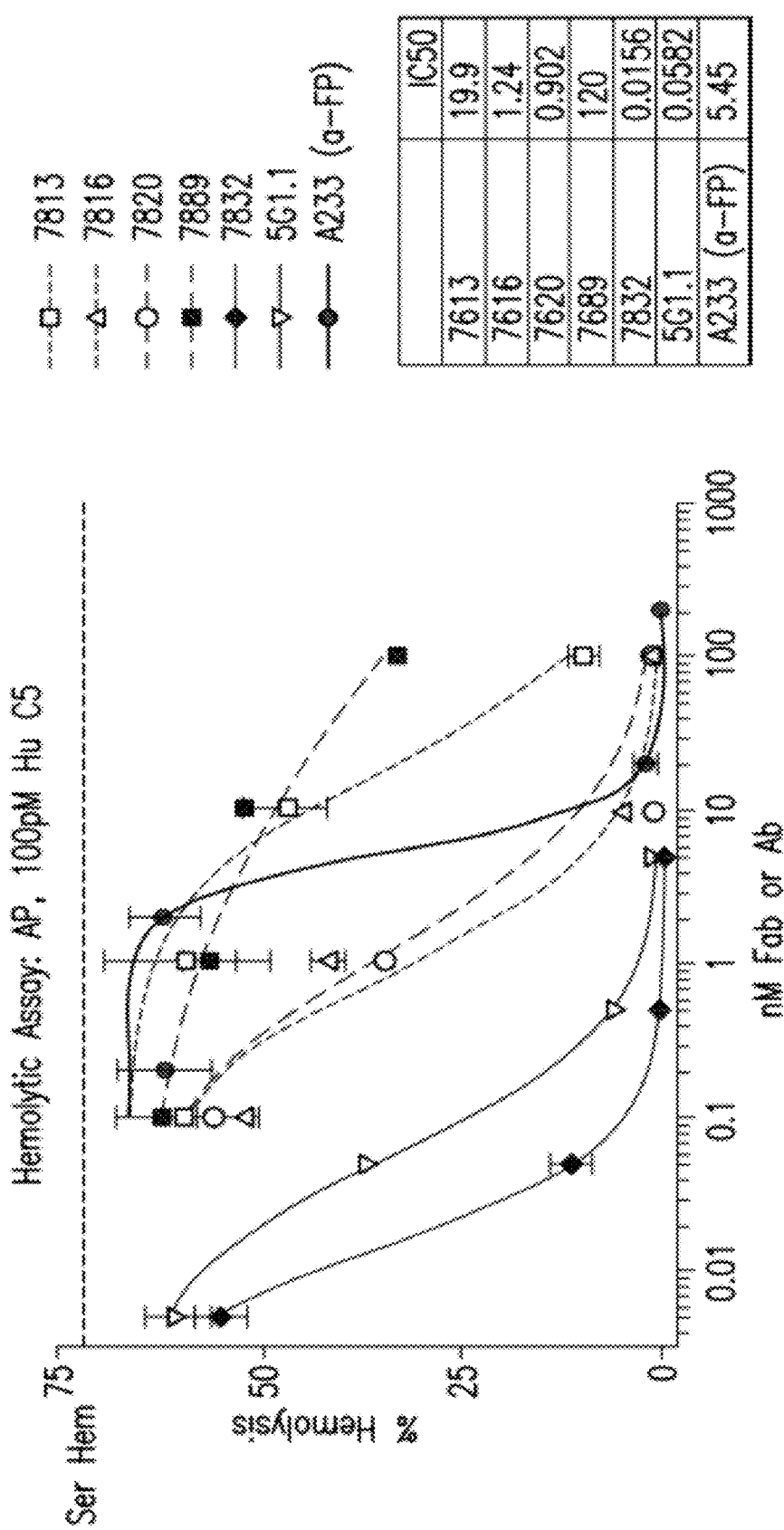
Figure 9J:
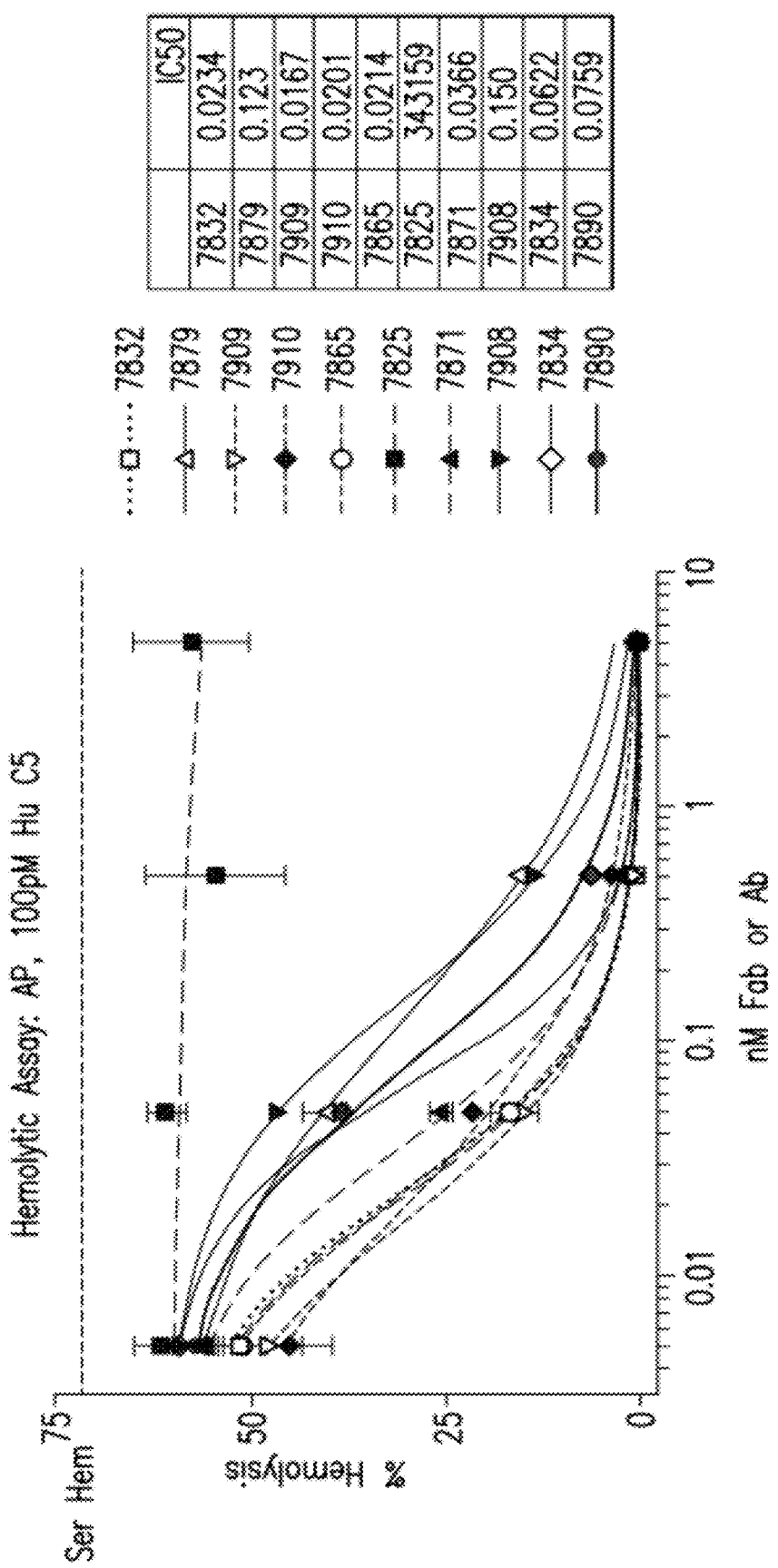
Figure 10A:
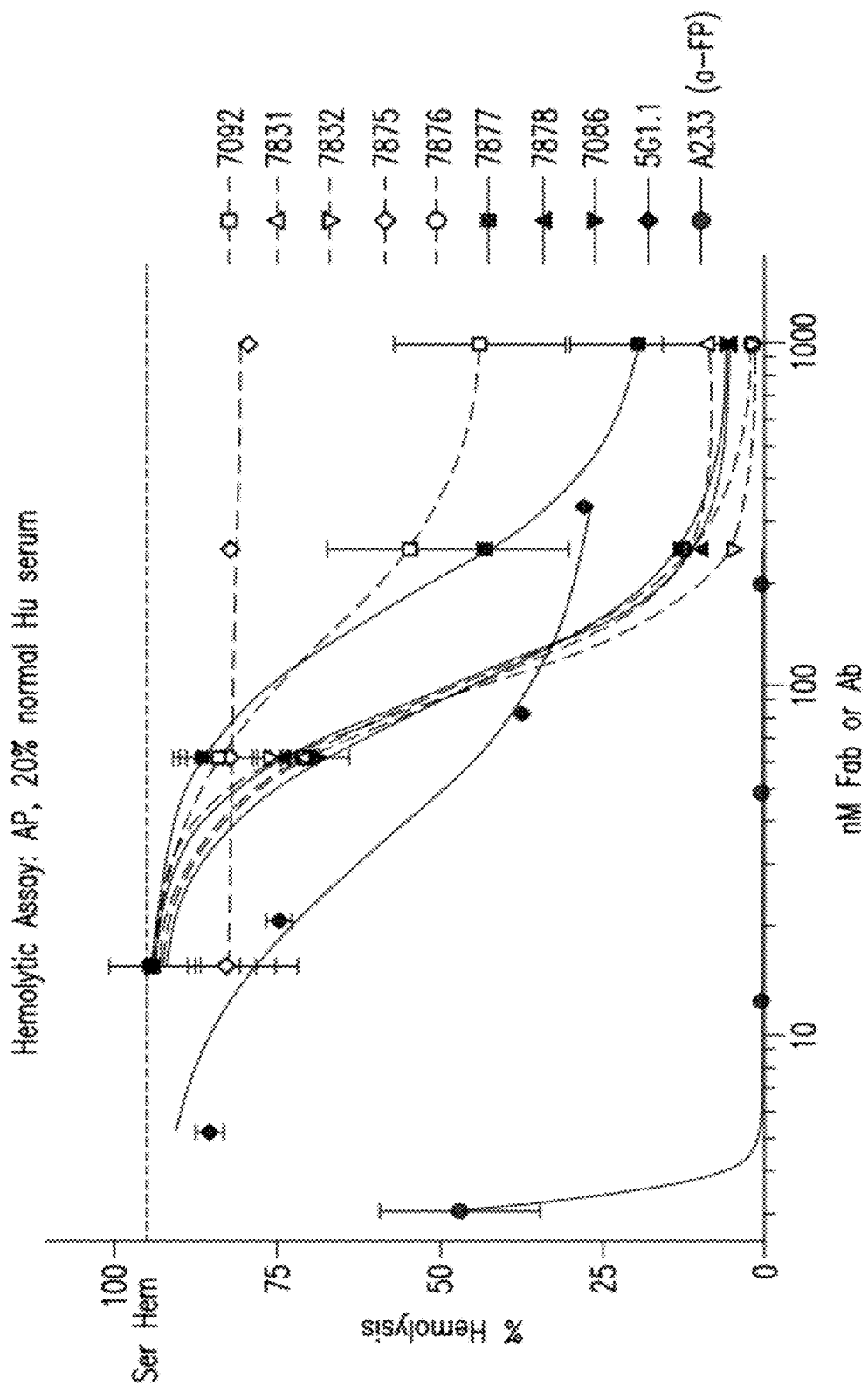
FIG. 10 shows affinity matured Fab characterization in alternative pathway hemolytic assay using 20% human serum.
Figure 10B:
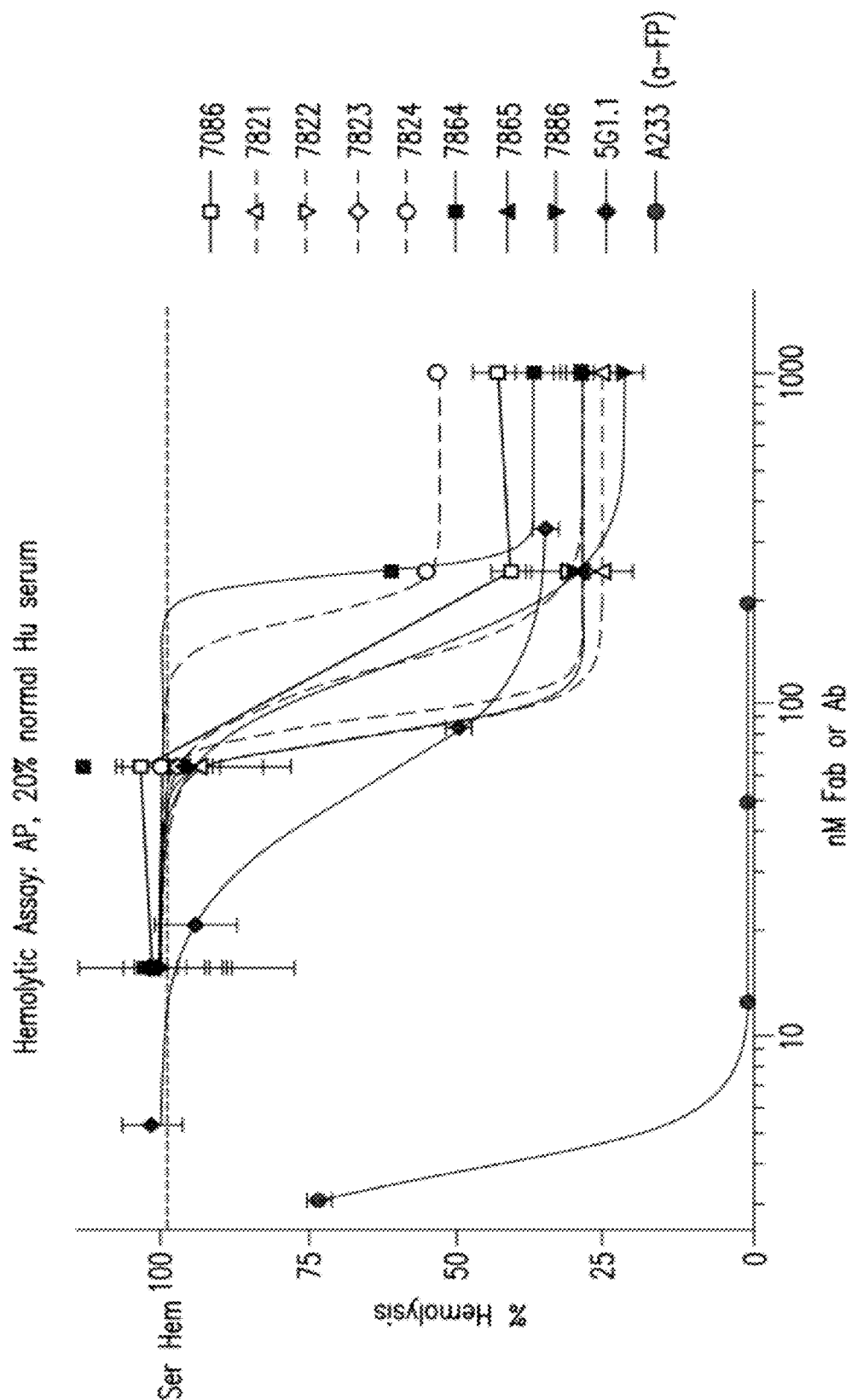
Figure 10C:
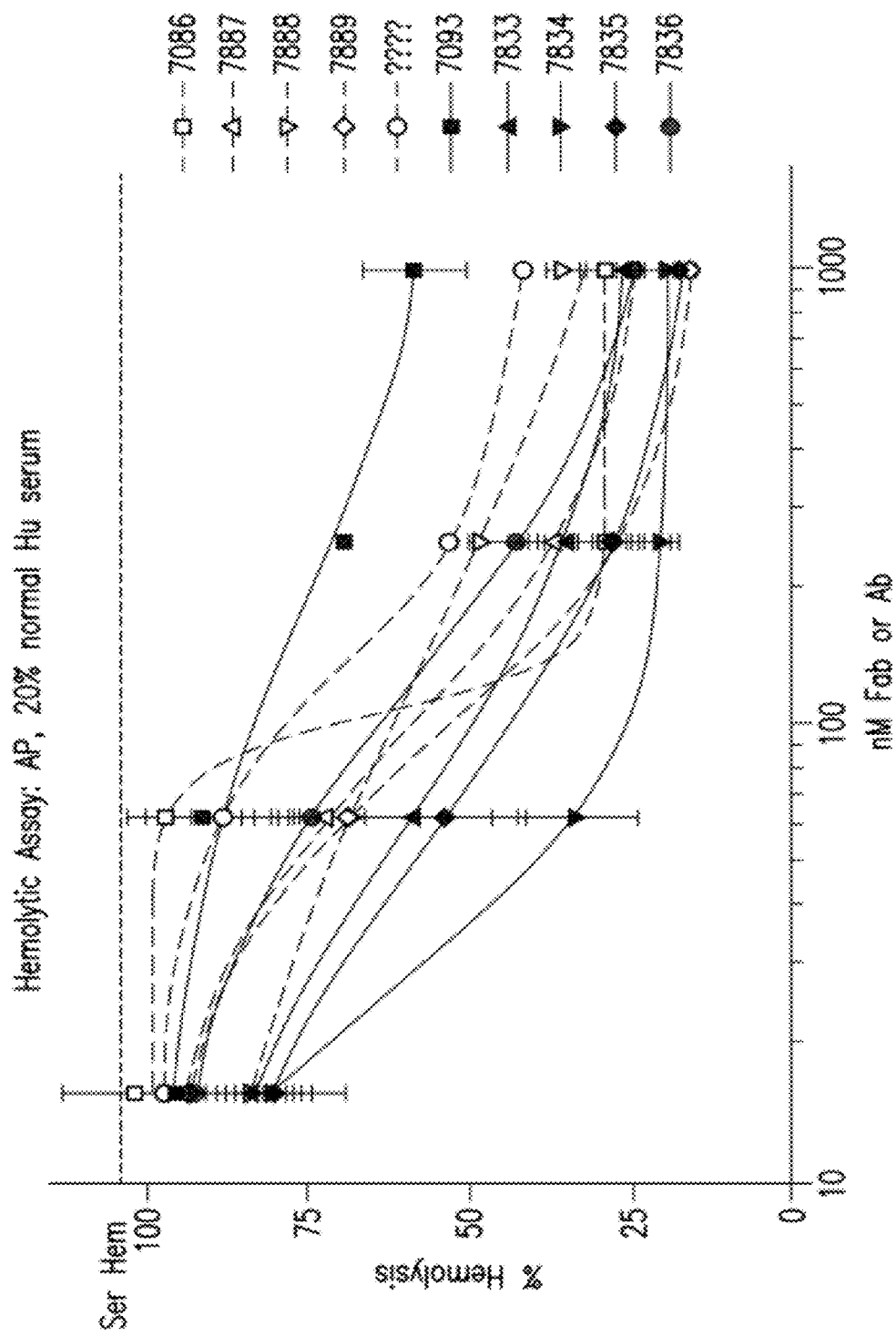
Figure 10D:
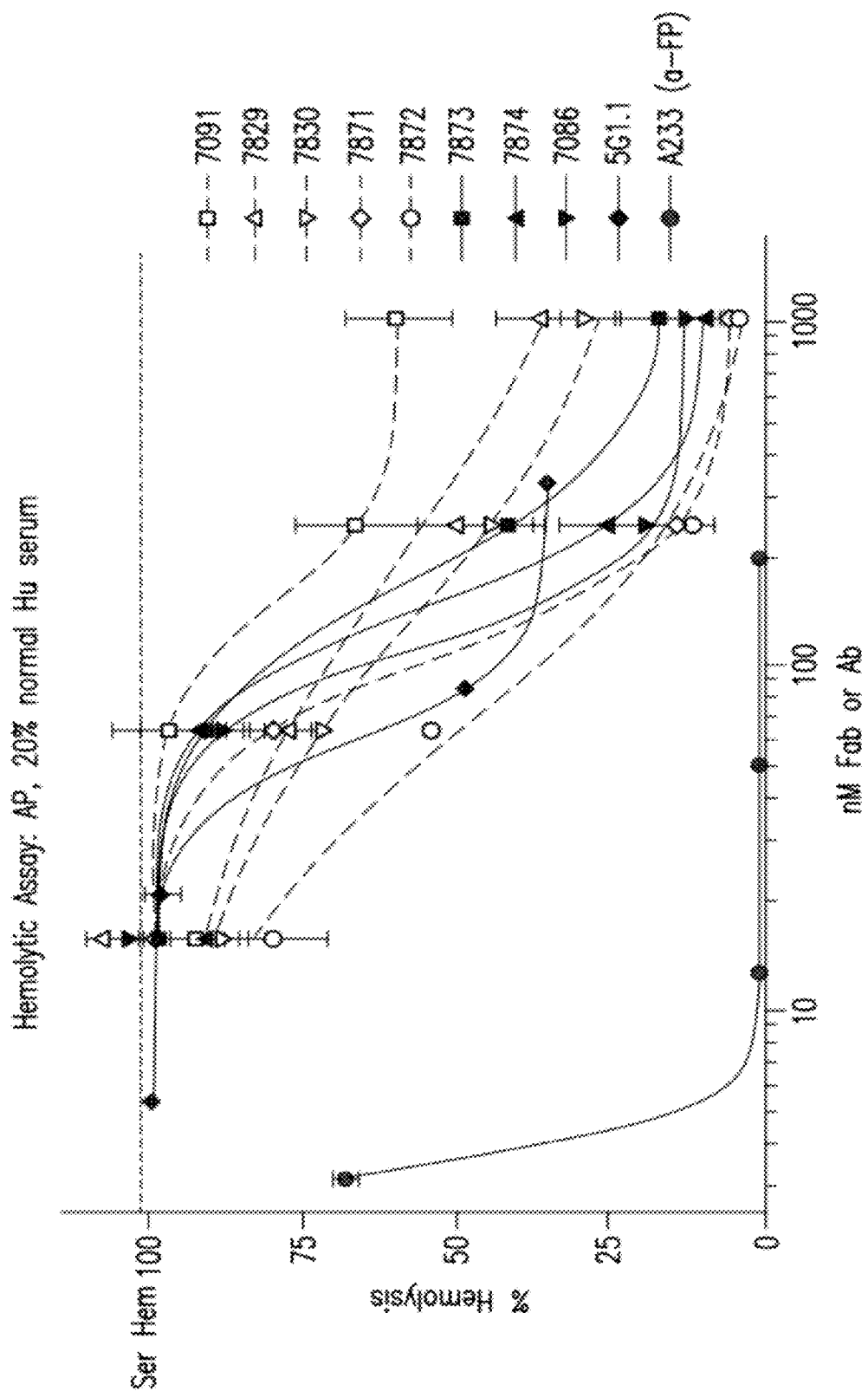
Figure 10F:
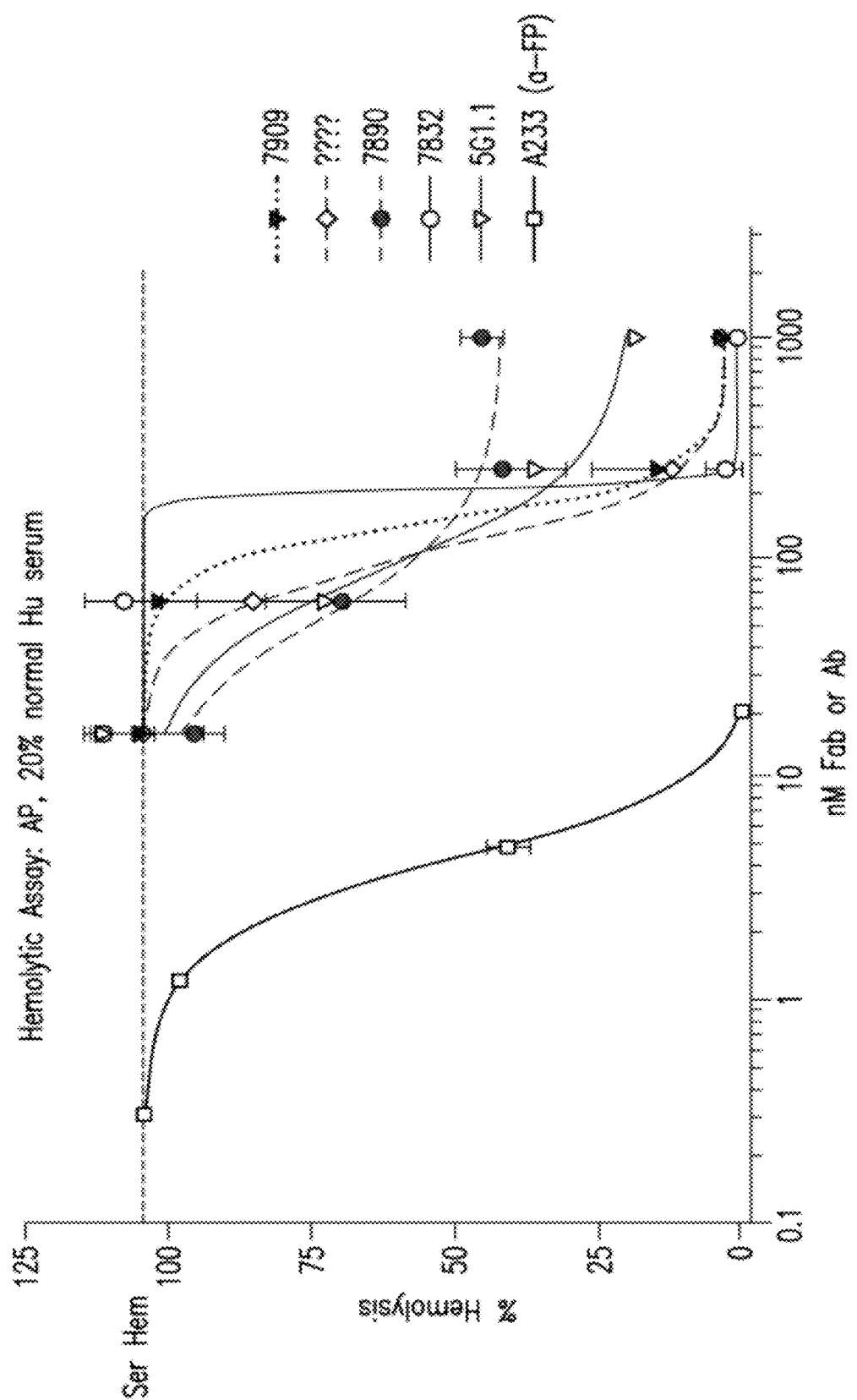
Figure 11A:
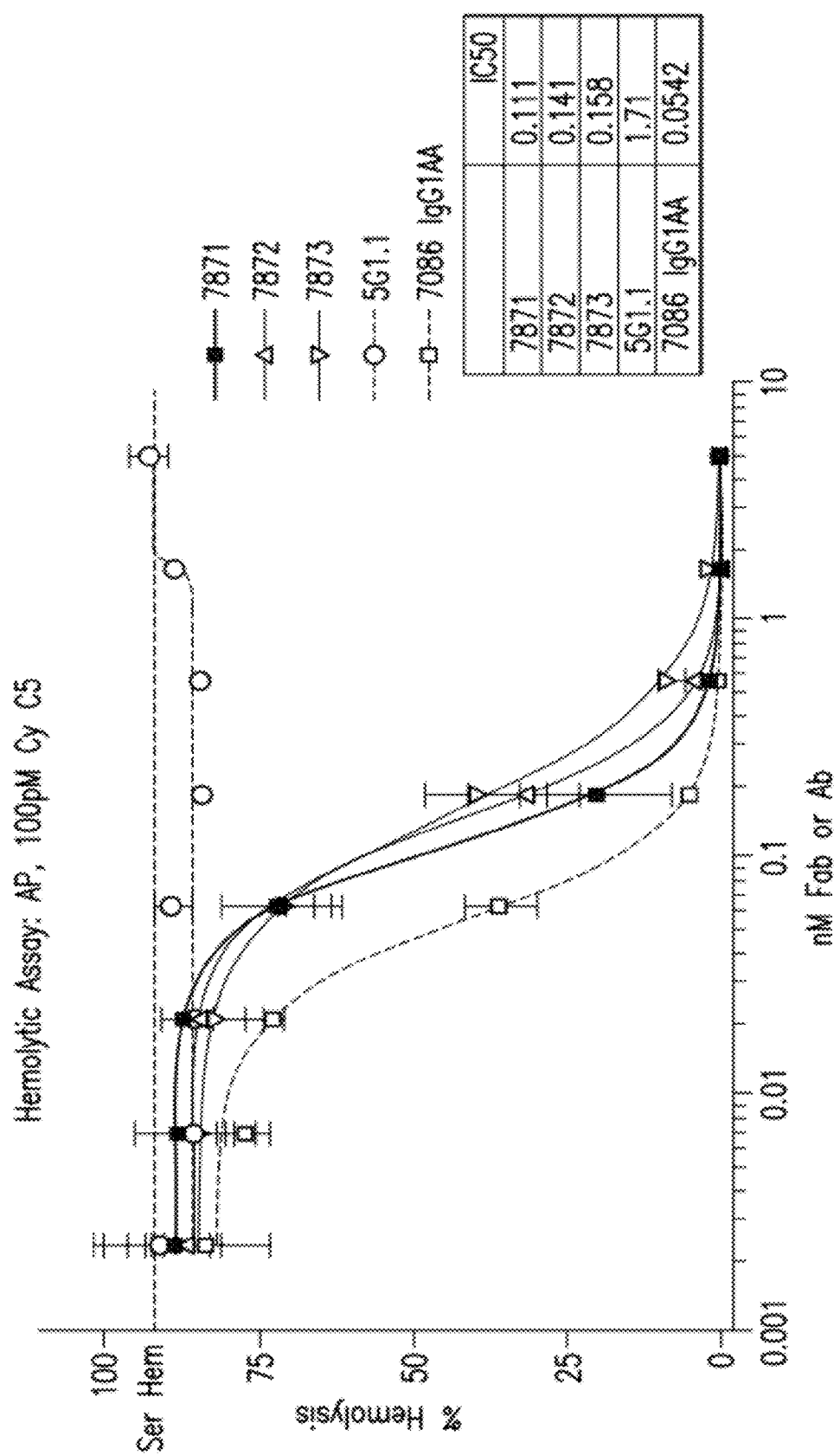
FIG. 11 shows affinity matured Fab characterization in alternative pathway hemolytic assay using 100 pM cynomolgus C5 added to 20% human C5-depleted serum.
Figure 11C:
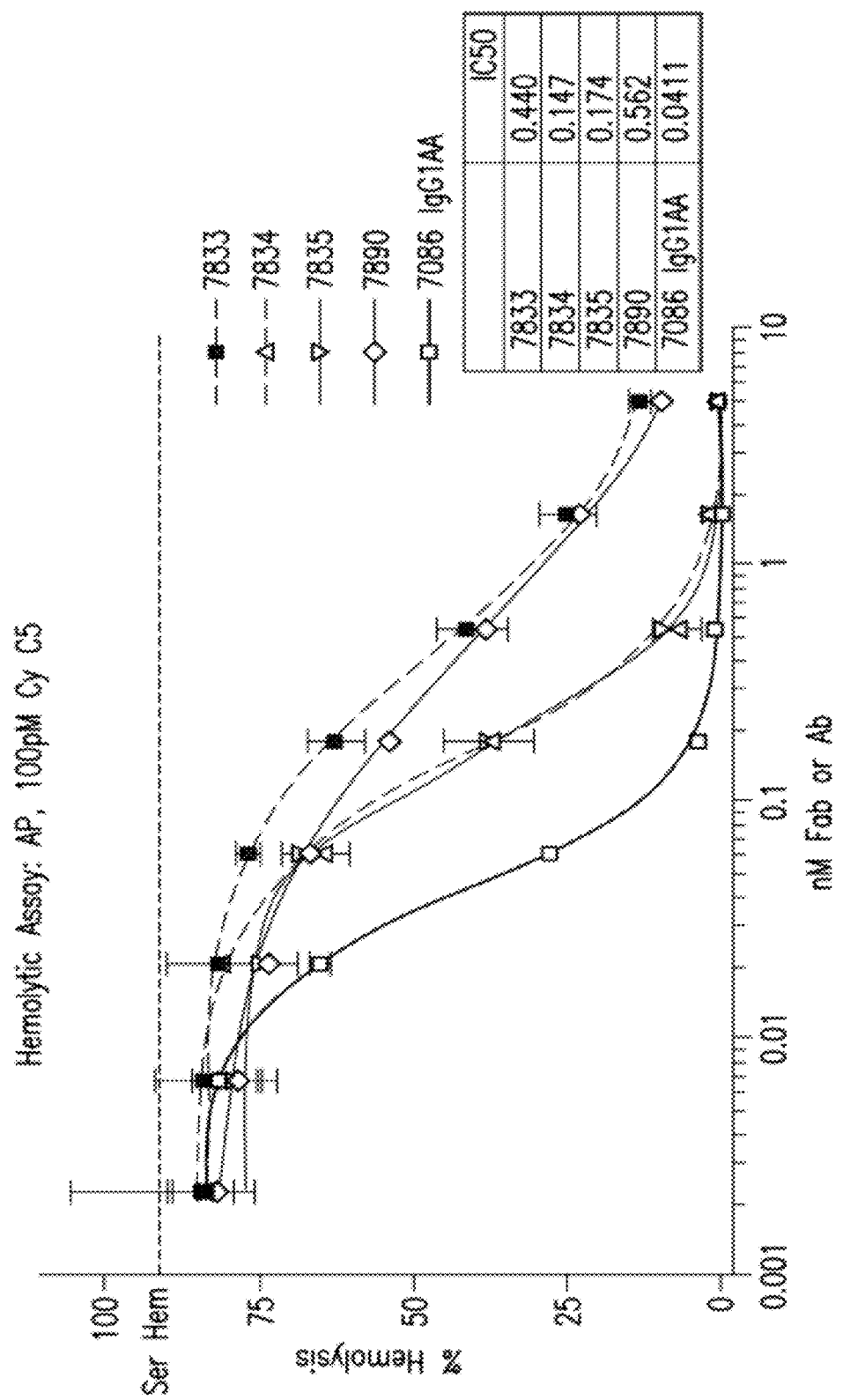
Figure 11D:
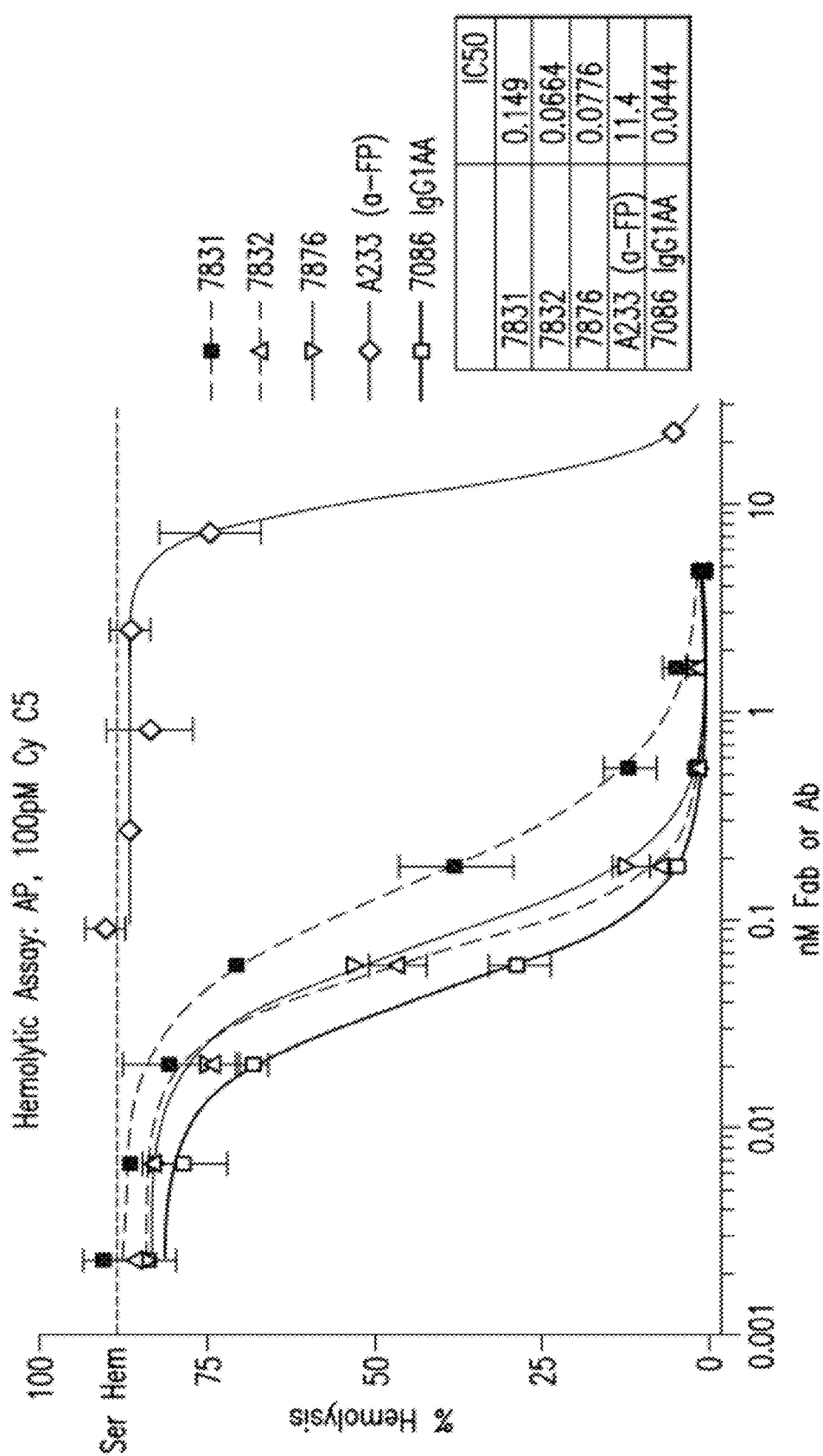
Figure 11E:
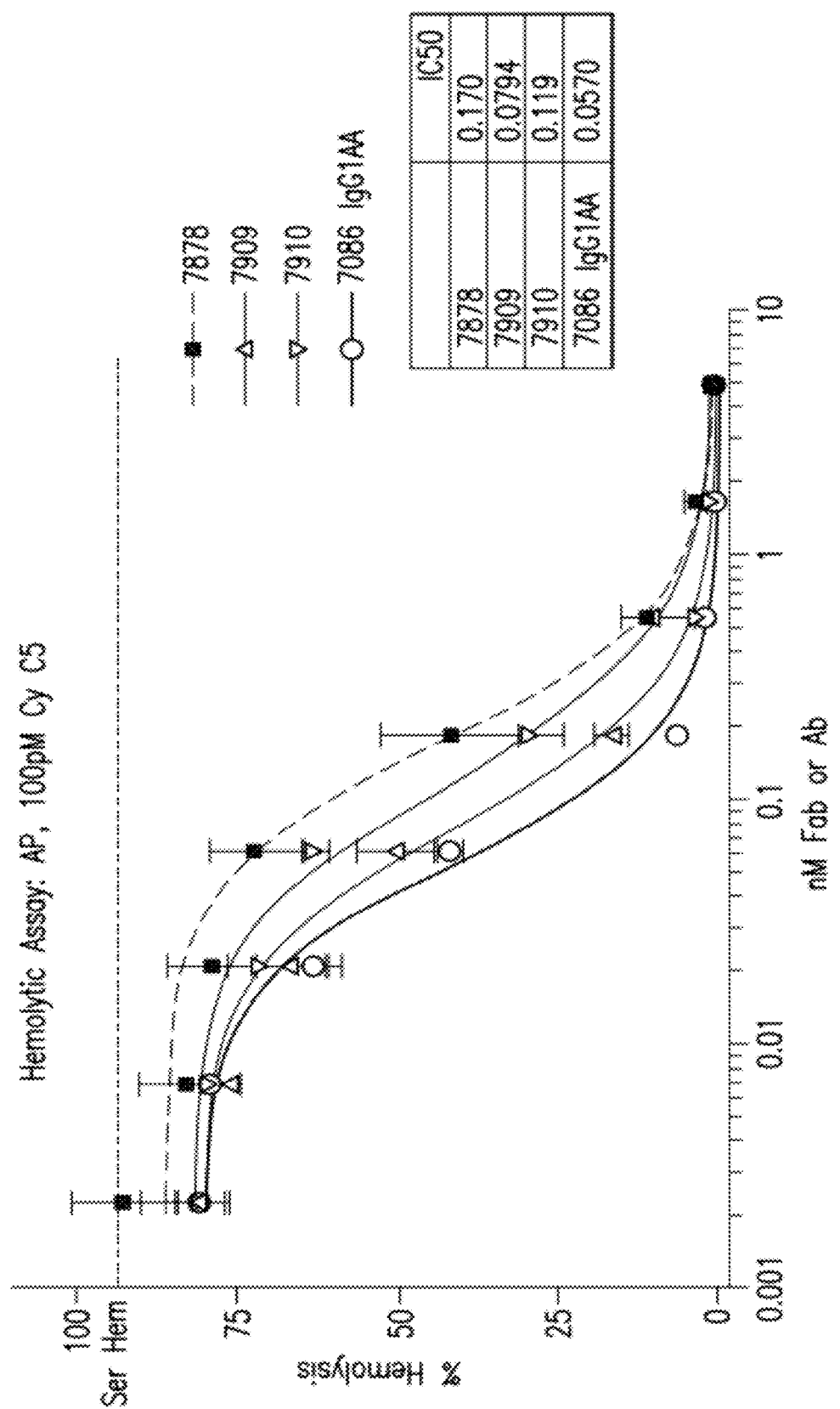
Figure 11F:
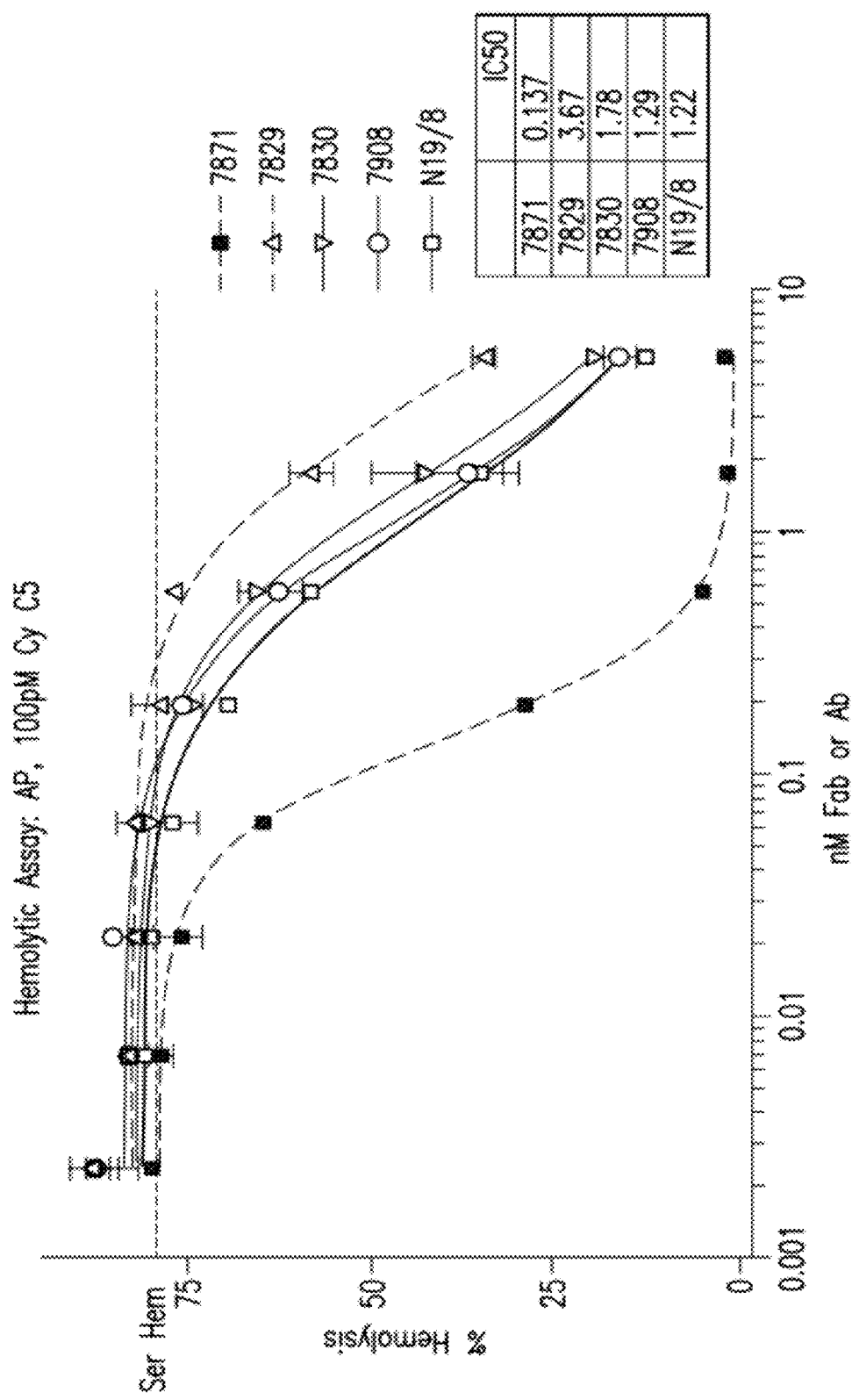

Assays of the complement pathway were also run in the presence of 5% cynomolgus serum in order to test for cross-reactivity. Derivatives of MOR07086, 7091, 7092 and 7093 could very effectively inhibit red blood cell lysis. The negative control, MOR03207 (anti-lysozyme Fab), had no impact on the complement pathway. Results of these assays are shown in FIG. 8.

Alternative Pathway (1) Alternative Pathway Using 100 pM Human C5

Matured Fabs were tested in the alternative pathway hemolytic assay with 100 pM human C5. Some derivatives of MOR06525, 6757, 6763, and 7087 showed potency improvement compared to their parentals. MOR07086-, 7091-, 7092-, 7093-, and 7094-derived Fabs showed highest potency (IC50 values in the low nM range). Descendants of MOR07091, 7092, 7093, and 7094 showed highly improved potency, many of which are more potent than reference antibody 5G1.1. FIG. 9 shows examples of hemolytic assay results for the affinity matured Fabs and 5G1.1.

(2) Alternative Pathway Using 20% Human Serum

Matured Fabs were tested in the alternative pathway hemolytic assay with 20% human serum. MOR07086-, 7091-, 7092- and 7093-derived Fabs showed best inhibitory activity. Many of these Fabs had better inhibitory activity than 5G1.1. FIG. 10 shows examples of hemolytic assay results for the affinity matured Fabs and reference antibody 5G1.1.

(3) Alternative Pathway Using 100 pM Cynomolgus C5

Matured Fabs were tested in the alternative pathway hemolytic assay using 100 pM cynomolgus C5 added to 20% human C5-depleted serum. MOR07091-, 7092- and 7093-derived Fabs showed best inhibitory activity; 5G1.1 does not crossreact with cynomolgus C5. FIG. 11 shows examples of hemolytic assay results for the affinity matured Fabs.

Figure 12:
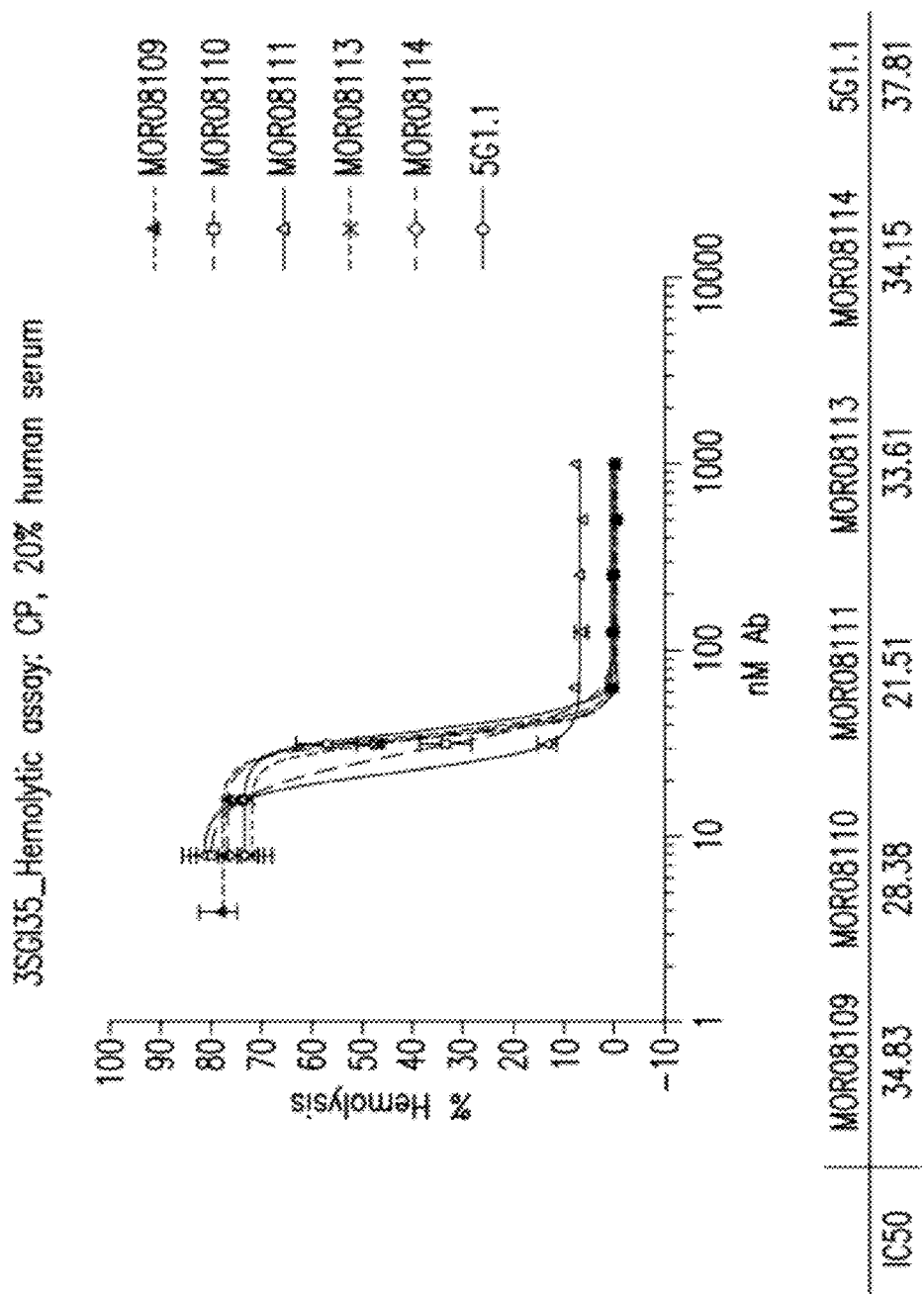
FIG. 12 shows characterization of germlined IgGs in classical pathway hemolytic assay using 20% human serum.

5. Hemolytic Assays with Germlined IgGs (Human IgG1AA Format) Classical Pathway (1) Classical Pathway Using 20% Human Serum Classical pathway assays using 20% human serum were run at MOR. IC50 values of the final germlined hu IgGAA—MOR08109, 8110, 8113, 8114—were better or similar to reference IgG 5G1.1 (see FIG. 12).

(2) Classical Pathway Using 5% Cynomolgus Serum

Figure 13:
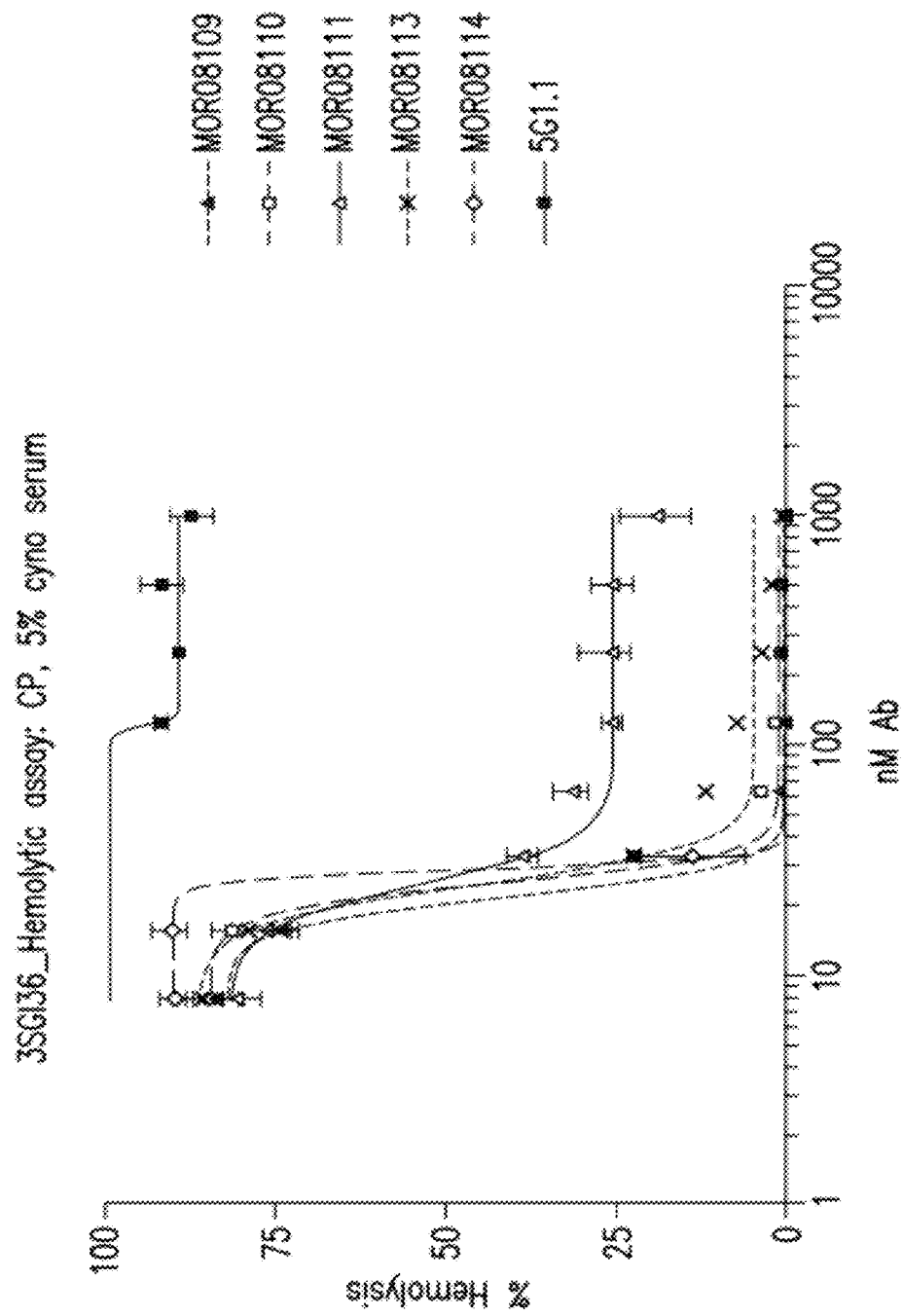
FIG. 13 shows characterization of germlined IgGs in classical pathway hemolytic assay using 5% cynomolgus serum.

A comparison to 5G1.1 in the classical pathway using 5% cynomolgus serum was not applicable, since this reference antibody does not recognize cynomolgus C5. The final germlined IgGs could completely inhibit lysis of the red blood cells induced by cynomolgus serum except MOR08111. Data are shown in FIG. 13.

Alternative Pathway (1) Alternative Pathway Using 100 pM Human C5

Figure 14C:
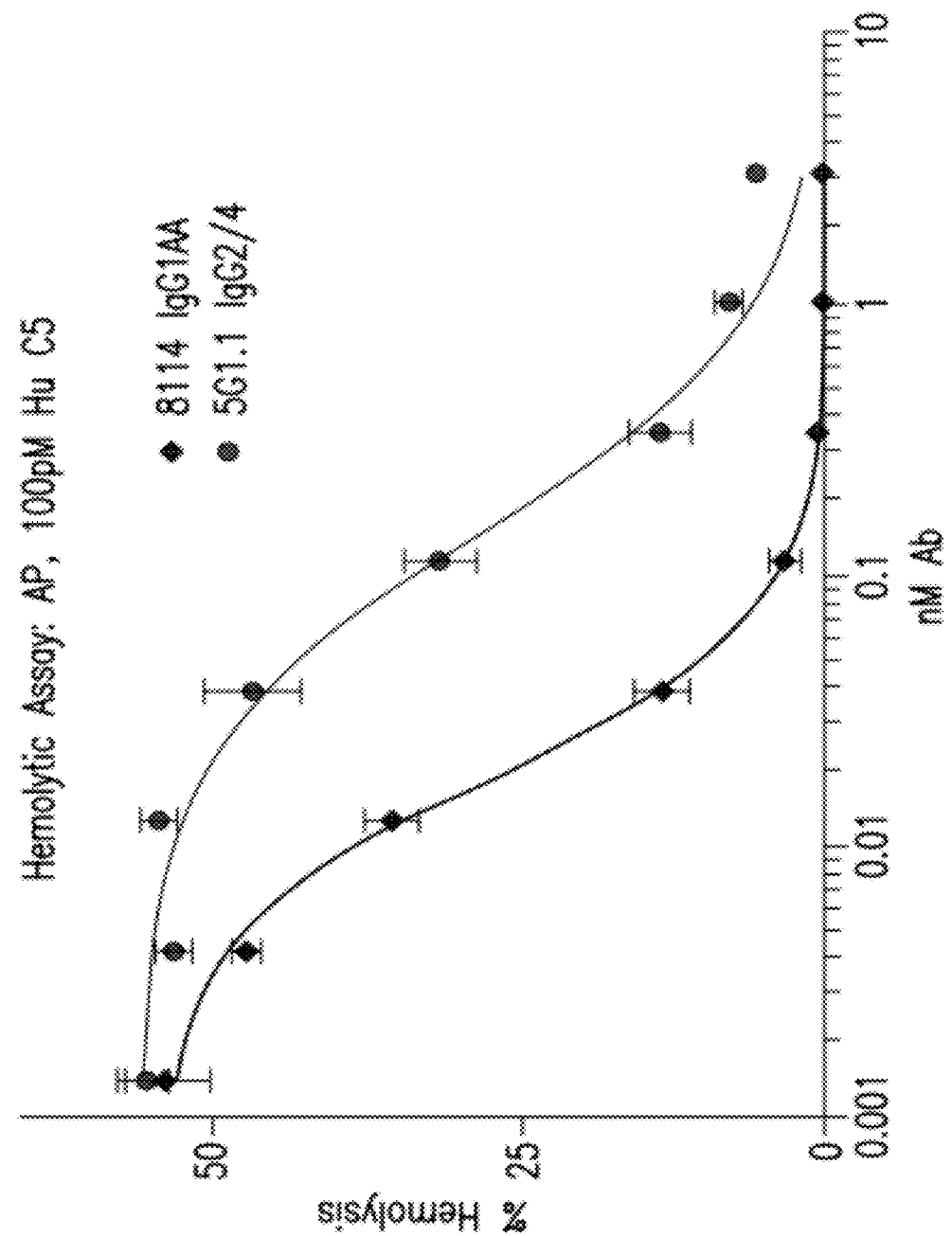
FIG. 14 shows characterization of germlined IgGs in alternative pathway hemolytic assay, 100 pM human C5.
Figure 15A:
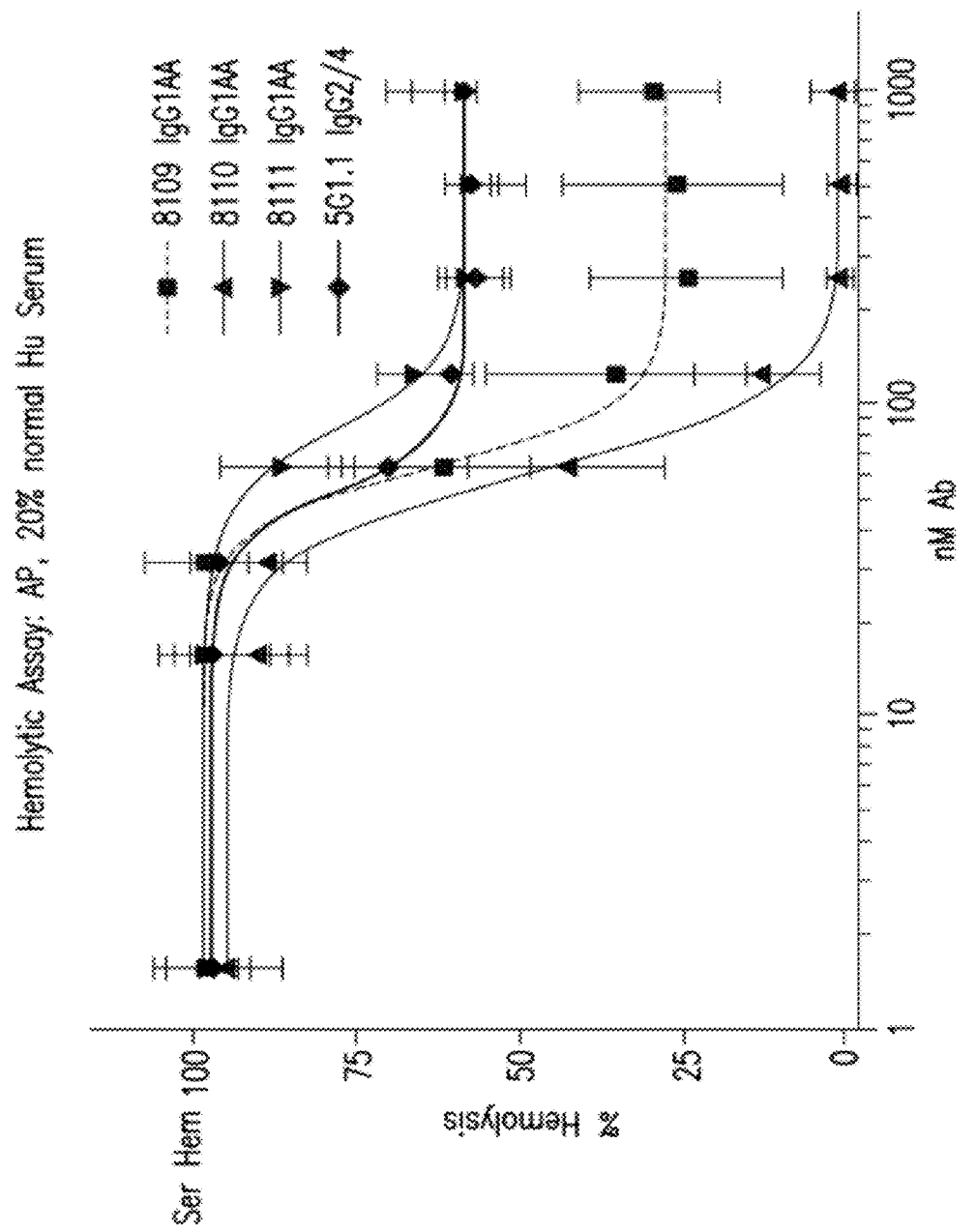
FIG. 15 shows characterization of final germlined IgGs in alternative pathway hemolytic assay and C5a generation ELISA using 20% human serum.
Figure 15B:
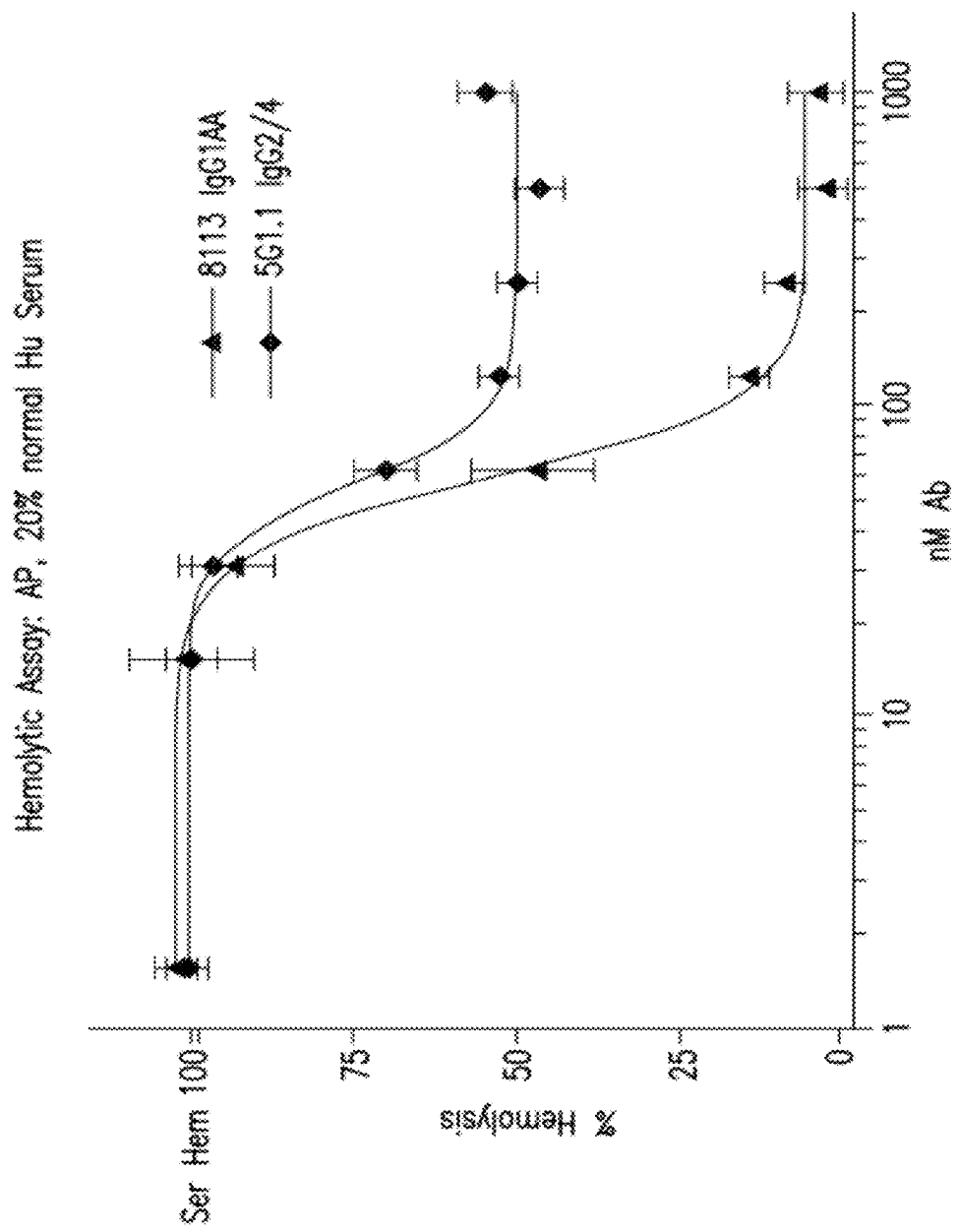
Figure 15C:
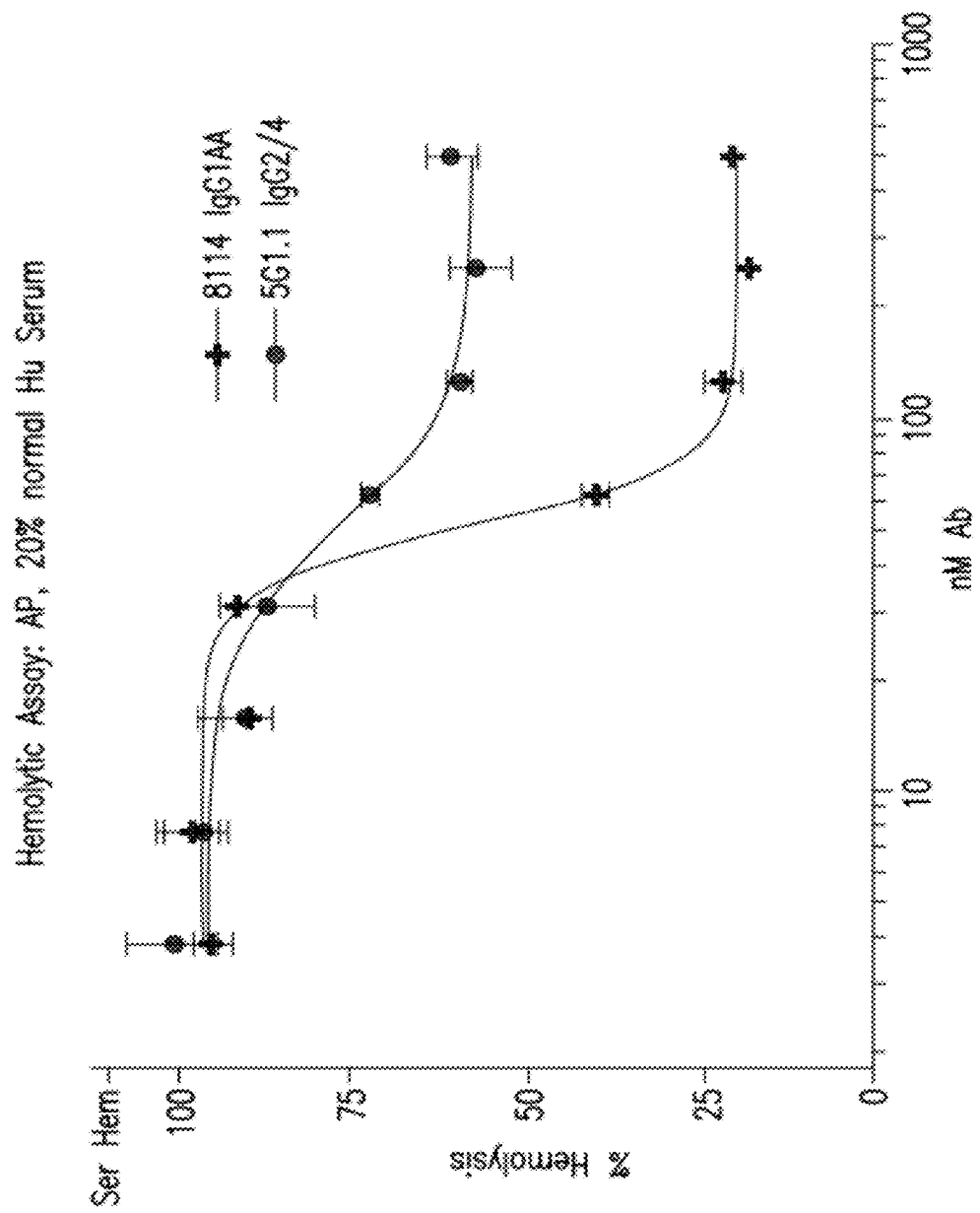
Figure 15D:
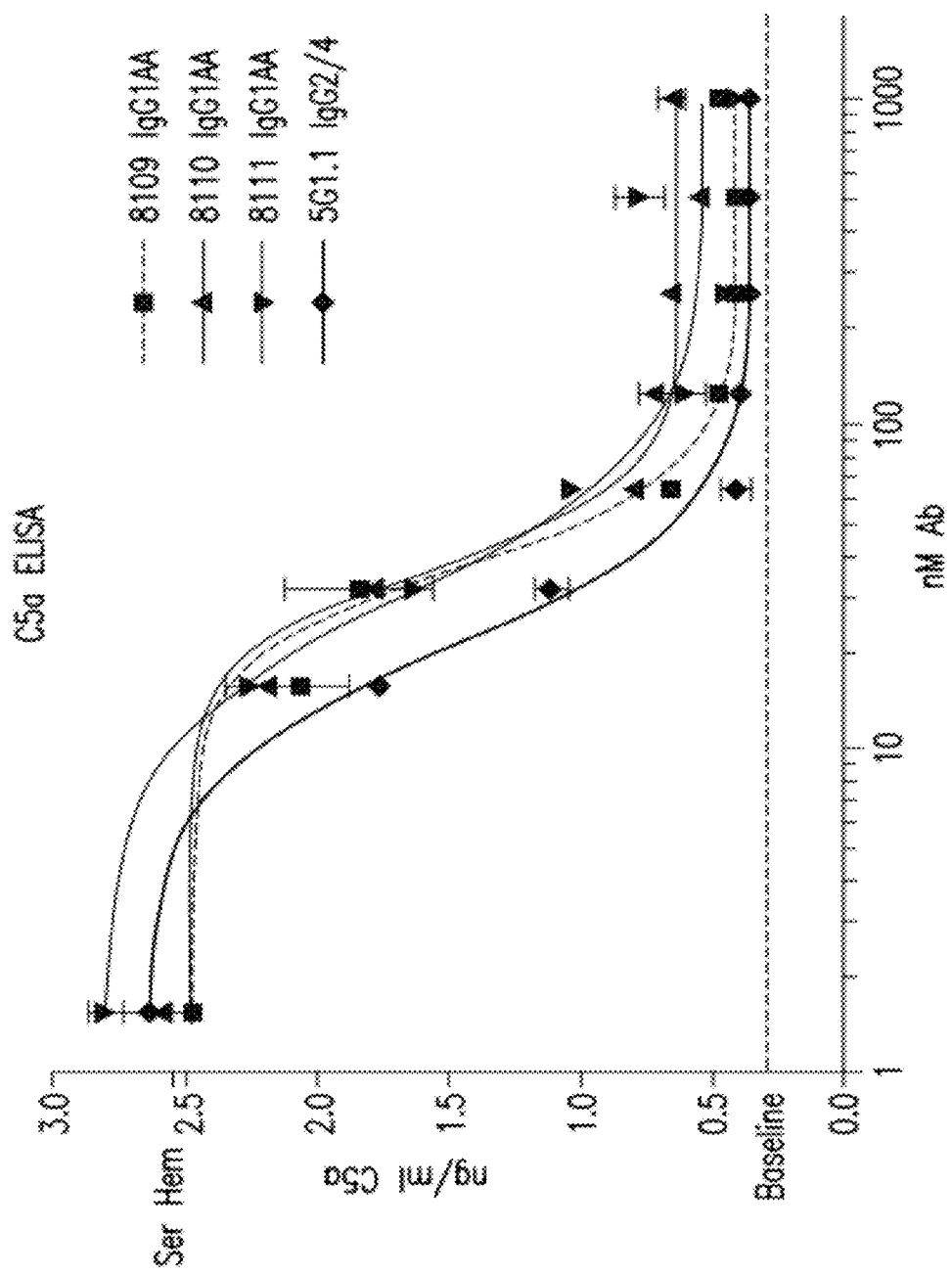
Figure 15E:
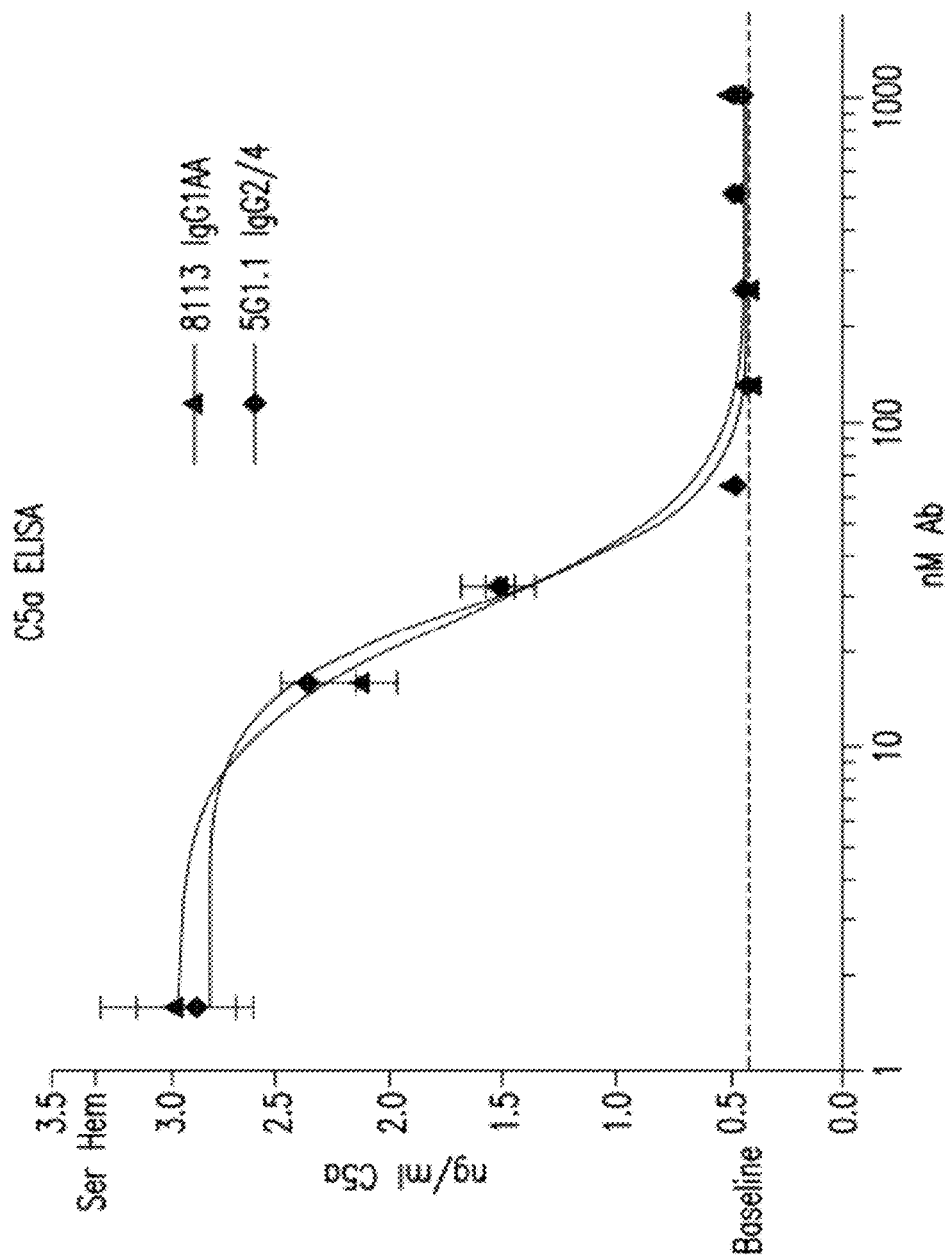
Figure 15F:
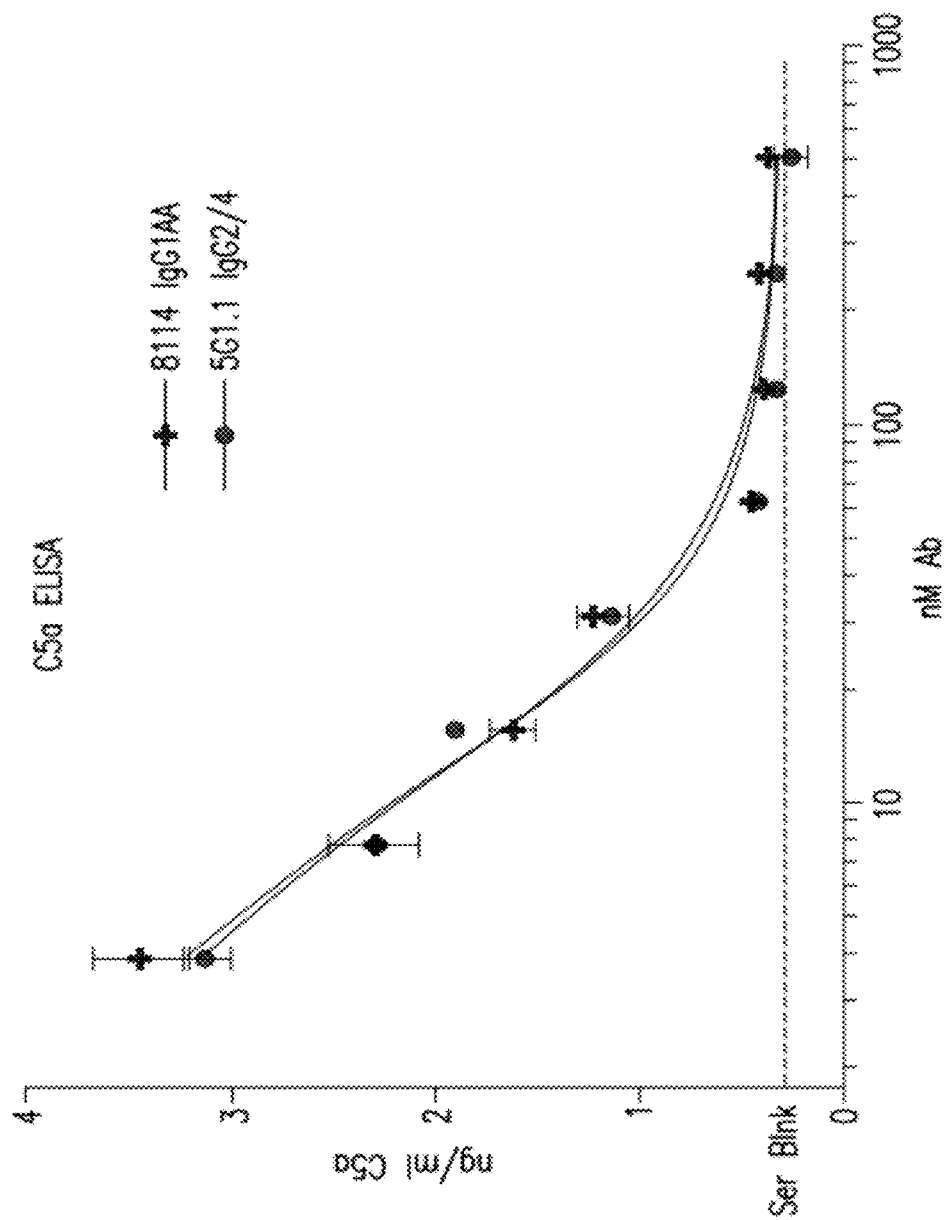

The germlined IgGs were tested in the alternative pathway hemolytic assay using 100 pM human C5. All antibodies showed potent inhibitory activity with IC50 values between 28 and 128 pM (with the exception of MOR08111, see FIG. 14), all were equal to or better than 5G1.1. FIG. 14 shows examples of hemolytic assay results for the IgGs.

(2) Alternative pathway Using 20% Human Serum and C5a Generation ELISA

The germlined IgGs were also tested in the alternative pathway hemolytic assay with 20% human serum. The majority of the antibodies tested achieve complete inhibition with 1050 values lower than 80 nM. Reference antibody 5G1.1 does not fully inhibit hemolysis in this assay. FIG. 15 shows examples of hemolytic assay results for the IgGs. Inhibition of C5a generation by the final IgGs was similar to 5G1.1 (1050 values in the low nM range).

(3) Alternative Pathway Using 100 pM Cynomolgus C5

Hemolytic assays of the alternative pathway in 20% human C5-depleted serum were reconstituted with 100 pM cynomolgus C5. Potency of the germlined final candidates against cynomolgus C5 was within 5-fold of that for human C5 (1050 values in the low pM range).

(4) Alternative Pathway Using 10% Cynomolgus Serum

In hemolytic assays of the alternative pathway using 10% cynomolgus serum ([C5]~40 nM) the potency of the germlined candidates was similar to the potency in human serum (success criterion was to have a potency not more than 5-fold weaker than for the fuctional assay using human C5).

Example 9

C5a Generation ELISA

C5a-des-Arg ELISA was developed to measure C5a generation during hemolysis to confirm that antibodies that were inhibitory in the hemolytic assay also inhibited cleavage of C5 into C5a and CSb.

A MaxiSorp® plate was coated with 100 µl/well mouse anti-human C5a-des-Arg (US Biologics) at 1 µg/ml in coating buffer (bicarbonate pH 9.5-9.8) and was incubated overnight at 4° C. After washing 3× with PBST, the plate was blocked with 300 µl/well diluent (Synblock, AbD Serotec) for 2 hours at room temperature. After aspirating the blocking solution, 100 µl samples or standards diluted with diluent were incubated for 1 hour at room temperature. Standards were prepared as follows: start was at 20 ng/ml standard (rC5a-des-Arg) and 1:4 serial dilutions were prepared for a 7-point curve. Samples of hemolytic assays were diluted 1:5 in diluent (hemolytic assay supernatants should be stored at −80° C. until used in C5a ELISA). In between the plate was washed 3× with PBST. 100 µl/well of 0.4 µg/ml detection antibody (biotin-goat anti-human c5a, R&D Systems) diluted in diluent was added and after 1 hour incubation at room temperature, 100 µl/well Strep-HRP (poly-HRP streptavidin) diluted 1:5000 in HRP diluent (poly-HRP diluent) was added for 30 minutes. After washing 4× with PBST, 100 µl/well TMB Substrate (Ultra TMB substrate solution) was added for 5-10 minutes. Reaction was stopped with 50 µl/well stop solution ($2NH_2SO_4$). Absorbance was read (A450-A570) and data were analyzed using SoftMax Pro.

Matured Fabs were tested for C5a generation during hemolysis to confirm that inhibitory activity was due to blocking C5 cleavage into C5a and C5b. The supernatants from hemolytic assays in 20% human serum were used for quantifying the C5a formation.

Figure 16A:
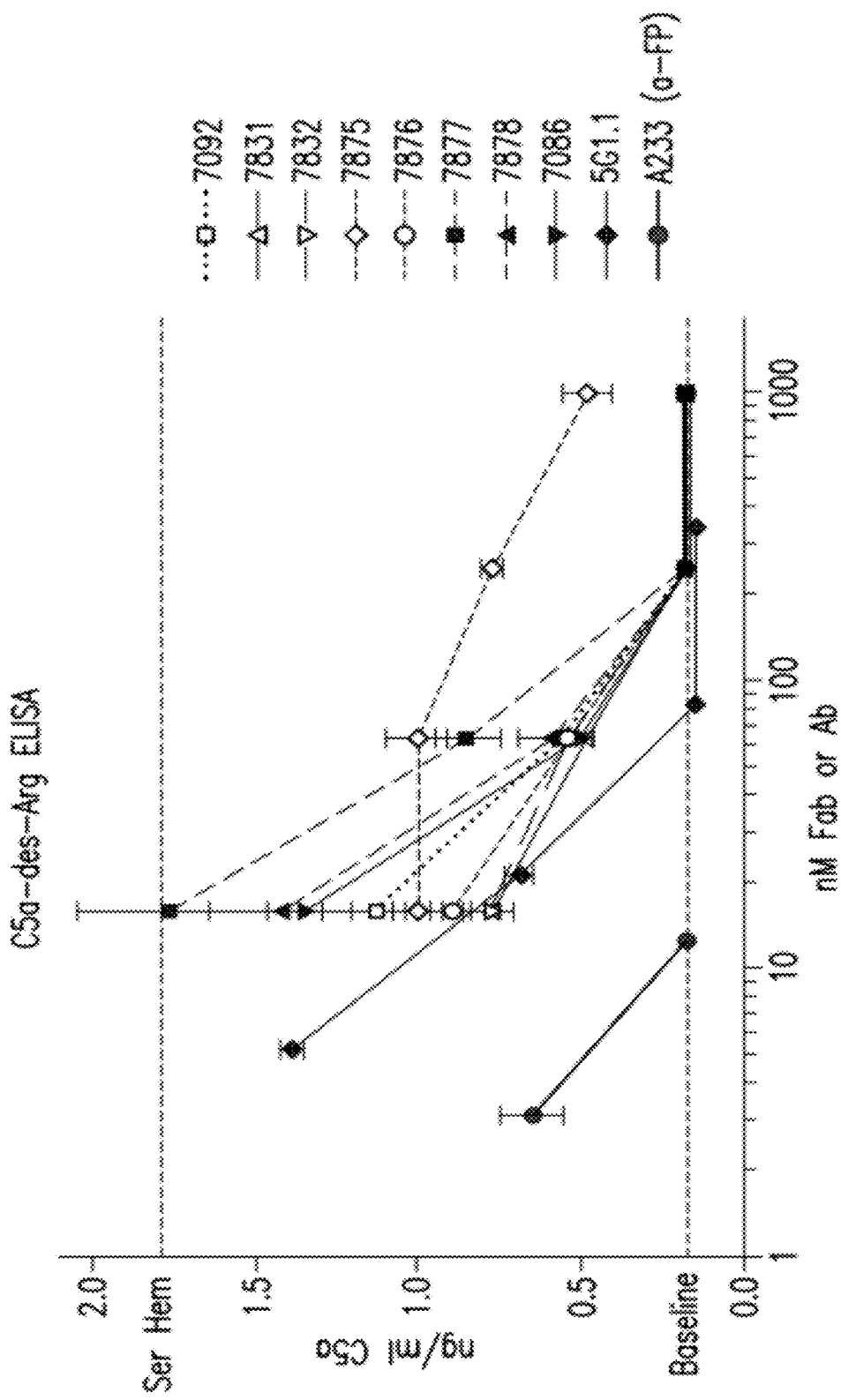
FIG. 16 shows affinity matured Fab characterization in the C5a ELISA using supernatant from 20% human serum hemolytic assays.
Figure 16B:
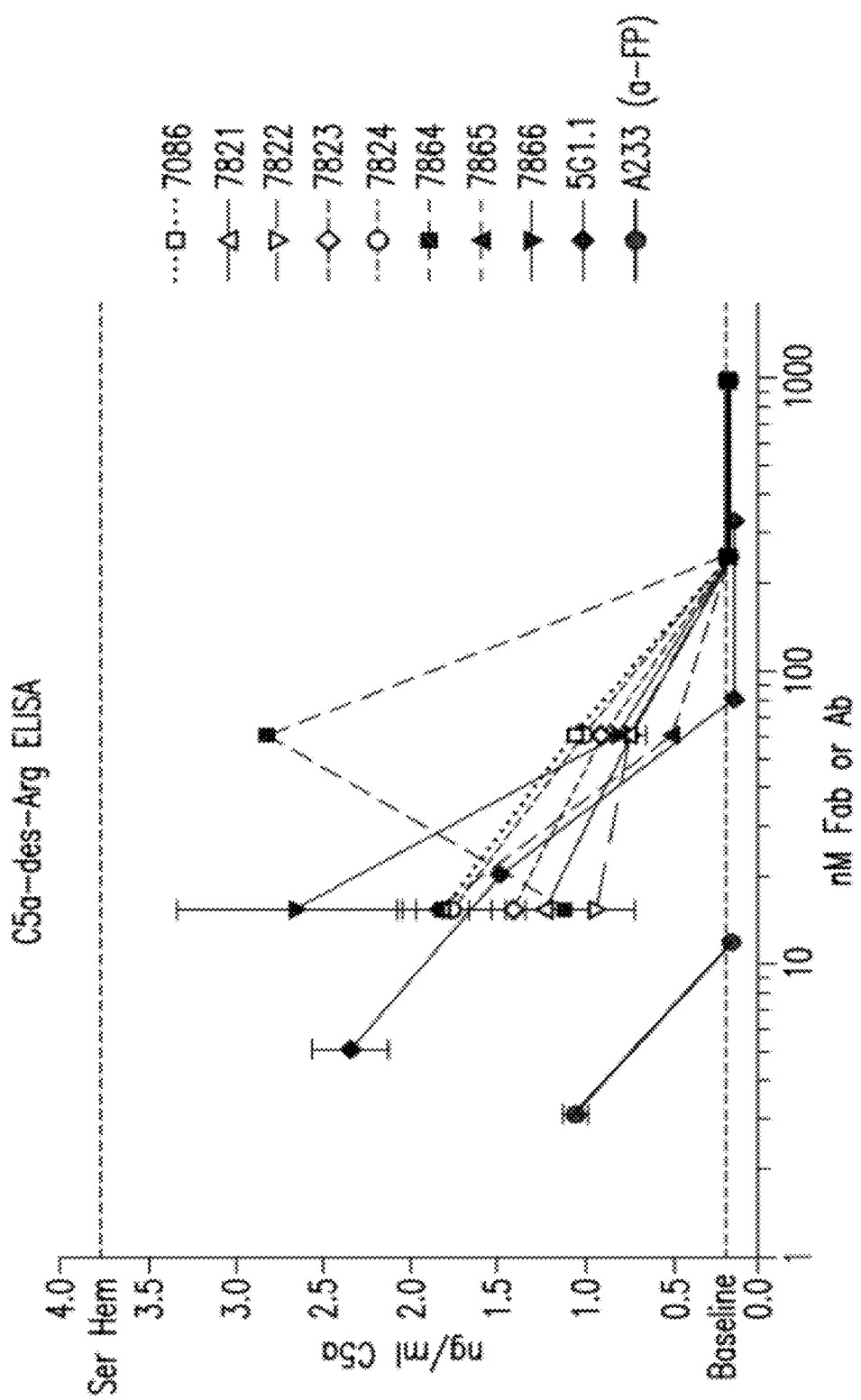
Figure 16D:
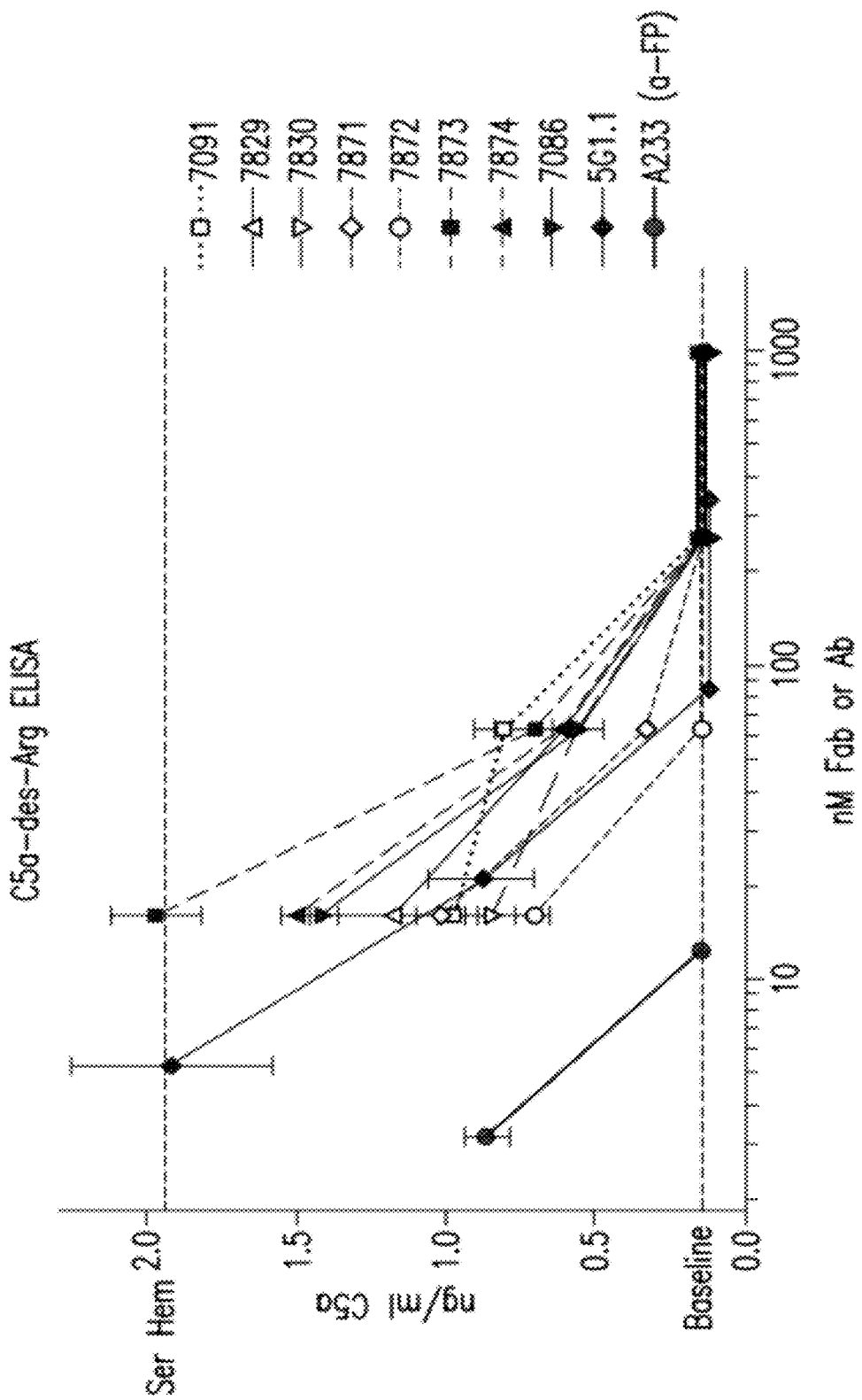

All Fabs tested brought C5a levels down to baseline. FIG. 16 shows examples of C5a ELISA results.

Example 10

Specificity ELISA on Human C3, C4, C5 and Cynomolgus C5

All purified Fabs were analyzed in a solution ELISA (method described above) for binding to human C3, C4 and C5. Fabs were incubated with biotinylated antigen on a Neutravidin plate and detected via the histidin tag.

Figures 1, 17:
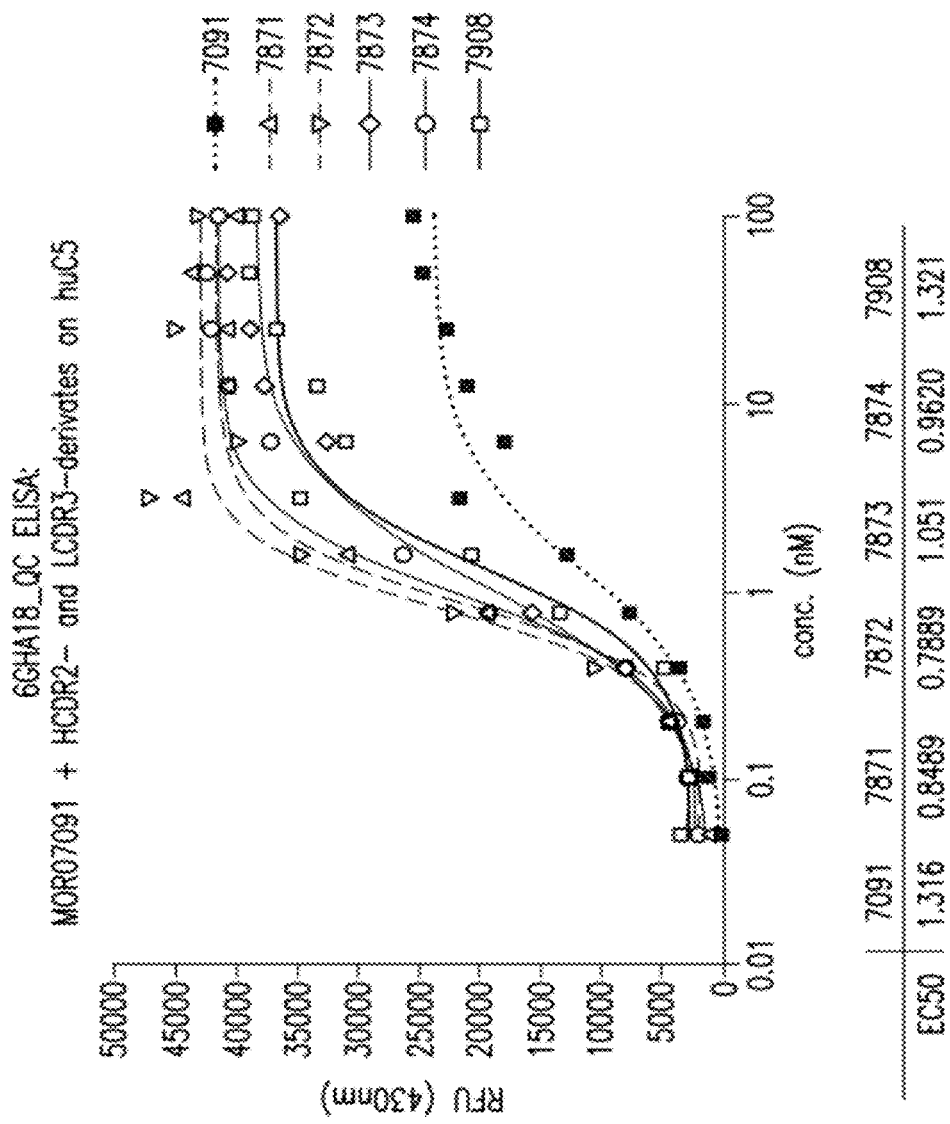
FIG. 17 shows specificity solution ELISA on human C3, C4, C5 and cynomolgus C5 testing antibody 7091 and its derivatives.
Figures 2, 17:
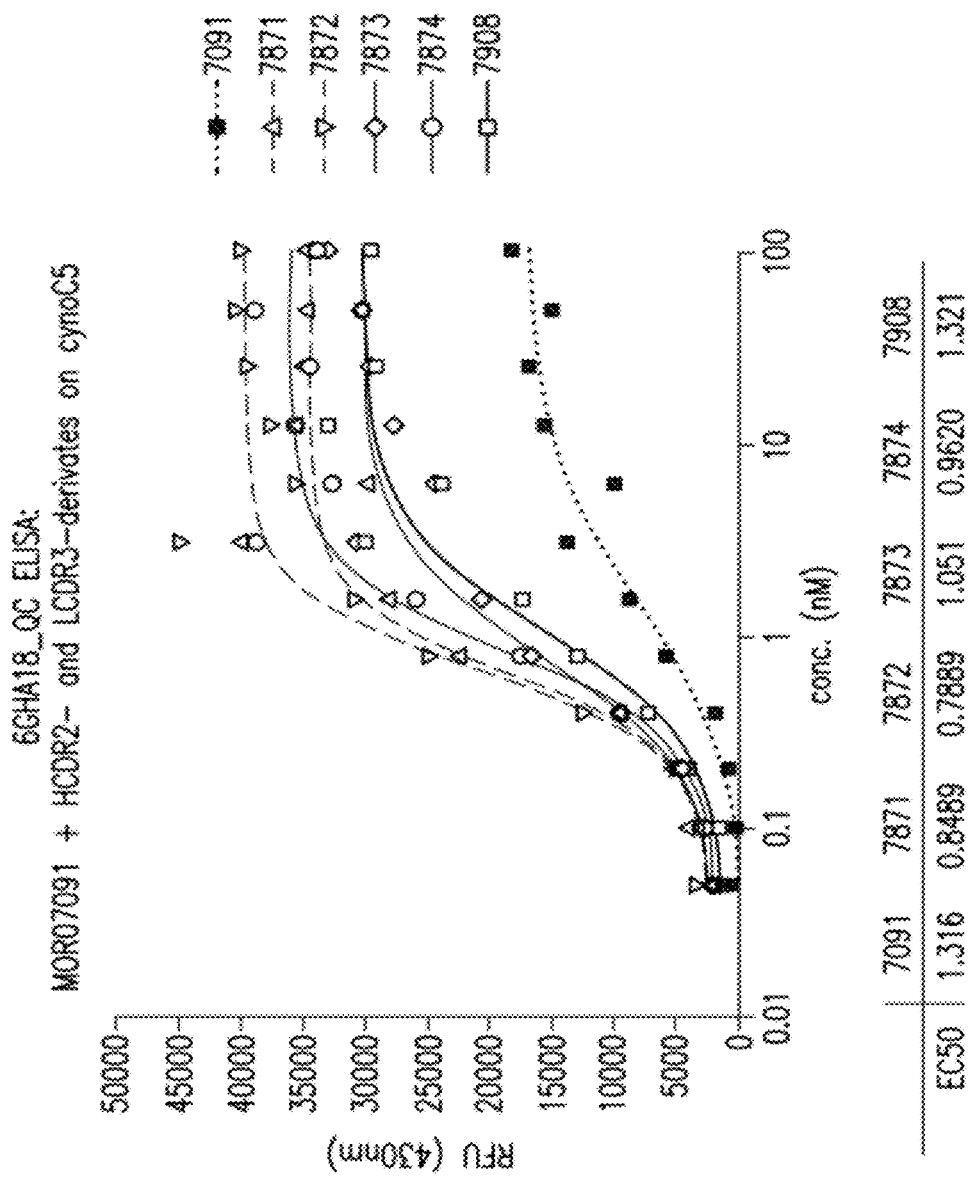
Figures 3, 17:
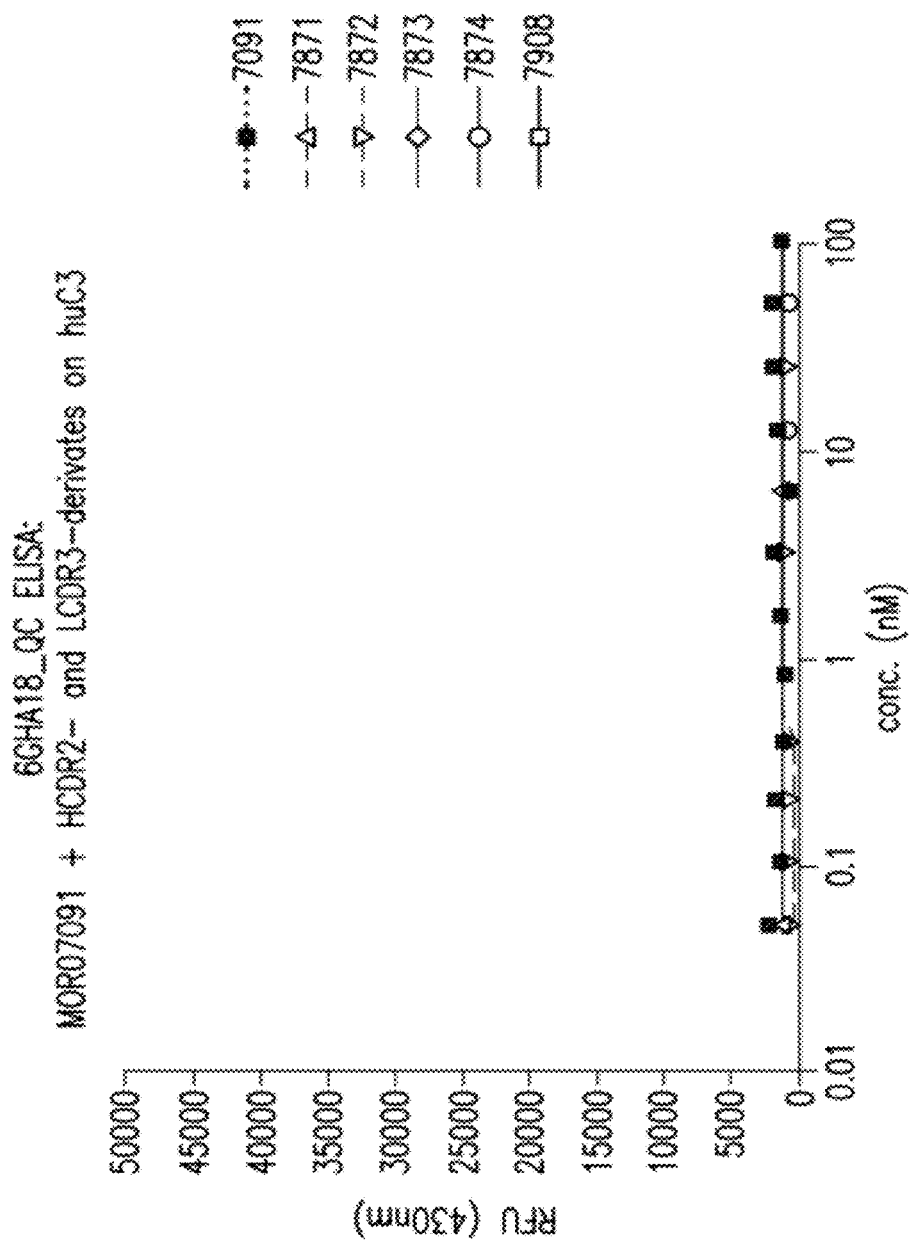
Figures 4, 17:
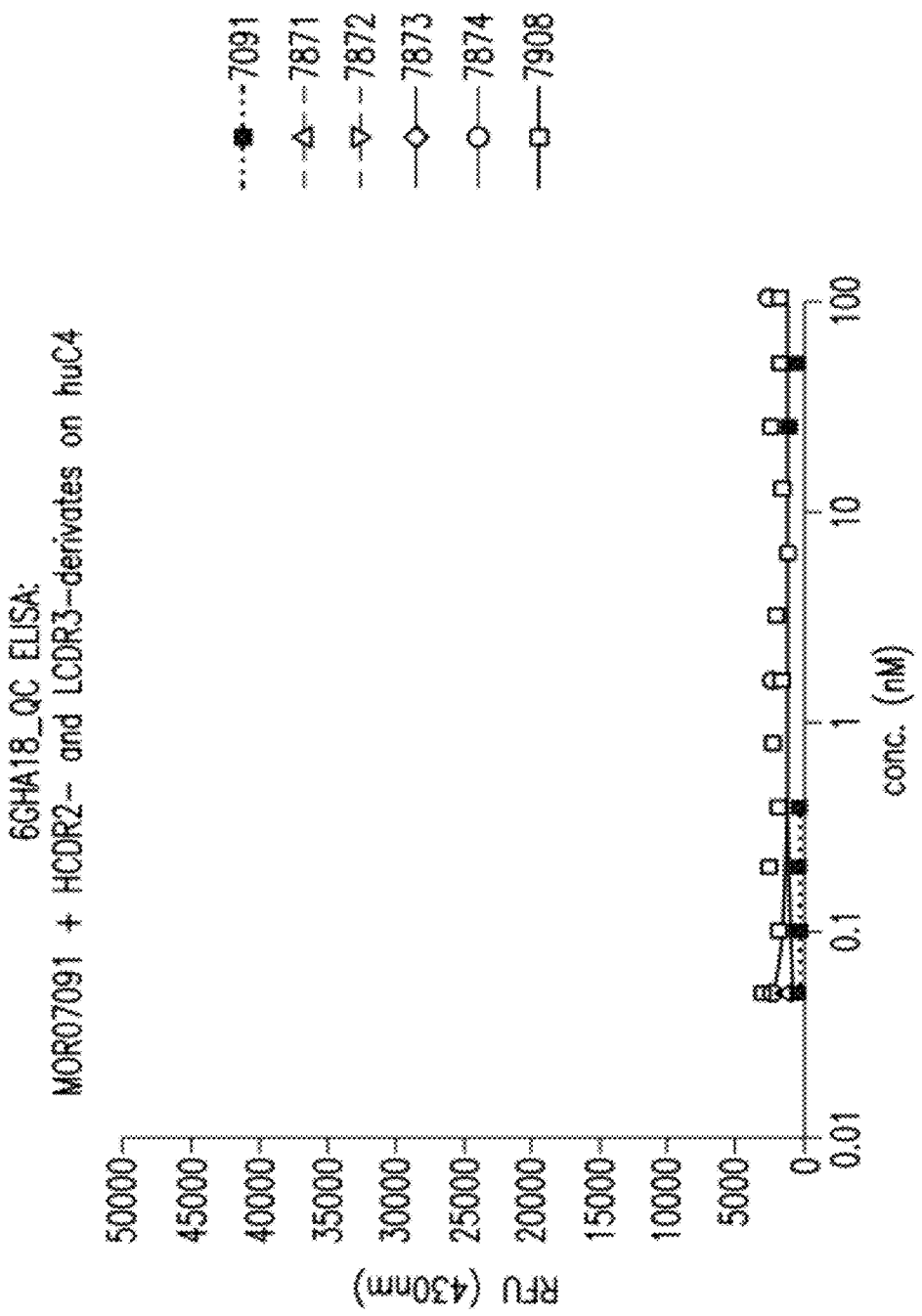

Improved binding was seen for almost all matured Fabs compared to their respective parental. No binding to the counter targets human C4 and C3 was detected up to 100 nM Fab. These results hit the success criteria for specificity: binding to human and cynomolgus C5 and no binding to human complement proteins C3 and C4. Examples for derivatives of parental Fab MOR07091 are shown in FIG. 17.

Example 11

Serum Stability Assays

Retained binding activity to human C5 in a binding assay at 50% human serum of C5-binding antibodies was determined as described below.

Antibodies (Fab format) were incubated up to 8 h at 37° C. with 100% human C5-depleted serum or with PBST/0.5% BSA (positive control). Wells of a blocked polypropylene plate were used for incubation to ensure no binding of the antibodies to the surface over the long incubation time. Samples were collected at different time points and stored at −20° C.

Samples were tested in a solution ELISA on NeutrAvidin plates to check binding ability to human C5. To the NeutrAvidin plates, which were blocked o/n with 1× ChemiBlocker-PBST. 20 µl of serial dilutions of the different collected samples were added. First dilution of the samples was 1:2 (final serum concentration 50%), followed by 1:3 dilutions steps. After 1 h incubation the plate was washed 3× with PBST and 20 µl biotinylated human C5 was applied to a concentration of 2.5 µg/ml. After 1 h plate was washed again 5× with PBST (0.05% Tween) and anti-HIS6—POD detection antibody for Fabs was added.

Fluorescence of the substrate (QuantaBlu™ or AttoPhos®) was measured after 5-10 min and retained binding activity was calculated compared with the respective maximum signal (antibody incubated with PBST/0.5% BSA).

One of the "must" criteria for the C5-binding antibodies is to retain 75-80% of binding activity in human serum i) in a functional assay at 10% serum and ii) in a binding assay at 50% serum. Because hemolytic assays were run in the presence of 20% serum it was only necessary to show retained binding in a binding assay at 50% serum.

Therefore matured final Fabs were incubated with 100% human C5-depleted serum at 37° C. for 8 h. Samples were collected at different time points and tested for binding to human C5 in a solution ELISA. Fab+serum samples used for ELISA were diluted to a concentration of 50% serum+10 nM Fab.

Figure 18:
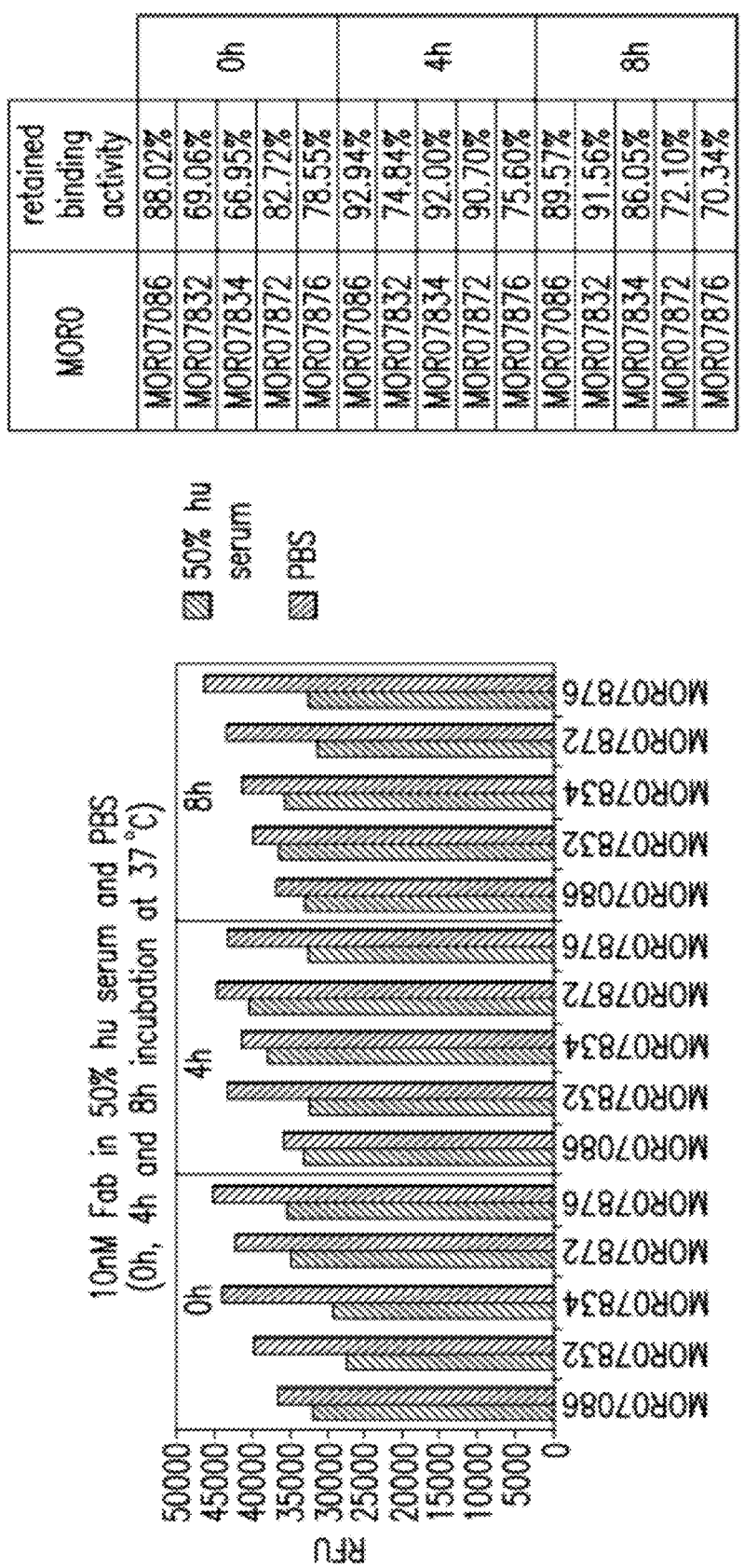
FIG. 18 shows serum stability assays (binding to human C5 in the presence of 50% serum) with the Fabs.

FIG. 18 illustrates the results of the final C5-binding final antibodies in the Fab format. 70-93% of the binding activity was retained after an 8 hour incubation time at 37° C. in 50% serum compared to incubation in PBS.

Example 12

Characterization by Epitope Binning

This procedure was used to group anti-human C5 Fabs into different epitope bins binding to the same or an overlapping epitope of the C5 protein.

Competition of each biotinylated anti-human C5 antibody with each unlabelled anti-human C5 antibody in 100-fold excess was tested in an ELISA (capture mode). It was compared with the highest signal of each antibody (biotinylated Fab without competition).

Human C5 was captured via a polyclonal anti-human C5 IgG (US Biological), which was coated previously o/n at 4° C. on a 384 well black MaxiSorp® plates. Next day the plate was washed twice with PBST and blocked for 2 h with 3% BSA-PBST. After washing 3× with PBST, 20 µl human C5 was added and incubated 2 h ar RT. The plate was washed 3× with PBST before adding the Fabs.

20 µl unlabelled Fab (200 µg/ml or 400 µg/ml) (100-fold excess) was added to the wells of a MaxiSorp® plate and subsequently 20 ng/ml or 40 ng/ml of biotinylated Fab. The biotinylated and unlabelled Fabs were incubated for 1 h at RT. The plate was washed 3× with PBST and Strep-AP Zynnax™ Streptavidin-Alkaline Phosphatase, ZYMED®, Code: 43-8322, Lot: 50799648 was added for detection of the biotinylated Fab binding via C5 to the plates. AttoPhos substrate (Roche) was added to the plates and Fluorescence was read after 5-10 min.

Parental Fabs

C5 was captured (via a polyclonal antibody) and unlabelled FabY was applied in excess to biotinylated FabX. Binding of biotinylated FabX to human C5 was detected. Six groups of Fabs could be defined: Group 1: MOR06952, 6961; Group 2: MOR06525, 6756, 6757, 6763;

Group 3: MOR07087; Group 4: MOR06764, 6776, 7081; Group 5: MOR07089; Group 6: MOR07082, 7083, 7084, 7086, 7088, 7090, 7091, 7092, 7093, 7095.

The Fabs were also divided into different epitope binding groups using a different method: FabX was immobilized, then FabY pre-incubated with biotinylated C5 was added. Following groups of Fabs could be defined: Group 1: MOR06952, 6961; Group 2:

MOR06525, 6757, 7083; Group 3: MOR07087; Group 4: MOR06763; Group 5: MOR07081; Group 6: MOR07082, 7083, 7084, 7086, 7088, 7091, 7092, 7093 (7089 competes with 7084). The conclusion was drawn that using two different methods, similar results could be obtained.

Matured Fabs

In order to complete Fab characterization competition of biotinylated Fab with unlabelled Fab (applied in 100-fold excess) was measured in solution ELISA. Results were compared with the highest signal (biotinylated Fab without competition).

As shown in FIG. 19, biotinylated Fabs compete with identical unlabelled Fabs and all Fabs compete for binding to the same or overlapping epitope. These results correlate with epitope binning data for the parental Fabs.

Example 13

Screening of C5 Alpha versus Beta Chain Binders and Competition Assays

Two ELISA experiments and hemolytic assays were performed to test if a Fab was an alpha or beta chain binder as described below.

In the first experiment, Fab was coated on a plate and purified C5 or supernatant from chimeric C5 preparation (human alpha, mouse beta chain) was added. As a next step 5G1.1 was applied and detection was done via an anti-human IgG.

In a second experiment, 5G1.1 was coated on a plate, purified C5 or supernatant from chimeric C5 preparation (human alpha, mouse beta chain) was added, then Fab, which was detected with an anti-Myc antibody.

Reference IgG 5G1.1 recognizes the alpha chain and was used to determine if the MorhpSys generated Fabs compete with 5G1.1 for binding. In the hemolytic assays supernatant from chimeric C5 preparation was added to human CS-depleted serum and Fabs were tested for inhibition of hemolysis.

Parental Fabs

Figure 20:
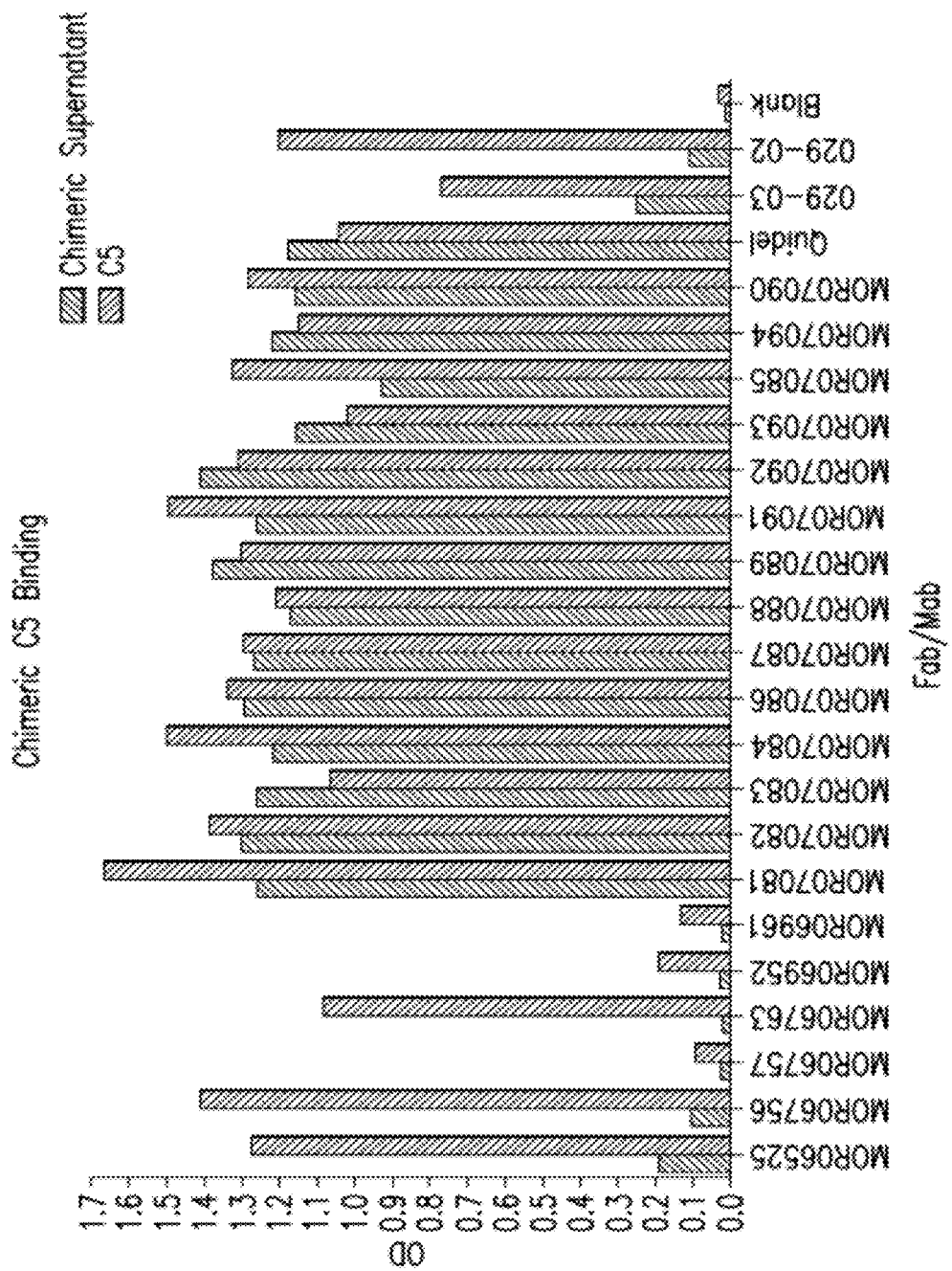
FIG. 20 shows an ELISA for antibody binding to mouse-human chimeric C5 or human C5 to determine alpha chain versus beta chain binders. C5 was presented by 5G1.1 to determine competition with 5G1.1.
Figure 21:
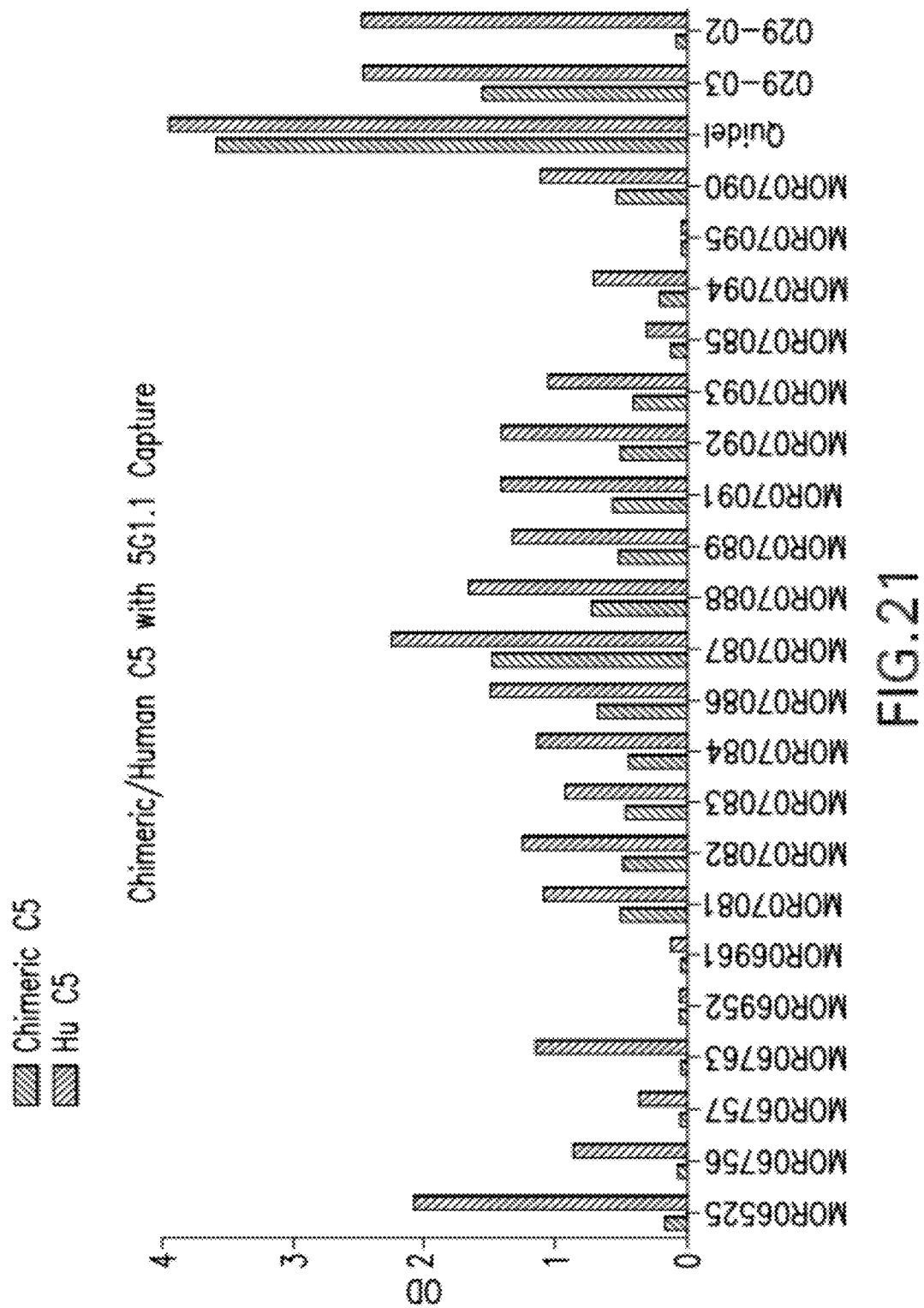
FIG. 21 shows ELISA for testing alpha chain versus beta chain binders with 5G1.1 capture.

FIG. 20 shows the results of an ELISA experiment where the Fabs were coated on a plate, C5 or supernatant of a chimeric C5 preparation (human alpha chain and mouse beta chain) was added, then 5G1.1. FIG. 21 shows the results of an ELISA experiment where purified C5 and supernatant from chimeric C5 were captured via 5G1.1.

Figures 1, 22:
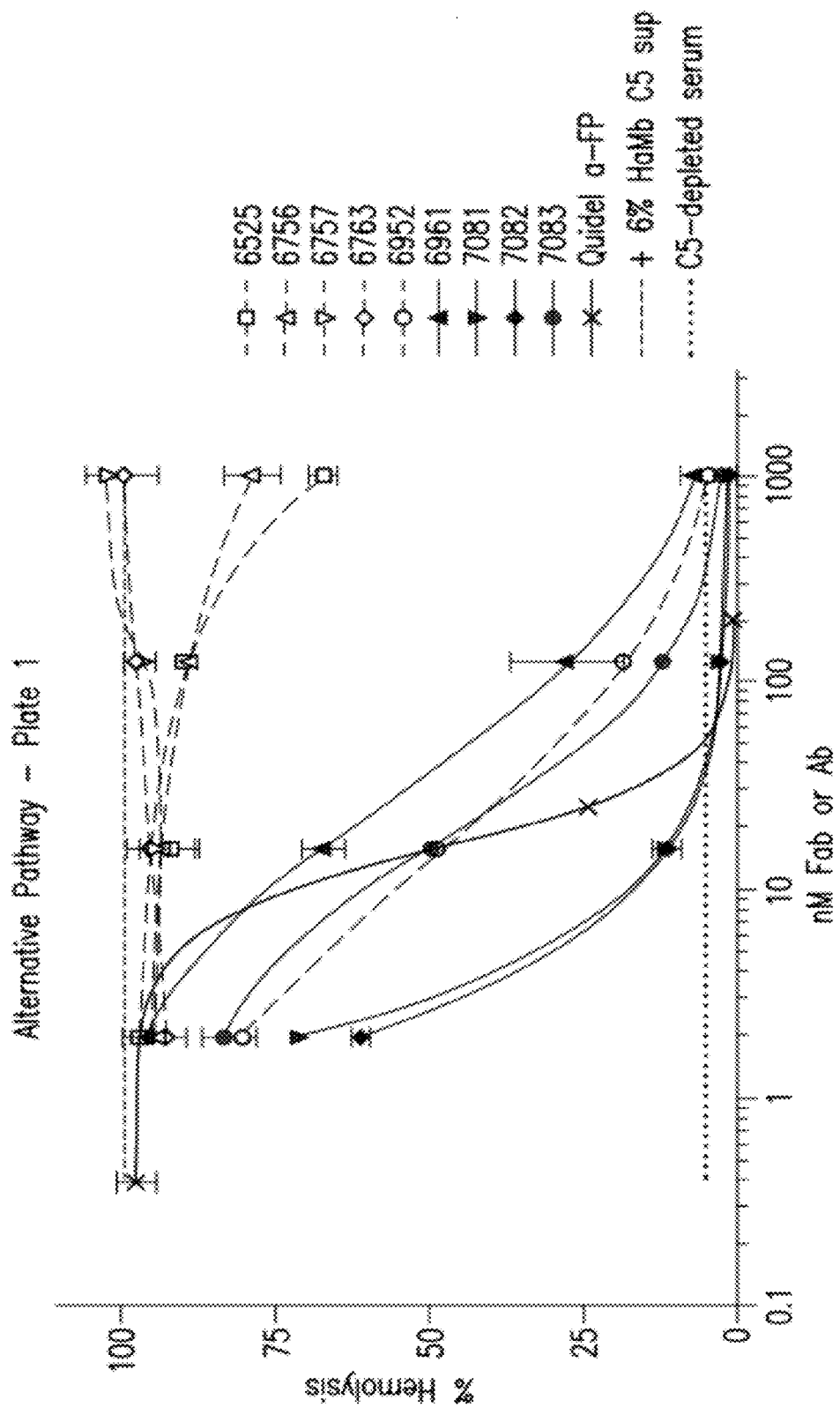
FIG. 22 shows results of hemolytic assay for testing alpha chain versus beta chain binders.
Figures 2, 22:
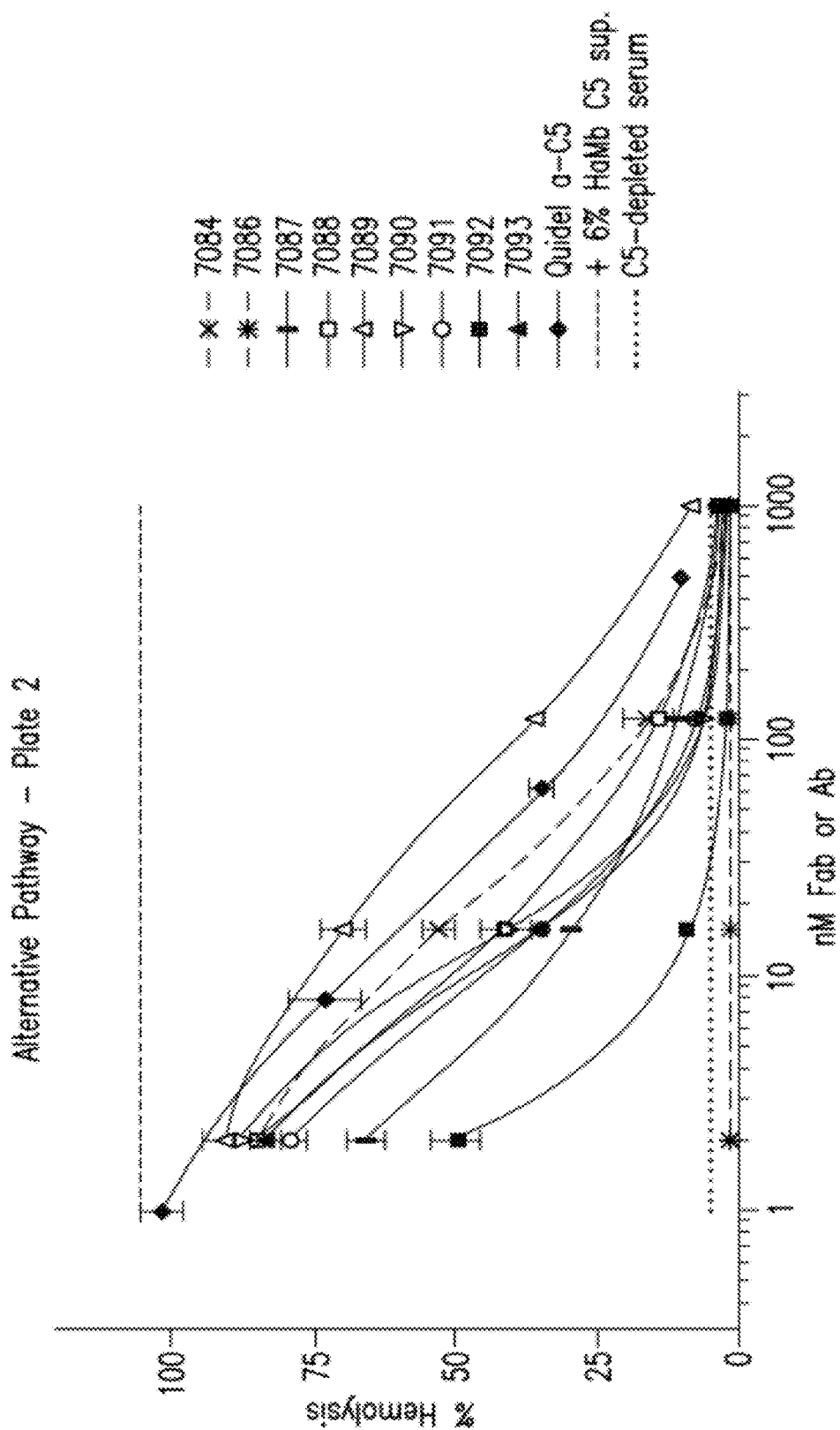

MOR06525, 6756, 6763 were beta chain binders (bind to C5 but not chimeric C5). Most MOR070XX Fabs (derived from solution pannings) are alpha chain binders (bind to C5 and chimeric C5). MOR06952 and 6961 compete with 5G1.1 so they are negative for both C5 and chimeric C5 and, thus, are most likely alpha chain binders as 5G1.1. MOR06757 behaves like MOR06952 and 6961, i.e. it likely is an alpha chain binder. However, MOR06757 does not inhibit hemolysis of chimeric C5 supernatant spiked into C5-depleted serum, while all the other alpha chain binders do (see FIG. 22).

In the hemolytic assay supernatant from chimeric C5 prep was added to human C5-depleted serum and Fabs were tested for inhibition of hemolysis. MOR06525, 6756, 6757 and 6763 did not inhibit hemolysis with chimeric C5 and thus, could be beta chain binders. MOR06952, 6961, 7081, 7082, 7083, 7084, 7086, 7087, 7088, 7089, 7090, 7091, 7092, 7093, 7094, 7095 inhibited hemolysis and thus could be alpha chain binders.

Example 14

Resistance to Proteolysis

To investigate the structural rigidity of Fabs, resistance of Fabs to proteolysis by thermolysin was performed (thermolysin bacterial protease, Calbiochem). Fab was incubated with thermolysin (Fab:thermolysin=3:1 (w/w), reaction volume of 8 µL) either at 37° C. or at 55° C. (thermolysin activity is optimal at 55° C.). The reaction was stopped by adding 4 µL of 0.5 M EDTA and 4 µL of 4×LDS sample buffer (Invitrogen) and the stopped samples were run on 4-12% SDS-PAGE at non-reducing condition. Proteolysis of Fabs was analyzed by monitoring the disappearance of Fab bands that were visualized by Coomassie staining.

Parental Fabs

Figure 23:
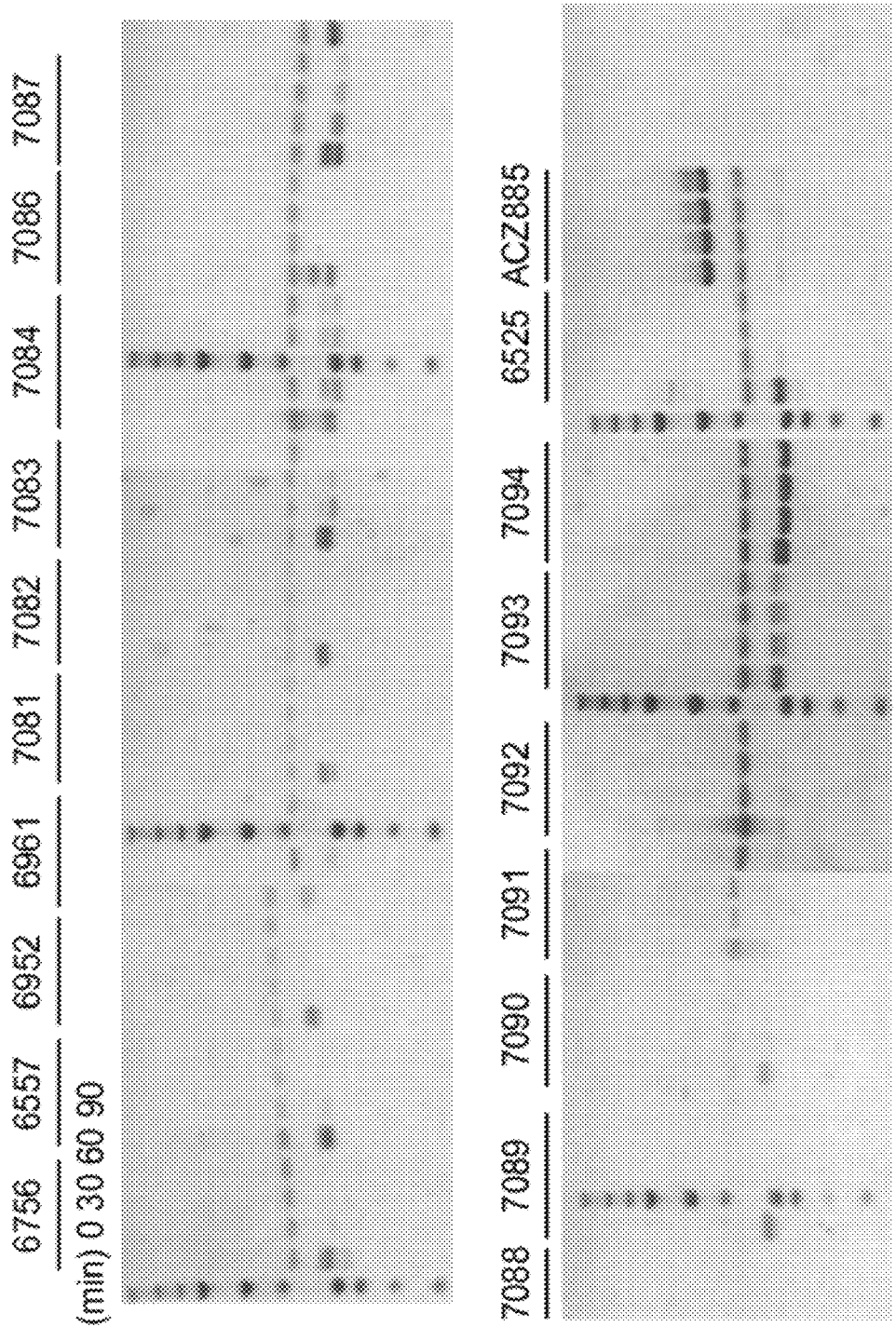
FIG. 23 show thermolysin proteolysis of parental Fabs at 37° C. (0, 30, 60 and 90 minutes).
Figure 24:
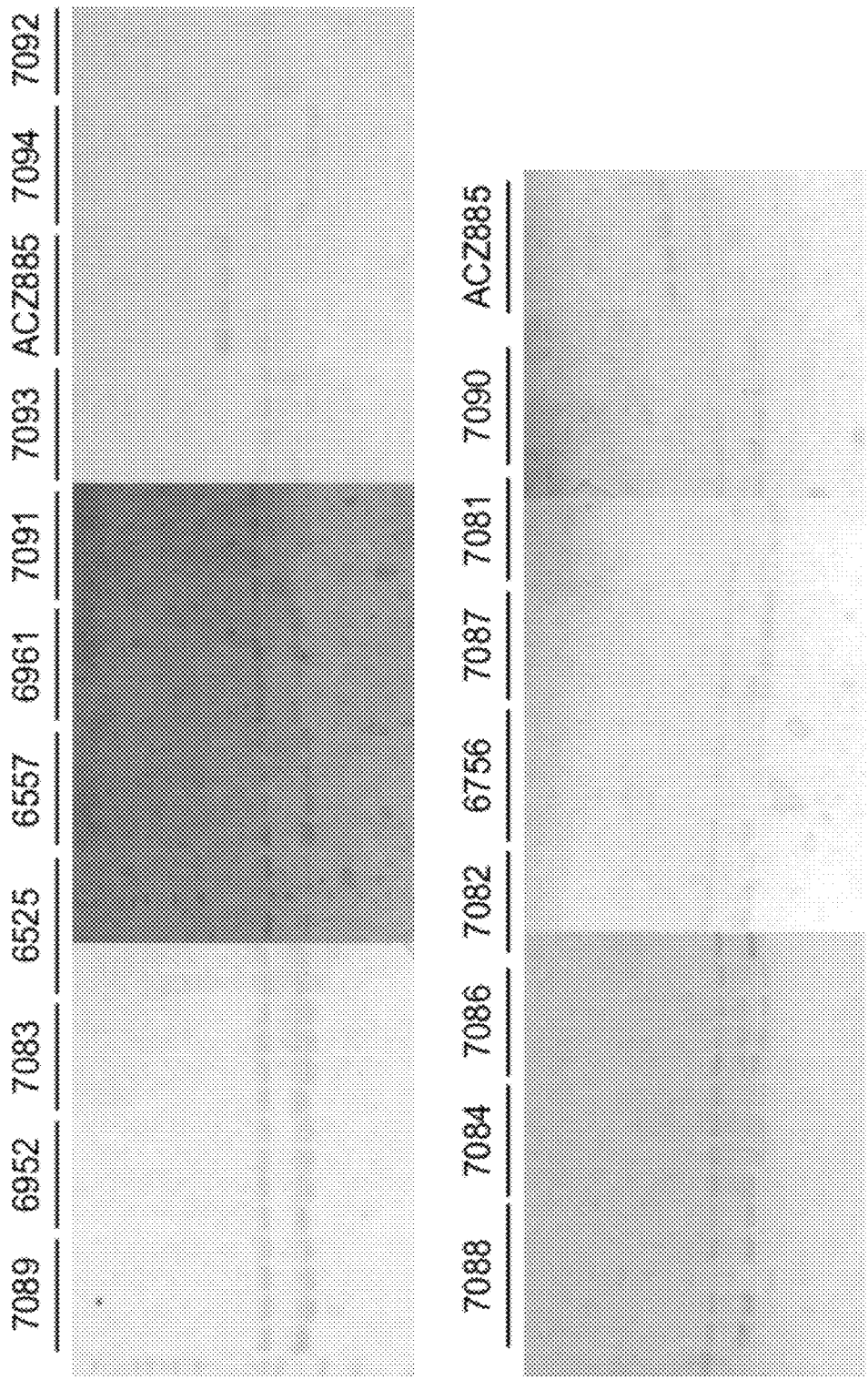
FIG. 24 show thermolysin proteolysis of parental Fabs at 55° C. (0, 30, 60 and 90 minutes).

Parental Fabs were tested for resistance to thermolysin proteolysis at 37° C. and 55° C. Fab from a humanized IL-1β antibody was used as control. Most tested Fabs were resistant to degradation by thermolysin at 37° C. up to 90 min. To further differentiate the structural rigidity of Fabs, proteolysis was performed at higher temperature of 55° C. Many of the Fabs tested were quickly degraded at 55° C. (>90% Fab was degraded within 30 min), while some Fabs were still resistant to proteolysis after 90 min (e.g., 7094). The resistant Fabs were suggested to have a more rigid structure such that they might show better in vivo pharmacokinetic properties. Results of these experiments are shown in the FIG. 23 and FIG. 24.

Matured Fabs

Figures 1, 25:
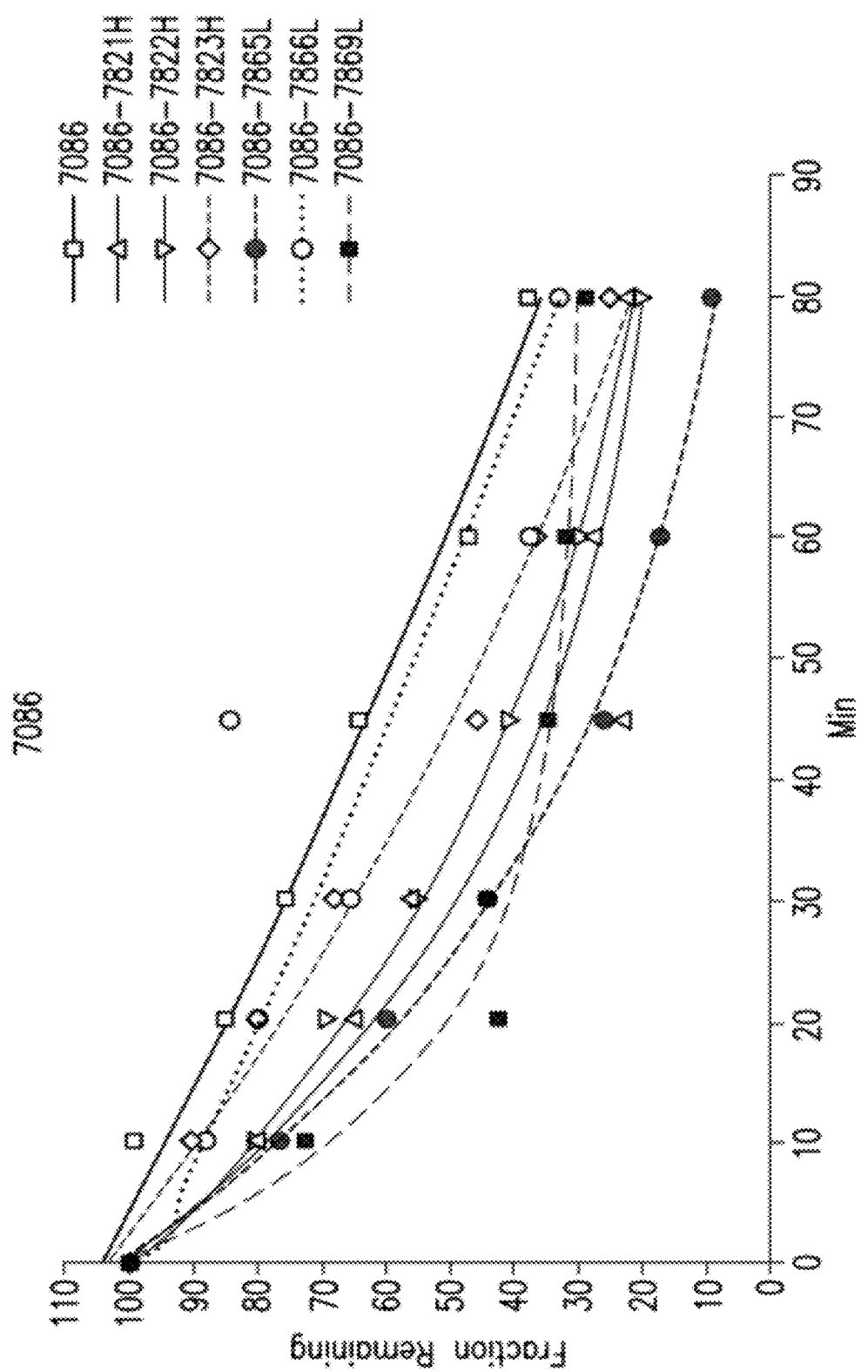
FIG. 25 shows thermolysin sensitivity of matured Fabs at 37° C.
Figures 2, 25:
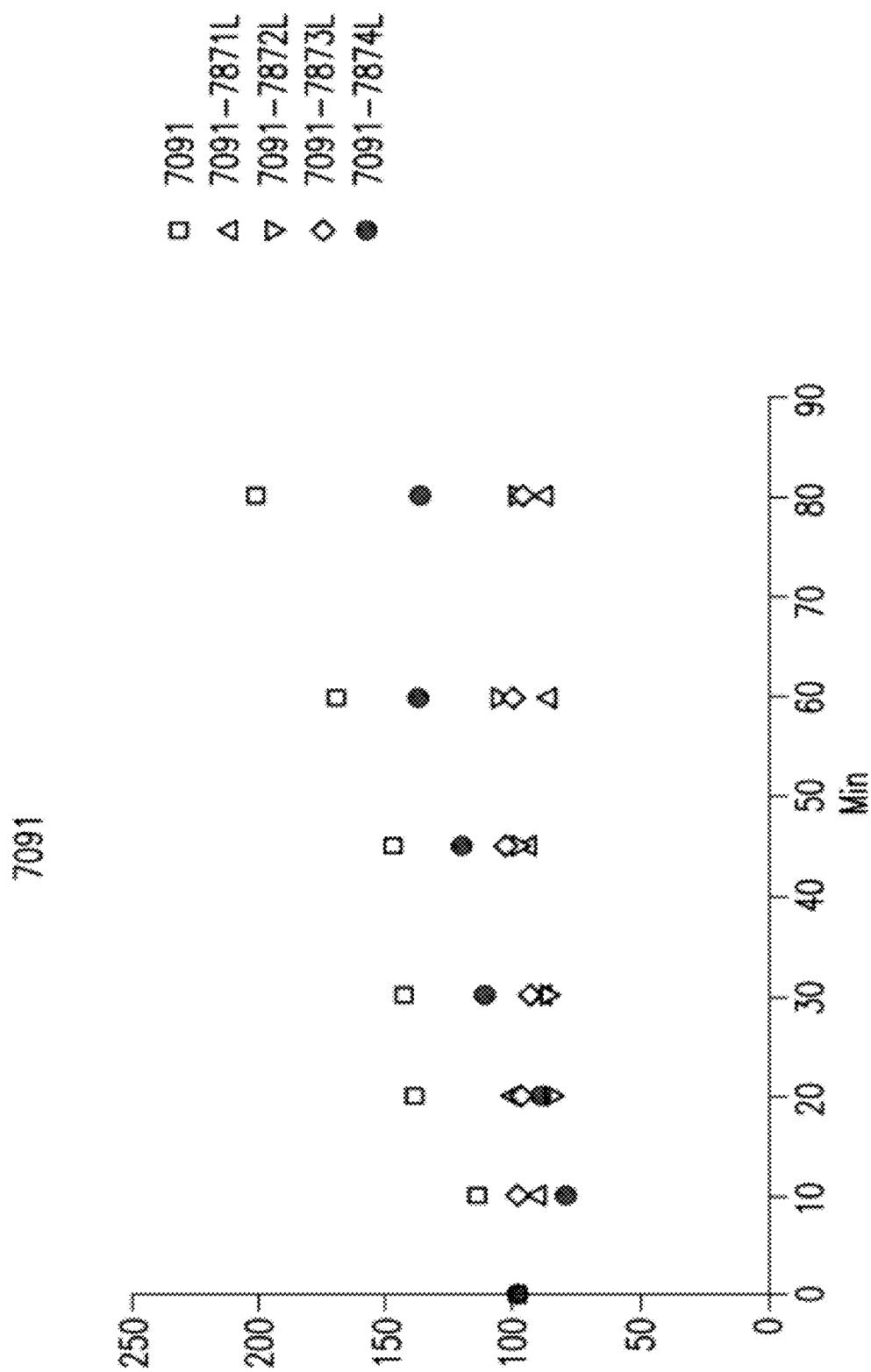
Figures 3, 25:
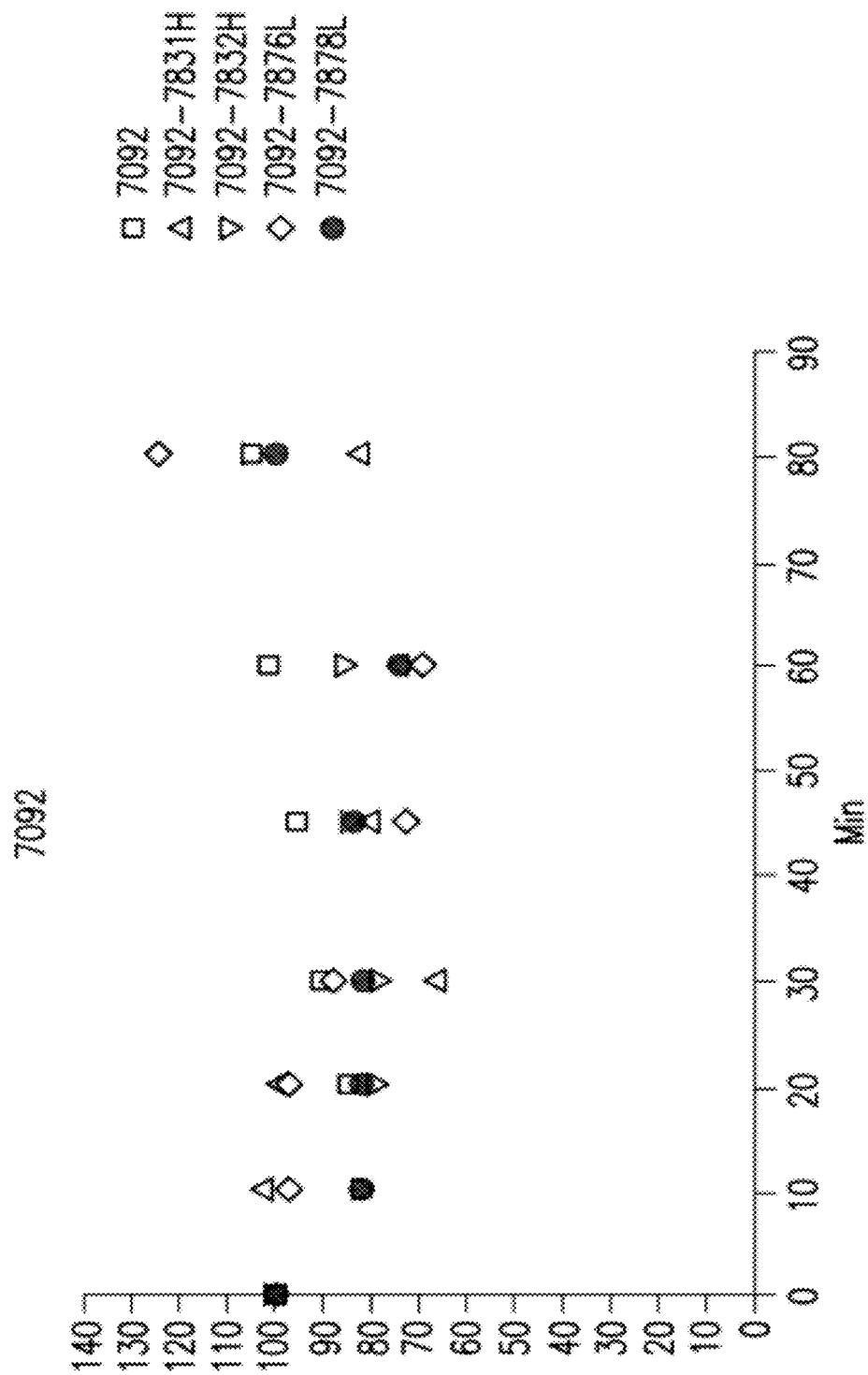
Figures 4, 25:
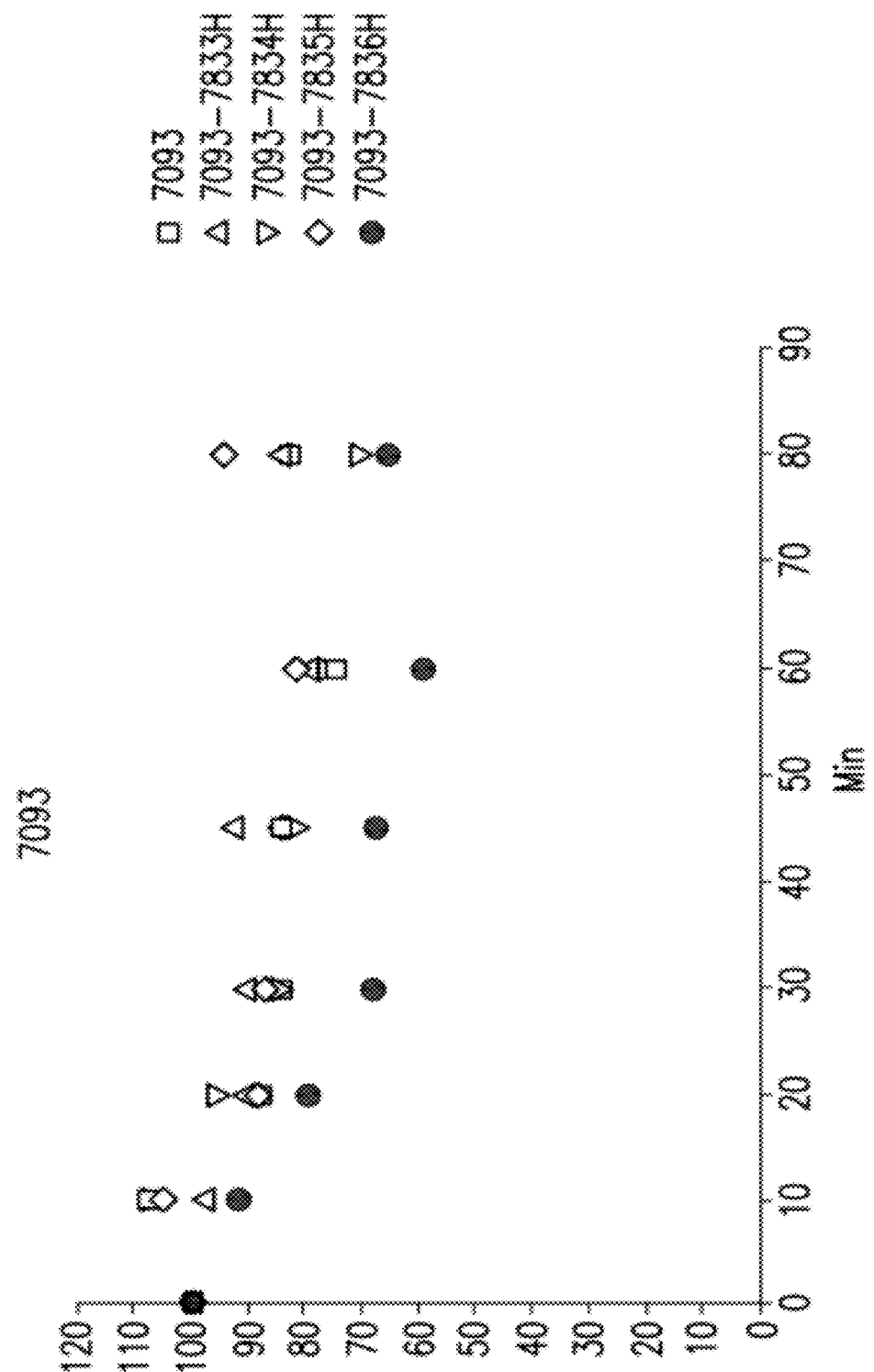
Figures 2, 26:
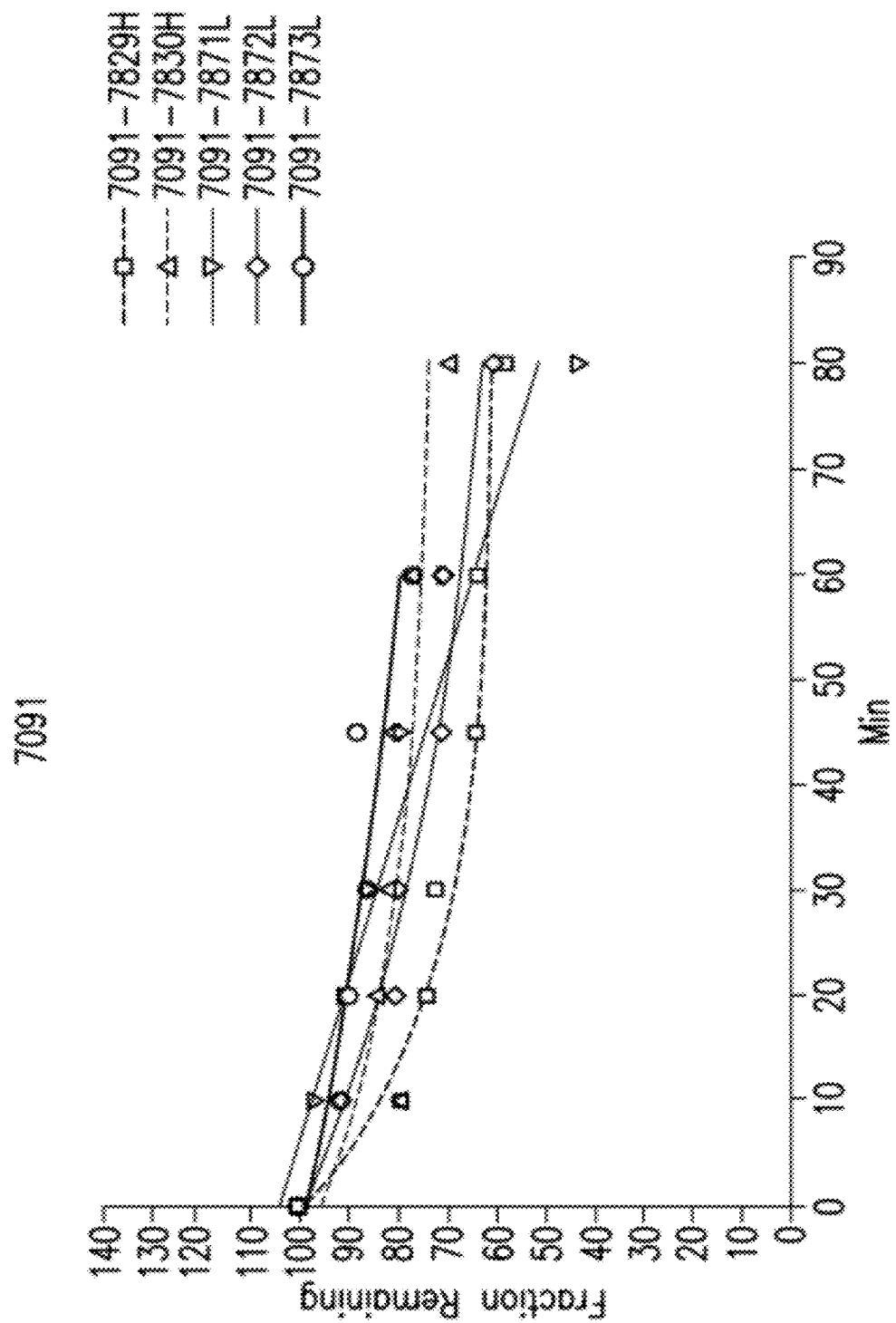
FIG. 26 shows thermolysin sensitivity of matured Fabs at 55° C.
Figures 3, 26:
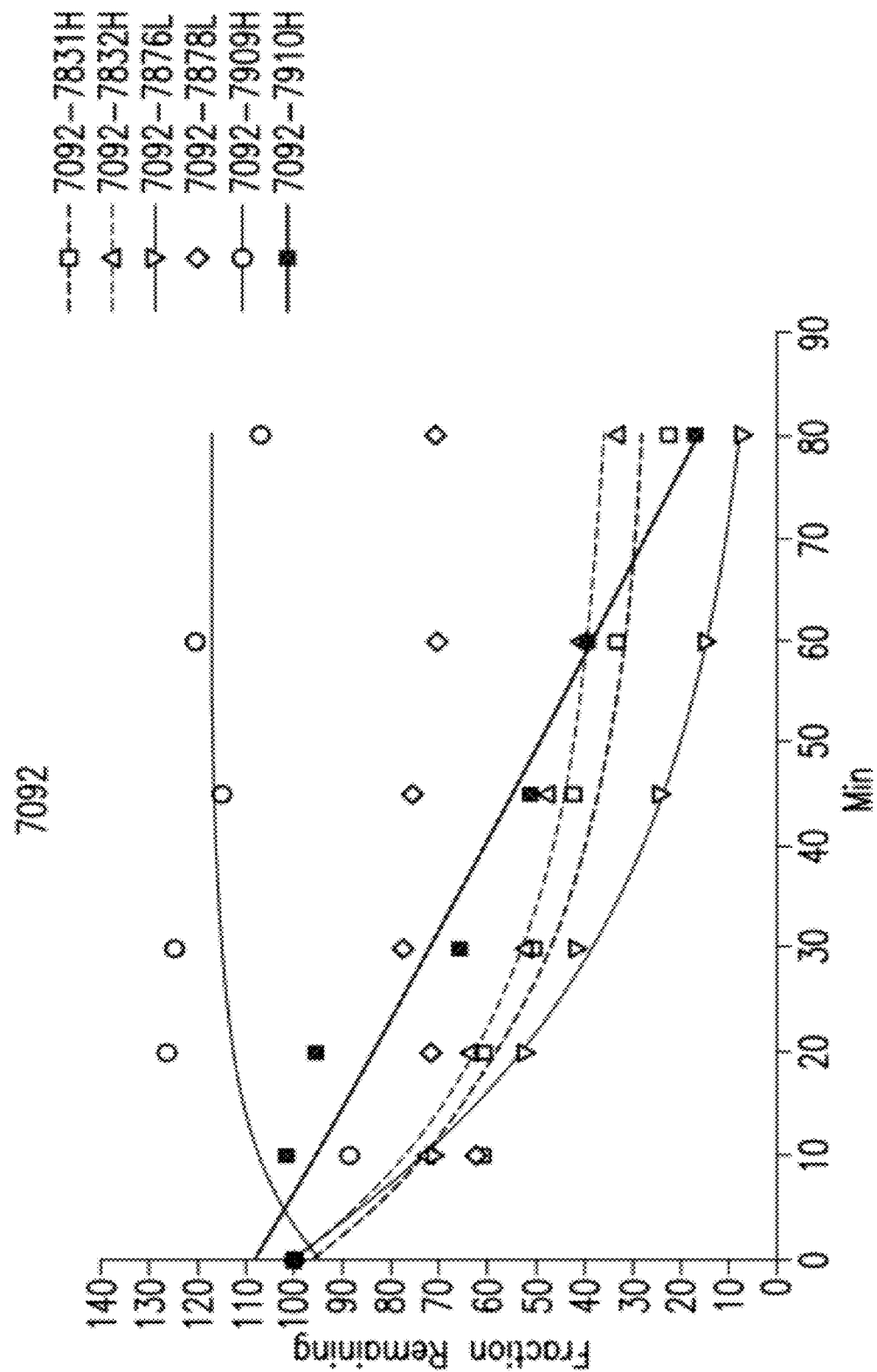

Fabs with the highest potency in hemolytic assays were tested for sensitivity to thermolysin at 37° C. and 55° C. In FIG. 25 and FIG. 26, experiments with derivatives of MOR07086, 7091, 7092 and 7093 are shown.

Results of these tests revealed that derivatives of parentals MOR07091, 7092 and 7093 were less sensitive to proteolysis, while MOR07086 derivatives were more sensitive to proteolysis.

Example 15

MAC Deposition Assay

As the terminal complement cascade ends up with formation of the MAC, inhibition of MAC formation was a further hint for the antibody ability to block the complement cascade. The rational was to have an additional set-up independent of cells and cell behaviour Zymosan (Sigma), which is an insoluble carbohydrate from the cell wall of yeast, used especially in the immunoassay of the alternative pathway, was coated to activate the Alternative Pathway and IgM (Sigma) was coated to activate the Classical Pathway for determination of MAC (membrane attack complex) deposition. Fabs were pre-incubated with human serum (6% for AP, 2% for CP) and added to plate. Percentage (%) inhibition of MAC deposition was calculated for each sample relative to baseline (EDTA treated human serum) and positive control (human serum), and used to generate the $IC_{50}$ curve with XLFit.

Parental Fabs

Figure 27:
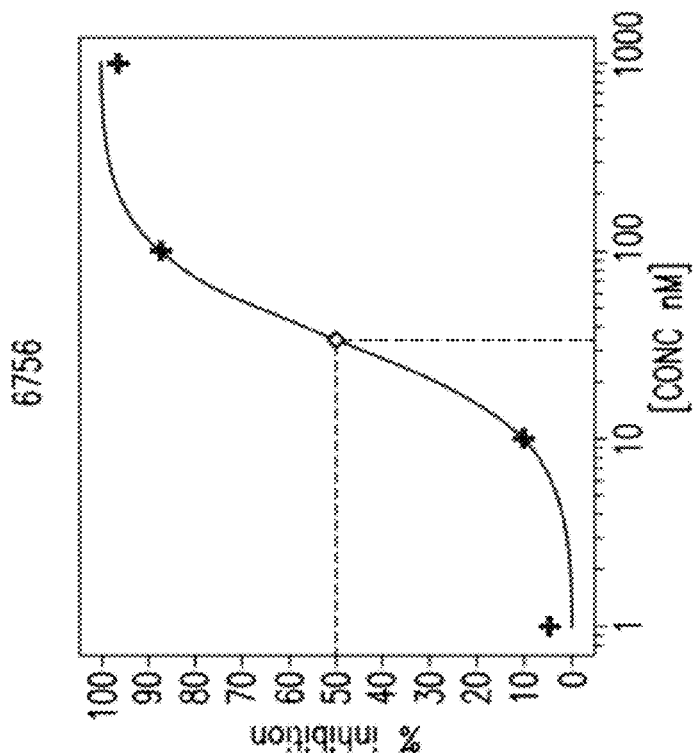
FIG. 27 shows examples of Fab inhibition of alternative pathway in MAC deposition assay.
Figure 27:
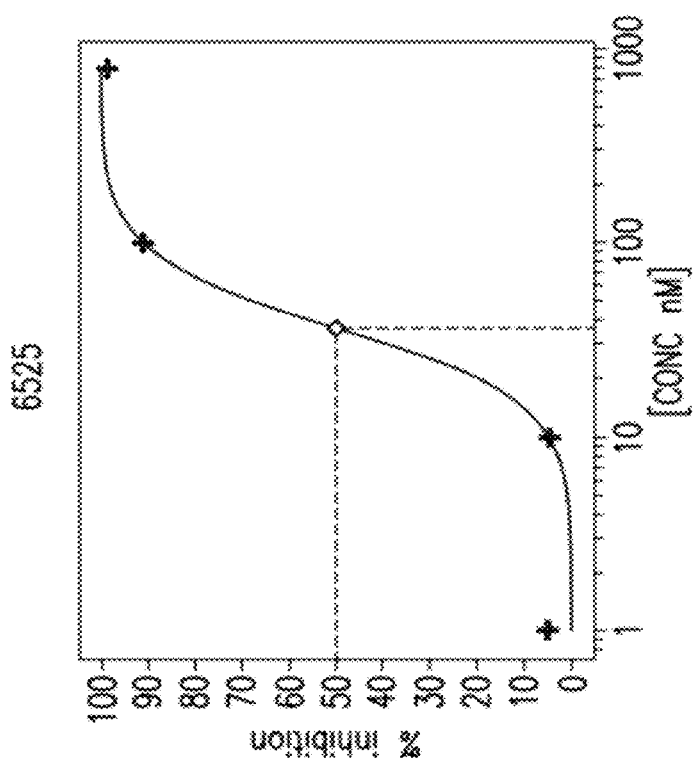

Parental Fabs were used in different concentrations and the maximal inhibition (if applicable also $IC_{50}$ values) were determined (example shown in FIG. 27). Most Fabs completely inhibited MAC deposition indicating blocking of C5 cleavage. Potency and ranking of Fabs were similar to data from hemolytic assays.

What is claimed is:

1. An isolated antibody or an antigen binding fragment thereof that specifically binds to a human complement C5 protein, said antibody or antigen binding fragment thereof comprising a HCDR1 sequence comprising the sequence of SEQ ID NO: 1, a HCDR2 sequence comprising the sequence of SEQ ID NO: 2, a HCDR3 sequence comprising the sequence of SEQ ID NO: 3, a LCDR1 sequence comprising the sequence of SEQ ID NO: 4, a LCDR2 sequence comprising the sequence of SEQ ID NO: 5, and a LCDR3 sequence comprising the sequence of SEQ ID NO: 6.

2. The antibody of claim 1, wherein said antibody is a monoclonal antibody.

3. The antibody of claim 2, wherein said antibody is a human or humanized antibody.

4. The antibody of claim 2, wherein said antibody is a chimeric antibody.

5. The antibody of claim 2, wherein said antibody comprises a human heavy chain constant region and a human light chain constant region.

6. The antibody of claim 2, wherein said antibody is a single chain antibody.

7. The antibody of claim 2, wherein said antibody is a Fab fragment.

8. The antibody of claim 2, wherein said antibody is a scFv.

9. The antibody of claim 2 binds to both human complement C5 and cynomolgus complement C5.

10. The antibody of claim 2 is an IgG isotype.

11. The antibody of claim 2, wherein said antibody comprises a framework in which amino acids have been substituted into the antibody framework from the respective human VH or VL germline sequences.

12. The antibody, or an antigen binding fragment thereof of claim 1, comprising a heavy chain variable region having at least 95% sequence identity to SEQ ID NO: 7.

13. The antibody, or an antigen binding fragment thereof of claim 1, comprising a light chain variable region having at least 95% sequence identity to SEQ ID NO: 8.

14. The antibody or antigen binding fragment thereof of claim 12, further comprising a light chain variable region having at least 95% sequence identity to SEQ ID NO: 8.

15. The antibody, or an antigen binding fragment thereof of claim 1, comprising a heavy chain having at least 95% sequence identity to SEQ ID NO: 9 wherein said antibody binds to human complement C5 protein.

16. The antibody, or an antigen binding fragment thereof of claim 1, comprising a light chain having at least 95% sequence identity to SEQ ID NO: 10, wherein said antibody binds to human complement C5 protein.

17. The antibody of claim 15, or an antigen binding fragment thereof, further comprising a light chain having at least 95% sequence identity to SEQ ID NO: 10.

18. A pharmaceutical composition comprising an antibody of claim 1 and a pharmaceutically acceptable carrier.

19. A monoclonal antibody, or antigen binding fragment thereof, that specifically binds to complement C5 protein, and cross competes with an antibody described in Table 1.

20. A monoclonal antibody, or antigen binding fragment thereof, that binds to the same epitope as an antibody described in Table 1.

* * * * *

SEQUENCE LISTING

```
<160> NUMBER OF SEQ ID NOS: 307

<210> SEQ ID NO 1
<211> LENGTH: 5
<212> TYPE: PRT
<213> ORGANISM: homo sapiens

<400> SEQUENCE: 1

Ser Tyr Ala Ile Ser
1               5

<210> SEQ ID NO 2
<211> LENGTH: 17
<212> TYPE: PRT
<213> ORGANISM: homo sapiens

<400> SEQUENCE: 2

Gly Ile Gly Pro Phe Phe Gly Thr Ala Asn Tyr Ala Gln Lys Phe Gln
1               5                   10                  15

Gly

<210> SEQ ID NO 3
<211> LENGTH: 7
<212> TYPE: PRT
<213> ORGANISM: homo sapiens

<400> SEQUENCE: 3

Asp Thr Pro Tyr Phe Asp Tyr
1               5

<210> SEQ ID NO 4
<211> LENGTH: 11
<212> TYPE: PRT
<213> ORGANISM: homo sapiens

<400> SEQUENCE: 4

Ser Gly Asp Ser Ile Pro Asn Tyr Tyr Val Tyr
1               5                   10

<210> SEQ ID NO 5
<211> LENGTH: 7
<212> TYPE: PRT
<213> ORGANISM: homo sapiens

<400> SEQUENCE: 5

Asp Asp Ser Asn Arg Pro Ser
1               5

<210> SEQ ID NO 6
<211> LENGTH: 11
<212> TYPE: PRT
<213> ORGANISM: homo sapiens

<400> SEQUENCE: 6
```

```
Gln Ser Phe Asp Ser Ser Leu Asn Ala Glu Val
1               5                   10
```

```
<210> SEQ ID NO 7
<211> LENGTH: 116
<212> TYPE: PRT
<213> ORGANISM: homo sapiens

<400> SEQUENCE: 7

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
            115
```

```
<210> SEQ ID NO 8
<211> LENGTH: 108
<212> TYPE: PRT
<213> ORGANISM: homo sapiens

<400> SEQUENCE: 8

Ser Tyr Glu Leu Thr Gln Pro Leu Ser Val Ser Val Ala Leu Gly Gln
1               5                   10                  15

Thr Ala Arg Ile Thr Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105
```

```
<210> SEQ ID NO 9
<211> LENGTH: 446
<212> TYPE: PRT
<213> ORGANISM: homo sapiens

<400> SEQUENCE: 9

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Ile Gly Pro Phe Phe Gly Thr Ala Asn Tyr Ala Gln Lys Phe
            50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Asp Thr Pro Tyr Phe Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
            130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
            195                 200                 205
Lys Val Asp Lys Arg Val Glu Pro Lys Ser Cys Asp Lys Thr His Thr
210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys
            435                 440                 445

<210> SEQ ID NO 10
<211> LENGTH: 214
<212> TYPE: PRT
```

<213> ORGANISM: homo sapiens

<400> SEQUENCE: 10

```
Ser Tyr Glu Leu Thr Gln Pro Leu Ser Val Ser Val Ala Leu Gly Gln
1               5                   10                  15

Thr Ala Arg Ile Thr Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 11
<211> LENGTH: 348
<212> TYPE: DNA
<213> ORGANISM: homo sapiens

<400> SEQUENCE: 11

| gaggtgcaat tggttcagtc tggcgcggaa gtgaaaaaac cgggcagcag cgtgaaagtg | 60 |
| agctgcaaag cctccggagg cacttttttct tcttatgcca tttcttgggt gcgccaagcc | 120 |
| cctgggcagg gtctcgagtg gatgggcggt atcggtccgt tttttggcac tgcgaattac | 180 |
| gcgcagaagt ttcagggccg ggtgaccatt accgcggatg aaagcaccag caccgcgtat | 240 |
| atggaactga gcagcctgcg tagcgaagat acggccgtgt attattgcgc gcgtgatact | 300 |
| ccttattttg attattgggg ccaaggcacc ctggtgacgg ttagctca | 348 |

<210> SEQ ID NO 12
<211> LENGTH: 324
<212> TYPE: DNA
<213> ORGANISM: homo sapiens

<400> SEQUENCE: 12

| tcctatgaac tcacacagcc cctgagcgtg agcgtggccc tgggccagac cgcccggatc | 60 |
| acctgctccg gcgacagcat ccccaactac tacgtgtact ggtaccagca gaagcccggc | 120 |
| caggccccg tgctggtgat ctacgacgac agcaaccggc ccagcggcat ccccgagcgg | 180 |

| | |
|---|---|
| ttcagcggca gcaacagcgg caacaccgcc accctgacca tttccagagc acaggcaggc | 240 |
| gacgaggccg actactactg ccagagcttc gacagcagcc tgaacgccga ggtgttcggc | 300 |
| ggagggacca agttaaccgt ccta | 324 |

<210> SEQ ID NO 13
<211> LENGTH: 1338
<212> TYPE: DNA
<213> ORGANISM: homo sapiens

<400> SEQUENCE: 13

| | |
|---|---|
| gaggtgcaat tggttcagtc tggcgcggaa gtgaaaaaac cgggcagcag cgtgaaagtg | 60 |
| agctgcaaag cctccggagg cacttttttct tcttatgcca tttcttgggt gcgccaagcc | 120 |
| cctgggcagg gtctcgagtg gatgggcggt atcggtccgt tttttggcac tgcgaattac | 180 |
| gcgcagaagt ttcagggccg ggtgaccatt accgcggatg aaagcaccag caccgcgtat | 240 |
| atggaactga gcagcctgcg tagcgaagat acggccgtgt attattgcgc gcgtgatact | 300 |
| ccttattttg attattgggg ccaaggcacc ctggtgacgg ttagctcagc ctccaccaag | 360 |
| ggtccatcgg tcttcccct ggcaccctcc tccaagagca cctctggggg cacagcggcc | 420 |
| ctgggctgcc tggtcaagga ctacttcccc gaaccggtga cggtgtcgtg aactcaggc | 480 |
| gccctgacca gcggcgtgca caccttcccg gctgtcctac agtcctcagg actctactcc | 540 |
| ctcagcagcg tggtgaccgt gccctccagc agcttgggca cccagaccta catctgcaac | 600 |
| gtgaatcaca gcccagcaa caccaaggtg gacaagagag ttgagcccaa atcttgtgac | 660 |
| aaaactcaca catgcccacc gtgcccagca cctgaagcag cggggggacc gtcagtcttc | 720 |
| ctcttccccc caaaacccaa ggacaccctc atgatctccc ggaccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgg | 900 |
| gtggtcagcg tcctcaccgt cctgcaccag gactggctga atggcaagga gtacaagtgc | 960 |
| aaggtctcca acaaagccct cccagccccc atcgagaaaa ccatctccaa agccaaaggg | 1020 |
| cagccccgag aaccacaggt gtacaccctg cccccatccc gggaggagat gaccaagaac | 1080 |
| caggtcagcc tgacctgcct ggtcaaaggc ttctatccca gcgacatcgc cgtggagtgg | 1140 |
| gagagcaatg ggcagccgga gaacaactac aagaccacgc ctcccgtgct ggactccgac | 1200 |
| ggctccttct tcctctacag caagctcacc gtggacaaga gcaggtggca gcaggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 14
<211> LENGTH: 642
<212> TYPE: DNA
<213> ORGANISM: homo sapiens

<400> SEQUENCE: 14

| | |
|---|---|
| tcctatgaac tcacacagcc cctgagcgtg agcgtggccc tgggccagac cgcccggatc | 60 |
| acctgctccg gcgacagcat ccccaactac tacgtgtact ggtaccagca gaagcccggc | 120 |
| caggcccccg tgctggtgat ctacgacgac agcaaccggc ccagcggcat ccccgagcgg | 180 |
| ttcagcggca gcaacagcgg caacaccgcc accctgacca tttccagagc acaggcaggc | 240 |
| gacgaggccg actactactg ccagagcttc gacagcagcc tgaacgccga ggtgttcggc | 300 |
| ggagggacca agttaaccgt cctaggtcag cccaaggctg cccctcggt cactctgttc | 360 |

```
ccgccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                      642
```

<210> SEQ ID NO 15
<211> LENGTH: 1338
<212> TYPE: DNA
<213> ORGANISM: homo sapiens

<400> SEQUENCE: 15

```
gaggtgcagc tggtgcagag cggagccgag gtgaagaagc ccggtagcag cgtcaaggtg     60
tcctgcaagg ccagcggcgg caccttcagc agctacgcca tcagctgggt gcggcaggcc    120
ccaggccagg gctggagtg gatgggcggc atcggcccat tcttcggcac cgccaactac    180
gcccagaagt tccagggcag ggtcaccatc accgccgacg agagcaccag caccgcctac    240
atggagctgt ccagcctgag aagcgaggac accgccgtgt actactgcgc cagagacacc    300
ccctacttcg actactgggg ccagggcacc ctggtgaccg tgagcagcgc tagcaccaag    360
ggccccagcg tgttccccct ggccccagc agcaagagca cctccggcgg cacagccgcc    420
ctgggctgcc tggtgaagga ctacttcccc gagcccgtga ccgtgtcctg aacagcgga    480 gccctgacca cgcgcgtgca caccttcccc gccgtgctgc agagcagcgg cctgtacagc    540
ctgtccagcg tggtgacagt gcccagcagc agcctgggca cccagaccta catctgcaac    600
gtgaaccaca agcccagcaa caccaaggtg gacaagagag tggagcccaa gagctgcgac    660
aagacccaca cctgcccccc ctgcccagcc cccgaagctg caggcggccc ttccgtgttc    720
ctgttccccc ccaagcccaa ggacaccctg atgatcagca ggaccccga ggtgacctgc    780 gtggtggtgg acgtgagcca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaaaga atacaagtgc    960
aaggtctcca acaaggccct gcctgccccc atcgaaaaga ccatcagcaa ggccaagggc   1020
cagccacggg agcccaggt gtacaccctg ccccccttctc gggaggagat gaccaagaac   1080
caggtgtccc tgacctgtct ggtgaagggc ttctacccca gcgacatcgc cgtggagtgg   1140
gagagcaacg gccagcccga gaacaactac aagaccaccc ccccagtgct ggacagcgac   1200
ggcagcttct tcctgtacag caagctgacc gtggacaaga gcaggtggca gcagggcaac   1260
gtgttcagct gcagcgtgat gcacgaggcc ctgcacaacc actacaccca gaagagcctg   1320
agcctgtcac ccggcaag                                                 1338
```

<210> SEQ ID NO 16
<211> LENGTH: 642
<212> TYPE: DNA
<213> ORGANISM: homo sapiens

<400> SEQUENCE: 16

```
agctacgagc tgacccagcc cctgagcgtg agcgtggccc tgggccagac cgccaggatc     60
acctgcagcg gcgacagcat ccccaactac tacgtgtact ggtatcagca gaagcccggc    120
caggcccccg tgctggtgat ctacgacgac agcaacaggc ccagcggcat ccccgagagg    180
ttcagcggca gcaacagcgg caacaccgcc accctgacca tcagcagagc ccaggccggc    240
```

```
gacgaggccg actactactg ccagagcttc gacagctcac tgaacgccga ggtgttcggc    300
ggagggacca agctgaccgt gctgggccag cctaaggctg cccccagcgt gaccctgttc    360 cccccagca gcgaggagct gcaggccaac aaggccaccc tggtgtgcct gatcagcgac    420
ttctacccag gcgccgtgac cgtggcctgg aaggccgaca gcagcccgt gaaggccggc    480 gtggagacca ccacccccag caagcagagc aacaacaagt acgccgccag cagctacctg    540
agcctgaccc ccgagcagtg gaagagccac aggtcctaca gctgccaggt gacccacgag    600
ggcagcaccg tggaaaagac cgtggcccca accgagtgca gc    642
```

```
<210> SEQ ID NO 17
<211> LENGTH: 4
<212> TYPE: PRT
<213> ORGANISM: homo sapiens

<400> SEQUENCE: 17

Asn Tyr Ile Ser
1

<210> SEQ ID NO 18
<211> LENGTH: 17
<212> TYPE: PRT
<213> ORGANISM: homo sapiens

<400> SEQUENCE: 18

Ile Ile Asp Pro Asp Asp Ser Tyr Thr Glu Tyr Ser Pro Ser Phe Gln
1               5                   10                  15
Gly

<210> SEQ ID NO 19
<211> LENGTH: 8
<212> TYPE: PRT
<213> ORGANISM: homo sapiens

<400> SEQUENCE: 19

Tyr Glu Tyr Gly Gly Phe Asp Ile
1               5

<210> SEQ ID NO 20
<211> LENGTH: 11
<212> TYPE: PRT
<213> ORGANISM: homo sapiens

<400> SEQUENCE: 20

Ser Gly Asp Asn Ile Gly Asn Ser Tyr Val His
1               5                   10

<210> SEQ ID NO 21
<211> LENGTH: 7
<212> TYPE: PRT
<213> ORGANISM: homo sapiens

<400> SEQUENCE: 21

Lys Asp Asn Asp Arg Pro Ser
1               5

<210> SEQ ID NO 22
<211> LENGTH: 9
<212> TYPE: PRT
<213> ORGANISM: homo sapiens

<400> SEQUENCE: 22

Gly Thr Tyr Asp Ile Glu Ser Tyr Val
```

-continued

<210> SEQ ID NO 23
<211> LENGTH: 116
<212> TYPE: PRT
<213> ORGANISM: homo sapiens

<400> SEQUENCE: 23

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

<210> SEQ ID NO 24
<211> LENGTH: 106
<212> TYPE: PRT
<213> ORGANISM: homo sapiens

<400> SEQUENCE: 24

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu
            100                 105

<210> SEQ ID NO 25
<211> LENGTH: 446
<212> TYPE: PRT
<213> ORGANISM: homo sapiens

<400> SEQUENCE: 25

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
 50                  55                  60

Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
                 85                  90                  95

Arg Tyr Glu Tyr Gly Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 26
<211> LENGTH: 212
<212> TYPE: PRT
<213> ORGANISM: homo sapiens

<400> SEQUENCE: 26

| | | | | | | | | | | | | | | | |
|---|---|---|---|---|---|---|---|---|---|---|---|---|---|---|---|
|Ser|Tyr|Glu|Leu|Thr|Gln|Pro|Pro|Ser|Val|Ser|Ala|Pro|Gly|Gln|
|1| | | |5| | | |10| | | | |15| |

Thr Ala Arg Ile Ser Cys Ser Gly Asp Asn Ile Gly Asn Ser Tyr Val
              20                  25                  30

His Trp Tyr Gln Gln Lys Pro Gly Gln Ala Pro Val Leu Val Ile Tyr
          35                  40                  45

Lys Asp Asn Asp Arg Pro Ser Gly Ile Pro Glu Arg Phe Ser Gly Ser
      50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 27
<211> LENGTH: 348
<212> TYPE: DNA
<213> ORGANISM: homo sapiens

<400> SEQUENCE: 27

```
gaggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatt gatcctgatg attcttatac tgagtattct     180
ccttcttttc agggtcaggt caccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctca                  348
```

<210> SEQ ID NO 28
<211> LENGTH: 318
<212> TYPE: DNA
<213> ORGANISM: homo sapiens

<400> SEQUENCE: 28

```
agttacgaac tgacccagcc gccttcagtg agcgttgcac aggtcagac cgcgcgtatc       60
tcgtgtagcg gcgataatat tggtaattct tatgttcatt ggtaccagca gaaacccggg     120
caggcgccag ttcttgtgat ttataaggat aatgatcgtc cctcaggcat cccggaacgc     180
tttagcggat ccaacagcgg caacaccgcg accctgacca ttagcggcac tcaggcggaa     240
```

```
gacgaagcgg attattattg cggtacttat gatattgagt cttatgtgtt tggcggcggc    300
acgaagttaa ccgtccta                                                 318

<210> SEQ ID NO 29
<211> LENGTH: 1338
<212> TYPE: DNA
<213> ORGANISM: homo sapiens

<400> SEQUENCE: 29
gaggtgcaat tggttcagag cggcgcggaa gtgaaaaaac cgggcgaaag cctgaaaatt     60
agctgcaaag gttccggata ttcctttact aattatattt cttgggtgcg ccagatgcct    120
gggaagggtc tcgagtggat gggcattatt gatcctgatg attcttatac tgagtattct    180 ccttctttc agggtcaggt caccattagc gcggataaaa gcattagcac cgcgtatctt    240
caatggagca gcctgaaagc gagcgatacg gccatgtatt attgcgcgcg ttatgagtat    300
ggtggttttg atatttgggg ccaaggcacc ctggtgacgg ttagctcagc ctccaccaag    360
ggtccatcgg tcttcccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaagcag cggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgg    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg ccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                1338

<210> SEQ ID NO 30
<211> LENGTH: 636
<212> TYPE: DNA
<213> ORGANISM: homo sapiens

<400> SEQUENCE: 30
agttacgaac tgacccagcc gccttcagtg agcgttgcac caggtcagac cgcgcgtatc     60
tcgtgtagcg gcgataatat tggtaattct tatgttcatt ggtaccagca gaaacccggg    120
caggcgccag ttcttgtgat ttataaggat aatgatcgtc cctcaggcat cccggaacgc    180
tttagcggat ccaacagcgg caacaccgcg accctgacca ttagcggcac tcaggcggaa    240
gacgaagcgg attattattg cggtacttat gatattgagt cttatgtgtt tggcggcggc    300
acgaagttaa ccgtcctagg tcagcccaag gctgccccct cggtcactct gttcccgccc    360
tcctctgagg agcttcaagc caacaaggcc acactggtgt gtctcataag tgacttctac    420
```

```
ccgggagccg tgacagtggc ctggaaggca gatagcagcc ccgtcaaggc gggagtggag      480
accaccacac cctccaaaca aagcaacaac aagtacgcgg ccagcagcta tctgagcctg      540
acgcctgagc agtggaagtc ccacagaagc tacagctgcc aggtcacgca tgaagggagc      600
accgtggaga agacagtggc ccctacagaa tgttca                               636

<210> SEQ ID NO 31
<211> LENGTH: 1338
<212> TYPE: DNA
<213> ORGANISM: homo sapiens

<400> SEQUENCE: 31
gaggtgcagc tggtgcagag cggagccgag gtgaaaaagc ccggtgagag cctgaagatc       60
agctgcaagg gcagcggcta cagcttcacc aactacatca gctgggtgcg gcagatgccc      120
ggcaagggcc tggagtggat gggcatcatc gaccccgacg acagctacac cgagtacagc      180
cccagcttcc agggccaggt gaccatcagc gccgacaaga gcatcagcac cgcctacctg      240
cagtggagca gcctgaaggc cagcgacacc gccatgtact actgcgccag atacgagtac      300
ggcggcttcg acatctgggg ccagggcacc ctggtgaccg tcagctcagc tagcaccaag      360
ggccccagcg tgttccccct ggcccccagc agcaagagca cctccggcgg cacagccgcc      420
ctgggctgcc tggtgaagga ctacttcccc gagcccgtga ccgtgtcctg gaacagcgga      480
gccctgacca gcggcgtgca caccttcccc gccgtgctgc agagcagcgg cctgtacagc      540
ctgtccagcg tggtgacagt gcccagcagc agcctgggca cccagaccta catctgcaac      600
gtgaaccaca agcccagcaa caccaaggtg gacaagagag tggagcccaa gagctgcgac      660
aagacccaca cctgcccccc ctgcccagcc ccgaagctg caggcggccc ttccgtgttc      720
ctgttccccc ccaagcccaa ggacaccctg atgatcagca ggacccccga ggtgacctgc      780
gtggtggtgg acgtgagcca cgaggaccca gaggtgaagt tcaactggta cgtggacggc      840
gtggaggtgc acaacgccaa gaccaagccc agagaggagc agtacaacag cacctacagg      900
gtggtgtccg tgctgaccgt gctgcaccag gactggctga acggcaaaga atacaagtgc      960
aaggtctcca acaaggccct gcctgccccc atcgaaaaga ccatcagcaa ggccaagggc     1020
cagccacggg agccccaggt gtacaccctg ccccttctc gggaggagat gaccaagaac     1080
caggtgtccc tgacctgtct ggtgaagggc ttctacccca gcgacatcgc cgtggagtgg     1140
gagagcaacg gccagcccga gaacaactac aagaccaccc cccagtgct ggacagcgac     1200 ggcagcttct tcctgtacag caagctgacc gtggacaaga gcaggtggca gcagggcaac     1260
gtgttcagct gcagcgtgat gcacgaggcc ctgcacaacc actacaccca gaagagcctg     1320
agcctgtcac ccggcaag                                                  1338

<210> SEQ ID NO 32
<211> LENGTH: 636
<212> TYPE: DNA
<213> ORGANISM: homo sapiens

<400> SEQUENCE: 32
agctacgagc tgacccagcc ccccagcgtg agcgtggccc caggccagac cgccaggatc       60
agctgcagcg gcgacaacat cggcaacagc tacgtgcact ggtatcagca gaagcccggc      120
caggcccccg tgctggtgat ctacaaggac aacgacaggc cagcggcat ccccgagagg      180 ttcagcggca gcaactccgg caacaccgcc accctgacca tcagcggcac ccaggccgag      240
gacgaggccg actactactg cggcacctac gacatcgagt catacgtgtt cggcggaggg      300
```

-continued

```
accaagctga ccgtgctggg ccagcctaag gctgccccca gcgtgaccct gttccccccc    360
agcagcgagg agctgcaggc caacaaggcc accctggtgt gcctgatcag cgacttctac    420
ccaggcgccg tgaccgtggc ctggaaggcc gacagcagcc ccgtgaaggc cggcgtggag    480
accaccaccc ccagcaagca gagcaacaac aagtacgccg ccagcagcta cctgagcctg    540 accccccgagc agtggaagag ccacaggtcc tacagctgcc aggtgaccca cgagggcagc    600
accgtggaaa agaccgtggc cccaaccgag tgcagc                              636
```

<210> SEQ ID NO 33
<211> LENGTH: 7
<212> TYPE: PRT
<213> ORGANISM: homo sapiens

<400> SEQUENCE: 33

Thr Ser Gly Gly Gly Val Ser
1               5

<210> SEQ ID NO 34
<211> LENGTH: 16
<212> TYPE: PRT
<213> ORGANISM: homo sapiens

<400> SEQUENCE: 34

Asn Ile Asp Asp Ala Asp Ile Lys Asp Tyr Ser Pro Ser Leu Lys Ser
1               5                   10                  15

<210> SEQ ID NO 35
<211> LENGTH: 7
<212> TYPE: PRT
<213> ORGANISM: homo sapiens

<400> SEQUENCE: 35

Gly Pro Tyr Gly Phe Asp Ser
1               5

<210> SEQ ID NO 36
<211> LENGTH: 14
<212> TYPE: PRT
<213> ORGANISM: homo sapiens

<400> SEQUENCE: 36

Thr Gly Thr Ser Ser Asp Ile Gly Thr Tyr Asn Tyr Val Ser
1               5                   10

<210> SEQ ID NO 37
<211> LENGTH: 7
<212> TYPE: PRT
<213> ORGANISM: homo sapiens

<400> SEQUENCE: 37

Asp Asp Ser Asn Arg Pro Ser
1               5

<210> SEQ ID NO 38
<211> LENGTH: 9
<212> TYPE: PRT
<213> ORGANISM: homo sapiens

<400> SEQUENCE: 38

Gln Ser Tyr Asp Ser Gln Ser Ile Val
1               5

```
<210> SEQ ID NO 39
<211> LENGTH: 117
<212> TYPE: PRT
<213> ORGANISM: homo sapiens

<400> SEQUENCE: 39

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Gly Gly Val Ser Trp Ile Arg Gln Pro Pro Gly Lys Ala Leu Glu
        35                  40                  45

Trp Leu Ala Asn Ile Asp Asp Ala Asp Ile Lys Asp Tyr Ser Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Pro Tyr Gly Phe Asp Ser Trp Gly Gln Gly Thr Leu
            100                 105                 110

Val Thr Val Ser Ser
        115

<210> SEQ ID NO 40
<211> LENGTH: 109
<212> TYPE: PRT
<213> ORGANISM: homo sapiens

<400> SEQUENCE: 40

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Asn Tyr Val Ser Trp Tyr Gln Gln His Pro Gly Lys Ala Pro Lys Leu
        35                  40                  45

Met Ile Tyr Asp Asp Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Gln
                85                  90                  95

Ser Ile Val Phe Gly Gly Gly Thr Lys Leu Thr Val Leu
            100                 105

<210> SEQ ID NO 41
<211> LENGTH: 447
<212> TYPE: PRT
<213> ORGANISM: homo sapiens

<400> SEQUENCE: 41

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Gly Gly Val Ser Trp Ile Arg Gln Pro Pro Gly Lys Ala Leu Glu
        35                  40                  45

Trp Leu Ala Asn Ile Asp Asp Ala Asp Ile Lys Asp Tyr Ser Pro Ser
    50                  55                  60
```

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Gly Pro Tyr Gly Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 215
<212> TYPE: PRT
<213> ORGANISM: homo sapiens

<400> SEQUENCE: 42
```

```
Glu Ser Ala Leu Thr Gln Pro Ala Val Ser Gly Ser Pro Gly Gln
 1               5                  10                  15

Ser Ile Thr Ile Ser Cys Thr Gly Thr Ser Ser Asp Ile Gly Thr Tyr
                20                  25                  30

Asn Tyr Val Ser Trp Tyr Gln Gln His Pro Gly Lys Ala Pro Lys Leu
            35                  40                  45

Met Ile Tyr Asp Asp Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Tyr Asp Ser Gln
                85                  90                  95

Ser Ile Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 43
<211> LENGTH: 351
<212> TYPE: DNA
<213> ORGANISM: homo sapiens

<400> SEQUENCE: 43
gaggtgacat tgaaagaaag cggcccggcc ctggtgaaac cgacccaaac cctgaccctg      60
acctgtacct tttccggatt tagcctgtct acttctggtg gtggtgtgtc ttggattcgc     120
cagccgcctg ggaaagccct cgagtggctg gctaatattg atgatgctga tattaaggat     180
tattctcctt ctcttaagtc tcgtctgacc attagcaaag atacttcgaa aaatcaggtg     240
gtgctgacta tgaccaacat ggacccggtg gatacggcca cctattattg cgcgcgtggt     300
ccttatggtt ttgattcttg gggccaaggc accctggtga cggttagctc a              351

<210> SEQ ID NO 44
<211> LENGTH: 327
<212> TYPE: DNA
<213> ORGANISM: homo sapiens

<400> SEQUENCE: 44
gaaagcgcac tgacccagcc agcttcagtg agcggctcac caggtcagag cattaccatc      60
tcgtgtacgg gtactagcag cgatattggt acttataatt atgtgtcttg gtaccagcag     120
catcccggga aggcgccgaa acttatgatt tatgatgatt ctaatcgtcc ctcaggcgtg     180
agcaaccgtt ttagcggatc caaaagcggc aacaccgcga gcctgaccat tagcggcctg     240
caagcggaag acgaagcgga ttattattgc agtcttatg attctcagtc tattgtgttt     300
```

```
ggcggcggca cgaagttaac cgtccta                                        327

<210> SEQ ID NO 45
<211> LENGTH: 1341
<212> TYPE: DNA
<213> ORGANISM: homo sapiens

<400> SEQUENCE: 45
gaggtgacat tgaaagaaag cggcccggcc ctggtgaaac cgacccaaac cctgaccctg     60
acctgtacct tttccggatt tagcctgtct acttctggtg gtggtgtgtc ttggattcgc    120
cagccgcctg gaaagccct cgagtggctg gctaatattg atgatgctga tattaaggat    180
tattctcctt ctcttaagtc tcgtctgacc attagcaaag atacttcgaa aaatcaggtg    240
gtgctgacta tgaccaacat ggacccggtg gatacggcca cctattattg cgcgcgtggt    300
ccttatggtt ttgattcttg gggccaaggc accctggtga cggttagctc agcctccacc    360
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaag cagcgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgggtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg   1260
aacgtcttct catgctccgt gatgcatgag gctctgcaca accactacac gcagaagagc   1320
ctctccctgt ctccgggtaa a                                             1341

<210> SEQ ID NO 46
<211> LENGTH: 645
<212> TYPE: DNA
<213> ORGANISM: homo sapiens

<400> SEQUENCE: 46
gaaagcgcac tgacccagcc agcttcagtg agcggctcac caggtcagag cattaccatc     60
tcgtgtacgg gtactagcag cgatattggt acttataatt atgtgtcttg gtaccagcag    120
catcccggga aggcgccgaa acttatgatt tatgatgatt ctaatcgtcc ctcaggcgtg    180
agcaaccgtt ttagcggatc caaaagcggc aacaccgcga gcctgaccat tagcggcctg    240
caagcggaag acgaagcgga ttattattgc cagtcttatg attctcagtc tattgtgttt    300
ggcggcggca cgaagttaac cgtcctaggt cagcccaagg ctgccccctc ggtcactctg    360
ttcccgccct cctctgagga gcttcaagcc aacaaggcca cactggtgtg tctcataagt    420
gacttctacc cgggagccgt gacagtggcc tggaaggcag atagcagccc cgtcaaggcg    480
```

| | |
|---|---|
| ggagtggaga ccaccacacc ctccaaacaa agcaacaaca agtacgcggc cagcagctat | 540 |
| ctgagcctga cgcctgagca gtggaagtcc cacagaagct acagctgcca ggtcacgcat | 600 |
| gaagggagca ccgtggagaa gacagtggcc cctacagaat gttca | 645 |

<210> SEQ ID NO 47
<211> LENGTH: 1341
<212> TYPE: DNA
<213> ORGANISM: homo sapiens

<400> SEQUENCE: 47

| | |
|---|---|
| gaggtgaccc tgaaggagag cggcccagcc ctggtgaagc ccacccagac cctgaccctg | 60 |
| acttgcacct tcagcggctt cagcctgagc accagcggag ggggcgtgag ctggatcagg | 120 |
| cagcccccag gtaaggccct ggagtggctg gccaatatcg acgacgccga tatcaaggac | 180 |
| tacagcccca gcctgaagag caggctgacc atcagcaagg acaccagcaa gaaccaggtg | 240 |
| gtgctgacca tgaccaatat ggaccccgtg acaccgcca cctactactg cgccagaggc | 300 |
| ccctacggct tcgacagctg ggccagggc accctggtga ccgtcagctc agctagcacc | 360 |
| aaggccccca cggtgttccc cctggccccc agcagcaaga gcacctccgg cggcacagcc | 420 |
| gccctgggct gcctggtgaa ggactacttc cccgagcccg tgaccgtgtc ctggaacagc | 480 |
| ggagccctga ccagcggcgt gcacaccttc cccgccgtgc tgcagagcag cggcctgtac | 540 |
| agcctgtcca gcgtggtgac agtgcccagc agcagcctgg gcacccagac ctacatctgc | 600 |
| aacgtgaacc acaagcccag caacaccaag gtggacaaga gagtggagcc caagagctgc | 660 |
| gacaagaccc acacctgccc ccctgccca gcccccgaag ctgcaggcgg cccttccgtg | 720 |
| ttcctgttcc ccccaagcc caaggacacc ctgatgatca gcaggacccc cgaggtgacc | 780 |
| tgcgtggtgg tggacgtgag ccacgaggac ccagaggtga agttcaactg gtacgtggac | 840 |
| ggcgtggagg tgcacaacgc caagaccaag cccagagagg agcagtacaa cagcacctac | 900 |
| agggtggtgt ccgtgctgac cgtgctgcac caggactggc tgaacggcaa agaatacaag | 960 |
| tgcaaggtct ccaacaaggc cctgcctgcc cccatcgaaa agaccatcag caaggccaag | 1020 |
| ggccagccac gggagcccca ggtgtacacc ctgccccctt ctcgggagga gatgaccaag | 1080 |
| aaccaggtgt ccctgacctg tctggtgaag ggcttctacc ccagcgacat cgccgtggag | 1140 |
| tgggagagca acggccagcc cgagaacaac tacaagacca ccccccccagt gctggacagc | 1200 |
| gacggcagct tcttcctgta cagcaagctg accgtggaca agagcaggtg gcagcagggc | 1260 |
| aacgtgttca gctgcagcgt gatgcacgag gccctgcaca accactacac ccagaagagc | 1320 |
| ctgagcctgt cacccggcaa g | 1341 |

<210> SEQ ID NO 48
<211> LENGTH: 645
<212> TYPE: DNA
<213> ORGANISM: homo sapiens

<400> SEQUENCE: 48

| | |
|---|---|
| gagagcgccc tgacccagcc cgccagcgtg agcggcagcc caggccagtc tatcacaatc | 60 |
| agctgcaccg gcacctccag cgatatcggc acctacaact acgtgagctg gtatcagcag | 120 |
| caccccggca aggcccccaa gctgatgatc tacgacgaca gcaacaggcc cagcggcgtg | 180 |
| agcaacaggt tcagcggcag caagagcggc aacaccgcca gcctgacaat cagcggcctg | 240 |
| caggccgagg acgaggccga ctactactgc cagagctacg acagccagtc aatcgtgttc | 300 |
| ggcggaggga ccaagctgac cgtgctgggc cagcctaagg ctgcccccag cgtgaccctg | 360 |

```
ttcccccccca gcagcgagga gctgcaggcc aacaaggcca ccctggtgtg cctgatcagc    420
gacttctacc caggcgccgt gaccgtggcc tggaaggccg acagcagccc cgtgaaggcc    480
ggcgtggaga ccaccacccc cagcaagcag agcaacaaca agtacgccgc cagcagctac    540
ctgagcctga cccccgagca gtggaagagc cacaggtcct acagctgcca ggtgacccac    600
gagggcagca ccgtggaaaa gaccgtggcc ccaaccgagt gcagc                    645
```

```
<210> SEQ ID NO 49
<211> LENGTH: 17
<212> TYPE: PRT
<213> ORGANISM: homo sapiens

<400> SEQUENCE: 49

Ile Ile Asp Pro Asp Asp Ser Tyr Thr Arg Tyr Ser Pro Ser Phe Gln
1               5                   10                  15

Gly

<210> SEQ ID NO 50
<211> LENGTH: 9
<212> TYPE: PRT
<213> ORGANISM: homo sapiens

<400> SEQUENCE: 50

Ala Thr Trp Gly Ser Glu Asp Gln Val
1               5

<210> SEQ ID NO 51
<211> LENGTH: 116
<212> TYPE: PRT
<213> ORGANISM: homo sapiens

<400> SEQUENCE: 51

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Asp Asp Ser Tyr Thr Arg Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
                100                 105                 110

Thr Val Ser Ser
        115

<210> SEQ ID NO 52
<211> LENGTH: 106
<212> TYPE: PRT
<213> ORGANISM: homo sapiens

<400> SEQUENCE: 52

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
                20                  25                  30
```

```
His Trp Tyr Gln Gln Lys Pro Gly Gln Ala Pro Val Leu Val Ile Tyr
             35                  40                  45

Lys Asp Asn Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Thr Trp Gly Ser Glu Asp Gln Val
                 85                  90                  95

Phe Gly Gly Gly Thr Lys Leu Thr Val Leu
                100                 105

<210> SEQ ID NO 53
<211> LENGTH: 446
<212> TYPE: PRT
<213> ORGANISM: homo sapiens

<400> SEQUENCE: 53

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
             20                  25                  30

Ile Ser Trp Val Arg Gln Met Pro Gly Lys Gly Leu Glu Trp Met Gly
             35                  40                  45

Ile Ile Asp Pro Asp Asp Ser Tyr Thr Arg Tyr Ser Pro Ser Phe Gln
 50                  55                  60

Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
                 85                  90                  95

Arg Tyr Glu Tyr Gly Gly Phe Asp Ile Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 54
<211> LENGTH: 212
<212> TYPE: PRT
<213> ORGANISM: homo sapiens

<400> SEQUENCE: 54

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Trp Gly Ser Glu Asp Gln Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 55
<211> LENGTH: 348
```

```
<212> TYPE: DNA
<213> ORGANISM: homo sapiens

<400> SEQUENCE: 55
gaggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatc gatccggatg atagctatac ccgttattct     180
ccgagctttc agggacaggt gaccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctca                  348

<210> SEQ ID NO 56
<211> LENGTH: 318
<212> TYPE: DNA
<213> ORGANISM: homo sapiens

<400> SEQUENCE: 56
agttacgaac tgacccagcc gccttcagtg agcgttgcac caggtcagac cgcgcgtatc      60
tcgtgtagcg gcgataatat tggtaattct tatgttcatt ggtaccagca gaaacccggg     120
caggcgccag ttcttgtgat ttataaggat aatgatcgtc cctcaggcat cccggaacgc     180
tttagcggat ccaacagcgg caacaccgcg accctgacca ttagcggcac tcaggcggaa     240
gacgaagcgg attattattg cgctacttgg ggttctgagg atcaggtgtt tggcggcggc     300
acgaagttaa ccgtccta                                                   318

<210> SEQ ID NO 57
<211> LENGTH: 1338
<212> TYPE: DNA
<213> ORGANISM: homo sapiens

<400> SEQUENCE: 57
gaggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatc gatccggatg atagctatac ccgttattct     180
ccgagctttc agggacaggt gaccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctcagc tccaccaag     360 ggtccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaagcag cggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgg     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggaggagat gaccaagaac    1080
```

| | |
|---|---|
| caggtcagcc tgacctgcct ggtcaaaggc ttctatccca gcgacatcgc cgtggagtgg | 1140 |
| gagagcaatg ggcagccgga gaacaactac aagaccacgc ctcccgtgct ggactccgac | 1200 |
| ggctccttct tcctctacag caagctcacc gtggacaaga gcaggtggca gcagggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 58
<211> LENGTH: 636
<212> TYPE: DNA
<213> ORGANISM: homo sapiens

<400> SEQUENCE: 58

| | |
|---|---|
| agttacgaac tgacccagcc gccttcagtg agcgttgcac caggtcagac cgcgcgtatc | 60 |
| tcgtgtagcg gcgataatat tggtaattct tatgttcatt ggtaccagca gaaacccggg | 120 |
| caggcgccag ttcttgtgat ttataaggat aatgatcgtc cctcaggcat cccggaacgc | 180 |
| tttagcggat ccaacagcgg caacaccgcg accctgacca ttagcggcac tcaggcggaa | 240 |
| gacgaagcgg attattattg cgctacttgg ggttctgagg atcaggtgtt tggcggcggc | 300 |
| acgaagttaa ccgtcctagg tcagcccaag gctgccccct cggtcactct gttcccgccc | 360 |
| tcctctgagg agcttcaagc caacaaggcc acactggtgt gtctcataag tgacttctac | 420 |
| ccgggagccg tgacagtggc ctggaaggca gatagcagcc ccgtcaaggc gggagtggag | 480 |
| accaccacac cctccaaaca aagcaacaac aagtacgcgg ccagcagcta tctgagcctg | 540 |
| acgcctgagc agtggaagtc ccacagaagc tacagctgcc aggtcacgca tgaagggagc | 600 |
| accgtggaga gacagtggcc cctacagaa tgttca | 636 |

<210> SEQ ID NO 59
<211> LENGTH: 1338
<212> TYPE: DNA
<213> ORGANISM: homo sapiens

<400> SEQUENCE: 59

| | |
|---|---|
| gaggtgcagc tggtgcagag cggagccgag gtgaaaaagc ccggtgagag cctgaagatc | 60 |
| agctgcaagg gcagcggcta cagcttcacc aactacatca gctgggtgcg gcagatgccc | 120 |
| ggcaagggcc tggagtggat gggcatcatc gaccccgacg acagctacac caggtacagc | 180 |
| cccagcttcc agggccaggt gaccatcagc gccgacaaga gcatcagcac cgcctacctg | 240 |
| cagtggagca gcctgaaggc cagcgacacc gccatgtact actgcgccag atacgagtac | 300 |
| ggcggcttcg acatctgggg ccagggcacc ctggtgaccg tcagctcagc tagcaccaag | 360 |
| ggcccagcg tgttcccct ggccccagc agcaagagca cctccggcgg cacagccgcc | 420 |
| ctgggctgcc tggtgaagga ctacttcccc gagcccgtga ccgtgtcctg gaacagcgga | 480 |
| gccctgacca gcggcgtgca caccttcccc gccgtgctgc agagcagcgg cctgtacagc | 540 |
| ctgtccagcg tggtgacagt gcccagcagc agcctgggca cccagaccta catctgcaac | 600 |
| gtgaaccaca agcccagcaa caccaaggtg gacaagagag tggagcccaa gagctgcgac | 660 |
| aagacccaca cctgcccccc ctgcccagcc cccgaagctg caggcggccc ttccgtgttc | 720 |
| ctgttccccc caagcccaa ggacaccctg atgatcagca ggacccccga ggtgacctgc | 780 |
| gtggtggtgg acgtgagcca cgaggaccca gaggtgaagt tcaactggta cgtggacggc | 840 |
| gtggaggtgc acaacgccaa gaccaagccc agagaggagc agtacaacag cacctacagg | 900 |
| gtggtgtccg tgctgaccgt gctgcaccag gactggctga acggcaaaga atacaagtgc | 960 |

```
aaggtctcca acaaggccct gcctgccccc atcgaaaaga ccatcagcaa ggccaagggc    1020
cagccacggg agccccaggt gtacaccctg ccccttctc gggaggagat gaccaagaac    1080
caggtgtccc tgacctgtct ggtgaagggc ttctacccca gcgacatcgc cgtggagtgg    1140
gagagcaacg gccagcccga gaacaactac aagaccaccc cccagtgct ggacagcgac    1200 ggcagcttct tcctgtacag caagctgacc gtggacaaga gcaggtggca gcagggcaac    1260
gtgttcagct gcagcgtgat gcacgaggcc ctgcacaacc actacaccca gaagagcctg    1320
agcctgtcac ccggcaag                                                 1338
```

\<210\> SEQ ID NO 60
\<211\> LENGTH: 636
\<212\> TYPE: DNA
\<213\> ORGANISM: homo sapiens

\<400\> SEQUENCE: 60

```
agctacgagc tgacccagcc ccccagcgtg agcgtggccc caggccagac cgccaggatc      60
agctgcagcg gcgacaatat cggcaacagc tacgtgcact ggtatcagca gaagcccggc     120
caggcccccg tgctggtgat ctacaaggac aacgacaggc ccagcggcat ccccgagagg     180
ttcagcggca gcaactccgg caacaccgcc accctgacaa tcagcggcac ccaggccgag     240
gacgaggcca ctactactg cgccacctgg ggctcagagg accaggtgtt cggcggaggg     300
accaagctga ccgtgctggg ccagcctaag gctgcccca gcgtgaccct gttccccccc     360
agcagcgagg agctgcaggc caacaaggcc accctggtgt gcctgatcag cgacttctac     420
ccaggcgccg tgaccgtggc ctggaaggcc gacagcagcc ccgtgaaggc cggcgtggag     480
accaccaccc ccagcaagca gagcaacaac aagtacgccg ccagcagcta cctgagcctg     540 accccccgagc agtggaagag ccacaggtcc tacagctgcc aggtgaccca cgagggcagc     600
accgtggaaa agaccgtggc cccaaccgag tgcagc                              636
```

\<210\> SEQ ID NO 61
\<211\> LENGTH: 5
\<212\> TYPE: PRT
\<213\> ORGANISM: homo sapiens

\<400\> SEQUENCE: 61

Ser Tyr Tyr Ile Gly
1               5

\<210\> SEQ ID NO 62
\<211\> LENGTH: 17
\<212\> TYPE: PRT
\<213\> ORGANISM: homo sapiens

\<400\> SEQUENCE: 62

Ile Ile Asp Pro Thr Asp Ser Gln Thr Ala Tyr Ser Pro Ser Phe Gln
1               5                   10                  15

Gly

\<210\> SEQ ID NO 63
\<211\> LENGTH: 8
\<212\> TYPE: PRT
\<213\> ORGANISM: homo sapiens

\<400\> SEQUENCE: 63

Tyr Met Met Arg Gly Phe Asp His
1               5

```
<210> SEQ ID NO 64
<211> LENGTH: 11
<212> TYPE: PRT
<213> ORGANISM: homo sapiens

<400> SEQUENCE: 64

Ser Gly Asp Ser Leu Gly Asp Tyr Tyr Ala Tyr
1               5                   10

<210> SEQ ID NO 65
<211> LENGTH: 7
<212> TYPE: PRT
<213> ORGANISM: homo sapiens

<400> SEQUENCE: 65

Lys Asp Asn Asn Arg Pro Ser
1               5

<210> SEQ ID NO 66
<211> LENGTH: 10
<212> TYPE: PRT
<213> ORGANISM: homo sapiens

<400> SEQUENCE: 66

Gln Thr Trp Asp Thr Gly Glu Ser Gly Val
1               5                   10

<210> SEQ ID NO 67
<211> LENGTH: 117
<212> TYPE: PRT
<213> ORGANISM: homo sapiens

<400> SEQUENCE: 67

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Tyr Ile Gly Trp Val Arg Gln Met Pro Gly Lys Gly Leu Glu Trp Met
            35                  40                  45

Gly Ile Ile Asp Pro Thr Asp Ser Gln Thr Ala Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Met Arg Gly Phe Asp His Trp Gly Gln Gly Thr Leu
            100                 105                 110

Val Thr Val Ser Ser
        115

<210> SEQ ID NO 68
<211> LENGTH: 107
<212> TYPE: PRT
<213> ORGANISM: homo sapiens

<400> SEQUENCE: 68

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
                20                  25                  30

Tyr Trp Tyr Gln Gln Lys Pro Gly Gln Ala Pro Val Leu Val Ile Tyr
```

```
              35                  40                  45
Lys Asp Asn Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Trp Asp Thr Gly Ser Gly
                 85                  90                  95

Val Phe Gly Gly Gly Thr Lys Leu Thr Val Leu
                100                 105

<210> SEQ ID NO 69
<211> LENGTH: 447
<212> TYPE: PRT
<213> ORGANISM: homo sapiens

<400> SEQUENCE: 69

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Tyr Ile Gly Trp Val Arg Gln Met Pro Gly Lys Gly Leu Glu Trp Met
             35                  40                  45

Gly Ile Ile Asp Pro Thr Asp Ser Gln Thr Ala Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Tyr Met Met Arg Gly Phe Asp His Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
```

```
                305                 310                 315                 320
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 70
<211> LENGTH: 213
<212> TYPE: PRT
<213> ORGANISM: homo sapiens

<400> SEQUENCE: 70

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
                20                  25                  30

Tyr Trp Tyr Gln Gln Lys Pro Gly Gln Ala Pro Val Leu Val Ile Tyr
                35                  40                  45

Lys Asp Asn Asn Arg Pro Ser Gly Ile Pro Glu Arg Phe Ser Gly Ser
                50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Thr Gly Glu Ser Gly
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Thr Leu Val Cys Leu Ile Ser Asp Phe Tyr Pro Gly Ala
                130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
                195                 200                 205

Pro Thr Glu Cys Ser
        210

<210> SEQ ID NO 71
<211> LENGTH: 351
<212> TYPE: DNA
```

<213> ORGANISM: homo sapiens

<400> SEQUENCE: 71

| | |
|---|---|
| gaggtgcaat tggttcagag cggcgcggaa gtgaaaaaac cgggcgaaag cctgaaaatt | 60 |
| agctgcaaag gttccggata ttcctttact tcttattata ttggttgggt gcgccagatg | 120 |
| cctgggaagg gtctcgagtg gatgggcatt attgatccta ctgattctca gactgcttat | 180 |
| tctccttctt ttcagggtca ggtgaccatt agcgcggata aaagcattag caccgcgtat | 240 |
| cttcaatgga gcagcctgaa agcgagcgat acggccatgt attattgcgc gcgttatatg | 300 |
| atgcgtggtt ttgatcattg gggccaaggc accctggtga cggttagctc a | 351 |

<210> SEQ ID NO 72
<211> LENGTH: 321
<212> TYPE: DNA
<213> ORGANISM: homo sapiens

<400> SEQUENCE: 72

| | |
|---|---|
| agttacgaac tgacccagcc gccttcagtg agcgttgcac caggtcagac cgcgcgtatc | 60 |
| tcgtgtagcg gcgattctct tggtgattat tatgcttatt ggtaccagca gaaacccggg | 120 |
| caggcgccag ttcttgtgat ttataaggat aataatcgtc cctcaggcat cccggaacgc | 180 |
| tttagcggat ccaacagcgg caacaccgcg accctgacca ttagcggcac tcaggcggaa | 240 |
| gacgaagcgg attattattg ccagacttgg gatactggtg agtctggtgt gtttggcggc | 300 |
| ggcacgaagt taaccgtcct a | 321 |

<210> SEQ ID NO 73
<211> LENGTH: 1341
<212> TYPE: DNA
<213> ORGANISM: homo sapiens

<400> SEQUENCE: 73

| | |
|---|---|
| gaggtgcaat tggttcagag cggcgcggaa gtgaaaaaac cgggcgaaag cctgaaaatt | 60 |
| agctgcaaag gttccggata ttcctttact tcttattata ttggttgggt gcgccagatg | 120 |
| cctgggaagg gtctcgagtg gatgggcatt attgatccta ctgattctca gactgcttat | 180 |
| tctccttctt ttcagggtca ggtgaccatt agcgcggata aaagcattag caccgcgtat | 240 |
| cttcaatgga gcagcctgaa agcgagcgat acggccatgt attattgcgc gcgttatatg | 300 |
| atgcgtggtt ttgatcattg gggccaaggc accctggtga cggttagctc agcctccacc | 360 |
| aagggtccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga gagttgagcc caaatcttgt | 660 |
| gacaaaactc acacatgccc accgtgccca gcacctgaag cagcgggggg accgtcagtc | 720 |
| ttcctcttcc cccaaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgggtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |

| | |
|---|---:|
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca gagcaggtg gcagcagggg | 1260 |
| aacgtcttct catgctccgt gatgcatgag gctctgcaca accactacac gcagaagagc | 1320 |
| ctctccctgt ctccgggtaa a | 1341 |

<210> SEQ ID NO 74
<211> LENGTH: 639
<212> TYPE: DNA
<213> ORGANISM: homo sapiens

<400> SEQUENCE: 74

| | |
|---|---:|
| agttacgaac tgacccagcc gccttcagtg agcgttgcac caggtcagac cgcgcgtatc | 60 |
| tcgtgtagcg gcgattctct tggtgattat tatgcttatt ggtaccagca gaaacccggg | 120 |
| caggcgccag ttcttgtgat ttataaggat aataatcgtc cctcaggcat cccggaacgc | 180 |
| tttagcggat ccaacagcgg caacaccgcg accctgacca ttagcggcac tcaggcggaa | 240 |
| gacgaagcgg attattattg ccagacttgg gatactggtg agtctggtgt gtttggcggc | 300 |
| ggcacgaagt taaccgtcct aggtcagccc aaggctgccc cctcggtcac tctgttcccg | 360 |
| ccctcctctg aggagcttca agccaacaag gccacactgg tgtgtctcat aagtgacttc | 420 |
| tacccgggag ccgtgacagt ggcctggaag gcagatagca gccccgtcaa ggcgggagtg | 480 |
| gagaccacca cccctccaa acaaagcaac aacaagtacg cggccagcag ctatctgagc | 540 |
| ctgacgcctg agcagtggaa gtcccacaga agctacagct gccaggtcac gcatgaaggg | 600 |
| agcaccgtgg agaagacagt ggcccctaca gaatgttca | 639 |

<210> SEQ ID NO 75
<211> LENGTH: 1341
<212> TYPE: DNA
<213> ORGANISM: homo sapiens

<400> SEQUENCE: 75

| | |
|---|---:|
| gaggtgcagc tggtgcagag cggagccgag gtgaaaaagc ccggtgagag cctgaagatc | 60 |
| agctgcaagg gcagcggcta cagcttcacc agctactaca tcggctgggt gcggcagatg | 120 |
| cccggcaagg gcctggagtg gatgggcatc atcgacccca ccgacagcca gaccgcctac | 180 |
| agccccagct ccagggcca ggtgaccatc agcgccgaca gagcatcag caccgcctac | 240 |
| ctgcagtgga gcagcctgaa ggccagcgac accgccatgt actactgcgc ccggtacatg | 300 |
| atgaggggct tcgaccactg gggtcagggc accctggtga ccgtcagctc agctagcacc | 360 |
| aagggcccca gcgtgttccc cctggccccc agcagcaaga gcacctccgg cggcacagcc | 420 |
| gccctgggct gcctggtgaa ggactacttc cccgagcccg tgaccgtgtc ctggaacagc | 480 |
| ggagccctga ccagcggcgt gcacaccttc ccgccgtgc tgcagagcag cggcctgtac | 540 |
| agcctgtcca gcgtggtgac agtgcccagc agcagcctgg gcacccagac ctacatctgc | 600 |
| aacgtgaacc acaagcccag caacaccaag gtggacaaga gagtggagcc caagagctgc | 660 |
| gacaagaccc acacctgccc ccctgccca gcccccgaag ctgcaggcgg cccttccgtg | 720 |
| ttcctgttcc cccccaagcc caaggacacc ctgatgatca gcaggaccccc gaggtgacc | 780 |
| tgcgtggtgg tggacgtgag ccacgaggac ccagaggtga agttcaactg gtacgtggac | 840 |
| ggcgtggagg tgcacaacgc caagaccaag cccagagagg agcagtacaa cagcacctac | 900 |
| agggtggtgt ccgtgctgac cgtgctgcac caggactggc tgaacggcaa agaatacaag | 960 |

```
tgcaaggtct ccaacaaggc cctgcctgcc cccatcgaaa agaccatcag caaggccaag      1020
ggccagccac gggagcccca ggtgtacacc ctgccccctt ctcgggagga gatgaccaag      1080
aaccaggtgt ccctgacctg tctggtgaag ggcttctacc ccagcgacat cgccgtggag      1140
tgggagagca acggccagcc cgagaacaac tacaagacca cccccccagt gctggacagc      1200
gacggcagct tcttcctgta cagcaagctg accgtggaca gagcaggtg gcagcagggc      1260 aacgtgttca gctgcagcgt gatgcacgag gccctgcaca accactacac ccagaagagc      1320
ctgagcctgt cacccggcaa g                                               1341

<210> SEQ ID NO 76
<211> LENGTH: 639
<212> TYPE: DNA
<213> ORGANISM: homo sapiens

<400> SEQUENCE: 76
agctacgagc tgacccagcc ccccagcgtg agcgtggccc caggccagac cgccaggatc        60
agctgcagcg gcgacagcct gggcgactac tacgcctact ggtatcagca gaagcccggc       120 caggccccc g tgctggtgat ctacaaggac aacaacaggc ccagcggcat ccccgagagg      180
ttcagcggca gcaacagcgg caacaccgcc accctgacaa tcagcggcac ccaggccgag       240
gacgaggccg actactactg ccagacctgg gacaccggcg agtcaggcgt gttcggcgga       300
gggaccaagc tgaccgtgct gggtcagcct aaggctgccc ccagcgtgac cctgttcccc       360
cccagcagcg aggagctgca ggccaacaag gccaccctgg tgtgcctgat cagcgacttc       420
tacccaggcg ccgtgaccgt ggcctggaag gccgacagca cccccgtgaa ggccggcgtg       480
gagaccacca ccccccagcaa gcagagcaac aacaagtacg ccgccagcag ctacctgagc       540 ctgaccccg agcagtggaa gagccacagg tcctacagct gccaggtgac ccacgagggc       600
agcaccgtgg aaaagaccgt ggccccaacc gagtgcagc                             639

<210> SEQ ID NO 77
<211> LENGTH: 17
<212> TYPE: PRT
<213> ORGANISM: homo sapiens

<400> SEQUENCE: 77

Ile Ile Asp Pro Ser Asp Ser His Thr Thr Tyr Ser Pro Ser Phe Gln
1               5                   10                  15

Gly

<210> SEQ ID NO 78
<211> LENGTH: 11
<212> TYPE: PRT
<213> ORGANISM: homo sapiens

<400> SEQUENCE: 78

Gln Thr Trp Asp Ile Leu Pro His Gly Leu Val
1               5                   10

<210> SEQ ID NO 79
<211> LENGTH: 117
<212> TYPE: PRT
<213> ORGANISM: homo sapiens

<400> SEQUENCE: 79

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
```

```
                    20                  25                  30
Tyr Ile Gly Trp Val Arg Gln Met Pro Gly Lys Gly Leu Glu Trp Met
             35                  40                  45
Gly Ile Ile Asp Pro Ser Asp Ser His Thr Thr Tyr Ser Pro Ser Phe
     50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                 85                  90                  95
Ala Arg Tyr Met Met Arg Gly Phe Asp His Trp Gly Gln Gly Thr Leu
             100                 105                 110
Val Thr Val Ser Ser
             115

<210> SEQ ID NO 80
<211> LENGTH: 108
<212> TYPE: PRT
<213> ORGANISM: homo sapiens

<400> SEQUENCE: 80

Ser Tyr Glu Leu Thr Gln Pro Pro Ser Val Ser Val Ala Pro Gly Gln
1               5                   10                  15
Thr Ala Arg Ile Ser Cys Ser Gly Asp Ser Leu Gly Asp Tyr Tyr Ala
             20                  25                  30
Tyr Trp Tyr Gln Gln Lys Pro Gly Gln Ala Pro Val Leu Val Ile Tyr
             35                  40                  45
Lys Asp Asn Asn Arg Pro Ser Gly Ile Pro Glu Arg Phe Ser Gly Ser
     50                  55                  60
Asn Ser Gly Asn Thr Ala Thr Leu Thr Ile Ser Gly Thr Gln Ala Glu
65                  70                  75                  80
Asp Glu Ala Asp Tyr Tyr Cys Gln Thr Trp Asp Ile Leu Pro His Gly
                 85                  90                  95
Leu Val Phe Gly Gly Gly Thr Lys Leu Thr Val Leu
             100                 105

<210> SEQ ID NO 81
<211> LENGTH: 447
<212> TYPE: PRT
<213> ORGANISM: homo sapiens

<400> SEQUENCE: 81

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
             20                  25                  30
Tyr Ile Gly Trp Val Arg Gln Met Pro Gly Lys Gly Leu Glu Trp Met
             35                  40                  45
Gly Ile Ile Asp Pro Ser Asp Ser His Thr Thr Tyr Ser Pro Ser Phe
     50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                 85                  90                  95
Ala Arg Tyr Met Met Arg Gly Phe Asp His Trp Gly Gln Gly Thr Leu
             100                 105                 110
Val Thr Val Ser Ser Ala Ser Thr Lys Gly Pro Ser Val Phe Pro Leu
             115                 120                 125
```

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 82
<211> LENGTH: 214
<212> TYPE: PRT
<213> ORGANISM: homo sapiens

<400> SEQUENCE: 82

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
50                  55                  60
```

```
Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Trp Asp Ile Leu Pro His Gly
                 85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 83
<211> LENGTH: 351
<212> TYPE: DNA
<213> ORGANISM: homo sapiens

<400> SEQUENCE: 83
gaggtgcaat tggttcagag cggcgcggaa gtgaaaaaac cgggcgaaag cctgaaaatt      60
agctgcaaag gttccggata ttcctttact tcttattata ttggttgggt cgccagatg     120 cctgggaagg gtctcgagtg gatgggcatt atcgatccgt ctgatagcca taccacttat     180
tctccgagct ttcagggcca ggtgaccatt agcgcggata aaagcattag caccgcgtat     240
cttcaatgga gcagcctgaa agcgagcgat acggccatgt attattgcgc gcgttatatg     300
atgcgtggtt ttgatcattg gggccaaggc accctggtga cggttagctc a              351

<210> SEQ ID NO 84
<211> LENGTH: 324
<212> TYPE: DNA
<213> ORGANISM: homo sapiens

<400> SEQUENCE: 84
agttacgaac tgacccagcc gccttcagtg agcgttgcac aggtcagac cgcgcgtatc       60 tcgtgtagcg gcgattctct tggtgattat tatgcttatt ggtaccagca gaaacccggg     120
caggcgccag ttcttgtgat ttataaggat aataatcgtc cctcaggcat cccgaacgc      180 tttagcggat ccaacagcgg caacaccgcg accctgacca ttagcggcac tcaggcggaa     240
gacgaagcgg attattattg ccagacttgg gatattcttc ctcatggtct tgtgtttggc     300
ggcggcacga agttaaccgt ccta                                            324

<210> SEQ ID NO 85
<211> LENGTH: 1341
<212> TYPE: DNA
<213> ORGANISM: homo sapiens

<400> SEQUENCE: 85
gaggtgcaat tggttcagag cggcgcggaa gtgaaaaaac cgggcgaaag cctgaaaatt      60
```

```
agctgcaaag gttccggata ttcctttact tcttattata ttggttgggt gcgccagatg    120
cctgggaagg gtctcgagtg gatgggcatt atcgatccgt ctgatagcca taccacttat    180
tctccgagct ttcagggcca ggtgaccatt agcgcggata aaagcattag caccgcgtat    240
cttcaatgga gcagcctgaa agcgagcgat acggccatgt attattgcgc gcgttatatg    300
atgcgtggtt ttgatcattg gggccaaggc accctggtga cggttagctc agcctccacc    360
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaag cagcgggggg accgtcagtc    720
ttcctcttcc cccaaaaccc aaggacaccc tcatgatctc ccggacccc tgaggtcaca    780 tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgggtggtca gcgtcctcac cgtcctgcac caggactggc tgaatggcaa ggagtacaag    960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320
ctctccctgt ctccgggtaa a                                               1341

<210> SEQ ID NO 86
<211> LENGTH: 642
<212> TYPE: DNA
<213> ORGANISM: homo sapiens

<400> SEQUENCE: 86
agttacgaac tgacccagcc gccttcagtg agcgttgcac caggtcagac cgcgcgtatc    60
tcgtgtagcg gcgattctct tggtgattat tatgcttatt ggtaccagca gaaacccggg    120
caggcgccag ttcttgtgat ttataaggat aataatcgtc cctcaggcat cccggaacgc    180
tttagcggat ccaacagcgg caacaccgcg accctgacca ttagcggcac tcaggcggaa    240
gacgaagcgg attattattg ccagacttgg gatattcttc ctcatggtct tgtgtttggc    300
ggcggcacga gttaaccgt cctaggtcag cccaaggctg cccctcggt cactctgttc    360 ccgccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtccac agaagctaca gctgccaggt cacgcatgaa    600
gggagcaccg tggagaagac agtggcccct acagaatgtt ca                        642

<210> SEQ ID NO 87
<211> LENGTH: 1341
<212> TYPE: DNA
<213> ORGANISM: homo sapiens
```

<400> SEQUENCE: 87

```
gaggtgcagc tggtgcagag cggagccgag gtgaaaaagc ccggtgagag cctgaagatc        60
agctgcaagg gcagcggcta cagcttcacc agctactaca tcggctgggt gcggcagatg       120
cccggcaagg gcctggagtg gatgggcatt atcgatccgt ctgatagcca taccacttat       180
tctccgagct ttcagggcca ggtgaccatc agcgccgaca agagcatcag caccgcctac       240
ctgcagtgga gcagcctgaa ggccagcgac accgccatgt actactgcgc ccggtacatg       300
atgaggggct tcgaccactg gggtcagggc accctggtga ccgtcagctc agctagcacc       360
aagggcccca gcgtgttccc cctggccccc agcagcaaga gcacctccgg cggcacagcc       420
gccctgggct gcctggtgaa ggactacttc cccgagcccg tgaccgtgtc ctggaacagc       480
ggagccctga ccagcggcgt gcacaccttc cccgccgtgc tgcagagcag cggcctgtac       540
agcctgtcca gcgtggtgac agtgcccagc agcagcctgg gcacccagac ctacatctgc       600
aacgtgaacc acaagcccag caacaccaag gtggacaaga gagtggagcc caagagctgc       660
gacaagaccc acacctgccc ccctgcccca gcccccgaag ctgcaggcgg cccttccgtg       720
ttcctgttcc cccccaagcc caaggacacc ctgatgatca gcaggacccc cgaggtgacc       780
tgcgtggtgg tggacgtgag ccacgaggac ccagaggtga agttcaactg gtacgtggac       840
ggcgtggagg tgcacaacgc caagaccaag cccagagagg agcagtacaa cagcacctac       900
agggtggtgt ccgtgctgac cgtgctgcac caggactggc tgaacggcaa agaatacaag       960
tgcaaggtct ccaacaaggc cctgcctgcc cccatcgaaa agaccatcag caaggccaag      1020
ggccagccac gggagcccca ggtgtacacc ctgcccccct tctcgggagga gatgaccaag      1080
aaccaggtgt ccctgacctg tctggtgaag ggcttctacc ccagcgacat cgccgtggag      1140
tgggagagca acggccagcc cgagaacaac tacaagacca cccccccagt gctggacagc      1200
gacggcagct tcttcctgta cagcaagctg accgtggaca gagcaggtg gcagcagggc      1260
aacgtgttca gctgcagcgt gatgcacgag gccctgcaca accactacac ccagaagagc      1320
ctgagcctgt cacccggcaa g                                                1341
```

<210> SEQ ID NO 88
<211> LENGTH: 642
<212> TYPE: DNA
<213> ORGANISM: homo sapiens

<400> SEQUENCE: 88

```
agctacgagc tgacccagcc ccccagcgtg agcgtggccc caggccagac cgccaggatc        60
agctgcagcg gcgacagcct gggcgactac tacgcctact ggtatcagca gaagcccggc       120
caggcccccg tgctggtgat ctacaaggac aacaacaggc ccagcggcat ccccgagagg       180
ttcagcggca gcaacagcgg caacaccgcc accctgacaa tcagcggcac ccaggccgag       240
gacgaggccg actactactg ccagacttgg gatattcttc ctcatggtct tgtgttcggc       300
ggagggacca agctgaccgt gctgggtcag cctaaggctg cccccagcgt gaccctgttc       360
cccccccagca gcgaggagct gcaggccaac aaggccaccc tggtgtgcct gatcagcgac       420
ttctacccag gcgccgtgac cgtggcctgg aaggcgaca gcagcccgt gaaggccggc       480
gtggagacca ccacccccag caagcagagc aacaacaagt acgccgccag cagctacctg       540
agcctgaccc ccgagcagtg gaagagccac aggtcctaca gctgccaggt gacccacgag       600
ggcagcaccg tggaaaagac cgtggccca accgagtgca gc                          642
```

-continued

```
<210> SEQ ID NO 89
<211> LENGTH: 11
<212> TYPE: PRT
<213> ORGANISM: homo sapiens

<400> SEQUENCE: 89

Gln Ala Trp Thr Asp Ser Pro Thr Gly Leu Val
1               5                   10

<210> SEQ ID NO 90
<211> LENGTH: 108
<212> TYPE: PRT
<213> ORGANISM: homo sapiens

<400> SEQUENCE: 90

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Trp Thr Asp Ser Pro Thr Gly
                85                  90                  95

Leu Val Phe Gly Gly Gly Thr Lys Leu Thr Val Leu
            100                 105

<210> SEQ ID NO 91
<211> LENGTH: 214
<212> TYPE: PRT
<213> ORGANISM: homo sapiens

<400> SEQUENCE: 91

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Trp Thr Asp Ser Pro Thr Gly
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175
```

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 92
<211> LENGTH: 324
<212> TYPE: DNA
<213> ORGANISM: homo sapiens

<400> SEQUENCE: 92

| | | | | | | |
|---|---|---|---|---|---|---|
| agttacgaac | tgacccagcc | gccttcagtg | agcgttgcac | caggtcagac | cgcgcgtatc | 60 |
| tcgtgtagcg | gcgattctct | tggtgattat | tatgcttatt | ggtaccagca | gaaacccggg | 120 |
| caggcgccag | ttcttgtgat | ttataaggat | aataatcgtc | cctcaggcat | cccggaacgc | 180 |
| tttagcggat | ccaacagcgg | caacaccgcg | accctgacca | ttagcggcac | tcaggcggaa | 240 |
| gacgaagcgg | attattattg | ccaggcttgg | actgattctc | ctactggtct | tgtgtttggc | 300 |
| ggcggcacga | agttaaccgt | ccta | | | | 324 |

<210> SEQ ID NO 93
<211> LENGTH: 642
<212> TYPE: DNA
<213> ORGANISM: homo sapiens

<400> SEQUENCE: 93

| | | | | | | |
|---|---|---|---|---|---|---|
| agttacgaac | tgacccagcc | gccttcagtg | agcgttgcac | caggtcagac | cgcgcgtatc | 60 |
| tcgtgtagcg | gcgattctct | tggtgattat | tatgcttatt | ggtaccagca | gaaacccggg | 120 |
| caggcgccag | ttcttgtgat | ttataaggat | aataatcgtc | cctcaggcat | cccggaacgc | 180 |
| tttagcggat | ccaacagcgg | caacaccgcg | accctgacca | ttagcggcac | tcaggcggaa | 240 |
| gacgaagcgg | attattattg | ccaggcttgg | actgattctc | ctactggtct | tgtgtttggc | 300 |
| ggcggcacga | agttaaccgt | cctaggtcag | cccaaggctg | ccccctcggt | cactctgttc | 360 |
| ccgccctcct | ctgaggagct | tcaagccaac | aaggccacac | tggtgtgtct | cataagtgac | 420 |
| ttctacccgg | gagccgtgac | agtggcctgg | aaggcagata | gcagccccgt | caaggcggga | 480 |
| gtggagacca | ccacaccctc | caaacaaagc | aacaacaagt | acgcggccag | cagctatctg | 540 |
| agcctgacgc | ctgagcagtg | gaagtcccac | agaagctaca | gctgccaggt | cacgcatgaa | 600 |
| gggagcaccg | tggagaagac | agtggccccct | acagaatgtt | ca | | 642 |

<210> SEQ ID NO 94
<211> LENGTH: 642
<212> TYPE: DNA
<213> ORGANISM: homo sapiens

<400> SEQUENCE: 94

| | | | | | | |
|---|---|---|---|---|---|---|
| agctacgagc | tgacccagcc | ccccagcgtg | agcgtggccc | caggccagac | cgccaggatc | 60 |
| agctgcagcg | gcgacagcct | gggcgactac | tacgcctact | ggtatcagca | gaagcccggc | 120 |
| caggcccccg | tgctggtgat | ctacaaggac | aacaacaggc | cagcggcat | ccccgagagg | 180 |
| ttcagcggca | gcaacagcgg | caacaccgcc | accctgacaa | tcagcggcac | ccaggccgag | 240 |
| gacgaggccg | actactactg | ccaggcttgg | actgattctc | ctactggtct | tgtgttcggc | 300 |
| ggagggacca | agctgaccgt | gctggtcag | cctaaggctg | ccccccagcgt | gaccctgttc | 360 |
| cccccccagca | gcgaggagct | gcaggccaac | aaggccaccc | tggtgtgcct | gatcagcgac | 420 |

```
ttctacccag cgccgtgac cgtggcctgg aaggccgaca gcagcccgt gaaggccggc    480 gtggagacca ccaccccag caagcagagc aacaacaagt acgccgccag cagctacctg    540
agcctgaccc ccgagcagtg gaagagccac aggtcctaca gctgccaggt gacccacgag    600
ggcagcaccg tggaaaagac cgtggcccca accgagtgca gc                      642
```

<210> SEQ ID NO 95  
<211> LENGTH: 17  
<212> TYPE: PRT  
<213> ORGANISM: homo sapiens

<400> SEQUENCE: 95

```
Ile Ile Asp Pro Thr Asp Ser Tyr Thr Val Tyr Ser Pro Ser Phe Gln
1               5                   10                  15

Gly
```

<210> SEQ ID NO 96  
<211> LENGTH: 117  
<212> TYPE: PRT  
<213> ORGANISM: homo sapiens

<400> SEQUENCE: 96

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Tyr Ile Gly Trp Val Arg Gln Met Pro Gly Lys Gly Leu Glu Trp Met
            35                  40                  45

Gly Ile Ile Asp Pro Thr Asp Ser Tyr Thr Val Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Met Arg Gly Phe Asp His Trp Gly Gln Gly Thr Leu
            100                 105                 110

Val Thr Val Ser Ser
        115
```

<210> SEQ ID NO 97  
<211> LENGTH: 447  
<212> TYPE: PRT  
<213> ORGANISM: homo sapiens

<400> SEQUENCE: 97

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Tyr Ile Gly Trp Val Arg Gln Met Pro Gly Lys Gly Leu Glu Trp Met
            35                  40                  45

Gly Ile Ile Asp Pro Thr Asp Ser Tyr Thr Val Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Tyr Met Met Arg Gly Phe Asp His Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Arg Val Glu Pro Lys Ser Cys Asp Lys Thr His
210                 215                 220
Thr Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 98
<211> LENGTH: 353
<212> TYPE: DNA
<213> ORGANISM: homo sapiens

<400> SEQUENCE: 98
gaggtgcaat tggttcagag cggcgcggaa gtgaaaaaac cgggcgaaag cctgaaaatt      60
agctgcaaag gttccggata ttcctttact tcttattata ttggttgggt gcgccagatg     120
cctgggaagg gtctcgagtg gatgggcatt attgatccta ctgattctta tactgtttat     180
```

| | |
|---|---:|
| tctccttctt ttcagggtca ggtgaccatt agcgcggata aaagcattag caccgcgtat | 240 |
| cttcaatgga gcagcctgaa agcgagcgat acggccatgt attattgcgc gcgttatatg | 300 |
| atgcgtggtt ttgatcattg gggccaaggc accctggtga cggttagctc agc | 353 |

<210> SEQ ID NO 99
<211> LENGTH: 1343
<212> TYPE: DNA
<213> ORGANISM: homo sapiens

<400> SEQUENCE: 99

| | |
|---|---:|
| gaggtgcaat tggttcagag cggcgcggaa gtgaaaaaac cgggcgaaag cctgaaaatt | 60 |
| agctgcaaag gttccggata ttcctttact tcttattata ttggttgggt gcgccagatg | 120 |
| cctgggaagg gtctcgagtg gatgggcatt attgatccta ctgattctta tactgtttat | 180 |
| tctccttctt ttcagggtca ggtgaccatt agcgcggata aaagcattag caccgcgtat | 240 |
| cttcaatgga gcagcctgaa agcgagcgat acggccatgt attattgcgc gcgttatatg | 300 |
| atgcgtggtt ttgatcattg gggccaaggc accctggtga cggttagctc agcgcctcca | 360 |
| ccaagggtcc atcggtcttc cccctggcac cctcctccaa gagcacctct ggggcacag | 420 |
| cggccctggg ctgcctggtc aaggactact ccccgaacc ggtgacggtg tcgtggaact | 480 |
| caggcgccct gaccagcggc gtgcacacct tcccggctgt cctacagtcc tcaggactct | 540 |
| actccctcag cagcgtggtg accgtgccct ccagcagctt gggcacccag acctacatct | 600 |
| gcaacgtgaa tcacaagccc agcaacacca aggtggacaa gagagttgag cccaaatctt | 660 |
| gtgacaaaac tcacacatgc ccaccgtgcc cagcacctga agcagcgggg ggaccgtcag | 720 |
| tcttcctctt ccccccaaaa cccaaggaca ccctcatgat ctcccggacc cctgaggtca | 780 |
| catgcgtggt ggtggacgtg agccacgaag accctgaggt caagttcaac tggtacgtgg | 840 |
| acggcgtgga ggtgcataat gccaagacaa agccgcggga ggagcagtac aacagcacgt | 900 |
| accgggtggt cagcgtcctc accgtcctgc accaggactg gctgaatggc aaggagtaca | 960 |
| agtgcaaggt ctccaacaaa gccctcccag ccccatcga aaaaccatc tccaaagcca | 1020 |
| aagggcagcc ccgagaacca caggtgtaca ccctgccccc atcccgggag gagatgacca | 1080 |
| agaaccaggt cagcctgacc tgcctggtca aaggcttcta tcccagcgac atcgccgtgg | 1140 |
| agtgggagag caatgggcag ccggagaaca actacaagac cacgcctccc gtgctggact | 1200 |
| ccgacggctc cttcttcctc tacagcaagc tcaccgtgga caagagcagg tggcagcagg | 1260 |
| ggaacgtctt ctcatgctcc gtgatgcatg aggctctgca caaccactac acgcagaaga | 1320 |
| gcctctccct gtctccgggt aaa | 1343 |

<210> SEQ ID NO 100
<211> LENGTH: 1341
<212> TYPE: DNA
<213> ORGANISM: homo sapiens

<400> SEQUENCE: 100

| | |
|---|---:|
| gaggtgcagc tggtgcagag cggagccgag gtgaaaaagc ccggtgagag cctgaagatc | 60 |
| agctgcaagg gcagcggcta cagcttcacc agctactaca tcggctgggt gcggcagatg | 120 |
| cccggcaagg gcctggagtg gatgggcatt attgatccta ctgattctta tactgttat | 180 |
| tctccttctt ttcagggtca ggtgaccatc agcgccgaca agagcatcag caccgcctac | 240 |
| ctgcagtgga gcagcctgaa ggccagcgac accgccatgt actactgcgc ccggtacatg | 300 |
| atgagggct tcgaccactg gggtcagggc accctggtga ccgtcagctc agctagcacc | 360 |

```
aagggcccca gcgtgttccc cctggccccc agcagcaaga gcacctccgg cggcacagcc    420
gccctgggct gcctggtgaa ggactacttc cccgagcccg tgaccgtgtc ctggaacagc    480
ggagccctga ccagcggcgt gcacaccttc ccgccgtgc tgcagagcag cggcctgtac    540
agcctgtcca gcgtggtgac agtgcccagc agcagcctgg gcacccagac ctacatctgc    600
aacgtgaacc acaagcccag caacaccaag gtggacaaga gagtggagcc caagagctgc    660
gacaagaccc acacctgccc ccctgccca gccccgaag ctgcaggcgg cccttccgtg    720
ttcctgttcc cccccaagcc caaggacacc ctgatgatca gcaggacccc cgaggtgacc    780
tgcgtggtgg tggacgtgag ccacgaggac ccagaggtga agttcaactg gtacgtggac    840
ggcgtggagg tgcacaacgc caagaccaag cccagagagg agcagtacaa cagcacctac    900
agggtggtgt ccgtgctgac cgtgctgcac caggactggc tgaacggcaa agaatacaag    960
tgcaaggtct ccaacaaggc cctgcctgcc cccatcgaaa agaccatcag caaggccaag   1020
ggccagccac gggagcccca ggtgtacacc ctgcccccctt ctcggggagga gatgaccaag   1080
aaccaggtgt ccctgacctg tctggtgaag ggcttctacc ccagcgacat cgccgtggag   1140
tgggagagca acggccagcc cgagaacaac tacaagacca ccccccccagt gctggacagc   1200
gacggcagct tcttcctgta cagcaagctg accgtggaca gagcaggtg gcagcagggc   1260
aacgtgttca gctgcagcgt gatgcacgag gccctgcaca accactacac ccagaagagc   1320
ctgagcctgt cacccggcaa g                                            1341
```

<210> SEQ ID NO 101
<211> LENGTH: 10
<212> TYPE: PRT
<213> ORGANISM: homo sapiens

<400> SEQUENCE: 101

Ser Thr Trp Asp Ile Glu Pro Thr Tyr Val
1               5                   10

<210> SEQ ID NO 102
<211> LENGTH: 107
<212> TYPE: PRT
<213> ORGANISM: homo sapiens

<400> SEQUENCE: 102

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Trp Asp Ile Glu Pro Thr Tyr
                85                  90                  95

Val Phe Gly Gly Gly Thr Lys Leu Thr Val Leu
            100                 105

<210> SEQ ID NO 103
<211> LENGTH: 213
<212> TYPE: PRT
<213> ORGANISM: homo sapiens -continued

<400> SEQUENCE: 103

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65              70                  75                  80

Asp Glu Ala Asp Tyr Tyr Cys Ser Thr Trp Asp Ile Glu Pro Thr Tyr
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 104
<211> LENGTH: 321
<212> TYPE: DNA
<213> ORGANISM: homo sapiens

<400> SEQUENCE: 104
agttacgaac tgacccagcc gccttcagtg agcgttgcac caggtcagac cgcgcgtatc      60
tcgtgtagcg gcgataatat tggtaattct tatgttcatt ggtaccagca gaaacccggg     120
caggcgccag ttcttgtgat ttataaggat aatgatcgtc cctcaggcat cccggaacgc     180
tttagcggat ccaacagcgg caacaccgcg accctgacca ttagcggcac tcaggcggaa     240
gacgaagcgg attattattg ctctacttgg gatattgagc ctacttatgt gtttggcggc     300
ggcacgaagt taaccgtcct a                                               321

<210> SEQ ID NO 105
<211> LENGTH: 639
<212> TYPE: DNA
<213> ORGANISM: homo sapiens

<400> SEQUENCE: 105
agttacgaac tgacccagcc gccttcagtg agcgttgcac caggtcagac cgcgcgtatc      60
tcgtgtagcg gcgataatat tggtaattct tatgttcatt ggtaccagca gaaacccggg     120
caggcgccag ttcttgtgat ttataaggat aatgatcgtc cctcaggcat cccggaacgc     180
tttagcggat ccaacagcgg caacaccgcg accctgacca ttagcggcac tcaggcggaa     240

```
gacgaagcgg attattattg ctctacttgg gatattgagc ctacttatgt gtttggcggc    300
ggcacgaagt taaccgtcct aggtcagccc aaggctgccc cctcggtcac tctgttcccg    360
ccctcctctg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cccctccaa acaaagcaac aacaagtacg cggccagcag ctatctgagc    540
ctgacgcctg agcagtggaa gtcccacaga agctacagct gccaggtcac gcatgaaggg    600
agcaccgtgg agaagacagt ggcccctaca gaatgttca                          639

<210> SEQ ID NO 106
<211> LENGTH: 639
<212> TYPE: DNA
<213> ORGANISM: homo sapiens

<400> SEQUENCE: 106
agctacgagc tgacccagcc ccccagcgtg agcgtggccc caggccagac cgccaggatc     60
agctgcagcg gcgacaatat cggcaacagc tacgtgcact ggtatcagca gaagcccggc    120
caggcccccg tgctggtgat ctacaaggac aacgacaggc ccagcggcat ccccgagagg    180
ttcagcggca gcaactccgg caacaccgcc accctgacaa tcagcggcac ccaggccgag    240
gacgaggccg actactactg ctctacttgg gatattgagc ctacttatgt gttcggcgga    300
gggaccaagc tgaccgtgct ggccagcct aaggctgccc ccagcgtgac cctgttcccc    360 ccagcagcg aggagctgca ggccaacaag gccaccctgg tgtgcctgat cagcgacttc    420
tacccaggcg ccgtgaccgt ggcctggaag gccgacagca gccccgtgaa ggccggcgtg    480
gagaccacca ccccccagcaa gcagagcaac aacaagtacg ccgccagcag ctacctgagc    540
ctgacccccg agcagtggaa gagccacagg tcctacagct gccaggtgac ccacgagggc    600
agcaccgtgg aaaagaccgt ggccccaacc gagtgcagc                          639

<210> SEQ ID NO 107
<211> LENGTH: 17
<212> TYPE: PRT
<213> ORGANISM: homo sapiens

<400> SEQUENCE: 107

Ile Ile Asp Pro Gln Asp Ser Tyr Thr Glu Tyr Ser Pro Ser Phe Gln
1               5                  10                  15

Gly

<210> SEQ ID NO 108
<211> LENGTH: 116
<212> TYPE: PRT
<213> ORGANISM: homo sapiens

<400> SEQUENCE: 108

Glu Val Gln Leu Val Gln Ser Gly Ala Glu Val Lys Lys Pro Gly Glu
1               5                  10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Gln Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80
```

-continued

```
Gln Trp Ser Ser Leu Lys Ala Ser Asp Thr Ala Met Tyr Tyr Cys Ala
                85                  90                  95
Arg Tyr Glu Tyr Gly Gly Phe Asp Ile Trp Gly Gln Gly Thr Leu Val
            100                 105                 110
Thr Val Ser Ser
        115

<210> SEQ ID NO 109
<211> LENGTH: 446
<212> TYPE: PRT
<213> ORGANISM: homo sapiens

<400> SEQUENCE: 109

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Asn Tyr
            20                  25                  30
Ile Ser Trp Val Arg Gln Met Pro Gly Lys Gly Leu Glu Trp Met Gly
        35                  40                  45
Ile Ile Asp Pro Gln Asp Ser Tyr Thr Glu Tyr Ser Pro Ser Phe Gln
50                  55                  60
Gly Gln Val Thr Ile Ser Ala Asp Lys Ser Ile Ser Thr Ala Tyr Leu
65                  70                  75                  80
Gln Trp Ser Ser Leu Lys Ala Ser Asp Thr Ala Met Tyr Tyr Cys Ala
                85                  90                  95
Arg Tyr Glu Tyr Gly Gly Phe Asp Ile Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445
```

<210> SEQ ID NO 110
<211> LENGTH: 348
<212> TYPE: DNA
<213> ORGANISM: homo sapiens

<400> SEQUENCE: 110

```
gaggtgcaat tggttcagag cggcgcggaa gtgaaaaaac cgggcgaaag cctgaaaatt    60
agctgcaaag gttccggata ttcctttact aattatattt cttgggtgcg ccagatgcct   120
gggaagggtc tcgagtggat gggcattatt gatcctcagg attcttatac tgagtattct   180
ccttcttttc agggtcaggt caccattagc gcggataaaa gcattagcac cgcgtatctt   240
caatggagca gcctgaaagc gagcgatacg ccatgtatt attgcgcgcg ttatgagtat   300
ggtggttttg atatttgggg ccaaggcacc ctggtgacgg ttagctca                348
```

<210> SEQ ID NO 111
<211> LENGTH: 1338
<212> TYPE: DNA
<213> ORGANISM: homo sapiens

<400> SEQUENCE: 111

```
gaggtgcaat tggttcagag cggcgcggaa gtgaaaaaac cgggcgaaag cctgaaaatt    60
agctgcaaag gttccggata ttcctttact aattatattt cttgggtgcg ccagatgcct   120
gggaagggtc tcgagtggat gggcattatt gatcctcagg attcttatac tgagtattct   180
ccttcttttc agggtcaggt caccattagc gcggataaaa gcattagcac cgcgtatctt   240
caatggagca gcctgaaagc gagcgatacg ccatgtatt attgcgcgcg ttatgagtat   300
ggtggttttg atatttgggg ccaaggcacc ctggtgacgg ttagctcagc ctccaccaag   360
ggtccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagagag ttgagcccaa atcttgtgac   660
aaaactcaca catgcccacc gtgcccagca cctgaagcag cggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgg   900
gtggtcagcg tcctcaccgt cctgcaccag gactggctga atggcaagga gtacaagtgc   960
```

-continued

```
aaggtctcca acaaagccct cccagccccc atcgagaaaa ccatctccaa agccaaaggg    1020
cagccccgag aaccacaggt gtacaccctg cccccatccc gggaggagat gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                 1338
```

<210> SEQ ID NO 112
<211> LENGTH: 1338
<212> TYPE: DNA
<213> ORGANISM: homo sapiens

<400> SEQUENCE: 112

```
gaggtgcagc tggtgcagag cggagccgag gtgaaaaagc ccggtgagag cctgaagatc      60
agctgcaagg gcagcggcta cagcttcacc aactacatca gctgggtgcg gcagatgccc     120
ggcaagggcc tggagtggat gggcatcatc gaccccaggg acagctacac cgagtacagc     180
cccagcttcc agggccaggt gaccatcagc gccgacaaga gcatcagcac cgcctacctg     240
cagtggagca gcctgaaggc cagcgacacc gccatgtact actgcgccag atacgagtac     300
ggcggcttcg acatctgggg ccagggcacc ctggtgaccg tcagctcagc tagcaccaag     360
ggccccagcg tgttcccccT ggcccccagc agcaagagca cctccggcgg cacagccgcc     420
ctgggctgcc tggtgaagga ctacttcccc gagcccgtga ccgtgtcctg aacagcggcgga    480 gccctgacca gcggcgtgca caccttcccc gccgtgctgc agagcagcgg cctgtacagc     540
ctgtccagcg tggtgacagt gcccagcagc agcctgggca cccagaccta catctgcaac     600
gtgaaccaca gcccagcaa caccaaggtg gacaagagag tggagcccaa gagctgcgac      660
aagacccaca cctgcccccc ctgcccagcc cccgaagctg caggcggccc ttccgtgttc     720
ctgttccccc ccaagcccaa ggacaccctg atgatcagca ggacccccga ggtgacctgc     780
gtggtggtgg acgtgagcca cgaggaccca gaggtgaagt tcaactggta cgtggacggc     840
gtggaggtgc acaacgccaa gaccaagccc agagaggagc agtacaacag cacctacagg     900
gtggtgtccg tgctgaccgt gctgcaccag gactggctga acggcaaaga atacaagtgc     960
aaggtctcca caaggccct gcctgccccc atcgaaaaga ccatcagcaa ggccaagggc     1020
cagccacggg agcccaggt gtacaccctg cccccttctc gggaggagat gaccaagaac     1080
caggtgtccc tgacctgtct ggtgaagggc ttctacccca gcgacatcgc cgtggagtgg    1140
gagagcaacg gccagcccga gaacaactac aagaccaccc cccagtgct ggacagcgac     1200 ggcagcttct tcctgtacag caagctgacc gtggacaaga gcaggtggca gcagggcaac    1260
gtgttcagct gcagcgtgat gcacgaggcc ctgcacaacc actacaccca gaagagcctg    1320
agcctgtcac ccggcaag                                                 1338
```

<210> SEQ ID NO 113
<211> LENGTH: 17
<212> TYPE: PRT
<213> ORGANISM: homo sapiens

<400> SEQUENCE: 113

```
Ile Ile Asp Pro Glu Asp Ser His Thr Glu Tyr Ser Pro Ser Phe Gln
1               5                   10                  15
```

Gly

<210> SEQ ID NO 114
<211> LENGTH: 116
<212> TYPE: PRT
<213> ORGANISM: homo sapiens

<400> SEQUENCE: 114

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Glu Asp Ser His Thr Glu Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
            115

<210> SEQ ID NO 115
<211> LENGTH: 446
<212> TYPE: PRT
<213> ORGANISM: homo sapiens

<400> SEQUENCE: 115

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Glu Asp Ser His Thr Glu Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 116
<211> LENGTH: 348
<212> TYPE: DNA
<213> ORGANISM: homo sapiens

<400> SEQUENCE: 116
gaggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatt gatcctgagg attctcatac tgagtattct     180
ccttcttttc agggtcaggt gaccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctca                  348

<210> SEQ ID NO 117
<211> LENGTH: 1338
<212> TYPE: DNA
<213> ORGANISM: homo sapiens

<400> SEQUENCE: 117
gaggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatt gatcctgagg attctcatac tgagtattct     180

```
ccttcttttc agggtcaggt gaccattagc gcggataaaa gcattagcac cgcgtatctt      240
caatggagca gcctgaaagc gagcgatacg gccatgtatt attgcgcgcg ttatgagtat      300
ggtggttttg atatttgggg ccaaggcacc ctggtgacgg ttagctcagc ctccaccaag      360
ggtccatcgg tcttcccccct ggcacccctcc tccaagagca cctctggggg cacagcggcc      420
ctgggctgcc tggtcaagga ctacttcccc gaaccggtga cggtgtcgtg aactcaggc      480 gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagagag ttgagcccaa atcttgtgac      660
aaaactcaca catgcccacc gtgcccagca cctgaagcag cggggggacc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgg      900
gtggtcagcg tcctcaccgt cctgcaccag gactggctga atggcaagga gtacaagtgc      960
aaggtctcca caaagccct cccagccccc atcgagaaaa ccatctccaa agccaaaggg     1020
cagccccgag aaccacaggt gtacaccctg cccccatccc gggaggagat gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct cctctacag caagctcacc gtggacaaga gcaggtggca gcaggggaac     1260
gtcttctcat gctccgtgat gcatgaggct ctgcacaacc actacacgca gaagagcctc     1320
tccctgtctc cgggtaaa                                                   1338

<210> SEQ ID NO 118
<211> LENGTH: 1338
<212> TYPE: DNA
<213> ORGANISM: homo sapiens

<400> SEQUENCE: 118
gaggtgcagc tggtgcagag cggagccgag gtgaaaaagc ccggtgagag cctgaagatc       60
agctgcaagg gcagcggcta cagcttcacc aactacatca gctgggtgcg gcagatgccc      120
ggcaagggcc tggagtggat gggcatcatc gaccccgagg acagccctac cgagtacagc      180
cccagcttcc agggccaggt gaccatcagc gccgacaaga gcatcagcac cgcctacctg      240
cagtggagca gcctgaaggc cagcgacacc gccatgtact actgcgccag atacgagtac      300
ggcggcttcg acatctgggg ccagggcacc ctggtgaccg tcagctcagc tagcaccaag      360
ggccccagcg tgttcccccct ggcccccagc agcaagagca cctccggcgg cacagccgcc      420
ctgggctgcc tggtcaagga ctacttcccc gagcccgtga ccgtgtcctg aacagcgga      480 gccctgacca gcggcgtgca caccttcccc gccgtgctgc agagcagcgg cctgtacagc      540
ctgtccagcg tggtgacagt gccccagcagc agcctgggca cccagaccta catctgcaac      600
gtgaaccaca gcccagcaa caccaaggtg gacaagagag tggagcccaa gagctgcgac      660
aagacccaca cctgcccccc ctgcccagcc ccgaagctg caggcggccc ttccgtgttc      720
ctgttccccc caagcccaa ggacaccctg atgatcagca ggaccccga ggtgacctgc      780 gtggtggtgg acgtgagcca cgaggaccca gaggtgaagt tcaactggta cgtggacggc      840
gtggaggtgc acaacgccaa gaccaagccc agagaggagc agtacaacag cacctacagg      900
gtggtgtccg tgctgaccgt gctgcaccag gactggctga acggcaaaga atacaagtgc      960
```

```
aaggtctcca acaaggccct gcctgccccc atcgaaaaga ccatcagcaa ggccaagggc    1020
cagccacggg agccccaggt gtacaccctg ccccctctc gggaggagat gaccaagaac    1080
caggtgtccc tgacctgtct ggtgaagggc ttctacccca gcgacatcgc cgtggagtgg    1140
gagagcaacg gccagcccga gaacaactac aagaccaccc ccccagtgct ggacagcgac    1200
ggcagcttct tcctgtacag caagctgacc gtggacaaga gcaggtggca gcagggcaac    1260
gtgttcagct gcagcgtgat gcacgaggcc ctgcacaacc actacaccca gaagagcctg    1320
agcctgtcac ccggcaag                                                 1338
```

<210> SEQ ID NO 119
<211> LENGTH: 17
<212> TYPE: PRT
<213> ORGANISM: homo sapiens

<400> SEQUENCE: 119

Asn Ile Gly Pro Phe Phe Gly Ile Ala Asn Tyr Ala Gln Lys Phe Gln
1               5                   10                  15

Gly

<210> SEQ ID NO 120
<211> LENGTH: 11
<212> TYPE: PRT
<213> ORGANISM: homo sapiens

<400> SEQUENCE: 120

Gln Thr Tyr Asp Asp Gly Ser Thr Ala Glu Val
1               5                   10

<210> SEQ ID NO 121
<211> LENGTH: 116
<212> TYPE: PRT
<213> ORGANISM: homo sapiens

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Asn Ile Gly Pro Phe Phe Gly Ile Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
        115

<210> SEQ ID NO 122
<211> LENGTH: 108
<212> TYPE: PRT
<213> ORGANISM: homo sapiens

<400> SEQUENCE: 122

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
                20                  25                  30

Tyr Trp Tyr Gln Gln Lys Pro Gly Gln Ala Pro Val Leu Val Ile Tyr
            35                  40                  45

Asp Asp Ser Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Asp Gly Ser Thr Ala
                85                  90                  95

Glu Val Phe Gly Gly Gly Thr Lys Leu Thr Val Leu
                100                 105

<210> SEQ ID NO 123
<211> LENGTH: 442
<212> TYPE: PRT
<213> ORGANISM: homo sapiens

<400> SEQUENCE: 123

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Asn Ile Gly Pro Phe Phe Gly Ile Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
                195                 200                 205

Lys Val Asp Lys Thr Val Glu Arg Lys Cys Cys Val Glu Cys Pro Pro
            210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

-continued

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 124
<211> LENGTH: 214
<212> TYPE: PRT
<213> ORGANISM: homo sapiens

<400> SEQUENCE: 124

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Asp Gly Ser Thr Ala
                85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 125
<211> LENGTH: 348
<212> TYPE: DNA
<213> ORGANISM: homo sapiens

<400> SEQUENCE: 125

```
caggtgcaat tggttcagtc tggcgcggaa gtgaaaaaac cgggcagcag cgtgaaagtg      60
agctgcaaag cctccggagg cacttttttct tcttatgcca tttcttgggt gcgccaagcc    120
cctgggcagg gtctcgagtg gatgggcaat atcggtccgt ttttttggcat tgcgaattac    180
gcgcagaagt ttcagggccg ggtgaccatt accgcggatg aaagcaccag caccgcgtat    240
atggaactga gcagcctgcg tagcgaagat acggccgtgt attattgcgc gcgtgatact    300
ccttattttg attattgggg ccaaggcacc ctggtgacgg ttagctca                 348
```

<210> SEQ ID NO 126
<211> LENGTH: 324
<212> TYPE: DNA
<213> ORGANISM: homo sapiens

<400> SEQUENCE: 126

```
gatatcgaac tgacccagcc gccttcagtg agcgttgcac caggtcagac cgcgcgtatc     60
tcgtgtagcg gcgattctat tcctaattat tatgtttatt ggtaccagca gaaacccggg    120
caggcgccag ttcttgtgat ttatgatgat tctaatcgtc cctcaggcat cccggaacgc    180
tttagcggat ccaacagcgg caacaccgcg accctgacca ttagcggcac tcaggcggaa    240
gacgaagcgg attattattg ccagacttat gatgatggtt ctactgctga ggtgtttggc    300
ggcggcacga gttaaccgt tctt                                             324
```

<210> SEQ ID NO 127
<211> LENGTH: 1326
<212> TYPE: DNA
<213> ORGANISM: homo sapiens

<400> SEQUENCE: 127

```
caggtgcaat tggttcagtc tggcgcggaa gtgaaaaaac cgggcagcag cgtgaaagtg      60
agctgcaaag cctccggagg cacttttttct tcttatgcca tttcttgggt gcgccaagcc    120
cctgggcagg gtctcgagtg gatgggcaat atcggtccgt ttttttggcat tgcgaattac    180
gcgcagaagt ttcagggccg ggtgaccatt accgcggatg aaagcaccag caccgcgtat    240
atggaactga gcagcctgcg tagcgaagat acggccgtgt attattgcgc gcgtgatact    300
ccttattttg attattgggg ccaaggcacc ctggtgacgg ttagctcagc ttccaccaag    360
ggcccagcg tgttcccct ggccccctgc agcagaagca ccagcgagag cacagccgcc      420
ctgggctgcc tggtgaagga ctacttcccc gagcccgtga ccgtgagctg aacagcgga    480
gccctgacca gcggcgtgca caccttcccc gccgtgctgc agagcagcgg cctgtacagc    540
ctgagcagcg tggtgaccgt gcccagcagc aacttcggca cccagaccta cacctgcaac    600
gtggaccaca agcccagcaa caccaaggtg gacaagaccg tggagcggaa gtgctgcgtg    660
gagtgccccc cctgccctgc cctcctgtg gccggaccct ccgtgttcct gttcccccc    720
aagcccaagg acaccctgat gatcagccgg accccgagg tgacctgcgt ggtggtggac    780
gtgagccacg aggaccccga ggtgcagttc aactggtacg tggacggcgt ggaggtgcac    840
aacgccaaga ccaagccccg ggaggaacag ttcaacagca ccttccgggt ggtgtccgtg    900
ctgaccgtgg tgcaccagga ctggctgaac ggcaaagaat acaagtgcaa ggtgtccaac    960
```

```
aagggcctgc ctgcccccat cgagaaaacc atcagcaaga caaagggcca gcccagggaa    1020
ccccaggtgt acaccctgcc ccccagccgg gaggaaatga ccaagaacca ggtgtccctg    1080
acctgtctgg tgaagggctt ctaccccagc gacatcgccg tggagtggga gagcaacggc    1140
cagcccgaga caactacaa gaccaccccc cccatgctgg acagcgacgg cagcttcttc    1200
ctgtacagca agctgacagt ggacaagagc cggtggcagc agggcaacgt gttcagctgc    1260
agcgtgatgc acgaggccct gcacaaccac tacacccaga gagcctgag cctgtccccc    1320 ggcaaa                                                              1326
```

<210> SEQ ID NO 128
<211> LENGTH: 642
<212> TYPE: DNA
<213> ORGANISM: homo sapiens
<400> SEQUENCE: 128

```
gatatcgaac tgacccagcc gccttcagtg agcgttgcac caggtcagac cgcgcgtatc      60
tcgtgtagcg gcgattctat tcctaattat tatgtttatt ggtaccagca gaaacccggg     120
caggcgccag ttcttgtgat ttatgatgat tctaatcgtc cctcaggcat cccggaacgc     180
tttagcggat ccaacagcgg caacaccgcg accctgacca ttagcggcac tcaggcggaa     240
gacgaagcgg attattattg ccagacttat gatgatggtt ctactgctga ggtgtttggc     300
ggcggcacga agttaaccgt tcttggtcag cccaaggctg cccccctcggt cactctgttc     360 ccgcccctcct ctgaggagct tcaagccaac aaggccacac tggtgtgtct cataagtgac     420
ttctacccgg gagccgtgac agtggcctgg aaggcagata gcagcccgt caaggcggga     480 gtggagacca ccacaccctc caaacaaagc aacaacaagt acgcggccag cagctatctg     540
agcctgacgc ctgagcagtg gaagtcccac agaagctaca gctgccaggt cacgcatgaa     600
gggagcaccg tggagaagac agtggcccct acagaatgtt ca                       642
```

<210> SEQ ID NO 129
<211> LENGTH: 1326
<212> TYPE: DNA
<213> ORGANISM: homo sapiens
<400> SEQUENCE: 129

```
caggtgcagc tggtgcagtc cggcgccgag gtgaagaagc ccggctcctc cgtgaaggtg      60
tcctgcaagg cctccggcgg caccttctcc tcctacgcca tctcctgggt gcggcaggcc     120
cccggccagg gcctggagtg gatgggcaac atcgcccct tcttcggcat cgccaactac     180
gcccagaagt tccagggccg ggtgaccatc accgccgacg agtccacctc caccgcctac     240
atggagctgt cctccctgcg gtccgaggac accgccgtgt actactgcgc ccgggacacc     300
ccctacttcg actactgggg ccagggcacc ctggtgaccg tgtcctccgc ctccaccaag     360 ggccccctccg tgttccccct ggccccctgc tccccggtcca cctccgagtc caccgccgcc     420
ctgggctgcc tggtgaagga ctacttcccc gagcccgtga ccgtgtcctg gaactccggc     480
gccctgacct ccggcgtgca caccttcccc gccgtgctgc agtcctccgg cctgtactcc     540
ctgtcctccg tggtgaccgt gccctcctcc aacttcggca cccagaccta cacctgcaac     600
gtggaccaca gccctccaa caccaaggtg gacaagaccg tggagcggaa gtgctgcgtg     660
gagtgccccc cctgccccgc ccccccccgtg gccggcccct ccgtgttcct gttccccccc     720
aagcccaagg acaccctgat gatctcccgg acccccgagg tgacctgcgt ggtggtggac     780
gtgtcccacg aggaccccga ggtgcagttc aactggtacg tggacggcgt ggaggtgcac     840
```

```
aacgccaaga ccaagccccg ggaggagcag ttcaactcca ccttccgggt ggtgtccgtg    900
ctgaccgtgg tgcaccagga ctggctgaac ggcaaggagt acaagtgcaa ggtgtccaac    960
aagggcctgc ccgcccccat cgagaagacc atctccaaga ccaagggcca gccccgggag   1020
ccccaggtgt acaccctgcc ccctcccgg gaggagatga ccaagaacca ggtgtccctg    1080
acctgcctgg tgaagggctt ctaccccctcc gacatcgccg tggagtggga gtccaacggc   1140
cagcccgaga caactacaa gaccaccccc cccatgctgg actccgacgg ctccttcttc    1200
ctgtactcca agctgaccgt ggacaagtcc cggtggcagc agggcaacgt gttctcctgc   1260
tccgtgatgc acgaggccct gcacaaccac tacacccaga gtccctgtc cctgtccccc    1320 ggcaag                                                                1326

<210> SEQ ID NO 130
<211> LENGTH: 642
<212> TYPE: DNA
<213> ORGANISM: homo sapiens

<400> SEQUENCE: 130
gacatcgagc tgacccagcc cccctccgtg tccgtggccc ccggccagac cgcccggatc     60
tcctgctccg gcgactccat ccccaactac tacgtgtact ggtaccagca gaagcccggc    120
caggcccccg tgctggtgat ctacgacgac tccaaccggc cctccggcat ccccgagcgg    180
ttctccggct ccaactccgg caacaccgcc accctgacca tctccggcac ccaggccgag    240
gacgaggccg actactactg ccagacctac gacgacggct ccaccgccga ggtgttcggc    300
ggcggcacca agctgaccgt gctgggccag cctaaggctg cccccagcgt gaccctgttc    360
cccccagcag cgaggagct gcaggccaac aaggccaccc tggtgtgcct gatcagcgac    420
ttctacccag cgccgtgac cgtggcctgg aaggccgaca gcagcccgt gaaggccggc    480 gtggagacca ccaccccag caagcagagc aacaacaagt acgccgccag cagctacctg    540
agcctgaccc ccgagcagtg gaagagccac aggtcctaca gctgccaggt gacccacgag    600
ggcagcaccg tggaaaagac cgtggcccca accgagtgca gc                       642

<210> SEQ ID NO 131
<211> LENGTH: 5
<212> TYPE: PRT
<213> ORGANISM: homo sapiens

<400> SEQUENCE: 131

Ser Tyr Trp Ile Ser
1               5

<210> SEQ ID NO 132
<211> LENGTH: 17
<212> TYPE: PRT
<213> ORGANISM: homo sapiens

<400> SEQUENCE: 132

Ile Ile Asp Pro Asp Asp Ser Lys Thr Asn Tyr Ser Pro Ser Phe Gln
1               5                   10                  15
Gly

<210> SEQ ID NO 133
<211> LENGTH: 8
<212> TYPE: PRT
<213> ORGANISM: homo sapiens

<400> SEQUENCE: 133
```

Arg Ser Tyr Tyr Pro Met Asp Tyr
1               5

<210> SEQ ID NO 134
<211> LENGTH: 15
<212> TYPE: PRT
<213> ORGANISM: homo sapiens

<400> SEQUENCE: 134

Thr Gly Thr Ser Ser Asp Val Val Gly Val Tyr Asn Phe Val Ser
1               5                   10                  15

<210> SEQ ID NO 135
<211> LENGTH: 7
<212> TYPE: PRT
<213> ORGANISM: homo sapiens

<400> SEQUENCE: 135

Tyr Val Asp Asn Arg Pro Ser
1               5

<210> SEQ ID NO 136
<211> LENGTH: 11
<212> TYPE: PRT
<213> ORGANISM: homo sapiens

<400> SEQUENCE: 136

Gln Ser Phe Asp Gly Phe Gly Ile Asp Met Val
1               5                   10

<210> SEQ ID NO 137
<211> LENGTH: 117
<212> TYPE: PRT
<213> ORGANISM: homo sapiens

<400> SEQUENCE: 137

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Asp Asp Ser Lys Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ser Tyr Tyr Pro Met Asp Tyr Trp Gly Gln Gly Thr Leu
            100                 105                 110

Val Thr Val Ser Ser
            115

<210> SEQ ID NO 138
<211> LENGTH: 112
<212> TYPE: PRT
<213> ORGANISM: homo sapiens

<400> SEQUENCE: 138

Asp Ile Ala Leu Thr Gln Pro Ala Ser Val Ser Gly Ser Pro Gly Gln
1               5                   10                  15

-continued

Ser Ile Thr Ile Ser Cys Thr Gly Thr Ser Ser Asp Val Gly Val
              20                  25                  30

Tyr Asn Phe Val Ser Trp Tyr Gln Gln His Pro Gly Lys Ala Pro Lys
         35                  40                  45

Leu Met Ile Tyr Tyr Val Asp Asn Arg Pro Ser Gly Val Ser Asn Arg
 50                  55                  60

Phe Ser Gly Ser Lys Ser Gly Asn Thr Ala Ser Leu Thr Ile Ser Gly
 65                  70                  75                  80

Leu Gln Ala Glu Asp Glu Ala Asp Tyr Tyr Cys Gln Ser Phe Asp Gly
              85                  90                  95

Phe Gly Ile Asp Met Val Phe Gly Gly Gly Thr Lys Leu Thr Val Leu
            100                 105                 110

<210> SEQ ID NO 139
<211> LENGTH: 220
<212> TYPE: PRT
<213> ORGANISM: homo sapiens
<220> FEATURE:
<221> NAME/KEY: MISC_FEATURE
<222> LOCATION: (220)..(220)
<223> OTHER INFORMATION: X can be C, EF, or CEF

<400> SEQUENCE: 139

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
              20                  25                  30

Trp Ile Ser Trp Val Arg Gln Met Pro Gly Lys Gly Leu Glu Trp Met
         35                  40                  45

Gly Ile Ile Asp Pro Asp Asp Ser Lys Thr Asn Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
              85                  90                  95

Ala Arg Arg Ser Tyr Tyr Pro Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Xaa
    210                 215                 220

<210> SEQ ID NO 140
<211> LENGTH: 217
<212> TYPE: PRT
<213> ORGANISM: homo sapiens
<220> FEATURE:
<221> NAME/KEY: MISC_FEATURE
<222> LOCATION: (217)..(217)

<223> OTHER INFORMATION: X can be CS or A

<400> SEQUENCE: 140

```
Asp Ile Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Val Gly Val
            20                  25                  30
Tyr Asn Phe Val Ser Trp Tyr Gln Gln His Pro Gly Lys Ala Pro Lys
        35                  40                  45
Leu Met Ile Tyr Tyr Val Asp Asn Arg Pro Ser Gly Val Ser Asn Arg
    50                  55                  60
Phe Ser Gly Ser Lys Ser Gly Asn Thr Ala Ser Leu Thr Ile Ser Gly
65                  70                  75                  80
Leu Gln Ala Glu Asp Glu Ala Asp Tyr Tyr Cys Gln Ser Phe Asp Gly
                85                  90                  95
Phe Gly Ile Asp Met Val Phe Gly Gly Gly Thr Lys Leu Thr Val Leu
            100                 105                 110
Gly Gln Pro Lys Ala Ala Pro Ser Val Thr Leu Phe Pro Pro Ser Ser
        115                 120                 125
Glu Glu Leu Gln Ala Asn Lys Ala Thr Leu Val Cys Leu Ile Ser Asp
    130                 135                 140
Phe Tyr Pro Gly Ala Val Thr Val Ala Trp Lys Ala Asp Ser Ser Pro
145                 150                 155                 160
Val Lys Ala Gly Val Glu Thr Thr Pro Ser Lys Gln Ser Asn Asn
                165                 170                 175
Lys Tyr Ala Ala Ser Ser Tyr Leu Ser Leu Thr Pro Glu Gln Trp Lys
            180                 185                 190
Ser His Arg Ser Tyr Ser Cys Gln Val Thr His Glu Gly Ser Thr Val
        195                 200                 205
Glu Lys Thr Val Ala Pro Thr Glu Xaa
    210                 215
```

<210> SEQ ID NO 141
<211> LENGTH: 351
<212> TYPE: DNA
<213> ORGANISM: homo sapiens

<400> SEQUENCE: 141

```
caggtgcaat tggttcagag cggcgcggaa gtgaaaaaac cgggcgaaag cctgaaaatt    60
agctgcaaag gttccggata ttcctttact tcttattgga tttcttgggt gcgccagatg   120
cctgggaagg gtctcgagtg gatgggcatt atcgatccgg atgatagcaa gaccaattat   180
tctccgagct tcagggccag gtgaccatta gcgcggata aaagcattag caccgcgtat   240
cttcaatgga gcagcctgaa agcgagcgat acggccatgt attattgcgc gcgtcgttct   300
tattatccta tggattattg gggccaaggc accctggtga cggttagctc a             351
```

<210> SEQ ID NO 142
<211> LENGTH: 336
<212> TYPE: DNA
<213> ORGANISM: homo sapiens

<400> SEQUENCE: 142

```
gatatcgcac tgacccagcc agcttcagtg agcggctcac caggtcagag cattaccatc    60
tcgtgtacgg gtactagcag cgatgttgtt ggtgtttata attttgtgtc ttggtaccag   120
cagcatcccg ggaaggcgcc gaaacttatg atttattatg ttgataatcg tccctcaggc   180
```

```
gtgagcaacc gttttagcgg atccaaaagc ggcaacaccg cgagcctgac cattagcggc    240
ctgcaagcgg aagacgaagc ggattattat tgccagtctt ttgatggttt tggtattgat    300
atggtgtttg gcggcggcac gaagttaacc gttctt                              336
```

```
<210> SEQ ID NO 143
<211> LENGTH: 658
<212> TYPE: DNA
<213> ORGANISM: homo sapiens
<220> FEATURE:
<221> NAME/KEY: misc_feature
<222> LOCATION: (658)..(658)
<223> OTHER INFORMATION: n can be TGC, GAATTC, or TGCGAATTC

<400> SEQUENCE: 143
```

```
caggtgcaat tggttcagag cggcgcggaa gtgaaaaaac cgggcgaaag cctgaaaatt     60
agctgcaaag gttccggata ttcctttact tcttattgga tttcttgggt gcgccagatg    120
cctgggaagg gtctcgagtg gatgggcatt atcgatccgg atgatagcaa gaccaattat    180
tctccgagct ttcagggcca ggtgaccatt agcgcggata aaagcattag caccgcgtat    240
cttcaatgga gcagcctgaa agcgagcgat acggccatgt attattgcgc gcgtcgttct    300
tattatccta tggattattg gggccaaggc accctggtga cggttagctc agcgtcgacc    360
aaaggtccaa gcgtgtttcc gctggctccg agcagcaaaa gcaccagcgg cggcacggct    420
gccctgggct gcctggttaa agattatttc ccggaaccag tcaccgtgag ctggaacagc    480
ggggcgctga ccagcggcgt gcatacccttt ccggcggtgc tgcaaagcag cggcctgtat    540
agcctgagca gcgttgtgac cgtgccgagc agcagcttag gcactcagac ctatatttgc    600
aacgtgaacc ataaaccgag caacaccaaa gtggataaaa aagtggaacc gaaaagcn     658
```

```
<210> SEQ ID NO 144
<211> LENGTH: 649
<212> TYPE: DNA
<213> ORGANISM: homo sapiens
<220> FEATURE:
<221> NAME/KEY: misc_feature
<222> LOCATION: (649)..(649)
<223> OTHER INFORMATION: n can be TGCAGC or GCC

<400> SEQUENCE: 144
```

```
gatatcgcac tgacccagcc agcttcagtg agcggctcac caggtcagag cattaccatc     60
tcgtgtacgg gtactagcag cgatgttgtt ggtgtttata attttgtgtc ttggtaccag    120
cagcatcccg ggaaggcgcc gaaacttatg atttattatg ttgataatcg tccctcaggc    180
gtgagcaacc gttttagcgg atccaaaagc ggcaacaccg cgagcctgac cattagcggc    240
ctgcaagcgg aagacgaagc ggattattat tgccagtctt ttgatggttt tggtattgat    300
atggtgtttg gcggcggcac gaagttaacc gttcttggcc agccgaaagc cgcaccgagt    360
gtgacgctgt ttccgccgag cagcgaagaa ttgcaggcga caaagcgac cctggtgtgc    420 ctgattagcg acttttatcc gggagccgtg acagtggcct ggaaggcaga tagcagcccc    480
gtcaaggcgg gagtggagac caccacaccc tccaaacaaa gcaacaacaa gtacgcggcc    540
agcagctatc tgagcctgac gcctgagcag tggaagtccc acagaagcta cagctgccag    600
gtcacgcatg aggggagcac cgtggaaaaa accgttgcgc cgactgagn               649
```

```
<210> SEQ ID NO 145
<211> LENGTH: 5
<212> TYPE: PRT
<213> ORGANISM: homo sapiens
```

```
<400> SEQUENCE: 145

Ser Tyr Trp Ile Ala
1               5

<210> SEQ ID NO 146
<211> LENGTH: 17
<212> TYPE: PRT
<213> ORGANISM: homo sapiens

<400> SEQUENCE: 146

Ile Ile Tyr Pro Gly Asp Ser Asp Thr Asn Tyr Ser Pro Ser Phe Gln
1               5                   10                  15

Gly

<210> SEQ ID NO 147
<211> LENGTH: 8
<212> TYPE: PRT
<213> ORGANISM: homo sapiens

<400> SEQUENCE: 147

Ser Lys Tyr Gly Ser Phe Asp Tyr
1               5

<210> SEQ ID NO 148
<211> LENGTH: 14
<212> TYPE: PRT
<213> ORGANISM: homo sapiens

<400> SEQUENCE: 148

Thr Gly Thr Ser Ser Asp Val Gly Gly Tyr Asn Tyr Val Ser
1               5                   10

<210> SEQ ID NO 149
<211> LENGTH: 7
<212> TYPE: PRT
<213> ORGANISM: homo sapiens

<400> SEQUENCE: 149

Asn Val Asn Ser Arg Pro Ser
1               5

<210> SEQ ID NO 150
<211> LENGTH: 11
<212> TYPE: PRT
<213> ORGANISM: homo sapiens

<400> SEQUENCE: 150

Gln Ser Tyr Asp Asp Gly Gln Asp Asn Glu Val
1               5                   10

<210> SEQ ID NO 151
<211> LENGTH: 117
<212> TYPE: PRT
<213> ORGANISM: homo sapiens

<400> SEQUENCE: 151

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Asn Tyr Ser Pro Ser Phe
```

```
                50                   55                   60
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                     85                  90                  95

Ala Arg Ser Lys Tyr Gly Ser Phe Asp Tyr Trp Gly Gln Gly Thr Leu
                100                 105                 110

Val Thr Val Ser Ser
                115

<210> SEQ ID NO 152
<211> LENGTH: 111
<212> TYPE: PRT
<213> ORGANISM: homo sapiens

<400> SEQUENCE: 152

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
             35                  40                  45

Met Ile Tyr Asn Val Asn Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Asp Gly
                 85                  90                  95

Gln Asp Asn Glu Val Phe Gly Gly Gly Thr Lys Leu Thr Val Leu
                100                 105                 110

<210> SEQ ID NO 153
<211> LENGTH: 220
<212> TYPE: PRT
<213> ORGANISM: homo sapiens
<220> FEATURE:
<221> NAME/KEY: MISC_FEATURE
<222> LOCATION: (220)..(220)
<223> OTHER INFORMATION: X can be C, EF, or CEF

<400> SEQUENCE: 153

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Trp Met
             35                  40                  45

Gly Ile Ile Tyr Pro Gly Asp Ser Asp Thr Asn Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Lys Tyr Gly Ser Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
```

```
                    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Xaa
210                 215                 220

<210> SEQ ID NO 154
<211> LENGTH: 216
<212> TYPE: PRT
<213> ORGANISM: homo sapiens
<220> FEATURE:
<221> NAME/KEY: MISC_FEATURE
<222> LOCATION: (216)..(216)
<223> OTHER INFORMATION: X can be CS or A

<400> SEQUENCE: 154

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asn Val Asn Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Asp Gly
                85                  90                  95

Gln Asp Asn Glu Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Xaa
210                 215

<210> SEQ ID NO 155
<211> LENGTH: 351
<212> TYPE: DNA
<213> ORGANISM: homo sapiens

<400> SEQUENCE: 155
caggtgcaat tggttcagag cggcgcggaa gtgaaaaaac cgggcgaaag cctgaaaatt      60
```

-continued

```
agctgcaaag gttccggata ttcctttact tcttattgga ttgcttgggt gcgccagatg    120
cctgggaagg gtctcgagtg gatgggcatt atctatccgg gtgatagcga taccaattat    180
tctccgagct ttcagggcca ggtgaccatt agcgcggata aaagcattag caccgcgtat    240
cttcaatgga gcagcctgaa agcgagcgat acggccatgt attattgcgc gcgttctaag    300
tatggttctt tgattattg gggccaaggc accctggtga cggttagctc a             351
```

<210> SEQ ID NO 156
<211> LENGTH: 333
<212> TYPE: DNA
<213> ORGANISM: homo sapiens

<400> SEQUENCE: 156

```
gatatcgcac tgacccagcc agcttcagtg agcggctcac caggtcagag cattaccatc     60
tcgtgtacgg gtactagcag cgatgttggt ggttataatt atgtgtcttg gtaccagcag    120
catcccggga aggcgccgaa acttatgatt tataatgtta attctcgtcc ctcaggcgtg    180
agcaaccgtt ttagcggatc caaaagcggc aacaccgcga gcctgaccat tagcggcctg    240
caagcggaag acgaagcgga ttattattgc cagtcttatg atgatggtca ggataatgag    300
gtgtttggcg gcggcacgaa gttaaccgtt ctt                                 333
```

<210> SEQ ID NO 157
<211> LENGTH: 658
<212> TYPE: DNA
<213> ORGANISM: homo sapiens
<220> FEATURE:
<221> NAME/KEY: misc_feature
<222> LOCATION: (658)..(658)
<223> OTHER INFORMATION: n can be TGC, GAATTC, or TGCGAATTC

<400> SEQUENCE: 157

```
caggtgcaat tggttcagag cggcgcggaa gtgaaaaaac cgggcgaaag cctgaaaatt     60
agctgcaaag gttccggata ttcctttact tcttattgga ttgcttgggt gcgccagatg    120
cctgggaagg gtctcgagtg gatgggcatt atctatccgg gtgatagcga taccaattat    180
tctccgagct ttcagggcca ggtgaccatt agcgcggata aaagcattag caccgcgtat    240
cttcaatgga gcagcctgaa agcgagcgat acggccatgt attattgcgc gcgttctaag    300
tatggttctt tgattattg gggccaaggc accctggtga cggttagctc agcgtcgacc    360
aaaggtccaa gcgtgtttcc gctggctccg agcagcaaaa gcaccagcgg cggcacggct    420
gccctgggct gcctggttaa agattatttc ccggaaccag tcaccgtgag ctggaacagc    480
ggggcgctga ccagcggcgt gcataccttt ccggcggtgc tgcaaagcag cggcctgtat    540
agcctgagca gcgttgtgac cgtgccgagc agcagcttag gcactcagac ctatatttgc    600
aacgtgaacc ataaaccgag caacaccaaa gtggataaaa aagtggaacc gaaaagcn     658
```

<210> SEQ ID NO 158
<211> LENGTH: 646
<212> TYPE: DNA
<213> ORGANISM: homo sapiens
<220> FEATURE:
<221> NAME/KEY: misc_feature
<222> LOCATION: (646)..(646)
<223> OTHER INFORMATION: n can be TGCAGC or GCC

<400> SEQUENCE: 158

```
gatatcgcac tgacccagcc agcttcagtg agcggctcac caggtcagag cattaccatc     60
tcgtgtacgg gtactagcag cgatgttggt ggttataatt atgtgtcttg gtaccagcag    120
```

```
catcccggga aggcgccgaa acttatgatt tataatgtta attctcgtcc ctcaggcgtg    180
agcaaccgtt ttagcggatc caaaagcggc aacaccgcga gcctgaccat tagcggcctg    240
caagcggaag acgaagcgga ttattattgc cagtcttatg atgatggtca ggataatgag    300
gtgtttggcg gcggcacgaa gttaaccgtt cttggccagc cgaaagccgc accgagtgtg    360
acgctgtttc cgccgagcag cgaagaattg caggcgaaca aagcgaccct ggtgtgcctg    420
attagcgact tttatccggg agccgtgaca gtggcctgga aggcagatag cagccccgtc    480
aaggcgggag tggagaccac cacaccctcc aaacaaagca acaacaagta cgcggccagc    540
agctatctga gcctgacgcc tgagcagtgg aagtcccaca aagctacag ctgccaggtc      600 acgcatgagg ggagcaccgt ggaaaaaacc gttgcgccga ctgagn               646
```

<210> SEQ ID NO 159
<211> LENGTH: 5
<212> TYPE: PRT
<213> ORGANISM: homo sapiens

<400> SEQUENCE: 159

Ser Tyr Ala Met His
1               5

<210> SEQ ID NO 160
<211> LENGTH: 17
<212> TYPE: PRT
<213> ORGANISM: homo sapiens

<400> SEQUENCE: 160

Ala Ile Ser Ser Ser Gly Ser Ser Thr Tyr Tyr Ala Asp Ser Val Lys
1               5                   10                  15

Gly

<210> SEQ ID NO 161
<211> LENGTH: 7
<212> TYPE: PRT
<213> ORGANISM: homo sapiens

<400> SEQUENCE: 161

Glu Ser Trp Phe Leu Asp Leu
1               5

<210> SEQ ID NO 162
<211> LENGTH: 11
<212> TYPE: PRT
<213> ORGANISM: homo sapiens

<400> SEQUENCE: 162

Arg Ala Ser Gln Ser Ile Ser Asn Trp Leu Ala
1               5                   10

<210> SEQ ID NO 163
<211> LENGTH: 7
<212> TYPE: PRT
<213> ORGANISM: homo sapiens

<400> SEQUENCE: 163

Leu Ala Ser Ser Leu Gln Ser
1               5

<210> SEQ ID NO 164
<211> LENGTH: 9
<212> TYPE: PRT

<213> ORGANISM: homo sapiens

<400> SEQUENCE: 164

Gln Gln Tyr Tyr Asp Phe Ser Asp Thr
1               5

<210> SEQ ID NO 165
<211> LENGTH: 116
<212> TYPE: PRT
<213> ORGANISM: homo sapiens

<400> SEQUENCE: 165

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Trp Phe Leu Asp Leu Trp Gly Gln Gly Thr Leu Val
            100                 105                 110

Thr Val Ser Ser
        115

<210> SEQ ID NO 166
<211> LENGTH: 107
<212> TYPE: PRT
<213> ORGANISM: homo sapiens

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Asp Phe Ser Asp
                85                  90                  95

Thr Phe Gly Gln Gly Thr Lys Val Glu Ile Lys
            100                 105

<210> SEQ ID NO 167
<211> LENGTH: 219
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: X can be C, EF, or CEF

<400> SEQUENCE: 167

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Ser Tyr
             20                  25                  30

Ala Met His Trp Val Arg Gln Ala Pro Gly Lys Gly Leu Glu Trp Val
         35                  40                  45

Ser Ala Ile Ser Ser Ser Gly Ser Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ser Trp Phe Leu Asp Leu Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Xaa
    210                 215

<210> SEQ ID NO 168
<211> LENGTH: 214
<212> TYPE: PRT
<213> ORGANISM: homo sapiens
<220> FEATURE:
<221> NAME/KEY: MISC_FEATURE
<222> LOCATION: (214)..(214)
<223> OTHER INFORMATION: X can be C or A

<400> SEQUENCE: 168

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Trp
             20                  25                  30

Leu Ala Trp Tyr Gln Gln Lys Pro Gly Lys Ala Pro Lys Leu Leu Ile
         35                  40                  45

Tyr Leu Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Asp Phe Ser Asp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Xaa
    210

<210> SEQ ID NO 169
<211> LENGTH: 348
<212> TYPE: DNA
<213> ORGANISM: homo sapiens

<400> SEQUENCE: 169
caggtgcaat tggtggaaag cggcggcggc ctggtgcaac cgggcggcag cctgcgtctg     60
agctgcgcgg cctccggatt tacctttact tcttatgcta tgcattgggt gcgccaagcc    120
cctgggaagg gtctcgagtg ggtgagcgct atctcttctt ctggtagctc taccattat    180 gcggatagcg tgaaaggccg ttttaccatt tcacgtgata attcgaaaaa caccctgtat    240
ctgcaaatga acagcctgcg tgcggaagat acggccgtgt attattgcgc gcgtgagtct    300
tggtttcttg atctttgggg ccaaggcacc ctggtgacgg ttagctca                 348

<210> SEQ ID NO 170
<211> LENGTH: 321
<212> TYPE: DNA
<213> ORGANISM: homo sapiens

<400> SEQUENCE: 170
gatatccaga tgacccagag cccgtctagc ctgagcgcga gcgtgggtga tcgtgtgacc     60
attacctgca gcgagcca gtctatttct aattggctgg cttggtacca gcagaaacca    120
ggtaaagcac cgaaactatt aatttatctt gcttcttctt tgcaaagcgg ggtcccgtcc    180
cgttttagcg gctctggatc cggcactgat tttaccctga ccattagcag cctgcaacct    240
gaagactttg cggtttatta ttgccagcag tattatgatt tttctgatac ctttggccag    300
ggtacgaaag ttgaaattaa a                                              321

<210> SEQ ID NO 171
<211> LENGTH: 655
<212> TYPE: DNA
<213> ORGANISM: homo sapiens
<220> FEATURE:
<221> NAME/KEY: misc_feature
<222> LOCATION: (655)..(655)
<223> OTHER INFORMATION: n can be TGC, TAATTC, or TGCGAATTC

<400> SEQUENCE: 171
caggtgcaat tggtggaaag cggcggcggc ctggtgcaac cgggcggcag cctgcgtctg     60
agctgcgcgg cctccggatt tacctttact tcttatgcta tgcattgggt gcgccaagcc    120
cctgggaagg gtctcgagtg ggtgagcgct atctcttctt ctggtagctc taccattat    180 gcggatagcg tgaaaggccg ttttaccatt tcacgtgata attcgaaaaa caccctgtat    240
ctgcaaatga acagcctgcg tgcggaagat acggccgtgt attattgcgc gcgtgagtct    300
tggtttcttg atctttgggg ccaaggcacc ctggtgacgg ttagctcagc gtcgaccaaa    360
```

```
ggtccaagcg tgtttccgct ggctccgagc agcaaaagca ccagcggcgg cacggctgcc    420
ctgggctgcc tggttaaaga ttatttcccg gaaccagtca ccgtgagctg aacagcggg     480 gcgctgacca gcggcgtgca tacctttccg gcggtgctgc aaagcagcgg cctgtatagc    540
ctgagcagcg ttgtgaccgt gccgagcagc agcttaggca ctcagaccta tatttgcaac    600
gtgaaccata aaccgagcaa caccaaagtg gataaaaaag tggaaccgaa aagcn         655
```

```
<210> SEQ ID NO 172
<211> LENGTH: 640
<212> TYPE: DNA
<213> ORGANISM: homo sapiens
<220> FEATURE:
<221> NAME/KEY: misc_feature
<222> LOCATION: (640)..(640)
<223> OTHER INFORMATION: n can be TGC or GCC

<400> SEQUENCE: 172
gatatccaga tgacccagag cccgtctagc ctgagcgcga gcgtgggtga tcgtgtgacc     60
attacctgca gagcgagcca gtctatttct aattggctgg cttggtacca gcagaaacca    120
ggtaaagcac cgaaactatt aatttatctt gcttcttctt tgcaaagcgg ggtcccgtcc    180
cgttttagcg gctctggatc cggcactgat tttaccctga ccattagcag cctgcaacct    240
gaagactttg cggtttatta ttgccagcag tattatgatt tttctgatac ctttggccag    300
ggtacgaaag ttgaaattaa acgtacggtg gctgctccga gcgtgtttat ttttccgccg    360
agcgatgaac aactgaaaag cggcacggcg agcgtggtgt gcctgctgaa caactttta    420 ccgcgtgaag cgaaagttca gtggaaagta gacaacgcgc tgcaaagcgg caacagccag    480
gaaagcgtga ccgaacagga tagcaaagat agcacctatt ctctgagcag cacctgacc    540 ctgagcaaag cggattatga aaaacataaa gtgtatgcgt gcgaagtgac ccatcaaggt    600
ctgagcagcc cggtgactaa atcttttaat cgtggcgagn                          640
```

```
<210> SEQ ID NO 173
<211> LENGTH: 5
<212> TYPE: PRT
<213> ORGANISM: homo sapiens

<400> SEQUENCE: 173

Asn Tyr Gly Met His
1               5
```

```
<210> SEQ ID NO 174
<211> LENGTH: 16
<212> TYPE: PRT
<213> ORGANISM: homo sapiens

<400> SEQUENCE: 174

Val Ser Tyr Ala Gly Ser Phe Thr Asn Tyr Ala Asp Ser Val Lys Gly
1               5                   10                  15
```

```
<210> SEQ ID NO 175
<211> LENGTH: 12
<212> TYPE: PRT
<213> ORGANISM: homo sapiens

<400> SEQUENCE: 175

Ser Trp Leu Phe Gly Tyr Pro Asp Ile Phe Asp Tyr
1               5                   10
```

```
<210> SEQ ID NO 176
<211> LENGTH: 14
```

```
<212> TYPE: PRT
<213> ORGANISM: homo sapiens

<400> SEQUENCE: 176

Thr Gly Thr Ser Ser Asp Val Gly Gly Tyr Asn Tyr Val Ser
1               5                   10

<210> SEQ ID NO 177
<211> LENGTH: 7
<212> TYPE: PRT
<213> ORGANISM: homo sapiens

<400> SEQUENCE: 177

Asp Val Asn Asn Arg Pro Ser
1               5

<210> SEQ ID NO 178
<211> LENGTH: 9
<212> TYPE: PRT
<213> ORGANISM: homo sapiens

<400> SEQUENCE: 178

Ser Ser Tyr Asp Lys Phe Gln Thr Val
1               5

<210> SEQ ID NO 179
<211> LENGTH: 120
<212> TYPE: PRT
<213> ORGANISM: homo sapiens

<400> SEQUENCE: 179

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Val Ser Tyr Ala Gly Ser Phe Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Trp Leu Phe Gly Tyr Pro Asp Ile Phe Asp Tyr Trp Gly Gln
            100                 105                 110

Gly Thr Leu Val Thr Val Ser Ser
        115                 120

<210> SEQ ID NO 180
<211> LENGTH: 109
<212> TYPE: PRT
<213> ORGANISM: homo sapiens

<400> SEQUENCE: 180

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
```

```
                    50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Lys Phe
                     85                  90                  95

Gln Thr Val Phe Gly Gly Gly Thr Lys Leu Thr Val Leu
                100                 105

<210> SEQ ID NO 181
<211> LENGTH: 223
<212> TYPE: PRT
<213> ORGANISM: homo sapiens
<220> FEATURE:
<221> NAME/KEY: MISC_FEATURE
<222> LOCATION: (223)..(223)
<223> OTHER INFORMATION: X can be C, EF, or CEF

<400> SEQUENCE: 181

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ser Val Ser Tyr Ala Gly Ser Phe Thr Asn Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ser Trp Leu Phe Gly Tyr Pro Asp Ile Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Xaa
    210                 215                 220

<210> SEQ ID NO 182
<211> LENGTH: 214
<212> TYPE: PRT
<213> ORGANISM: homo sapiens
<220> FEATURE:
<221> NAME/KEY: MISC_FEATURE
<222> LOCATION: (214)..(214)
<223> OTHER INFORMATION: X can be CS or A

<400> SEQUENCE: 182

Asp Ile Ala Leu Thr Gln Pro Ala Ser Val Ser Gly Ser Pro Gly Gln
  1               5                  10                  15
```

```
Ser Ile Thr Ile Ser Cys Thr Gly Thr Ser Ser Asp Val Gly Gly Tyr
        20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Gly Val Ser Asn Arg Phe
        50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Lys Phe
                85                  90                  95

Gln Thr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Xaa
        210

<210> SEQ ID NO 183
<211> LENGTH: 360
<212> TYPE: DNA
<213> ORGANISM: homo sapiens

<400> SEQUENCE: 183
caggtgcaat tggtggaaag cggcggcggc ctggtgcaac cgggcggcag cctgcgtctg      60
agctgcgcgg cctccggatt taccttttct aattatggta tgcattgggt gcgccaagcc     120
cctgggaagg gtctcgagtg ggtgagcgtt tcttatgctg gtagctttac caattatgcg     180
gatagcgtga aaggccgttt taccatttca cgtgataatt cgaaaaacac cctgtatctg     240
caaatgaaca gcctgcgtgc ggaagatacg gccgtgtatt attgcgcgcg ttcttggctt     300
tttggttatc ctgatatttt tgattattgg ggccaaggca ccctggtgac ggttagctca     360

<210> SEQ ID NO 184
<211> LENGTH: 327
<212> TYPE: DNA
<213> ORGANISM: homo sapiens

<400> SEQUENCE: 184
gatatcgcac tgacccagcc agcttcagtg agcggctcac caggtcagag cattaccatc      60
tcgtgtacgg gtactagcag cgatgttggt ggttataatt atgtgtcttg gtaccagcag     120
catcccggga aggcgccgaa acttatgatt tatgatgtta ataatcgtcc ctcaggcgtg     180
agcaaccgtt ttagcggatc caaaagcggc aacaccgcga gcctgaccat tagcggcctg     240
caagcggaag acgaagcgga ttattattgc tcttcttatg ataagtttca gactgtgttt     300
ggcggcggca cgaagttaac cgttctt                                         327
```

```
<210> SEQ ID NO 185
<211> LENGTH: 667
<212> TYPE: DNA
<213> ORGANISM: homo sapiens
<220> FEATURE:
<221> NAME/KEY: misc_feature
<222> LOCATION: (667)..(667)
<223> OTHER INFORMATION: n can be TGC, TAATTC, or TGCGAATTC

<400> SEQUENCE: 185
caggtgcaat tggtggaaag cggcggcggc ctggtgcaac cgggcggcag cctgcgtctg      60
agctgcgcgg cctccggatt tacctttct aattatggta tgcattgggt gcgccaagcc     120
cctgggaagg gtctcgagtg ggtgagcgtt tcttatgctg gtagctttac caattatgcg     180
gatagcgtga aaggccgttt taccatttca cgtgataatt cgaaaaacac cctgtatctg     240
caaatgaaca gcctgcgtgc ggaagatacg gccgtgtatt attgcgcgcg ttcttggctt     300
tttggttatc ctgatatttt tgattattgg ggccaaggca ccctggtgac ggttagctca     360
gcgtcgacca aaggtccaag cgtgtttccg ctggctccga gcagcaaaag caccagcggc     420
ggcacggctg ccctgggctg cctggttaaa gattatttcc cggaaccagt caccgtgagc     480
tggaacagcg gggcgctgac cagcggcgtg cataccttc cggcggtgct gcaaagcagc     540
ggcctgtata gcctgagcag cgttgtgacc gtgccgagca gcagcttagg cactcagacc     600
tatatttgca acgtgaacca taaaccgagc aacaccaaag tggataaaaa agtggaaccg     660 aaaagcn                                                              667

<210> SEQ ID NO 186
<211> LENGTH: 640
<212> TYPE: DNA
<213> ORGANISM: homo sapiens
<220> FEATURE:
<221> NAME/KEY: misc_feature
<222> LOCATION: (640)..(640)
<223> OTHER INFORMATION: n can be TGCAGC or GCC

<400> SEQUENCE: 186
gatatcgcac tgacccagcc agcttcagtg agcggctcac caggtcagag cattaccatc      60
tcgtgtacgg gtactagcag cgatgttggt ggttataatt atgtgtcttg gtaccagcag     120
catcccggga aggcgccgaa acttatgatt tatgatgtta ataatcgtcc ctcaggcgtg     180
agcaaccgtt ttagcggatc caaaagcggc aacaccgcga gcctgaccat tagcggcctg     240
caagcggaag acgaagcgga ttattattgc tcttcttatg ataagtttca gactgtgttt     300
ggcggcggca cgaagttaac cgttcttggc cagccgaaag ccgcaccgag tgtgacgctg     360
tttccgccga gcagcgaaga attgcaggcg aacaaagcga ccctggtgtg cctgattagc     420 gactttatc cgggagccgt gacagtggcc tggaaggcag atagcagccc cgtcaaggcg     480
ggagtggaga ccaccacacc ctccaaacaa agcaacaaca agtacgcggc cagcagctat     540
ctgagcctga cgcctgagca gtggaagtcc cacagaagct acagctgcca ggtcacgcat     600 gagggagca ccgtggaaaa aaccgttgcg ccgactgagn                            640

<210> SEQ ID NO 187
<211> LENGTH: 116
<212> TYPE: PRT
<213> ORGANISM: homo sapiens

<400> SEQUENCE: 187

Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
        115

<210> SEQ ID NO 188
<211> LENGTH: 108
<212> TYPE: PRT
<213> ORGANISM: homo sapiens

<400> SEQUENCE: 188

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
            35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105

<210> SEQ ID NO 189
<211> LENGTH: 219
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: X can be C, EF, or CEF

<400> SEQUENCE: 189

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Asp Thr Pro Tyr Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Xaa
    210                 215

<210> SEQ ID NO 190
<211> LENGTH: 213
<212> TYPE: PRT
<213> ORGANISM: homo sapiens
<220> FEATURE:
<221> NAME/KEY: MISC_FEATURE
<222> LOCATION: (213)..(213)
<223> OTHER INFORMATION: X can be CS or A

<400> SEQUENCE: 190

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Xaa
    210

<210> SEQ ID NO 191
```

<211> LENGTH: 348
<212> TYPE: DNA
<213> ORGANISM: homo sapiens

<400> SEQUENCE: 191

| caggtgcaat | tggttcagtc | tggcgcggaa | gtgaaaaaac | cgggcagcag | cgtgaaagtg | 60 |
| agctgcaaag | cctccggagg | cacttttttct | tcttatgcca | tttcttgggt | gcgccaagcc | 120 |
| cctgggcagg | gtctcgagtg | gatgggcggt | atcggtccgt | tttttggcac | tgcgaattac | 180 |
| gcgcagaagt | ttcagggccg | ggtgaccatt | accgcggatg | aaagcaccag | caccgcgtat | 240 |
| atggaactga | gcagcctgcg | tagcgaagat | acggccgtgt | attattgcgc | gcgtgatact | 300 |
| ccttatttg | attattgggg | ccaaggcacc | ctggtgacgg | ttagctca | | 348 |

<210> SEQ ID NO 192
<211> LENGTH: 324
<212> TYPE: DNA
<213> ORGANISM: homo sapiens

<400> SEQUENCE: 192

| gatatcgaac | tgacccagcc | gccttcagtg | agcgttgcac | caggtcagac | cgcgcgtatc | 60 |
| tcgtgtagcg | gcgattctat | tcctaattat | tatgtttatt | ggtaccagca | gaaacccggg | 120 |
| caggcgccag | ttcttgtgat | ttatgatgat | tctaatcgtc | cctcaggcat | cccgaacgc | 180 |
| tttagcggat | ccaacagcgg | caacaccgcg | accctgacca | ttagcggcac | tcaggcggaa | 240 |
| gacgaagcgg | attattattg | ccagtctttt | gattcttctc | ttaatgctga | ggtgtttggc | 300 |
| ggcggcacga | agttaaccgt | tctt | | | | 324 |

<210> SEQ ID NO 193
<211> LENGTH: 655
<212> TYPE: DNA
<213> ORGANISM: homo sapiens
<220> FEATURE:
<221> NAME/KEY: misc_feature
<222> LOCATION: (655)..(655)
<223> OTHER INFORMATION: n can be TGC, GAATTC, or TGCGAATTC

<400> SEQUENCE: 193

| caggtgcaat | tggttcagtc | tggcgcggaa | gtgaaaaaac | cgggcagcag | cgtgaaagtg | 60 |
| agctgcaaag | cctccggagg | cacttttttct | tcttatgcca | tttcttgggt | gcgccaagcc | 120 |
| cctgggcagg | gtctcgagtg | gatgggcggt | atcggtccgt | tttttggcac | tgcgaattac | 180 |
| gcgcagaagt | ttcagggccg | ggtgaccatt | accgcggatg | aaagcaccag | caccgcgtat | 240 |
| atggaactga | gcagcctgcg | tagcgaagat | acggccgtgt | attattgcgc | gcgtgatact | 300 |
| ccttatttg | attattgggg | ccaaggcacc | ctggtgacgg | ttagctcagc | gtcgaccaaa | 360 |
| ggtccaagcg | tgtttccgct | ggctccgagc | agcaaaagca | ccagcggcgg | cacggctgcc | 420 |
| ctgggctgcc | tggttaaaga | ttatttcccg | gaaccagtca | ccgtgagctg | gaacagcggg | 480 |
| gcgctgacca | gcggcgtgca | tacctttccg | gcggtgctgc | aaagcagcgg | cctgtatagc | 540 |
| ctgagcagcg | ttgtgaccgt | gccgagcagc | agcttaggca | ctcagaccta | tatttgcaac | 600 |
| gtgaaccata | aaccgagcaa | caccaaagtg | gataaaaaag | tggaaccgaa | aagcn | 655 |

<210> SEQ ID NO 194
<211> LENGTH: 637
<212> TYPE: DNA
<213> ORGANISM: homo sapiens
<220> FEATURE:
<221> NAME/KEY: misc_feature
<222> LOCATION: (637)..(637)

-continued

<223> OTHER INFORMATION: n can be TGCAGC or GCC

<400> SEQUENCE: 194

```
gatatcgaac tgacccagcc gccttcagtg agcgttgcac caggtcagac cgcgcgtatc    60
tcgtgtagcg gcgattctat tcctaattat tatgtttatt ggtaccagca gaaacccggg   120
caggcgccag ttcttgtgat ttatgatgat tctaatcgtc cctcaggcat cccggaacgc   180
tttagcggat ccaacagcgg caacaccgcg accctgacca ttagcggcac tcaggcggaa   240
gacgaagcgg attattattg ccagtctttt gattcttctc ttaatgctga ggtgtttggc   300
ggcggcacga agttaaccgt tcttggccag ccgaaagccg caccgagtgt gacgctgttt   360
ccgccgagca gcgaagaatt gcaggcgaac aaagcgaccc tggtgtgcct gattagcgac   420
ttttatccgg gagccgtgac agtggcctgg aaggcagata gcagcccgt caaggcggga   480
gtggagacca ccacaccctc caaacaaagc aacaacaagt acgcggccag cagctatctg   540
agcctgacgc ctgagcagtg gaagtcccac agaagctaca gctgccaggt cacgcatgag   600
gggagcaccg tggaaaaaac cgttgcgccg actgagn                            637
```

<210> SEQ ID NO 195
<211> LENGTH: 5
<212> TYPE: PRT
<213> ORGANISM: homo sapiens

<400> SEQUENCE: 195

Ser Tyr Tyr Ile Ser
1               5

<210> SEQ ID NO 196
<211> LENGTH: 17
<212> TYPE: PRT
<213> ORGANISM: homo sapiens

<400> SEQUENCE: 196

Gly Ile Ile Pro Ile Phe Gly Thr Ala Asn Tyr Ala Gln Lys Phe Gln
1               5                   10                  15

Gly

<210> SEQ ID NO 197
<211> LENGTH: 19
<212> TYPE: PRT
<213> ORGANISM: homo sapiens

<400> SEQUENCE: 197

Gly Glu Ile Trp His Val His Gln Pro Tyr Lys Ser Gly Val Tyr Gly
1               5                   10                  15

Ala Ala Tyr

<210> SEQ ID NO 198
<211> LENGTH: 11
<212> TYPE: PRT
<213> ORGANISM: homo sapiens

<400> SEQUENCE: 198

Arg Ala Ser Gln Gly Ile Ser Asn Trp Leu Asn
1               5                   10

<210> SEQ ID NO 199
<211> LENGTH: 7
<212> TYPE: PRT
<213> ORGANISM: homo sapiens

<400> SEQUENCE: 199

Gly Thr Ser Ser Leu Gln Ser
1               5

<210> SEQ ID NO 200
<211> LENGTH: 9
<212> TYPE: PRT
<213> ORGANISM: homo sapiens

<400> SEQUENCE: 200

Gln Gln Leu Asp Ser Phe Pro Ala Thr
1               5

<210> SEQ ID NO 201
<211> LENGTH: 128
<212> TYPE: PRT
<213> ORGANISM: homo sapiens

<400> SEQUENCE: 201

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Ile Trp His Val His Gln Pro Tyr Lys Ser Gly Val
            100                 105                 110

Tyr Gly Ala Ala Tyr Trp Gly Gln Gly Thr Leu Val Thr Val Ser Ser
        115                 120                 125

<210> SEQ ID NO 202
<211> LENGTH: 107
<212> TYPE: PRT
<213> ORGANISM: homo sapiens

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Asn Trp Tyr Gln Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asp Ser Phe Pro Ala
                85                  90                  95

Thr Phe Gly Gln Gly Thr Lys Val Glu Ile Lys
            100                 105

<210> SEQ ID NO 203
<211> LENGTH: 231

```
<212> TYPE: PRT
<213> ORGANISM: homo sapiens
<220> FEATURE:
<221> NAME/KEY: MISC_FEATURE
<222> LOCATION: (231)..(231)
<223> OTHER INFORMATION: X can be C, EF, or CEF

<400> SEQUENCE: 203

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Tyr Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Ile Trp His Val His Gln Pro Tyr Lys Ser Gly Val
            100                 105                 110

Tyr Gly Ala Ala Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Xaa
225                 230

<210> SEQ ID NO 204
<211> LENGTH: 214
<212> TYPE: PRT
<213> ORGANISM: homo sapiens
<220> FEATURE:
<221> NAME/KEY: MISC_FEATURE
<222> LOCATION: (214)..(214)
<223> OTHER INFORMATION: X can be C or A

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Asn Trp Tyr Gln Gln Lys Pro Gly Lys Ala Pro Lys Leu Leu Ile
            35                  40                  45

Tyr Gly Thr Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Leu Asp Ser Phe Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Xaa
    210

<210> SEQ ID NO 205
<211> LENGTH: 384
<212> TYPE: DNA
<213> ORGANISM: homo sapiens

<400> SEQUENCE: 205
caggtgcaat tggttcagtc tggcgcggaa gtgaaaaaac cgggcagcag cgtgaaagtg      60
agctgcaaag cctccggagg cacttttttct tcttattata tttcttgggt gcgccaagcc    120
cctgggcagg gtctcgagtg gatgggcggt atcattccga ttttttggcac tgcgaattac    180 gcgcagaagt ttcagggccg ggtgaccatt accgcggatg aaagcaccag caccgcgtat    240
atggaactga gcagcctgcg tagcgaagat acggccgtgt attattgcgc gcgtggtgag    300
atttggcatg ttcatcagcc ttataagtct ggtgtttatg gtgctgctta ttggggccaa    360
ggcacccctg gtgacggttag ctca                                          384

<210> SEQ ID NO 206
<211> LENGTH: 321
<212> TYPE: DNA
<213> ORGANISM: homo sapiens

<400> SEQUENCE: 206
gatatccaga tgacccagag cccgtctagc ctgagcgcga gcgtgggtga tcgtgtgacc      60
attacctgca gcgagcca gggtatttct aattggctga attggtacca gcagaaacca      120
ggtaaagcac cgaaactatt aatttatggt acttcttctt tgcaaagcgg ggtcccgtcc    180
cgttttagcg gctctggatc cggcactgat tttaccctga ccattagcag cctgcaacct    240
gaagactttg cgacttatta ttgccagcag cttgattctt ttcctgctac ctttggccag    300
ggtacgaaag ttgaaattaa a                                               321

<210> SEQ ID NO 207
<211> LENGTH: 691
<212> TYPE: DNA
<213> ORGANISM: homo sapiens
<220> FEATURE:
<221> NAME/KEY: misc_feature
<222> LOCATION: (691)..(691)
<223> OTHER INFORMATION: n can be TGC, GAATTC, or TGCGAATTC -continued

<400> SEQUENCE: 207

```
caggtgcaat tggttcagtc tggcgcggaa gtgaaaaaac cgggcagcag cgtgaaagtg        60
agctgcaaag cctccggagg cacttttct tcttattata tttcttgggt gcgccaagcc       120
cctgggcagg tctcgagtg gatgggcggt atcattccga tttttggcac tgcgaattac       180
gcgcagaagt tcagggccg ggtgaccatt accgcggatg aaagcaccag caccgcgtat       240
atggaactga gcagcctgcg tagcgaagat acggccgtgt attattgcgc gcgtggtgag       300
atttggcatg ttcatcagcc ttataagtct ggtgtttatg gtgctgctta ttggggccaa       360
ggcaccctgg tgacggttag ctcagcgtcg accaaaggtc caagcgtgtt ccgctggct        420
ccgagcagca aaagcaccag cggcggcacg gctgccctgg gctgcctggt taaagattat       480
ttcccggaac cagtcaccgt gagctggaac agcggggcgc tgaccagcgg cgtgcatacc       540
tttccggcgg tgctgcaaag cagcggcctg tatagcctga gcagcgttgt gaccgtgccg       600
agcagcagct taggcactca gacctatatt tgcaacgtga accataaacc gagcaacacc       660
aaagtggata aaaagtgga accgaaaagc n                                       691
```

<210> SEQ ID NO 208
<211> LENGTH: 640
<212> TYPE: DNA
<213> ORGANISM: homo sapiens
<220> FEATURE:
<221> NAME/KEY: misc_feature
<222> LOCATION: (640)..(640)
<223> OTHER INFORMATION: n can be TGC or GCC

<400> SEQUENCE: 208

```
gatatccaga tgacccagag cccgtctagc ctgagcgcga gcgtgggtga tcgtgtgacc        60
attacctgca gcgcagcca gggtatttct aattggctga attggtacca gcagaaacca       120
ggtaaagcac cgaaactatt aatttatggt acttcttctt tgcaaagcgg ggtcccgtcc       180
cgttttagcg gctctggatc cggcactgat tttaccctga ccattagcag cctgcaacct       240
gaagactttg cgacttatta ttgccagcag cttgattctt ttcctgctac ctttggccag       300
ggtacgaaag ttgaaattaa acgtacggtg gctgctccga gcgtgtttat ttttccgccg       360
agcgatgaac aactgaaaag cggcacggcg agcgtggtgt gcctgctgaa caacttttat       420
ccgcgtgaag cgaaagttca gtggaaagta gacaacgcgc tgcaaagcgg caacagccag       480
gaaagcgtga ccgaacagga tagcaaagat agcacctatt ctctgagcag caccctgacc       540
ctgagcaaag cggattatga aaaacataaa gtgtatgcgt gcgaagtgac ccatcaaggt       600
ctgagcagcc cggtgactaa atcttttaat cgtggcgagn                             640
```

<210> SEQ ID NO 209
<211> LENGTH: 11
<212> TYPE: PRT
<213> ORGANISM: homo sapiens

<400> SEQUENCE: 209

Gln Ser Trp Thr Asp Ser Pro Asn Thr Leu Val
1               5                   10

<210> SEQ ID NO 210
<211> LENGTH: 117
<212> TYPE: PRT
<213> ORGANISM: homo sapiens

<400> SEQUENCE: 210

Gln Val Gln Leu Val Gln Ser Gly Ala Glu Val Lys Lys Pro Gly Glu

```
                1               5                  10                 15
Ser Leu Lys Ile Ser Cys Lys Gly Ser Gly Tyr Ser Phe Thr Ser Tyr
                20                          25                 30

Tyr Ile Gly Trp Val Arg Gln Met Pro Gly Lys Gly Leu Glu Trp Met
                35                          40                 45

Gly Ile Ile Asp Pro Ser Asp Ser His Thr Thr Tyr Ser Pro Ser Phe
                50                          55                 60

Gln Gly Gln Val Thr Ile Ser Ala Asp Lys Ser Ile Ser Thr Ala Tyr
65                              70                 75                 80

Leu Gln Trp Ser Ser Leu Lys Ala Ser Asp Thr Ala Met Tyr Tyr Cys
                85                          90                 95

Ala Arg Tyr Met Met Arg Gly Phe Asp His Trp Gly Gln Gly Thr Leu
                100                         105                110

Val Thr Val Ser Ser
                115
```

<210> SEQ ID NO 211
<211> LENGTH: 108
<212> TYPE: PRT
<213> ORGANISM: homo sapiens

<400> SEQUENCE: 211

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
                20                          25                  30

Tyr Trp Tyr Gln Gln Lys Pro Gly Gln Ala Pro Val Leu Val Ile Tyr
                35                          40                  45

Lys Asp Asn Asn Arg Pro Ser Gly Ile Pro Glu Arg Phe Ser Gly Ser
                50                          55                  60

Asn Ser Gly Asn Thr Ala Thr Leu Thr Ile Ser Gly Thr Gln Ala Glu
65                              70                  75                  80

Asp Glu Ala Asp Tyr Tyr Cys Gln Ser Trp Thr Asp Ser Pro Asn Thr
                85                          90                  95

Leu Val Phe Gly Gly Gly Thr Lys Leu Thr Val Leu
                100                         105
```

<210> SEQ ID NO 212
<211> LENGTH: 220
<212> TYPE: PRT
<213> ORGANISM: homo sapiens
<220> FEATURE:
<221> NAME/KEY: MISC_FEATURE
<222> LOCATION: (220)..(220)
<223> OTHER INFORMATION: X can be C, EF, or CEF

<400> SEQUENCE: 212

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                          25                  30

Tyr Ile Gly Trp Val Arg Gln Met Pro Gly Lys Gly Leu Glu Trp Met
                35                          40                  45

Gly Ile Ile Asp Pro Ser Asp Ser His Thr Thr Tyr Ser Pro Ser Phe
                50                          55                  60

Gln Gly Gln Val Thr Ile Ser Ala Asp Lys Ser Ile Ser Thr Ala Tyr
65                              70                  75                  80

Leu Gln Trp Ser Ser Leu Lys Ala Ser Asp Thr Ala Met Tyr Tyr Cys
```

```
                   85                  90                  95
Ala Arg Tyr Met Met Arg Gly Phe Asp His Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Xaa
    210                 215                 220

<210> SEQ ID NO 213
<211> LENGTH: 213
<212> TYPE: PRT
<213> ORGANISM: homo sapiens
<220> FEATURE:
<221> NAME/KEY: MISC_FEATURE
<222> LOCATION: (213)..(213)
<223> OTHER INFORMATION: X can be CS or A

<400> SEQUENCE: 213

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Thr Asp Ser Pro Asn Thr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Xaa
    210
```

```
<210> SEQ ID NO 214
<211> LENGTH: 351
<212> TYPE: DNA
<213> ORGANISM: homo sapiens

<400> SEQUENCE: 214
caggtgcaat tggttcagag cggcgcggaa gtgaaaaaac cgggcgaaag cctgaaaatt      60
agctgcaaag gttccggata ttcctttact tcttattata ttggttgggt gcgccagatg     120
cctgggaagg gtctcgagtg gatgggcatt atcgatccgt ctgatagcca taccacttat     180
tctccgagct ttcagggcca ggtgaccatt agcgcggata aaagcattag caccgcgtat     240
cttcaatgga gcagcctgaa agcgagcgat acggccatgt attattgcgc gcgttatatg     300
atgcgtggtt ttgatcattg gggccaaggc accctggtga cggttagctc a              351

<210> SEQ ID NO 215
<211> LENGTH: 324
<212> TYPE: DNA
<213> ORGANISM: homo sapiens

<400> SEQUENCE: 215
gatatcgaac tgacccagcc gccttcagtg agcgttgcac caggtcagac cgcgcgtatc      60
tcgtgtagcg gcgattctct tggtgattat tatgcttatt ggtaccagca gaaacccggg     120
caggcgccag ttcttgtgat ttataaggat aataatcgtc cctcaggcat cccggaacgc     180
tttagcggat ccaacagcgg caacaccgcg accctgacca ttagcggcac tcaggcggaa     240
gacgaagcgg attattattg ccagtcttgg actgattctc ctaatactct tgtgtttggc     300
ggcggcacga agttaaccgt tctt                                            324

<210> SEQ ID NO 216
<211> LENGTH: 658
<212> TYPE: DNA
<213> ORGANISM: homo sapiens
<220> FEATURE:
<221> NAME/KEY: misc_feature
<222> LOCATION: (658)..(658)
<223> OTHER INFORMATION: n can be TGC, GAATTC, or TGCGAATTC

<400> SEQUENCE: 216
caggtgcaat tggttcagag cggcgcggaa gtgaaaaaac cgggcgaaag cctgaaaatt      60
agctgcaaag gttccggata ttcctttact tcttattata ttggttgggt gcgccagatg     120
cctgggaagg gtctcgagtg gatgggcatt atcgatccgt ctgatagcca taccacttat     180
tctccgagct ttcagggcca ggtgaccatt agcgcggata aaagcattag caccgcgtat     240
cttcaatgga gcagcctgaa agcgagcgat acggccatgt attattgcgc gcgttatatg     300
atgcgtggtt ttgatcattg gggccaaggc accctggtga cggttagctc agcgtcgacc     360
aaaggtccaa gcgtgtttcc gctggctccg agcagcaaaa gcaccagcgg cggcacggct     420
gccctgggct gcctggttaa agattatttc ccggaaccag tcaccgtgag ctggaacagc     480
ggggcgctga ccagcggcgt gcataccttt ccggcggtgc tgcaaagcag cggcctgtat     540
agcctgagca gcgttgtgac cgtgccgagc agcagcttag cactcagac ctatatttgc     600 aacgtgaacc ataaaccgag caacaccaaa gtggataaaa agtggaacc gaaaagcn       658

<210> SEQ ID NO 217
<211> LENGTH: 637
<212> TYPE: DNA
<213> ORGANISM: homo sapiens
<220> FEATURE:
```

<221> NAME/KEY: misc_feature
<222> LOCATION: (637)..(637)
<223> OTHER INFORMATION: n can be TGCAGC or GCC

<400> SEQUENCE: 217

```
gatatcgaac tgacccagcc gccttcagtg agcgttgcac caggtcagac cgcgcgtatc    60
tcgtgtagcg gcgattctct tggtgattat tatgcttatt ggtaccagca gaaacccggg   120
caggcgccag ttcttgtgat ttataaggat aataatcgtc cctcaggcat cccgaacgc    180
tttagcggat ccaacagcgg caacaccgcg accctgacca ttagcggcac tcaggcggaa   240
gacgaagcgg attattattg ccagtcttgg actgattctc ctaatactct tgtgtttggc   300
ggcggcacga agttaaccgt tcttggccag ccgaaagccg caccgagtgt gacgctgttt   360
ccgccgagca gcgaagaatt gcaggcgaac aaagcgaccc tggtgtgcct gattagcgac   420
ttttatccgg gagccgtgac agtggcctgg aaggcagata gcagcccgt caaggcggga    480
gtggagacca ccacaccctc caaacaaagc aacaacaagt acgcggccag cagctatctg   540
agcctgacgc ctgagcagtg gaagtcccac agaagctaca gctgccaggt cacgcatgag   600
gggagcaccg tggaaaaaac cgttgcgccg actgagn                            637
```

<210> SEQ ID NO 218
<211> LENGTH: 116
<212> TYPE: PRT
<213> ORGANISM: homo sapiens

<400> SEQUENCE: 218

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Asp Asp Ser Tyr Thr Arg Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115
```

<210> SEQ ID NO 219
<211> LENGTH: 106
<212> TYPE: PRT
<213> ORGANISM: homo sapiens

<400> SEQUENCE: 219

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
                20                  25                  30

His Trp Tyr Gln Gln Lys Pro Gly Gln Ala Pro Val Leu Val Ile Tyr
            35                  40                  45

Lys Asp Asn Asp Arg Pro Ser Gly Ile Pro Glu Arg Phe Ser Gly Ser
        50                  55                  60
```

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu
            100                 105

<210> SEQ ID NO 220
<211> LENGTH: 219
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: X can be C, EF, or CEF

<400> SEQUENCE: 220

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Asp Asp Ser Tyr Thr Arg Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Xaa
    210                 215

<210> SEQ ID NO 221
<211> LENGTH: 211
<212> TYPE: PRT
<213> ORGANISM: homo sapiens
<220> FEATURE:
<221> NAME/KEY: MISC_FEATURE
<222> LOCATION: (211)..(211)
<223> OTHER INFORMATION: X can be CS or A

<400> SEQUENCE: 221

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
                20                  25                  30

His Trp Tyr Gln Gln Lys Pro Gly Gln Ala Pro Val Leu Val Ile Tyr
            35                  40                  45

Lys Asp Asn Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Thr Tyr Asp Ile Glu Ser Tyr Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Xaa
    210

<210> SEQ ID NO 222
<211> LENGTH: 348
<212> TYPE: DNA
<213> ORGANISM: homo sapiens

<400> SEQUENCE: 222
caggtgcaat tggttcagag cggcgcggaa gtgaaaaaac cgggcgaaag cctgaaaatt    60
agctgcaaag ttccggata ttcctttact aattatattt cttgggtgcg ccagatgcct   120
gggaagggtc tcgagtggat gggcattatc gatccggatg atagctatac ccgttattct   180
ccgagctttc agggacaggt gaccattagc gcggataaaa gcattagcac cgcgtatctt   240
caatggagca gcctgaaagc gagcgatacg gccatgtatt attgcgcgcg ttatgagtat   300
ggtggttttg atatttgggg ccaaggcacc ctggtgacgg ttagctca              348

<210> SEQ ID NO 223
<211> LENGTH: 318
<212> TYPE: DNA
<213> ORGANISM: homo sapiens

<400> SEQUENCE: 223
gatatcgaac tgacccagcc gccttcagtg agcgttgcac aggtcagac cgcgcgtatc    60 tcgtgtagcg gcgataatat tggtaattct tatgttcatt ggtaccagca gaaacccggg   120
caggcgccag ttcttgtgat ttataaggat aatgatcgtc cctcaggcat cccggaacgc   180
tttagcggat ccaacagcgg caacaccgcg accctgacca ttagcggcac tcaggcggaa   240
gacgaagcgg attattattg cggtacttat gatattgagt cttatgtgtt tggcggcggc   300
acgaagttaa ccgttctt                                                318

<210> SEQ ID NO 224
<211> LENGTH: 655

```
<212> TYPE: DNA
<213> ORGANISM: homo sapiens
<220> FEATURE:
<221> NAME/KEY: misc_feature
<222> LOCATION: (655)..(655)
<223> OTHER INFORMATION: n can be TGC, GAATTC, or TGCGAATTC

<400> SEQUENCE: 224
caggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatc gatccggatg atagctatac ccgttattct     180
ccgagctttc agggacaggt gaccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctcagc gtcgaccaaa     360
ggtccaagcg tgtttccgct ggctccgagc agcaaaagca ccagcggcgg cacggctgcc     420
ctgggctgcc tggttaaaga ttatttcccg gaaccagtca ccgtgagctg gaacagcggg     480
gcgctgacca gcggcgtgca tacctttccg gcggtgctgc aaagcagcgg cctgtatagc     540
ctgagcagcg ttgtgaccgt gccgagcagc agcttaggca ctcagaccta tatttgcaac     600
gtgaaccata aaccgagcaa caccaaagtg gataaaaaag tggaaccgaa aagcn          655

<210> SEQ ID NO 225
<211> LENGTH: 631
<212> TYPE: DNA
<213> ORGANISM: homo sapiens
<220> FEATURE:
<221> NAME/KEY: misc_feature
<222> LOCATION: (631)..(631)
<223> OTHER INFORMATION: n can be TGCAGC or GCC

<400> SEQUENCE: 225
gatatcgaac tgacccagcc gccttcagtg agcgttgcac caggtcagac cgcgcgtatc      60
tcgtgtagcg gcgataatat tggtaattct tatgttcatt ggtaccagca gaaacccggg     120
caggcgccag ttcttgtgat ttataaggat aatgatcgtc cctcaggcat cccggaacgc     180
tttagcggat ccaacagcgg caacaccgcg accctgacca ttagcggcac tcaggcggaa     240
gacgaagcgg attattattg cggtacttat gatattgagt cttatgtgtt tggcggcggc     300
acgaagttaa ccgttcttgg ccagccgaaa gccgcaccga gtgtgacgct gtttccgccg     360
agcagcgaag aattgcaggc gaacaaagcg accctggtgt gcctgattag cgactttttat    420 ccgggagccg tgacagtggc ctggaaggca gatagcagcc ccgtcaaggc gggagtggag     480
accaccacac cctccaaaca aagcaacaac aagtacgcgg ccagcagcta tctgagcctg     540
acgcctgagc agtggaagtc ccacagaagc tacagctgcc aggtcacgca tgaggggagc     600
accgtggaaa aaaccgttgc gccgactgag n                                     631

<210> SEQ ID NO 226
<211> LENGTH: 16
<212> TYPE: PRT
<213> ORGANISM: homo sapiens

<400> SEQUENCE: 226

His Ile Phe Ser Asp Asp Asp Lys Tyr Tyr Ser Thr Ser Leu Lys Thr
1               5                   10                  15

<210> SEQ ID NO 227
<211> LENGTH: 117
<212> TYPE: PRT
```

<213> ORGANISM: homo sapiens

<400> SEQUENCE: 227

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Gly Gly Val Ser Trp Ile Arg Gln Pro Pro Gly Lys Ala Leu Glu
        35                  40                  45

Trp Leu Ala His Ile Phe Ser Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Pro Tyr Gly Phe Asp Ser Trp Gly Gln Gly Thr Leu
            100                 105                 110

Val Thr Val Ser Ser
            115

<210> SEQ ID NO 228
<211> LENGTH: 109
<212> TYPE: PRT
<213> ORGANISM: homo sapiens

<400> SEQUENCE: 228

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Asn Tyr Val Ser Trp Tyr Gln Gln His Pro Gly Lys Ala Pro Lys Leu
        35                  40                  45

Met Ile Tyr Asp Asp Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Gln
                85                  90                  95

Ser Ile Val Phe Gly Gly Gly Thr Lys Leu Thr Val Leu
            100                 105

<210> SEQ ID NO 229
<211> LENGTH: 220
<212> TYPE: PRT
<213> ORGANISM: homo sapiens
<220> FEATURE:
<221> NAME/KEY: MISC_FEATURE
<222> LOCATION: (220)..(220)
<223> OTHER INFORMATION: X can be C, EF, or CEF

<400> SEQUENCE: 229

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Gly Gly Val Ser Trp Ile Arg Gln Pro Pro Gly Lys Ala Leu Glu
        35                  40                  45

Trp Leu Ala His Ile Phe Ser Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Pro Tyr Gly Phe Asp Ser Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Xaa
            210                 215                 220

<210> SEQ ID NO 230
<211> LENGTH: 214
<212> TYPE: PRT
<213> ORGANISM: homo sapiens
<220> FEATURE:
<221> NAME/KEY: MISC_FEATURE
<222> LOCATION: (214)..(214)
<223> OTHER INFORMATION: X can be CS or A

<400> SEQUENCE: 230

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Asn Tyr Val Ser Trp Tyr Gln Gln His Pro Gly Lys Ala Pro Lys Leu
            35                  40                  45

Met Ile Tyr Asp Asp Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Gln
            85                  90                  95

Ser Ile Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
            130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr

```
                195                 200                 205
Val Ala Pro Thr Glu Xaa
                210

<210> SEQ ID NO 231
<211> LENGTH: 351
<212> TYPE: DNA
<213> ORGANISM: homo sapiens

<400> SEQUENCE: 231
caggtgcaat tgaaagaaag cggcccggcc ctggtgaaac cgacccaaac cctgaccctg      60
acctgtacct tttccggatt tagcctgtct acttctggtg gtggtgtgtc ttggattcgc     120
cagccgcctg ggaaagccct cgagtggctg gctcatatct tttctgatga tgataagtat     180
tatagcacca gcctgaaaac gcgtctgacc attagcaaag atacttcgaa aaatcaggtg     240
gtgctgacta tgaccaacat ggacccggtg gatacggcca cctattattg cgcgcgtggt     300
ccttatggtt ttgattcttg gggccaaggc accctggtga cggttagctc a              351

<210> SEQ ID NO 232
<211> LENGTH: 327
<212> TYPE: DNA
<213> ORGANISM: homo sapiens

<400> SEQUENCE: 232
gatatcgcac tgacccagcc agcttcagtg agcggctcac caggtcagag cattaccatc      60
tcgtgtacgg gtactagcag cgatattggt acttataatt atgtgtcttg gtaccagcag     120
catcccggga aggcgccgaa acttatgatt tatgatgatt ctaatcgtcc ctcaggcgtg     180
agcaaccgtt ttagcggatc caaaagcggc aacaccgcga gcctgaccat tagcggcctg     240
caagcggaag acgaagcgga ttattattgc cagtcttatg attctcagtc tattgtgttt     300
ggcggcggca cgaagttaac cgttctt                                         327

<210> SEQ ID NO 233
<211> LENGTH: 658
<212> TYPE: DNA
<213> ORGANISM: homo sapiens
<220> FEATURE:
<221> NAME/KEY: misc_feature
<222> LOCATION: (658)..(658)
<223> OTHER INFORMATION: n can be TGC, GAATTC, or TGCGAATTC

<400> SEQUENCE: 233
caggtgcaat tgaaagaaag cggcccggcc ctggtgaaac cgacccaaac cctgaccctg      60
acctgtacct tttccggatt tagcctgtct acttctggtg gtggtgtgtc ttggattcgc     120
cagccgcctg ggaaagccct cgagtggctg gctcatatct tttctgatga tgataagtat     180
tatagcacca gcctgaaaac gcgtctgacc attagcaaag atacttcgaa aaatcaggtg     240
gtgctgacta tgaccaacat ggacccggtg gatacggcca cctattattg cgcgcgtggt     300
ccttatggtt ttgattcttg gggccaaggc accctggtga cggttagctc agcgtcgacc     360
aaaggtccaa gcgtgtttcc gctggctccg agcagcaaaa gcaccagcgg cggcacggct     420
gccctgggct gcctggttaa agattatttc ccggaaccag tcaccgtgag ctggaacagc     480
ggggcgctga ccagcggcgt gcataccttt ccggcggtgc tgcaaagcag cggcctgtat     540
agcctgagca gcgttgtgac cgtgccgagc agcagcttag gcactcagac ctatatttgc     600
aacgtgaacc ataaaccgag caacaccaaa gtggataaaa agtggaaacc gaaaagcn     658
```

<210> SEQ ID NO 234
<211> LENGTH: 640
<212> TYPE: DNA
<213> ORGANISM: homo sapiens
<220> FEATURE:
<221> NAME/KEY: misc_feature
<222> LOCATION: (640)..(640)
<223> OTHER INFORMATION: n can be TGCAGC or GCC

<400> SEQUENCE: 234

```
gatatcgcac tgacccagcc agcttcagtg agcggctcac caggtcagag cattaccatc      60
tcgtgtacgg gtactagcag cgatattggt acttataatt atgtgtcttg gtaccagcag     120
catcccggga aggcgccgaa acttatgatt tatgatgatt ctaatcgtcc ctcaggcgtg     180
agcaaccgtt ttagcggatc caaaagcggc aacaccgcga gcctgaccat tagcggcctg     240
caagcggaag acgaagcgga ttattattgc cagtcttatg attctcagtc tattgtgttt     300
ggcggcggca cgaagttaac cgttcttggc cagccgaaag ccgcaccgag tgtgacgctg     360
tttccgccga gcagcgaaga attgcaggcg aacaaagcga ccctggtgtg cctgattagc     420
gactttatc cgggagccgt gacagtggcc tggaaggcag atagcagccc cgtcaaggcg     480
ggagtggaga ccaccacacc ctccaaacaa agcaacaaca agtacgcggc cagcagctat     540
ctgagcctga cgcctgagca gtggaagtcc cacagaagct acagctgcca ggtcacgcat     600
gagggggagca ccgtggaaaa aaccgttgcg ccgactgagn                          640
```

<210> SEQ ID NO 235
<211> LENGTH: 7
<212> TYPE: PRT
<213> ORGANISM: homo sapiens

<400> SEQUENCE: 235

Thr Ser Gly Met Ser Val Gly
1               5

<210> SEQ ID NO 236
<211> LENGTH: 16
<212> TYPE: PRT
<213> ORGANISM: homo sapiens

<400> SEQUENCE: 236

Leu Ile Asp Trp Asp Glu Asp Lys Ser Tyr Ser Thr Ser Leu Lys Thr
1               5                   10                  15

<210> SEQ ID NO 237
<211> LENGTH: 11
<212> TYPE: PRT
<213> ORGANISM: homo sapiens

<400> SEQUENCE: 237

Tyr Asn Trp Tyr Asn Pro Pro Gly Phe Asp Asn
1               5                   10

<210> SEQ ID NO 238
<211> LENGTH: 13
<212> TYPE: PRT
<213> ORGANISM: homo sapiens

<400> SEQUENCE: 238

Ser Gly Ser Ser Ser Asn Ile Gly Ser Asn Tyr Val Ser
1               5                   10

<210> SEQ ID NO 239
<211> LENGTH: 7

<212> TYPE: PRT
<213> ORGANISM: homo sapiens

<400> SEQUENCE: 239

Arg Asn Asp Lys Arg Pro Ser
1               5

<210> SEQ ID NO 240
<211> LENGTH: 9
<212> TYPE: PRT
<213> ORGANISM: homo sapiens

<400> SEQUENCE: 240

Gln Ser Ala Asp Ser Ser Ser Met Val
1               5

<210> SEQ ID NO 241
<211> LENGTH: 121
<212> TYPE: PRT
<213> ORGANISM: homo sapiens

<400> SEQUENCE: 241

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Leu Ile Asp Trp Asp Glu Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Asn Trp Tyr Asn Pro Pro Gly Phe Asp Asn Trp Gly
            100                 105                 110

Gln Gly Thr Leu Val Thr Val Ser Ser
        115                 120

<210> SEQ ID NO 242
<211> LENGTH: 108
<212> TYPE: PRT
<213> ORGANISM: homo sapiens

<400> SEQUENCE: 242

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Arg Asn Asp Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Ala Asp Ser Ser Ser
                85                  90                  95

Met Val Phe Gly Gly Gly Thr Lys Leu Thr Val Leu
            100                 105

-continued

```
<210> SEQ ID NO 243
<211> LENGTH: 224
<212> TYPE: PRT
<213> ORGANISM: homo sapiens
<220> FEATURE:
<221> NAME/KEY: MISC_FEATURE
<222> LOCATION: (224)..(224)
<223> OTHER INFORMATION: X can be C, EF, or CEF

<400> SEQUENCE: 243

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Leu Ile Asp Trp Asp Glu Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Asn Trp Tyr Asn Pro Pro Gly Phe Asp Asn Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Xaa
    210                 215                 220

<210> SEQ ID NO 244
<211> LENGTH: 213
<212> TYPE: PRT
<213> ORGANISM: homo sapiens
<220> FEATURE:
<221> NAME/KEY: MISC_FEATURE
<222> LOCATION: (213)..(213)
<223> OTHER INFORMATION: X can be CS or A

<400> SEQUENCE: 244

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Arg Asn Asp Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80
```

```
Ser Glu Asp Glu Ala Asp Tyr Tyr Cys Gln Ser Ala Asp Ser Ser
             85                  90                  95
Met Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
            115                 120                 125
Ala Asn Lys Ala Thr Leu Val Cys Leu Ile Ser Asp Phe Tyr Pro Gly
        130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Xaa
        210

<210> SEQ ID NO 245
<211> LENGTH: 363
<212> TYPE: DNA
<213> ORGANISM: homo sapiens

<400> SEQUENCE: 245
caggtgcaat tgaaagaaag cggcccggcc ctggtgaaac cgacccaaac cctgaccctg      60
acctgtacct tttccggatt tagcctgtct acttctggta tgtctgtggg ttggattcgc     120
cagccgcctg ggaaagccct cgagtggctg gctcttatcg attgggatga ggataagtct     180
tatagcacca gcctgaaaac gcgtctgacc attagcaaag atacttcgaa aaatcaggtg     240
gtgctgacta tgaccaacat ggacccggtg atacggcca cctattattg cgcgcgttat     300
aattggtata tcctcctgg ttttgataat tggggccaag gcaccctggt gacggttagc     360
tca                                                                  363

<210> SEQ ID NO 246
<211> LENGTH: 324
<212> TYPE: DNA
<213> ORGANISM: homo sapiens

<400> SEQUENCE: 246
gatatcgtgc tgacccagcc gccttcagtg agtggcgcac aggtcagcg tgtgaccatc       60 tcgtgtagcg gcagcagcag caacattggt tctaattatg tgtcttggta ccagcagttg     120
cccgggacgg cgccgaaact tctgatttat cgtaatgata gcgtccctc aggcgtgccg      180 gatcgtttta gcggatccaa aagcggcacc agcgcgagcc ttgcgattac gggcctgcaa     240
agcgaagacg aagcggatta ttattgccag tctgctgatt cttcttctat ggtgtttggc     300
ggcggcacga agttaaccgt tctt                                           324

<210> SEQ ID NO 247
<211> LENGTH: 670
<212> TYPE: DNA
<213> ORGANISM: homo sapiens
<220> FEATURE:
<221> NAME/KEY: misc_feature
<222> LOCATION: (670)..(670)
<223> OTHER INFORMATION: n can be TGC, GAATTC, or TGCGAATTC
```

-continued

<400> SEQUENCE: 247

```
caggtgcaat tgaaagaaag cggcccggcc ctggtgaaac cgacccaaac cctgaccctg      60
acctgtacct tttccggatt tagcctgtct acttctggta tgtctgtggg ttggattcgc     120
cagccgcctg ggaaagccct cgagtggctg gctcttatcg attgggatga ggataagtct     180
tatagcacca gcctgaaaac gcgtctgacc attagcaaag atacttcgaa aaatcaggtg     240
gtgctgacta tgaccaacat ggacccgtg gatacggcca cctattattg cgcgcgttat      300
aattggtata atcctcctgg ttttgataat tggggccaag caccctggt gacggttagc      360
tcagcgtcga ccaaaggtcc aagcgtgttt ccgctggctc cgagcagcaa aagcaccagc     420
ggcggcacgg ctgccctggg ctgcctggtt aaagattatt tcccggaacc agtcaccgtg     480
agctggaaca gcggggcgct gaccagcggc gtgcatacct tccggcggt gctgcaaagc      540
agcggcctgt atagcctgag cagcgttgtg accgtgccga gcagcagctt aggcactcag     600
acctatattt gcaacgtgaa ccataaaccg agcaacacca agtggataa aaaagtggaa      660
ccgaaaagcn                                                            670
```

<210> SEQ ID NO 248
<211> LENGTH: 637
<212> TYPE: DNA
<213> ORGANISM: homo sapiens
<220> FEATURE:
<221> NAME/KEY: misc_feature
<222> LOCATION: (637)..(637)
<223> OTHER INFORMATION: n can be TGCAGC or GCC

<400> SEQUENCE: 248

```
gatatcgtgc tgacccagcc gccttcagtg agtggcgcac caggtcagcg tgtgaccatc      60
tcgtgtagcg gcagcagcag caacattggt tctaattatg tgtcttggta ccagcagttg     120
cccgggacgg cgccgaaact tctgatttat cgtaatgata agcgtccctc aggcgtgccg     180
gatcgttta gcggatccaa aagcggcacc agcgcgagcc ttgcgattac gggcctgcaa      240
agcgaagacg aagcggatta ttattgccag tctgctgatt cttcttctat ggtgtttggc     300
ggcggcacga agttaaccgt tcttggccag ccgaaagccg caccgagtgt gacgctgttt     360
ccgccgagca gcgaagaatt gcaggcgaac aaagcgaccc tggtgtgcct gattagcgac     420
ttttatccgg gagccgtgac agtggcctgg aaggcagata gcagccccgt caaggcggga     480
gtggagacca ccacaccctc caaacaaagc aacaacaagt acgcggccag cagctatctg     540
agcctgacgc ctgagcagtg gaagtccac agaagctaca gctgccaggt cacgcatgag      600
gggagcaccg tggaaaaaac cgttgcgccg actgagn                              637
```

<210> SEQ ID NO 249
<211> LENGTH: 219
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: X can be C, EF, or CEF

<400> SEQUENCE: 249

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

Gly Asn Ile Gly Pro Phe Phe Gly Ile Ala Asn Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Xaa
    210                 215

<210> SEQ ID NO 250
<211> LENGTH: 655
<212> TYPE: DNA
<213> ORGANISM: homo sapiens
<220> FEATURE:
<221> NAME/KEY: misc_feature
<222> LOCATION: (655)..(655)
<223> OTHER INFORMATION: n can be TGC, GAATTC, or TGCGAATTC

<400> SEQUENCE: 250
caggtgcaat tggttcagtc tggcgcggaa gtgaaaaaac cgggcagcag cgtgaaagtg      60
agctgcaaag cctccggagg cacttttttct tcttatgcca tttcttgggt gcgccaagcc    120
cctgggcagg gtctcgagtg gatgggcaat atcggtccgt tttttggcat tgcgaattac    180
gcgcagaagt tcagggccg gtgaccatt accgcggatg aaagcaccag caccgcgtat     240
atggaactga gcagcctgcg tagcgaagat acggccgtgt attattgcgc gcgtgatact    300
ccttattttg attattgggg ccaaggcacc ctggtgacgg ttagctcagc gtcgaccaaa    360
ggtccaagcg tgtttccgct ggctccgagc agcaaaagca ccagcggcgg cacggctgcc    420
ctgggctgcc tggttaaaga ttatttcccg gaaccagtca ccgtgagctg aacagcggg    480 gcgctgacca gcggcgtgca tacctttccg gcggtgctgc aaagcagcgg cctgtatagc    540
ctgagcagcg ttgtgaccgt gccgagcagc agcttaggca ctcagaccta tatttgcaac    600
gtgaaccata aaccgagcaa caccaaagtg gataaaaaag tggaaccgaa aagcn         655

<210> SEQ ID NO 251
<211> LENGTH: 213
<212> TYPE: PRT
<213> ORGANISM: homo sapiens
<220> FEATURE:
<221> NAME/KEY: MISC_FEATURE
<222> LOCATION: (213)..(213)
<223> OTHER INFORMATION: X can be CS or A

<400> SEQUENCE: 251

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Asp Gly Ser Thr Ala
                85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Xaa
    210

<210> SEQ ID NO 252
<211> LENGTH: 637
<212> TYPE: DNA
<213> ORGANISM: homo sapiens
<220> FEATURE:
<221> NAME/KEY: misc_feature
<222> LOCATION: (637)..(637)
<223> OTHER INFORMATION: n can be TGCAGC or GCC

<400> SEQUENCE: 252
gatatcgaac tgacccagcc gccttcagtg agcgttgcac caggtcagac cgcgcgtatc      60
tcgtgtagcg gcgattctat tcctaattat tatgtttatt ggtaccagca gaaacccggg     120
caggcgccag ttcttgtgat ttatgatgat tctaatcgtc cctcaggcat cccggaacgc     180
tttagcggat ccaacagcgg caacaccgcg accctgacca ttagcggcac tcaggcggaa     240
gacgaagcgg attattattg ccagacttat gatgatggtt ctactgctga ggtgtttggc     300
ggcggcacga agttaaccgt tcttggccag ccgaaagccg caccgagtgt gacgctgttt     360
ccgccgagca gcgaagaatt gcaggcgaac aaagcgaccc tggtgtgcct gattagcgac     420
ttttatccgg gagccgtgac agtggcctgg aaggcagata gcagcccgt caaggcggga     480 gtggagacca ccacaccctc aaacaaagc aacaacaagt acgcggccag cagctatctg     540
agcctgacgc ctgagcagtg gaagtcccac agaagctaca gctgccaggt cacgcatgag     600
gggagcaccg tggaaaaaac cgttgcgccg actgagn                              637

<210> SEQ ID NO 253
<211> LENGTH: 117
<212> TYPE: PRT
```

<213> ORGANISM: homo sapiens

<400> SEQUENCE: 253

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Tyr Ile Gly Trp Val Arg Gln Met Pro Gly Lys Gly Leu Glu Trp Met
        35                  40                  45

Gly Ile Ile Asp Pro Thr Asp Ser Gln Thr Ala Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Met Arg Gly Phe Asp His Trp Gly Gln Gly Thr Leu
            100                 105                 110

Val Thr Val Ser Ser
        115
```

<210> SEQ ID NO 254
<211> LENGTH: 220
<212> TYPE: PRT
<213> ORGANISM: homo sapiens
<220> FEATURE:
<221> NAME/KEY: MISC_FEATURE
<222> LOCATION: (220)..(220)
<223> OTHER INFORMATION: X can be C, EF, or CEF

<400> SEQUENCE: 254

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Tyr Ile Gly Trp Val Arg Gln Met Pro Gly Lys Gly Leu Glu Trp Met
        35                  40                  45

Gly Ile Ile Asp Pro Thr Asp Ser Gln Thr Ala Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Met Arg Gly Phe Asp His Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Xaa
```

<210> SEQ ID NO 255
<211> LENGTH: 351
<212> TYPE: DNA
<213> ORGANISM: homo sapiens

<400> SEQUENCE: 255
caggtgcaat tggttcagag cggcgcggaa gtgaaaaaac cgggcgaaag cctgaaaatt      60
agctgcaaag gttccggata ttcctttact tcttattata ttggttgggt gcgccagatg     120
cctgggaagg gtctcgagtg gatgggcatt attgatccta ctgattctca gactgcttat     180
tctccttctt ttcagggtca ggtgaccatt agcgcggata aaagcattag caccgcgtat     240
cttcaatgga gcagcctgaa agcgagcgat acggccatgt attattgcgc gcgttatatg     300
atgcgtggtt ttgatcattg gggccaaggc accctggtga cggttagctc a             351

<210> SEQ ID NO 256
<211> LENGTH: 658
<212> TYPE: DNA
<213> ORGANISM: homo sapiens
<220> FEATURE:
<221> NAME/KEY: misc_feature
<222> LOCATION: (658)..(658)
<223> OTHER INFORMATION: n can be TGC, GAATTC, or TGCGAATTC

<400> SEQUENCE: 256
caggtgcaat tggttcagag cggcgcggaa gtgaaaaaac cgggcgaaag cctgaaaatt      60
agctgcaaag gttccggata ttcctttact tcttattata ttggttgggt gcgccagatg     120
cctgggaagg gtctcgagtg gatgggcatt attgatccta ctgattctca gactgcttat     180
tctccttctt ttcagggtca ggtgaccatt agcgcggata aaagcattag caccgcgtat     240
cttcaatgga gcagcctgaa agcgagcgat acggccatgt attattgcgc gcgttatatg     300
atgcgtggtt ttgatcattg gggccaaggc accctggtga cggttagctc agcgtcgacc     360
aaaggtccaa gcgtgtttcc gctggctccg agcagcaaaa gcaccagcgg cggcacggct     420
gccctgggct gcctggttaa agattatttc ccggaaccag tcaccgtgag ctggaacagc     480
ggggcgctga ccagcggcgt gcataccttt ccggcggtgc tgcaaagcag cggcctgtat     540
agcctgagca cgttgtgac cgtgccgagc agcagcttag gcactcagac ctatatttgc     600
aacgtgaacc ataaaccgag caacaccaaa gtggataaaa aagtggaacc gaaaagcn     658

<210> SEQ ID NO 257
<211> LENGTH: 117
<212> TYPE: PRT
<213> ORGANISM: homo sapiens

<400> SEQUENCE: 257

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Tyr Ile Gly Trp Val Arg Gln Met Pro Gly Lys Gly Leu Glu Trp Met
        35                  40                  45

Gly Ile Ile Asp Pro Thr Asp Ser Gln Thr Ala Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys

```
                    85                  90                  95
Ala Arg Tyr Met Met Arg Gly Phe Asp His Trp Gly Gln Gly Thr Leu
                100                 105                 110

Val Thr Val Ser Ser
        115

<210> SEQ ID NO 258
<211> LENGTH: 220
<212> TYPE: PRT
<213> ORGANISM: homo sapiens
<220> FEATURE:
<221> NAME/KEY: MISC_FEATURE
<222> LOCATION: (220)..(220)
<223> OTHER INFORMATION: X can be C, EF, or CEF

<400> SEQUENCE: 258

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Tyr Ile Gly Trp Val Arg Gln Met Pro Gly Lys Gly Leu Glu Trp Met
        35                  40                  45

Gly Ile Ile Asp Pro Thr Asp Ser Tyr Thr Val Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Met Arg Gly Phe Asp His Trp Gly Gln Gly Thr Leu
                100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Xaa
    210                 215                 220

<210> SEQ ID NO 259
<211> LENGTH: 351
<212> TYPE: DNA
<213> ORGANISM: homo sapiens

<400> SEQUENCE: 259
caggtgcaat tggttcagag cggcgcggaa gtgaaaaaac cgggcgaaag cctgaaaatt      60
agctgcaaag gttccggata ttcctttact tcttattata ttggttgggt gcgccagatg     120
cctgggaagg gtctcgagtg gatgggcatt attgatccta ctgattctta tactgtttat     180
tctccttctt ttcagggtca ggtgaccatt agcgcggata aaagcattag caccgcgtat     240
cttcaatgga gcagcctgaa agcgagcgat acggccatgt attattgcgc gcgttatatg     300
```

```
atgcgtggtt ttgatcattg gggccaaggc accctggtga cggttagctc a         351
```

<210> SEQ ID NO 260
<211> LENGTH: 658
<212> TYPE: DNA
<213> ORGANISM: homo sapiens
<220> FEATURE:
<221> NAME/KEY: misc_feature
<222> LOCATION: (658)..(658)
<223> OTHER INFORMATION: n can be TGC, GAATTC, or TGCGAATTC

<400> SEQUENCE: 260

```
caggtgcaat tggttcagag cggcgcggaa gtgaaaaaac cgggcgaaag cctgaaaatt    60
agctgcaaag gttccggata ttcctttact tcttattata ttggttgggt gcgccagatg   120
cctgggaagg gtctcgagtg gatgggcatt attgatccta ctgattctta tactgtttat   180
tctccttctt ttcagggtca ggtgaccatt agcgcggata aaagcattag caccgcgtat   240
cttcaatgga gcagcctgaa agcgagcgat acggccatgt attattgcgc gcgttatatg   300
atgcgtggtt ttgatcattg gggccaaggc accctggtga cggttagctc agcgtcgacc   360
aaaggtccaa gcgtgtttcc gctggctccg agcagcaaaa gcaccagcgg cggcacggct   420
gccctgggct gcctggttaa agattatttc ccggaaccag tcaccgtgag ctggaacagc   480
ggggcgctga ccagcggcgt gcataccttt ccggcggtgc tgcaaagcag cggcctgtat   540
agcctgagca gcgttgtgac cgtgccgagc agcagcttag gcactcagac ctatatttgc   600
aacgtgaacc ataaaccgag caacaccaaa gtggataaaa agtggaacc gaaaagcn    658
```

<210> SEQ ID NO 261
<211> LENGTH: 107
<212> TYPE: PRT
<213> ORGANISM: homo sapiens

<400> SEQUENCE: 261

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
                20                  25                  30

Tyr Trp Tyr Gln Gln Lys Pro Gly Gln Ala Pro Val Leu Val Ile Tyr
            35                  40                  45

Lys Asp Asn Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Thr Gly Glu Ser Gly
                85                  90                  95

Val Phe Gly Gly Gly Thr Lys Leu Thr Val Leu
            100                 105

<210> SEQ ID NO 262
<211> LENGTH: 212
<212> TYPE: PRT
<213> ORGANISM: homo sapiens
<220> FEATURE:
<221> NAME/KEY: MISC_FEATURE
<222> LOCATION: (212)..(212)
<223> OTHER INFORMATION: X can be CS or A

<400> SEQUENCE: 262

Asp Ile Glu Leu Thr Gln Pro Pro Ser Val Ser Val Ala Pro Gly Gln
1               5                   10                  15

```
Thr Ala Arg Ile Ser Cys Ser Gly Asp Ser Leu Gly Asp Tyr Tyr Ala
             20                  25                  30
Tyr Trp Tyr Gln Gln Lys Pro Gly Gln Ala Pro Val Leu Val Ile Tyr
         35                  40                  45
Lys Asp Asn Asn Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Glu
 65                  70                  75                  80
Asp Glu Ala Asp Tyr Tyr Cys Gln Thr Trp Asp Thr Gly Glu Ser Gly
                 85                  90                  95
Val Phe Gly Gly Gly Thr Lys Leu Thr Val Leu Gly Gln Pro Lys Ala
            100                 105                 110
Ala Pro Ser Val Thr Leu Phe Pro Pro Ser Ser Glu Glu Leu Gln Ala
        115                 120                 125
Asn Lys Ala Thr Leu Val Cys Leu Ile Ser Asp Phe Tyr Pro Gly Ala
130                 135                 140
Val Thr Val Ala Trp Lys Ala Asp Ser Ser Pro Val Lys Ala Gly Val
145                 150                 155                 160
Glu Thr Thr Thr Pro Ser Lys Gln Ser Asn Asn Lys Tyr Ala Ala Ser
                165                 170                 175
Ser Tyr Leu Ser Leu Thr Pro Glu Gln Trp Lys Ser His Arg Ser Tyr
            180                 185                 190
Ser Cys Gln Val Thr His Glu Gly Ser Thr Val Glu Lys Thr Val Ala
        195                 200                 205
Pro Thr Glu Xaa
    210

<210> SEQ ID NO 263
<211> LENGTH: 321
<212> TYPE: DNA
<213> ORGANISM: homo sapiens

<400> SEQUENCE: 263
gatatcgaac tgacccagcc gccttcagtg agcgttgcac caggtcagac cgcgcgtatc      60
tcgtgtagcg gcgattctct tggtgattat tatgcttatt ggtaccagca gaaacccggg     120
caggcgccag ttcttgtgat ttataaggat aataatcgtc cctcaggcat cccggaacgc     180
tttagcggat ccaacagcgg caacaccgcg accctgacca ttagcggcac tcaggcggaa     240
gacgaagcgg attattattg ccagacttgg gatactggtg agtctggtgt gtttggcggc     300
ggcacgaagt taaccgttct t                                                321

<210> SEQ ID NO 264
<211> LENGTH: 634
<212> TYPE: DNA
<213> ORGANISM: homo sapiens
<220> FEATURE:
<221> NAME/KEY: misc_feature
<222> LOCATION: (634)..(634)
<223> OTHER INFORMATION: n can be TGCAGC or GCC

<400> SEQUENCE: 264
gatatcgaac tgacccagcc gccttcagtg agcgttgcac caggtcagac cgcgcgtatc      60
tcgtgtagcg gcgattctct tggtgattat tatgcttatt ggtaccagca gaaacccggg     120
caggcgccag ttcttgtgat ttataaggat aataatcgtc cctcaggcat cccggaacgc     180
tttagcggat ccaacagcgg caacaccgcg accctgacca ttagcggcac tcaggcggaa     240
gacgaagcgg attattattg ccagacttgg gatactggtg agtctggtgt gtttggcggc     300
```

```
ggcacgaagt taaccgttct tggccagccg aaagccgcac cgagtgtgac gctgtttccg    360
ccgagcagcg aagaattgca ggcgaacaaa gcgaccctgg tgtgcctgat tagcgacttt    420
tatccgggag ccgtgacagt ggcctggaag gcagatagca gccccgtcaa ggcgggagtg    480
gagaccacca caccctccaa acaaagcaac aacaagtacg cggccagcag ctatctgagc    540
ctgacgcctg agcagtggaa gtcccacaga agctacagct gccaggtcac gcatgagggg    600
agcaccgtgg aaaaaaccgt tgcgccgact gagn                                634
```

<210> SEQ ID NO 265
<211> LENGTH: 108
<212> TYPE: PRT
<213> ORGANISM: homo sapiens

<400> SEQUENCE: 265

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Ile Leu Pro His Gly
                85                  90                  95

Leu Val Phe Gly Gly Gly Thr Lys Leu Thr Val Leu
            100                 105
```

<210> SEQ ID NO 266
<211> LENGTH: 213
<212> TYPE: PRT
<213> ORGANISM: homo sapiens
<220> FEATURE:
<221> NAME/KEY: MISC_FEATURE
<222> LOCATION: (213)..(213)
<223> OTHER INFORMATION: X can be CS or A

<400> SEQUENCE: 266

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Ile Leu Pro His Gly
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140
```

```
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Xaa
    210

<210> SEQ ID NO 267
<211> LENGTH: 324
<212> TYPE: DNA
<213> ORGANISM: homo sapiens

<400> SEQUENCE: 267
gatatcgaac tgacccagcc gccttcagtg agcgttgcac caggtcagac cgcgcgtatc    60
tcgtgtagcg gcgattctct tggtgattat tatgcttatt ggtaccagca gaaacccggg   120
caggcgccag ttcttgtgat ttataaggat aataatcgtc cctcaggcat cccggaacgc   180
tttagcggat ccaacagcgg caacaccgcg accctgacca ttagcggcac tcaggcggaa   240
gacgaagcgg attattattg ccagacttgg gatattcttc ctcatggtct tgtgtttggc   300
ggcggcacga agttaaccgt tctt                                          324

<210> SEQ ID NO 268
<211> LENGTH: 637
<212> TYPE: DNA
<213> ORGANISM: homo sapiens
<220> FEATURE:
<221> NAME/KEY: misc_feature
<222> LOCATION: (637)..(637)
<223> OTHER INFORMATION: n can be TGCAGC or GCC

<400> SEQUENCE: 268
gatatcgaac tgacccagcc gccttcagtg agcgttgcac caggtcagac cgcgcgtatc    60
tcgtgtagcg gcgattctct tggtgattat tatgcttatt ggtaccagca gaaacccggg   120
caggcgccag ttcttgtgat ttataaggat aataatcgtc cctcaggcat cccggaacgc   180
tttagcggat ccaacagcgg caacaccgcg accctgacca ttagcggcac tcaggcggaa   240
gacgaagcgg attattattg ccagacttgg gatattcttc ctcatggtct tgtgtttggc   300
ggcggcacga agttaaccgt tcttggccag ccgaaagccg caccgagtgt gacgctgttt   360
ccgccgagca gcgaagaatt gcaggcgaac aaagcgaccc tggtgtgcct gattagcgac   420
ttttatccgg gagccgtgac agtggcctgg aaggcagata gcagcccgt caaggcggga    480 gtggagacca ccacccctc caaacaaagc aacaacaagt acgcggccag cagctatctg   540
agcctgacgc ctgagcagtg gaagtcccac agaagctaca gctgccaggt cacgcatgag   600
gggagcaccg tggaaaaaac cgttgcgccg actgagn                            637

<210> SEQ ID NO 269
<211> LENGTH: 108
<212> TYPE: PRT
<213> ORGANISM: homo sapiens

<400> SEQUENCE: 269

Asp Ile Glu Leu Thr Gln Pro Pro Ser Val Ser Val Ala Pro Gly Gln
1               5                   10                  15
```

```
Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ala Trp Thr Asp Ser Pro Thr Gly
                85                  90                  95

Leu Val Phe Gly Gly Gly Thr Lys Leu Thr Val Leu
            100                 105
```

```
<210> SEQ ID NO 270
<211> LENGTH: 213
<212> TYPE: PRT
<213> ORGANISM: homo sapiens
<220> FEATURE:
<221> NAME/KEY: MISC_FEATURE
<222> LOCATION: (213)..(213)
<223> OTHER INFORMATION: X can be CS or A

<400> SEQUENCE: 270

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ala Trp Thr Asp Ser Pro Thr Gly
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Xaa
    210
```

```
<210> SEQ ID NO 271
<211> LENGTH: 324
<212> TYPE: DNA
<213> ORGANISM: homo sapiens

<400> SEQUENCE: 271
```

```
gatatcgaac tgacccagcc gccttcagtg agcgttgcac caggtcagac cgcgcgtatc    60
tcgtgtagcg gcgattctct tggtgattat tatgcttatt ggtaccagca gaaacccggg   120
caggcgccag ttcttgtgat ttataaggat aataatcgtc cctcaggcat cccggaacgc   180
tttagcggat ccaacagcgg caacaccgcg accctgacca ttagcggcac tcaggcggaa   240
gacgaagcgg attattattg ccaggcttgg actgattctc ctactggtct tgtgtttggc   300
ggcggcacga agttaaccgt tctt                                          324
```

<210> SEQ ID NO 272
<211> LENGTH: 637
<212> TYPE: DNA
<213> ORGANISM: homo sapiens
<220> FEATURE:
<221> NAME/KEY: misc_feature
<222> LOCATION: (637)..(637)
<223> OTHER INFORMATION: n can be TGCAGC or GCC

<400> SEQUENCE: 272

```
gatatcgaac tgacccagcc gccttcagtg agcgttgcac caggtcagac cgcgcgtatc    60
tcgtgtagcg gcgattctct tggtgattat tatgcttatt ggtaccagca gaaacccggg   120
caggcgccag ttcttgtgat ttataaggat aataatcgtc cctcaggcat cccggaacgc   180
tttagcggat ccaacagcgg caacaccgcg accctgacca ttagcggcac tcaggcggaa   240
gacgaagcgg attattattg ccaggcttgg actgattctc ctactggtct tgtgtttggc   300
ggcggcacga agttaaccgt tcttggccag ccgaaagccg caccgagtgt gacgctgttt   360
ccgccgagca gcgaagaatt gcaggcgaac aaagcgaccc tggtgtgcct gattagcgac   420
ttttatccgg gagccgtgac agtggcctgg aaggcagata gcagcccgt caaggcggga   480 gtggagacca ccacaccctc caaacaaagc aacaacaagt acgcggccag cagctatctg   540
agcctgacgc ctgagcagtg gaagtcccac agaaagctaca gctgccaggt cacgcatgag   600
gggagcaccg tggaaaaaac cgttgcgccg actgagn                            637
```

<210> SEQ ID NO 273
<211> LENGTH: 116
<212> TYPE: PRT
<213> ORGANISM: homo sapiens

<400> SEQUENCE: 273

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Asp Asp Ser Tyr Thr Glu Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

```
<210> SEQ ID NO 274
<211> LENGTH: 219
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: X can be C, EF, or CEF

<400> SEQUENCE: 274
```

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Xaa
210                 215

```
<210> SEQ ID NO 275
<211> LENGTH: 348
<212> TYPE: DNA
<213> ORGANISM: homo sapiens

<400> SEQUENCE: 275
```
caggtgcaat tggttcagag cggcgcggaa gtgaaaaaac cgggcgaaag cctgaaaatt        60
agctgcaaag gttccggata ttcctttact aattatattt cttgggtgcg ccagatgcct       120
gggaagggtc tcgagtggat gggcattatt gatcctgatg attcttatac tgagtattct       180
ccttcttttc agggtcaggt caccattagc gcggataaaa gcattagcac cgcgtatctt       240
caatggagca gcctgaaagc gagcgatacg gccatgtatt attgcgcgcg ttatgagtat       300
ggtggttttg atatttgggg ccaaggcacc ctggtgacgg ttagctca                    348

```
<210> SEQ ID NO 276
<211> LENGTH: 655
<212> TYPE: DNA
<213> ORGANISM: homo sapiens
<220> FEATURE:
<221> NAME/KEY: misc_feature
```

<222> LOCATION: (655)..(655)
<223> OTHER INFORMATION: n can be TGC, GAATTC, or TGCGAATTC

<400> SEQUENCE: 276

```
caggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatt gatcctgatg attcttatac tgagtattct     180
ccttcttttc agggtcaggt caccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctcagc gtcgaccaaa     360
ggtccaagcg tgtttccgct ggctccgagc agcaaaagca ccagcggcgg cacggctgcc     420
ctgggctgcc tggttaaaga ttatttcccg aaccagtca ccgtgagctg aacagcggg      480
gcgctgacca gcggcgtgca tacctttccg gcggtgctgc aaagcagcgg cctgtatagc     540
ctgagcagcg ttgtgaccgt gccgagcagc agcttaggca ctcagaccta tatttgcaac     600
gtgaaccata aaccgagcaa caccaaagtg gataaaaaag tggaaccgaa aagcn          655
```

<210> SEQ ID NO 277
<211> LENGTH: 116
<212> TYPE: PRT
<213> ORGANISM: homo sapiens

<400> SEQUENCE: 277

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Gln Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115
```

<210> SEQ ID NO 278
<211> LENGTH: 219
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: X can be C, EF, or CEF

<400> SEQUENCE: 278

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45
```

```
Ile Ile Asp Pro Gln Asp Ser Tyr Thr Glu Tyr Ser Pro Ser Phe Gln
 50                  55                  60

Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
                 85                  90                  95

Arg Tyr Glu Tyr Gly Gly Phe Asp Ile Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Xaa
            210                 215
```

<210> SEQ ID NO 279
<211> LENGTH: 348
<212> TYPE: DNA
<213> ORGANISM: homo sapiens

<400> SEQUENCE: 279

```
caggtgcaat tggttcagag cggcgcggaa gtgaaaaaac cgggcgaaag cctgaaaatt    60
agctgcaaag gttccggata ttcctttact aattatattt cttgggtgcg ccagatgcct   120
gggaagggtc tcgagtggat gggcattatt gatcctcagg attcttatac tgagtattct   180
ccttcttttc agggtcaggt caccattagc gcggataaaa gcattagcac cgcgtatctt   240
caatggagca gcctgaaagc gagcgatacg gccatgtatt attgcgcgcg ttatgagtat   300
ggtggttttg atatttgggg ccaaggcacc ctggtgacgg ttagctca                348
```

<210> SEQ ID NO 280
<211> LENGTH: 655
<212> TYPE: DNA
<213> ORGANISM: homo sapiens
<220> FEATURE:
<221> NAME/KEY: misc_feature
<222> LOCATION: (655)..(655)
<223> OTHER INFORMATION: n can be TGC, GAATTC, TGCGAATTC

<400> SEQUENCE: 280

```
caggtgcaat tggttcagag cggcgcggaa gtgaaaaaac cgggcgaaag cctgaaaatt    60
agctgcaaag gttccggata ttcctttact aattatattt cttgggtgcg ccagatgcct   120
gggaagggtc tcgagtggat gggcattatt gatcctcagg attcttatac tgagtattct   180
ccttcttttc agggtcaggt caccattagc gcggataaaa gcattagcac cgcgtatctt   240
caatggagca gcctgaaagc gagcgatacg gccatgtatt attgcgcgcg ttatgagtat   300
ggtggttttg atatttgggg ccaaggcacc ctggtgacgg ttagctcagc gtcgaccaaa   360
ggtccaagcg tgtttccgct ggctccgagc agcaaaagca ccagcggcgg cacggctgcc   420
ctgggctgcc tggttaaaga ttatttcccg gaaccagtca ccgtgagctg gaacagcggg   480
```

```
gcgctgacca gcggcgtgca tacctttccg gcggtgctgc aaagcagcgg cctgtatagc   540
ctgagcagcg ttgtgaccgt gccgagcagc agcttaggca ctcagaccta tatttgcaac   600
gtgaaccata aaccgagcaa caccaaagtg gataaaaaag tggaaccgaa aagcn        655
```

<210> SEQ ID NO 281
<211> LENGTH: 116
<212> TYPE: PRT
<213> ORGANISM: homo sapiens

<400> SEQUENCE: 281

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Glu Asp Ser His Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
            115
```

<210> SEQ ID NO 282
<211> LENGTH: 219
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: X can be C, EF, or CEF

<400> SEQUENCE: 282

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Glu Asp Ser His Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Xaa
    210                 215

<210> SEQ ID NO 283
<211> LENGTH: 348
<212> TYPE: DNA
<213> ORGANISM: homo sapiens

<400> SEQUENCE: 283
caggtgcaat tggttcagag cggcgcggaa gtgaaaaaac cgggcgaaag cctgaaaatt       60
agctgcaaag gttccggata ttcctttact aattatattt cttgggtgcg ccagatgcct      120
gggaagggtc tcgagtggat gggcattatt gatcctgagg attctcatac tgagtattct      180
ccttcttttc agggtcaggt gaccattagc gcggataaaa gcattagcac cgcgtatctt      240
caatggagca gcctgaaagc gagcgatacg gccatgtatt attgcgcgcg ttatgagtat      300
ggtggttttg atatttgggg ccaaggcacc ctggtgacgg ttagctca                   348

<210> SEQ ID NO 284
<211> LENGTH: 655
<212> TYPE: DNA
<213> ORGANISM: homo sapiens
<220> FEATURE:
<221> NAME/KEY: misc_feature
<222> LOCATION: (655)..(655)
<223> OTHER INFORMATION: n can be TGC, GAATTC, or TGCGAATTC

<400> SEQUENCE: 284
caggtgcaat tggttcagag cggcgcggaa gtgaaaaaac cgggcgaaag cctgaaaatt       60
agctgcaaag gttccggata ttcctttact aattatattt cttgggtgcg ccagatgcct      120
gggaagggtc tcgagtggat gggcattatt gatcctgagg attctcatac tgagtattct      180
ccttcttttc agggtcaggt gaccattagc gcggataaaa gcattagcac cgcgtatctt      240
caatggagca gcctgaaagc gagcgatacg gccatgtatt attgcgcgcg ttatgagtat      300
ggtggttttg atatttgggg ccaaggcacc ctggtgacgg ttagctcagc gtcgaccaaa      360
ggtccaagcg tgtttccgct ggctccgagc agcaaaagca ccagcggcgg cacggctgcc      420
ctgggctgcc tggttaaaga ttatttcccg gaaccagtca ccgtgagctg gaacagcggg      480
gcgctgacca gcggcgtgca tacctttccg gcggtgctgc aaagcagcgg cctgtatagc      540
ctgagcagcg ttgtgaccgt gccgagcagc agcttaggca ctcagaccta tatttgcaac      600
gtgaaccata aaccgagcaa caccaaagtg gataaaaaag tggaaccgaa aagcn          655

<210> SEQ ID NO 285
<211> LENGTH: 106
<212> TYPE: PRT
<213> ORGANISM: homo sapiens

<400> SEQUENCE: 285

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30
```

```
His Trp Tyr Gln Gln Lys Pro Gly Gln Ala Pro Val Leu Val Ile Tyr
            35                  40                  45

Lys Asp Asn Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Thr Trp Gly Ser Glu Asp Gln Val
                 85                  90                  95

Phe Gly Gly Gly Thr Lys Leu Thr Val Leu
                100                 105

<210> SEQ ID NO 286
<211> LENGTH: 211
<212> TYPE: PRT
<213> ORGANISM: homo sapiens
<220> FEATURE:
<221> NAME/KEY: MISC_FEATURE
<222> LOCATION: (211)..(211)
<223> OTHER INFORMATION: X can be CS or A

<400> SEQUENCE: 286

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Asn Ser Tyr Val
                20                  25                  30

His Trp Tyr Gln Gln Lys Pro Gly Gln Ala Pro Val Leu Val Ile Tyr
            35                  40                  45

Lys Asp Asn Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Thr Trp Gly Ser Glu Asp Gln Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
                115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
                195                 200                 205

Thr Glu Xaa
    210

<210> SEQ ID NO 287
<211> LENGTH: 318
<212> TYPE: DNA
<213> ORGANISM: homo sapiens

<400> SEQUENCE: 287
gatatcgaac tgacccagcc gccttcagtg agcgttgcac caggtcagac cgcgcgtatc    60
```

```
tcgtgtagcg gcgataatat tggtaattct tatgttcatt ggtaccagca gaaacccggg    120
caggcgccag ttcttgtgat ttataaggat aatgatcgtc cctcaggcat cccggaacgc    180
tttagcggat ccaacagcgg caacaccgcg accctgacca ttagcggcac tcaggcggaa    240
gacgaagcgg attattattg cgctacttgg ggttctgagg atcaggtgtt tggcggcggc    300
acgaagttaa ccgttctt                                                  318
```

```
<210> SEQ ID NO 288
<211> LENGTH: 631
<212> TYPE: DNA
<213> ORGANISM: homo sapiens
<220> FEATURE:
<221> NAME/KEY: misc_feature
<222> LOCATION: (631)..(631)
<223> OTHER INFORMATION: n can be TGCAGC or GCC

<400> SEQUENCE: 288
```

```
gatatcgaac tgacccagcc gccttcagtg agcgttgcac caggtcagac cgcgcgtatc     60
tcgtgtagcg gcgataatat tggtaattct tatgttcatt ggtaccagca gaaacccggg    120
caggcgccag ttcttgtgat ttataaggat aatgatcgtc cctcaggcat cccggaacgc    180
tttagcggat ccaacagcgg caacaccgcg accctgacca ttagcggcac tcaggcggaa    240
gacgaagcgg attattattg cgctacttgg ggttctgagg atcaggtgtt tggcggcggc    300
acgaagttaa ccgttcttgg ccagccgaaa gccgcaccga gtgtgacgct gtttccgccg    360
agcagcgaag aattgcaggc gaacaaagcg accctggtgt gcctgattag cgactttat    420 ccgggagccg tgacagtggc ctggaaggca gatagcagcc ccgtcaaggc gggagtggag    480
accaccacac cctccaaaca aagcaacaac aagtacgcgg ccagcagcta tctgagcctg    540
acgcctgagc agtggaagtc ccacagaagc tacagctgcc aggtcacgca tgagggagc    600 accgtggaaa aaaccgttgc gccgactgag n                                   631
```

```
<210> SEQ ID NO 289
<211> LENGTH: 107
<212> TYPE: PRT
<213> ORGANISM: homo sapiens

<400> SEQUENCE: 289
```

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Trp Asp Ile Glu Pro Thr Tyr
                85                  90                  95

Val Phe Gly Gly Gly Thr Lys Leu Thr Val Leu
            100                 105

```
<210> SEQ ID NO 290
<211> LENGTH: 212
<212> TYPE: PRT
<213> ORGANISM: homo sapiens
<220> FEATURE:
<221> NAME/KEY: MISC_FEATURE
```

<222> LOCATION: (212)..(212)
<223> OTHER INFORMATION: X can be CS or A

<400> SEQUENCE: 290

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Trp Asp Ile Glu Pro Thr Tyr
                85                  90                  95

Val Phe Gly Gly Gly Thr Lys Leu Thr Val Leu Gly Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Xaa
    210

<210> SEQ ID NO 291
<211> LENGTH: 321
<212> TYPE: DNA
<213> ORGANISM: homo sapiens

<400> SEQUENCE: 291
gatatcgaac tgacccagcc gccttcagtg agcgttgcac caggtcagac cgcgcgtatc      60
tcgtgtagcg gcgataatat tggtaattct tatgttcatt ggtaccagca gaaacccggg     120
caggcgccag ttcttgtgat ttataaggat aatgatcgtc cctcaggcat cccggaacgc     180
tttagcggat ccaacagcgg caacaccgcg accctgacca ttagcggcac tcaggcggaa     240
gacgaagcgg attattattg ctctacttgg gatattgagc ctacttatgt gtttggcggc     300
ggcacgaagt taaccgttct t                                              321

<210> SEQ ID NO 292
<211> LENGTH: 634
<212> TYPE: DNA
<213> ORGANISM: homo sapiens
<220> FEATURE:
<221> NAME/KEY: misc_feature
<222> LOCATION: (634)..(634)
<223> OTHER INFORMATION: n can be TGCAGC or GCC

<400> SEQUENCE: 292
gatatcgaac tgacccagcc gccttcagtg agcgttgcac caggtcagac cgcgcgtatc      60

```
tcgtgtagcg gcgataatat tggtaattct tatgttcatt ggtaccagca gaaacccggg      120
caggcgccag ttcttgtgat ttataaggat aatgatcgtc cctcaggcat cccggaacgc      180
tttagcggat ccaacagcgg caacaccgcg accctgacca ttagcggcac tcaggcggaa      240
gacgaagcgg attattattg ctctacttgg gatattgagc ctacttatgt gtttggcggc      300
ggcacgaagt taaccgttct tggccagccg aaagccgcac cgagtgtgac gctgtttccg      360
ccgagcagcg aagaattgca ggcgaacaaa gcgaccctgg tgtgcctgat tagcgacttt      420
tatccgggag ccgtgacagt ggcctggaag gcagatagca gccccgtcaa ggcgggagtg      480
gagaccacca caccctccaa acaaagcaac aacaagtacg cggccagcag ctatctgagc      540
ctgacgcctg agcagtggaa gtcccacaga agctacagct gccaggtcac gcatgagggg      600
agcaccgtgg aaaaaaccgt tgcgccgact gagn                                 634
```

<210> SEQ ID NO 293
<211> LENGTH: 228
<212> TYPE: PRT
<213> ORGANISM: homo sapiens

<400> SEQUENCE: 293

```
Cys Asp Lys Thr His Thr Cys Pro Pro Cys Pro Ala Pro Glu Ala Ala
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 294
<211> LENGTH: 103
<212> TYPE: PRT
<213> ORGANISM: homo sapiens
<220> FEATURE:

```
<221> NAME/KEY: misc_feature
<222> LOCATION: (103)..(103)
<223> OTHER INFORMATION: Xaa can be any naturally occurring amino acid

<400> SEQUENCE: 294

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Xaa
            100

<210> SEQ ID NO 295
<211> LENGTH: 326
<212> TYPE: PRT
<213> ORGANISM: homo sapiens

<400> SEQUENCE: 295

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

-continued

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 296
<211> LENGTH: 1676
<212> TYPE: PRT
<213> ORGANISM: homo sapiens

<400> SEQUENCE: 296

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

-continued

Asn Thr Met Leu Ile Asn Gly Ile Ala Gln Val Thr Phe Asp Ser Glu
290                     295                 300

Thr Ala Val Lys Glu Leu Ser Tyr Tyr Ser Leu Glu Asp Leu Asn Asn
305                     310                 315                 320

Lys Tyr Leu Tyr Ile Ala Val Thr Val Ile Glu Ser Thr Gly Gly Phe
                325                     330                 335

Ser Glu Glu Ala Glu Ile Pro Gly Ile Lys Tyr Val Leu Ser Pro Tyr
            340                     345                 350

Lys Leu Asn Leu Val Ala Thr Pro Leu Phe Leu Lys Pro Gly Ile Pro
        355                     360                 365

Tyr Pro Ile Lys Val Gln Val Lys Asp Ser Leu Asp Gln Leu Val Gly
370                     375                 380

Gly Val Pro Val Thr Leu Asn Ala Gln Thr Ile Asp Val Asn Gln Glu
385                     390                 395                 400

Thr Ser Asp Leu Asp Pro Ser Lys Ser Val Thr Arg Val Asp Asp Gly
                405                     410                 415

Val Ala Ser Phe Val Leu Asn Leu Pro Ser Gly Val Thr Val Leu Glu
            420                     425                 430

Phe Asn Val Lys Thr Asp Ala Pro Asp Leu Pro Glu Glu Asn Gln Ala
        435                     440                 445

Arg Glu Gly Tyr Arg Ala Ile Ala Tyr Ser Ser Leu Ser Gln Ser Tyr
450                     455                 460

Leu Tyr Ile Asp Trp Thr Asp Asn His Lys Ala Leu Leu Val Gly Glu
465                     470                 475                 480

His Leu Asn Ile Ile Val Thr Pro Lys Ser Pro Tyr Ile Asp Lys Ile
                485                     490                 495

Thr His Tyr Asn Tyr Leu Ile Leu Ser Lys Gly Lys Ile Ile His Phe
            500                     505                 510

Gly Thr Arg Glu Lys Phe Ser Asp Ala Ser Tyr Gln Ser Ile Asn Ile
        515                     520                 525

Pro Val Thr Gln Asn Met Val Pro Ser Ser Arg Leu Leu Val Tyr Tyr
530                     535                 540

Ile Val Thr Gly Glu Gln Thr Ala Glu Leu Val Ser Asp Ser Val Trp
545                     550                 555                 560

Leu Asn Ile Glu Glu Lys Cys Gly Asn Gln Leu Gln Val His Leu Ser
                565                     570                 575

Pro Asp Ala Asp Ala Tyr Ser Pro Gly Gln Thr Val Ser Leu Asn Met
            580                     585                 590

Ala Thr Gly Met Asp Ser Trp Val Ala Leu Ala Ala Val Asp Ser Ala
        595                     600                 605

Val Tyr Gly Val Gln Arg Gly Ala Lys Lys Pro Leu Glu Arg Val Phe
610                     615                 620

Gln Phe Leu Glu Lys Ser Asp Leu Gly Cys Gly Ala Gly Gly Gly Leu
625                     630                 635                 640

Asn Asn Ala Asn Val Phe His Leu Ala Gly Leu Thr Phe Leu Thr Asn
                645                     650                 655

Ala Asn Ala Asp Asp Ser Gln Glu Asn Asp Glu Pro Cys Lys Glu Ile
            660                     665                 670

Leu Arg Pro Arg Arg Thr Leu Gln Lys Lys Ile Glu Glu Ile Ala Ala
        675                     680                 685

Lys Tyr Lys His Ser Val Val Lys Cys Cys Tyr Asp Gly Ala Cys
690                     695                 700

Val Asn Asn Asp Glu Thr Cys Glu Gln Arg Ala Ala Arg Ile Ser Leu
705                     710                 715                 720

-continued

Gly Pro Arg Cys Ile Lys Ala Phe Thr Glu Cys Cys Val Val Ala Ser
                725                 730                 735
Gln Leu Arg Ala Asn Ile Ser His Lys Asp Met Gln Leu Gly Arg Leu
                740                 745                 750
His Met Lys Thr Leu Leu Pro Val Ser Lys Pro Glu Ile Arg Ser Tyr
                755                 760                 765
Phe Pro Glu Ser Trp Leu Trp Glu Val His Leu Val Pro Arg Arg Lys
                770                 775                 780
Gln Leu Gln Phe Ala Leu Pro Asp Ser Leu Thr Thr Trp Glu Ile Gln
785                 790                 795                 800
Gly Val Gly Ile Ser Asn Thr Gly Ile Cys Val Ala Asp Thr Val Lys
                805                 810                 815
Ala Lys Val Phe Lys Asp Val Phe Leu Glu Met Asn Ile Pro Tyr Ser
                820                 825                 830
Val Val Arg Gly Glu Gln Ile Gln Leu Lys Gly Thr Val Tyr Asn Tyr
                835                 840                 845
Arg Thr Ser Gly Met Gln Phe Cys Val Lys Met Ser Ala Val Glu Gly
                850                 855                 860
Ile Cys Thr Ser Glu Ser Pro Val Ile Asp His Gln Gly Thr Lys Ser
865                 870                 875                 880
Ser Lys Cys Val Arg Gln Lys Val Glu Gly Ser Ser Ser His Leu Val
                885                 890                 895
Thr Phe Thr Val Leu Pro Leu Glu Ile Gly Leu His Asn Ile Asn Phe
                900                 905                 910
Ser Leu Glu Thr Trp Phe Gly Lys Glu Ile Leu Val Lys Thr Leu Arg
                915                 920                 925
Val Val Pro Glu Gly Val Lys Arg Glu Ser Tyr Ser Gly Val Thr Leu
                930                 935                 940
Asp Pro Arg Gly Ile Tyr Gly Thr Ile Ser Arg Arg Lys Glu Phe Pro
945                 950                 955                 960
Tyr Arg Ile Pro Leu Asp Leu Val Pro Lys Thr Glu Ile Lys Arg Ile
                965                 970                 975
Leu Ser Val Lys Gly Leu Leu Val Gly Glu Ile Leu Ser Ala Val Leu
                980                 985                 990
Ser Gln Glu Gly Ile Asn Ile Leu Thr His Leu Pro Lys Gly Ser Ala
                995                 1000                1005
Glu Ala Glu Leu Met Ser Val Val Pro Val Phe Tyr Val Phe His
                1010                1015                1020
Tyr Leu Glu Thr Gly Asn His Trp Asn Ile Phe His Ser Asp Pro
                1025                1030                1035
Leu Ile Glu Lys Gln Lys Leu Lys Lys Lys Leu Lys Glu Gly Met
                1040                1045                1050
Leu Ser Ile Met Ser Tyr Arg Asn Ala Asp Tyr Ser Tyr Ser Val
                1055                1060                1065
Trp Lys Gly Gly Ser Ala Ser Thr Trp Leu Thr Ala Phe Ala Leu
                1070                1075                1080
Arg Val Leu Gly Gln Val Asn Lys Tyr Val Glu Gln Asn Gln Asn
                1085                1090                1095
Ser Ile Cys Asn Ser Leu Leu Trp Leu Val Glu Asn Tyr Gln Leu
                1100                1105                1110
Asp Asn Gly Ser Phe Lys Glu Asn Ser Gln Tyr Gln Pro Ile Lys
                1115                1120                1125
Leu Gln Gly Thr Leu Pro Val Glu Ala Arg Glu Asn Ser Leu Tyr

|  |  |  |  |  |  |  |  |  |  |
|---|---|---|---|---|---|---|---|---|---|
| | | | 1130 | | | 1135 | | | 1140 |
| Leu | Thr | Ala | Phe | Thr | Val | Ile | Gly | Ile | Arg | Lys | Ala | Phe | Asp | Ile |
| 1145 | | | | | 1150 | | | | | 1155 |
| Cys | Pro | Leu | Val | Lys | Ile | Asp | Thr | Ala | Leu | Ile | Lys | Ala | Asp | Asn |
| 1160 | | | | | 1165 | | | | | 1170 |
| Phe | Leu | Leu | Glu | Asn | Thr | Leu | Pro | Ala | Gln | Ser | Thr | Phe | Thr | Leu |
| 1175 | | | | | 1180 | | | | | 1185 |
| Ala | Ile | Ser | Ala | Tyr | Ala | Leu | Ser | Leu | Gly | Asp | Lys | Thr | His | Pro |
| 1190 | | | | | 1195 | | | | | 1200 |
| Gln | Phe | Arg | Ser | Ile | Val | Ser | Ala | Leu | Lys | Arg | Glu | Ala | Leu | Val |
| 1205 | | | | | 1210 | | | | | 1215 |
| Lys | Gly | Asn | Pro | Pro | Ile | Tyr | Arg | Phe | Trp | Lys | Asp | Asn | Leu | Gln |
| 1220 | | | | | 1225 | | | | | 1230 |
| His | Lys | Asp | Ser | Ser | Val | Pro | Asn | Thr | Gly | Thr | Ala | Arg | Met | Val |
| 1235 | | | | | 1240 | | | | | 1245 |
| Glu | Thr | Thr | Ala | Tyr | Ala | Leu | Leu | Thr | Ser | Leu | Asn | Leu | Lys | Asp |
| 1250 | | | | | 1255 | | | | | 1260 |
| Ile | Asn | Tyr | Val | Asn | Pro | Val | Ile | Lys | Trp | Leu | Ser | Glu | Glu | Gln |
| 1265 | | | | | 1270 | | | | | 1275 |
| Arg | Tyr | Gly | Gly | Gly | Phe | Tyr | Ser | Thr | Gln | Asp | Thr | Ile | Asn | Ala |
| 1280 | | | | | 1285 | | | | | 1290 |
| Ile | Glu | Gly | Leu | Thr | Glu | Tyr | Ser | Leu | Leu | Val | Lys | Gln | Leu | Arg |
| 1295 | | | | | 1300 | | | | | 1305 |
| Leu | Ser | Met | Asp | Ile | Asp | Val | Ser | Tyr | Lys | His | Lys | Gly | Ala | Leu |
| 1310 | | | | | 1315 | | | | | 1320 |
| His | Asn | Tyr | Lys | Met | Thr | Asp | Lys | Asn | Phe | Leu | Gly | Arg | Pro | Val |
| 1325 | | | | | 1330 | | | | | 1335 |
| Glu | Val | Leu | Leu | Asn | Asp | Asp | Leu | Ile | Val | Ser | Thr | Gly | Phe | Gly |
| 1340 | | | | | 1345 | | | | | 1350 |
| Ser | Gly | Leu | Ala | Thr | Val | His | Val | Thr | Thr | Val | Val | His | Lys | Thr |
| 1355 | | | | | 1360 | | | | | 1365 |
| Ser | Thr | Ser | Glu | Glu | Val | Cys | Ser | Phe | Tyr | Leu | Lys | Ile | Asp | Thr |
| 1370 | | | | | 1375 | | | | | 1380 |
| Gln | Asp | Ile | Glu | Ala | Ser | His | Tyr | Arg | Gly | Tyr | Gly | Asn | Ser | Asp |
| 1385 | | | | | 1390 | | | | | 1395 |
| Tyr | Lys | Arg | Ile | Val | Ala | Cys | Ala | Ser | Tyr | Lys | Pro | Ser | Arg | Glu |
| 1400 | | | | | 1405 | | | | | 1410 |
| Glu | Ser | Ser | Ser | Gly | Ser | Ser | His | Ala | Val | Met | Asp | Ile | Ser | Leu |
| 1415 | | | | | 1420 | | | | | 1425 |
| Pro | Thr | Gly | Ile | Ser | Ala | Asn | Glu | Glu | Asp | Leu | Lys | Ala | Leu | Val |
| 1430 | | | | | 1435 | | | | | 1440 |
| Glu | Gly | Val | Asp | Gln | Leu | Phe | Thr | Asp | Tyr | Gln | Ile | Lys | Asp | Gly |
| 1445 | | | | | 1450 | | | | | 1455 |
| His | Val | Ile | Leu | Gln | Leu | Asn | Ser | Ile | Pro | Ser | Ser | Asp | Phe | Leu |
| 1460 | | | | | 1465 | | | | | 1470 |
| Cys | Val | Arg | Phe | Arg | Ile | Phe | Glu | Leu | Phe | Glu | Val | Gly | Phe | Leu |
| 1475 | | | | | 1480 | | | | | 1485 |
| Ser | Pro | Ala | Thr | Phe | Thr | Val | Tyr | Glu | Tyr | His | Arg | Pro | Asp | Lys |
| 1490 | | | | | 1495 | | | | | 1500 |
| Gln | Cys | Thr | Met | Phe | Tyr | Ser | Thr | Ser | Asn | Ile | Lys | Ile | Gln | Lys |
| 1505 | | | | | 1510 | | | | | 1515 |
| Val | Cys | Glu | Gly | Ala | Ala | Cys | Lys | Cys | Val | Glu | Ala | Asp | Cys | Gly |
| 1520 | | | | | 1525 | | | | | 1530 |

-continued

```
Gln Met Gln Glu Glu Leu Asp Leu Thr Ile Ser Ala Glu Thr Arg
1535                1540                1545

Lys Gln Thr Ala Cys Lys Pro Glu Ile Ala Tyr Ala Tyr Lys Val
    1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 297
<211> LENGTH: 1676
<212> TYPE: PRT
<213> ORGANISM: homo sapiens

<400> SEQUENCE: 297

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
            35                  40                  45

Ala Phe Asp Ala Thr Ile Ser Ile Lys Ser Tyr Pro Asp Lys Lys Phe
        50                  55                  60

Ser Tyr Ser Ser Gly His Val His Leu Ser Ser Glu Asn Lys Phe Gln
65                  70                  75                  80

Asn Ser Ala Val Leu Thr Ile Gln Pro Lys Gln Leu Pro Gly Gly Gln
                85                  90                  95

Asn Gln Val Ser Tyr Val Tyr Leu Glu Val Val Ser His Phe Ser
            100                 105                 110

Lys Ser Lys Lys Ile Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Ile Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Gln Ala Lys Tyr Lys Glu Asp
        195                 200                 205

Phe Ser Thr Thr Gly Thr Ala Phe Phe Glu Val Lys Glu Tyr Val Leu
    210                 215                 220
```

```
Pro His Phe Ser Val Ser Val Glu Pro Glu Ser Asn Phe Ile Gly Tyr
225                 230                 235                 240

Lys Asn Phe Lys Asn Phe Glu Ile Thr Ile Lys Ala Arg Tyr Phe Tyr
            245                 250                 255

Asn Lys Val Val Thr Glu Ala Asp Val Tyr Ile Thr Phe Gly Ile Arg
        260                 265                 270

Glu Asp Leu Lys Asp Asp Gln Lys Glu Met Met Gln Thr Ala Met Gln
    275                 280                 285

Asn Thr Met Leu Ile Asn Gly Ile Ala Gln Val Thr Phe Asp Ser Glu
290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
            355                 360                 365

Tyr Ser Ile Lys Val Gln Val Lys Asp Ala Leu Asp Gln Leu Val Gly
370                 375                 380

Gly Val Pro Val Thr Leu Asn Ala Gln Thr Ile Asp Val Asn Gln Glu
385                 390                 395                 400

Thr Ser Asp Leu Glu Pro Arg Lys Ser Val Thr Arg Val Asp Asp Gly
            405                 410                 415

Val Ala Ser Phe Val Val Asn Leu Pro Ser Gly Val Thr Val Leu Glu
                420                 425                 430

Phe Asn Val Lys Thr Asp Ala Pro Asp Leu Pro Asp Glu Asn Gln Ala
            435                 440                 445

Arg Glu Gly Tyr Arg Ala Ile Ala Tyr Ser Ser Leu Ser Gln Ser Tyr
450                 455                 460

Leu Tyr Ile Asp Trp Thr Asp Asn His Lys Ala Leu Leu Val Gly Glu
465                 470                 475                 480

Tyr Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Leu Ser Asp Ala Ser Tyr Gln Ser Ile Asn Ile
            515                 520                 525

Pro Val Thr Gln Asn Met Val Pro Ser Ser Arg Leu Leu Val Tyr Tyr
            530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Thr Tyr Ser Pro Gly Gln Thr Val Ser Leu Asn Met
            580                 585                 590

Val Thr Gly Met Asp Ser Trp Val Ala Leu Thr Ala Val Asp Ser Ala
            595                 600                 605

Val Tyr Gly Val Gln Arg Arg Ala Lys Lys Pro Leu Glu Arg Val Phe
            610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655
```

```
Ala Asn Ala Asp Asp Ser Gln Glu Asn Asp Glu Pro Cys Lys Glu Ile
            660                 665                 670

Ile Arg Pro Arg Arg Met Leu Gln Glu Lys Ile Glu Glu Ile Ala Ala
        675                 680                 685

Lys Tyr Lys His Leu Val Val Lys Lys Cys Cys Tyr Asp Gly Val Arg
    690                 695                 700

Ile Asn His Asp Glu Thr Cys Glu Gln Arg Ala Ala Arg Ile Ser Val
705                 710                 715                 720

Gly Pro Arg Cys Val Lys Ala Phe Thr Glu Cys Cys Val Val Ala Ser
                725                 730                 735

Gln Leu Arg Ala Asn Asn Ser His Lys Asp Leu Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
    770                 775                 780

Gln Leu Gln Phe Ala Leu Pro Asp Ser Val Thr Thr Trp Glu Ile Gln
785                 790                 795                 800

Gly Val Gly Ile Ser Asn Ser Gly Ile Cys Val Ala Asp Thr Ile Lys
                805                 810                 815

Ala Lys Val Phe Lys Asp Val Phe Leu Glu Met Asn Ile Pro Tyr Ser
            820                 825                 830

Val Val Arg Gly Glu Gln Val Gln Leu Lys Gly Thr Val Tyr Asn Tyr
        835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser Asn His Leu Val
                885                 890                 895

Thr Phe Thr Val Leu Pro Leu Glu Ile Gly Leu Gln Asn Ile Asn Phe
            900                 905                 910

Ser Leu Glu Thr Ser Phe Gly Lys Glu Ile Leu Val Lys Ser Leu Arg
        915                 920                 925

Val Val Pro Glu Gly Val Lys Arg Glu Ser Tyr Ser Gly Ile Thr Leu
    930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Arg Glu Gly Ile Asn Ile Leu Thr His Leu Pro Lys Gly Ser Ala
        995                 1000                1005

Glu Ala Glu Leu Met Ser Val Val Pro Val Phe Tyr Val Phe His
   1010             1015                1020

Tyr Leu Glu Thr Gly Asn His Trp Asn Ile Phe His Ser Asp Pro
   1025             1030                1035

Leu Ile Glu Lys Arg Asn Leu Glu Lys Lys Leu Lys Glu Gly Met
   1040             1045                1050

Val Ser Ile Met Ser Tyr Arg Asn Ala Asp Tyr Ser Tyr Ser Val
   1055             1060                1065

Trp Lys Gly Gly Ser Ala Ser Thr Trp Leu Thr Ala Phe Ala Leu
```

-continued

```
                1070                1075                1080
Arg Val Leu Gly Gln Val His Lys Tyr Val Glu Gln Asn Gln Asn
1085                1090                1095
Ser Ile Cys Asn Ser Leu Leu Trp Leu Val Glu Asn Tyr Gln Leu
1100                1105                1110
Asp Asn Gly Ser Phe Lys Glu Asn Ser Gln Tyr Gln Pro Ile Lys
1115                1120                1125
Leu Gln Gly Thr Leu Pro Val Glu Ala Arg Glu Asn Ser Leu Tyr
1130                1135                1140
Leu Thr Ala Phe Thr Val Ile Gly Ile Arg Lys Ala Phe Asp Ile
1145                1150                1155
Cys Pro Leu Val Lys Ile Asn Thr Ala Leu Ile Lys Ala Asp Thr
1160                1165                1170
Phe Leu Leu Glu Asn Thr Leu Pro Ala Gln Ser Thr Phe Thr Leu
1175                1180                1185
Ala Ile Ser Ala Tyr Ala Leu Ser Leu Gly Asp Lys Thr His Pro
1190                1195                1200
Gln Phe Arg Ser Ile Val Ser Ala Leu Lys Arg Glu Ala Leu Val
1205                1210                1215
Lys Gly Asn Pro Pro Ile Tyr Arg Phe Trp Lys Asp Ser Leu Gln
1220                1225                1230
His Lys Asp Ser Ser Val Pro Asn Thr Gly Thr Ala Arg Met Val
1235                1240                1245
Glu Thr Thr Ala Tyr Ala Leu Leu Thr Ser Leu Asn Leu Lys Asp
1250                1255                1260
Ile Asn Tyr Val Asn Pro Ile Ile Lys Trp Leu Ser Glu Glu Gln
1265                1270                1275
Arg Tyr Gly Gly Gly Phe Tyr Ser Thr Gln Asp Thr Ile Asn Ala
1280                1285                1290
Ile Glu Gly Leu Thr Glu Tyr Ser Leu Leu Val Lys Gln Leu Arg
1295                1300                1305
Leu Asn Met Asp Ile Asp Val Ala Tyr Lys His Lys Gly Pro Leu
1310                1315                1320
His Asn Tyr Lys Met Thr Asp Lys Asn Phe Leu Gly Arg Pro Val
1325                1330                1335
Glu Val Leu Leu Asn Asp Asp Leu Val Val Ser Thr Gly Phe Gly
1340                1345                1350
Ser Gly Leu Ala Thr Val His Val Thr Thr Val Val His Lys Thr
1355                1360                1365
Ser Thr Ser Glu Glu Val Cys Ser Phe Tyr Leu Lys Ile Asp Thr
1370                1375                1380
Gln Asp Ile Glu Ala Ser His Tyr Arg Gly Tyr Gly Asn Ser Asp
1385                1390                1395
Tyr Lys Arg Ile Val Ala Cys Ala Ser Tyr Lys Pro Ser Lys Glu
1400                1405                1410
Glu Ser Ser Ser Gly Ser Ser His Ala Val Met Asp Ile Ser Leu
1415                1420                1425
Pro Thr Gly Ile Asn Ala Asn Glu Glu Asp Leu Lys Ala Leu Val
1430                1435                1440
Glu Gly Val Asp Gln Leu Phe Thr Asp Tyr Gln Ile Lys Asp Gly
1445                1450                1455
His Val Ile Leu Gln Leu Asn Ser Ile Pro Ser Ser Asp Phe Leu
1460                1465                1470
```

```
Cys Val Arg Phe Arg Ile Phe Glu Leu Phe Glu Val Gly Phe Leu
    1475                1480                1485

Ser Pro Ala Thr Phe Thr Val Tyr Glu Tyr His Arg Pro Asp Lys
    1490                1495                1500

Gln Cys Thr Met Phe Tyr Ser Thr Ser Asn Ile Lys Ile Gln Lys
    1505                1510                1515

Val Cys Glu Gly Ala Thr Cys Lys Cys Ile Glu Ala Asp Cys Gly
    1520                1525                1530

Gln Met Gln Lys Glu Leu Asp Leu Thr Ile Ser Ala Glu Thr Arg
    1535                1540                1545

Lys Gln Thr Ala Cys Asn Pro Glu Ile Ala Tyr Ala Tyr Lys Val
    1550                1555                1560

Ile Ile Thr Ser Ile Thr Thr Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Thr Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 298
<211> LENGTH: 98
<212> TYPE: PRT
<213> ORGANISM: Homo sapiens

<400> SEQUENCE: 298

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 299
<211> LENGTH: 95
<212> TYPE: PRT
<213> ORGANISM: Homo sapiens

<400> SEQUENCE: 299

Ser Tyr Glu Leu Thr Gln Pro Leu Ser Val Ser Val Ala Leu Gly Gln
1               5                   10                  15
```

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95

<210> SEQ ID NO 300
<211> LENGTH: 98
<212> TYPE: PRT
<213> ORGANISM: Homo sapiens

<400> SEQUENCE: 300

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 301
<211> LENGTH: 95
<212> TYPE: PRT
<213> ORGANISM: Homo sapiens

<400> SEQUENCE: 301

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95

<210> SEQ ID NO 302
<211> LENGTH: 99
<212> TYPE: PRT
<213> ORGANISM: Homo sapiens

<400> SEQUENCE: 302

Gln Val Thr Leu Lys Glu Ser Gly Pro Ala Leu Val Lys Pro Thr Gln
1               5                   10                  15

-continued

```
Thr Leu Thr Leu Thr Cys Thr Phe Ser Gly Phe Ser Leu Ser Thr Ser
            20                  25                  30
Gly Met Arg Val Ser Trp Ile Arg Gln Pro Pro Gly Lys Ala Leu Glu
        35                  40                  45
Trp Leu Ala Arg Ile Asp Trp Asp Asp Lys Phe Tyr Ser Thr Ser
    50                  55                  60
Leu Lys Thr Arg Leu Thr Ile Ser Lys Asp Thr Ser Lys Asn Gln Val
 65                  70                  75                  80
Val Leu Thr Met Thr Asn Met Asp Pro Val Asp Thr Ala Thr Tyr Tyr
                85                  90                  95
Cys Ala Arg

<210> SEQ ID NO 303
<211> LENGTH: 99
<212> TYPE: PRT
<213> ORGANISM: Homo sapiens

<400> SEQUENCE: 303

Gln Ser Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Glu Val Ser Asn Arg Pro Ser Gly Val Ser Asn Arg Phe
    50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Thr Ser Ser
                85                  90                  95
Ser Thr Leu

<210> SEQ ID NO 304
<211> LENGTH: 98
<212> TYPE: PRT
<213> ORGANISM: Homo sapiens

<400> SEQUENCE: 304

Glu Val Gln Leu Val Gln Ser Gly Ala Glu Val Lys Lys Pro Gly Glu
 1               5                  10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                85                  90                  95
Ala Arg

<210> SEQ ID NO 305
<211> LENGTH: 95
<212> TYPE: PRT
<213> ORGANISM: Homo sapiens
```

<400> SEQUENCE: 305

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95

<210> SEQ ID NO 306
<211> LENGTH: 98
<212> TYPE: PRT
<213> ORGANISM: Homo sapiens

<400> SEQUENCE: 306

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 307
<211> LENGTH: 95
<212> TYPE: PRT
<213> ORGANISM: Homo sapiens

<400> SEQUENCE: 307

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95